United States Patent
Nicolaou et al.

(10) Patent No.: US 10,808,007 B2
(45) Date of Patent: Oct. 20, 2020

(54) DESACETOXYTUBULYSIN H AND ANALOGS THEREOF

(71) Applicant: WILLIAM MARSH RICE UNIVERSITY, Houston, TX (US)

(72) Inventors: Kyriacos C. Nicolaou, Houston, TX (US); Dionisios Vourloumis, Athens (GR); Jun Yin, Houston, TX (US); Rohan Erande, Houston, TX (US); Debashis Mandal, Fremont, CA (US); Phillipp Klahn, Munster (DE)

(73) Assignee: William Marsh Rice University, Houston, TX (US)

( * ) Notice: Subject to any disclaimer, the term of this patent is extended or adjusted under 35 U.S.C. 154(b) by 0 days.

(21) Appl. No.: 15/553,674

(22) PCT Filed: Feb. 25, 2016

(86) PCT No.: PCT/US2016/019604
§ 371 (c)(1),
(2) Date: Aug. 25, 2017

(87) PCT Pub. No.: WO2016/138288
PCT Pub. Date: Sep. 1, 2016

(65) Prior Publication Data
US 2018/0127463 A1 May 10, 2018

Related U.S. Application Data

(60) Provisional application No. 62/120,613, filed on Feb. 25, 2015, provisional application No. 62/275,667, filed on Jan. 6, 2016.

(51) Int. Cl.
| | | |
|---|---|---|
| *A61K 38/00* | (2006.01) | |
| *C07K 5/078* | (2006.01) | |
| *C07D 277/56* | (2006.01) | |
| *C07D 417/12* | (2006.01) | |
| *C07D 417/14* | (2006.01) | |
| *C07D 401/12* | (2006.01) | |
| *C07K 5/02* | (2006.01) | |
| *C07D 453/02* | (2006.01) | |
| *A61P 35/00* | (2006.01) | |

(52) U.S. Cl.
CPC .......... *C07K 5/06139* (2013.01); *A61P 35/00* (2018.01); *C07D 277/56* (2013.01); *C07D 401/12* (2013.01); *C07D 417/12* (2013.01); *C07D 417/14* (2013.01); *C07D 453/02* (2013.01); *C07K 5/021* (2013.01); *C07K 5/06165* (2013.01); *A61K 38/00* (2013.01)

(58) Field of Classification Search
None
See application file for complete search history.

(56) References Cited

U.S. PATENT DOCUMENTS

| | | | |
|---|---|---|---|
| 7,816,377 B2 | 10/2010 | Dömling et al. | |
| 8,772,244 B2 | 7/2014 | Richter | |
| 2005/0239713 A1 | 10/2005 | Domling et al. | |
| 2005/0249740 A1 | 11/2005 | Dömling et al. | |
| 2010/0240701 A1 | 9/2010 | Radoslavov et al. | |
| 2011/0027274 A1 | 2/2011 | Cheng et al. | |
| 2011/0200581 A1 | 8/2011 | Zanda et al. | |
| 2013/0137139 A1 | 5/2013 | Vlahov et al. | |
| 2014/0227295 A1 | 8/2014 | Cong et al. | |
| 2014/0323690 A1 | 10/2014 | Cheng et al. | |

FOREIGN PATENT DOCUMENTS

| | | |
|---|---|---|
| CN | 102725001 A | 10/2012 |
| CN | 105073139 A | 11/2015 |
| CO | 12034850 | 2/2012 |
| EP | 2174947 | 4/2010 |
| EP | 2409983 | 1/2012 |
| JP | 2011-037846 | 2/2011 |
| JP | 2013-501055 | 1/2013 |
| WO | WO 2004/005326 | 1/2004 |
| WO | WO 2004/005327 | 1/2004 |
| WO | WO 2008/106080 | 9/2008 |
| WO | WO 2008/138561 | 11/2008 |

(Continued)

OTHER PUBLICATIONS

Chen et al. Molecules. Aug. 2017; 22(8): 1281.*
Balasubramanian, R. et al., "Tubulysin analogs incorporating desmethyl and dimethyl tubuphenylalanine derivatives." *Bioorg. Med. Chem. Lett.* 18, 2996-2999; 2008.
Burkhart, J. L. et al., "A straightforward click-approach towards pretubulysin-analogs." *RSC Advances*. 2, 3785-3790; 2012.
Burkhart, J. L. et al., "Syntheses and evaluation of simplified pretubulysin analogs." *Eur. J. Org. Chem.* 3050-3059; 2011.
Chai, Y. et al., "Discovery of 23 natural tubulysins from *Angiococcus disciformis* An d48 and *Cystobacter* SBCb004", *Chem. Biol.* 17, 296-309; 2010.

(Continued)

Primary Examiner — Jeanette M Lieb
(74) Attorney, Agent, or Firm — Parker Highlander PLLC

(57) ABSTRACT

In one aspect, the present disclosure provides tubulysin analogs of the formula (I) wherein $R_1$, $R_2$, $R_3$, $R_4$, $X_1$, $X_2$, $X_3$, and $A_1$ are as defined herein. In another aspect, the present disclosure also provides methods of preparing the compounds disclosed herein. In another aspect, the present disclosure also provides pharmaceutical compositions and methods of use of the compounds disclosed herein.

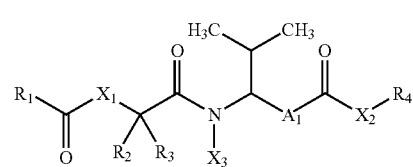

(I)

18 Claims, 87 Drawing Sheets

(56) References Cited

FOREIGN PATENT DOCUMENTS

| WO | WO 2009/012958 | 1/2009 |
|---|---|---|
| WO | WO 2009/055562 | 4/2009 |
| WO | WO 2010/034724 | 4/2010 |
| WO | WO 2011/017249 | 2/2011 |
| WO | WO 2011/069116 | 6/2011 |
| WO | WO 2012/010287 | 1/2012 |
| WO | WO 2012/019123 | 2/2012 |
| WO | WO 2013/149185 | 10/2013 |
| WO | WO 2014/126836 | 8/2014 |
| WO | WO2015157594 | 11/2016 |

OTHER PUBLICATIONS

Dömling, A. et al., "Total synthesis of tubulysin U and V", *Angew. Chem. Int. Ed.*, 45:7235-7239; 2006.

Dömling, A. et al., "Myxobacterial epothilones and tubulysins as promising anticancer agents." *Molecular Diversity* 9, 141-147; 2005.

Eirich, J. et al., "Pretubulysin derived probes as novel tools for monitoring the microtubule network via activity-based protein profiling and fluorescence microscopy." *Mol. BioSyst.*, 8, 2067-2075; 2012.

Floyd, W. C., III et al., "Chemotherapeutic evaluation of a synthetic tubulysin analogue-dendrimer conjugate in c26 tumor bearing mice." *ChemMedChem*, 6, 49-53; 2011.

Höfle, G. et al., "Semisynthesis and degradation of the tubulin inhibitors epothilone and tubulysin." *Pure Appl. Chem.*, 75, 167-178; 2003.

International Preliminary Report on Patentability issued in in International Application No. PCT/US2016/019604, dated Sep. 8, 2017.

International Search Report and Written Opinion issued in International Application No. PCT/US2016/019604, dated Jun. 6, 2016.

Kazmaier, U. et al., "Hoffmann, J Synthetic Approaches Towards Tubulysins and Derivatives Thereof." *The Open Natural Products Journal*, 6, 12-30; 2013.

Khalil, M. W. et al., "Mechanism of action of tubulysin, an antimitotic peptide from myxobacteria." *ChemBioChem*, 7, 678-683; 2006.

Kubicek, K. et al., "The tubulin-bound structure of the antimitotic drug tubulysin", *Angew. Chem. Int. Ed.*, 49:4809-4812, 2010

Neri, D. et al., "Efforts toward the Total Synthesis of Tubulysins: New Hopes for a More Effective Targeted Drug Delivery to Tumors." *ChemMedChem*, 1, 175-180; 2006.

Pando, O. et al., "First total synthesis of tubulysin B." *Org. Lett.*, 11, 5567-5569; 2009.

Pando, O. et al., "The multiple multicomponent approach natural product mimics: Tubugis, N-substituted anticancer peptides with picomolar activity." *J. Am. Chem. Soc.*, 133, 7692-7695; 2011.

Patterson, A. W. et al., "Design, Synthesis, and Biological Properties of Highly Potent Tubulysin D Analogs." *Chem. Eur. J.*, 13, 9534-9541; 2007.

Patterson, A.W. et al., "Expedient Synthesis of N-Methyl Tubulysin Analogues with High Cytotoxicity." *J. Org. Chem*; 73, 4362-4369; 2008.

Peltier, H. M. et al., "The total synthesis of tubulysin D", *J. Am. Chem. Soc.*, 128:16018-16019, 2006.

Raghavan, B. et al., "Cytotoxic simplified tubulysin analogs." *J. Med. Chem.*, 51, 1530-1533; 2008.

Rath, S. et al., "Anti-angiogenic effects of the tubulysin precursor pretubulysin and of simplified pretubulysin derivatives." *Br. J. Pharmacol.*, 167, 1048-1061; 2012.

Rautio et al., "Prodrugs: design and clinical applications", *Nat. Rev.*, 7:255-270, 2008.

Sandmann, A. et al., "Identification and analysis of the core biosynthetic machinery of tubulysin, a potent cytotoxin with potential anticancer activity." *Chem. Biol.*, 11, 1071-1079; 2004.

Sani, M. et al., "Total synthesis of tubulysins U and V." *Angew. Chem. Int. Ed.*, 46:3526-3529; 2007.

Sasse, F. et al., Success in tubulysin D synthesis. *Nat. Chem. Biol.*, 3, 87-89; 2007.

Sasse, F. et al., "Tubulysins, new cytostatic peptides from myxobacteria acting on microtubuli." *J. Antibiot.*, 53, 879-885; 2000.

Shankar S. P. et al., "Total synthesis and cytotoxicity evaluation of an oxazole analogue of tubulysin U." *Synlett*, 1673-1676; 2011.

Shankar, S. P. et al., "Synthesis and structure-activity relationship studies of novel tubulysin U analogs-effect on cytotoxicity of structural variations in the tubuvaline fragment." *Org. Biomol. Chem.*, 2273-2287; 2013.

Shibue, T. et al., "Synthesis and biological evaluation of tubulysin D analogs related to stereoisomers of tubuvaline." *Bioorg. Med. Chem. Lett.*, 21, 431-434; 2011.

Shibue, T. et al., "Total syntheses of tubulysins." *Chem. Eur. J.*, 16, 11678-11688; 2010.

Steinmetz, H. et al., "Isolation, crystal and solution structure determination and biosynthesis of tubulysins-powerful inhibitors of tubulin polymerization from myxobacteria." *Angew. Chem.*, 116, 4996-5000; 2004.

Third Party Observation issued in corresponding PCT Application No. PCT/US2016/019604, dated Mar. 3, 2017.

Ullrich, A. et al., "Pretubulysin, a potent and chemically accessible tubulysin precursor from Angiococcus disciformis", *Angew. Chem. Int. Ed.*, 48:4422-4425, 2009.

Wang, R. et al., "Stereoselective total synthesis of tubulysin V." *Chin. J. Chem*, 31, 40-48; 2013.

Wang, Z. et al., "Structure-activity and High-content Imaging Analyses of Novel Tubulysins." *Chem Biol Drug Des*, 70: 75-862007; 2007.

WIKI-2013-HATU, Dec. 20, 2013.

Wipf, P. et al.; "Total Synthesis of N14-Desacetoxytubulysin H." *Org. Lett.* 9, 1605-1607; 2007.

Yang, X et al., "Design, synthesis, and biological activities of triazole tubulysin V analogue." *Tetrahedron Lett.* 54, 2986-2988; 2013.

Yang, X, et al., "Total Synthesis of Tubulysin U and Its C-4 Epimer." *Chem Asian J.*, 8, 1213-1222; 2013.

Search Report/Patentability Examination dated Jun. 5, 2019 in Colombian Examination Report dated Jun. 18, 2019 issued in corresponding Colombian Application No. NC2017/0008600.

Office Action and Search Report issued in Chinese Application No. 201680023813, dated Nov. 28, 2019, with English language translation.

Office Action issued in Japanese Application No. 2017-545239, dated Dec. 12, 2019, with English language translation.

\* cited by examiner

| NSC : D - 784013 / 1 | | | | | | | | | Experiment ID : 1509RS55 | | | | Test Type : 08 | | Units : Molar |
|---|---|---|---|---|---|---|---|---|---|---|---|---|---|---|---|
| Report Date : November 04, 2015 | | | | | | | | | Test Date : September 08, 2015 | | | | QNS : | MC : | |
| COMI : KCN-TB1 | | | | | | | | | Stain Reagent : SRB Dual-Pass Related | | | | SSPL : 0ZAS | | |
| | Time | | | | Log10 Concentration | | | | | | Percent Growth | | | | |
| | | | | Mean Optical Densities | | | | | | | | | | | |
| Panel/Cell Line | Zero | Ctrl | -11.0 | -10.0 | -9.0 | -8.0 | -7.0 | -11.0 | -10.0 | -9.0 | -8.0 | -7.0 | GI50 | TGI | LC50 |
| Leukemia | | | | | | | | | | | | | | | |
| CCRF-CEM | 0.854 | 3.295 | 3.234 | 3.021 | 1.425 | 1.083 | 1.073 | 97 | 89 | 23 | 9 | 9 | 3.92E-10 | > 1.00E-7 | > 1.00E-7 |
| HL-60(TB) | 0.734 | 3.086 | 3.035 | 3.057 | 1.130 | 0.568 | 0.585 | 98 | 99 | 17 | -23 | -20 | 3.94E-10 | 2.67E-9 | > 1.00E-7 |
| K-562 | 0.259 | 2.366 | 2.424 | 2.085 | 0.584 | 0.405 | 0.411 | 103 | 87 | 15 | 7 | 7 | 3.27E-10 | > 1.00E-7 | > 1.00E-7 |
| MOLT-4 | 0.951 | 3.266 | 3.255 | 3.228 | 2.735 | 1.645 | 1.323 | 100 | 98 | 77 | 30 | 16 | 3.76E-9 | > 1.00E-7 | > 1.00E-7 |
| RPMI-8226 | 0.482 | 1.736 | 1.627 | 1.462 | 0.627 | 0.579 | 0.670 | 91 | 78 | 12 | 8 | 15 | 2.64E-10 | > 1.00E-7 | > 1.00E-7 |
| SR | 0.285 | 0.812 | 0.808 | 0.674 | 0.415 | 0.328 | 0.326 | 99 | 74 | 25 | 8 | 8 | 3.05E-10 | > 1.00E-7 | > 1.00E-7 |

*FIG. 9*

| | | | | | | | | | | | |
|---|---|---|---|---|---|---|---|---|---|---|---|
| Non-Small Cell Lung Cancer | | | | | | | | | | | |
| A549/ATCC | 0.397 | 1.896 | 1.815 | 1.840 | 1.243 | 0.723 | 0.608 | 95 | 96 | 56 | 22 | 14 | 1.53E-9 | > 1.00E-7 | > 1.00E-7 |
| EKVX | 0.829 | 2.020 | 1.956 | 1.923 | 1.420 | 1.255 | 1.252 | 95 | 92 | 50 | 36 | 36 | 9.80E-10 | > 1.00E-7 | > 1.00E-7 |
| HOP-62 | 0.551 | 1.594 | 1.622 | 1.620 | 1.049 | 0.796 | 0.624 | 103 | 102 | 48 | 23 | 7 | 9.10E-10 | > 1.00E-7 | > 1.00E-7 |
| HOP-92 | 1.496 | 1.940 | 1.890 | 1.822 | 1.619 | 1.846 | 1.751 | 89 | 73 | 28 | 79 | 57 | | | |
| NCI-H226 | 0.568 | 1.501 | 1.466 | 1.483 | 1.087 | 1.045 | 0.860 | 96 | 98 | 56 | 51 | 31 | 1.13E-8 | > 1.00E-7 | > 1.00E-7 |
| NCI-H23 | 0.617 | 1.889 | 1.853 | 1.733 | 1.227 | 0.911 | 0.823 | 97 | 88 | 48 | 23 | 16 | 8.87E-10 | > 1.00E-7 | > 1.00E-7 |
| NCI-H322M | 0.662 | 2.055 | 2.039 | 1.981 | 1.313 | 1.182 | 1.108 | 99 | 95 | 47 | 37 | 32 | 8.54E-10 | > 1.00E-7 | > 1.00E-7 |
| NCI-H460 | 0.217 | 2.495 | 2.542 | 2.450 | 0.521 | 0.324 | 0.300 | 102 | 98 | 13 | 5 | 4 | 3.69E-10 | > 1.00E-7 | > 1.00E-7 |
| NCI-H522 | 0.922 | 2.903 | 2.816 | 2.507 | 1.407 | 0.948 | 0.836 | 96 | 80 | 24 | 1 | -9 | 3.47E-10 | 1.33E-8 | > 1.00E-7 |
| Colon Cancer | | | | | | | | | | | | | | | |
| COLO 205 | 0.482 | 1.602 | 1.633 | 1.557 | 0.693 | 0.367 | 0.220 | 103 | 96 | 19 | -24 | -54 | 3.94E-10 | 2.75E-9 | 7.14E-8 |
| HCC-2998 | 0.664 | 2.228 | 2.167 | 2.196 | 1.535 | 0.763 | 0.727 | 96 | 98 | 56 | 6 | 4 | 1.30E-9 | > 1.00E-7 | > 1.00E-7 |
| HCT-116 | 0.329 | 2.816 | 2.853 | 2.563 | 0.930 | 0.580 | 0.450 | 101 | 90 | 24 | 10 | 5 | 4.04E-10 | > 1.00E-7 | > 1.00E-7 |
| HCT-15 | 0.237 | 1.334 | 1.312 | 1.296 | 0.842 | 0.385 | 0.251 | 98 | 96 | 55 | 13 | 1 | 1.33E-9 | > 1.00E-7 | > 1.00E-7 |
| HT29 | 0.374 | 2.585 | 2.496 | 2.528 | 0.625 | 0.435 | 0.377 | 96 | 97 | 11 | 3 | | 3.56E-10 | > 1.00E-7 | > 1.00E-7 |
| KM12 | 0.429 | 2.591 | 2.535 | 2.071 | 0.766 | 0.571 | 0.413 | 97 | 76 | 16 | 7 | -4 | 2.69E-10 | 4.33E-8 | > 1.00E-7 |
| SW-620 | 0.230 | 2.066 | 1.999 | 1.637 | 0.698 | 0.608 | 0.612 | 96 | 77 | 25 | 21 | 21 | 3.32E-10 | > 1.00E-7 | > 1.00E-7 |

*FIG. 9 (Cont'd)*

| | | | | | | | | | | |
|---|---|---|---|---|---|---|---|---|---|---|
| CNS Cancer | | | | | | | | | | |
| SF-268 | 0.431 | 1.693 | 1.681 | 1.672 | 1.010 | 0.799 | 0.659 | 99 | 98 | 46 | 29 | 18 | 8.34E-10 | > 1.00E-7 |
| SF-295 | 0.834 | 2.625 | 2.561 | 2.393 | 1.023 | 0.727 | 0.665 | 96 | 87 | 11 | -13 | -20 | 3.05E-10 | 2.82E-9 |
| SF-539 | 0.954 | 2.670 | 2.627 | 2.589 | 1.568 | 0.855 | 0.789 | 97 | 95 | 36 | -10 | -17 | 5.76E-10 | 5.96E-9 |
| SNB-19 | 0.499 | 1.872 | 1.795 | 1.690 | 1.039 | 0.800 | 0.730 | 94 | 87 | 39 | 22 | 17 | 5.95E-10 | > 1.00E-7 |
| SNB-75 | 0.861 | 1.765 | 1.656 | 1.630 | 1.210 | 1.011 | 1.010 | 88 | 85 | 39 | 17 | 16 | 5.68E-10 | > 1.00E-7 |
| U251 | 0.301 | 1.398 | 1.353 | 1.325 | 0.628 | 0.509 | 0.498 | 96 | 93 | 30 | 19 | 18 | 4.80E-10 | > 1.00E-7 |
| Melanoma | | | | | | | | | | |
| LOX IMVI | 0.426 | 2.725 | 2.680 | 2.530 | 1.314 | 1.091 | 0.774 | 98 | 92 | 39 | 29 | 15 | 6.09E-10 | > 1.00E-7 |
| MALME-3M | 0.729 | 1.420 | 1.396 | 1.231 | 1.046 | 1.078 | 1.063 | 96 | 73 | 46 | 50 | 48 | . | > 1.00E-7 |
| M14 | 0.602 | 2.642 | 2.593 | 2.264 | 1.047 | 0.798 | 0.954 | 98 | 81 | 22 | 10 | 17 | 3.37E-10 | > 1.00E-7 |
| MDA-MB-435 | 0.472 | 2.589 | 2.435 | 1.401 | 0.326 | 0.240 | 0.266 | 93 | 44 | -31 | -49 | -44 | 7.49E-11 | 3.86E-10 |
| SK-MEL-2 | 0.964 | 2.273 | 2.245 | 2.116 | 1.527 | 1.400 | 1.365 | 98 | 88 | 43 | 33 | 31 | 7.00E-10 | > 1.00E-7 |
| SK-MEL-28 | 0.780 | 2.247 | 2.239 | 1.971 | 1.510 | 1.553 | 1.579 | 99 | 81 | 50 | 53 | 54 | . | > 1.00E-7 |
| SK-MEL-5 | 0.839 | 2.875 | 2.891 | 1.937 | 1.243 | 0.845 | 0.595 | 101 | 54 | 20 | . | -29 | 1.30E-10 | 1.02E-8 |
| UACC-62 | 0.703 | 2.577 | 2.336 | 1.786 | 0.971 | 0.981 | 0.998 | 87 | 58 | 14 | 15 | 16 | 1.51E-10 | > 1.00E-7 |
| Ovarian Cancer | | | | | | | | | | |
| IGROV1 | 0.829 | 2.274 | 2.333 | 2.239 | 1.802 | 1.482 | 1.192 | 104 | 98 | 67 | 45 | 25 | 6.04E-9 | > 1.00E-7 |
| OVCAR-3 | 0.442 | 1.649 | 1.678 | 1.306 | 0.603 | 0.460 | 0.360 | 102 | 72 | 13 | 1 | -19 | 2.34E-10 | 1.19E-8 |
| OVCAR-4 | 0.661 | 1.513 | 1.482 | 1.443 | 1.245 | 1.140 | 1.005 | 96 | 92 | 68 | 56 | 40 | 2.45E-8 | > 1.00E-7 |
| OVCAR-5 | 0.754 | 2.034 | 1.985 | 1.960 | 1.560 | 1.235 | 1.117 | 96 | 94 | 63 | 38 | 28 | 3.24E-9 | > 1.00E-7 |
| OVCAR-8 | 0.496 | 2.052 | 2.052 | 2.084 | 1.664 | 0.839 | 0.669 | 100 | 102 | 75 | 22 | 11 | 2.97E-9 | > 1.00E-7 |
| NCI/ADR-RES | 0.560 | 1.851 | 1.885 | 1.799 | 1.587 | 1.022 | 0.482 | 103 | 96 | 80 | 36 | -14 | 4.73E-9 | 5.23E-8 |
| SK-OV-3 | 0.802 | 1.534 | 1.527 | 1.510 | 1.133 | 0.831 | 0.763 | 99 | 97 | 45 | 4 | -5 | 8.07E-10 | 2.78E-8 |

*FIG. 9 (Cont'd)*

| | | | | | | | | | | |
|---|---|---|---|---|---|---|---|---|---|---|
| Renal Cancer | | | | | | | | | | |
| 786-0 | 0.605 | 2.513 | 2.438 | 2.373 | 1.538 | 1.033 | 0.904 | 96 | 93 | 49 | 22 | 16 | 9.42E-10 | > 1.00E-7 | > 1.00E-7 |
| A498 | 1.169 | 2.045 | 1.977 | 2.002 | 1.467 | 1.360 | 1.349 | 92 | 95 | 34 | 22 | 21 | 5.48E-10 | > 1.00E-7 | > 1.00E-7 |
| ACHN | 0.483 | 2.035 | 2.025 | 2.047 | 1.473 | 1.159 | 0.946 | 99 | 101 | 64 | 44 | 30 | 4.81E-9 | > 1.00E-7 | > 1.00E-7 |
| CAKI-1 | 0.592 | 2.292 | 2.117 | 2.144 | 1.584 | 1.104 | 1.076 | 90 | 91 | 58 | 30 | 28 | 1.97E-9 | > 1.00E-7 | > 1.00E-7 |
| RXF 393 | 0.963 | 1.694 | 1.646 | 1.600 | 1.301 | 0.924 | 1.132 | 93 | 87 | 46 | -4 | 23 | 8.07E-10 | | > 1.00E-7 |
| SN12C | 0.648 | 2.227 | 2.152 | 2.182 | 1.648 | 1.207 | 1.064 | 95 | 97 | 63 | 35 | 26 | 3.00E-9 | > 1.00E-7 | > 1.00E-7 |
| TK-10 | 0.762 | 2.015 | 1.796 | 1.766 | 1.690 | 1.486 | 1.394 | 82 | 80 | 74 | 58 | 50 | > 1.00E-7 | > 1.00E-7 | > 1.00E-7 |
| UO-31 | 0.811 | 2.294 | 2.115 | 2.053 | 1.911 | 1.511 | 1.388 | 88 | 84 | 74 | 47 | 39 | 7.88E-9 | > 1.00E-7 | > 1.00E-7 |
| Prostate Cancer | | | | | | | | | | |
| PC-3 | 0.649 | 2.449 | 2.369 | 1.993 | 1.157 | 0.895 | 0.881 | 96 | 75 | 28 | 14 | 13 | 3.39E-10 | > 1.00E-7 | > 1.00E-7 |
| DU-145 | 0.284 | 1.434 | 1.507 | 1.436 | 0.583 | 0.368 | 0.366 | 106 | 100 | 26 | 7 | 7 | 4.75E-10 | > 1.00E-7 | > 1.00E-7 |
| Breast Cancer | | | | | | | | | | |
| MCF7 | 0.405 | 2.143 | 2.072 | 1.409 | 0.607 | 0.560 | 0.521 | 96 | 58 | 12 | 9 | 7 | 1.47E-10 | > 1.00E-7 | > 1.00E-7 |
| MDA-MB-231/ATCC | 0.619 | 1.824 | 1.781 | 1.717 | 1.320 | 0.997 | 0.764 | 96 | 91 | 58 | 31 | 12 | 2.01E-9 | > 1.00E-7 | > 1.00E-7 |
| HS 578T | 1.054 | 2.230 | 2.189 | 2.121 | 1.643 | 1.381 | 1.221 | 97 | 91 | 50 | 28 | 14 | 1.01E-9 | > 1.00E-7 | > 1.00E-7 |
| BT-549 | 1.183 | 2.466 | 2.404 | 2.243 | 1.739 | 1.504 | 0.955 | 95 | 83 | 43 | 25 | -19 | 6.76E-10 | 3.67E-8 | > 1.00E-7 |
| T-47D | 0.750 | 1.499 | 1.508 | 1.437 | 1.015 | 1.090 | 1.212 | 101 | 92 | 35 | 45 | 62 | > 1.00E-7 | > 1.00E-7 | > 1.00E-7 |
| MDA-MB-468 | 0.794 | 1.670 | 1.623 | 1.500 | 1.037 | 0.904 | 0.835 | 95 | 81 | 28 | 13 | 5 | 3.78E-10 | > 1.00E-7 | > 1.00E-7 |

*FIG. 9 (Cont'd)*

National Cancer Institute Developmental Therapeutics Program
In-Vitro Testing Results

| NSC: D-784014 / 1 | | | | | | | Experiment ID: 1509RS55 | | | | | Test Type: 08 | | Units: Molar |
|---|---|---|---|---|---|---|---|---|---|---|---|---|---|---|
| Report Date: November 04, 2015 | | | | | | | Test Date: September 08, 2015 | | | | | QNS: | | MC: |
| COMI: KCN-Tb2 | | | | | | | Stain Reagent: SRB Dual-Pass Related | | | | | SSPL: OZAS | | |

| | Time | | | | Mean Optical Densities | | | | | | Percent Growth | | | | | |
| | | | | | | | | | Log10 Concentration | | | | | | | |
| Panel/Cell Line | Zero | Ctrl | -11.0 | -10.0 | -9.0 | -8.0 | -7.0 | -11.0 | -10.0 | -9.0 | -8.0 | -7.0 | GI50 | TGI | LC50 |
| Leukemia | | | | | | | | | | | | | | | |
| CCRF-CEM | 0.854 | 3.131 | 3.169 | 3.176 | 1.580 | 1.043 | 1.035 | 102 | 102 | 32 | 8 | 8 | 5.52E-10 | > 1.00E-7 | > 1.00E-7 |
| HL-60(TB) | 0.734 | 3.174 | 3.121 | 2.972 | 0.634 | 0.606 | 0.584 | 98 | 92 | -14 | -17 | -21 | 2.49E-10 | 7.42E-10 | > 1.00E-7 |
| K-562 | 0.259 | 2.433 | 2.425 | 2.057 | 0.455 | 0.412 | 0.414 | 100 | 83 | 9 | 7 | 7 | 2.78E-10 | > 1.00E-7 | > 1.00E-7 |
| MOLT-4 | 0.951 | 3.355 | 3.316 | 3.361 | 2.889 | 1.473 | 1.293 | 98 | 100 | 81 | 22 | 14 | 3.31E-9 | > 1.00E-7 | > 1.00E-7 |
| RPMI-8226 | 0.482 | 1.755 | 1.708 | 1.438 | 0.537 | 0.605 | 0.671 | 96 | 75 | 4 | 10 | 15 | 2.26E-10 | > 1.00E-7 | > 1.00E-7 |
| SR | 0.285 | 0.866 | 0.834 | 0.545 | 0.353 | 0.325 | 0.308 | 94 | 45 | 12 | 7 | 4 | 7.86E-11 | > 1.00E-7 | > 1.00E-7 |

*FIG. 10*

| | | | | | | | | | |
|---|---|---|---|---|---|---|---|---|---|
| Non-Small Cell Lung Cancer | | | | | | | | | |
| A549/ATCC | 0.397 | 1.781 | 1.757 | 1.824 | 0.801 | 0.580 | 0.539 | 98 | 103 | 29 | 13 | 10 | 5.23E-10 | 1.00E-7 | > 1.00E-7 |
| EKVX | 0.829 | 2.119 | 2.066 | 1.992 | 1.401 | 1.329 | 1.290 | 96 | 90 | 44 | 39 | 36 | 7.51E-10 | 1.00E-7 | > 1.00E-7 |
| HOP-62 | 0.551 | 1.639 | 1.654 | 1.574 | 0.905 | 0.797 | 0.615 | 101 | 94 | 33 | 23 | 6 | 5.20E-10 | 1.00E-7 | > 1.00E-7 |
| HOP-92 | 1.496 | 1.921 | 1.849 | 1.800 | 1.668 | 1.834 | 1.740 | 83 | 71 | 40 | 79 | 57 | | 1.00E-7 | > 1.00E-7 |
| NCI-H226 | 0.568 | 1.470 | 1.456 | 1.344 | 1.074 | 0.927 | 0.808 | 98 | 86 | 56 | 40 | 27 | 2.34E-9 | 1.00E-7 | > 1.00E-7 |
| NCI-H23 | 0.617 | 1.914 | 1.919 | 1.770 | 1.178 | 1.025 | 1.003 | 100 | 89 | 43 | 31 | 30 | 7.10E-10 | 1.00E-7 | > 1.00E-7 |
| NCI-H322M | 0.662 | 2.064 | 2.018 | 2.041 | 1.203 | 1.231 | 1.155 | 97 | 98 | 39 | 41 | 35 | 6.44E-10 | 1.00E-7 | > 1.00E-7 |
| NCI-H460 | 0.217 | 2.564 | 2.624 | 2.298 | 0.369 | 0.299 | 0.300 | 103 | 89 | 6 | 3 | 4 | 2.95E-10 | 1.00E-7 | > 1.00E-7 |
| NCI-H522 | 0.922 | 2.948 | 2.627 | 2.621 | 1.088 | 0.978 | 0.755 | 84 | 84 | 8 | 3 | -18 | 2.80E-10 | 1.35E-8 | |
| Colon Cancer | | | | | | | | | |
| COLO 205 | 0.482 | 1.622 | 1.663 | 1.298 | 0.527 | 0.249 | 0.179 | 104 | 72 | 4 | -48 | -63 | 2.08E-10 | 1.19E-9 | 1.30E-8 |
| HCC-2998 | 0.664 | 2.254 | 2.259 | 2.010 | 0.919 | 0.945 | 0.851 | 100 | 85 | 16 | 18 | 12 | 3.20E-10 | 1.00E-7 | > 1.00E-7 |
| HCT-116 | 0.329 | 2.807 | 2.637 | 2.648 | 0.696 | 0.455 | 0.401 | 93 | 94 | 15 | 5 | 3 | 3.57E-10 | 1.00E-7 | > 1.00E-7 |
| HCT-15 | 0.237 | 1.394 | 1.343 | 1.142 | 0.515 | 0.289 | 0.224 | 96 | 78 | 24 | 4 | -6 | 3.32E-10 | 2.75E-8 | |
| HT29 | 0.374 | 2.478 | 2.494 | 2.088 | 0.435 | 0.409 | 0.335 | 101 | 81 | 3 | 2 | -10 | 2.51E-10 | 1.37E-8 | |
| KM12 | 0.429 | 2.516 | 2.438 | 1.648 | 0.767 | 0.572 | 0.487 | 96 | 58 | 16 | 7 | 3 | 1.58E-10 | 1.00E-7 | > 1.00E-7 |
| SW-620 | 0.230 | 2.044 | 1.885 | 1.443 | 0.575 | 0.578 | 0.611 | 91 | 67 | 19 | 19 | 21 | 2.25E-10 | 1.00E-7 | > 1.00E-7 |

*FIG. 10 (Cont'd)*

| | | | | | | | | | | |
|---|---|---|---|---|---|---|---|---|---|---|
| CNS Cancer | | | | | | | | | | |
| SF-268 | 0.431 | 1.634 | 1.601 | 1.590 | 0.756 | 0.712 | 0.573 | 97 | 96 | 27 | 23 | 12 | 4.66E-10 | > 1.00E-7 | > 1.00E-7 |
| SF-295 | 0.834 | 2.706 | 2.605 | 2.357 | 0.743 | 0.688 | 0.654 | 95 | 81 | -11 | -18 | -22 | 2.19E-10 | 7.62E-10 | > 1.00E-7 |
| SF-539 | 0.954 | 2.631 | 2.565 | 2.601 | 1.418 | 0.806 | 0.778 | 96 | 98 | 28 | -16 | -18 | 4.82E-10 | 4.37E-9 | > 1.00E-7 |
| SNB-19 | 0.499 | 1.831 | 1.750 | 1.634 | 0.895 | 0.761 | 0.758 | 94 | 85 | 30 | 20 | 19 | 4.31E-10 | > 1.00E-7 | > 1.00E-7 |
| SNB-75 | 0.861 | 1.603 | 1.498 | 1.515 | 0.976 | 0.876 | 0.858 | 86 | 88 | 15 | 2 | | 3.34E-10 | 7.06E-8 | > 1.00E-7 |
| U251 | 0.301 | 1.287 | 1.282 | 1.231 | 0.471 | 0.461 | 0.438 | 99 | 94 | 17 | 16 | 14 | 3.76E-10 | > 1.00E-7 | > 1.00E-7 |
| Melanoma | | | | | | | | | | |
| LOX IMVI | 0.426 | 2.766 | 2.713 | 2.609 | 1.220 | 1.090 | 0.795 | 98 | 93 | 34 | 28 | 16 | 5.36E-10 | > 1.00E-7 | > 1.00E-7 |
| MALME-3M | 0.729 | 1.413 | 1.395 | 1.180 | 1.038 | 1.152 | 1.114 | 97 | 66 | 45 | 62 | 56 | | | > 1.00E-7 |
| M14 | 0.602 | 2.647 | 2.625 | 2.410 | 0.898 | 0.976 | 1.023 | 99 | 88 | 14 | 18 | 21 | 3.31E-10 | > 1.00E-7 | > 1.00E-7 |
| MDA-MB-435 | 0.472 | 2.523 | 2.242 | 0.708 | 0.202 | 0.268 | 0.306 | 86 | 11 | -57 | -43 | -35 | 3.06E-11 | 1.47E-10 | > 1.00E-7 |
| SK-MEL-2 | 0.964 | 2.274 | 2.177 | 1.991 | 1.432 | 1.501 | 1.459 | 93 | 78 | 36 | 41 | 38 | 4.63E-10 | > 1.00E-7 | > 1.00E-7 |
| SK-MEL-28 | 0.780 | 2.241 | 2.217 | 1.967 | 1.519 | 1.538 | 1.534 | 98 | 81 | 51 | 52 | 52 | > 1.00E-7 | > 1.00E-7 | > 1.00E-7 |
| SK-MEL-5 | 0.839 | 3.003 | 2.936 | 1.878 | 1.152 | 0.776 | 0.647 | 97 | 48 | 14 | -8 | -23 | 9.09E-11 | 4.55E-9 | > 1.00E-7 |
| UACC-62 | 0.703 | 2.542 | 2.265 | 1.544 | 0.888 | 0.928 | 0.989 | 85 | 46 | 10 | 12 | 16 | 7.77E-11 | > 1.00E-7 | > 1.00E-7 |
| Ovarian Cancer | | | | | | | | | | |
| IGROV1 | 0.829 | 2.358 | 2.380 | 2.179 | 1.689 | 1.371 | 1.153 | 101 | 88 | 56 | 35 | 21 | 2.00E-9 | > 1.00E-7 | > 1.00E-7 |
| OVCAR-3 | 0.442 | 1.625 | 1.594 | 0.701 | 0.536 | 0.456 | 0.367 | 97 | 22 | 8 | 1 | -17 | 4.24E-11 | 1.16E-8 | > 1.00E-7 |
| OVCAR-4 | 0.661 | 1.328 | 1.337 | 1.236 | 1.084 | 0.953 | 0.941 | 101 | 86 | 63 | 44 | 42 | 4.79E-9 | > 1.00E-7 | > 1.00E-7 |
| OVCAR-5 | 0.754 | 2.005 | 1.938 | 1.833 | 1.241 | 1.248 | 1.180 | 95 | 86 | 39 | 39 | 34 | 5.83E-10 | > 1.00E-7 | > 1.00E-7 |
| OVCAR-8 | 0.496 | 1.934 | 1.915 | 1.846 | 0.911 | 0.593 | 0.590 | 99 | 94 | 29 | 7 | 7 | 4.73E-10 | > 1.00E-7 | > 1.00E-7 |
| NCI/ADR-RES | 0.560 | 1.953 | 1.921 | 1.898 | 1.706 | 1.200 | 0.713 | 98 | 96 | 82 | 46 | 11 | 7.72E-9 | > 1.00E-7 | > 1.00E-7 |
| SK-OV-3 | 0.802 | 1.604 | 1.595 | 1.379 | 0.962 | 0.952 | 0.855 | 99 | 72 | 20 | 19 | 7 | 2.64E-10 | > 1.00E-7 | > 1.00E-7 |

*FIG. 10 (Cont'd)*

| | | | | | | | | | | |
|---|---|---|---|---|---|---|---|---|---|---|
| Renal Cancer | | | | | | | | | | |
| 786-0 | 0.605 | 2.315 | 2.217 | 2.135 | 0.937 | 0.880 | 0.828 | 94 | 89 | 19 | 16 | 13 | 3.66E-10 | > 1.00E-7 | > 1.00E-7 |
| A498 | 1.169 | 1.981 | 1.996 | 1.812 | 1.256 | 1.296 | 1.322 | 102 | 79 | 11 | 16 | 19 | 2.67E-10 | > 1.00E-7 | > 1.00E-7 |
| ACHN | 0.483 | 2.012 | 1.999 | 1.856 | 1.171 | 0.960 | 0.808 | 99 | 90 | 45 | 31 | 21 | 7.73E-10 | > 1.00E-7 | > 1.00E-7 |
| CAKI-1 | 0.592 | 2.115 | 2.000 | 1.915 | 1.290 | 0.962 | 0.903 | 92 | 87 | 46 | 24 | 20 | 7.92E-10 | > 1.00E-7 | > 1.00E-7 |
| RXF 393 | 0.963 | 1.639 | 1.585 | 1.480 | 0.947 | 0.968 | 1.074 | 92 | 76 | -2 | 1 | 16 | 2.18E-10 | | > 1.00E-7 |
| SN12C | 0.648 | 2.263 | 2.159 | 2.111 | 1.367 | 1.208 | 0.919 | 94 | 91 | 45 | 35 | 17 | 7.60E-10 | > 1.00E-7 | > 1.00E-7 |
| TK-10 | 0.762 | 1.946 | 1.825 | 1.828 | 1.397 | 1.403 | 1.282 | 90 | 90 | 54 | 54 | 44 | 2.54E-8 | > 1.00E-7 | > 1.00E-7 |
| UO-31 | 0.811 | 2.317 | 2.097 | 2.058 | 1.619 | 1.511 | 1.316 | 85 | 83 | 54 | 46 | 33 | 3.20E-9 | > 1.00E-7 | > 1.00E-7 |
| Prostate Cancer | | | | | | | | | | |
| PC-3 | 0.649 | 2.352 | 2.342 | 1.662 | 0.890 | 0.865 | 0.871 | 99 | 60 | 14 | 13 | 13 | 1.62E-10 | > 1.00E-7 | > 1.00E-7 |
| DU-145 | 0.284 | 1.384 | 1.419 | 1.081 | 0.305 | 0.358 | 0.293 | 103 | 72 | 2 | 7 | 1 | 2.08E-10 | > 1.00E-7 | > 1.00E-7 |
| Breast Cancer | | | | | | | | | | |
| MCF7 | 0.405 | 2.175 | 1.963 | 0.906 | 0.580 | 0.539 | 0.500 | 88 | 28 | 10 | 8 | 5 | 4.33E-11 | > 1.00E-7 | > 1.00E-7 |
| MDA-MB-231/ATCC | 0.619 | 1.808 | 1.720 | 1.695 | 1.217 | 0.796 | 0.744 | 93 | 90 | 50 | 15 | 10 | 1.02E-9 | > 1.00E-7 | > 1.00E-7 |
| HS 578T | 1.054 | 2.237 | 2.191 | 2.193 | 1.414 | 1.293 | 1.196 | 96 | 96 | 30 | 20 | 12 | 5.04E-10 | > 1.00E-7 | > 1.00E-7 |
| BT-549 | 1.183 | 2.342 | 2.242 | 2.137 | 1.497 | 1.297 | 0.787 | 91 | 82 | 27 | 10 | -33 | 3.85E-10 | 1.69E-8 | > 1.00E-7 |
| T-47D | 0.750 | 1.486 | 1.488 | 1.343 | 0.927 | 1.182 | 1.195 | 100 | 81 | 24 | 59 | 60 | | > 1.00E-7 | > 1.00E-7 |
| MDA-MB-468 | 0.794 | 1.688 | 1.647 | 1.399 | 0.979 | 0.993 | 0.875 | 95 | 68 | 21 | 22 | 9 | 2.38E-10 | > 1.00E-7 | > 1.00E-7 |

*FIG. 10 (Cont'd)*

| National Cancer Institute Developmental Therapeutics Program In-Vitro Testing Results ||||||||||||||
|---|---|---|---|---|---|---|---|---|---|---|---|---|---|
| NSC: D - 784527 / 1 ||| Experiment ID: 1506NS12 |||||| Test Type: 08 ||| Units: Molar |
| Report Date: July 21, 2015 ||| Test Date: June 29, 2015 |||||| QNS: ||| MC: |
| COMI: KCN-Tb3 ||| Stain Reagent: SRB Dual-Pass Related |||||| SSPL: 0ZAS ||||
| | Time | | | Mean Optical Densities | | | | | Percent Growth | | | | |
| | | | | | | | Log10 Concentration | | | | | | |
| Panel/Cell Line | Zero | Ctrl | -8.0 | -7.0 | -6.0 | -5.0 | -4.0 | -8.0 | -7.0 | -6.0 | -5.0 | -4.0 | |
| | | | | | | | | | | | | | GI50 | TGI | LC50 |
| Leukemia | | | | | | | | | | | | | | | | |
| CCRF-CEM | 0.854 | 2.421 | 2.385 | 2.310 | 2.474 | 1.965 | 0.769 | 98 | 94 | 103 | 73 | 3 | 2.15E-5 | > 1.00E-4 | > 1.00E-4 |
| HL-60(TB) | 1.590 | 3.663 | 3.797 | . | 3.612 | 2.513 | 1.331 | 106 | . | 98 | 45 | -16 | 7.89E-6 | 5.40E-5 | > 1.00E-4 |
| K-562 | 0.209 | 2.003 | 2.050 | 2.011 | 2.041 | 1.346 | 0.360 | 103 | 100 | 102 | 63 | 8 | 1.75E-5 | > 1.00E-4 | > 1.00E-4 |
| MOLT-4 | 1.439 | 3.735 | 3.813 | . | 3.657 | 3.392 | 1.382 | 103 | . | 97 | 85 | -4 | 2.47E-5 | 9.02E-5 | > 1.00E-4 |
| RPMI-8226 | 1.573 | 3.023 | 3.106 | 3.084 | 3.131 | 2.144 | 1.616 | 106 | 104 | 107 | 39 | 3 | 6.96E-6 | > 1.00E-4 | > 1.00E-4 |
| SR | 0.409 | 2.203 | 2.022 | 2.018 | 1.937 | 0.866 | 0.399 | 90 | 90 | 85 | 25 | -3 | 3.88E-6 | 8.10E-5 | > 1.00E-4 |

*FIG. 11*

| | | | | | | | | | | |
|---|---|---|---|---|---|---|---|---|---|---|
| Non-Small Cell Lung Cancer | | | | | | | | | | |
| A549/ATCC | 0.501 | 1.862 | 1.845 | 1.810 | 1.889 | 1.944 | 0.836 | 99 | 95 | 102 | 106 | 25 | 4.89E-5 | > 1.00E-4 | > 1.00E-4 |
| EKVX | 0.616 | 2.432 | 2.309 | 2.256 | 2.264 | 2.080 | 1.055 | 93 | 90 | 92 | 81 | 25 | 3.53E-5 | > 1.00E-4 | > 1.00E-4 |
| HOP-62 | 0.652 | 1.751 | 1.753 | 1.695 | 1.758 | 1.535 | 0.734 | 100 | 95 | 101 | 80 | 7 | 2.61E-5 | > 1.00E-4 | > 1.00E-4 |
| HOP-92 | 1.325 | 1.962 | 1.882 | 1.875 | 1.812 | 1.611 | 1.265 | 87 | 85 | 76 | 45 | -5 | 6.89E-6 | 8.09E-5 | > 1.00E-4 |
| NCI-H226 | 0.723 | 1.540 | 1.589 | 1.539 | 1.545 | 1.497 | 0.938 | 106 | 100 | 101 | 95 | 26 | 4.50E-5 | > 1.00E-4 | > 1.00E-4 |
| NCI-H23 | 0.872 | 2.373 | 2.336 | 2.321 | 2.217 | 1.953 | 1.093 | 98 | 97 | 90 | 73 | 15 | 2.46E-5 | > 1.00E-4 | > 1.00E-4 |
| NCI-H322M | 0.853 | 2.108 | 2.036 | 2.075 | 2.002 | 1.866 | 1.187 | 94 | 97 | 92 | 81 | 27 | 3.69E-5 | > 1.00E-4 | > 1.00E-4 |
| NCI-H460 | 0.221 | 2.321 | 2.298 | 2.236 | 2.358 | 1.850 | 0.166 | 99 | 96 | 102 | 78 | -25 | 1.86E-5 | 5.69E-5 | > 1.00E-4 |
| NCI-H522 | 1.054 | 2.456 | 2.529 | 2.380 | 2.383 | 1.728 | 0.712 | 105 | 95 | 95 | 48 | -33 | 8.93E-6 | 3.89E-5 | > 1.00E-4 |
| Colon Cancer | | | | | | | | | | |
| COLO 205 | 0.430 | 1.462 | 1.458 | 1.387 | 1.458 | 1.236 | 0.227 | 100 | 93 | 100 | 78 | -47 | 1.68E-5 | 4.20E-5 | > 1.00E-4 |
| HCC-2998 | 0.866 | 2.901 | 2.831 | 2.939 | 2.789 | 2.242 | 0.966 | 97 | 102 | 95 | 68 | 5 | 1.91E-5 | > 1.00E-4 | > 1.00E-4 |
| HCT-116 | 0.314 | 2.268 | 2.342 | 2.338 | 2.405 | 1.367 | 0.242 | 104 | 104 | 107 | 54 | -23 | 1.12E-5 | 5.03E-5 | > 1.00E-4 |
| HCT-15 | 0.268 | 2.209 | 2.180 | 2.125 | 2.165 | 1.659 | 0.411 | 99 | 95 | 98 | 72 | 7 | 2.17E-5 | > 1.00E-4 | > 1.00E-4 |
| HT29 | 0.253 | 1.506 | 1.483 | 1.548 | 1.460 | 1.324 | 0.266 | 98 | 103 | 96 | 85 | 1 | 2.63E-5 | > 1.00E-4 | > 1.00E-4 |
| KM12 | 0.530 | 2.957 | 2.888 | 2.929 | 2.963 | 1.619 | 0.658 | 97 | 99 | 100 | 45 | 5 | 8.08E-6 | > 1.00E-4 | > 1.00E-4 |
| SW-620 | 0.250 | 1.730 | 1.660 | 1.657 | 1.585 | 1.303 | 0.444 | 95 | 95 | 90 | 71 | 13 | 2.31E-5 | > 1.00E-4 | > 1.00E-4 |

*FIG. 11 (Cont'd)*

| | | | | | | | | | | | | | | | |
|---|---|---|---|---|---|---|---|---|---|---|---|---|---|---|---|
| CNS Cancer | | | | | | | | | | | | | | | |
| SF-268 | 0.597 | 1.989 | 1.954 | 1.962 | 1.954 | 1.807 | 0.695 | 98 | 98 | 97 | 87 | 7 | 2.90E-5 | >1.00E-4 | >1.00E-4 |
| SF-295 | 0.647 | 2.480 | 2.411 | 2.292 | 2.318 | 1.954 | 0.795 | 96 | 90 | 91 | 71 | 8 | 2.17E-5 | >1.00E-4 | >1.00E-4 |
| SF-539 | 1.084 | 2.845 | 2.854 | 2.674 | 2.751 | 2.401 | 0.746 | 100 | 90 | 95 | 75 | -31 | 1.71E-5 | 5.08E-4 | >1.00E-4 |
| SNB-19 | 0.964 | 2.477 | 2.410 | 2.407 | 2.388 | 2.036 | 1.439 | 96 | 95 | 94 | 71 | 31 | 3.38E-5 | >1.00E-4 | >1.00E-4 |
| SNB-75 | 0.818 | 1.657 | 1.507 | 1.471 | 1.476 | 1.162 | 0.815 | 82 | 78 | 78 | 41 | - | 5.73E-5 | 9.80E-4 | >1.00E-4 |
| U251 | 0.354 | 1.648 | 1.673 | 1.599 | 1.572 | 1.424 | 0.493 | 102 | 96 | 94 | 83 | 11 | 2.85E-5 | >1.00E-4 | >1.00E-4 |
| Melanoma | | | | | | | | | | | | | | | |
| LOX IMVI | 0.342 | 2.459 | 2.373 | 2.293 | 2.350 | 1.873 | 0.514 | 96 | 92 | 95 | 72 | 8 | 2.23E-5 | >1.00E-4 | >1.00E-4 |
| MALME-3M | 0.760 | 1.253 | 1.216 | 1.240 | 1.156 | 1.010 | 0.992 | 93 | 97 | 80 | 51 | 47 | 1.57E-5 | >1.00E-4 | >1.00E-4 |
| M14 | 0.497 | 1.936 | 1.902 | 1.844 | 1.738 | 1.198 | 0.325 | 98 | 94 | 86 | 49 | -35 | 9.25E-5 | 3.84E-4 | >1.00E-4 |
| MDA-MB-435 | 0.561 | 2.671 | 2.564 | 2.516 | 2.393 | 0.400 | 0.239 | 95 | 93 | 87 | -29 | -57 | 2.08E-5 | 5.64E-4 | 5.52E-5 |
| SK-MEL-2 | 0.949 | 2.423 | 2.372 | 2.399 | 2.327 | 1.746 | 1.197 | 97 | 98 | 94 | 54 | 17 | 1.28E-5 | >1.00E-4 | >1.00E-4 |
| SK-MEL-28 | 0.950 | 2.488 | 2.529 | 2.420 | 2.440 | 1.953 | 1.524 | 103 | 96 | 97 | 65 | 37 | 3.51E-5 | >1.00E-4 | >1.00E-4 |
| SK-MEL-5 | 0.629 | 2.499 | 2.515 | 2.491 | 2.432 | 1.607 | 0.434 | 101 | 100 | 96 | 52 | -31 | 1.07E-5 | 4.24E-4 | >1.00E-4 |
| UACC-257 | 0.888 | 1.988 | 1.918 | 1.926 | 1.827 | 1.636 | 1.286 | 94 | 94 | 85 | 68 | 36 | 3.68E-5 | >1.00E-4 | >1.00E-4 |
| UACC-62 | 1.077 | 2.955 | 2.881 | 2.818 | 2.699 | 1.662 | 1.183 | 96 | 93 | 86 | 31 | 6 | 4.56E-5 | >1.00E-4 | >1.00E-4 |
| Ovarian Cancer | | | | | | | | | | | | | | | |
| IGROV1 | 0.707 | 2.307 | 2.413 | 2.386 | 2.319 | 1.550 | 0.890 | 107 | 105 | 101 | 53 | 11 | 1.16E-5 | >1.00E-4 | >1.00E-4 |
| OVCAR-3 | 0.495 | 1.816 | 1.808 | 1.880 | 1.859 | 1.201 | 0.326 | 99 | 105 | 103 | 53 | -34 | 1.09E-05 | 4.07E-5 | >1.00E-4 |
| OVCAR-4 | 0.769 | 1.796 | 1.788 | 1.699 | 1.723 | 1.600 | 0.955 | 99 | 91 | 93 | 81 | 18 | 3.11E-5 | >1.00E-4 | >1.00E-4 |
| OVCAR-5 | 0.571 | 1.437 | 1.429 | 1.301 | 1.325 | 1.192 | 0.771 | 100 | 84 | 87 | 72 | 23 | 2.79E-5 | >1.00E-4 | >1.00E-4 |
| OVCAR-8 | 0.484 | 1.974 | 1.973 | 1.948 | 1.977 | 1.874 | 0.639 | 98 | 98 | 100 | 93 | 10 | 3.33E-5 | >1.00E-4 | >1.00E-4 |
| NCI/ADR-RES | 0.530 | 1.811 | 1.820 | 1.751 | 1.714 | 1.587 | 0.555 | 101 | 95 | 92 | 82 | 2 | 2.53E-5 | >1.00E-4 | >1.00E-4 |
| SK-OV-3 | 1.101 | 2.062 | 2.122 | 2.081 | 2.174 | 2.003 | 1.198 | 106 | 102 | 112 | 94 | 10 | 3.34E-5 | >1.00E-4 | >1.00E-4 |

*FIG. 11 (Cont'd)*

| | | | | | | | | | | |
|---|---|---|---|---|---|---|---|---|---|---|
| Renal Cancer | | | | | | | | | | |
| 786-0 | 0.641 | 2.183 | 2.086 | 0.641 | 0.641 | 0.641 | 94 | 89 | 90 | 68 | -20 | 1.61E-5 | 5.97E-5 |
| ACHN | 0.573 | 2.398 | 2.396 | 0.573 | 0.573 | 0.573 | 100 | 93 | 94 | 83 | 7 | 2.73E-5 | >1.00E-4 |
| CAKI-1 | 0.813 | 3.246 | 3.145 | 0.813 | 0.813 | 0.813 | 96 | 91 | 94 | 84 | 14 | 3.06E-5 | >1.00E-4 |
| RXF 393 | 1.108 | 1.659 | 1.682 | 1.108 | 1.108 | 1.108 | 104 | 103 | 77 | 45 | -13 | 7.56E-5 | 5.04E-5 |
| SN12C | 0.675 | 2.399 | 2.258 | 0.675 | 0.675 | 0.675 | 92 | 91 | 94 | 87 | 10 | 3.00E-5 | >1.00E-4 |
| TK-10 | 0.869 | 1.789 | 1.708 | 0.869 | 0.869 | 0.869 | 91 | 93 | 88 | 87 | 37 | 5.41E-5 | >1.00E-4 |
| UO-31 | 1.089 | 2.558 | 2.381 | 1.089 | 1.089 | 1.089 | 88 | 89 | 85 | 64 | 10 | 1.80E-5 | >1.00E-4 |
| Prostate Cancer | | | | | | | | | | |
| PC-3 | 0.620 | 2.049 | 2.055 | 2.049 | 2.048 | 1.728 | 0.574 | 100 | 100 | 100 | 78 | 4 | 2.36E-5 | >1.00E-4 |
| DU-145 | 0.455 | 2.052 | 2.054 | 2.086 | 2.156 | 2.030 | 0.592 | 101 | 102 | 107 | 99 | 9 | 3.47E-5 | >1.00E-4 |
| Breast Cancer | | | | | | | | | | |
| MCF7 | 0.359 | 2.760 | 2.565 | 2.420 | 2.463 | 1.158 | 0.625 | 92 | 86 | 88 | 33 | 11 | 4.92E-5 | >1.00E-4 |
| MDA-MB-231/ATCC | 0.730 | 1.628 | 1.599 | 1.600 | 1.563 | 1.359 | 0.493 | 97 | 97 | 93 | 70 | -33 | 1.57E-5 | 4.82E-5 |
| HS 578T | 1.234 | 2.272 | 2.129 | 2.151 | 2.166 | 1.853 | 0.855 | 86 | 89 | 90 | 60 | -31 | 1.28E-5 | 4.57E-5 |
| BT-549 | 1.156 | 2.251 | 2.277 | 2.154 | 2.283 | 1.758 | 0.780 | 102 | 91 | 103 | 55 | -33 | 1.14E-5 | 4.25E-5 |
| T-47D | 0.680 | 1.358 | 1.404 | 1.291 | 1.277 | 1.096 | 0.975 | 107 | 90 | 88 | 61 | 43 | 4.30E-5 | >1.00E-4 |
| MDA-MB-468 | 0.851 | 1.393 | 1.369 | 1.425 | 1.411 | 0.874 | 0.774 | 96 | 105 | 103 | 2 | -10 | 3.38E-5 | 1.54E-5 |

*FIG. 11 (Cont'd)*

National Cancer Institute Developmental Therapeutics Program
In-Vitro Testing Results

| NSC: D-784528/1 | | | | | | Experiment ID: 1506NS12 | | | | | Test Type: 08 | | Units: Molar |
|---|---|---|---|---|---|---|---|---|---|---|---|---|---|
| Report Date: July 21, 2015 | | | | | | Test Date: June 29, 2015 | | | | | QNS: | | MC: |
| COMI: KCN-Tb4 | | | | | | Stain Reagent: SRB Dual-Pass Related | | | | | SSPL: OZAS | | |

| | Time | | | Mean Optical Densities | | | | | Percent Growth | | | | | |
|---|---|---|---|---|---|---|---|---|---|---|---|---|---|---|
| | | | | | Log10 Concentration | | | | | | | | | |
| Panel/Cell Line | Zero | Ctrl | -8.0 | -7.0 | -6.0 | -5.0 | -4.0 | -8.0 | -7.0 | -6.0 | -5.0 | -4.0 | GI50 | TGI | LC50 |
| Leukemia | | | | | | | | | | | | | | | |
| CCRF-CEM | 0.713 | 2.422 | 2.524 | 2.106 | 2.017 | 1.988 | 0.878 | 106 | 82 | 76 | 75 | 10 | 2.39E-5 | > 1.00E-4 | > 1.00E-4 |
| RPMI-8226 | 1.573 | 3.089 | 3.112 | 3.056 | 3.073 | 2.285 | 1.791 | 101 | 98 | 99 | 47 | 14 | 8.74E-6 | > 1.00E-4 | > 1.00E-4 |
| Non-Small Cell Lung Cancer | | | | | | | | | | | | | | | |
| A549/ATCC | 0.501 | 1.835 | 1.788 | 1.818 | 1.838 | 1.938 | 1.008 | 96 | 99 | 100 | 108 | 38 | 6.73E-5 | > 1.00E-4 | > 1.00E-4 |
| EKVX | 0.616 | 2.276 | 2.180 | 2.138 | 2.132 | 2.022 | 1.019 | 94 | 92 | 91 | 85 | 24 | 3.75E-5 | > 1.00E-4 | > 1.00E-4 |
| HOP-62 | 0.652 | 1.880 | 1.904 | 1.875 | 1.872 | 1.731 | 0.835 | 102 | 100 | 99 | 88 | 15 | 3.30E-5 | > 1.00E-4 | > 1.00E-4 |
| HOP-92 | 1.325 | 1.996 | 1.921 | 1.925 | 1.855 | 1.677 | 1.294 | 89 | 79 | 79 | 52 | -2 | 1.11E-5 | 9.05E-5 | > 1.00E-4 |
| NCI-H226 | 0.723 | 1.596 | 1.565 | 1.560 | 1.551 | 1.511 | 0.966 | 97 | 96 | 95 | 90 | 28 | 4.41E-5 | > 1.00E-4 | > 1.00E-4 |

FIG. 12

| | | | | | | | | | | | |
|---|---|---|---|---|---|---|---|---|---|---|---|
| NCI-H23 | 0.872 | 2.440 | 2.370 | 2.292 | 2.214 | 2.102 | 1.112 | 96 | 91 | 86 | 78 | 15 | 2.82E-5 | > 1.00E-4 | > 1.00E-4 |
| NCI-H322M | 0.853 | 2.209 | 2.144 | 2.158 | 2.105 | 1.978 | 1.294 | 95 | 96 | 92 | 83 | 32 | 4.50E-5 | > 1.00E-4 | > 1.00E-4 |
| NCI-H460 | 0.221 | 2.278 | 2.343 | 2.291 | 2.312 | 2.039 | 0.217 | 103 | 101 | 102 | 88 | -2 | 2.66E-5 | 9.55E-5 | > 1.00E-4 |
| NCI-H522 | 1.064 | 2.325 | 2.334 | 2.351 | 2.310 | 1.834 | 0.674 | 101 | 102 | 99 | 61 | -37 | 1.30E-5 | 4.21E-5 | > 1.00E-4 |
| Colon Cancer | | | | | | | | | | | | | | | |
| COLO 205 | 0.430 | 1.508 | 1.551 | 1.479 | 1.469 | 1.331 | 0.315 | 104 | 97 | 96 | 84 | -27 | 2.01E-5 | 5.71E-5 | > 1.00E-4 |
| HCC-2998 | 0.866 | 2.982 | 2.963 | 2.984 | 2.980 | 2.745 | 0.956 | 99 | 100 | 100 | 89 | 4 | 2.88E-5 | > 1.00E-4 | > 1.00E-4 |
| HCT-116 | 0.314 | 2.235 | 2.478 | 2.328 | 2.328 | 1.928 | 0.262 | 113 | 105 | 105 | 84 | -17 | 2.18E-5 | 6.84E-5 | > 1.00E-4 |
| HCT-15 | 0.268 | 2.179 | 2.134 | 1.924 | 2.068 | 1.778 | 0.409 | 98 | 87 | 94 | 79 | 7 | 2.54E-5 | > 1.00E-4 | > 1.00E-4 |
| HT29 | 0.253 | 1.465 | 1.471 | 1.507 | 1.437 | 1.337 | 0.279 | 101 | 103 | 98 | 89 | 2 | 2.83E-5 | > 1.00E-4 | > 1.00E-4 |
| KM12 | 0.530 | 3.074 | 3.068 | 3.032 | 2.928 | 2.236 | 0.502 | 100 | 98 | 94 | 67 | -5 | 1.72E-5 | 8.43E-5 | > 1.00E-4 |
| SW-620 | 0.250 | 1.638 | 1.600 | 1.583 | 1.510 | 1.307 | 0.445 | 97 | 96 | 91 | 76 | 14 | 2.64E-5 | > 1.00E-4 | > 1.00E-4 |
| CNS Cancer | | | | | | | | | | | | | | | |
| SF-268 | 0.597 | 2.066 | 2.031 | 2.056 | 2.000 | 1.819 | 0.788 | 98 | 99 | 96 | 83 | 13 | 2.97E-5 | > 1.00E-4 | > 1.00E-4 |
| SF-295 | 0.647 | 2.349 | 2.251 | 2.174 | 2.208 | 2.008 | 0.758 | 94 | 90 | 92 | 80 | 7 | 2.56E-5 | > 1.00E-4 | > 1.00E-4 |
| SF-539 | 1.084 | 2.805 | 2.759 | 2.619 | 2.705 | 2.531 | 0.785 | 97 | 89 | 94 | 84 | -28 | 2.02E-5 | 5.66E-5 | > 1.00E-4 |
| SNB-19 | 0.964 | 2.473 | 2.352 | 2.350 | 2.317 | 2.066 | 1.304 | 92 | 92 | 90 | 73 | 23 | 2.86E-5 | > 1.00E-4 | > 1.00E-4 |
| SNB-75 | 0.818 | 1.737 | 1.516 | 1.516 | 1.480 | 1.348 | 0.848 | 76 | 76 | 72 | 58 | 3 | 1.38E-5 | > 1.00E-4 | > 1.00E-4 |
| U251 | 0.354 | 1.602 | 1.588 | 1.557 | 1.575 | 1.503 | 0.493 | 99 | 96 | 98 | 92 | 11 | 3.31E-5 | > 1.00E-4 | > 1.00E-4 |

*FIG. 12 (Cont'd)*

| | | | | | | | | | | | |
|---|---|---|---|---|---|---|---|---|---|---|---|
| Melanoma | | | | | | | | | | | |
| LOX IMVI | 0.342 | 2.501 | 2.444 | 2.361 | 2.317 | 2.165 | 0.650 | 97 | 93 | 91 | 84 | 14 | 3.09E-5 | > 1.00E-4 | > 1.00E-4 |
| MALME-3M | 0.760 | 1.314 | 1.277 | 1.275 | 1.239 | 1.157 | 1.046 | 93 | 93 | 86 | 72 | 52 | > 1.00E-4 | > 1.00E-4 | > 1.00E-4 |
| M14 | 0.497 | 1.885 | 1.850 | 1.857 | 1.778 | 1.492 | 0.321 | 97 | 98 | 92 | 72 | -35 | 1.59E-5 | 4.67E-5 | > 1.00E-4 |
| MDA-MB-435 | 0.561 | 2.740 | 2.648 | 2.537 | 2.568 | 0.786 | 0.146 | 96 | 91 | 92 | 10 | -74 | 3.27E-6 | 1.33E-5 | 5.19E-5 |
| SK-MEL-2 | 0.949 | 2.313 | 2.221 | 2.263 | 2.215 | 1.789 | 1.190 | 93 | 96 | 93 | 62 | 18 | 1.83E-5 | > 1.00E-4 | > 1.00E-4 |
| SK-MEL-28 | 0.950 | 2.459 | 2.441 | 2.388 | 2.422 | 1.987 | 1.567 | 99 | 95 | 98 | 69 | 41 | 4.70E-5 | > 1.00E-4 | > 1.00E-4 |
| SK-MEL-5 | 0.629 | 2.619 | 2.590 | 2.631 | 2.566 | 1.866 | 0.373 | 99 | 101 | 97 | 62 | -41 | 1.31E-5 | 4.02E-5 | > 1.00E-4 |
| UACC-257 | 0.888 | 1.958 | 1.781 | 1.818 | 1.789 | 1.720 | 1.438 | 83 | 87 | 84 | 78 | 51 | > 1.00E-4 | > 1.00E-4 | > 1.00E-4 |
| UACC-62 | 1.077 | 2.952 | 2.832 | 2.831 | 2.799 | 1.868 | 1.339 | 94 | 94 | 92 | 42 | 14 | 6.96E-6 | > 1.00E-4 | > 1.00E-4 |
| Ovarian Cancer | | | | | | | | | | | |
| IGROV1 | 0.707 | 2.351 | 2.392 | 2.433 | 2.430 | 1.781 | 0.992 | 102 | 105 | 105 | 65 | 17 | 2.09E-5 | > 1.00E-4 | > 1.00E-4 |
| OVCAR-3 | 0.495 | 1.788 | 1.793 | 1.766 | 1.822 | 1.511 | 0.262 | 100 | 98 | 103 | 79 | -47 | 1.69E-5 | 4.22E-5 | > 1.00E-4 |
| OVCAR-4 | 0.769 | 1.842 | 1.872 | 1.709 | 1.719 | 1.733 | 1.003 | 103 | 88 | 88 | 90 | 22 | 3.85E-5 | > 1.00E-4 | > 1.00E-4 |
| OVCAR-5 | 0.571 | 1.422 | 1.360 | 1.287 | 1.321 | 1.200 | 0.744 | 93 | 84 | 88 | 74 | 20 | 2.79E-5 | > 1.00E-4 | > 1.00E-4 |
| OVCAR-8 | 0.484 | 1.861 | 1.909 | 1.881 | 1.885 | 1.850 | 0.615 | 103 | 101 | 102 | 99 | 10 | 3.54E-5 | > 1.00E-4 | > 1.00E-4 |
| NCI/ADR-RES | 0.530 | 1.844 | 1.846 | 1.800 | 1.801 | 1.732 | 0.908 | 100 | 97 | 97 | 91 | 29 | 4.58E-5 | > 1.00E-4 | > 1.00E-4 |
| SK-OV-3 | 1.101 | 2.111 | 2.146 | 2.138 | 2.226 | 2.155 | 1.277 | 103 | 103 | 111 | 104 | 17 | 4.22E-5 | > 1.00E-4 | > 1.00E-4 |

*FIG. 12 (Cont'd)*

| | | | | | | | | | | |
|---|---|---|---|---|---|---|---|---|---|---|
| Renal Cancer | | | | | | | | | | |
| 786-0 | 0.641 | 2.170 | 2.194 | 2.018 | 2.152 | 1.899 | 0.592 | 102 | 90 | 99 | 82 | -8 | 2.29E-5 | 8.22E-5 | |
| ACHN | 0.573 | 2.365 | 2.366 | 2.243 | 2.298 | 2.086 | 0.764 | 100 | 93 | 96 | 84 | 11 | 2.93E-5 | > 1.00E-4 | > 1.00E-4 |
| CAKI-1 | 0.813 | 3.178 | 3.053 | 2.959 | 3.028 | 2.927 | 1.295 | 95 | 91 | 94 | 89 | 20 | 3.72E-5 | > 1.00E-4 | > 1.00E-4 |
| RXF 393 | 1.108 | 1.609 | 1.568 | 1.577 | 1.604 | 1.417 | 0.890 | 92 | 94 | 99 | 62 | -20 | 1.39E-5 | 5.73E-5 | |
| SN12C | 0.675 | 2.269 | 2.229 | 2.234 | 2.208 | 2.188 | 1.148 | 97 | 98 | 96 | 95 | 30 | 4.88E-5 | > 1.00E-4 | > 1.00E-4 |
| TK-10 | 0.869 | 1.784 | 1.708 | 1.685 | 1.664 | 1.632 | 1.206 | 92 | 89 | 87 | 83 | 37 | 5.20E-5 | > 1.00E-4 | > 1.00E-4 |
| UO-31 | 1.089 | 2.658 | 2.468 | 2.500 | 2.420 | 2.207 | 1.387 | 88 | 90 | 85 | 71 | 19 | 2.55E-5 | > 1.00E-4 | > 1.00E-4 |
| Prostate Cancer | | | | | | | | | | |
| PC-3 | 0.620 | 2.116 | 2.095 | 2.105 | 2.095 | 1.852 | 0.750 | 99 | 99 | 99 | 82 | 9 | 2.75E-5 | > 1.00E-4 | > 1.00E-4 |
| DU-145 | 0.455 | 2.041 | 2.113 | 2.099 | 2.040 | 1.989 | 0.554 | 105 | 104 | 100 | 97 | 6 | 3.28E-5 | > 1.00E-4 | > 1.00E-4 |
| Breast Cancer | | | | | | | | | | |
| MCF7 | 0.359 | 2.525 | 2.414 | 2.287 | 2.344 | 1.298 | 0.634 | 95 | 89 | 92 | 43 | 13 | 7.28E-6 | > 1.00E-4 | > 1.00E-4 |
| MDA-MB-231/ATCC | 0.730 | 1.584 | 1.607 | 1.566 | 1.614 | 1.434 | 0.584 | 103 | 98 | 103 | 82 | -20 | 2.07E-5 | 6.38E-5 | |
| HS 578T | 1.234 | 2.318 | 2.143 | 2.197 | 2.191 | 1.974 | 0.959 | 84 | 89 | 88 | 68 | -22 | 1.59E-5 | 5.67E-5 | |
| BT-549 | 1.156 | 2.225 | 2.278 | 2.156 | 2.260 | 2.015 | 1.023 | 105 | 94 | 103 | 80 | -12 | 2.14E-5 | 7.49E-5 | |
| T-47D | 0.680 | 1.288 | 1.279 | 1.269 | 1.319 | 1.239 | 0.982 | 99 | 97 | 105 | 92 | 50 | 9.79E-5 | > 1.00E-4 | > 1.00E-4 |
| MDA-MB-468 | 0.861 | 1.407 | 1.426 | 1.452 | 1.411 | 0.913 | 0.736 | 103 | 108 | 101 | 10 | -15 | 3.60E-6 | 2.49E-5 | |

*FIG. 12 (Cont'd)*

National Cancer Institute Developmental Therapeutics Program
In-Vitro Testing Results

| NSC: D-784529/1 | | | Experiment ID: 1506NS12 | | | | Test Type: 08 | | Units: Molar |
|---|---|---|---|---|---|---|---|---|---|
| Report Date: July 21, 2015 | | | Test Date: June 29, 2015 | | | | QNS: | | MC: |
| COMI: KCN-Tb5 | | | Stain Reagent: SRB Dual-Pass Related | | | | SSPL: 0ZAS | | |

| | Time | | | Mean Optical Densities | | | | | | Percent Growth | | | | | |
| | | | | | | Log10 Concentration | | | | | | | | | |
| Panel/Cell Line | Zero | Ctrl | -8.0 | -7.0 | -6.0 | -5.0 | -4.0 | -8.0 | -7.0 | -6.0 | -5.0 | -4.0 | GI50 | TGI | LC50 |
| Leukemia | | | | | | | | | | | | | | | |
| CCRF-CEM | 0.713 | 2.422 | 1.965 | 2.316 | 1.944 | 0.878 | 0.888 | 73 | 94 | 72 | 10 | 10 | 2.25E-6 | > 1.00E-4 | > 1.00E-4 |
| RPMI-8226 | 1.573 | 3.089 | 3.065 | 3.073 | 2.463 | 2.034 | 1.664 | 98 | 99 | 59 | 30 | 6 | 2.03E-6 | > 1.00E-4 | > 1.00E-4 |
| Non-Small Cell Lung Cancer | | | | | | | | | | | | | | | |
| A549/ATCC | 0.501 | 1.835 | 1.773 | 1.734 | 1.756 | 1.084 | 0.913 | 95 | 92 | 94 | 44 | 31 | 7.49E-6 | > 1.00E-4 | > 1.00E-4 |
| EKVX | 0.616 | 2.276 | 2.069 | 2.141 | 2.066 | 1.217 | 1.062 | 87 | 92 | 87 | 36 | 27 | 5.36E-6 | > 1.00E-4 | > 1.00E-4 |
| HOP-62 | 0.652 | 1.880 | 1.721 | 1.833 | 1.682 | 0.945 | 0.895 | 87 | 96 | 84 | 24 | 20 | 3.66E-6 | > 1.00E-4 | > 1.00E-4 |
| HOP-92 | 1.325 | 1.996 | 1.880 | 1.848 | 1.694 | 1.433 | 1.272 | 83 | 78 | 55 | 16 | -4 | 1.34E-6 | 6.29E-5 | > 1.00E-4 |
| NCI-H226 | 0.723 | 1.596 | 1.526 | 1.603 | 1.576 | 1.136 | 1.020 | 92 | 101 | 98 | 47 | 34 | 8.83E-6 | > 1.00E-4 | > 1.00E-4 |

*FIG. 13*

| | | | | | | | | | | | |
|---|---|---|---|---|---|---|---|---|---|---|---|
| NCI-H23 | 0.872 | 2.440 | 2.274 | 2.278 | 2.176 | 1.495 | 1.236 | 89 | 90 | 83 | 40 | 23 | 5.80E-6 | >1.00E-4 | >1.00E-4 |
| NCI-H322M | 0.853 | 2.209 | 2.052 | 2.053 | 2.022 | 1.471 | 1.341 | 88 | 88 | 86 | 46 | 36 | 7.78E-6 | >1.00E-4 | >1.00E-4 |
| NCI-H460 | 0.221 | 2.278 | 2.348 | 2.378 | 2.015 | 0.323 | 0.225 | 103 | 105 | 87 | 5 | . | 2.83E-6 | >1.00E-4 | >1.00E-4 |
| NCI-H522 | 1.064 | 2.325 | 2.131 | 2.206 | 1.808 | 1.169 | 0.880 | 85 | 91 | 59 | 8 | -17 | 1.50E-6 | 2.11E-5 | >1.00E-4 |
| Colon Cancer | | | | | | | | | | | | | | | |
| COLO 205 | 0.430 | 1.508 | 1.409 | 1.461 | 1.384 | 0.556 | 0.287 | 91 | 96 | 88 | 12 | -33 | 3.17E-6 | 1.82E-5 | >1.00E-4 |
| HCC-2998 | 0.866 | 2.982 | 2.939 | 2.858 | 2.653 | 1.308 | 1.162 | 98 | 94 | 84 | 21 | 14 | 3.48E-6 | >1.00E-4 | >1.00E-4 |
| HCT-116 | 0.314 | 2.235 | 2.188 | 2.366 | 2.178 | 0.450 | 0.338 | 98 | 107 | 97 | 7 | 1 | 3.33E-6 | >1.00E-4 | >1.00E-4 |
| HCT-15 | 0.268 | 2.179 | 1.927 | 2.004 | 1.904 | 0.674 | 0.458 | 87 | 91 | 86 | 21 | 10 | 3.58E-6 | >1.00E-4 | >1.00E-4 |
| HT29 | 0.253 | 1.465 | 1.303 | 1.390 | 1.442 | 0.327 | 0.292 | 87 | 94 | 98 | 6 | 3 | 3.33E-6 | >1.00E-4 | >1.00E-4 |
| KM12 | 0.530 | 3.074 | 3.050 | 2.986 | 2.266 | 0.819 | 0.613 | 99 | 97 | 68 | 11 | 3 | 2.09E-6 | >1.00E-4 | >1.00E-4 |
| SW-620 | 0.250 | 1.638 | 1.558 | 1.655 | 1.430 | 0.553 | 0.452 | 94 | 101 | 85 | 22 | 15 | 3.58E-6 | >1.00E-4 | >1.00E-4 |
| CNS Cancer | | | | | | | | | | | | | | | |
| SF-268 | 0.597 | 2.066 | 2.084 | 1.965 | 2.022 | 1.049 | 0.838 | 101 | 93 | 97 | 31 | 16 | 5.13E-6 | >1.00E-4 | >1.00E-4 |
| SF-295 | 0.647 | 2.349 | 2.143 | 2.180 | 1.968 | 0.904 | 0.813 | 88 | 90 | 78 | 15 | 10 | 2.76E-6 | >1.00E-4 | >1.00E-4 |
| SF-539 | 1.084 | 2.805 | 2.603 | 2.685 | 2.643 | 0.891 | 0.878 | 88 | 93 | 91 | -18 | -19 | 2.37E-6 | 6.84E-6 | >1.00E-4 |
| SNB-19 | 0.964 | 2.473 | 2.419 | 2.444 | 2.236 | 1.501 | 1.552 | 96 | 98 | 84 | 36 | 39 | 5.06E-6 | >1.00E-4 | >1.00E-4 |
| SNB-75 | 0.818 | 1.737 | 1.436 | 1.553 | 1.436 | 0.815 | 0.927 | 67 | 80 | 67 | . | 12 | 1.80E-6 | . | >1.00E-4 |
| U251 | 0.354 | 1.602 | 1.552 | 1.513 | 1.421 | 0.534 | 0.461 | 96 | 93 | 85 | 14 | 9 | 3.16E-6 | >1.00E-4 | >1.00E-4 |

*FIG. 13 (Cont'd)*

| | | | | | | | | | | | |
|---|---|---|---|---|---|---|---|---|---|---|---|
| Melanoma | | | | | | | | | | | |
| LOX IMVI | 0.342 | 2.501 | 2.433 | 2.341 | 2.270 | 1.018 | 0.795 | 97 | 93 | 89 | 31 | 21 | 4.76E-6 | | > 1.00E-4 |
| MALME-3M | 0.760 | 1.314 | 1.227 | 1.227 | 1.161 | 1.098 | 1.037 | 84 | 84 | 72 | 61 | 50 | 9.81E-5 | | > 1.00E-4 |
| M14 | 0.497 | 1.885 | 1.639 | 1.816 | 1.746 | 0.361 | 0.362 | 82 | 95 | 90 | -27 | -27 | 2.19E-6 | 5.84E-6 | > 1.00E-4 |
| MDA-MB-435 | 0.561 | 2.740 | 2.468 | 2.544 | 1.102 | 0.185 | 0.183 | 88 | 91 | 25 | -67 | -67 | 4.16E-7 | 1.86E-6 | 6.53E-6 |
| SK-MEL-2 | 0.949 | 2.313 | 2.213 | 2.233 | 1.843 | 1.421 | 1.142 | 93 | 94 | 66 | 35 | 14 | 3.17E-6 | > 1.00E-4 | > 1.00E-4 |
| SK-MEL-28 | 0.950 | 2.459 | 2.221 | 2.359 | 2.100 | 1.715 | 1.705 | 84 | 93 | 76 | 51 | 50 | > 1.00E-4 | > 1.00E-4 | > 1.00E-4 |
| SK-MEL-5 | 0.629 | 2.619 | 2.542 | 2.509 | 1.900 | 0.741 | 0.284 | 96 | 94 | 64 | 6 | -55 | 1.73E-6 | 1.24E-5 | 8.31E-5 |
| UACC-257 | 0.888 | 1.958 | 1.656 | 1.777 | 1.775 | 1.534 | 1.525 | 72 | 83 | 83 | 60 | 60 | > 1.00E-4 | > 1.00E-4 | > 1.00E-4 |
| UACC-62 | 1.077 | 2.952 | 2.870 | 2.877 | 2.058 | 1.637 | 1.453 | 96 | 96 | 52 | 30 | 20 | 1.27E-6 | > 1.00E-4 | > 1.00E-4 |
| Ovarian Cancer | | | | | | | | | | | |
| IGROV1 | 0.707 | 2.351 | 2.378 | 2.422 | 1.904 | 1.177 | 0.960 | 102 | 104 | 73 | 29 | 15 | 3.28E-6 | > 1.00E-4 | > 1.00E-4 |
| OVCAR-3 | 0.495 | 1.788 | 1.750 | 1.887 | 1.717 | 0.360 | 0.317 | 97 | 108 | 95 | -27 | -36 | 2.32E-6 | 5.96E-6 | > 1.00E-4 |
| OVCAR-4 | 0.769 | 1.842 | 1.757 | 1.808 | 1.727 | 1.189 | 1.004 | 92 | 97 | 89 | 39 | 22 | 6.06E-6 | > 1.00E-4 | > 1.00E-4 |
| OVCAR-5 | 0.571 | 1.422 | 1.231 | 1.286 | 1.257 | 1.014 | 0.779 | 78 | 84 | 81 | 52 | 24 | 1.19E-5 | > 1.00E-4 | > 1.00E-4 |
| OVCAR-8 | 0.484 | 1.861 | 1.838 | 1.890 | 1.821 | 0.855 | 0.691 | 98 | 102 | 97 | 27 | 15 | 4.69E-6 | > 1.00E-4 | > 1.00E-4 |
| NCI/ADR-RES | 0.530 | 1.844 | 1.856 | 1.819 | 1.820 | 1.429 | 1.099 | 101 | 98 | 98 | 68 | 43 | 5.42E-5 | > 1.00E-4 | > 1.00E-4 |
| SK-OV-3 | 1.101 | 2.111 | 1.938 | 2.121 | 2.015 | 1.439 | 1.297 | 83 | 101 | 90 | 33 | 19 | 5.13E-6 | > 1.00E-4 | > 1.00E-4 |

*FIG. 13 (Cont'd)*

| | | | | | | | | | | |
|---|---|---|---|---|---|---|---|---|---|---|
| Renal Cancer | | | | | | | | | | |
| 786-0 | 0.641 | 2.170 | 1.939 | 2.010 | 2.029 | 0.899 | 0.711 | 85 | 90 | 91 | 17 | 5 | 3.56E-6 | > 1.00E-4 | > 1.00E-4 |
| ACHN | 0.573 | 2.365 | 2.250 | 2.383 | 2.323 | 1.382 | 0.824 | 94 | 101 | 98 | 45 | 14 | 8.09E-6 | > 1.00E-4 | > 1.00E-4 |
| CAKI-1 | 0.813 | 3.178 | 2.932 | 3.014 | 2.985 | 1.949 | 1.251 | 90 | 93 | 92 | 48 | 18 | 9.01E-6 | > 1.00E-4 | > 1.00E-4 |
| RXF 393 | 1.108 | 1.609 | 1.563 | 1.600 | 1.486 | 0.972 | 1.042 | 91 | 98 | 76 | -12 | -6 | 1.95E-6 | 7.25E-6 | > 1.00E-4 |
| SN12C | 0.675 | 2.269 | 2.310 | 2.340 | 2.306 | 1.399 | 1.244 | 103 | 104 | 102 | 45 | 36 | 8.31E-6 | > 1.00E-4 | > 1.00E-4 |
| TK-10 | 0.869 | 1.784 | 1.690 | 1.656 | 1.679 | 1.320 | 1.147 | 90 | 86 | 89 | 49 | 30 | 9.56E-6 | > 1.00E-4 | > 1.00E-4 |
| UO-31 | 1.089 | 2.658 | 2.389 | 2.392 | 2.398 | 1.769 | 1.553 | 83 | 83 | 83 | 43 | 30 | 6.82E-6 | > 1.00E-4 | > 1.00E-4 |
| Prostate Cancer | | | | | | | | | | |
| PC-3 | 0.620 | 2.116 | 2.072 | 1.943 | 1.918 | 0.901 | 0.845 | 97 | 88 | 87 | 19 | 15 | 3.47E-6 | > 1.00E-4 | > 1.00E-4 |
| DU-145 | 0.455 | 2.041 | 2.116 | 2.095 | 2.072 | 0.689 | 0.624 | 105 | 103 | 102 | 15 | 11 | 3.94E-6 | > 1.00E-4 | > 1.00E-4 |
| Breast Cancer | | | | | | | | | | |
| MCF7 | 0.359 | 2.525 | 2.333 | 2.267 | 1.528 | 0.710 | 0.570 | 91 | 88 | 54 | 16 | 10 | 1.27E-6 | > 1.00E-4 | > 1.00E-4 |
| MDA-MB-231/ATCC | 0.730 | 1.584 | 1.581 | 1.620 | 1.559 | 0.795 | 0.625 | 100 | 104 | 97 | 8 | -14 | 3.35E-6 | 2.21E-5 | > 1.00E-4 |
| HS 578T | 1.234 | 2.316 | 2.215 | 2.241 | 2.165 | 1.168 | 1.095 | 90 | 93 | 86 | -5 | -11 | 2.47E-6 | 8.73E-6 | > 1.00E-4 |
| BT-549 | 1.156 | 2.225 | 2.098 | 2.161 | 2.035 | 1.332 | 1.037 | 88 | 94 | 82 | 16 | -10 | 3.09E-6 | 4.12E-5 | > 1.00E-4 |
| T-47D | 0.680 | 1.288 | 1.150 | 1.215 | 1.122 | 0.924 | 1.191 | 77 | 88 | 73 | 40 | 84 | | > 1.00E-4 | > 1.00E-4 |
| MDA-MB-468 | 0.861 | 1.407 | 1.321 | 1.389 | 1.030 | 0.817 | 0.747 | 84 | 97 | 31 | -5 | -13 | 5.14E-7 | 7.22E-6 | > 1.00E-4 |

*FIG. 13 (Cont'd)*

National Cancer Institute Developmental Therapeutics Program
In-Vitro Testing Results

| NSC : D - 784530 / 1 | | | | | | | | Experiment ID : 1509RS64 | | | | Test Type : 08 | | Units : Molar |
|---|---|---|---|---|---|---|---|---|---|---|---|---|---|---|
| Report Date : November 04, 2015 | | | | | | | | Test Date : September 21, 2015 | | | | QNS : | | MC : |
| COMI : KCN-Tb6 | | | | | | | | Stain Reagent : SRB Dual-Pass Related | | | | SSPL : 0ZAS | | |

| | Time | | Log10 Concentration | | | | | | | | Percent Growth | | | | | |
|---|---|---|---|---|---|---|---|---|---|---|---|---|---|---|---|---|
| | | | Mean Optical Densities | | | | | | | | | | | | | |
| Panel/Cell Line | Zero | Ctrl | -8.6 | -7.6 | -6.6 | -5.6 | -4.6 | -8.6 | -7.6 | -6.6 | -5.6 | -4.6 | GI50 | TGI | LC50 |
| Leukemia | | | | | | | | | | | | | | | |
| CCRF-CEM | 0.527 | 3.088 | 3.082 | 3.146 | 2.812 | 0.918 | 0.780 | 100 | 102 | 89 | 15 | 10 | 8.48E-7 | > 2.50E-5 | > 2.50E-5 |
| HL-60(TB) | 0.819 | 3.205 | 3.186 | 3.190 | 2.369 | 0.742 | 0.699 | 99 | 99 | 65 | -9 | -15 | 3.97E-7 | 1.87E-6 | > 2.50E-5 |
| K-562 | 0.252 | 2.446 | 2.462 | 2.462 | 1.637 | 0.484 | 0.426 | 101 | 101 | 63 | 11 | 8 | 4.44E-7 | > 2.50E-5 | > 2.50E-5 |
| MOLT-4 | 0.566 | 2.766 | 2.799 | 2.803 | 2.612 | 0.921 | 0.841 | 102 | 102 | 93 | 16 | 13 | 9.06E-7 | > 2.50E-5 | > 2.50E-5 |
| RPMI-8226 | 0.481 | 1.716 | 1.801 | 1.757 | 1.134 | 0.541 | 0.429 | 107 | 103 | 53 | 5 | -11 | 2.86E-7 | 5.11E-6 | > 2.50E-5 |
| SR | 0.310 | 1.521 | 1.414 | 1.345 | 0.643 | 0.441 | 0.354 | 91 | 85 | 27 | 11 | 4 | 1.02E-7 | > 2.50E-5 | > 2.50E-5 |

FIG. 14

| | | | | | | | | | | | |
|---|---|---|---|---|---|---|---|---|---|---|---|
| Non-Small Cell Lung Cancer | | | | | | | | | | | |
| A549/ATCC | 0.477 | 1.816 | 1.767 | 1.811 | 1.768 | 0.888 | 0.591 | 96 | 100 | 96 | 31 | 9 | 1.27E-6 | > 2.50E-5 | > 2.50E-5 |
| EKVX | 0.844 | 2.572 | 2.484 | 2.498 | 2.401 | 1.355 | 1.200 | 95 | 96 | 90 | 30 | 21 | 1.15E-6 | > 2.50E-5 | > 2.50E-5 |
| HOP-62 | 0.653 | 1.788 | 1.800 | 1.833 | 1.591 | 0.785 | 0.719 | 101 | 104 | 83 | 12 | 6 | 7.20E-7 | > 2.50E-5 | > 2.50E-5 |
| HOP-92 | 0.966 | 1.626 | 1.641 | 1.634 | 1.415 | 1.305 | 1.127 | 102 | 101 | 68 | 51 | 24 | 2.81E-6 | > 2.50E-5 | > 2.50E-5 |
| NCI-H226 | 0.825 | 2.187 | 2.105 | 2.118 | 2.002 | 1.402 | 1.102 | 94 | 95 | 86 | 42 | 20 | 1.67E-6 | > 2.50E-5 | > 2.50E-5 |
| NCI-H23 | 0.803 | 2.299 | 2.214 | 2.174 | 1.952 | 1.135 | 1.052 | 94 | 92 | 77 | 22 | 17 | 7.74E-7 | > 2.50E-5 | > 2.50E-5 |
| NCI-H322M | 0.830 | 2.575 | 2.453 | 2.450 | 2.331 | 1.377 | 1.425 | 93 | 93 | 86 | 31 | 34 | 1.14E-6 | > 2.50E-5 | > 2.50E-5 |
| NCI-H460 | 0.320 | 3.008 | 3.065 | 3.046 | 2.533 | 0.445 | 0.344 | 102 | 101 | 82 | 5 | 1 | 6.52E-7 | > 2.50E-5 | > 2.50E-5 |
| NCI-H522 | 1.026 | 2.083 | 2.066 | 2.074 | 1.439 | 0.854 | 0.806 | 98 | 99 | 39 | -17 | -21 | 1.64E-7 | 1.25E-6 | > 2.50E-5 |
| Colon Cancer | | | | | | | | | | | |
| COLO 205 | 0.545 | 2.048 | 2.144 | 2.094 | 1.767 | 0.325 | 0.188 | 106 | 103 | 81 | -40 | -66 | 4.52E-7 | 1.16E-6 | 5.99E-6 |
| HCC-2998 | 0.663 | 2.618 | 2.576 | 2.415 | 1.744 | 0.963 | 0.677 | 98 | 90 | 55 | 15 | 1 | 3.39E-7 | > 2.50E-5 | > 2.50E-5 |
| HCT-116 | 0.252 | 2.151 | 2.050 | 1.959 | 1.469 | 0.267 | 0.261 | 95 | 90 | 64 | 1 | | 4.17E-7 | > 2.50E-5 | > 2.50E-5 |
| HCT-15 | 0.325 | 2.054 | 2.077 | 2.056 | 1.819 | 0.327 | 0.311 | 101 | 100 | 86 | | -4 | 6.60E-7 | 2.66E-6 | > 2.50E-5 |
| HT29 | 0.183 | 1.192 | 1.145 | 1.182 | 1.028 | 0.187 | 0.178 | 99 | 99 | 84 | | -3 | 6.34E-7 | 3.17E-6 | > 2.50E-5 |
| KM12 | 0.556 | 3.140 | 3.051 | 2.972 | 2.224 | 0.963 | 0.738 | 95 | 93 | 65 | 16 | 7 | 4.97E-7 | > 2.50E-5 | > 2.50E-5 |
| SW-620 | 0.347 | 2.472 | 2.371 | 2.393 | 1.862 | 0.766 | 0.675 | 97 | 96 | 71 | 20 | 15 | 6.47E-7 | > 2.50E-5 | > 2.50E-5 |

*FIG. 14 (Cont'd)*

| | | | | | | | | | | |
|---|---|---|---|---|---|---|---|---|---|---|
| CNS Cancer | | | | | | | | | | |
| SF-268 | 0.549 | 2.127 | 2.028 | 2.007 | 1.874 | 0.880 | 0.750 | 94 | 92 | 84 | 21 | 13 | 8.66E-7 | > 2.50E-5 | > 2.50E-5 |
| SF-295 | 0.546 | 1.885 | 1.773 | 1.833 | 1.570 | 0.491 | 0.521 | 92 | 96 | 76 | -10 | -5 | 5.05E-7 | 1.91E-6 | > 2.50E-5 |
| SF-539 | 1.222 | 3.085 | 3.051 | 3.000 | 2.930 | 1.009 | 0.942 | 98 | 95 | 92 | -17 | -23 | 6.02E-7 | 1.73E-6 | > 2.50E-5 |
| SNB-19 | 0.766 | 2.501 | 2.424 | 2.436 | 2.130 | 1.379 | 1.282 | 96 | 96 | 79 | 35 | 30 | 1.14E-6 | > 2.50E-5 | > 2.50E-5 |
| SNB-75 | 0.969 | 1.858 | 1.638 | 1.579 | 1.491 | 1.174 | 1.079 | 75 | 69 | 59 | 23 | 12 | 4.39E-7 | > 2.50E-5 | > 2.50E-5 |
| U251 | 0.376 | 1.635 | 1.633 | 1.660 | 1.463 | 0.554 | 0.524 | 100 | 102 | 86 | 14 | 12 | 7.96E-7 | > 2.50E-5 | > 2.50E-5 |
| Melanoma | | | | | | | | | | |
| LOX IMVI | 0.518 | 3.269 | 3.169 | 3.142 | 2.874 | 1.015 | 0.741 | 96 | 95 | 86 | 18 | 8 | 8.42E-7 | > 2.50E-5 | > 2.50E-5 |
| MALME-3M | 0.915 | 1.869 | 1.779 | 1.718 | 1.500 | 1.343 | 1.280 | 91 | 84 | 61 | 45 | 38 | 1.22E-6 | > 2.50E-5 | > 2.50E-5 |
| M14 | 0.490 | 1.740 | 1.695 | 1.692 | 1.411 | 0.406 | 0.307 | 96 | 96 | 74 | -17 | -37 | 4.56E-7 | 1.62E-6 | > 2.50E-5 |
| MDA-MB-435 | 0.476 | 2.806 | 2.743 | 2.669 | 0.714 | 0.170 | 0.250 | 97 | 94 | 10 | -64 | -48 | 8.39E-8 | 3.42E-7 | > 2.50E-5 |
| SK-MEL-2 | 0.956 | 1.973 | 2.044 | 1.923 | 1.599 | 1.293 | 1.185 | 107 | 95 | 63 | 33 | 22 | 6.88E-7 | > 2.50E-5 | > 2.50E-5 |
| SK-MEL-28 | 0.749 | 2.017 | 2.000 | 1.972 | 1.675 | 1.412 | 1.283 | 99 | 96 | 73 | 52 | 42 | 4.21E-6 | > 2.50E-5 | > 2.50E-5 |
| SK-MEL-5 | 0.934 | 3.249 | 3.180 | 3.192 | 1.836 | 0.466 | 0.187 | 97 | 98 | 39 | -50 | -80 | 1.62E-7 | 6.84E-7 | 2.49E-6 |
| UACC-62 | 0.879 | 3.094 | 3.001 | 3.023 | 1.689 | 1.458 | 1.300 | 96 | 97 | 37 | 26 | 19 | 1.49E-7 | > 2.50E-5 | > 2.50E-5 |
| Ovarian Cancer | | | | | | | | | | |
| IGROV1 | 0.758 | 2.458 | 2.481 | 2.442 | 1.744 | 1.130 | 0.996 | 101 | 99 | 58 | 22 | 14 | 4.16E-7 | > 2.50E-5 | > 2.50E-5 |
| OVCAR-3 | 0.467 | 1.681 | 1.732 | 1.739 | 0.797 | 0.274 | 0.282 | 104 | 105 | 27 | -41 | -40 | 1.27E-7 | 6.23E-7 | > 2.50E-5 |
| OVCAR-4 | 0.689 | 1.539 | 1.506 | 1.478 | 1.416 | 0.984 | 0.870 | 96 | 93 | 86 | 35 | 21 | 1.25E-6 | > 2.50E-5 | > 2.50E-5 |
| OVCAR-5 | 0.656 | 2.040 | 1.972 | 1.894 | 1.866 | 1.108 | 0.925 | 95 | 89 | 87 | 33 | 19 | 1.20E-6 | > 2.50E-5 | > 2.50E-5 |
| OVCAR-8 | 0.453 | 1.861 | 1.899 | 1.944 | 1.863 | 0.678 | 0.725 | 103 | 106 | 100 | 16 | 19 | 9.85E-7 | > 2.50E-5 | > 2.50E-5 |
| NCI/ADR-RES | 0.575 | 2.056 | 2.000 | 1.969 | 1.931 | 1.206 | 0.605 | 96 | 94 | 92 | 43 | 2 | 1.76E-6 | > 2.50E-5 | > 2.50E-5 |
| SK-OV-3 | 0.872 | 1.725 | 1.774 | 1.767 | 1.489 | 1.072 | 1.012 | 106 | 105 | 72 | 23 | 16 | 7.15E-7 | > 2.50E-5 | > 2.50E-5 |

*FIG. 14 (Cont'd)*

| | | | | | | | | | | |
|---|---|---|---|---|---|---|---|---|---|---|
| Renal Cancer | | | | | | | | | | |
| 786-0 | 0.474 | 1.866 | 1.770 | 1.771 | 1.429 | 0.507 | 0.396 | 93 | 93 | 69 | 2 | | 4.77E-7 | 3.33E-6 | > 2.50E-5 |
| A498 | 1.487 | 2.393 | 2.260 | 2.305 | 1.843 | 1.521 | 1.307 | 85 | 90 | 39 | 4 | -16 | 1.54E-7 | 4.31E-6 | > 2.50E-5 |
| ACHN | 0.442 | 1.942 | 1.930 | 1.904 | 1.828 | 0.880 | 0.509 | 99 | 97 | 92 | 29 | -12 | 1.17E-6 | > 2.50E-5 | > 2.50E-5 |
| CAKI-1 | 0.620 | 2.737 | 2.479 | 2.480 | 2.489 | 1.239 | 0.731 | 88 | 88 | 88 | 29 | 4 | 1.11E-6 | > 2.50E-5 | > 2.50E-5 |
| RXF 393 | 0.948 | 1.588 | 1.556 | 1.596 | 1.349 | 1.016 | 0.995 | 95 | 101 | 63 | 11 | 5 | 4.36E-7 | > 2.50E-5 | > 2.50E-5 |
| SN12C | 0.609 | 2.459 | 2.400 | 2.354 | 2.274 | 1.088 | 0.804 | 97 | 94 | 90 | 26 | 7 | 1.05E-6 | > 2.50E-5 | > 2.50E-5 |
| TK-10 | 0.895 | 1.796 | 1.737 | 1.689 | 1.619 | 1.264 | 0.951 | 93 | 88 | 80 | 41 | 6 | 1.48E-6 | > 2.50E-5 | > 2.50E-5 |
| UO-31 | 1.010 | 2.618 | 2.428 | 2.335 | 2.255 | 1.626 | 1.268 | 88 | 82 | 77 | 38 | 16 | 1.25E-6 | > 2.50E-5 | > 2.50E-5 |
| Prostate Cancer | | | | | | | | | | |
| PC-3 | 0.508 | 2.381 | 2.323 | 2.326 | 1.928 | 0.831 | 0.677 | 97 | 97 | 76 | 17 | 9 | 6.89E-7 | > 2.50E-5 | > 2.50E-5 |
| DU-145 | 0.442 | 2.141 | 2.144 | 2.127 | 1.963 | 0.494 | 0.456 | 100 | 99 | 90 | 3 | 1 | 7.16E-7 | > 2.50E-5 | > 2.50E-5 |
| Breast Cancer | | | | | | | | | | |
| MCF7 | 0.468 | 2.813 | 2.705 | 2.685 | 1.018 | 0.723 | 0.566 | 95 | 95 | 23 | 11 | 4 | 1.06E-7 | > 2.50E-5 | > 2.50E-5 |
| MDA-MB-231/ATCC | 0.775 | 2.106 | 2.131 | 2.123 | 1.996 | 0.850 | 0.629 | 102 | 101 | 92 | 6 | -19 | 7.64E-7 | 4.24E-6 | > 2.50E-5 |
| HS 578T | 1.129 | 2.045 | 2.042 | 2.042 | 1.931 | 1.217 | 1.049 | 100 | 100 | 88 | 10 | -7 | 7.57E-7 | 9.34E-6 | > 2.50E-5 |
| BT-549 | 0.793 | 1.623 | 1.564 | 1.560 | 1.155 | 0.594 | 0.344 | 93 | 92 | 44 | -25 | -57 | 1.85E-7 | 1.08E-6 | 1.54E-5 |
| T-47D | 0.687 | 1.474 | 1.466 | 1.474 | 1.109 | 1.127 | 1.092 | 99 | 100 | 54 | 56 | 51 | > 2.50E-5 | > 2.50E-5 | > 2.50E-5 |
| MDA-MB-468 | 0.914 | 2.076 | 1.969 | 1.989 | 0.907 | 0.695 | 0.633 | 91 | 93 | | -24 | -31 | 7.14E-8 | 2.45E-7 | |

*FIG. 14 (Cont'd)*

National Cancer Institute Developmental Therapeutics Program
In-Vitro Testing Results

| NSC: D-784531/1 | | | | | Experiment ID: 1509RS64 | | | | | | Test Type: 08 | | | Units: Molar |
|---|---|---|---|---|---|---|---|---|---|---|---|---|---|---|
| Report Date: November 04, 2015 | | | | | Test Date: September 21, 2015 | | | | | | QNS: | | | MC: |
| COMI: KCN-Tb7 | | | | | Stain Reagent: SRB Dual-Pass Related | | | | | | SSPL: 0ZAS | | | |
| | Time | | Log10 Concentration | | | | | | | | | | | |
| | | | Mean Optical Densities | | | | | Percent Growth | | | | | | |
| Panel/Cell Line | Zero | Ctrl | -8.8 | -7.8 | -6.8 | -5.8 | -4.8 | -8.8 | -7.8 | -6.8 | -5.8 | -4.8 | GI50 | TGI | LC50 |
| Leukemia | | | | | | | | | | | | | | | |
| CCRF-CEM | 0.527 | 3.167 | 3.057 | 3.049 | 2.111 | 0.715 | 0.576 | 96 | 96 | 60 | 7 | 2 | 2.58E-7 | >1.67E-5 | >1.67E-5 |
| HL-60(TB) | 0.819 | 3.337 | 3.305 | 3.328 | 1.003 | 0.614 | 0.637 | 99 | 100 | 7 | -25 | -22 | 5.76E-8 | 2.81E-7 | >1.67E-5 |
| K-562 | 0.252 | 2.600 | 2.408 | 2.389 | 1.080 | 0.460 | 0.377 | 92 | 91 | 35 | 9 | 5 | 9.08E-8 | >1.67E-5 | >1.67E-5 |
| MOLT-4 | 0.566 | 2.840 | 2.659 | 2.793 | 2.650 | 1.177 | 0.765 | 92 | 98 | 92 | 27 | 9 | 7.34E-7 | >1.67E-5 | >1.67E-5 |
| RPMI-8226 | 0.481 | 1.571 | 1.517 | 1.423 | 0.491 | 0.479 | 0.388 | 95 | 86 | 1 | . | -19 | 4.45E-8 | 7.94E-7 | >1.67E-5 |
| SR | 0.310 | 1.536 | 1.459 | 0.933 | 0.489 | 0.443 | 0.422 | 94 | 51 | 15 | 11 | 9 | 1.76E-8 | >1.67E-5 | >1.67E-5 |

*FIG. 15*

| | | | | | | | | | | | |
|---|---|---|---|---|---|---|---|---|---|---|---|
| Non-Small Cell Lung Cancer | | | | | | | | | | | |
| A549/ATCC | 0.477 | 1.956 | 1.667 | 1.675 | 1.651 | 1.020 | 0.691 | 80 | 81 | 79 | 37 | 14 | 8.16E-7 | > 1.67E-5 |
| EKVX | 0.844 | 2.488 | 2.409 | 2.309 | 2.130 | 1.547 | 1.378 | 95 | 89 | 78 | 43 | 32 | 1.04E-6 | > 1.67E-5 |
| HOP-62 | 0.653 | 1.776 | 1.662 | 1.669 | 1.378 | 0.783 | 0.600 | 90 | 90 | 65 | 12 | -8 | 3.14E-7 | 6.42E-6 |
| HOP-92 | 0.966 | 1.562 | 1.500 | 1.532 | 1.294 | 1.319 | 1.240 | 90 | 95 | 55 | 59 | 46 | 8.36E-6 | > 1.67E-5 |
| NCI-H226 | 0.825 | 2.157 | 2.023 | 2.018 | 1.956 | 1.571 | 1.311 | 90 | 90 | 85 | 56 | 36 | 3.40E-6 | > 1.67E-5 |
| NCI-H23 | 0.803 | 2.150 | 2.053 | 2.023 | 1.704 | 1.261 | 1.101 | 93 | 91 | 67 | 34 | 22 | 5.44E-7 | > 1.67E-5 |
| NCI-H322M | 0.830 | 2.482 | 2.381 | 2.380 | 2.200 | 1.425 | 1.352 | 94 | 94 | 83 | 36 | 32 | 8.40E-7 | > 1.67E-5 |
| NCI-H460 | 0.320 | 2.994 | 3.083 | 3.047 | 1.997 | 0.503 | 0.350 | 103 | 102 | 63 | 7 | 1 | 2.82E-7 | > 1.67E-5 |
| NCI-H522 | 1.026 | 2.194 | 2.207 | 2.032 | 1.250 | 0.866 | 0.633 | 101 | 86 | 19 | -16 | -38 | 5.78E-8 | 5.93E-7 |
| Colon Cancer | | | | | | | | | | | |
| COLO 205 | 0.545 | 1.844 | 1.860 | 1.817 | 1.011 | 0.389 | 0.127 | 101 | 98 | 36 | -29 | -77 | 9.88E-8 | 4.64E-6 |
| HCC-2998 | 0.663 | 2.452 | 2.414 | 2.462 | 1.541 | 0.949 | 0.730 | 98 | 101 | 49 | 16 | 4 | 1.60E-7 | > 1.67E-5 |
| HCT-116 | 0.252 | 2.173 | 2.147 | 2.134 | 0.954 | 0.419 | 0.317 | 99 | 98 | 37 | 9 | 3 | 1.01E-7 | > 1.67E-5 |
| HCT-15 | 0.325 | 1.964 | 1.919 | 1.857 | 1.573 | 0.935 | 0.480 | 97 | 93 | 76 | 37 | 9 | 7.83E-7 | > 1.67E-5 |
| HT29 | 0.183 | 1.141 | 1.130 | 1.103 | 0.323 | 0.186 | 0.169 | 99 | 96 | 15 | | -8 | 6.13E-8 | 1.82E-6 |
| KM12 | 0.556 | 3.094 | 3.057 | 3.076 | 1.947 | 1.016 | 0.760 | 99 | 99 | 55 | 18 | 8 | 2.26E-7 | > 1.67E-5 |
| SW-620 | 0.347 | 2.471 | 2.386 | 2.246 | 1.061 | 0.695 | 0.594 | 96 | 89 | 34 | 16 | 12 | 8.49E-8 | > 1.67E-5 |

*FIG. 15 (Cont'd)*

| | | | | | | | | | | |
|---|---|---|---|---|---|---|---|---|---|---|
| CNS Cancer | | | | | | | | | | |
| SF-268 | 0.549 | 2.182 | 2.117 | 1.831 | 1.135 | 0.762 | 96 | 97 | 78 | 36 | 13 | 7.77E-7 | >1.67E-5 | >1.67E-5 |
| SF-295 | 0.546 | 1.840 | 1.748 | 1.436 | 0.544 | 0.489 | 93 | 89 | 69 | · | | 3.12E-7 | 1.65E-6 | >1.67E-5 |
| SF-539 | 1.222 | 3.044 | 3.069 | 3.041 | 0.987 | 1.038 | 101 | 100 | 100 | -19 | -11 | 4.38E-7 | 1.15E-6 | >1.67E-5 |
| SNB-19 | 0.766 | 2.387 | 2.343 | 1.868 | 1.422 | 1.260 | 97 | 92 | 68 | 40 | -15 | 7.51E-7 | >1.67E-5 | >1.67E-5 |
| SNB-75 | 0.969 | 1.999 | 1.820 | 1.526 | 1.170 | 1.246 | 83 | 86 | 54 | 20 | 30 | 2.19E-7 | >1.67E-5 | >1.67E-5 |
| U251 | 0.376 | 1.575 | 1.504 | 1.245 | 0.574 | 0.496 | 94 | 91 | 72 | 17 | 27 10 | 4.21E-7 | >1.67E-5 | >1.67E-5 |
| | | | | | | | | | | | |
| Melanoma | | | | | | | | | | | |
| LOX IMVI | 0.518 | 3.188 | 3.122 | 3.096 | 1.423 | 0.847 | 98 | 97 | 67 | 34 | 12 | 5.40E-7 | >1.67E-5 | >1.67E-5 |
| MALME-3M | 0.915 | 1.774 | 1.712 | 1.666 | 1.299 | 1.310 | 93 | 87 | 50 | 45 | 46 | 1.78E-7 | >1.67E-5 | >1.67E-5 |
| M14 | 0.490 | 1.855 | 1.799 | 1.813 | 0.401 | 0.551 | 96 | 97 | 55 | -18 | 4 | 1.94E-7 | | >1.67E-5 |
| MDA-MB-435 | 0.476 | 2.846 | 2.708 | 2.209 | 0.251 | 0.252 | 94 | 73 | -11 | -47 | -47 | 3.14E-8 | 1.23E-7 | >1.67E-5 |
| SK-MEL-2 | 0.956 | 1.769 | 1.813 | 1.770 | 1.141 | 1.013 | 105 | 100 | 23 | 5 | 7 | 7.41E-8 | >1.67E-5 | >1.67E-5 |
| SK-MEL-28 | 0.749 | 1.953 | 1.918 | 1.873 | 1.333 | 1.298 | 97 | 93 | 72 | 48 | 46 | 1.44E-6 | >1.67E-5 | >1.67E-5 |
| SK-MEL-5 | 0.934 | 3.252 | 3.213 | 3.077 | 1.319 | 0.587 | 98 | 92 | 35 | 17 | -37 | 9.25E-8 | 3.40E-6 | >1.67E-5 |
| UACC-62 | 0.879 | 3.044 | 2.873 | 2.746 | 1.395 | 1.330 | 92 | 86 | 30 | 24 | 21 | 7.32E-8 | >1.67E-5 | >1.67E-5 |
| | | | | | | | | | | | |
| Ovarian Cancer | | | | | | | | | | | |
| IGROV1 | 0.758 | 2.372 | 2.381 | 2.310 | 1.393 | 1.052 | 101 | 96 | 60 | 39 | 18 | 4.97E-7 | >1.67E-5 | >1.67E-5 |
| OVCAR-3 | 0.467 | 1.733 | 1.759 | 1.638 | 0.331 | 0.252 | 102 | 93 | 1 | -29 | -46 | 4.85E-8 | 1.76E-7 | >1.67E-5 |
| OVCAR-4 | 0.689 | 1.665 | 1.686 | 1.564 | 1.051 | 0.945 | 102 | 90 | 63 | 37 | 26 | 5.21E-7 | >1.67E-5 | >1.67E-5 |
| OVCAR-5 | 0.656 | 1.979 | 1.923 | 1.895 | 1.133 | 1.051 | 96 | 94 | 88 | 36 | 30 | 9.05E-7 | >1.67E-5 | >1.67E-5 |
| OVCAR-8 | 0.453 | 1.773 | 1.738 | 1.720 | 0.652 | 0.539 | 97 | 96 | 77 | 15 | 6 | 4.59E-7 | >1.67E-5 | >1.67E-5 |
| NCI/ADR-RES | 0.575 | 1.908 | 1.846 | 1.858 | 1.663 | 1.526 | 95 | 96 | 89 | 82 | 71 | >1.67E-5 | >1.67E-5 | >1.67E-5 |
| SK-OV-3 | 0.872 | 1.637 | 1.602 | 1.578 | 0.997 | 0.790 | 95 | 92 | 61 | 16 | -9 | 2.98E-7 | 7.16E-6 | >1.67E-5 |

*FIG. 15 (Cont'd)*

| | | | | | | | | | | |
|---|---|---|---|---|---|---|---|---|---|---|
| Renal Cancer | | | | | | | | | | |
| 786-0 | 0.474 | 2.011 | 1.935 | 1.927 | 1.171 | 0.760 | 0.642 | 95 | 95 | 45 | 19 | 11 | 1.34E-7 | > 1.67E-5 | > 1.67E-5 |
| A498 | 1.487 | 2.409 | 2.376 | 2.120 | 2.030 | 1.466 | 1.298 | 96 | 69 | 59 | -1 | -13 | 2.34E-7 | 1.58E-6 | > 1.67E-5 |
| ACHN | 0.442 | 1.871 | 1.938 | 1.940 | 1.605 | 1.024 | 0.833 | 105 | 105 | 81 | 41 | 27 | 9.86E-7 | > 1.67E-5 | > 1.67E-5 |
| CAKI-1 | 0.620 | 2.851 | 2.666 | 2.649 | 2.630 | 2.270 | 1.524 | 92 | 91 | 90 | 74 | 41 | 8.68E-6 | > 1.67E-5 | > 1.67E-5 |
| RXF 393 | 0.948 | 1.660 | 1.613 | 1.523 | 1.327 | 0.916 | 1.098 | 93 | 81 | 53 | -3 | 21 | 1.90E-7 | | > 1.67E-5 |
| SN12C | 0.609 | 2.414 | 2.293 | 2.254 | 2.005 | 1.302 | 1.008 | 93 | 91 | 77 | 38 | 22 | 8.40E-7 | > 1.67E-5 | > 1.67E-5 |
| TK-10 | 0.895 | 1.722 | 1.657 | 1.652 | 1.542 | 1.296 | 1.250 | 92 | 92 | 78 | 48 | 43 | 1.48E-6 | > 1.67E-5 | > 1.67E-5 |
| UO-31 | 1.010 | 2.519 | 2.325 | 2.359 | 2.279 | 1.890 | 1.562 | 87 | 89 | 84 | 58 | 37 | 4.02E-6 | > 1.67E-5 | > 1.67E-5 |
| Prostate Cancer | | | | | | | | | | |
| PC-3 | 0.508 | 2.386 | 2.320 | 2.217 | 1.255 | 0.857 | 0.754 | 96 | 91 | 40 | 19 | 13 | 1.05E-7 | > 1.67E-5 | > 1.67E-5 |
| DU-145 | 0.442 | 2.164 | 2.215 | 2.251 | 1.247 | 0.524 | 0.461 | 103 | 105 | 47 | 5 | 1 | 1.47E-7 | > 1.67E-5 | > 1.67E-5 |
| Breast Cancer | | | | | | | | | | |
| MCF7 | 0.468 | 2.813 | 2.661 | 2.202 | 0.829 | 0.792 | 0.623 | 93 | 74 | 15 | 14 | 7 | 4.28E-8 | > 1.67E-5 | > 1.67E-5 |
| MDA-MB-231/ATCC | 0.775 | 2.086 | 2.063 | 2.010 | 1.745 | 1.065 | 0.789 | 98 | 94 | 74 | 22 | 1 | 4.84E-7 | > 1.67E-5 | > 1.67E-5 |
| HS 578T | 1.129 | 2.127 | 2.068 | 2.032 | 1.931 | 1.188 | 1.065 | 94 | 90 | 80 | 6 | -6 | 4.27E-7 | 5.41E-6 | > 1.67E-5 |
| BT-549 | 0.793 | 1.740 | 1.752 | 1.683 | 1.152 | 0.890 | 0.609 | 101 | 94 | 38 | 10 | -23 | 1.02E-7 | 3.38E-6 | > 1.67E-5 |
| T-47D | 0.687 | 1.460 | 1.416 | 1.393 | 0.894 | 1.096 | 1.154 | 94 | 91 | 27 | 53 | 60 | | > 1.67E-5 | > 1.67E-5 |
| MDA-MB-468 | 0.914 | 2.066 | 1.964 | 1.829 | 1.169 | 1.007 | 0.838 | 91 | 79 | 22 | 8 | -8 | 5.44E-8 | 5.18E-6 | > 1.67E-5 |

*FIG. 15 (Cont'd)*

| NSC: D - 784015 / 1 | | | | | | | | | Experiment ID: 1509RS55 | | | | | Test Type: 08 | | | Units: Molar |
|---|---|---|---|---|---|---|---|---|---|---|---|---|---|---|---|---|---|
| Report Date: November 04, 2015 | | | | | | | | | Test Date: September 08, 2015 | | | | | QNS: | | | MC: |
| COMI: KCN-Tb8 | | | | | | | | | Stain Reagent: SRB Dual-Pass Related | | | | | SSPL: OZAS | | | |
| | Time | | Log10 Concentration | | | | | | | | Percent Growth | | | | | | |
| | Zero | Ctrl | -8.6 | -7.6 | -6.6 | -5.6 | -4.6 | -8.6 | -7.6 | -6.6 | -5.6 | -4.6 | GI50 | TGI | LC50 | | |
| Panel/Cell Line | | | | Mean Optical Densities | | | | | | | | | | | | | |
| Leukemia | | | | | | | | | | | | | | | | | |
| CCRF-CEM | 0.854 | 3.312 | 3.281 | 3.228 | 2.129 | 0.881 | 0.756 | 99 | 97 | 52 | 1 | -11 | 2.72E-7 | 3.05E-6 | > 2.50E-5 | | |
| HL-60(TB) | 0.734 | 3.216 | 3.108 | 2.846 | 0.607 | 0.542 | 0.528 | 96 | 85 | -17 | -26 | -28 | 5.50E-8 | 1.69E-7 | > 2.50E-5 | | |
| K-562 | 0.259 | 2.492 | 2.442 | 1.855 | 0.653 | 0.445 | 0.362 | 98 | 71 | 18 | 8 | 5 | 6.26E-8 | > 2.50E-5 | > 2.50E-5 | | |
| MOLT-4 | 0.951 | 3.349 | 3.290 | 3.292 | 2.851 | 1.361 | 1.112 | 98 | 79 | 79 | 17 | 7 | 7.38E-7 | > 2.50E-5 | > 2.50E-5 | | |
| RPMI-8226 | 0.482 | 1.797 | 1.743 | 1.623 | 0.618 | 0.584 | 0.447 | 96 | 87 | 10 | 8 | -7 | 7.57E-8 | 8.15E-6 | > 2.50E-5 | | |
| SR | 0.285 | 0.889 | 0.804 | 0.434 | 0.366 | 0.323 | 0.285 | 86 | 25 | 13 | 6 | . | 9.62E-9 | > 2.50E-5 | > 2.50E-5 | | |

*FIG. 16*

| Cell Line | | | | | | | | | | | | | | |
|---|---|---|---|---|---|---|---|---|---|---|---|---|---|---|
| Non-Small Cell Lung Cancer | | | | | | | | | | | | | | |
| A549/ATCC | 0.397 | 1.901 | 1.849 | 1.722 | 0.777 | 0.575 | 97 | 98 | 88 | 25 | 12 | 1.01E-6 | > 2.50E-5 | > 2.50E-5 |
| EKVX | 0.829 | 2.047 | 2.026 | 1.864 | 1.443 | 1.311 | 98 | 96 | 75 | 50 | 40 | 2.73E-6 | > 2.50E-5 | > 2.50E-5 |
| HOP-62 | 0.551 | 1.603 | 1.639 | 2.001 | 0.699 | 0.563 | 103 | 99 | 67 | 14 | 1 | 5.17E-7 | > 2.50E-5 | > 2.50E-5 |
| HOP-92 | 1.496 | 1.921 | 1.807 | 1.590 | 1.251 | 1.398 | 73 | 48 | 38 | 67 | -7 | . | 2.04E-5 | > 2.50E-5 |
| NCI-H226 | 0.568 | 1.469 | 1.396 | 1.699 | 1.783 | 0.833 | 92 | 93 | 79 | 41 | 29 | 1.46E-6 | > 2.50E-5 | > 2.50E-5 |
| NCI-H23 | 0.617 | 1.864 | 1.870 | 1.408 | 0.939 | 0.835 | 101 | 95 | 71 | 31 | 17 | 8.47E-7 | > 2.50E-5 | > 2.50E-5 |
| NCI-H322M | 0.662 | 2.015 | 1.997 | 1.801 | 1.010 | 1.076 | 99 | 97 | 84 | 39 | 31 | 1.43E-6 | > 2.50E-5 | > 2.50E-5 |
| NCI-H460 | 0.217 | 2.565 | 2.607 | 1.977 | 1.192 | 0.222 | 102 | 102 | 52 | 5 | . | 2.81E-7 | > 2.50E-5 | > 2.50E-5 |
| NCI-H522 | 0.922 | 3.062 | 2.952 | 2.612 | 1.448 | 0.340 | 95 | 85 | 25 | -7 | -35 | 9.67E-8 | 1.50E-6 | > 2.50E-5 |
| | | | | 2.751 | 1.459 | 0.596 | | | | | | | | |
| Colon Cancer | | | | | | | | | | | | | | |
| COLO 205 | 0.482 | 1.571 | 1.591 | 1.509 | 1.073 | 0.445 | 102 | 94 | 54 | -8 | -59 | 2.93E-7 | > 2.50E-5 | 1.64E-5 |
| HCC-2998 | 0.664 | 2.373 | 2.323 | 2.287 | 1.653 | 0.196 | 97 | 95 | 58 | 24 | 4 | 4.26E-7 | > 2.50E-5 | > 2.50E-5 |
| HCT-116 | 0.329 | 2.749 | 2.772 | 2.655 | 1.072 | 0.733 | 101 | 96 | 29 | 10 | 6 | 1.21E-7 | > 2.50E-5 | > 2.50E-5 |
| HCT-15 | 0.237 | 1.436 | 1.360 | 1.388 | 1.028 | 0.466 | 94 | 96 | 80 | 24 | -12 | 8.63E-7 | 1.17E-5 | > 2.50E-5 |
| HT29 | 0.374 | 2.821 | 2.824 | 2.773 | 1.198 | 0.209 | 100 | 98 | 46 | . | -21 | 2.10E-7 | 2.43E-6 | > 2.50E-5 |
| KM12 | 0.429 | 2.684 | 2.722 | 2.574 | 1.502 | 0.297 | 102 | 95 | 50 | 14 | 7 | 2.55E-7 | > 2.50E-5 | > 2.50E-5 |
| SW-620 | 0.230 | 2.019 | 1.986 | 1.980 | 1.563 | 0.595 | 98 | 98 | 41 | 19 | 16 | 1.75E-7 | > 2.50E-5 | > 2.50E-5 |
| | | | | | 0.969 | 0.523 | | | | | | | | |

*FIG. 16 (Cont'd)*

| | | | | | | | | | |
|---|---|---|---|---|---|---|---|---|---|
| CNS Cancer | | | | | | | | | |
| SF-268 | 0.431 | 1.710 | 1.668 | 1.202 | 0.686 | 0.472 | 97 | 94 | 60 | 20 | 3 | 4.49E-7 | > 2.50E-5 | > 2.50E-5 |
| SF-295 | 0.834 | 2.778 | 2.641 | 2.078 | 0.799 | 0.782 | 93 | 92 | 64 | -4 | -6 | 4.01E-7 | 2.17E-6 | > 2.50E-5 |
| SF-539 | 0.954 | 2.713 | 2.617 | 2.636 | 0.826 | 0.774 | 95 | 96 | 74 | -13 | -19 | 4.68E-7 | 1.75E-6 | > 2.50E-5 |
| SNB-19 | 0.499 | 1.834 | 1.745 | 2.251 | 0.772 | 0.714 | 93 | 90 | 47 | 20 | 16 | 2.10E-7 | > 2.50E-5 | > 2.50E-5 |
| SNB-75 | 0.861 | 1.808 | 1.663 | 1.124 | 0.970 | 0.907 | 85 | 85 | 29 | 12 | 5 | 1.05E-7 | > 2.50E-5 | > 2.50E-5 |
| U251 | 0.301 | 1.427 | 1.424 | 1.137 | 0.498 | 0.463 | 100 | 98 | 56 | 17 | 14 | 3.65E-7 | > 2.50E-5 | > 2.50E-5 |
| Melanoma | | | | | | | | | |
| LOX IMVI | 0.426 | 2.788 | 2.715 | 2.643 | 0.866 | 0.579 | 97 | 94 | 48 | 19 | 6 | 2.26E-7 | > 2.50E-5 | > 2.50E-5 |
| MALME-3M | 0.729 | 1.399 | 1.385 | 1.328 | 1.129 | 1.002 | 98 | 89 | 60 | 42 | 41 | 8.61E-7 | > 2.50E-5 | > 2.50E-5 |
| M14 | 0.602 | 2.727 | 2.676 | 2.692 | 1.008 | 1.013 | 98 | 98 | 64 | 21 | 19 | 5.31E-7 | > 2.50E-5 | > 2.50E-5 |
| MDA-MB-435 | 0.472 | 2.614 | 2.539 | 1.697 | 1.057 | 0.389 | 97 | 57 | . | -27 | -18 | 3.33E-8 | 2.45E-7 | > 2.50E-5 |
| SK-MEL-2 | 0.964 | 2.151 | 2.113 | 1.959 | 1.959 | 1.230 | 97 | 99 | 58 | 29 | 22 | 4.81E-7 | > 2.50E-5 | > 2.50E-5 |
| SK-MEL-28 | 0.780 | 2.282 | 2.296 | 2.143 | 1.657 | 1.307 | 101 | 94 | 65 | 44 | 39 | 1.31E-6 | > 2.50E-5 | > 2.50E-5 |
| SK-MEL-5 | 0.839 | 2.768 | 2.776 | 2.194 | 1.440 | 1.368 | 100 | 87 | 30 | -12 | -43 | 1.11E-7 | 1.31E-6 | > 2.50E-5 |
| UACC-62 | 0.703 | 2.604 | 2.388 | 2.520 | 1.417 | 0.482 | 89 | 76 | 24 | 10 | 5 | 8.00E-8 | > 2.50E-5 | > 2.50E-5 |
| Ovarian Cancer | | | | | | | | | |
| IGROV1 | 0.829 | 2.295 | 2.300 | 2.011 | 1.597 | 1.189 | 100 | 81 | 52 | 25 | 6 | 3.05E-7 | > 2.50E-5 | > 2.50E-5 |
| OVCAR-3 | 0.442 | 1.697 | 1.754 | 1.531 | 0.564 | 0.414 | 105 | 87 | 10 | -6 | -37 | 7.50E-8 | 9.98E-7 | > 2.50E-5 |
| OVCAR-4 | 0.661 | 1.508 | 1.484 | 1.502 | 1.428 | 0.281 | 97 | 99 | 91 | 56 | 44 | 7.67E-6 | > 2.50E-5 | > 2.50E-5 |
| OVCAR-5 | 0.754 | 2.069 | 2.053 | 1.987 | 1.907 | 1.035 | 99 | 94 | 88 | 38 | 27 | 1.43E-6 | > 2.50E-5 | > 2.50E-5 |
| OVCAR-8 | 0.496 | 2.039 | 1.994 | 1.984 | 1.643 | 1.106 | 97 | 96 | 74 | 10 | 7 | 5.99E-7 | > 2.50E-5 | > 2.50E-5 |
| NCI/ADR-RES | 0.560 | 1.980 | 1.977 | 1.954 | 1.898 | 1.749 | 100 | 98 | 94 | 84 | 65 | > 2.50E-5 | > 2.50E-5 | > 2.50E-5 |
| SK-OV-3 | 0.802 | 1.481 | 1.457 | 1.460 | 1.310 | 0.962 | 0.817 | 96 | 97 | 75 | 23 | 2 | 7.60E-7 | > 2.50E-5 | > 2.50E-5 |

*FIG. 16 (Cont'd)*

| | | | | | | | | | | | |
|---|---|---|---|---|---|---|---|---|---|---|---|
| Renal Cancer | | | | | | | | | | | |
| 786-0 | 0.605 | 2.502 | 2.312 | 2.304 | 1.540 | 0.982 | 0.679 | 90 | 90 | 49 | 20 | | 2.40E-7 | > 2.50E-5 | > 2.50E-5 |
| A498 | 1.169 | 1.994 | 2.022 | 1.900 | 1.765 | 1.225 | 1.204 | 103 | 89 | 72 | 7 | 4 | 5.46E-7 | > 2.50E-5 | > 2.50E-5 |
| ACHN | 0.483 | 2.082 | 2.094 | 2.117 | 1.948 | 1.168 | 0.753 | 101 | 102 | 92 | 43 | 4 | 1.78E-6 | > 2.50E-5 | > 2.50E-5 |
| CAKI-1 | 0.592 | 2.359 | 2.189 | 2.195 | 2.161 | 1.775 | 1.045 | 90 | 91 | 89 | 67 | 17 | 6.42E-6 | > 2.50E-5 | > 2.50E-5 |
| RXF 393 | 0.963 | 1.673 | 1.659 | 1.626 | 1.249 | 0.937 | 1.035 | 98 | 93 | 40 | -3 | 26 | 1.64E-7 | | > 2.50E-5 |
| SN12C | 0.648 | 2.307 | 2.274 | 2.262 | 1.721 | 1.220 | 0.922 | 98 | 97 | 65 | 34 | 10 | 7.66E-7 | > 2.50E-5 | > 2.50E-5 |
| TK-10 | 0.762 | 1.941 | 1.821 | 1.866 | 1.614 | 1.375 | 1.240 | 90 | 94 | 72 | 52 | 17 | 3.70E-6 | > 2.50E-5 | > 2.50E-5 |
| UO-31 | 0.811 | 2.312 | 2.107 | 2.009 | 2.119 | 1.528 | 1.147 | 86 | 80 | 87 | 48 | 41 | 2.19E-6 | > 2.50E-5 | > 2.50E-5 |
| Prostate Cancer | | | | | | | | | | | | | | | |
| PC-3 | 0.649 | 2.486 | 2.417 | 2.225 | 1.284 | 0.887 | 0.703 | 96 | 86 | 35 | 13 | 3 | 1.25E-7 | > 2.50E-5 | > 2.50E-5 |
| DU-145 | 0.284 | 1.435 | 1.503 | 1.479 | 0.913 | 0.367 | 0.262 | 106 | 104 | 55 | 7 | -8 | 3.13E-7 | 7.49E-6 | |
| Breast Cancer | | | | | | | | | | | | | | | |
| MCF7 | 0.405 | 2.271 | 2.194 | 1.666 | 0.639 | 0.603 | 0.491 | 96 | 68 | 13 | 11 | 5 | 5.21E-8 | > 2.50E-5 | > 2.50E-5 |
| MDA-MB-231/ATCC | 0.619 | 1.833 | 1.772 | 1.783 | 1.378 | 0.718 | 0.629 | 95 | 96 | 63 | 8 | 1 | 4.25E-7 | > 2.50E-5 | > 2.50E-5 |
| HS 578T | 1.054 | 2.178 | 2.180 | 2.114 | 1.581 | 1.128 | 1.025 | 100 | 94 | 47 | 7 | -3 | 2.15E-7 | 1.26E-5 | > 2.50E-5 |
| BT-549 | 1.183 | 2.418 | 2.421 | 2.284 | 1.593 | 1.091 | 0.797 | 100 | 89 | 33 | -8 | -33 | 1.25E-7 | 1.61E-6 | > 2.50E-5 |
| T-47D | 0.750 | 1.486 | 1.490 | 1.411 | 1.002 | 1.116 | 1.194 | 101 | 90 | 34 | 50 | 60 | | > 2.50E-5 | > 2.50E-5 |
| MDA-MB-468 | 0.794 | 1.609 | 1.510 | 1.442 | 0.934 | 0.814 | 0.793 | 88 | 79 | 17 | 2 | | 7.43E-8 | 2.12E-5 | > 2.50E-5 |

*FIG. 16 (Cont'd)*

National Cancer Institute Developmental Therapeutics Program
In-Vitro Testing Results

| NSC : D - 784532 / 1 | | | | | | | | | | Test Type : 08 | | Units : Molar |
|---|---|---|---|---|---|---|---|---|---|---|---|---|
| Report Date : November 04, 2015 | | | | | | | | | | Experiment ID : 1509RS64 | | |
| | | | | | | | | | | Test Date : September 21, 2015 | QNS : | MC : |
| COMI : KCN-Tb9 | | | | | | | | | | Stain Reagent : SRB Dual-Pass Related | SSPL : OZAS | |

| | Time | | | Mean Optical Densities | | | | | Percent Growth | | | | | | | |
|---|---|---|---|---|---|---|---|---|---|---|---|---|---|---|---|---|
| Panel/Cell Line | Zero | Ctrl | -8.8 | -7.8 | -6.8 | -5.8 | -4.8 | -8.8 | -7.8 | -6.8 | -5.8 | -4.8 | GI50 | TGI | LC50 |
| Leukemia | | | | | | | | | | | | | | | |
| CCRF-CEM | 0.527 | 3.167 | 3.169 | 3.224 | 2.879 | 0.880 | 0.790 | 100 | 102 | 89 | 13 | 10 | 4.69E-7 | > 1.43E-5 | > 1.43E-5 |
| HL-60(TB) | 0.819 | 3.337 | 3.350 | 3.352 | 1.726 | 0.686 | 0.770 | 100 | 101 | 36 | -16 | -6 | 8.68E-8 | 6.98E-7 | > 1.43E-5 |
| K-562 | 0.252 | 2.600 | 2.613 | 2.561 | 1.459 | 0.543 | 0.464 | 101 | 98 | 51 | 12 | 9 | 1.55E-7 | > 1.43E-5 | > 1.43E-5 |
| MOLT-4 | 0.566 | 2.840 | 2.915 | 2.841 | 2.726 | 1.216 | 0.888 | 103 | 100 | 95 | 29 | 14 | 6.80E-7 | > 1.43E-5 | > 1.43E-5 |
| RPMI-8226 | 0.481 | 1.571 | 1.623 | 1.604 | 0.798 | 0.564 | 0.414 | 105 | 103 | 29 | 8 | -14 | 7.44E-8 | 3.22E-6 | > 1.43E-5 |
| SR | 0.310 | 1.536 | 1.411 | 1.043 | 0.519 | 0.478 | 0.432 | 90 | 60 | 17 | 14 | 10 | 2.42E-8 | > 1.43E-5 | > 1.43E-5 |

Log10 Concentration

*FIG. 17*

| | | | | | | | | | | | |
|---|---|---|---|---|---|---|---|---|---|---|---|
| Non-Small Cell Lung Cancer | | | | | | | | | | | |
| A549/ATCC | 0.477 | 1.956 | 1.803 | 1.871 | 1.816 | 1.416 | 0.786 | 90 | 94 | 91 | 63 | 21 | 2.97E-6 | > 1.43E-5 | > 1.43E-5 |
| EKVX | 0.844 | 2.488 | 2.450 | 2.464 | 2.332 | 1.852 | 1.482 | 98 | 99 | 91 | 61 | 39 | 4.54E-6 | > 1.43E-5 | > 1.43E-5 |
| HOP-62 | 0.653 | 1.776 | 1.718 | 1.747 | 1.639 | 0.934 | 0.746 | 95 | 97 | 88 | 25 | 8 | 5.71E-7 | > 1.43E-5 | > 1.43E-5 |
| HOP-92 | 0.966 | 1.562 | 1.540 | 1.585 | 1.409 | 1.333 | 1.302 | 96 | 104 | 74 | 62 | 56 | > 1.43E-5 | > 1.43E-5 | > 1.43E-5 |
| NCI-H226 | 0.825 | 2.157 | 2.130 | 2.097 | 2.095 | 1.676 | 1.398 | 98 | 96 | 95 | 64 | 43 | 6.60E-6 | > 1.43E-5 | > 1.43E-5 |
| NCI-H23 | 0.803 | 2.150 | 2.077 | 2.045 | 1.919 | 1.392 | 1.151 | 95 | 92 | 83 | 44 | 26 | 9.89E-7 | > 1.43E-5 | > 1.43E-5 |
| NCI-H322M | 0.830 | 2.482 | 2.335 | 2.299 | 2.250 | 1.519 | 1.523 | 91 | 89 | 86 | 42 | 42 | 9.29E-7 | > 1.43E-5 | > 1.43E-5 |
| NCI-H460 | 0.320 | 2.994 | 3.010 | 2.994 | 2.820 | 0.582 | 0.406 | 101 | 100 | 93 | 10 | 3 | 4.73E-7 | > 1.43E-5 | > 1.43E-5 |
| NCI-H522 | 1.026 | 2.194 | 2.268 | 2.027 | 1.484 | 0.920 | 0.730 | 106 | 86 | 39 | -10 | -29 | 8.36E-8 | 8.84E-7 | > 1.43E-5 |
| Colon Cancer | | | | | | | | | | | |
| COLO 205 | 0.545 | 1.844 | 1.972 | 1.949 | 1.724 | 0.626 | 0.259 | 110 | 108 | 91 | 6 | -52 | 4.34E-7 | 1.83E-6 | 1.30E-5 |
| HCC-2998 | 0.663 | 2.452 | 2.466 | 2.353 | 1.796 | 1.042 | 0.744 | 101 | 94 | 63 | 21 | 5 | 2.96E-7 | > 1.43E-5 | > 1.43E-5 |
| HCT-116 | 0.252 | 2.173 | 2.191 | 2.089 | 1.655 | 0.533 | 0.316 | 101 | 96 | 73 | 15 | 3 | 3.54E-7 | > 1.43E-5 | > 1.43E-5 |
| HCT-15 | 0.325 | 1.964 | 1.966 | 1.981 | 1.827 | 1.245 | 0.487 | 100 | 101 | 92 | 56 | 10 | 1.94E-6 | > 1.43E-5 | > 1.43E-5 |
| HT29 | 0.183 | 1.141 | 1.126 | 1.119 | 0.987 | 0.178 | 0.157 | 98 | 98 | 84 | -3 | -14 | 3.52E-7 | 1.33E-6 | > 1.43E-5 |
| KM12 | 0.556 | 3.094 | 3.066 | 3.010 | 2.456 | 1.089 | 0.809 | 99 | 97 | 75 | 21 | 10 | 4.14E-7 | > 1.43E-5 | > 1.43E-5 |
| SW-620 | 0.347 | 2.471 | 2.339 | 2.352 | 1.711 | 0.883 | 0.636 | 94 | 94 | 64 | 25 | 14 | 3.31E-7 | > 1.43E-5 | > 1.43E-5 |

*FIG. 17 (Cont'd)*

| | | | | | | | | | | |
|---|---|---|---|---|---|---|---|---|---|---|
| CNS Cancer | | | | | | | | | | |
| SF-268 | 0.549 | 2.182 | 2.114 | 2.090 | 1.888 | 1.109 | 0.820 | 96 | 94 | 82 | 34 | 17 | 6.69E-7 | > 1.43E-5 | > 1.43E-5 |
| SF-295 | 0.546 | 1.840 | 1.807 | 1.832 | 1.781 | 0.780 | 0.611 | 97 | 99 | 95 | 18 | 5 | 5.52E-7 | > 1.43E-5 | > 1.43E-5 |
| SF-539 | 1.222 | 3.044 | 2.972 | 2.972 | 2.912 | 1.013 | 1.086 | 96 | 96 | 93 | -17 | -11 | 3.50E-7 | 9.99E-7 | > 1.43E-5 |
| SNB-19 | 0.766 | 2.387 | 2.356 | 2.397 | 2.110 | 1.436 | 1.472 | 98 | 101 | 83 | 41 | 44 | 8.83E-7 | > 1.43E-5 | > 1.43E-5 |
| SNB-75 | 0.969 | 1.999 | 1.780 | 1.749 | 1.575 | 1.189 | 1.433 | 79 | 76 | 59 | 21 | 45 | 2.46E-7 | > 1.43E-5 | > 1.43E-5 |
| U251 | 0.376 | 1.575 | 1.598 | 1.596 | 1.444 | 0.627 | 0.548 | 102 | 102 | 89 | 21 | 14 | 5.35E-7 | > 1.43E-5 | > 1.43E-5 |
| Melanoma | | | | | | | | | | | | | | | |
| LOX IMVI | 0.518 | 3.188 | 3.123 | 3.116 | 2.490 | 1.319 | 0.817 | 98 | 97 | 74 | 30 | 11 | 5.00E-7 | > 1.43E-5 | > 1.43E-5 |
| MALME-3M | 0.915 | 1.774 | 1.697 | 1.665 | 1.445 | 1.255 | 1.317 | 91 | 87 | 62 | 40 | 47 | 4.83E-7 | > 1.43E-5 | > 1.43E-5 |
| M14 | 0.490 | 1.855 | 1.800 | 1.763 | 1.512 | 0.506 | 0.475 | 96 | 93 | 75 | 1 | -3 | 3.11E-7 | 2.63E-6 | > 1.43E-5 |
| MDA-MB-435 | 0.476 | 2.846 | 2.776 | 2.558 | 0.809 | 0.270 | 0.338 | 97 | 88 | 14 | -43 | -29 | 4.66E-8 | 2.51E-7 | > 1.43E-5 |
| SK-MEL-2 | 0.956 | 1.769 | 1.789 | 1.713 | 1.382 | 0.979 | 0.992 | 102 | 93 | 52 | 3 | 4 | 1.60E-7 | > 1.43E-5 | > 1.43E-5 |
| SK-MEL-28 | 0.749 | 1.953 | 1.936 | 1.919 | 1.599 | 1.373 | 1.405 | 99 | 97 | 71 | 52 | 54 | > 1.43E-5 | > 1.43E-5 | > 1.43E-5 |
| SK-MEL-5 | 0.934 | 3.252 | 3.220 | 3.218 | 2.439 | 1.345 | 0.746 | 99 | 99 | 65 | 18 | -20 | 2.96E-7 | 4.20E-6 | > 1.43E-5 |
| UACC-62 | 0.879 | 3.044 | 2.894 | 2.927 | 1.979 | 1.326 | 1.359 | 93 | 95 | 51 | 21 | 22 | 1.52E-7 | > 1.43E-5 | > 1.43E-5 |
| Ovarian Cancer | | | | | | | | | | | | | | | |
| IGROV1 | 0.758 | 2.372 | 2.446 | 2.272 | 1.741 | 1.382 | 1.081 | 105 | 94 | 61 | 39 | 20 | 4.41E-7 | > 1.43E-5 | > 1.43E-5 |
| OVCAR-3 | 0.467 | 1.733 | 1.809 | 1.710 | 0.742 | 0.427 | 0.319 | 106 | 98 | 22 | -9 | -32 | 6.10E-8 | 7.41E-7 | > 1.43E-5 |
| OVCAR-4 | 0.689 | 1.665 | 1.621 | 1.623 | 1.596 | 1.193 | 1.049 | 95 | 96 | 93 | 52 | 37 | 1.85E-6 | > 1.43E-5 | > 1.43E-5 |
| OVCAR-5 | 0.656 | 1.979 | 1.901 | 1.857 | 1.826 | 1.637 | 1.071 | 94 | 91 | 88 | 74 | 31 | 5.24E-6 | > 1.43E-5 | > 1.43E-5 |
| OVCAR-8 | 0.453 | 1.773 | 1.777 | 1.857 | 1.815 | 0.797 | 0.693 | 100 | 106 | 103 | 26 | 18 | 7.00E-7 | > 1.43E-5 | > 1.43E-5 |
| NCI/ADR-RES | 0.575 | 1.908 | 1.860 | 1.827 | 1.839 | 1.814 | 1.610 | 96 | 94 | 95 | 93 | 78 | > 1.43E-5 | > 1.43E-5 | > 1.43E-5 |
| SK-OV-3 | 0.872 | 1.637 | 1.672 | 1.715 | 1.583 | 1.155 | 1.029 | 105 | 110 | 93 | 37 | 21 | 8.37E-7 | > 1.43E-5 | > 1.43E-5 |

*FIG. 17 (Cont'd)*

| | | | | | | | | | | |
|---|---|---|---|---|---|---|---|---|---|---|
| Renal Cancer | | | | | | | | | | |
| 786-0 | 0.474 | 2.011 | 1.966 | 1.937 | 0.889 | 0.700 | 97 | 95 | 82 | 27 | 15 | 5.46E-7 | > 1.43E-5 |
| A498 | 1.487 | 2.409 | 2.359 | 2.401 | 1.641 | 1.445 | 95 | 99 | 90 | 17 | -3 | 5.03E-7 | 1.02E-5 |
| ACHN | 0.442 | 1.871 | 1.870 | 1.854 | 1.848 | 0.788 | 100 | 99 | 98 | 64 | 24 | 3.19E-6 | > 1.43E-5 |
| CAKI-1 | 0.620 | 2.851 | 2.643 | 2.593 | 2.590 | 1.462 | 91 | 88 | 88 | 87 | 38 | 8.08E-6 | > 1.43E-5 |
| RXF 393 | 0.948 | 1.660 | 1.596 | 1.598 | 1.424 | 0.865 | 91 | 91 | 67 | -9 | 36 | 2.38E-7 | |
| SN12C | 0.609 | 2.414 | 2.375 | 2.372 | 2.169 | 1.203 | 98 | 98 | 86 | 42 | 24 | 9.58E-7 | > 1.43E-5 |
| TK-10 | 0.895 | 1.722 | 1.679 | 1.611 | 1.564 | 1.037 | 95 | 87 | 81 | 46 | 46 | 1.11E-6 | > 1.43E-5 |
| UO-31 | 1.010 | 2.519 | 2.261 | 2.283 | 2.033 | 1.274 | 83 | 84 | 83 | 68 | 43 | 7.29E-6 | > 1.43E-5 |
| Prostate Cancer | | | | | | | | | | |
| PC-3 | 0.508 | 2.386 | 2.325 | 2.354 | 2.018 | 0.892 | 97 | 98 | 80 | 20 | 13 | 4.59E-7 | > 1.43E-5 |
| DU-145 | 0.442 | 2.164 | 2.250 | 2.161 | 2.082 | 0.587 | 105 | 100 | 95 | 8 | 5 | 4.74E-7 | > 1.43E-5 |
| Breast Cancer | | | | | | | | | | |
| MCF7 | 0.468 | 2.813 | 2.782 | 2.565 | 0.946 | 0.881 | 99 | 89 | 20 | 18 | 11 | 5.32E-8 | > 1.43E-5 |
| MDA-MB-231/ATCC | 0.775 | 2.086 | 2.092 | 2.123 | 1.958 | 1.043 | 100 | 103 | 90 | 20 | | 5.39E-7 | > 1.43E-5 |
| HS 578T | 1.129 | 2.127 | 2.059 | 2.125 | 2.005 | 1.229 | 93 | 100 | 88 | 10 | 4 | 4.37E-7 | > 1.43E-5 |
| BT-549 | 0.793 | 1.740 | 1.713 | 1.681 | 1.358 | 0.920 | 97 | 94 | 60 | 13 | -19 | 2.31E-7 | 3.71E-6 |
| T-47D | 0.687 | 1.460 | 1.452 | 1.487 | 1.108 | 1.128 | 99 | 104 | 54 | 57 | 67 | > 1.43E-5 | > 1.43E-5 |
| MDA-MB-468 | 0.914 | 2.066 | 2.002 | 1.972 | 1.404 | 0.943 | 0.926 | 94 | 92 | 42 | 3 | 1 | 1.01E-7 | > 1.43E-5 |

*FIG. 17 (Cont'd)*

| | | | | | | | | | | | | | |
|---|---|---|---|---|---|---|---|---|---|---|---|---|---|
| NSC : D - 784533 / 1 | | | | | Experiment ID : 1507NS15 | | | | Test Type : 08 | | | Units : Molar | |
| Report Date : September 10, 2015 | | | | | Test Date : July 06, 2015 | | | | QNS : | | | MC : | |
| COMI : KCN-Tb10 | | | | | Stain Reagent : SRB Dual-Pass Related | | | | SSPL : OZAS | | | | |
| | Time | | | Mean Optical Densities | | | | | Percent Growth | | | | |
| | | | | | Log10 Concentration | | | | | | | | |
| Panel/Cell Line | Zero | Ctrl | -8.8 | -7.8 | -6.8 | -5.8 | -4.8 | -8.8 | -7.8 | -6.8 | -5.8 | -4.8 | GI50 | TGI | LC50 |
| Leukemia | | | | | | | | | | | | | | | |
| CCRF-CEM | 0.692 | 2.692 | 2.667 | 2.630 | 2.449 | 0.970 | 0.799 | 99 | 97 | 88 | 14 | 5 | 4.65E-7 | > 1.43E-5 | > 1.43E-5 |
| HL-60(TB) | 0.841 | 2.650 | 2.727 | 2.775 | 1.146 | 0.607 | 0.680 | 104 | 107 | 17 | -28 | -19 | 6.13E-8 | 3.41E-7 | > 1.43E-5 |
| K-562 | 0.295 | 2.134 | 2.181 | 2.139 | 1.427 | 0.607 | 0.488 | 103 | 100 | 62 | 17 | 10 | 2.60E-7 | > 1.43E-5 | > 1.43E-5 |
| MOLT-4 | 0.637 | 2.558 | 2.581 | 2.568 | 2.485 | 1.321 | 0.886 | 101 | 101 | 96 | 36 | 13 | 8.28E-7 | > 1.43E-5 | > 1.43E-5 |
| RPMI-8226 | 0.825 | 2.349 | 2.372 | 2.378 | 1.661 | 1.189 | 0.870 | 102 | 102 | 55 | 24 | 3 | 2.05E-7 | > 1.43E-5 | > 1.43E-5 |
| SR | 0.433 | 1.985 | 1.903 | 1.798 | 1.016 | 0.814 | 0.575 | 95 | 88 | 38 | 25 | 9 | 8.09E-8 | > 1.43E-5 | > 1.43E-5 |

FIG. 18

| | | | | | | | | | | |
|---|---|---|---|---|---|---|---|---|---|---|
| Non-Small Cell Lung Cancer | | | | | | | | | | |
| A549/ATCC | 0.461 | 2.370 | 2.267 | 2.273 | 2.293 | 1.967 | 0.942 | 95 | 95 | 96 | 79 | 25 | 4.93E-6 | > 1.43E-5 | > 1.43E-5 |
| EKVX | 0.686 | 2.236 | 2.125 | 2.057 | 2.056 | 1.541 | 1.173 | 93 | 88 | 88 | 55 | 31 | 2.35E-6 | > 1.43E-5 | > 1.43E-5 |
| HOP-62 | 0.802 | 1.823 | 1.699 | 1.599 | 1.558 | 1.348 | 1.203 | 88 | 78 | 74 | 53 | 39 | 2.50E-6 | > 1.43E-5 | > 1.43E-5 |
| HOP-92 | 1.384 | 2.310 | 2.195 | 2.175 | 2.049 | 2.051 | 1.862 | 88 | 85 | 72 | 72 | 52 | > 1.43E-5 | > 1.43E-5 | > 1.43E-5 |
| NCI-H226 | 0.817 | 2.097 | 1.989 | 2.014 | 1.995 | 1.651 | 1.546 | 92 | 94 | 92 | 65 | 57 | > 1.43E-5 | > 1.43E-5 | > 1.43E-5 |
| NCI-H23 | 0.712 | 2.187 | 2.136 | 2.113 | 1.919 | 1.282 | 0.955 | 97 | 95 | 82 | 39 | 16 | 7.80E-7 | > 1.43E-5 | > 1.43E-5 |
| NCI-H322M | 0.574 | 1.630 | 1.629 | 1.654 | 1.511 | 0.982 | 1.038 | 100 | 102 | 89 | 39 | 44 | 8.48E-7 | > 1.43E-5 | > 1.43E-5 |
| NCI-H460 | 0.322 | 3.189 | 3.186 | 3.217 | 3.093 | 1.067 | 0.515 | 100 | 101 | 97 | 26 | 7 | 6.53E-7 | > 1.43E-5 | > 1.43E-5 |
| NCI-H522 | 0.945 | 2.834 | 2.728 | 2.725 | 1.388 | 0.958 | 0.768 | 94 | 94 | 23 | 1 | -19 | 6.02E-8 | 1.55E-6 | > 1.43E-5 |
| Colon Cancer | | | | | | | | | | |
| COLO 205 | 0.441 | 1.894 | 1.862 | 1.739 | 1.597 | 0.755 | 0.290 | 98 | 89 | 80 | 22 | -34 | 4.63E-7 | 3.48E-6 | > 1.43E-5 |
| HCC-2998 | 0.472 | 1.829 | 1.793 | 1.883 | 1.471 | 0.794 | 0.648 | 97 | 104 | 74 | 24 | 13 | 4.25E-7 | > 1.43E-5 | > 1.43E-5 |
| HCT-15 | 0.529 | 2.973 | 2.874 | 2.841 | 2.895 | 1.980 | 0.806 | 96 | 95 | 97 | 59 | 11 | 2.24E-6 | > 1.43E-5 | > 1.43E-5 |
| HT29 | 0.349 | 2.277 | 2.213 | 2.285 | 1.790 | 0.582 | 0.480 | 97 | 100 | 75 | 12 | 7 | 3.55E-7 | > 1.43E-5 | > 1.43E-5 |
| KM12 | 0.710 | 3.324 | 3.346 | 3.350 | 2.961 | 1.497 | 1.036 | 101 | 101 | 86 | 30 | 12 | 6.31E-7 | > 1.43E-5 | > 1.43E-5 |
| SW-620 | 0.265 | 2.104 | 1.982 | 1.939 | 1.629 | 0.866 | 0.706 | 93 | 91 | 74 | 33 | 24 | 5.47E-7 | > 1.43E-5 | > 1.43E-5 |

*FIG. 18 (Cont'd)*

| | | | | | | | | | | |
|---|---|---|---|---|---|---|---|---|---|---|
| CNS Cancer | | | | | | | | | | |
| SF-268 | 0.682 | 2.297 | 2.190 | 2.207 | 1.551 | 93 | 94 | 85 | 54 | 21 | 1.87E-6 | > 1.43E-5 |
| SF-295 | 0.986 | 2.828 | 2.690 | 2.747 | 1.470 | 92 | 96 | 92 | 26 | 6 | 6.25E-7 | > 1.43E-5 |
| SF-539 | 1.258 | 2.990 | 2.982 | 2.884 | 1.098 | 100 | 94 | 98 | 26 | 4 | 6.67E-7 | > 1.43E-5 |
| SNB-19 | 0.660 | 2.072 | 1.990 | 2.013 | 1.326 | 94 | 96 | 80 | 39 | 35 | 7.84E-7 | > 1.43E-5 |
| SNB-75 | 0.955 | 2.066 | 1.743 | 1.766 | 1.158 | 71 | 73 | 62 | 19 | 29 | 2.71E-7 | > 1.43E-5 |
| U251 | 0.407 | 1.997 | 1.864 | 1.910 | 1.281 | 92 | 94 | 92 | 27 | 13 | 6.40E-7 | > 1.43E-5 |
| | | | | | 0.611 | | | | | | | |
| Melanoma | | | | | | | | | | | |
| LOX IMVI | 0.258 | 2.008 | 1.892 | 1.928 | 1.361 | 93 | 95 | 63 | 25 | 8 | 3.14E-7 | > 1.43E-5 |
| MALME-3M | 0.719 | 1.210 | 1.195 | 1.157 | 1.019 | 97 | 89 | 61 | 51 | 73 | > 1.43E-5 | > 1.43E-5 |
| M14 | 0.435 | 1.838 | 1.716 | 1.752 | 0.968 | 91 | 94 | 73 | 29 | -8 | 4.72E-7 | 8.74E-6 |
| MDA-MB-435 | 0.448 | 2.734 | 2.581 | 2.322 | 1.458 | 93 | 82 | 23 | -22 | -67 | 4.95E-8 | 4.64E-7 |
| SK-MEL-2 | 1.098 | 2.801 | 2.751 | 2.730 | 0.838 | 97 | 96 | 60 | 37 | 20 | 3.90E-7 | > 1.43E-5 |
| SK-MEL-28 | 0.467 | 1.408 | 1.378 | 1.343 | 0.351 | 97 | 93 | 75 | 42 | 39 | 8.34E-7 | > 1.43E-5 |
| SK-MEL-5 | 0.550 | 2.611 | 2.701 | 2.582 | 1.734 | 104 | 99 | 49 | 19 | -31 | 1.38E-7 | 3.43E-6 |
| UACC-257 | 1.075 | 2.447 | 2.289 | 2.266 | 0.864 | 88 | 87 | 77 | 36 | 31 | 6.55E-7 | > 1.43E-5 |
| UACC-62 | 0.748 | 2.340 | 2.201 | 2.143 | 0.938 | 91 | 88 | 50 | 24 | 20 | 1.46E-7 | > 1.43E-5 |
| | | | | | 1.502 | | | | | | | |
| | | | | | 1.059 | | | | | | | |
| | | | | | 0.401 | | | | | | | |
| | | | | | 1.078 | | | | | | | |
| | | | | | 0.401 | | | | | | | |
| | | | | | 0.148 | | | | | | | |
| | | | | | 1.437 | | | | | | | |
| | | | | | 0.833 | | | | | | | |
| | | | | | 0.381 | | | | | | | |
| | | | | | 1.568 | | | | | | | |
| | | | | | 1.134 | | | | | | | |
| Ovarian Cancer | | | | | | | | | | | |
| IGROV1 | 0.790 | 2.519 | 2.603 | 2.528 | 1.857 | 105 | 101 | 62 | 48 | 26 | 9.97E-7 | > 1.43E-5 |
| OVCAR-3 | 0.501 | 1.767 | 1.764 | 1.787 | 0.983 | 100 | 102 | 38 | -6 | -46 | 9.26E-8 | 1.05E-6 |
| OVCAR-4 | 0.595 | 1.479 | 1.372 | 1.388 | 1.301 | 88 | 90 | 80 | 56 | 30 | 2.49E-6 | > 1.43E-5 |
| OVCAR-5 | 0.953 | 1.841 | 1.748 | 1.694 | 1.536 | 90 | 83 | 87 | 66 | 63 | > 1.43E-5 | > 1.43E-5 |
| OVCAR-8 | 0.501 | 2.265 | 2.221 | 2.191 | 1.126 | 97 | 96 | 88 | 35 | 9 | 7.52E-7 | > 1.43E-5 |
| NCI/ADR-RES | 0.536 | 1.749 | 1.786 | 1.750 | 0.666 | 103 | 100 | 102 | 85 | 33 | 6.69E-6 | > 1.43E-5 |
| SK-OV-3 | 0.857 | 2.244 | 2.242 | 2.178 | 0.935 | 100 | 95 | 77 | 43 | 32 | 8.71E-7 | > 1.43E-5 |
| | | | | | 1.297 | | | | | | | |
| | | | | | 1.513 | | | | | | | |
| | | | | | 1.449 | | | | | | | |
| | | | | | 1.564 | | | | | | | |
| | | | | | 1.238 | | | | | | | |
| | | | | | 0.272 | | | | | | | |
| | | | | | 0.862 | | | | | | | |

*FIG. 18 (Cont'd)*

| | | | | | | | | | | |
|---|---|---|---|---|---|---|---|---|---|---|
| Renal Cancer | | | | | | | | | | |
| 786-0 | 1.179 | 2.967 | 2.880 | 2.777 | 2.016 | 1.544 | 95 | 97 | 89 | 47 | 20 | 1.20E-6 | > 1.43E-5 | > 1.43E-5 |
| ACHN | 0.564 | 2.415 | 2.463 | 2.357 | 1.515 | 1.177 | 103 | 94 | 97 | 51 | 33 | 1.70E-6 | > 1.43E-5 | > 1.43E-5 |
| CAKI-1 | 0.621 | 3.110 | 2.861 | 2.751 | 2.695 | 1.411 | 90 | 88 | 86 | 83 | 32 | 6.33E-6 | > 1.43E-5 | > 1.43E-5 |
| RXF 393 | 0.947 | 1.724 | 1.677 | 1.546 | 1.090 | 1.196 | 94 | 100 | 77 | 18 | 32 | 4.13E-7 | > 1.43E-5 | > 1.43E-5 |
| SN12C | 0.653 | 2.226 | 2.194 | 2.108 | 1.366 | 1.047 | 98 | 99 | 92 | 45 | 25 | 1.14E-6 | > 1.43E-5 | > 1.43E-5 |
| TK-10 | 0.816 | 1.886 | 1.783 | 1.686 | 1.434 | 1.359 | 90 | 91 | 81 | 58 | 51 | > 1.43E-5 | > 1.43E-5 | > 1.43E-5 |
| UO-31 | 0.783 | 2.240 | 2.231 | 2.099 | 1.761 | 1.352 | 99 | 89 | 90 | 67 | 39 | 5.83E-6 | > 1.43E-5 | > 1.43E-5 |
| Prostate Cancer | | | | | | | | | | |
| PC-3 | 0.474 | 1.511 | 1.468 | 1.336 | 0.935 | 0.844 | 96 | 94 | 83 | 44 | 36 | 1.03E-6 | > 1.43E-5 | > 1.43E-5 |
| DU-145 | 0.429 | 1.982 | 1.988 | 1.865 | 0.653 | 0.503 | 100 | 103 | 92 | 14 | 5 | 5.00E-7 | > 1.43E-5 | > 1.43E-5 |
| Breast Cancer | | | | | | | | | | |
| MCF7 | 0.571 | 2.909 | 2.760 | 2.527 | 1.347 | 1.074 | 0.960 | 94 | 84 | 33 | 22 | 17 | 6.64E-8 | > 1.43E-5 | > 1.43E-5 |
| MDA-MB-231/ATCC | 0.572 | 1.347 | 1.320 | 1.316 | 1.285 | 0.801 | 0.638 | 96 | 96 | 92 | 30 | 9 | 6.73E-7 | > 1.43E-5 | > 1.43E-5 |
| HS 578T | 0.984 | 2.179 | 2.061 | 2.097 | 2.029 | 1.476 | 1.214 | 90 | 93 | 87 | 41 | 19 | 9.22E-7 | > 1.43E-5 | > 1.43E-5 |
| BT-549 | 0.701 | 1.613 | 1.489 | 1.538 | 1.226 | 0.993 | 0.506 | 86 | 92 | 58 | 32 | -28 | 2.82E-7 | 4.90E-6 | > 1.43E-5 |
| T-47D | 0.892 | 1.934 | 1.903 | 1.893 | 1.689 | 1.499 | 1.648 | 93 | 92 | 73 | 56 | 69 | > 1.43E-5 | > 1.43E-5 | > 1.43E-5 |
| MDA-MB-468 | 0.579 | 1.239 | 1.199 | 1.202 | 0.997 | 0.677 | 0.695 | 94 | 94 | 63 | 15 | 18 | 2.69E-7 | > 1.43E-5 | > 1.43E-5 |

*FIG. 18 (Cont'd)*

National Cancer Institute Developmental Therapeutics Program
In-Vitro Testing Results

| NSC: D - 784016 / 1 | | | | | Experiment ID: 1509RS55 | | | | | Test Type: 08 | | Units: Molar |
|---|---|---|---|---|---|---|---|---|---|---|---|---|
| Report Date: November 04, 2015 | | | | | Test Date: September 08, 2015 | | | | | QNS: | | MC: |
| COMI: KCN-Tb11 | | | | | Stain Reagent: SRB Dual-Pass Related | | | | | SSPL: OZAS | | |

| | Time | | Log10 Concentration | | | | | | Percent Growth | | | | | | |
|---|---|---|---|---|---|---|---|---|---|---|---|---|---|---|---|
| | | | Mean Optical Densities | | | | | | | | | | | | |
| Panel/Cell Line | Zero | Ctrl | -11.0 | -10.0 | -9.0 | -8.0 | -7.0 | -11.0 | -10.0 | -9.0 | -8.0 | -7.0 | GI50 | TGI | LC50 |
| Leukemia | | | | | | | | | | | | | | | |
| CCRF-CEM | 0.854 | 3.312 | 3.296 | 3.302 | 2.804 | 1.135 | 1.125 | 99 | 100 | 79 | 11 | 11 | 2.70E-9 | > 1.00E-7 | > 1.00E-7 |
| HL-60(TB) | 0.734 | 3.216 | 3.157 | 3.092 | 0.861 | 0.644 | 0.638 | 98 | 95 | 5 | -12 | -13 | 3.17E-9 | 1.96E-9 | > 1.00E-7 |
| K-562 | 0.259 | 2.492 | 2.431 | 2.417 | 1.353 | 0.477 | 0.484 | 97 | 97 | 49 | 10 | 10 | 9.52E-10 | > 1.00E-7 | > 1.00E-7 |
| MOLT-4 | 0.951 | 3.349 | 3.343 | 3.310 | 3.212 | 1.663 | 1.403 | 100 | 98 | 94 | 30 | 19 | 4.85E-9 | > 1.00E-7 | > 1.00E-7 |
| RPMI-8226 | 0.482 | 1.797 | 1.749 | 1.726 | 1.345 | 0.650 | 0.649 | 96 | 95 | 66 | 13 | 13 | 1.97E-9 | > 1.00E-7 | > 1.00E-7 |
| SR | 0.285 | 0.889 | 0.849 | 0.631 | 0.414 | 0.399 | 0.365 | 93 | 57 | 21 | 19 | 13 | 1.59E-10 | > 1.00E-7 | > 1.00E-7 |

*FIG. 19*

| | | | | | | | | | | |
|---|---|---|---|---|---|---|---|---|---|---|
| Non-Small Cell Lung Cancer | | | | | | | | | | |
| A549/ATCC | 0.397 | 1.901 | 1.827 | 1.811 | 1.737 | 1.114 | 0.681 | 95 | 94 | 89 | 48 | 19 | 8.79E-9 | > 1.00E-7 | > 1.00E-7 |
| EKVX | 0.829 | 2.047 | 1.947 | 1.924 | 1.833 | 1.499 | 1.358 | 92 | 90 | 82 | 55 | 43 | 2.70E-8 | > 1.00E-7 | > 1.00E-7 |
| HOP-62 | 0.551 | 1.603 | 1.580 | 1.589 | 1.228 | 0.871 | 0.694 | 98 | 99 | 64 | 30 | 14 | 2.65E-9 | > 1.00E-7 | > 1.00E-7 |
| HOP-92 | 1.496 | 1.921 | 1.778 | 1.795 | 1.716 | 1.683 | 1.778 | 66 | 70 | 52 | 44 | 66 | | > 1.00E-7 | > 1.00E-7 |
| NCI-H226 | 0.568 | 1.469 | 1.415 | 1.373 | 1.319 | 1.084 | 0.924 | 94 | 89 | 83 | 57 | 39 | 2.56E-8 | > 1.00E-7 | > 1.00E-7 |
| NCI-H23 | 0.617 | 1.864 | 1.834 | 1.756 | 1.560 | 1.042 | 0.866 | 98 | 91 | 76 | 34 | 20 | 4.14E-9 | > 1.00E-7 | > 1.00E-7 |
| NCI-H322M | 0.662 | 2.015 | 1.857 | 1.925 | 1.856 | 1.139 | 1.111 | 88 | 93 | 88 | 35 | 33 | 5.26E-9 | > 1.00E-7 | > 1.00E-7 |
| NCI-H460 | 0.217 | 2.565 | 2.579 | 2.523 | 2.256 | 0.442 | 0.318 | 101 | 98 | 87 | 10 | 4 | 3.00E-9 | > 1.00E-7 | > 1.00E-7 |
| NCI-H522 | 0.922 | 3.062 | 2.999 | 2.720 | 1.321 | 1.038 | 0.893 | 97 | 84 | 19 | 5 | -3 | 3.31E-10 | 4.28E-8 | > 1.00E-7 |
| Colon Cancer | | | | | | | | | | |
| COLO 205 | 0.482 | 1.571 | 1.567 | 1.536 | 1.267 | 0.767 | 0.461 | 100 | 97 | 72 | 26 | -4 | 3.03E-9 | 7.15E-8 | > 1.00E-7 |
| HCC-2998 | 0.664 | 2.373 | 2.313 | 2.251 | 2.011 | 1.074 | 0.905 | 97 | 93 | 79 | 24 | 14 | 3.36E-9 | > 1.00E-7 | > 1.00E-7 |
| HCT-116 | 0.329 | 2.749 | 2.730 | 2.889 | 2.498 | 0.755 | 0.612 | 99 | 106 | 90 | 18 | 12 | 3.55E-9 | > 1.00E-7 | > 1.00E-7 |
| HCT-15 | 0.237 | 1.436 | 1.420 | 1.410 | 1.252 | 0.782 | 0.338 | 99 | 98 | 85 | 45 | 8 | 7.63E-9 | > 1.00E-7 | > 1.00E-7 |
| HT29 | 0.374 | 2.821 | 2.846 | 2.575 | 1.666 | 0.447 | 0.371 | 101 | 90 | 53 | 3 | . | 1.14E-9 | 6.12E-8 | > 1.00E-7 |
| KM12 | 0.429 | 2.684 | 2.638 | 2.548 | 2.213 | 0.874 | 0.719 | 98 | 94 | 79 | 20 | 13 | 3.09E-9 | > 1.00E-7 | > 1.00E-7 |
| SW-620 | 0.230 | 2.019 | 1.966 | 1.942 | 1.246 | 0.550 | 0.516 | 97 | 96 | 57 | 18 | 16 | 1.49E-9 | > 1.00E-7 | > 1.00E-7 |

*FIG. 19 (Cont'd)*

| Cell Line | | | | | | | | | | | | | | | |
|---|---|---|---|---|---|---|---|---|---|---|---|---|---|---|---|
| CNS Cancer | | | | | | | | | | | | | | | |
| SF-268 | 0.431 | 1.710 | 1.665 | 1.578 | 1.282 | 0.807 | 0.685 | 96 | 90 | 67 | 29 | 20 | 2.79E-9 | >1.00E-7 | >1.00E-7 |
| SF-295 | 0.834 | 2.778 | 2.581 | 2.498 | 2.251 | 1.149 | 0.831 | 90 | 86 | 73 | 16 | — | 2.53E-9 | 9.44E-8 | >1.00E-7 |
| SF-539 | 0.954 | 2.713 | 2.623 | 2.546 | 1.889 | 0.973 | 0.778 | 95 | 91 | 53 | 1 | -18 | 1.15E-9 | 1.14E-8 | >1.00E-7 |
| SNB-19 | 0.499 | 1.834 | 1.826 | 1.811 | 1.561 | 0.901 | 0.841 | 99 | 98 | 80 | 30 | 26 | 3.96E-9 | >1.00E-7 | >1.00E-7 |
| SNB-75 | 0.861 | 1.808 | 1.614 | 1.572 | 1.374 | 0.968 | 1.022 | 80 | 75 | 54 | 11 | 17 | 1.25E-9 | >1.00E-7 | >1.00E-7 |
| U251 | 0.301 | 1.427 | 1.385 | 1.381 | 1.309 | 0.600 | 0.600 | 96 | 96 | 90 | 27 | 27 | 4.24E-9 | >1.00E-7 | >1.00E-7 |
| Melanoma | | | | | | | | | | | | | | | |
| LOX IMVI | 0.426 | 2.788 | 2.720 | 2.642 | 1.621 | 1.218 | 0.789 | 97 | 94 | 51 | 34 | 15 | 1.08E-9 | >1.00E-7 | >1.00E-7 |
| MALME-3M | 0.729 | 1.399 | 1.347 | 1.309 | 1.129 | 0.988 | 0.973 | 92 | 87 | 60 | 39 | 36 | 2.88E-9 | >1.00E-7 | >1.00E-7 |
| M14 | 0.602 | 2.727 | 2.738 | 2.667 | 2.365 | 1.544 | 1.094 | 101 | 97 | 83 | 44 | 23 | 7.13E-9 | >1.00E-7 | >1.00E-7 |
| MDA-MB-435 | 0.472 | 2.614 | 2.559 | 2.233 | 0.962 | 0.337 | 0.389 | 97 | 82 | 23 | -29 | -18 | 3.49E-10 | 2.78E-9 | >1.00E-7 |
| SK-MEL-2 | 0.964 | 2.151 | 2.099 | 2.007 | 1.628 | 1.365 | 1.348 | 96 | 88 | 56 | 34 | 32 | 1.85E-9 | >1.00E-7 | >1.00E-7 |
| SK-MEL-28 | 0.780 | 2.282 | 2.274 | 2.221 | 1.932 | 1.680 | 1.556 | 99 | 96 | 77 | 60 | 52 | >1.00E-7 | >1.00E-7 | >1.00E-7 |
| SK-MEL-5 | 0.839 | 2.768 | 2.722 | 2.600 | 1.738 | 1.086 | 0.666 | 98 | 91 | 47 | 13 | -21 | 8.38E-10 | 2.41E-8 | >1.00E-7 |
| UACC-62 | 0.703 | 2.604 | 2.454 | 2.514 | 1.680 | 1.023 | 1.031 | 92 | 95 | 51 | 17 | 17 | 1.10E-9 | >1.00E-7 | >1.00E-7 |
| Ovarian Cancer | | | | | | | | | | | | | | | |
| IGROV1 | 0.829 | 2.295 | 2.189 | 2.211 | 1.637 | 1.442 | 1.246 | 93 | 94 | 55 | 42 | 28 | 2.42E-9 | >1.00E-7 | >1.00E-7 |
| OVCAR-3 | 0.442 | 1.697 | 1.697 | 1.664 | 0.801 | 0.464 | 0.438 | 100 | 97 | 29 | 2 | — | 4.89E-10 | 4.51E-8 | >1.00E-7 |
| OVCAR-4 | 0.661 | 1.508 | 1.489 | 1.444 | 1.433 | 1.327 | 1.185 | 98 | 92 | 91 | 79 | 62 | >1.00E-7 | >1.00E-7 | >1.00E-7 |
| OVCAR-5 | 0.754 | 2.069 | 1.938 | 1.879 | 1.855 | 1.751 | 1.350 | 90 | 86 | 84 | 76 | 45 | 7.02E-8 | >1.00E-7 | >1.00E-7 |
| OVCAR-8 | 0.496 | 2.039 | 2.038 | 2.084 | 1.462 | 0.834 | 0.708 | 100 | 103 | 63 | 22 | 14 | 2.04E-9 | >1.00E-7 | >1.00E-7 |
| NCI/ADR-RES | 0.560 | 1.980 | 1.954 | 1.875 | 1.856 | 1.670 | 1.188 | 98 | 93 | 91 | 78 | 44 | 6.76E-8 | >1.00E-7 | >1.00E-7 |
| SK-OV-3 | 0.802 | 1.481 | 1.441 | 1.429 | 1.391 | 1.143 | 0.970 | 94 | 92 | 87 | 50 | 25 | 1.02E-8 | >1.00E-7 | >1.00E-7 |

*FIG. 19 (Cont'd)*

| | | | | | | | | | | |
|---|---|---|---|---|---|---|---|---|---|---|
| Renal Cancer | | | | | | | | | | |
| 786-0 | 0.605 | 2.502 | 2.426 | 2.408 | 1.939 | 1.244 | 1.041 | 96 | 95 | 70 | 34 | 23 | 3.58E-9 | | |
| A498 | 1.169 | 1.994 | 1.981 | 1.927 | 1.774 | 1.628 | 1.304 | 98 | 92 | 73 | 56 | 16 | 1.39E-8 | > 1.00E-7 | > 1.00E-7 |
| ACHN | 0.483 | 2.082 | 2.097 | 2.036 | 1.854 | 1.349 | 1.109 | 101 | 97 | 86 | 54 | 39 | 1.89E-8 | > 1.00E-7 | > 1.00E-7 |
| CAKI-1 | 0.592 | 2.359 | 2.203 | 2.150 | 2.007 | 1.539 | 1.227 | 91 | 88 | 80 | 54 | 36 | 1.60E-8 | > 1.00E-7 | > 1.00E-7 |
| RXF 393 | 0.963 | 1.673 | 1.608 | 1.577 | 1.285 | 0.944 | 0.904 | 91 | 86 | 45 | -2 | -6 | 7.68E-10 | 9.06E-9 | > 1.00E-7 |
| SN12C | 0.648 | 2.307 | 2.271 | 2.305 | 1.571 | 1.258 | 1.076 | 98 | 100 | 56 | 37 | 26 | 1.99E-9 | > 1.00E-7 | > 1.00E-7 |
| TK-10 | 0.762 | 1.941 | 1.827 | 1.799 | 1.564 | 1.226 | 1.183 | 90 | 88 | 68 | 39 | 36 | 4.24E-9 | > 1.00E-7 | > 1.00E-7 |
| UO-31 | 0.811 | 2.312 | 1.996 | 2.098 | 2.075 | 1.707 | 1.445 | 79 | 86 | 84 | 60 | 42 | 3.58E-8 | > 1.00E-7 | > 1.00E-7 |
| Prostate Cancer | | | | | | | | | | |
| PC-3 | 0.649 | 2.486 | 2.375 | 2.362 | 1.926 | 1.072 | 0.929 | 94 | 93 | 69 | 23 | 15 | 2.63E-9 | > 1.00E-7 | |
| DU-145 | 0.284 | 1.435 | 1.478 | 1.428 | 0.885 | 0.427 | 0.380 | 104 | 99 | 52 | 12 | 8 | 1.13E-9 | > 1.00E-7 | |
| Breast Cancer | | | | | | | | | | |
| MCF7 | 0.405 | 2.271 | 2.140 | 2.094 | 1.081 | 0.602 | 0.601 | 93 | 91 | 36 | 11 | 10 | 5.57E-10 | > 1.00E-7 | > 1.00E-7 |
| MDA-MB-231/ATCC | 0.619 | 1.833 | 1.832 | 1.790 | 1.483 | 1.077 | 0.747 | 100 | 96 | 71 | 38 | 11 | 4.29E-9 | > 1.00E-7 | > 1.00E-7 |
| HS 578T | 1.054 | 2.178 | 2.100 | 2.086 | 1.551 | 1.171 | 1.165 | 93 | 92 | 44 | 10 | 10 | 7.54E-10 | > 1.00E-7 | > 1.00E-7 |
| BT-549 | 1.183 | 2.418 | 2.409 | 2.356 | 1.967 | 1.657 | 1.135 | 99 | 95 | 64 | 38 | -4 | 3.44E-9 | 8.01E-8 | > 1.00E-7 |
| T-47D | 0.750 | 1.486 | 1.428 | 1.463 | 1.207 | 1.005 | 1.111 | 92 | 97 | 62 | 35 | 49 | 2.75E-9 | > 1.00E-7 | > 1.00E-7 |
| MDA-MB-468 | 0.794 | 1.609 | 1.529 | 1.473 | 1.043 | 0.749 | 0.738 | 90 | 83 | 31 | -6 | -7 | 4.28E-10 | 6.95E-9 | > 1.00E-7 |

*FIG. 19 (Cont'd)*

National Cancer Institute Developmental Therapeutics Program
In-Vitro Testing Results

| NSC: D-784812/1 | | | | | Experiment ID: 1509RS64 | | | | | Test Type: 08 | | Units: Molar |
|---|---|---|---|---|---|---|---|---|---|---|---|---|
| Report Date: November 04, 2015 | | | | | Test Date: September 21, 2015 | | | | | QNS: | | MC: |
| COMI: KCN-Tb13 | | | | | Stain Reagent: SRB Dual-Pass Related | | | | | SSPL: OZAS | | |

| | Time | | | Mean Optical Densities | | | | | Percent Growth | | | | | | |
| | Zero | Ctrl | -8.5 | -7.5 | -6.5 | -5.5 | -4.5 | -8.5 | -7.5 | -6.5 | -5.5 | -4.5 | GI50 | TGI | LC50 |
|---|---|---|---|---|---|---|---|---|---|---|---|---|---|---|---|
| Panel/Cell Line | | | | | | | | | | | | | | | |
| Leukemia | | | | | | | | | | | | | | | |
| CCRF-CEM | 0.527 | 3.022 | 3.091 | 3.081 | 1.396 | 0.820 | 0.673 | 103 | 102 | 35 | 12 | 6 | 1.98E-7 | > 3.32E-5 | > 3.32E-5 |
| HL-60(TB) | 0.819 | 3.259 | 3.264 | 3.246 | 0.771 | 0.669 | 0.625 | 100 | 99 | -6 | -18 | -24 | 9.79E-8 | 2.92E-7 | > 3.32E-5 |
| K-562 | 0.252 | 2.261 | 2.308 | 2.064 | 0.802 | 0.488 | 0.473 | 102 | 90 | 27 | 12 | 11 | 1.45E-7 | > 3.32E-5 | > 3.32E-5 |
| MOLT-4 | 0.566 | 2.588 | 2.738 | 2.641 | 1.380 | 0.904 | 0.822 | 107 | 103 | 40 | 17 | 13 | 2.32E-7 | > 3.32E-5 | > 3.32E-5 |
| RPMI-8226 | 0.481 | 1.476 | 1.533 | 1.464 | 0.490 | 0.486 | 0.450 | 106 | 99 | 1 | 1 | -6 | 1.05E-6 | 3.92E-6 | > 3.32E-5 |
| SR | 0.310 | 1.375 | 1.215 | 0.613 | 0.508 | 0.451 | 0.365 | 85 | 28 | 19 | 13 | 5 | 1.38E-8 | > 3.32E-5 | > 3.32E-5 |

Log10 Concentration

FIG. 20

| | | | | | | | | | | |
|---|---|---|---|---|---|---|---|---|---|---|
| Non-Small Cell Lung Cancer | | | | | | | | | | |
| A549/ATCC | 0.477 | 1.889 | 1.871 | 1.860 | 1.692 | 1.116 | 0.844 | 99 | 98 | 86 | 45 | 26 | 2.54E-6 | > 3.32E-5 | > 3.32E-5 |
| EKVX | 0.844 | 2.586 | 2.502 | 2.510 | 2.174 | 1.706 | 1.538 | 95 | 96 | 76 | 49 | 40 | 3.18E-6 | > 3.32E-5 | > 3.32E-5 |
| HOP-62 | 0.653 | 1.863 | 1.913 | 1.889 | 1.357 | 0.951 | 0.774 | 104 | 102 | 58 | 25 | 10 | 5.81E-7 | > 3.32E-5 | > 3.32E-5 |
| HOP-92 | 0.966 | 1.449 | 1.395 | 1.422 | 1.294 | 1.297 | 1.266 | 89 | 94 | 68 | 69 | 62 | > 3.32E-5 | > 3.32E-5 | > 3.32E-5 |
| NCI-H226 | 0.825 | 2.160 | 2.094 | 2.179 | 2.006 | 1.763 | 1.502 | 95 | 101 | 88 | 70 | 51 | > 3.32E-5 | > 3.32E-5 | > 3.32E-5 |
| NCI-H23 | 0.803 | 2.330 | 2.250 | 2.158 | 1.863 | 1.448 | 1.244 | 95 | 89 | 69 | 42 | 29 | 1.72E-6 | > 3.32E-5 | > 3.32E-5 |
| NCI-H322M | 0.830 | 2.432 | 2.262 | 2.255 | 2.100 | 1.322 | 1.370 | 89 | 89 | 79 | 31 | 34 | 1.33E-6 | > 3.32E-5 | > 3.32E-5 |
| NCI-H460 | 0.320 | 2.808 | 2.911 | 2.963 | 2.278 | 0.574 | 0.436 | 104 | 106 | 79 | 10 | 5 | 8.71E-7 | > 3.32E-5 | > 3.32E-5 |
| NCI-H522 | 1.026 | 2.347 | 2.273 | 2.001 | 1.502 | 1.200 | 1.061 | 94 | 74 | 36 | 13 | 3 | 1.42E-7 | > 3.32E-5 | > 3.32E-5 |
| Colon Cancer | | | | | | | | | | |
| COLO 205 | 0.545 | 1.915 | 2.009 | 1.956 | 1.075 | 0.613 | 0.211 | 107 | 103 | 39 | 5 | -61 | 2.21E-7 | > 3.32E-5 | 2.24E-5 |
| HCC-2998 | 0.663 | 2.546 | 2.443 | 2.472 | 1.863 | 1.125 | 0.840 | 95 | 96 | 64 | 25 | 9 | 7.43E-7 | > 3.32E-5 | > 3.32E-5 |
| HCT-116 | 0.252 | 1.974 | 2.027 | 2.046 | 0.854 | 0.427 | 0.323 | 103 | 104 | 35 | 10 | 4 | 2.01E-7 | > 3.32E-5 | > 3.32E-5 |
| HCT-15 | 0.325 | 2.148 | 2.135 | 2.107 | 1.721 | 0.679 | 0.480 | 99 | 98 | 77 | 19 | 8 | 9.68E-7 | > 3.32E-5 | > 3.32E-5 |
| HT29 | 0.183 | 1.063 | 1.118 | 1.046 | 0.298 | 0.204 | 0.189 | 106 | 98 | 13 | 2 | 1 | 1.22E-7 | > 3.32E-5 | > 3.32E-5 |
| KM12 | 0.556 | 2.765 | 2.695 | 2.667 | 1.784 | 1.022 | 0.705 | 97 | 96 | 56 | 21 | 7 | 4.82E-7 | > 3.32E-5 | > 3.32E-5 |
| SW-620 | 0.347 | 2.361 | 2.379 | 2.312 | 1.225 | 0.819 | 0.772 | 101 | 98 | 44 | 23 | 21 | 2.52E-7 | > 3.32E-5 | > 3.32E-5 |

*FIG. 20 (Cont'd)*

| Cell Line | | | | | | | | | | | | | | |
|---|---|---|---|---|---|---|---|---|---|---|---|---|---|---|
| CNS Cancer | | | | | | | | | | | | | | |
| SF-268 | 0.549 | 2.020 | 1.991 | 1.916 | 1.337 | 1.028 | 0.833 | 98 | 93 | 54 | 33 | 19 | 4.89E-7 | > 3.32E-5 | > 3.32E-5 |
| SF-295 | 0.546 | 1.878 | 1.785 | 1.846 | 1.301 | 0.753 | 0.633 | 93 | 98 | 57 | 16 | 7 | 4.81E-7 | > 3.32E-5 | > 3.32E-5 |
| SF-539 | 1.222 | 3.055 | 3.009 | 2.942 | 2.191 | 1.257 | 1.155 | 97 | 94 | 53 | 2 | -5 | 3.78E-7 | 5.98E-6 | > 3.32E-5 |
| SNB-19 | 0.766 | 2.309 | 2.299 | 2.318 | 2.136 | 1.348 | 1.370 | 99 | 101 | 89 | 38 | 39 | 1.91E-6 | > 3.32E-5 | > 3.32E-5 |
| SNB-75 | 0.969 | 1.809 | 1.637 | 1.607 | 1.209 | 1.149 | 1.282 | 79 | 76 | 29 | 21 | 37 | 1.17E-7 | > 3.32E-5 | > 3.32E-5 |
| U251 | 0.376 | 1.551 | 1.545 | 1.550 | 1.211 | 0.653 | 0.575 | 100 | 100 | 71 | 24 | 17 | 9.23E-7 | > 3.32E-5 | > 3.32E-5 |
| Melanoma | | | | | | | | | | | | | | | |
| LOX IMVI | 0.518 | 3.269 | 3.199 | 3.132 | 2.054 | 1.368 | 1.060 | 97 | 95 | 56 | 31 | 20 | 5.69E-7 | > 3.32E-5 | > 3.32E-5 |
| MALME-3M | 0.915 | 1.722 | 1.667 | 1.551 | 1.296 | 1.182 | 1.203 | 93 | 79 | 47 | 33 | 36 | 2.70E-7 | > 3.32E-5 | > 3.32E-5 |
| M14 | 0.490 | 1.774 | 1.756 | 1.623 | 0.935 | 0.511 | 0.519 | 99 | 88 | 35 | 2 | 2 | 1.72E-7 | > 3.32E-5 | > 3.32E-5 |
| MDA-MB-435 | 0.476 | 2.647 | 2.545 | 1.679 | 0.430 | 0.244 | 0.204 | 95 | 55 | -10 | -49 | -57 | 4.02E-8 | 2.35E-7 | 4.57E-6 |
| SK-MEL-2 | 0.956 | 1.887 | 1.926 | 1.864 | 1.589 | 1.257 | 1.275 | 104 | 98 | 68 | 32 | 34 | 1.06E-6 | > 3.32E-5 | > 3.32E-5 |
| SK-MEL-28 | 0.749 | 1.883 | 1.895 | 1.741 | 1.450 | 1.286 | 1.304 | 101 | 87 | 62 | 47 | 49 | 2.17E-6 | > 3.32E-5 | > 3.32E-5 |
| SK-MEL-5 | 0.934 | 3.317 | 3.298 | 3.254 | 2.336 | 1.263 | 0.675 | 99 | 97 | 59 | 14 | -28 | 5.22E-7 | 7.13E-6 | > 3.32E-5 |
| UACC-62 | 0.879 | 2.981 | 2.870 | 2.762 | 1.795 | 1.366 | 1.383 | 95 | 90 | 44 | 23 | 24 | 2.40E-7 | > 3.32E-5 | > 3.32E-5 |
| Ovarian Cancer | | | | | | | | | | | | | | | |
| IGROV1 | 0.758 | 2.295 | 2.296 | 2.038 | 1.589 | 1.315 | 0.996 | 100 | 83 | 54 | 36 | 15 | 5.59E-7 | > 3.32E-5 | > 3.32E-5 |
| OVCAR-3 | 0.467 | 1.640 | 1.677 | 1.612 | 0.543 | 0.449 | 0.376 | 103 | 98 | 6 | -4 | -19 | 1.11E-7 | 1.41E-6 | > 3.32E-5 |
| OVCAR-4 | 0.689 | 1.532 | 1.545 | 1.474 | 1.382 | 1.093 | 0.942 | 102 | 93 | 82 | 48 | 30 | 2.88E-6 | > 3.32E-5 | > 3.32E-5 |
| OVCAR-5 | 0.656 | 1.952 | 1.910 | 1.880 | 1.786 | 1.300 | 1.013 | 97 | 94 | 87 | 50 | 28 | 3.25E-6 | > 3.32E-5 | > 3.32E-5 |
| OVCAR-8 | 0.453 | 1.811 | 1.851 | 1.833 | 1.252 | 0.772 | 0.652 | 103 | 102 | 59 | 23 | 15 | 5.90E-7 | > 3.32E-5 | > 3.32E-5 |
| NCI/ADR-RES | 0.575 | 2.016 | 2.010 | 1.939 | 1.860 | 1.733 | 1.072 | 100 | 95 | 89 | 80 | 34 | 1.52E-5 | > 3.32E-5 | > 3.32E-5 |
| SK-OV-3 | 0.872 | 1.608 | 1.648 | 1.668 | 1.503 | 1.289 | 1.174 | 105 | 108 | 86 | 57 | 41 | 8.86E-6 | > 3.32E-5 | > 3.32E-5 |

| | | | | | | | | | | |
|---|---|---|---|---|---|---|---|---|---|---|
| Renal Cancer | | | | | | | | | | |
| 786-0 | 0.474 | 1.887 | 1.924 | 1.713 | 0.955 | 0.782 | 0.556 | 103 | 88 | 34 | 22 | 6 | 1.67E-7 | > 3.32E-5 | > 3.32E-5 |
| A498 | 1.487 | 2.329 | 2.281 | 2.240 | 2.089 | 1.708 | 1.397 | 94 | 89 | 72 | 26 | -6 | 9.93E-7 | 2.15E-5 | > 3.32E-5 |
| ACHN | 0.442 | 1.787 | 1.793 | 1.834 | 1.420 | 1.038 | 0.654 | 100 | 104 | 73 | 44 | 16 | 2.10E-6 | > 3.32E-5 | > 3.32E-5 |
| CAKI-1 | 0.620 | 2.637 | 2.400 | 2.365 | 2.320 | 1.685 | 1.190 | 88 | 87 | 84 | 53 | 28 | 4.31E-6 | > 3.32E-5 | > 3.32E-5 |
| RXF 393 | 0.948 | 1.650 | 1.575 | 1.577 | 1.295 | 0.970 | 1.087 | 89 | 90 | 49 | 3 | 20 | 3.21E-7 | > 3.32E-5 | > 3.32E-5 |
| SN12C | 0.609 | 2.259 | 2.280 | 2.134 | 1.422 | 1.157 | 0.621 | 101 | 92 | 49 | 33 | 1 | 3.20E-7 | > 3.32E-5 | > 3.32E-5 |
| TK-10 | 0.895 | 1.759 | 1.708 | 1.623 | 1.518 | 1.430 | 1.293 | 94 | 84 | 72 | 62 | 46 | 1.87E-5 | > 3.32E-5 | > 3.32E-5 |
| UO-31 | 1.010 | 2.446 | 2.235 | 2.206 | 2.173 | 1.725 | 1.567 | 85 | 83 | 81 | 50 | 39 | 3.27E-6 | > 3.32E-5 | > 3.32E-5 |
| Prostate Cancer | | | | | | | | | | |
| PC-3 | 0.508 | 2.291 | 2.254 | 2.208 | 1.517 | 0.856 | 0.764 | 98 | 95 | 57 | 20 | 14 | 4.99E-7 | > 3.32E-5 | > 3.32E-5 |
| DU-145 | 0.442 | 1.980 | 2.028 | 1.955 | 0.896 | 0.498 | 0.554 | 103 | 98 | 29 | 4 | 7 | 1.67E-7 | > 3.32E-5 | > 3.32E-5 |
| Breast Cancer | | | | | | | | | | |
| MCF7 | 0.468 | 2.851 | 2.749 | 2.718 | 0.991 | 0.940 | 0.804 | 96 | 94 | 22 | 20 | 14 | 1.36E-7 | > 3.32E-5 | > 3.32E-5 |
| MDA-MB-231/ATCC | 0.775 | 2.012 | 2.040 | 2.016 | 1.540 | 0.966 | 0.643 | 102 | 100 | 62 | 15 | -17 | 5.96E-7 | 9.92E-6 | > 3.32E-5 |
| HS 578T | 1.129 | 2.129 | 2.062 | 2.029 | 1.410 | 1.291 | 1.215 | 93 | 90 | 28 | 16 | 9 | 1.47E-7 | > 3.32E-5 | > 3.32E-5 |
| BT-549 | 0.793 | 1.758 | 1.752 | 1.693 | 1.202 | 0.920 | 0.713 | 99 | 93 | 42 | 13 | -10 | 2.35E-7 | 1.22E-5 | > 3.32E-5 |
| T-47D | 0.687 | 1.478 | 1.466 | 1.473 | 1.121 | 1.165 | 1.297 | 98 | 99 | 55 | 60 | 77 | > 3.32E-5 | > 3.32E-5 | > 3.32E-5 |
| MDA-MB-468 | 0.914 | 2.140 | 2.055 | 1.969 | 1.372 | 1.055 | 1.021 | 93 | 86 | 37 | 11 | 9 | 1.83E-7 | > 3.32E-5 | > 3.32E-5 |

National Cancer Institute Developmental Therapeutics Program
In-Vitro Testing Results

| NSC: D-784017/1 | | | | | | Experiment ID: 15009RS55 | | | | | Test Type: 08 | | Units: Molar |
|---|---|---|---|---|---|---|---|---|---|---|---|---|---|
| Report Date: November 04, 2015 | | | | | | Test Date: September 08, 2015 | | | | | QNS: | | MC: |
| COMI: KCN-Tb14 | | | | | | Stain Reagent: SRB Dual-Pass Related | | | | | SSPL: OZAS | | |

| | Time | | Mean Optical Densities | | | | | Percent Growth | | | | | | |
|---|---|---|---|---|---|---|---|---|---|---|---|---|---|---|
| | | | | | Log10 Concentration | | | | | | | | | |
| Panel/Cell Line | Zero | Ctrl | -11.0 | -10.0 | -9.0 | -8.0 | -7.0 | -11.0 | -10.0 | -9.0 | -8.0 | -7.0 | GI50 | TGI | LC50 |
| Leukemia | | | | | | | | | | | | | | | |
| CCRF-CEM | 0.854 | 3.357 | 3.333 | 3.172 | 1.407 | 1.053 | 1.016 | 99 | 93 | 22 | 8 | 6 | 4.02E-10 | >1.00E-7 | >1.00E-7 |
| HL-60(TB) | 0.734 | 3.125 | 3.048 | 2.487 | 0.635 | 0.590 | 0.610 | 97 | 73 | -14 | -20 | -17 | 1.86E-10 | 6.98E-10 | >1.00E-7 |
| K-562 | 0.259 | 2.591 | 2.611 | 2.023 | 0.540 | 0.471 | 0.446 | 101 | 76 | 12 | 9 | 8 | 2.53E-10 | >1.00E-7 | >1.00E-7 |
| MOLT-4 | 0.951 | 3.347 | 3.367 | 3.333 | 1.928 | 1.358 | 1.332 | 101 | 99 | 41 | 17 | 16 | 6.96E-10 | >1.00E-7 | >1.00E-7 |
| RPMI-8226 | 0.482 | 1.800 | 1.808 | 1.671 | 0.644 | 0.570 | 0.646 | 101 | 90 | 12 | 7 | 12 | 3.28E-10 | >1.00E-7 | >1.00E-7 |
| SR | 0.285 | 0.815 | 0.815 | 0.489 | 0.352 | 0.348 | 0.324 | 100 | 38 | 13 | 12 | 7 | 6.49E-11 | >1.00E-7 | >1.00E-7 |

*FIG. 21*

| | | | | | | | | | | | |
|---|---|---|---|---|---|---|---|---|---|---|---|
| Non-Small Cell Lung Cancer | | | | | | | | | | | |
| A549/ATCC | 0.397 | 1.882 | 1.829 | 1.861 | 1.519 | 0.862 | 0.575 | 96 | 99 | 76 | 31 | 12 | 3.78E-9 | > 1.00E-7 |
| EKVX | 0.829 | 2.118 | 2.056 | 2.073 | 1.797 | 1.539 | 1.443 | 95 | 96 | 75 | 55 | 48 | 4.75E-8 | > 1.00E-7 |
| HOP-62 | 0.551 | 1.593 | 1.595 | 1.508 | 0.911 | 0.678 | 0.546 | 100 | 92 | 35 | 12 | - | 5.38E-10 | 8.40E-8 |
| HOP-92 | 1.496 | 1.907 | 1.841 | 1.831 | 1.682 | 1.623 | 1.574 | 84 | 81 | 45 | 31 | 19 | 7.34E-10 | > 1.00E-7 |
| NCI-H226 | 0.568 | 1.493 | 1.462 | 1.451 | 1.326 | 1.031 | 0.930 | 97 | 95 | 82 | 50 | 39 | 1.00E-8 | > 1.00E-7 |
| NCI-H23 | 0.617 | 1.844 | 1.828 | 1.822 | 1.463 | 1.135 | 1.014 | 99 | 98 | 69 | 42 | 32 | 5.11E-9 | > 1.00E-7 |
| NCI-H322M | 0.662 | 2.059 | 2.018 | 2.004 | 1.781 | 1.160 | 1.081 | 97 | 96 | 80 | 36 | 30 | 4.76E-9 | > 1.00E-7 |
| NCI-H460 | 0.217 | 2.537 | 2.658 | 2.644 | 1.146 | 0.384 | 0.299 | 105 | 105 | 40 | 7 | 4 | 7.01E-10 | > 1.00E-7 |
| NCI-H522 | 0.922 | 2.900 | 2.580 | 2.164 | 0.895 | 0.821 | 0.756 | 84 | 63 | -3 | -11 | -18 | 1.56E-10 | 9.01E-10 |
| Colon Cancer | | | | | | | | | | | |
| COLO 205 | 0.482 | 1.553 | 1.554 | 1.471 | 1.088 | 0.700 | 0.374 | 100 | 92 | 57 | 20 | -22 | 1.52E-9 | 2.99E-8 |
| HCC-2998 | 0.664 | 2.231 | 2.174 | 2.270 | 1.844 | 1.011 | 0.924 | 96 | 102 | 75 | 22 | 17 | 2.99E-9 | > 1.00E-7 |
| HCT-116 | 0.329 | 2.870 | 2.681 | 2.897 | 1.522 | 0.673 | 0.455 | 93 | 101 | 47 | 14 | 5 | 8.78E-10 | > 1.00E-7 |
| HCT-15 | 0.237 | 1.513 | 1.486 | 1.458 | 1.178 | 0.599 | 0.346 | 98 | 96 | 74 | 28 | 9 | 3.33E-9 | > 1.00E-7 |
| HT29 | 0.374 | 2.594 | 2.650 | 2.344 | 0.994 | 0.376 | 0.345 | 103 | 89 | 28 | - | -8 | 4.33E-8 | 1.03E-8 |
| KM12 | 0.429 | 2.740 | 2.650 | 2.647 | 2.319 | 0.860 | 0.664 | 96 | 96 | 82 | 19 | 10 | 3.19E-9 | > 1.00E-7 |
| SW-620 | 0.230 | 2.028 | 2.001 | 1.755 | 0.757 | 0.573 | 0.572 | 99 | 85 | 29 | 19 | 19 | 4.24E-10 | > 1.00E-7 |

*FIG. 21 (Cont'd)*

| | | | | | | | | | | |
|---|---|---|---|---|---|---|---|---|---|---|
| CNS Cancer | | | | | | | | | | |
| SF-268 | 0.431 | 1.679 | 1.662 | 1.630 | 1.038 | 0.630 | 99 | 96 | 49 | 28 | 16 | 9.37E-10 | > 1.00E-7 | > 1.00E-7 |
| SF-295 | 0.834 | 2.680 | 2.653 | 2.643 | 1.850 | 0.801 | 99 | 98 | 55 | 8 | -4 | 1.28E-9 | 4.61E-8 | > 1.00E-7 |
| SF-539 | 0.954 | 2.640 | 2.661 | 2.632 | 1.508 | 0.702 | 101 | 100 | 33 | -4 | -26 | 5.53E-10 | 7.79E-9 | > 1.00E-7 |
| SNB-19 | 0.499 | 1.862 | 1.813 | 1.780 | 1.187 | 0.788 | 96 | 94 | 50 | 29 | 21 | 1.05E-9 | > 1.00E-7 | > 1.00E-7 |
| SNB-75 | 0.861 | 1.673 | 1.572 | 1.550 | 1.064 | 0.978 | 88 | 85 | 25 | 7 | 14 | 3.82E-10 | > 1.00E-7 | > 1.00E-7 |
| U251 | 0.301 | 1.443 | 1.399 | 1.374 | 0.828 | 0.494 | 96 | 94 | 46 | 22 | 17 | 8.31E-10 | > 1.00E-7 | > 1.00E-7 |
| Melanoma | | | | | | | | | | |
| LOX IMVI | 0.426 | 2.776 | 2.680 | 2.504 | 1.272 | 0.796 | 96 | 88 | 36 | 30 | 16 | 5.40E-10 | > 1.00E-7 | > 1.00E-7 |
| MALME-3M | 0.729 | 1.470 | 1.415 | 1.301 | 1.186 | 1.011 | 93 | 77 | 62 | 48 | 38 | 7.57E-9 | > 1.00E-7 | > 1.00E-7 |
| M14 | 0.602 | 2.740 | 2.697 | 2.604 | 2.136 | 1.093 | 98 | 94 | 72 | 42 | 23 | 5.54E-9 | > 1.00E-7 | > 1.00E-7 |
| MDA-MB-435 | 0.472 | 2.533 | 2.411 | 1.664 | 0.485 | 0.283 | 94 | 58 | 1 | -41 | -40 | 1.37E-10 | 1.04E-9 | > 1.00E-7 |
| SK-MEL-2 | 0.964 | 2.168 | 2.178 | 2.052 | 1.568 | 1.228 | 101 | 90 | 50 | 29 | 22 | 1.02E-9 | > 1.00E-7 | > 1.00E-7 |
| SK-MEL-28 | 0.780 | 2.331 | 2.263 | 2.151 | 1.318 | 1.508 | 96 | 88 | 66 | 54 | 47 | 3.56E-8 | > 1.00E-7 | > 1.00E-7 |
| SK-MEL-5 | 0.839 | 2.770 | 2.729 | 2.418 | 1.614 | 0.728 | 98 | 82 | 45 | 12 | -13 | 7.48E-10 | 2.99E-8 | > 1.00E-7 |
| UACC-62 | 0.703 | 2.621 | 2.398 | 2.257 | 1.716 | 1.071 | 88 | 81 | 42 | 20 | 13 | 6.14E-10 | > 1.00E-7 | > 1.00E-7 |
| Ovarian Cancer | | | | | | | | | | |
| IGROV1 | 0.829 | 2.341 | 2.362 | 2.077 | 1.502 | 0.953 | 101 | 83 | 51 | 40 | 26 | 1.32E-9 | > 1.00E-7 | > 1.00E-7 |
| OVCAR-3 | 0.442 | 1.670 | 1.631 | 1.364 | 1.095 | 1.230 | 97 | 75 | 14 | 3 | -13 | 2.56E-10 | 1.58E-8 | > 1.00E-7 |
| OVCAR-4 | 0.661 | 1.452 | 1.425 | 1.382 | 0.611 | 0.387 | 96 | 91 | 85 | 62 | 43 | 4.24E-8 | > 1.00E-7 | > 1.00E-7 |
| OVCAR-5 | 0.754 | 2.078 | 2.043 | 2.079 | 1.337 | 1.000 | 97 | 100 | 87 | 64 | 36 | 3.15E-8 | > 1.00E-7 | > 1.00E-7 |
| OVCAR-8 | 0.496 | 2.066 | 2.007 | 1.911 | 1.152 | 1.228 | 96 | 93 | 35 | 11 | 9 | 5.60E-10 | > 1.00E-7 | > 1.00E-7 |
| NCI/ADR-RES | 0.560 | 1.962 | 1.981 | 1.053 | 1.603 | 0.630 | 101 | 99 | 90 | 78 | 39 | 5.22E-8 | > 1.00E-7 | > 1.00E-7 |
| SK-OV-3 | 0.802 | 1.481 | 1.491 | 1.457 | 1.254 | 0.863 | 101 | 96 | 66 | 18 | 9 | 2.20E-9 | > 1.00E-7 | > 1.00E-7 |

*FIG. 21 (Cont'd)*

| | | | | | | | | | | | |
|---|---|---|---|---|---|---|---|---|---|---|---|
| Renal Cancer | | | | | | | | | | | |
| 786-0 | 0.605 | 2.420 | 2.342 | 2.328 | 1.317 | 1.008 | 0.889 | 96 | 95 | 39 | 22 | 16 | 6.40E-10 | > 1.00E-7 |
| A498 | 1.169 | 2.008 | 1.924 | 1.849 | 1.972 | 1.526 | 1.344 | 90 | 81 | 96 | 43 | 21 | 7.23E-9 | > 1.00E-7 |
| ACHN | 0.483 | 2.028 | 2.053 | 2.016 | 1.710 | 1.209 | 1.024 | 102 | 99 | 79 | 47 | 35 | 8.06E-9 | > 1.00E-7 |
| CAKI-1 | 0.592 | 2.262 | 2.114 | 2.105 | 1.704 | 1.300 | 1.080 | 91 | 91 | 67 | 42 | 29 | 4.85E-9 | > 1.00E-7 |
| RXF 393 | 0.963 | 1.664 | 1.628 | 1.557 | 1.124 | 0.932 | 0.981 | 95 | 85 | 23 | -3 | 3 | 3.64E-10 |  |
| SN12C | 0.648 | 2.323 | 2.200 | 2.111 | 1.345 | 1.203 | 1.000 | 93 | 87 | 42 | 33 | 21 | 6.54E-10 | > 1.00E-7 |
| TK-10 | 0.762 | 1.928 | 1.885 | 1.897 | 1.621 | 1.359 | 1.338 | 96 | 97 | 74 | 51 | 49 | 4.58E-8 | > 1.00E-7 |
| UO-31 | 0.811 | 2.274 | 2.050 | 2.053 | 2.067 | 1.551 | 1.351 | 85 | 85 | 86 | 51 | 37 | 1.09E-8 | > 1.00E-7 |
| Prostate Cancer | | | | | | | | | | | |
| PC-3 | 0.649 | 2.564 | 2.514 | 2.451 | 1.687 | 0.960 | 0.915 | 97 | 94 | 54 | 16 | 14 | 1.29E-9 | > 1.00E-7 |
| DU-145 | 0.284 | 1.424 | 1.505 | 1.493 | 0.514 | 0.406 | 0.314 | 107 | 106 | 20 | 11 | 3 | 4.49E-10 | > 1.00E-7 |
| Breast Cancer | | | | | | | | | | | |
| MCF7 | 0.405 | 2.339 | 2.237 | 1.892 | 0.675 | 0.640 | 0.587 | 95 | 77 | 14 | 12 | 9 | 2.67E-10 | > 1.00E-7 |
| MDA-MB-231/ATCC | 0.619 | 1.784 | 1.725 | 1.684 | 1.287 | 0.887 | 0.649 | 95 | 91 | 57 | 23 | 3 | 1.63E-9 | > 1.00E-7 |
| HS 578T | 1.054 | 2.152 | 2.146 | 2.005 | 1.322 | 1.203 | 1.211 | 99 | 87 | 24 | 14 | 14 | 3.88E-10 | > 1.00E-7 |
| BT-549 | 1.183 | 2.256 | 2.295 | 2.191 | 1.499 | 1.413 | 0.810 | 104 | 94 | 29 | 21 | -32 | 4.80E-10 | 2.53E-8 |
| T-47D | 0.750 | 1.559 | 1.499 | 1.516 | 0.999 | 1.024 | 1.063 | 92 | 95 | 31 | 34 | 39 | 4.99E-10 | > 1.00E-7 |
| MDA-MB-468 | 0.794 | 1.649 | 1.639 | 1.436 | 0.976 | 0.870 | 0.782 | 99 | 75 | 21 | 9 | -2 | 2.92E-10 | 7.14E-8 |

*FIG. 21 (Cont'd)*

National Cancer Institute Developmental Therapeutics Program
In-Vitro Testing Results

| NSC : D - 784814 / 1 | | | | | | | | Experiment ID : 1509RS64 | | | | Test Type : 08 | | Units : Molar |
|---|---|---|---|---|---|---|---|---|---|---|---|---|---|---|
| Report Date : November 04, 2015 | | | | | | | | Test Date : September 21, 2015 | | | | QNS : | | MC : |
| COMI : KCN-Tb16 | | | | | | | | Stain Reagent : SRB Dual-Pass Related | | | | SSPL : 0ZAS | | |

| | Time | | | | | | | | | | | | | | |
|---|---|---|---|---|---|---|---|---|---|---|---|---|---|---|---|
| | Zero | Ctrl | -8.6 | -7.6 | -6.6 | -5.6 | -4.6 | -8.6 | -7.6 | -6.6 | -5.6 | -4.6 | GI50 | TGI | LC50 |
| | | | Mean Optical Densities | | | | | Percent Growth | | | | | | | |
| | | | | | Log10 Concentration | | | | | | | | | | |
| Panel/Cell Line | | | | | | | | | | | | | | | |
| Leukemia | | | | | | | | | | | | | | | |
| CCRF-CEM | 0.527 | 3.127 | 3.126 | 3.070 | 1.284 | 0.892 | 0.766 | 100 | 98 | 29 | 14 | 9 | 1.24E-7 | > 2.50E-5 | > 2.50E-5 |
| HL-60(TB) | 0.819 | 3.297 | 3.322 | 3.156 | 0.826 | 0.717 | 0.704 | 101 | 94 | | -13 | -14 | 7.40E-8 | 2.63E-7 | > 2.50E-5 |
| K-562 | 0.252 | 2.472 | 2.478 | 2.024 | 0.848 | 0.541 | 0.533 | 100 | 80 | 27 | 13 | 13 | 9.14E-8 | > 2.50E-5 | > 2.50E-5 |
| MOLT-4 | 0.566 | 2.848 | 2.876 | 2.571 | 1.384 | 0.976 | 0.913 | 101 | 88 | 36 | 18 | 15 | 1.34E-7 | > 2.50E-5 | > 2.50E-5 |
| RPMI-8226 | 0.481 | 1.687 | 1.655 | 1.650 | 0.566 | 0.552 | 0.578 | 97 | 97 | 7 | 6 | 8 | 8.31E-8 | > 2.50E-5 | > 2.50E-5 |
| SR | 0.310 | 1.504 | 1.317 | 0.792 | 0.526 | 0.498 | 0.453 | 84 | 40 | 18 | 16 | 12 | 1.51E-8 | > 2.50E-5 | > 2.50E-5 |

FIG. 22

| | | | | | | | | | | |
|---|---|---|---|---|---|---|---|---|---|---|
| Non-Small Cell Lung Cancer | | | | | | | | | | |
| A549/ATCC | 0.477 | 1.802 | 1.783 | 1.832 | 1.833 | 1.028 | 0.854 | 99 | 102 | 102 | 42 | 28 | 1.81E-6 | > 2.50E-5 | > 2.50E-5 |
| EKVX | 0.844 | 2.499 | 2.497 | 2.510 | 2.186 | 1.680 | 1.512 | 100 | 101 | 81 | 50 | 40 | 2.79E-6 | > 2.50E-5 | > 2.50E-5 |
| HOP-62 | 0.653 | 1.880 | 1.896 | 1.867 | 1.453 | 1.004 | 0.837 | 101 | 99 | 65 | 29 | 15 | 6.49E-7 | > 2.50E-5 | > 2.50E-5 |
| HOP-92 | 0.966 | 1.622 | 1.593 | 1.619 | 1.489 | 1.385 | 1.401 | 96 | 99 | 80 | 64 | 66 | > 2.50E-5 | > 2.50E-5 | > 2.50E-5 |
| NCI-H226 | 0.825 | 2.117 | 2.095 | 2.139 | 2.042 | 1.716 | 1.547 | 98 | 102 | 94 | 69 | 56 | > 2.50E-5 | > 2.50E-5 | > 2.50E-5 |
| NCI-H23 | 0.803 | 2.252 | 2.180 | 2.133 | 1.912 | 1.425 | 1.234 | 95 | 92 | 77 | 43 | 30 | 1.54E-6 | > 2.50E-5 | > 2.50E-5 |
| NCI-H322M | 0.830 | 2.560 | 2.410 | 2.405 | 2.373 | 1.447 | 1.422 | 91 | 91 | 89 | 36 | 34 | 1.35E-6 | > 2.50E-5 | > 2.50E-5 |
| NCI-H460 | 0.320 | 2.842 | 2.841 | 2.934 | 2.778 | 0.630 | 0.474 | 100 | 104 | 97 | 12 | 6 | 9.02E-7 | > 2.50E-5 | > 2.50E-5 |
| NCI-H522 | 1.026 | 2.338 | 2.124 | 1.930 | 1.463 | 1.025 | 0.928 | 84 | 69 | 33 | . | -10 | 8.50E-8 | 2.48E-6 | > 2.50E-5 |
| Colon Cancer | | | | | | | | | | |
| COLO 205 | 0.545 | 1.984 | 1.998 | 1.982 | 1.075 | 0.587 | 0.293 | 101 | 100 | 37 | 3 | -46 | 1.55E-7 | 2.86E-6 | > 2.50E-5 |
| HCC-2998 | 0.663 | 2.480 | 2.412 | 2.503 | 2.147 | 1.076 | 1.006 | 96 | 101 | 82 | 23 | 19 | 8.61E-7 | > 2.50E-5 | > 2.50E-5 |
| HCT-116 | 0.252 | 1.976 | 1.966 | 1.823 | 1.265 | 0.439 | 0.297 | 99 | 91 | 59 | 11 | 3 | 3.81E-7 | > 2.50E-5 | > 2.50E-5 |
| HCT-15 | 0.325 | 2.205 | 2.099 | 2.126 | 1.764 | 0.836 | 0.480 | 94 | 96 | 77 | 27 | 8 | 8.61E-7 | > 2.50E-5 | > 2.50E-5 |
| HT29 | 0.183 | 1.078 | 1.123 | 1.007 | 0.373 | 0.219 | 0.209 | 105 | 92 | 21 | 4 | 3 | 9.81E-8 | > 2.50E-5 | > 2.50E-5 |
| KM12 | 0.556 | 3.031 | 2.990 | 2.906 | 2.366 | 1.113 | 0.933 | 98 | 95 | 73 | 23 | 15 | 7.16E-7 | > 2.50E-5 | > 2.50E-5 |
| SW-620 | 0.347 | 2.298 | 2.263 | 2.392 | 1.281 | 0.827 | 0.743 | 98 | 105 | 48 | 25 | 20 | 2.29E-7 | > 2.50E-5 | > 2.50E-5 |

*FIG. 22 (Cont'd)*

| | | | | | | | | | | | |
|---|---|---|---|---|---|---|---|---|---|---|---|
| CNS Cancer | | | | | | | | | | | |
| SF-268 | 0.549 | 2.114 | 2.024 | 1.995 | 1.464 | 1.156 | 0.889 | 94 | 92 | 58 | 39 | 22 | 6.74E-7 | > 2.50E-5 |
| SF-295 | 0.546 | 1.894 | 1.844 | 1.822 | 1.607 | 0.738 | 0.626 | 96 | 95 | 79 | 14 | 6 | 6.96E-7 | > 2.50E-5 |
| SF-539 | 1.222 | 3.142 | 3.045 | 3.032 | 2.304 | 1.044 | 1.107 | 95 | 94 | 56 | -15 | -9 | 3.07E-7 | 1.56E-6 |
| SNB-19 | 0.766 | 2.386 | 2.361 | 2.377 | 2.135 | 1.342 | 1.386 | 98 | 99 | 84 | 36 | 38 | 1.27E-6 | > 2.50E-5 |
| SNB-75 | 0.969 | 1.932 | 1.756 | 1.718 | 1.340 | 1.234 | 1.431 | 82 | 78 | 38 | 28 | 48 | 1.27E-7 | > 2.50E-5 |
| U251 | 0.376 | 1.589 | 1.590 | 1.611 | 1.333 | 0.643 | 0.615 | 100 | 102 | 79 | 22 | 20 | 8.05E-7 | > 2.50E-5 |
| Melanoma | | | | | | | | | | | | | | |
| LOX IMVI | 0.518 | 3.269 | 3.186 | 3.108 | 2.179 | 1.504 | 1.053 | 97 | 94 | 60 | 36 | 19 | 6.62E-7 | > 2.50E-5 |
| MALME-3M | 0.915 | 1.817 | 1.733 | 1.661 | 1.487 | 1.336 | 1.271 | 91 | 83 | 63 | 47 | 39 | 1.58E-6 | > 2.50E-5 |
| M14 | 0.490 | 1.691 | 1.672 | 1.549 | 0.908 | 0.427 | 0.470 | 98 | 88 | 35 | -13 | -4 | 1.29E-7 | 1.34E-6 |
| MDA-MB-435 | 0.476 | 2.728 | 2.681 | 2.677 | 0.566 | 0.247 | 0.364 | 98 | 67 | 4 | -48 | -24 | 4.61E-8 | 2.98E-6 |
| SK-MEL-2 | 0.956 | 1.920 | 1.967 | 1.908 | 1.866 | 1.386 | 1.319 | 105 | 99 | 94 | 45 | 38 | 1.94E-6 | > 2.50E-5 |
| SK-MEL-28 | 0.749 | 1.972 | 1.971 | 1.841 | 1.588 | 1.404 | 1.359 | 100 | 89 | 69 | 54 | 50 | 2.35E-5 | > 2.50E-5 |
| SK-MEL-5 | 0.934 | 3.270 | 3.240 | 3.212 | 2.669 | 1.094 | 0.686 | 99 | 98 | 74 | 7 | -27 | 5.72E-7 | 4.00E-6 |
| UACC-62 | 0.879 | 3.023 | 2.868 | 2.881 | 2.133 | 1.414 | 1.557 | 93 | 93 | 58 | 25 | 32 | 4.48E-7 | > 2.50E-5 |
| Ovarian Cancer | | | | | | | | | | | | | | |
| IGROV1 | 0.758 | 2.442 | 2.464 | 2.245 | 1.791 | 1.442 | 1.250 | 101 | 88 | 61 | 41 | 29 | 8.79E-7 | > 2.50E-5 |
| OVCAR-3 | 0.467 | 1.731 | 1.761 | 1.694 | 0.700 | 0.517 | 0.483 | 102 | 97 | 18 | 4 | 1 | 9.91E-8 | > 2.50E-5 |
| OVCAR-4 | 0.689 | 1.588 | 1.533 | 1.537 | 1.569 | 1.204 | 1.065 | 94 | 94 | 98 | 57 | 42 | 7.32E-6 | > 2.50E-5 |
| OVCAR-5 | 0.656 | 1.953 | 1.887 | 1.820 | 1.771 | 1.221 | 0.960 | 95 | 90 | 86 | 44 | 23 | 1.76E-6 | > 2.50E-5 |
| OVCAR-8 | 0.453 | 1.830 | 1.894 | 1.907 | 1.577 | 0.807 | 0.785 | 105 | 106 | 82 | 26 | 24 | 9.20E-7 | > 2.50E-5 |
| NCI/ADR-RES | 0.575 | 1.997 | 1.950 | 1.914 | 1.894 | 1.789 | 1.451 | 97 | 94 | 93 | 85 | 62 | > 2.50E-5 | > 2.50E-5 |
| SK-OV-3 | 0.872 | 1.693 | 1.716 | 1.734 | 1.647 | 1.226 | 1.158 | 103 | 105 | 94 | 43 | 35 | 1.83E-6 | > 2.50E-5 |

*FIG. 22 (Cont'd)*

| | | | | | | | | | | |
|---|---|---|---|---|---|---|---|---|---|---|
| Renal Cancer | | | | | | | | | | |
| 786-0 | 0.474 | 1.715 | 1.697 | 1.648 | 1.013 | 0.740 | 0.697 | 99 | 95 | 43 | 21 | | 1.86E-7 | > 2.50E-5 |
| A498 | 1.487 | 2.403 | 2.213 | 2.304 | 2.261 | 1.851 | 1.489 | 79 | 89 | 84 | 40 | | 1.47E-6 | > 2.50E-5 |
| ACHN | 0.442 | 1.892 | 1.886 | 1.869 | 1.737 | 1.178 | 0.814 | 100 | 98 | 89 | 51 | 18 | 2.68E-6 | > 2.50E-5 |
| CAKI-1 | 0.620 | 2.765 | 2.582 | 2.516 | 2.492 | 2.077 | 1.451 | 91 | 88 | 87 | 68 | 26 | 1.03E-5 | > 2.50E-5 |
| RXF 393 | 0.948 | 1.606 | 1.571 | 1.571 | 1.264 | 0.852 | 1.099 | 95 | 95 | 48 | -10 | 39 | 2.27E-7 | > 2.50E-5 |
| SN12C | 0.609 | 2.311 | 2.316 | 2.317 | 1.536 | 1.228 | 1.049 | 100 | 100 | 54 | 36 | 23 | 4.40E-7 | > 2.50E-5 |
| TK-10 | 0.895 | 1.765 | 1.702 | 1.652 | 1.536 | 1.357 | 1.357 | 93 | 87 | 74 | 53 | 26 | > 2.50E-5 | > 2.50E-5 |
| UO-31 | 1.010 | 2.528 | 2.303 | 2.273 | 2.297 | 1.995 | 1.690 | 85 | 83 | 85 | 65 | 53 | 1.38E-5 | > 2.50E-5 |
| Prostate Cancer | | | | | | | | | | | | | | |
| PC-3 | 0.508 | 2.346 | 2.251 | 2.153 | 1.824 | 0.931 | 0.851 | 95 | 89 | 72 | 23 | 19 | 6.96E-7 | > 2.50E-5 |
| DU-145 | 0.442 | 2.111 | 2.149 | 2.077 | 1.340 | 0.576 | 0.547 | 102 | 98 | 54 | 8 | 6 | 3.03E-7 | > 2.50E-5 |
| Breast Cancer | | | | | | | | | | | | | | |
| MCF7 | 0.468 | 2.862 | 2.759 | 2.809 | 1.153 | 0.951 | 0.883 | 96 | 98 | 29 | 20 | 17 | 1.23E-7 | > 2.50E-5 |
| MDA-MB-231/ATCC | 0.775 | 2.051 | 2.053 | 2.030 | 1.629 | 1.003 | 0.807 | 100 | 98 | 67 | 18 | 2 | 5.52E-7 | > 2.50E-5 |
| HS 578T | 1.129 | 2.097 | 2.002 | 2.073 | 1.465 | 1.353 | 1.379 | 90 | 98 | 35 | 23 | 26 | 1.45E-7 | > 2.50E-5 |
| BT-549 | 0.793 | 1.651 | 1.607 | 1.592 | 1.140 | 0.937 | 0.655 | 95 | 93 | 40 | 17 | -17 | 1.65E-7 | 7.73E-6 |
| T-47D | 0.687 | 1.553 | 1.498 | 1.533 | 1.251 | 1.080 | 1.215 | 94 | 98 | 65 | 45 | 61 | > 2.50E-5 | > 2.50E-5 |
| MDA-MB-468 | 0.914 | 2.132 | 2.047 | 1.977 | 1.343 | 0.935 | 0.921 | 93 | 87 | 35 | 2 | 1 | 1.30E-7 | > 2.50E-5 |

*FIG. 22 (Cont'd)*

National Cancer Institute Developmental Therapeutics Program
In-Vitro Testing Results

| NSC: D-784020 / 1 | | | | | Experiment ID: 1509RS55 | | | | | Test Type: 08 | | Units: Molar |
|---|---|---|---|---|---|---|---|---|---|---|---|---|
| Report Date: November 04, 2015 | | | | | Test Date: September 08, 2015 | | | | | QNS: | | MC: |
| COMI: KCN-Tb20 | | | | | Stain Reagent: SRB Dual-Pass Related | | | | | SSPL: 0ZAS | | |

| | Time | | Mean Optical Densities | | | | | Percent Growth | | | | | | |
|---|---|---|---|---|---|---|---|---|---|---|---|---|---|---|
| | | | | | Log10 Concentration | | | | | | | | | |
| Panel/Cell Line | Zero | Ctrl | -11.0 | -10.0 | -9.0 | -8.0 | -7.0 | -11.0 | -10.0 | -9.0 | -8.0 | -7.0 | GI50 | TGI | LC50 |
| Leukemia | | | | | | | | | | | | | | | |
| CCRF-CEM | 0.854 | 3.313 | 3.273 | 3.243 | 1.781 | 1.101 | 1.086 | 98 | 97 | 38 | 10 | 9 | 6.21E-10 | > 1.00E-7 | > 1.00E-7 |
| HL-60(TB) | 0.734 | 3.178 | 3.132 | 2.775 | 0.684 | 0.622 | 0.596 | 98 | 84 | -7 | -15 | -19 | 2.35E-10 | 8.39E-10 | > 1.00E-7 |
| K-562 | 0.259 | 2.487 | 2.493 | 2.153 | 0.581 | 0.428 | 0.434 | 100 | 85 | 14 | 8 | 8 | 3.13E-10 | > 1.00E-7 | > 1.00E-7 |
| MOLT-4 | 0.951 | 3.355 | 3.326 | 3.359 | 3.074 | 1.693 | 1.378 | 99 | 100 | 88 | 31 | 18 | 4.64E-9 | > 1.00E-7 | > 1.00E-7 |
| RPMI-8226 | 0.482 | 1.765 | 1.764 | 1.428 | 0.566 | 0.620 | 0.676 | 100 | 74 | 7 | 11 | 15 | 2.25E-10 | > 1.00E-7 | > 1.00E-7 |
| SR | 0.285 | 0.862 | 0.865 | 0.572 | 0.383 | 0.352 | 0.333 | 101 | 50 | 17 | 12 | 8 | 9.85E-11 | > 1.00E-7 | > 1.00E-7 |

*FIG. 23*

| | | | | | | | | | | | |
|---|---|---|---|---|---|---|---|---|---|---|---|
| Non-Small Cell Lung Cancer | | | | | | | | | | | |
| A549/ATCC | 0.397 | 1.871 | 1.796 | 1.822 | 1.470 | 0.690 | 0.571 | 95 | 97 | 73 | 20 | 12 | 2.70E-9 | > 1.00E-7 | > 1.00E-7 |
| EKVX | 0.829 | 2.025 | 2.012 | 1.946 | 1.589 | 1.345 | 1.300 | 99 | 93 | 64 | 43 | 39 | 4.61E-9 | > 1.00E-7 | > 1.00E-7 |
| HOP-62 | 0.551 | 1.514 | 1.516 | 1.462 | 0.970 | 0.738 | 0.619 | 100 | 95 | 43 | 19 | 7 | 7.45E-10 | > 1.00E-7 | > 1.00E-7 |
| HOP-92 | 1.496 | 1.895 | 1.811 | 1.782 | 1.610 | 1.681 | 1.596 | 79 | 72 | 29 | 46 | 25 | 3.19E-10 | > 1.00E-7 | > 1.00E-7 |
| NCI-H226 | 0.568 | 1.517 | 1.446 | 1.432 | 1.152 | 1.037 | 0.924 | 93 | 91 | 62 | 49 | 38 | 9.00E-9 | > 1.00E-7 | > 1.00E-7 |
| NCI-H23 | 0.617 | 1.818 | 1.735 | 1.597 | 1.074 | 0.852 | 0.783 | 93 | 82 | 38 | 20 | 14 | 5.32E-10 | > 1.00E-7 | > 1.00E-7 |
| NCI-H322M | 0.662 | 1.996 | 1.975 | 1.939 | 1.401 | 1.113 | 1.028 | 98 | 96 | 55 | 34 | 27 | 1.78E-9 | > 1.00E-7 | > 1.00E-7 |
| NCI-H460 | 0.217 | 2.591 | 2.623 | 2.566 | 0.485 | 0.350 | 0.313 | 101 | 99 | 11 | 6 | 4 | 3.62E-10 | > 1.00E-7 | > 1.00E-7 |
| NCI-H522 | 0.922 | 2.702 | 2.547 | 2.394 | 0.918 | 0.770 | 0.612 | 91 | 83 | . | -16 | -34 | 2.47E-10 | 9.88E-10 | > 1.00E-7 |
| Colon Cancer | | | | | | | | | | | |
| COLO 205 | 0.482 | 1.527 | 1.514 | 1.421 | 0.686 | 0.398 | 0.185 | 99 | 90 | 19 | -18 | -62 | 3.69E-10 | 3.36E-9 | 5.43E-8 |
| HCC-2998 | 0.664 | 2.134 | 2.088 | 1.897 | 0.955 | 0.823 | 0.706 | 97 | 84 | 20 | 11 | 3 | 3.38E-10 | > 1.00E-7 | > 1.00E-7 |
| HCT-116 | 0.329 | 2.613 | 2.696 | 2.668 | 0.778 | 0.540 | 0.477 | 104 | 102 | 20 | 9 | 6 | 4.30E-10 | > 1.00E-7 | > 1.00E-7 |
| HCT-15 | 0.237 | 1.373 | 1.315 | 1.267 | 0.858 | 0.416 | 0.297 | 95 | 91 | 55 | 16 | 5 | 1.31E-9 | 1.35E-9 | > 1.00E-7 |
| HT29 | 0.374 | 2.392 | 2.319 | 2.090 | 0.410 | 0.330 | 0.329 | 96 | 85 | 2 | -12 | -12 | 2.63E-10 | 1.35E-9 | > 1.00E-7 |
| KM12 | 0.429 | 2.564 | 2.508 | 2.161 | 0.835 | 0.714 | 0.539 | 97 | 81 | 19 | 13 | 5 | 3.17E-10 | > 1.00E-7 | > 1.00E-7 |
| SW-620 | 0.230 | 2.074 | 1.979 | 1.591 | 0.649 | 0.582 | 0.617 | 95 | 74 | 23 | 19 | 21 | 2.92E-10 | > 1.00E-7 | > 1.00E-7 |

*FIG. 23 (Cont'd)*

| | | | | | | | | | | | |
|---|---|---|---|---|---|---|---|---|---|---|---|
| CNS Cancer | | | | | | | | | | | |
| SF-268 | 0.431 | 1.699 | 1.694 | 1.589 | 0.912 | 0.777 | 0.642 | 100 | 91 | 38 | 27 | 17 | 5.94E-10 | >1.00E-7 | >1.00E-7 |
| SF-295 | 0.834 | 2.642 | 2.526 | 2.426 | 1.147 | 0.724 | 0.759 | 94 | 88 | 17 | -13 | -9 | 3.45E-10 | 3.69E-9 | >1.00E-7 |
| SF-539 | 0.954 | 2.481 | 2.449 | 2.404 | 1.853 | 0.653 | 0.672 | 98 | 95 | 59 | -32 | -30 | 1.25E-9 | 4.48E-9 | >1.00E-7 |
| SNB-19 | 0.499 | 1.838 | 1.791 | 1.645 | 1.003 | 0.784 | 0.731 | 96 | 86 | 38 | 21 | 17 | 5.52E-10 | >1.00E-7 | >1.00E-7 |
| SNB-75 | 0.861 | 1.564 | 1.487 | 1.513 | 0.999 | 0.866 | 0.933 | 89 | 93 | 20 | 1 | 10 | 3.83E-10 | >1.00E-7 | >1.00E-7 |
| U251 | 0.301 | 1.364 | 1.362 | 1.294 | 0.595 | 0.461 | 0.431 | 100 | 93 | 28 | 15 | 12 | 4.57E-10 | >1.00E-7 | >1.00E-7 |
| Melanoma | | | | | | | | | | | |
| LOX IMVI | 0.426 | 2.594 | 2.465 | 2.380 | 1.219 | 1.083 | 0.688 | 94 | 90 | 37 | 30 | 12 | 5.62E-10 | >1.00E-7 | >1.00E-7 |
| MALME-3M | 0.729 | 1.389 | 1.376 | 1.145 | 0.972 | 1.033 | 1.040 | 98 | 63 | 37 | 46 | 47 | 3.12E-10 | >1.00E-7 | >1.00E-7 |
| M14 | 0.602 | 2.499 | 2.441 | 2.385 | 1.117 | 0.802 | 0.957 | 97 | 94 | 27 | 11 | 19 | 4.55E-10 | >1.00E-7 | >1.00E-7 |
| MDA-MB-435 | 0.472 | 2.465 | 2.293 | 0.797 | 0.220 | 0.286 | 0.329 | 91 | 16 | -53 | -40 | -30 | 3.55E-11 | 1.71E-10 | >1.00E-7 |
| SK-MEL-2 | 0.964 | 2.033 | 2.037 | 1.840 | 1.204 | 1.178 | 1.183 | 100 | 82 | 22 | 20 | 20 | 3.44E-10 | >1.00E-7 | >1.00E-7 |
| SK-MEL-28 | 0.780 | 2.182 | 2.191 | 1.944 | 1.467 | 1.340 | 1.427 | 101 | 83 | 49 | 40 | 46 | 9.34E-10 | >1.00E-7 | >1.00E-7 |
| SK-MEL-5 | 0.839 | 2.859 | 2.825 | 1.969 | 1.235 | 0.944 | 0.570 | 98 | 56 | 20 | 5 | -32 | 1.46E-10 | 1.38E-8 | >1.00E-7 |
| UACC-62 | 0.703 | 2.593 | 2.351 | 1.759 | 1.017 | 0.983 | 0.990 | 87 | 56 | 17 | 15 | 15 | 1.41E-10 | >1.00E-7 | >1.00E-7 |
| Ovarian Cancer | | | | | | | | | | | |
| IGROV1 | 0.829 | 2.274 | 2.328 | 1.944 | 1.557 | 1.245 | 1.079 | 104 | 77 | 50 | 29 | 17 | 1.04E-9 | >1.00E-7 | >1.00E-7 |
| OVCAR-3 | 0.442 | 1.606 | 1.590 | 0.778 | 0.531 | 0.418 | 0.356 | 99 | 29 | 8 | -6 | -20 | 4.97E-11 | 3.79E-9 | >1.00E-7 |
| OVCAR-4 | 0.661 | 1.353 | 1.363 | 1.303 | 1.132 | 1.002 | 0.995 | 101 | 93 | 68 | 49 | 48 | 9.09E-9 | >1.00E-7 | >1.00E-7 |
| OVCAR-5 | 0.754 | 1.955 | 1.950 | 1.846 | 1.706 | 1.104 | 1.056 | 100 | 91 | 79 | 29 | 25 | 3.84E-9 | >1.00E-7 | >1.00E-7 |
| OVCAR-8 | 0.496 | 2.060 | 2.077 | 1.998 | 1.097 | 0.583 | 0.548 | 101 | 96 | 38 | 6 | 3 | 6.29E-10 | >1.00E-7 | >1.00E-7 |
| NCI/ADR-RES | 0.560 | 1.744 | 1.758 | 1.641 | 1.539 | 1.397 | 1.041 | 101 | 91 | 83 | 71 | 41 | 4.88E-8 | >1.00E-7 | >1.00E-7 |
| SK-OV-3 | 0.802 | 1.441 | 1.433 | 1.333 | 1.062 | 0.966 | 0.850 | 99 | 83 | 41 | 26 | 7 | 6.04E-10 | >1.00E-7 | >1.00E-7 |

*FIG. 23 (Cont'd)*

| | | | | | | | | | | | |
|---|---|---|---|---|---|---|---|---|---|---|---|
| Renal Cancer | | | | | | | | | | | |
| 786-0 | 0.605 | 2.431 | 2.379 | 2.270 | 1.129 | 1.007 | 0.888 | 97 | 91 | 29 | 22 | 15 | 4.56E-10 | > 1.00E-7 |
| A498 | 1.169 | 2.063 | 2.086 | 1.923 | 1.595 | 1.269 | 1.305 | 103 | 84 | 48 | 11 | 15 | 8.62E-10 | > 1.00E-7 |
| ACHN | 0.483 | 1.930 | 1.875 | 1.863 | 1.209 | 1.069 | 0.838 | 96 | 95 | 50 | 41 | 25 | 1.04E-9 | > 1.00E-7 |
| CAKI-1 | 0.592 | 2.198 | 2.021 | 2.031 | 1.789 | 1.271 | 1.037 | 89 | 90 | 75 | 42 | 28 | 5.77E-9 | > 1.00E-7 |
| RXF 393 | 0.963 | 1.657 | 1.595 | 1.496 | 1.065 | 0.959 | 1.089 | 91 | 77 | 15 | | 18 | 2.70E-10 | |
| SN12C | 0.648 | 2.282 | 2.221 | 2.136 | 1.478 | 1.270 | 1.036 | 96 | 91 | 51 | 38 | 24 | 1.15E-9 | > 1.00E-7 |
| TK-10 | 0.762 | 1.699 | 1.660 | 1.662 | 1.335 | 1.291 | 1.273 | 96 | 96 | 61 | 56 | 55 | > 1.00E-7 | > 1.00E-7 |
| UO-31 | 0.811 | 2.248 | 1.892 | 1.954 | 1.887 | 1.386 | 1.328 | 75 | 80 | 75 | 40 | 36 | 5.16E-9 | > 1.00E-7 |
| Prostate Cancer | | | | | | | | | | | |
| PC-3 | 0.649 | 2.467 | 2.324 | 1.861 | 0.926 | 0.874 | 0.773 | 92 | 67 | 15 | 12 | 7 | 2.11E-10 | > 1.00E-7 |
| DU-145 | 0.284 | 1.410 | 1.450 | 1.320 | 0.361 | 0.384 | 0.338 | 104 | 92 | 7 | 9 | 5 | 3.11E-10 | > 1.00E-7 |
| Breast Cancer | | | | | | | | | | | |
| MCF7 | 0.405 | 2.157 | 2.053 | 0.858 | 0.604 | 0.560 | 0.524 | 94 | 26 | 11 | 9 | 7 | 4.42E-11 | > 1.00E-7 |
| MDA-MB-231/ATCC | 0.619 | 1.894 | 1.834 | 1.801 | 1.319 | 0.920 | 0.712 | 95 | 93 | 55 | 24 | 7 | 1.43E-9 | > 1.00E-7 |
| HS 578T | 1.054 | 2.211 | 2.166 | 2.171 | 1.652 | 1.245 | 1.209 | 96 | 97 | 52 | 17 | 13 | 1.12E-9 | > 1.00E-7 |
| BT-549 | 1.183 | 2.283 | 2.256 | 2.124 | 1.569 | 1.418 | 0.902 | 98 | 86 | 35 | 21 | -24 | 5.06E-10 | 2.98E-8 |
| T-47D | 0.750 | 1.470 | 1.399 | 1.318 | 0.883 | 1.076 | 1.125 | 90 | 79 | 18 | 45 | 52 | > 1.00E-7 | > 1.00E-7 |
| MDA-MB-468 | 0.794 | 1.660 | 1.544 | 1.273 | 0.870 | 0.884 | 0.831 | 87 | 55 | 9 | 10 | 4 | 1.30E-10 | > 1.00E-7 |

*FIG. 23 (Cont'd)*

National Cancer Institute Developmental Therapeutics Program
In-Vitro Testing Results

| NSC : D - 784021 / 1 | | | Experiment ID : 150RS55 | | | | Test Type : 08 | | Units : Molar |
|---|---|---|---|---|---|---|---|---|---|
| Report Date : November 04, 2015 | | | Test Date : September 08, 2015 | | | | QNS: | | MC: |
| COMI : KCN-Tb21 | | | Stain Reagent : SRB Dual-Pass Related | | | | SSPL : 0ZAS | | |

| | Time | | Log10 Concentration | | | | | | | | | | |
|---|---|---|---|---|---|---|---|---|---|---|---|---|---|
| | | | Mean Optical Densities | | | | | Percent Growth | | | | | |
| Panel/Cell Line | Zero | Ctrl | -8.8 | -7.8 | -6.8 | -5.8 | -4.8 | -8.8 | -7.8 | -6.8 | -5.8 | -4.8 | GI50 | TGI | LC50 |
| Leukemia | | | | | | | | | | | | | | | |
| CCRF-CEM | 0.854 | 3.295 | 3.251 | 2.824 | 1.139 | 1.065 | 0.891 | 98 | 81 | 12 | 9 | 2 | 4.59E-8 | >1.65E-5 | >1.65E-5 |
| HL-60(TB) | 0.734 | 3.086 | 2.648 | 0.714 | 0.593 | 0.580 | 0.593 | 81 | -3 | -19 | -21 | -19 | 3.89E-9 | 1.53E-8 | >1.65E-5 |
| K-562 | 0.259 | 2.366 | 1.846 | 0.812 | 0.455 | 0.433 | 0.438 | 75 | 26 | 9 | 8 | 8 | 5.41E-9 | >1.65E-5 | >1.65E-5 |
| MOLT-4 | 0.951 | 3.266 | 3.234 | 2.947 | 1.738 | 1.350 | 1.214 | 99 | 86 | 34 | 17 | 11 | 8.14E-8 | >1.65E-5 | >1.65E-5 |
| RPMI-8226 | 0.482 | 1.736 | 1.625 | 0.869 | 0.635 | 0.694 | 0.646 | 91 | 31 | 12 | 17 | 13 | 7.93E-9 | >1.65E-5 | >1.65E-5 |
| SR | 0.285 | 0.812 | 0.421 | 0.337 | 0.334 | 0.334 | 0.302 | 26 | 10 | 9 | 9 | 3 | <1.65E-9 | >1.65E-5 | >1.65E-5 |

*FIG. 24*

| | | | | | | | | | | | |
|---|---|---|---|---|---|---|---|---|---|---|---|
| Non-Small Cell Lung Cancer | | | | | | | | | | | |
| A549/ATCC | 0.397 | 1.896 | 1.826 | 1.818 | 1.219 | 0.706 | 0.634 | 95 | 95 | 55 | 21 | 16 | 2.28E-7 | > 1.65E-5 | > 1.65E-5 |
| EKVX | 0.829 | 2.020 | 1.881 | 1.779 | 1.442 | 1.336 | 1.277 | 88 | 80 | 51 | 43 | 38 | 2.39E-7 | > 1.65E-5 | > 1.65E-5 |
| HOP-62 | 0.551 | 1.594 | 1.530 | 1.384 | 0.873 | 0.752 | 0.670 | 94 | 80 | 31 | 19 | 11 | 6.71E-8 | > 1.65E-5 | > 1.65E-5 |
| HOP-92 | 1.496 | 1.940 | 1.856 | 1.780 | 1.681 | 1.772 | 1.684 | 81 | 64 | 42 | 62 | 42 | | > 1.65E-5 | > 1.65E-5 |
| NCI-H226 | 0.568 | 1.501 | 1.403 | 1.321 | 1.089 | 0.982 | 0.894 | 89 | 81 | 56 | 44 | 35 | 5.32E-7 | > 1.65E-5 | > 1.65E-5 |
| NCI-H23 | 0.617 | 1.889 | 1.706 | 1.509 | 1.087 | 0.991 | 0.950 | 86 | 70 | 37 | 29 | 26 | 6.66E-8 | > 1.65E-5 | > 1.65E-5 |
| NCI-H322M | 0.662 | 2.055 | 1.898 | 1.881 | 1.136 | 1.091 | 1.153 | 89 | 88 | 34 | 31 | 35 | 8.30E-8 | > 1.65E-5 | > 1.65E-5 |
| NCI-H460 | 0.217 | 2.495 | 2.521 | 2.166 | 0.428 | 0.326 | 0.306 | 101 | 86 | 9 | 5 | 4 | 4.83E-8 | > 1.65E-5 | > 1.65E-5 |
| NCI-H522 | 0.922 | 2.903 | 2.244 | 1.695 | 1.341 | 1.136 | 0.910 | 67 | 39 | 21 | 11 | -1 | 6.62E-9 | 1.28E-5 | > 1.65E-5 |
| Colon Cancer | | | | | | | | | | | |
| COLO 205 | 0.482 | 1.602 | 1.635 | 1.390 | 0.768 | 0.448 | 0.236 | 103 | 81 | 26 | -7 | -51 | 5.98E-8 | 1.00E-6 | 1.55E-5 |
| HCC-2998 | 0.664 | 2.228 | 2.138 | 1.724 | 1.171 | 0.995 | 0.866 | 94 | 68 | 32 | 21 | 13 | 5.24E-8 | > 1.65E-5 | > 1.65E-5 |
| HCT-116 | 0.329 | 2.816 | 2.897 | 1.960 | 0.810 | 0.681 | 0.537 | 103 | 66 | 19 | 14 | 8 | 3.58E-8 | > 1.65E-5 | > 1.65E-5 |
| HCT-15 | 0.237 | 1.334 | 1.260 | 1.102 | 0.677 | 0.344 | 0.241 | 93 | 79 | 40 | 10 | | 9.16E-8 | > 1.65E-5 | > 1.65E-5 |
| HT29 | 0.374 | 2.585 | 2.486 | 1.836 | 0.466 | 0.417 | 0.430 | 96 | 66 | 4 | 2 | 3 | 3.00E-8 | > 1.65E-5 | > 1.65E-5 |
| KM12 | 0.429 | 2.591 | 2.438 | 1.896 | 0.791 | 0.659 | 0.558 | 93 | 68 | 17 | 11 | 6 | 3.68E-8 | > 1.65E-5 | > 1.65E-5 |
| SW-620 | 0.230 | 2.066 | 1.994 | 1.240 | 0.670 | 0.628 | 0.589 | 96 | 55 | 24 | 22 | 19 | 2.39E-8 | > 1.65E-5 | > 1.65E-5 |

*FIG. 24 (Cont'd)*

| | | | | | | | | | | | |
|---|---|---|---|---|---|---|---|---|---|---|---|
| CNS Cancer | | | | | | | | | | | |
| SF-268 | 0.431 | 1.693 | 1.627 | 0.820 | 0.699 | 0.660 | 95 | 73 | 31 | 21 | 18 | 5.83E-8 | > 1.65E-5 |
| SF-295 | 0.834 | 2.625 | 2.428 | 0.929 | 0.706 | 0.745 | 89 | 80 | 5 | -15 | -11 | 4.18E-8 | 2.97E-7 |
| SF-539 | 0.954 | 2.670 | 2.545 | 0.793 | 0.796 | 0.758 | 93 | 82 | -17 | -17 | -21 | 3.47E-8 | 1.11E-7 |
| SNB-19 | 0.499 | 1.872 | 1.811 | 0.913 | 0.895 | 0.862 | 96 | 71 | 30 | 29 | 26 | 5.32E-8 | > 1.65E-5 |
| SNB-75 | 0.861 | 1.765 | 1.669 | 0.852 | 0.981 | 1.018 | 89 | 60 | -1 | 13 | 17 | 2.41E-8 | |
| U251 | 0.301 | 1.398 | 1.366 | 0.542 | 0.510 | 0.475 | 97 | 83 | 22 | 19 | 16 | 5.76E-8 | > 1.65E-5 |
| Melanoma | | | | | | | | | | | |
| LOX IMVI | 0.426 | 2.725 | 2.611 | 1.183 | 0.795 | 0.788 | 95 | 69 | 33 | 16 | 16 | 5.52E-8 | > 1.65E-5 |
| MALME-3M | 0.729 | 1.420 | 1.305 | 0.992 | 1.033 | 1.048 | 83 | 67 | 38 | 44 | 46 | 6.34E-8 | > 1.65E-5 |
| M14 | 0.602 | 2.642 | 2.540 | 0.952 | 1.050 | 1.055 | 95 | 77 | 17 | 22 | 22 | 4.69E-8 | > 1.65E-5 |
| MDA-MB-435 | 0.472 | 2.589 | 1.665 | 0.267 | 0.340 | 0.267 | 56 | 8 | -43 | -28 | -44 | 2.23E-9 | 2.33E-8 |
| SK-MEL-2 | 0.964 | 2.273 | 2.231 | 1.600 | 1.661 | 1.572 | 97 | 79 | 49 | 53 | 46 | | > 1.65E-5 |
| SK-MEL-28 | 0.780 | 2.247 | 2.163 | 1.435 | 1.544 | 1.492 | 94 | 79 | 45 | 52 | 49 | | > 1.65E-5 |
| SK-MEL-5 | 0.839 | 2.875 | 2.674 | 1.199 | 0.759 | 0.679 | 90 | 53 | 18 | -10 | -19 | 1.97E-8 | 7.36E-7 |
| UACC-62 | 0.703 | 2.577 | 2.307 | 1.133 | 1.119 | 1.107 | 86 | 52 | 23 | 22 | 22 | 1.94E-8 | > 1.65E-5 |
| Ovarian Cancer | | | | | | | | | | | |
| IGROV1 | 0.829 | 2.274 | 1.955 | 1.371 | 1.213 | 1.075 | 78 | 64 | 38 | 27 | 17 | 5.47E-8 | > 1.65E-5 |
| OVCAR-3 | 0.442 | 1.649 | 1.519 | 0.495 | 0.458 | 0.468 | 89 | 17 | 4 | 1 | 2 | 5.79E-9 | > 1.65E-5 |
| OVCAR-4 | 0.661 | 1.513 | 1.463 | 1.275 | 1.088 | 1.079 | 94 | 91 | 72 | 50 | 49 | 1.88E-6 | > 1.65E-5 |
| OVCAR-5 | 0.754 | 2.034 | 1.982 | 1.658 | 1.213 | 1.150 | 96 | 92 | 71 | 36 | 31 | 6.45E-7 | > 1.65E-5 |
| OVCAR-8 | 0.496 | 2.052 | 1.982 | 0.843 | 0.742 | 0.733 | 95 | 82 | 22 | 16 | 15 | 5.72E-8 | > 1.65E-5 |
| NCI/ADR-RES | 0.560 | 1.851 | 1.864 | 1.725 | 1.602 | 1.154 | 101 | 92 | 90 | 81 | 46 | 1.26E-5 | > 1.65E-5 |
| SK-OV-3 | 0.802 | 1.534 | 1.492 | 1.207 | 1.072 | 0.993 | 94 | 77 | 55 | 37 | 26 | 3.17E-7 | > 1.65E-5 |

*FIG. 24 (Cont'd)*

| | | | | | | | | | | |
|---|---|---|---|---|---|---|---|---|---|---|
| Renal Cancer | | | | | | | | | | |
| 786-0 | 0.605 | 2.513 | 2.448 | 2.029 | 1.259 | 1.009 | 0.956 | 97 | 75 | 34 | 21 | 18 | 6.72E-8 | > 1.65E-5 | > 1.65E-5 |
| A498 | 1.169 | 2.045 | 1.994 | 1.955 | 1.730 | 1.358 | 1.352 | 94 | 90 | 64 | 22 | 21 | 3.52E-7 | > 1.65E-5 | > 1.65E-5 |
| ACHN | 0.483 | 2.035 | 2.016 | 1.881 | 1.211 | 1.078 | 0.809 | 99 | 90 | 47 | 38 | 21 | 1.40E-7 | > 1.65E-5 | > 1.65E-5 |
| CAKI-1 | 0.592 | 2.292 | 2.129 | 2.079 | 1.880 | 1.392 | 0.956 | 90 | 87 | 76 | 47 | 21 | 1.30E-6 | > 1.65E-5 | > 1.65E-5 |
| RXF 393 | 0.963 | 1.694 | 1.554 | 1.397 | 0.925 | 1.034 | 1.092 | 81 | 59 | -4 | 10 | 18 | 2.32E-8 | | |
| SN12C | 0.648 | 2.227 | 2.226 | 1.833 | 1.274 | 1.147 | 1.062 | 100 | 75 | 40 | 32 | 26 | 8.40E-8 | > 1.65E-5 | > 1.65E-5 |
| TK-10 | 0.762 | 2.015 | 1.787 | 1.671 | 1.435 | 1.358 | 1.343 | 82 | 73 | 54 | 48 | 46 | 6.59E-7 | > 1.65E-5 | > 1.65E-5 |
| UO-31 | 0.811 | 2.294 | 2.036 | 2.074 | 1.807 | 1.346 | 1.357 | 83 | 85 | 67 | 36 | 37 | 5.89E-7 | > 1.65E-5 | > 1.65E-5 |
| Prostate Cancer | | | | | | | | | | |
| PC-3 | 0.649 | 2.449 | 2.293 | 1.823 | 0.971 | 0.921 | 0.880 | 91 | 65 | 18 | 15 | 13 | 3.46E-8 | > 1.65E-5 | > 1.65E-5 |
| DU-145 | 0.284 | 1.434 | 1.428 | 1.181 | 0.385 | 0.356 | 0.357 | 99 | 78 | 9 | 6 | 6 | 4.19E-8 | > 1.65E-5 | > 1.65E-5 |
| Breast Cancer | | | | | | | | | | |
| MCF7 | 0.405 | 2.143 | 1.658 | 0.670 | 0.592 | 0.548 | 0.538 | 72 | 15 | 11 | 8 | 8 | 4.04E-9 | > 1.65E-5 | > 1.65E-5 |
| MDA-MB-231/ATCC | 0.619 | 1.824 | 1.845 | 1.636 | 0.969 | 0.766 | 0.639 | 102 | 84 | 29 | 12 | 2 | 6.90E-8 | > 1.65E-5 | > 1.65E-5 |
| HS 578T | 1.054 | 2.230 | 2.150 | 1.880 | 1.191 | 1.276 | 1.198 | 93 | 70 | 12 | 19 | 12 | 3.65E-8 | > 1.65E-5 | > 1.65E-5 |
| BT-549 | 1.183 | 2.466 | 2.406 | 1.879 | 1.410 | 1.123 | 0.967 | 95 | 54 | 18 | -5 | -18 | 2.15E-8 | 9.85E-7 | > 1.65E-5 |
| T-47D | 0.750 | 1.499 | 1.413 | 1.181 | 1.126 | 1.149 | 1.289 | 89 | 58 | 50 | 53 | 72 | > 1.65E-5 | > 1.65E-5 | > 1.65E-5 |
| MDA-MB-468 | 0.794 | 1.670 | 1.495 | 1.212 | 0.930 | 0.916 | 0.874 | 80 | 48 | 15 | 14 | 9 | 1.40E-8 | > 1.65E-5 | > 1.65E-5 |

*FIG. 24 (Cont'd)*

| National Cancer Institute Developmental Therapeutics Program |
|:---:|
| In-Vitro Testing Results |

| NSC: D-784022 / 1 | | | | | | | | Experiment ID: 1509RS55 | | | | Test Type: 08 | | Units: Molar |
|---|---|---|---|---|---|---|---|---|---|---|---|---|---|---|
| Report Date: November 04, 2015 | | | | | | | | Test Date: September 08, 2015 | | | | QNS: | | MC: |
| COMI: KCN-Tb23 | | | | | | | | Stain Reagent: SRB Dual-Pass Related | | | | SSPL: 0ZAS | | |

| | Time | | Mean Optical Densities | | | | | Log10 Concentration Percent Growth | | | | | | |
|---|---|---|---|---|---|---|---|---|---|---|---|---|---|---|
| Panel/Cell Line | Zero | Ctrl | -8.8 | -7.8 | -6.8 | -5.8 | -4.8 | -8.8 | -7.8 | -6.8 | -5.8 | -4.8 | | |
| | | | | | | | | | | | | | GI50 | TGI | LC50 |
| Leukemia | | | | | | | | | | | | | | | |
| CCRF-CEM | 0.854 | 3.131 | 3.201 | 3.212 | 2.739 | 1.037 | 0.787 | 103 | 104 | 83 | 8 | -8 | 4.12E-7 | 4.80E-6 | > 1.50E-5 |
| HL-60(TB) | 0.734 | 3.174 | 3.078 | 3.009 | 0.761 | 0.577 | 0.619 | 96 | 93 | 1 | -21 | -16 | 4.42E-8 | 1.68E-7 | > 1.50E-5 |
| K-562 | 0.259 | 2.433 | 2.462 | 2.371 | 1.037 | 0.457 | 0.384 | 101 | 97 | 36 | 9 | 6 | 8.80E-8 | > 1.50E-5 | > 1.50E-5 |
| MOLT-4 | 0.951 | 3.355 | 3.312 | 3.357 | 3.134 | 1.295 | 1.158 | 98 | 100 | 91 | 14 | 9 | 5.12E-7 | > 1.50E-5 | > 1.50E-5 |
| RPMI-8226 | 0.482 | 1.755 | 1.742 | 1.683 | 0.824 | 0.590 | 0.360 | 99 | 94 | 27 | 8 | -25 | 6.81E-8 | 2.67E-6 | > 1.50E-5 |
| SR | 0.285 | 0.866 | 0.860 | 0.583 | 0.369 | 0.339 | 0.295 | 99 | 51 | 14 | 9 | 2 | 1.63E-8 | > 1.50E-5 | > 1.50E-5 |

FIG. 25

| | | | | | | | | | | | |
|---|---|---|---|---|---|---|---|---|---|---|---|
| Non-Small Cell Lung Cancer | | | | | | | | | | | |
| A549/ATCC | 0.397 | 1.781 | 1.712 | 1.704 | 1.812 | 1.103 | 0.599 | 95 | 94 | 102 | 51 | 15 | 1.60E-6 | > 1.50E-5 | > 1.50E-5 |
| EKVX | 0.829 | 2.119 | 1.993 | 1.947 | 1.918 | 1.509 | 1.354 | 90 | 87 | 84 | 53 | 41 | 2.51E-6 | > 1.50E-5 | > 1.50E-5 |
| HOP-62 | 0.551 | 1.639 | 1.607 | 1.619 | 1.457 | 0.797 | 0.636 | 97 | 98 | 83 | 23 | 8 | 5.30E-7 | > 1.50E-5 | > 1.50E-5 |
| HOP-92 | 1.496 | 1.921 | 1.820 | 1.846 | 1.692 | 1.728 | 1.183 | 76 | 82 | 46 | 54 | -21 | | 7.91E-6 | > 1.50E-5 |
| NCI-H226 | 0.568 | 1.470 | 1.434 | 1.379 | 1.338 | 0.949 | 0.768 | 96 | 90 | 85 | 42 | 22 | 9.90E-7 | > 1.50E-5 | > 1.50E-5 |
| NCI-H23 | 0.617 | 1.914 | 1.827 | 1.724 | 1.559 | 0.928 | 0.747 | 93 | 85 | 73 | 24 | 10 | 4.38E-7 | > 1.50E-5 | > 1.50E-5 |
| NCI-H322M | 0.662 | 2.064 | 1.881 | 1.963 | 1.853 | 1.108 | 1.154 | 87 | 93 | 85 | 32 | 35 | 6.81E-7 | > 1.50E-5 | > 1.50E-5 |
| NCI-H460 | 0.217 | 2.564 | 2.550 | 2.517 | 2.443 | 0.420 | 0.287 | 99 | 98 | 95 | 9 | 3 | 4.97E-7 | > 1.50E-5 | > 1.50E-5 |
| NCI-H522 | 0.922 | 2.948 | 2.634 | 2.755 | 1.663 | 1.049 | 0.739 | 84 | 90 | 37 | 6 | -20 | 8.45E-8 | 2.60E-6 | > 1.50E-5 |
| Colon Cancer | | | | | | | | | | | |
| COLO 205 | 0.482 | 1.622 | 1.648 | 1.657 | 1.589 | 0.755 | 0.251 | 102 | 103 | 97 | 24 | -48 | 6.60E-7 | 3.22E-6 | > 1.50E-5 |
| HCC-2998 | 0.664 | 2.254 | 2.055 | 2.074 | 1.556 | 0.835 | 0.237 | 87 | 89 | 56 | 11 | -64 | 2.04E-7 | 2.09E-6 | 9.65E-6 |
| HCT-116 | 0.329 | 2.807 | 2.736 | 2.711 | 1.909 | 0.472 | 0.450 | 97 | 96 | 64 | 6 | 5 | 2.59E-7 | > 1.50E-5 | > 1.50E-5 |
| HCT-15 | 0.237 | 1.394 | 1.332 | 1.310 | 1.189 | 0.623 | 0.264 | 95 | 93 | 82 | 33 | 2 | 6.86E-7 | > 1.50E-5 | > 1.50E-5 |
| HT29 | 0.374 | 2.478 | 2.467 | 2.347 | 2.009 | 0.396 | 0.331 | 99 | 94 | 78 | 1 | -12 | 3.45E-7 | 1.81E-6 | > 1.50E-5 |
| KM12 | 0.429 | 2.516 | 2.453 | 2.381 | 1.814 | 0.625 | 0.421 | 97 | 94 | 66 | 9 | -2 | 2.91E-7 | 1.02E-5 | > 1.50E-5 |
| SW-620 | 0.230 | 2.044 | 1.956 | 1.864 | 1.221 | 0.634 | 0.535 | 95 | 90 | 55 | 22 | 17 | 2.08E-7 | > 1.50E-5 | > 1.50E-5 |

*FIG. 25 (Cont'd)*

| | | | | | | | | | | |
|---|---|---|---|---|---|---|---|---|---|---|
| CNS Cancer | | | | | | | | | | |
| SF-268 | 0.431 | 1.634 | 1.561 | 1.262 | 0.588 | 0.407 | 94 | 99 | 69 | 13 | -6 | 3.28E-7 | 7.52E-6 | >1.50E-5 |
| SF-295 | 0.834 | 2.706 | 2.580 | 2.350 | 0.791 | 0.785 | 93 | 88 | 81 | -5 | -6 | 3.43E-7 | 1.31E-6 | >1.50E-5 |
| SF-539 | 0.954 | 2.631 | 2.524 | 2.371 | 0.750 | 0.765 | 94 | 93 | 84 | -21 | -20 | 3.17E-7 | 9.42E-7 | >1.50E-5 |
| SNB-19 | 0.499 | 1.831 | 1.795 | 1.439 | 0.864 | 0.823 | 97 | 107 | 71 | 27 | 24 | 4.48E-7 | >1.50E-5 | >1.50E-5 |
| SNB-75 | 0.861 | 1.603 | 1.508 | 1.208 | 0.834 | 0.766 | 87 | 79 | 47 | -3 | -11 | 1.19E-7 | 1.30E-6 | >1.50E-5 |
| U251 | 0.301 | 1.287 | 1.254 | 1.175 | 0.530 | 0.475 | 97 | 98 | 89 | 23 | 18 | 5.84E-7 | >1.50E-5 | >1.50E-5 |
| Melanoma | | | | | | | | | | |
| LOX IMVI | 0.426 | 2.766 | 2.682 | 2.578 | 0.772 | 0.448 | 96 | 92 | 57 | 15 | 1 | 2.23E-7 | >1.50E-5 | >1.50E-5 |
| MALME-3M | 0.729 | 1.413 | 1.342 | 1.357 | 1.038 | 0.772 | 90 | 92 | 61 | 45 | 6 | 7.48E-7 | >1.50E-5 | >1.50E-5 |
| M14 | 0.602 | 2.647 | 2.554 | 2.540 | 0.964 | 0.643 | 95 | 95 | 79 | 18 | 2 | 4.42E-7 | >1.50E-5 | >1.50E-5 |
| MDA-MB-435 | 0.472 | 2.523 | 2.417 | 2.220 | 0.243 | 0.382 | 95 | 85 | 12 | -49 | -19 | 4.51E-8 | 2.34E-7 | >1.50E-5 |
| SK-MEL-2 | 0.964 | 2.274 | 2.324 | 2.239 | 1.548 | 1.040 | 104 | 97 | 65 | 45 | 6 | 8.08E-7 | >1.50E-5 | >1.50E-5 |
| SK-MEL-28 | 0.780 | 2.241 | 2.207 | 2.165 | 1.530 | 1.286 | 98 | 95 | 76 | 51 | 35 | 1.81E-6 | >1.50E-5 | >1.50E-5 |
| SK-MEL-5 | 0.839 | 3.003 | 2.916 | 2.754 | 0.924 | 0.444 | 96 | 88 | 50 | 4 | -47 | 1.48E-7 | 1.79E-6 | >1.50E-5 |
| UACC-62 | 0.703 | 2.542 | 2.443 | 2.423 | 0.967 | 0.405 | 95 | 94 | 40 | 14 | -42 | 9.61E-8 | 2.69E-6 | >1.50E-5 |
| Ovarian Cancer | | | | | | | | | | |
| IGROV1 | 0.829 | 2.358 | 2.247 | 2.205 | 1.162 | 0.810 | 93 | 90 | 57 | 22 | -2 | 2.40E-7 | 1.20E-5 | >1.50E-5 |
| OVCAR-3 | 0.442 | 1.625 | 1.578 | 1.550 | 0.412 | 0.379 | 96 | 94 | 16 | -7 | -14 | 5.49E-8 | 7.60E-7 | >1.50E-5 |
| OVCAR-4 | 0.661 | 1.328 | 1.306 | 1.296 | 0.956 | 0.823 | 97 | 95 | 95 | 44 | 24 | 1.15E-6 | >1.50E-5 | >1.50E-5 |
| OVCAR-5 | 0.754 | 2.005 | 1.909 | 1.892 | 1.476 | 1.027 | 92 | 91 | 87 | 58 | 22 | 2.46E-6 | >1.50E-5 | >1.50E-5 |
| OVCAR-8 | 0.496 | 1.934 | 1.968 | 1.861 | 0.699 | 0.752 | 102 | 95 | 90 | 14 | 18 | 5.02E-7 | >1.50E-5 | >1.50E-5 |
| NCI/ADR-RES | 0.560 | 1.953 | 1.826 | 1.732 | 1.397 | 98 | 91 | 92 | 84 | 60 | >1.50E-5 | >1.50E-5 | >1.50E-5 |
| SK-OV-3 | 0.802 | 1.604 | 1.524 | 1.447 | 1.069 | 1.017 | 95 | 90 | 80 | 33 | 27 | 6.63E-7 | >1.50E-5 | >1.50E-5 |

*FIG. 25 (Cont'd)*

| | | | | | | | | | | |
|---|---|---|---|---|---|---|---|---|---|---|
| Renal Cancer | | | | | | | | | | |
| 786-0 | 0.605 | 2.315 | 2.235 | 2.262 | 2.049 | 1.084 | 0.736 | 95 | 97 | 84 | 28 | 8 | 6.12E-7 | > 1.50E-5 | > 1.50E-5 |
| A498 | 1.169 | 1.981 | 1.912 | 1.975 | 1.901 | 1.591 | 1.289 | 91 | 99 | 90 | 52 | 15 | 1.69E-6 | > 1.50E-5 | > 1.50E-5 |
| ACHN | 0.483 | 2.012 | 2.021 | 1.969 | 1.857 | 1.161 | 0.748 | 101 | 97 | 90 | 44 | 17 | 1.13E-6 | > 1.50E-5 | > 1.50E-5 |
| CAKI-1 | 0.592 | 2.115 | 1.951 | 1.843 | 1.814 | 1.525 | 0.868 | 89 | 82 | 80 | 61 | 18 | 2.73E-6 | > 1.50E-5 | > 1.50E-5 |
| RXF 393 | 0.963 | 1.639 | 1.609 | 1.505 | 1.332 | 0.960 | 0.959 | 96 | 80 | 55 | . | . | 1.81E-7 | 1.48E-6 | > 1.50E-5 |
| SN12C | 0.648 | 2.263 | 2.284 | 2.314 | 2.005 | 1.154 | 0.812 | 101 | 103 | 84 | 31 | 10 | 6.63E-7 | > 1.50E-5 | > 1.50E-5 |
| TK-10 | 0.762 | 1.946 | 1.860 | 1.786 | 1.559 | 1.202 | 1.062 | 93 | 86 | 67 | 37 | 25 | 5.62E-7 | > 1.50E-5 | > 1.50E-5 |
| UO-31 | 0.811 | 2.317 | 2.074 | 2.079 | 2.017 | 1.701 | 1.331 | 84 | 84 | 80 | 59 | 34 | 3.50E-6 | > 1.50E-5 | > 1.50E-5 |
| Prostate Cancer | | | | | | | | | | |
| PC-3 | 0.649 | 2.352 | 2.278 | 2.293 | 1.778 | 0.891 | 0.730 | 96 | 97 | 66 | 14 | 5 | 3.08E-7 | > 1.50E-5 | > 1.50E-5 |
| DU-145 | 0.284 | 1.384 | 1.437 | 1.403 | 1.214 | 0.348 | 0.324 | 105 | 102 | 85 | 6 | 4 | 4.12E-7 | > 1.50E-5 | > 1.50E-5 |
| Breast Cancer | | | | | | | | | | |
| MCF7 | 0.405 | 2.175 | 2.053 | 1.910 | 0.604 | 0.519 | 0.533 | 93 | 85 | 11 | 6 | 7 | 4.47E-8 | > 1.50E-5 | > 1.50E-5 |
| MDA-MB-231/ATCC | 0.619 | 1.808 | 1.792 | 1.808 | 1.601 | 0.659 | 0.510 | 99 | 100 | 83 | 3 | -18 | 3.87E-7 | 2.16E-6 | > 1.50E-5 |
| HS 578T | 1.054 | 2.237 | 2.156 | 2.131 | 1.855 | 1.180 | 1.065 | 93 | 91 | 68 | 11 | 1 | 3.05E-7 | > 1.50E-5 | > 1.50E-5 |
| BT-549 | 1.183 | 2.342 | 2.287 | 2.301 | 1.738 | 0.952 | 0.482 | 95 | 96 | 48 | -20 | -59 | 1.36E-7 | 7.70E-7 | 8.77E-6 |
| T-47D | 0.750 | 1.486 | 1.517 | 1.499 | 1.142 | 1.186 | 0.939 | 104 | 102 | 53 | 59 | 26 | 2.81E-6 | > 1.50E-5 | > 1.50E-5 |
| MDA-MB-468 | 0.794 | 1.688 | 1.570 | 1.512 | 1.133 | 0.828 | 0.326 | 87 | 80 | 38 | 4 | -59 | 7.78E-8 | 1.72E-6 | 1.08E-5 |

*FIG. 25 (Cont'd)*

DESACETOXYTUBULYSIN H AND ANALOGS THEREOF

This application is a national phase application under 35 U.S.C. § 371 of International Application No. PCT/US2016/019604 filed on Feb. 25, 2016 and claims the benefit of priority to U.S. Provisional Application Ser. No. 62/120,613, filed on Feb. 25, 2015 and U.S. Provisional Application Ser. No. 62/275,667, filed Jan. 6, 2016, the entire contents of which are hereby incorporated by reference.

BACKGROUND

1. Field

This disclosure relates to the fields of medicine, pharmacology, chemistry, and oncology. In particular, new compounds, compositions, methods of treatment, and methods of synthesis relating to analogues of tubulysin are disclosed.

2. Related Art

Tubulysins constitute an important class of potent antitumor agents, whose potential in cancer chemotherapy has been recognized and extensively explored (Dömling and Richter, 2005; Sasse et al., 2000; Sandmann et al., 2004; Chai et al., 2010; Khalil et al., 2006; Kubicek et al., 2010a; Kubicek et al., 2010b; Steinmetz et al., 2004: Steinmetz 2004; Ullrich et al., 2009a; Ullrich, et al., 2009b. As a result of these studies a number of the naturally occurring tubulysins (Neri et al., 2006; Kazmaier et al., 2013 and Höfle et al., 2003) tubulysin A-I, (Pando et al., 2009: Shibue et al., 2010; Sasse and Menche, 2007; Peltier et al., 2006) tubulysins U, (Yang et al., 2013; Shibue et al., 2010; Sani et al., 2007a; Sani et al., 2007b: Dömling et al., 2006a and Dömling et al., 2006b) and V, (Shibue et al., 2010; Wang et al., 2013; Sani et al., 2007a; Sani et al., 2007b; Dömling et al., 2006a and Dömling et al., 2006b) pretubulysin D (Ullrich et al., 2009a; Ullrich et al., 2009b) and tubulysins (I)-(X), (Chai et al., 2010 FIG. 1) have been synthesized and so have a large number of their analogues (Wipf and Wang, 2007; Raghavan et al., 2008; Floyd et al., 2011; Patterson et al., 2007; Rath et al., 2012; Eirich et al., 2012; Burkhart et al., 2011; Shibue et al., 2011; Pando et al., 2011; Shankar et al., 2011; Wang et al., 2007; Shankar et al., 2013; Burkhart et al., 2012; Yang et al., 2013; Balasubramanian et al., 2008; Patterson et al., 2008; US 2010/0240701 A1; US 2011/0027274 A1; U.S. Pat. No. 7,816,377 B2; WO 2009/012958 A2; WO 2009/055562 A1; EP 2 174 947 A1; WO 2013/149185 A1; EP 2 409 983 A1, 2012; WO 2012/010287 A1; WO 2012/019123 A1; WO 2004/005326 A2, 2004; WO 2004/005327 A1; WO 2008/106080 A2). Exerting their cytotoxicity through a microtubule de-polymerization mechanism (Khalil et al., 2006; Kubicek et al., 2010a; Kubicek et al., 2010b; Steinmetz et al., 2004; Steinmetz, 2004; Neri et al., 2006), these compounds are of particular interest as payloads on antibody drug conjugates (ADCs). The development of tubulysin analogs is of clinical importance.

SUMMARY

The present disclosure provides analogs of tubulysin which may be useful in the treatment of cancer.

Thus, there is provided compounds of the formula:

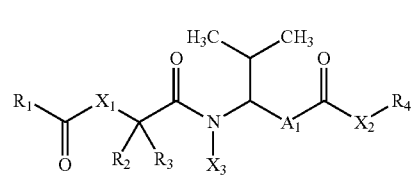

(I)

wherein: $R_1$ is heteroaryl$_{(C \leq 12)}$, heterocycloalkyl$_{(C \leq 12)}$, arylamino$_{(C \leq 12)}$, aralkylamino$_{(C \leq 12)}$, alkanediyl$_{(C \leq 12)}$-$Y_2$, fused cycloalkyl$_{(C \leq 12)}$-$Y_2$, or a substituted version of any of these groups, wherein $Y_2$ is amino, alkylamino$_{(C \leq 12)}$, dialkylamino$_{(C \leq 12)}$, amido$_{(C \leq 12)}$, substituted alkylamino$_{(C \leq 12)}$, substituted dialkylamino$_{(C \leq 12)}$, or substituted amido$_{(C \leq 12)}$; $R_2$ and $R_3$ are each independently selected from hydrogen, alkyl$_{(C \leq 12)}$, cycloalkyl$_{(C \leq 12)}$, fused cycloalkyl$_{(C \leq 12)}$, aryl$_{(C \leq 12)}$, heterocycloalkyl$_{(C \leq 12)}$, -alkanediyl$_{(C \leq 12)}$-cycloalkyl$_{(C \leq 12)}$, or a substituted version of any of these groups; or $R_2$ and $R_3$ are taken together and are alkanediyl$_{(C \leq 12)}$, alkoxydiyl$_{(C \leq 12)}$, alkylthiodiyl$_{(C \leq 12)}$, or alkylaminodiyl$_{(C \leq 12)}$; $R_4$ is cycloalkyl$_{(C \leq 12)}$, fused cycloalkyl$_{(C \leq 12)}$, aralkyl$_{(C \leq 12)}$, substituted cycloalkyl$_{(C \leq 12)}$, substituted fused cycloalkyl$_{(C \leq 12)}$, substituted aralkyl$_{(C \leq 12)}$, fused cycloalkylamino$_{(C \leq 12)}$, substituted fused cycloalkylamino$_{(C \leq 12)}$, or a structure of the formula:

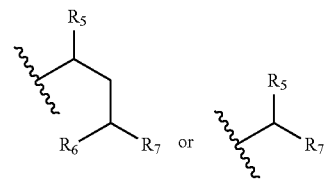

wherein: $R_5$ is aryl$_{(C \leq 12)}$, aralkyl$_{(C \leq 12)}$, heteroaryl$_{(C \leq 12)}$, heteroaralkyl$_{(C \leq 12)}$, or a substituted version of any of these groups; or is -alkanediyl$_{(C \leq 6)}$-arenediyl$_{(C \leq 22)}$-$Y_3$ or a substituted version of any of these groups; wherein: $Y_3$ is alkoxy$_{(C \leq 12)}$, aryloxy$_{(C \leq 12)}$, an oxygen linked antibody, —C(O)-alkoxy$_{(C \leq 12)}$, —C(O)-alkylamino$_{(C \leq 12)}$, —C(O)-dialkylamino$_{(C \leq 12)}$, —C(O)-aryloxy$_{(C \leq 12)}$, —C(O)-arylamino$_{(C \leq 12)}$, —C(O)—$Y_4$; or a substituted version of any of these groups; wherein: $Y_4$ is a nitrogen linked antibody or an oxygen linked antibody; $R_6$ is hydrogen, alkyl$_{(C \leq 8)}$, or substituted alkyl$_{(C \leq 8)}$; $R_7$ is —C(O)—$Y_5$; wherein $Y_5$ is amino, hydroxy, alkoxy$_{(C \leq 12)}$, substituted alkoxy$_{(C \leq 12)}$, alkylamino$_{(C \leq 12)}$, substituted alkylamino$_{(C \leq 12)}$, dialkylamino$_{(C \leq 12)}$, substituted dialkylamino$_{(C \leq 12)}$, an oxygen linked antibody, or a nitrogen linked antibody; $X_1$ and $X_2$ are each independently selected from a covalent bond, —O—, —S—, —NR$_8$—, or —NR$_9$NR$_{10}$—, wherein: $R_8$, $R_9$, and $R_{10}$ are each independently selected from hydrogen, alkyl$_{(C \leq 12)}$, substituted alkyl$_{(C \leq 12)}$, cycloalkyl$_{(C \leq 12)}$, or substituted cycloalkyl$_{(C \leq 12)}$; $X_3$ is hydrogen, alkyl$_{(C \leq 12)}$, or substituted alkyl$_{(C \leq 12)}$; and A$_1$ is —C(O)NR$_{13}$-fused cycloalkanediyl$_{(C \leq 12)}$, -alkanediyl$_{(C \leq 12)}$-heteroarenediyl$_{(C \leq 12)}$, -alkanediyl$_{(C \leq 12)}$-heteroarenediyl$_{(C \leq 12)}$, wherein the alkanediyl is substituted with an amido$_{(C \leq 8)}$ or acyloxy$_{(C \leq 8)}$ group, or a substituted version of any of these groups, wherein: $R_{13}$ is hydrogen, alkyl$_{(C \leq 12)}$, substituted alkyl$_{(C \leq 12)}$, cycloalkyl$_{(C \leq 12)}$, or substituted cycloalkyl$_{(C \leq 12)}$; provided that $X_3$ is not hydrogen, methyl, hydroxymethyl, or acetoxymethyl, when $R_2$ or $R_3$ is sec-butyl, $R_5$ is benzyl, $R_7$ is —$CO_2H$, and $R_1$ is 2-N-methylpiperidinyl; or a pharmaceutically acceptable salt thereof. In some embodiments, the compounds are further defined as:

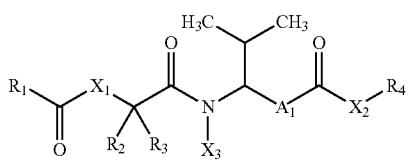

(I)

wherein: $R_1$ is heteroaryl$_{(C\leq12)}$, heterocycloalkyl$_{(C\leq12)}$, arylamino$_{(C\leq12)}$, aralkylamino$_{(C\leq12)}$, alkanediyl$_{(C\leq12)}$-$Y_2$, fused cycloalkyl$_{(C\leq12)}$-$Y_2$, or a substituted version of any of these groups, wherein $Y_2$ is amino, alkylamino$_{(C\leq12)}$, dialkylamino$_{(C\leq12)}$, amido$_{(C\leq12)}$, substituted alkylamino$_{(C\leq12)}$, substituted dialkylamino$_{(C\leq12)}$, or substituted amido$_{(C\leq12)}$; $R_2$ and $R_3$ are each independently selected from hydrogen, alkyl$_{(C\leq12)}$, cycloalkyl$_{(C\leq12)}$, fused cycloalkyl$_{(C\leq12)}$, heterocycloalkyl$_{(C\leq12)}$, -alkanediyl$_{(C\leq12)}$-cycloalkyl$_{(C\leq12)}$, or a substituted version of any of these groups; or $R_2$ and $R_3$ are taken together and are alkanediyl$_{(C\leq12)}$, alkoxydiyl$_{(C\leq12)}$, alkylthiodiyl$_{(C\leq12)}$, or alkylaminodiyl$_{(C\leq12)}$; $R_4$ is fused cycloalkylamino$_{(C\leq12)}$, substituted fused cycloalkylamino$_{(C\leq12)}$, or a structure of the formula:

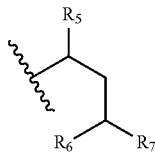

wherein: $R_5$ is aryl$_{(C\leq12)}$, aralkyl$_{(C\leq12)}$, heteroaryl$_{(C\leq12)}$, heteroaralkyl$_{(C\leq12)}$, or a substituted version of any of these groups; or is -alkanediyl$_{(C\leq6)}$-arenediyl$_{(C\leq12)}$-$Y_3$ or a substituted version of any of these groups; wherein: $Y_3$ is alkoxy$_{(C\leq12)}$, aryloxy$_{(C\leq12)}$, an oxygen linked antibody, —C(O)-alkoxy$_{(C\leq12)}$, —C(O)-alkylamino$_{(C\leq12)}$, —C(O)-dialkylamino$_{(C\leq12)}$, —C(O)-aryloxy$_{(C\leq12)}$, —C(O)-arylamino$_{(C\leq12)}$, —C(O)—$Y_4$; or a substituted version of any of these groups; wherein: $Y_1$ is a nitrogen linked antibody or an oxygen linked antibody; $R_6$ is hydrogen, alkyl$_{(C\leq8)}$, or substituted alkyl$_{(C\leq8)}$; $R_7$ is —C(O)—$Y_5$; wherein $Y_5$ is amino, hydroxy, alkoxy$_{(C\leq12)}$, substituted alkoxy$_{(C\leq12)}$, alkylamino$_{(C\leq12)}$, substituted alkylamino$_{(C\leq12)}$, dialkylamino$_{(C\leq12)}$, substituted dialkylamino$_{(C\leq12)}$, an oxygen linked antibody, or a nitrogen linked antibody; $X_1$ and $X_2$ are each independently selected from —O—, —S—, —$NR_8$—, or —$NR_9NR_{10}$—, wherein: $R_8$, $R_9$, and $R_{10}$ are each independently selected from hydrogen, alkyl$_{(C\leq12)}$, substituted alkyl$_{(C\leq12)}$, cycloalkyl$_{(C\leq12)}$, or substituted cycloalkyl$_{(C\leq12)}$; $X_3$ is hydrogen, alkyl$_{(C\leq12)}$, or substituted alkyl$_{(C\leq12)}$; and $A_1$ is —C(O)$NR_{13}$-fused cycloalkanediyl$_{(C\leq12)}$, -alkanediyl$_{(C\leq12)}$-heteroarene-diyl$_{(C\leq12)}$, -alkanediyl$_{(C\leq12)}$-heteroarenediyl$_{(C\leq12)}$, wherein the alkanediyl is substituted with an amido$_{(C\leq8)}$ or acyloxy$_{(C\leq8)}$ group, or a substituted version of any of these groups, wherein: $R_{13}$ is hydrogen, alkyl$_{(C\leq12)}$, substituted alkyl$_{(C\leq12)}$, cycloalkyl$_{(C\leq12)}$, or substituted cycloalkyl$_{(C\leq12)}$; provided that $X_3$ is not hydrogen, methyl, hydroxymethyl, or acetoxymethyl, when $R_2$ or $R_3$ is sec-butyl, $R_5$ is benzyl, $R_7$ is —$CO_2H$, and $R_1$ is 2-N-methylpiperidinyl; or a pharmaceutically acceptable salt thereof. In some embodiments, the formula is further defined as:

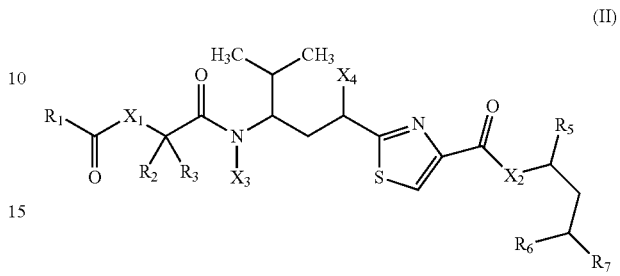

(II)

wherein: $R_1$ is heteroaryl$_{(C\leq12)}$, heterocycloalkyl$_{(C\leq12)}$, arylamino$_{(C\leq12)}$, aralkylamino$_{(C\leq12)}$, alkanediyl$_{(C\leq12)}$-$Y_2$, fused cycloalkyl$_{(C\leq12)}$-$Y_2$, or a substituted version of any of these groups, wherein $Y_2$ is amino, alkylamino$_{(C\leq12)}$, dialkylamino$_{(C\leq12)}$, amido$_{(C\leq12)}$, substituted alkylamino$_{(C\leq12)}$, substituted dialkylamino$_{(C\leq12)}$, or substituted amido$_{(C\leq12)}$; $R_2$ and $R_3$ are each independently selected from hydrogen, cycloalkyl$_{(C\leq12)}$, fused cycloalkyl$_{(C\leq12)}$, heterocycloalkyl$_{(C\leq12)}$, -alkanediyl$_{(C\leq12)}$, -cycloalkyl$_{(C\leq12)}$, or a substituted version of any of these groups; or $R_2$ and $R_3$ are taken together and are alkanediyl$_{(C\leq12)}$, alkoxydiyl$_{(C\leq12)}$, alkylthiodiyl$_{(C\leq12)}$, or alkylaminodiyl$_{(C\leq12)}$; $R_5$ is aryl$_{(C\leq12)}$, aralkyl$_{(C\leq12)}$, heteroaryl$_{(C\leq12)}$, heteroaralkyl$_{(C\leq12)}$, or a substituted version of any of these groups; or is -alkanediyl$_{(C\leq6)}$-arenediyl$_{(C\leq12)}$-$Y_3$ or a substituted version of any of these groups; wherein: $Y_3$ is alkoxy$_{(C\leq12)}$, aryloxy$_{(C\leq12)}$, an oxygen linked antibody, —C(O)-alkoxy$_{(C\leq12)}$, —C(O)-alkylamino$_{(C\leq12)}$, —C(O)-dialkylamino$_{(C\leq12)}$, —C(O)-aryloxy$_{(C\leq12)}$, —C(O)-arylamino$_{(C\leq12)}$, —C(O)—$Y_4$; or a substituted version of any of these groups; wherein: $Y_4$ is a nitrogen or an oxygen linked antibody; $R_6$ is hydrogen, alkyl$_{(C\leq8)}$, or substituted alkyl$_{(C\leq8)}$; $R_7$ is —C(O)—$Y_5$; wherein $Y_5$ is amino, hydroxy, alkoxy$_{(C\leq12)}$, substituted alkoxy$_{(C\leq12)}$, alkylamino$_{(C\leq12)}$, substituted alkylamino$_{(C\leq12)}$, dialkylamino$_{(C\leq12)}$, substituted dialkylamino$_{(C\leq12)}$, an oxygen linked antibody, or a nitrogen linked antibody; $X_1$ and $X_2$ are each independently selected from —O—, —S—, —$NR_8$—, or —$NR_9NR_{10}$—, wherein: $R_8$, $R_9$, and $R_{10}$ are each independently selected from hydrogen, alkyl$_{(C\leq12)}$, substituted alkyl$_{(C\leq12)}$, cycloalkyl$_{(C\leq12)}$, or substituted cycloalkyl$_{(C\leq12)}$; $X_3$ is hydrogen, alkyl$_{(C\leq12)}$, or substituted alkyl$_{(C\leq12)}$; and $X_4$ is amino, hydroxy, acyloxy$_{(C\leq8)}$, substituted acyloxy$_{(C\leq8)}$, amido$_{(C\leq8)}$, substituted amido$_{(C\leq8)}$; or a pharmaceutically acceptable salt thereof. In some embodiments, the formula is further defined as:

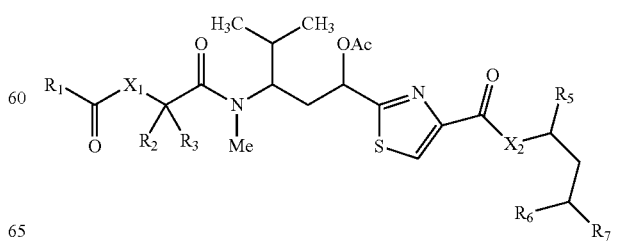

(III)

wherein: $R_1$ is heteroaryl$_{(C≤12)}$, heterocycloalkyl$_{(C≤12)}$, arylamino$_{(C≤12)}$, aralkylamino$_{(C≤12)}$, alkanediyl$_{(C≤12)}$-$Y_2$, fused cycloalkyl$_{(C≤12)}$-$Y_2$, or a substituted version of any of these groups, wherein $Y_2$ is amino, alkylamino$_{(C≤12)}$, dialkylamino$_{(C≤12)}$, amido$_{(C≤12)}$, substituted alkylamino$_{(C≤12)}$, substituted dialkylamino$_{(C≤12)}$, or substituted amido$_{(C≤12)}$; $R_2$ and $R_3$ are each independently selected from hydrogen, cycloalkyl$_{(C≤12)}$, fused cycloalkyl$_{(C≤12)}$, heterocycloalkyl$_{(C≤12)}$, -alkanediyl$_{(C≤12)}$-cycloalkyl$_{(C≤12)}$, or a substituted version of any of these groups; or $R_2$ and $R_3$ are taken together and are alkanediyl$_{(C≤12)}$, alkoxydiyl$_{(C≤12)}$, alkylthiodiyl$_{(C≤12)}$, or alkylaminodiyl$_{(C≤12)}$; $R_5$ is aryl$_{(C≤12)}$, aralkyl$_{(C≤12)}$, heteroaryl$_{(C≤12)}$, heteroaralkyl$_{(C≤12)}$, or a substituted version of any of these groups; or is -alkanediyl$_{(C≤6)}$-arenediyl$_{(C≤12)}$-$Y_3$ or a substituted version of any of these groups; wherein: $Y_3$ is alkoxy$_{(C≤12)}$, aryloxy$_{(C≤12)}$, an oxygen linked antibody, —C(O)-alkoxy$_{(C≤12)}$, —C(O)-alkylamino$_{(C≤12)}$, —C(O)-dialkylamino$_{(C≤12)}$, —C(O)-aryloxy$_{(C≤12)}$, —C(O)-arylamino$_{(C≤12)}$, —C(O)—$Y_4$; or a substituted version of any of these groups; wherein: $Y_4$ is a nitrogen or an oxygen linked antibody; and $R_6$ is hydrogen, alkyl$_{(C≤8)}$, or substituted alkyl$_{(C≤8)}$; $R_7$ is —C(O)—$Y_5$; wherein $Y_5$ is amino, hydroxy, alkoxy$_{(C≤12)}$, substituted alkoxy$_{(C≤12)}$, alkylamino$_{(C≤12)}$, substituted alkylamino$_{(C≤12)}$, dialkylamino$_{(C≤12)}$, substituted dialkylamino$_{(C≤12)}$, an oxygen linked antibody, or a nitrogen linked antibody; $X_1$ and $X_2$ are each independently selected from —O—, —S—, —NR$_8$—, or —NR$_9$NR$_{10}$—, wherein: $R_8$, $R_9$, and $R_{10}$ are each independently selected from hydrogen, alkyl$_{(C≤12)}$, substituted alkyl$_{(C≤12)}$, cycloalkyl$_{(C≤12)}$, or substituted cycloalkyl$_{(C≤12)}$; or a pharmaceutically acceptable salt thereof. In some embodiments, the formula is further defined as:

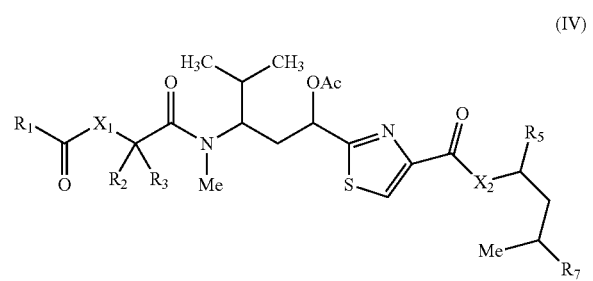

(IV)

wherein: $R_1$ is heteroaryl$_{(C≤12)}$, heterocycloalkyl$_{(C≤12)}$, arylamino$_{(C≤12)}$, aralkylamino$_{(C≤12)}$, alkanediyl$_{(C≤12)}$-$Y_2$, fused cycloalkyl$_{(C≤12)}$-$Y_2$, or a substituted version of any of these groups, wherein $Y_2$ is amino, alkylamino$_{(C≤12)}$, dialkylamino$_{(C≤12)}$, amido$_{(C≤12)}$, substituted alkylamino$_{(C≤12)}$, substituted dialkylamino$_{(C≤12)}$, or substituted amido$_{(C≤12)}$; $R_2$ and $R_3$ are each independently selected from hydrogen, cycloalkyl$_{(C≤12)}$, fused cycloalkyl$_{(C≤12)}$, heterocycloalkyl$_{(C≤12)}$, -alkanediyl$_{(C≤12)}$-cycloalkyl$_{(C≤12)}$, or a substituted version of any of these groups; or $R_2$ and $R_3$ are taken together and are alkanediyl$_{(C≤12)}$, alkoxydiyl$_{(C≤12)}$, alkylthiodiyl$_{(C≤12)}$, or alkylaminodiyl$_{(C≤12)}$; $R_5$ is aryl$_{(C≤12)}$, aralkyl$_{(C≤12)}$, heteroaryl$_{(C≤12)}$, heteroaralkyl$_{(C≤12)}$, or a substituted version of any of these groups; or is -alkanediyl$_{(C≤6)}$-arenediyl$_{(C≤12)}$-$Y_3$ or a substituted version of any of these groups; wherein: $Y_3$ is alkoxy$_{(C≤12)}$, aryloxy$_{(C≤12)}$, an oxygen linked antibody, —C(O)-alkoxy$_{(C≤12)}$, —C(O)-alkylamino$_{(C≤12)}$, —C(O)-dialkylamino$_{(C≤12)}$, —C(O)-aryloxy$_{(C≤12)}$, —C(O)-arylamino$_{(C≤12)}$, —C(O)—$Y_4$; or a substituted version of any of these groups; wherein: $Y_4$ is a nitrogen or an oxygen linked antibody; $R_7$ is —C(O)—$Y_5$; wherein $Y_5$ is amino, hydroxy, alkoxy$_{(C≤12)}$, substituted alkoxy$_{(C≤12)}$, alkylamino$_{(C≤12)}$, substituted alkylamino$_{(C≤12)}$, dialkylamino$_{(C≤12)}$, substituted dialkylamino$_{(C≤12)}$, an oxygen linked antibody, or a nitrogen linked antibody; and $X_1$ and $X_2$ are each independently selected from —O—, —S—, —NR$_8$—, or —NR$_9$NR$_{10}$—, wherein: $R_8$, $R_9$, and $R_{10}$ are each independently selected from hydrogen, alkyl$_{(C≤12)}$, substituted alkyl$_{(C≤12)}$, cycloalkyl$_{(C≤12)}$, or substituted cycloalkyl$_{(C≤12)}$; or a pharmaceutically acceptable salt thereof. In some embodiments, the formula is further defined as:

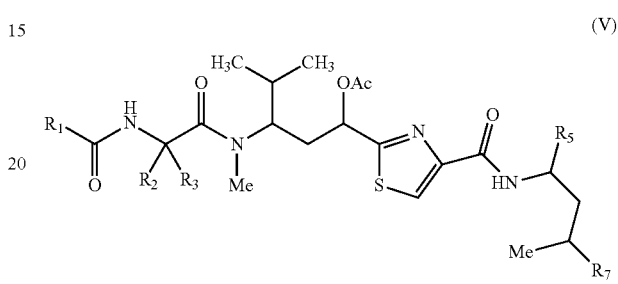

(V)

wherein: $R_1$ is heteroaryl$_{(C≤12)}$, heterocycloalkyl$_{(C≤12)}$, arylamino$_{(C≤12)}$, aralkylamino$_{(C≤12)}$, alkanediyl$_{(C≤12)}$-$Y_2$, fused cycloalkyl$_{(C≤12)}$-$Y_2$, or a substituted version of any of these groups, wherein $Y_2$ is amino, alkylamino$_{(C≤12)}$, dialkylamino$_{(C≤12)}$, amido$_{(C≤12)}$, substituted alkylamino$_{(C≤12)}$, substituted dialkylamino$_{(C≤12)}$, or substituted amido$_{(C≤12)}$; $R_2$ and $R_3$ are each independently selected from hydrogen, cycloalkyl$_{(C≤12)}$, fused cycloalkyl$_{(C≤12)}$, heterocycloalkyl$_{(C≤12)}$, -alkanediyl$_{(C≤12)}$-cycloalkyl$_{(C≤12)}$, or a substituted version of any of these groups; or $R_2$ and $R_3$ are taken together and are alkanediyl$_{(C≤12)}$, alkoxydiyl$_{(C≤12)}$, alkylthiodiyl$_{(C≤12)}$, or alkylaminodiyl$_{(C≤12)}$; $R_5$ is aryl$_{(C≤12)}$, aralkyl$_{(C≤12)}$, heteroaryl$_{(C≤12)}$, heteroaralkyl$_{(C≤12)}$, or a substituted version of any of these groups; or is -alkanediyl$_{(C≤6)}$-arenediyl$_{(C≤12)}$-$Y_3$ or a substituted version of any of these groups; wherein: $Y_3$ is alkoxy$_{(C≤12)}$, aryloxy$_{(C≤12)}$, an oxygen linked antibody, —C(O)-alkoxy$_{(C≤12)}$, —C(O)-alkylamino$_{(C≤12)}$, —C(O)-dialkylamino$_{(C≤12)}$, —C(O)-aryloxy$_{(C≤12)}$, —C(O)-arylamino$_{(C≤12)}$, —C(O)—$Y_4$; or a substituted version of any of these groups; wherein: $Y_4$ is a nitrogen or an oxygen linked antibody; and $R_7$ is —C(O)—$Y_5$; wherein $Y_5$ is amino, hydroxy, alkoxy$_{(C≤12)}$, substituted alkoxy$_{(C≤12)}$, alkylamino$_{(C≤12)}$, substituted alkylamino$_{(C≤12)}$, dialkylamino$_{(C≤12)}$, substituted dialkylamino$_{(C≤12)}$, an oxygen linked antibody, or a nitrogen linked antibody; or a pharmaceutically acceptable salt thereof. In some embodiments, the formula is further defined as:

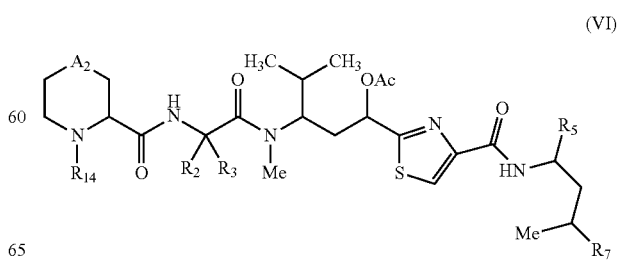

(VI)

wherein: $R_2$ and $R_3$ are each independently selected from hydrogen, cycloalkyl$_{(C\leq12)}$, fused cycloalkyl$_{(C\leq12)}$, heterocycloalkyl$_{(C\leq12)}$, -alkanediyl$_{(C\leq12)}$-cycloalkyl$_{(C\leq12)}$, or a substituted version of any of these groups; or $R_2$ and $R_3$ are taken together and are alkanediyl$_{(C\leq12)}$, alkoxydiyl$_{(C\leq12)}$, alkylthiodiyl$_{(C\leq12)}$, or alkylaminodiyl$_{(C\leq12)}$; $R_5$ is aryl$_{(C\leq12)}$, aralkyl$_{(C\leq12)}$, heteroaryl$_{(C\leq12)}$, heteroaralkyl$_{(C\leq12)}$, or a substituted version of any of these groups; or is -alkanediyl$_{(C\leq6)}$-arenediyl$_{(C\leq12)}$-$Y_3$ or a substituted version of any of these groups; wherein: $Y_3$ is alkoxy$_{(C\leq12)}$, aryloxy$_{(C\leq12)}$, an oxygen linked antibody, —C(O)-alkoxy$_{(C\leq12)}$, —C(O)-alkylamino$_{(C\leq12)}$, —C(O)-dialkylamino$_{(C\leq12)}$, —C(O)-aryloxy$_{(C\leq12)}$, —C(O)-arylamino$_{(C\leq12)}$, —C(O)—$Y_4$; or a substituted version of any of these groups; wherein: $Y_4$ is a nitrogen or an oxygen linked antibody; $R_7$ is —C(O)—$Y_5$; wherein $Y_5$ is amino, hydroxy, alkoxy$_{(C\leq12)}$, substituted alkoxy$_{(C\leq12)}$, alkylamino$_{(C\leq12)}$, substituted alkylamino$_{(C\leq12)}$, dialkylamino$_{(C\leq12)}$, substituted dialkylamino$_{(C\leq12)}$, an oxygen linked antibody, or a nitrogen linked antibody; $A_2$ is —CH$_2$—, —CHR$_{15}$—, —O—, —NH—, or —NMe-; and $R_{14}$ is alkyl$_{(C\leq6)}$ or substituted alkyl$_{(C\leq6)}$; wherein $R_{14}$ and $R_{15}$ are taken together and are alkanediyl$_{(C\leq6)}$ or substituted alkanediyl$_{(C\leq6)}$; or a pharmaceutically acceptable salt thereof. In some embodiments, the formula is further defined as:

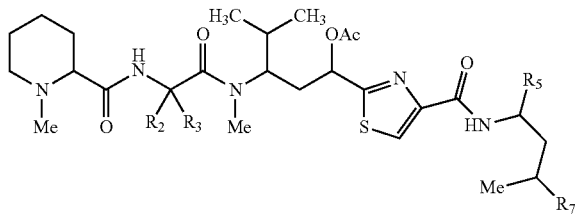

(VII)

wherein: $R_2$ and $R_3$ are each independently selected from hydrogen, cycloalkyl$_{(C\leq12)}$, fused cycloalkyl$_{(C\leq12)}$, heterocycloalkyl$_{(C\leq12)}$, -alkanediyl$_{(C\leq12)}$-cycloalkyl$_{(C\leq12)}$, or a substituted version of any of these groups; or $R_2$ and $R_3$ are taken together and are alkanediyl$_{(C\leq12)}$, alkoxydiyl$_{(C\leq12)}$, alkylthiodiyl$_{(C\leq12)}$, or alkylaminodiyl$_{(C\leq12)}$; $R_5$ is aryl$_{(C\leq12)}$, aralkyl$_{(C\leq12)}$, heteroaryl$_{(C\leq12)}$, heteroaralkyl$_{(C\leq12)}$, or a substituted version of any of these groups; or is -alkanediyl$_{(C\leq6)}$-arenediyl$_{(C\leq12)}$-$Y_3$ or a substituted version of any of these groups; wherein: $Y_3$ is alkoxy$_{(C\leq12)}$, aryloxy$_{(C\leq12)}$, an oxygen linked antibody, —C(O)-alkoxy$_{(C\leq12)}$, —C(O)-alkylamino$_{(C\leq12)}$, —C(O)-dialkylamino$_{(C\leq12)}$, —C(O)-aryloxy$_{(C\leq12)}$, —C(O)-arylamino$_{(C\leq12)}$, —C(O)—$Y_4$; or a substituted version of any of these groups; wherein: $Y_4$ is a nitrogen or an oxygen linked antibody; and $R_7$ is —C(O)—$Y_5$; wherein $Y_5$ is amino, hydroxy, alkoxy$_{(C\leq12)}$, substituted alkoxy$_{(C\leq12)}$, alkylamino$_{(C\leq12)}$, substituted alkylamino$_{(C\leq12)}$, dialkylamino$_{(C\leq12)}$, substituted dialkylamino$_{(C\leq12)}$, an oxygen linked antibody, or a nitrogen linked antibody; or a pharmaceutically acceptable salt thereof. In some embodiments, the formula is further defined as:

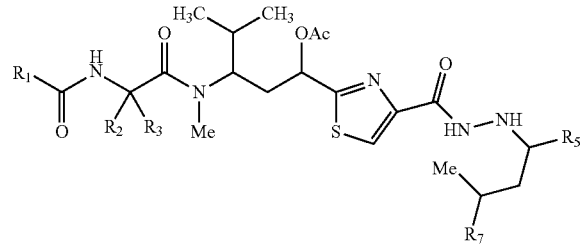

(VIII)

wherein: $R_1$ is heteroaryl$_{(C\leq12)}$, heterocycloalkyl$_{(C\leq12)}$, alkanediyl$_{(C\leq12)}$-$Y_2$, fused cycloalkyl$_{(C\leq12)}$-$Y_2$, or a substituted version of any of these groups, wherein $Y_2$ is amino, alkylamino$_{(C\leq12)}$, dialkylamino$_{(C\leq12)}$, amido$_{(C\leq12)}$, substituted alkylamino$_{(C\leq12)}$, substituted dialkylamino$_{(C\leq12)}$, or substituted amido$_{(C\leq12)}$; $R_2$ and $R_3$ are each independently selected from hydrogen, alkyl$_{(C\leq12)}$, cycloalkyl$_{(C\leq12)}$, fused cycloalkyl$_{(C\leq12)}$, heterocycloalkyl$_{(C\leq12)}$, -alkanediyl$_{(C\leq12)}$-cycloalkyl$_{(C\leq12)}$, or a substituted version of any of these groups; or $R_2$ and $R_3$ are taken together and are alkanediyl$_{(C\leq12)}$, alkoxydiyl$_{(C\leq12)}$, alkylthiodiyl$_{(C\leq12)}$, or alkylaminodiyl$_{(C\leq12)}$; $R_5$ is aryl$_{(C\leq12)}$, aralkyl$_{(C\leq12)}$, heteroaryl$_{(C\leq12)}$, heteroaralkyl$_{(C\leq12)}$, or a substituted version of any of these groups; or is -alkanediyl$_{(C\leq8)}$-arenediyl$_{(C\leq12)}$-$Y_3$ or a substituted version of any of these groups; wherein: $Y_3$ is alkoxy$_{(C\leq12)}$, aryloxy$_{(C\leq12)}$, an oxygen linked antibody, —C(O)-alkoxy$_{(C\leq12)}$, —C(O)-alkylamino$_{(C\leq12)}$, —C(O)-dialkylamino$_{(C\leq12)}$, —C(O)-aryloxy$_{(C\leq12)}$, —C(O)-arylamino$_{(C\leq12)}$, —C(O)—$Y_4$; or a substituted version of any of these groups; wherein: $Y_4$ is a nitrogen or an oxygen linked antibody; and $R_7$ is —C(O)—$Y_5$; wherein $Y_5$ is amino, hydroxy, alkoxy$_{(C\leq12)}$, substituted alkoxy$_{(C\leq12)}$, alkylamino$_{(C\leq12)}$, substituted alkylamino$_{(C\leq12)}$, dialkylamino$_{(C\leq12)}$, substituted dialkylamino$_{(C\leq12)}$, an oxygen linked antibody, or a nitrogen linked antibody; or a pharmaceutically acceptable salt thereof. In some embodiments, the formula is further defined as:

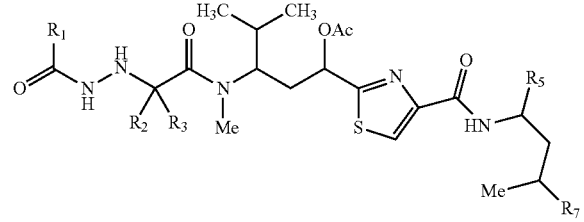

(IX)

wherein: $R_1$ is heteroaryl$_{(C\leq12)}$, heterocycloalkyl$_{(C\leq12)}$, alkanediyl$_{(C\leq12)}$-$Y_2$, fused cycloalkyl$_{(C\leq12)}$-$Y_2$, or a substituted version of any of these groups, wherein $Y_2$ is amino, alkylamino$_{(C\leq12)}$, dialkylamino$_{(C\leq12)}$, amido$_{(C\leq12)}$, substituted alkylamino$_{(C\leq12)}$, substituted dialkylamino$_{(C\leq12)}$, or substituted amido$_{(C\leq12)}$; $R_2$ and $R_3$ are each independently selected from hydrogen, alkyl$_{(C\leq12)}$, cycloalkyl$_{(C\leq12)}$, fused cycloalkyl$_{(C\leq12)}$, heterocycloalkyl$_{(C\leq12)}$, -alkanediyl$_{(C\leq12)}$-cycloalkyl$_{(C\leq12)}$, or a substituted version of any of these groups; or $R_2$ and $R_3$ are taken together and are alkanediyl$_{(C\leq12)}$, alkoxydiyl$_{(C\leq12)}$, alkylthiodiyl$_{(C\leq12)}$, or alkylaminodiyl$_{(C\leq12)}$; $R_5$ is aryl$_{(C\leq12)}$, aralkyl$_{(C\leq12)}$, heteroaryl$_{(C\leq12)}$, heteroaralkyl$_{(C\leq12)}$, or a substituted version of any of these groups; or is -alkanediyl$_{(C≤6)}$-arenediyl$_{(C≤12)}$-Y$_3$ or a substituted version of any of these groups; wherein: Y$_3$ is alkoxy$_{(C≤12)}$, aryloxy$_{(C≤12)}$, an oxygen linked antibody, —C(O)-alkoxy$_{(C≤12)}$, —C(O)-alkylamino$_{(C≤12)}$, —C(O)-dialkylamino$_{(C≤12)}$, —C(O)-aryloxy$_{(C≤12)}$, —C(O)-arylamino$_{(C≤12)}$, —C(O)—Y$_4$; or a substituted version of any of these groups; wherein: Y$_4$ is a nitrogen or an oxygen linked antibody; and R$_7$ is —C(O)—Y$_5$; wherein Y$_5$ is amino, hydroxy, alkoxy$_{(C≤12)}$, substituted alkoxy$_{(C≤12)}$, alkylamino$_{(C≤12)}$, substituted alkylamino$_{(C≤12)}$, dialkylamino$_{(C≤12)}$, substituted dialkylamino$_{(C≤12)}$, an oxygen linked antibody, or a nitrogen linked antibody; or a pharmaceutically acceptable salt thereof. In some embodiments, the formula is further defined as:

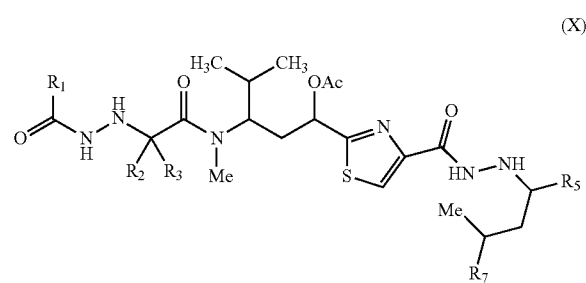

(X)

wherein: R$_1$ is heteroaryl$_{(C≤12)}$, heterocycloalkyl$_{(C≤12)}$, alkanediyl$_{(C≤12)}$-Y$_2$, fused cycloalkyl$_{(C≤12)}$-Y$_2$, or a substituted version of any of these groups, wherein Y$_2$ is amino, alkylamino$_{(C≤12)}$, dialkylamino$_{(C≤12)}$, amido$_{(C≤12)}$, substituted alkylamino$_{(C≤12)}$, substituted dialkylamino)$_{(C≤12)}$, or substituted amido$_{(C≤12)}$; R$_2$ and R$_3$ are each independently selected from hydrogen, alkyl$_{(C≤12)}$, cycloalkyl$_{(C≤12)}$, fused cycloalkyl$_{(C≤12)}$, heterocycloalkyl$_{(C≤12)}$, -alkanediyl$_{(C≤12)}$-cycloalkyl$_{(C≤12)}$, or a substituted version of any of these groups; or R$_2$ and R$_3$ are taken together and are alkanediyl$_{(C≤12)}$, alkoxydiyl$_{(C≤12)}$, alkylthiodiyl$_{(C≤12)}$, or alkylaminodiyl$_{(C≤12)}$; R$_5$ is aryl$_{(C≤12)}$, aralkyl$_{(C≤12)}$, heteroaryl$_{(C≤12)}$, heteroaralkyl$_{(C≤12)}$, or a substituted version of any of these groups; or is -alkanediyl$_{(C≤8)}$, -arenediyl$_{(C≤12)}$-Y$_3$ or a substituted version of any of these groups; wherein: Y$_3$ is alkoxy$_{(C≤12)}$, aryloxy$_{(C≤12)}$, an oxygen linked antibody, —C(O)-alkoxy$_{(C≤12)}$, —C(O)-alkylamino$_{(C≤12)}$, —C(O)-dialkylamino$_{(C≤12)}$, —C(O)-aryloxy$_{(C≤12)}$, —C(O)-arylamino$_{(C≤12)}$, —C(O)—Y$_4$; or a substituted version of any of these groups; wherein: Y$_4$ is a nitrogen or an oxygen linked antibody; and R$_7$ is —C(O)—Y$_5$; wherein Y$_5$ is amino, hydroxy, alkoxy$_{(C≤12)}$, substituted alkoxy$_{(C≤12)}$, alkylamino$_{(C≤12)}$, substituted alkylamino$_{(C≤12)}$, dialkylamino$_{(C≤12)}$, substituted dialkylamino$_{(C≤12)}$, an oxygen linked antibody, or a nitrogen linked antibody; or a pharmaceutically acceptable salt thereof.

In some embodiments, R$_1$ is heterocycloalkyl$_{(C≤12)}$ or substituted heterocycloalkyl$_{(C≤12)}$. In some embodiments, R$_1$ is 2-N-methyl-pyrrolidinyl, 2-N-methyl-morpholinyl, 2-N-methyl-piperidinyl, 2-N-ethyl-piperidinyl, 2-N-isopropyl-piperidinyl, 2-quinuclidinyl, 2-N,N'-dimethyl-piperazinyl, or 2-N-methyl-azepanyl. In some embodiments, R$_1$ is 2-N-methyl-piperidinyl, 2-N-ethyl-piperidinyl, or 2-N-isopropyl-piperidinyl.

In some embodiments, R$_2$ is cycloalkyl$_{(C≤12)}$ or substituted cycloalkyl$_{(C≤12)}$. In some embodiments, R$_2$ is cyclopropyl or cyclobutyl. In some embodiments, R$_2$ is cyclopropyl. In other embodiments, R$_2$ is heterocycloalkyl$_{(C≤12)}$ or substituted heterocycloalkyl$_{(C≤12)}$. In some embodiments, R$_2$ is oxetanyl or thietanyl. In other embodiments, R$_2$ is fused cycloalkyl$_{(C≤12)}$ or substituted fused cycloalkyl$_{(C≤12)}$. In some embodiments, R$_2$ is 3-t-butylpropellanyl or 3-trifluoromethylpropellanyl. In other embodiments, R$_2$ is -alkanediyl$_{(C≤12)}$-cycloalkyl$_{(C≤12)}$ or a substituted version thereof. In some embodiments, the alkanediyl$_{(C≤12)}$ or substituted alkanediyl$_{(C≤12)}$ is —CH$_2$— or —CH(CH$_3$)—. In some embodiments, the cycloalkyl$_{(C≤12)}$ or substituted cycloalkyl$_{(C≤12)}$ is cyclopropyl. In some embodiments, R$_2$ is alkyl$_{(C≤12)}$ or substituted alkyl$_{(C≤12)}$. In other embodiments, R$_2$ is alkyl$_{(C≤12)}$. In some embodiments, R$_2$ is butyl. In other embodiments, R$_2$ is aryl$_{(C≤12)}$ or substituted aryl$_{(C≤12)}$. In some embodiments, R$_2$ is phenyl or 4-fluorophenyl. In some embodiments, R$_2$ is sec-butyl. In other embodiments, R$_2$ is substituted alkyl$_{(C≤12)}$. In some embodiments, R$_2$ is 2,2,2-trifluoroethyl or 2,2,2,2',2',2'-hexafluoroisopropyl. In other embodiments, R$_2$ and R$_3$ are taken together and are alkanediyl$_{(C≤12)}$ or substituted alkanediyl$_{(C≤12)}$. In some embodiments, R$_2$ and R$_3$ are taken together and are alkanediyl$_{(C≤12)}$. In some embodiments, R$_2$ and R$_3$ are taken together and are —CH$_2$CH$_2$— or —CH$_2$CH$_2$CH$_2$—. In other embodiments, R$_2$ and R$_3$ are taken together and are alkoxydiyl$_{(C≤12)}$ or substituted alkoxydiyl$_{(C≤12)}$. In some embodiments, R$_2$ and R$_3$ are taken together and are —CH$_2$OCH$_2$—. In other embodiments, R$_2$ and R$_3$ are taken together and are alkylthiodiyl$_{(C≤12)}$ or substituted alkylthiodiyl$_{(C≤12)}$. In some embodiments, R$_2$ and R$_3$ are taken together and are —CH$_2$SCH$_2$—. In some embodiments, R$_3$ is hydrogen.

In some embodiments, R$_4$ is fused cycloalkylamino$_{(C≤12)}$ or substituted fused cycloalkylamino$_{(C≤12)}$. In some embodiments, R$_4$ is 1-(4-methyl carboxylatecubanyl)amino or 1-(3-methyl carboxylatepropellanyl)amino. In other embodiments, R$_4$ is cycloalkyl$_{(C≤12)}$ or substituted cycloalkyl$_{(C≤12)}$. In some embodiments, R$_4$ is substituted cycloalkyl$_{(C≤12)}$ such as 4-carboxycyclohexyl or 4-methyl carboxylatecyclohexyl. In other embodiments, R$_4$ is fused cycloalkyl$_{(C≤12)}$ or substituted fused cycloalkyl$_{(C≤12)}$ such as 4-methyl carboxylatecubanyl, 3-carboxymethyl carboxylatepropellanyl, or 3-methyl carboxylatepropellanyl. In other embodiments, R$_4$ is:

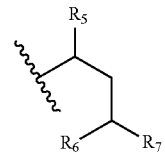

wherein: R$_5$ is aryl$_{(C≤12)}$, aralkyl$_{(C≤12)}$, heteroaryl$_{(C≤12)}$, heteroaralkyl$_{(C≤12)}$, or a substituted version of any of these groups; or is -alkanediyl(c)-arenediyl$_{(C≤12)}$-Y$_3$ or a substituted version of any of these groups; wherein: Y$_3$ is alkoxy$_{(C≤12)}$, aryloxy$_{(C≤12)}$, an oxygen linked antibody, —C(O)-alkoxy$_{(C≤12)}$, —C(O)-alkylamino$_{(C≤12)}$, —C(O)-dialkylamino$_{(C≤12)}$, —C(O)-aryloxy$_{(C≤12)}$, —C(O)-arylamino$_{(C≤12)}$, —C(O)—Y$_4$; or a substituted version of any of these groups; wherein: Y$_4$ is a nitrogen linked antibody or an oxygen linked antibody; R$_6$ is hydrogen, alkyl$_{(C≤8)}$, or substituted alkyl$_{(C≤8)}$; R$_7$ is —C(O)—Y$_5$; wherein Y$_5$ is amino, hydroxy, alkoxy$_{(C≤12)}$, substituted alkoxy$_{(C≤12)}$, alkylamino$_{(C≤12)}$, substituted alkylamino$_{(C≤12)}$, dialkylamino$_{(C≤12)}$, substituted dialkylamino$_{(C≤12)}$, an oxygen linked antibody, or a nitrogen linked antibody. In other embodiments, R$_4$ is:

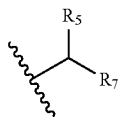

wherein: $R_5$ is aryl$_{(C\le12)}$, aralkyl$_{(C\le12)}$, heteroaryl$_{(C\le12)}$, heteroaralkyl$_{(C\le12)}$, or a substituted version of any of these groups; or is -alkanediyl$_{(C\le6)}$-arenediyl$_{(C\le12)}$-$Y_3$ or a substituted version of any of these groups; wherein: $Y_3$ is alkoxy$_{(C\le12)}$, aryloxy$_{(C\le12)}$, an oxygen linked antibody, —C(O)-alkoxy$_{(C\le12)}$, —C(O)-alkylamino$_{(C\le12)}$, —C(O)-dialkylamino$_{(C\le12)}$, —C(O)-aryloxy$_{(C\le12)}$, —C(O)-arylamino$_{(C\le12)}$, —C(O)—$Y_4$; or a substituted version of any of these groups; wherein: $Y_4$ is a nitrogen linked antibody or an oxygen linked antibody; and $R_7$ is —C(O)—$Y_5$; wherein $Y_5$ is amino, hydroxy, alkoxy$_{(C\le12)}$, substituted alkoxy$_{(C\le12)}$, alkylamino$_{(C\le12)}$, substituted alkylamino$_{(C\le12)}$, dialkylamino$_{(C\le12)}$, substituted dialkylamino$_{(C\le12)}$, an oxygen linked antibody, or a nitrogen linked antibody.

In some embodiments, $R_5$ is aralkyl$_{(C\le12)}$ or substituted aralkyl$_{(C\le12)}$. In some embodiments, $R_5$ is aralkyl$_{(C\le12)}$. In some embodiments, $R_5$ is benzyl. In other embodiments, $R_5$ is substituted aralkyl$_{(C\le12)}$. In some embodiments, $R_5$ is 2-fluorophenylmethyl, 3,5-difluorophenylmethyl, 2,4,6-trifluorophenylmethyl, 4-trifluoromethylphenylmethyl. In other embodiments, $R_5$ is heteroaralkyl$_{(C\le12)}$ or substituted heteroaralkyl$_{(C\le12)}$. In other embodiments, $R_5$ is heteroaralkyl$_{(C\le12)}$. In some embodiments, $R_5$ is 4-pyridinylmethyl, 5-(N-methylindolyl)methyl, 2-pyrimidinylmethyl, 2-(5-methylpyrimidinyl)methyl, 2-thiazolylmethyl, or 2-(4-methylthiazolyl)methyl. In other embodiments, $R_5$ is substituted heteroaralkyl$_{(C\le12)}$. In some embodiments, $R_5$ is 2-(5-trifluoromethylpyrimidinyl)methyl or 2-(4-trifluoromethylthiazolyl)methyl.

In some embodiments, $R_6$ is alkyl$_{(C\le12)}$ or substituted alkyl$_{(C\le12)}$. In some embodiments, $R_6$ is alkyl$_{(C\le12)}$. In some embodiments, $R_6$ is methyl. In some embodiments, $R_7$ is —CO$_2$H. In other embodiments, $R_7$ is —C(O)—$Y_5$ wherein $Y_5$ is alkoxy$_{(C\le12)}$ or substituted alkoxy$_{(C\le12)}$. In some embodiments, $R_7$ is —C(O)—$Y_5$ wherein $Y_5$ is alkoxy$_{(C\le12)}$. In some embodiments, $R_7$ is —CO$_2$Me. In other embodiments, $R_7$ is —C(O)—$Y_5$ wherein $Y_5$ is an oxygen linked antibody or a nitrogen linked antibody.

In some embodiments, $X_1$ is —NR$_8$—, wherein $R_8$ is hydrogen, alkyl$_{(C\le12)}$, substituted alkyl$_{(C\le12)}$, cycloalkyl$_{(C\le12)}$), or substituted cycloalkyl$_{(C\le12)}$. In some embodiments, $X_1$ is —NH—. In other embodiments, $X_1$ is —NR$_9$NR$_{10}$—, wherein $R_9$ and $R_{10}$ are each independently selected from hydrogen, alkyl$_{(C\le12)}$, substituted alkyl$_{(C\le12)}$, cycloalkyl$_{(C\le12)}$, or substituted cycloalkyl$_{(C\le12)}$. In some embodiments, $X_1$ is —NHNH—. In some embodiments, $X_2$ is —NR$_8$—, wherein $R_8$ is hydrogen, alkyl$_{(C\le12)}$, substituted alkyl$_{(C\le12)}$, cycloalkyl$_{(C\le12)}$, or substituted cycloalkyl$_{(C\le12)}$. In some embodiments, $X_2$ is —NH—. In other embodiments, $X_2$ is —NR$_9$NR$_{10}$—, wherein $R_9$ and $R_{10}$ are each independently selected from hydrogen, alkyl$_{(C\le12)}$, substituted alkyl$_{(C\le12)}$, cycloalkyl$_{(C\le12)}$, or substituted cycloalkyl$_{(C\le12)}$. In some embodiments, $X_2$ is —NHNH—.

In some embodiments, $X_3$ is alkyl$_{(C\le12)}$ or substituted alkyl$_{(C\le12)}$. In some embodiments, $X_3$ is alkyl$_{(C\le12)}$. In some embodiments, $X_3$ is methyl. In some embodiments, $A_1$ is —C(O)NR$_{13}$-fused cycloalkanediyl$_{(C\le12)}$ or a substituted version thereof. In some embodiments, $A_1$ is —C(O)NH-cubanyl or —C(O)NH-propellanyl. In other embodiments, $A_1$ is -alkanediyl$_{(C\le12)}$-heteroarenediyl$_{(C\le12)}$, wherein the alkanediyl is substituted with an amido$_{(C\le8)}$ or acyloxy$_{(C\le8)}$ group or a substituted version thereof. In some embodiments, the heteroarenediyl$_{(C\le12)}$ is 2,4-thiazolediyl. In some embodiments, the alkanediyl$_{(C\le12)}$ is a ethylene or a substituted ethylene further substituted with an amido$_{(C\le8)}$, or acyloxy$_{(C\le8)}$ group or a substituted version of either of these two groups. In some embodiments, the alkanediyl$_{(C\le12)}$ is ethylene substituted with an acyloxy$_{(C\le12)}$ or a substituted acyloxy$_{(C\le12)}$. In some embodiments, the alkanediyl$_{(C\le12)}$ is —CH$_2$CH(OAc)—. In some embodiments, $X_4$ is acyloxy$_{(C\le12)}$ or substituted acyloxy$_{(C\le12)}$. In some embodiments, $X_4$ is acetyl.

In some embodiments, the formula is further defined as:

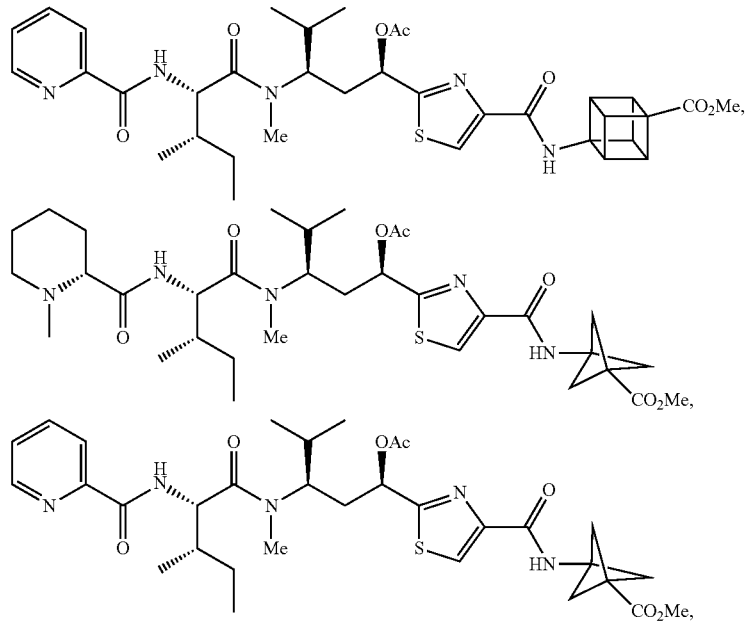

-continued
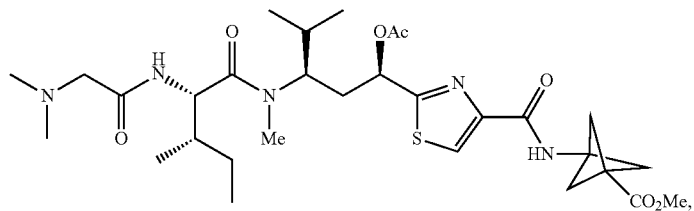
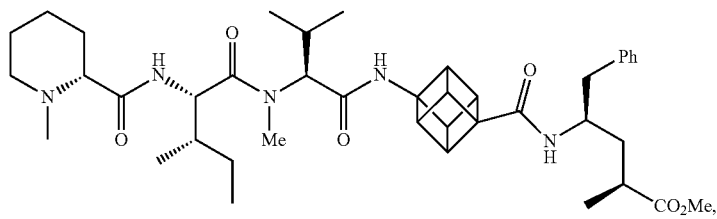
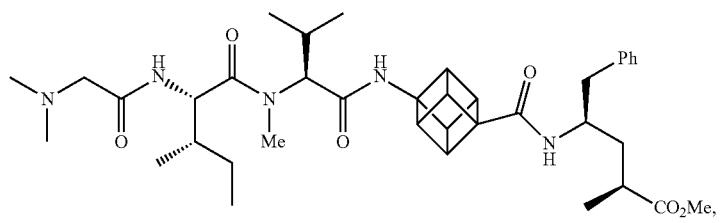
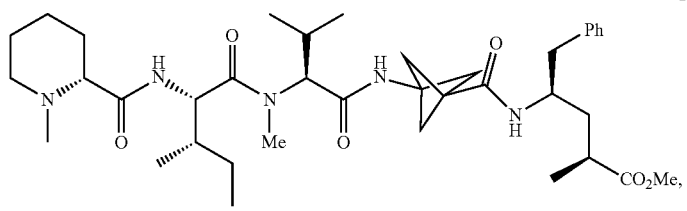
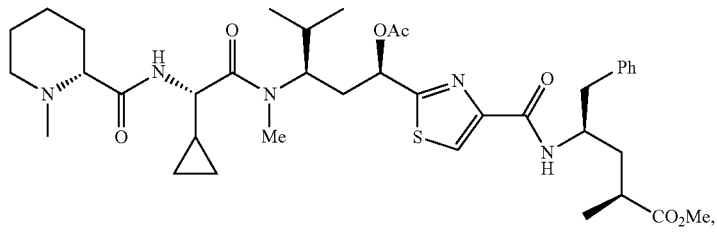
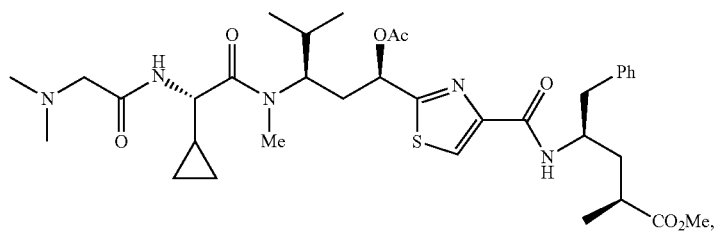
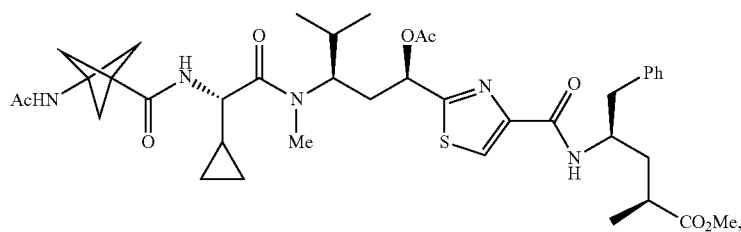

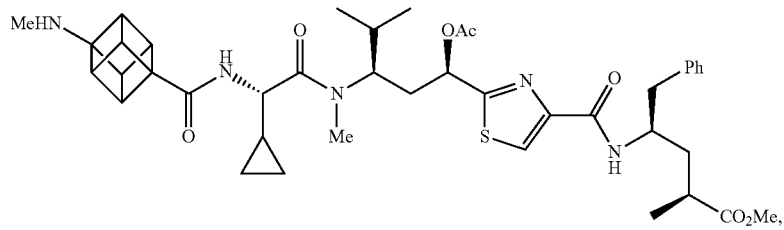
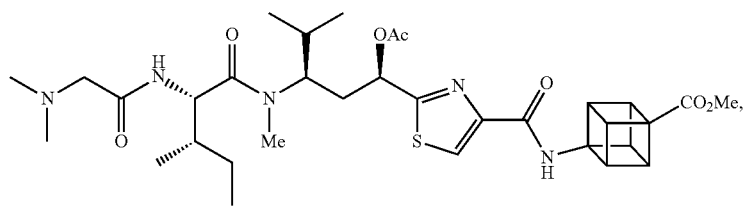
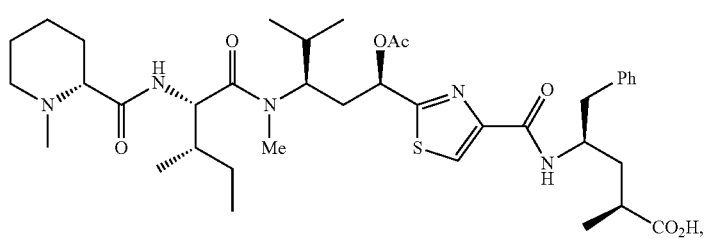
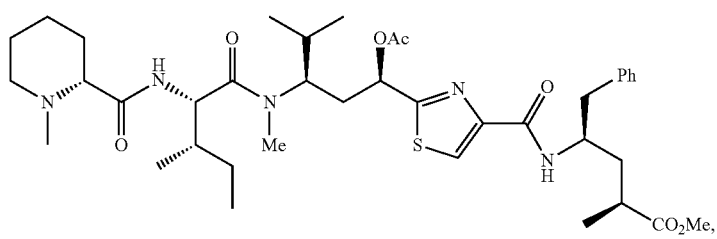
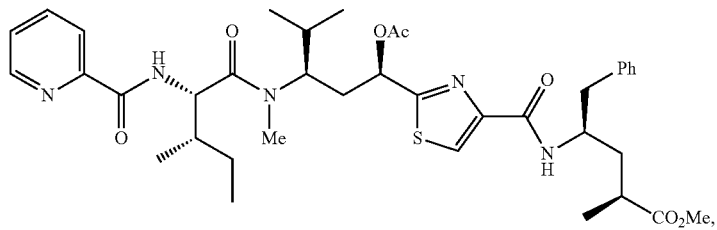
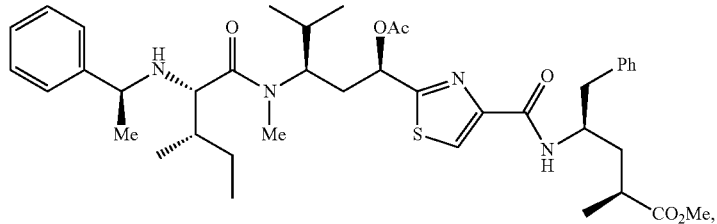
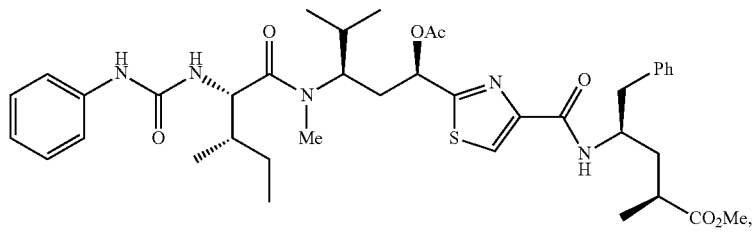

-continued
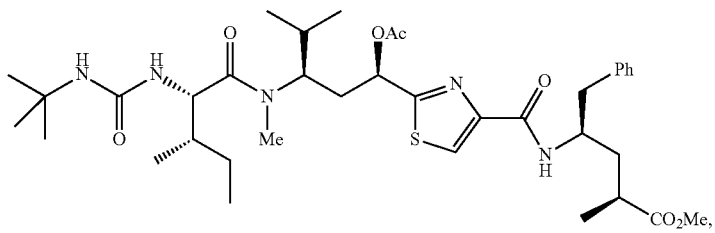
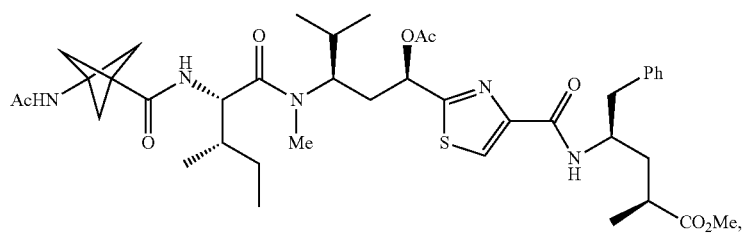
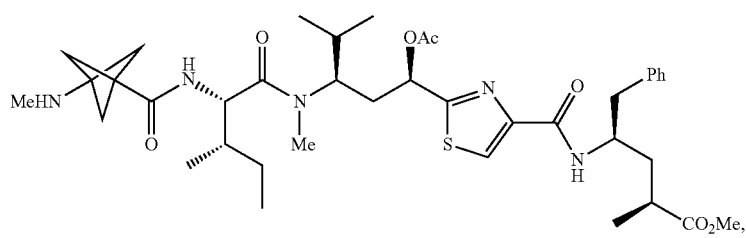
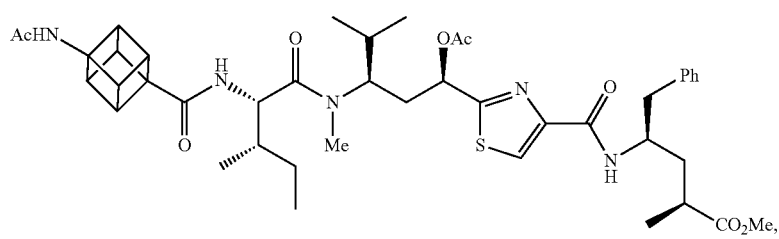
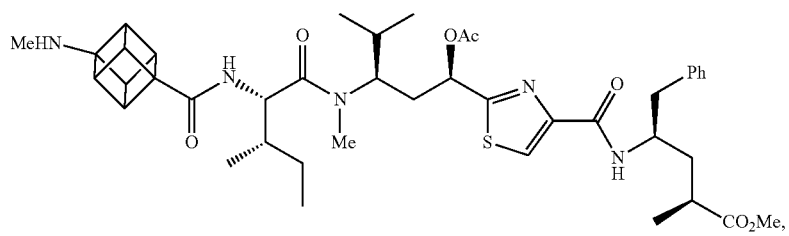
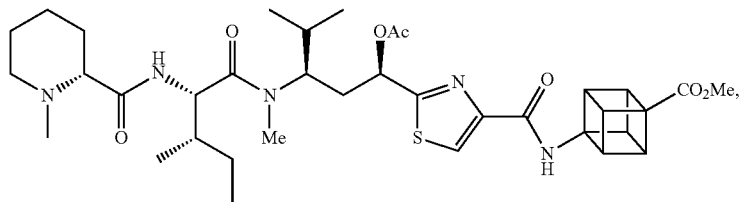
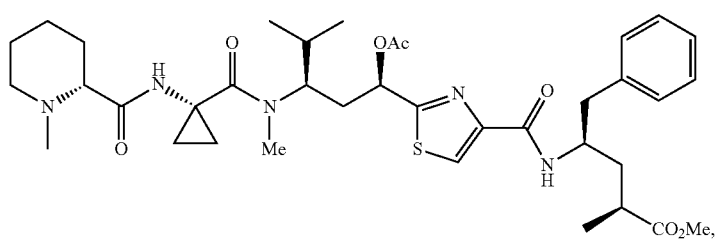

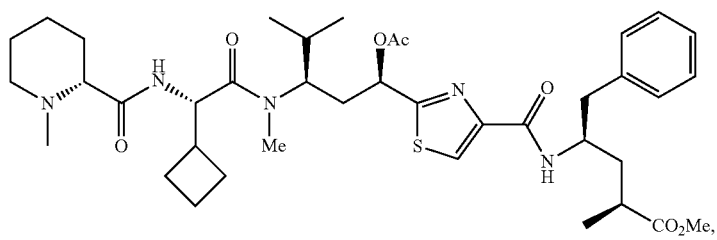
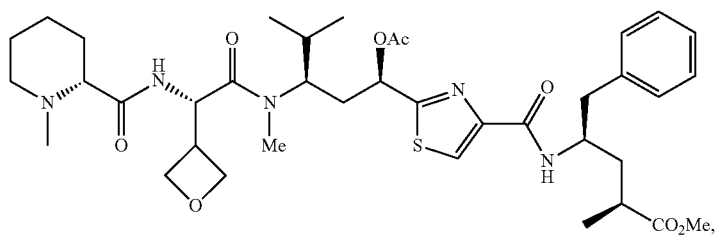
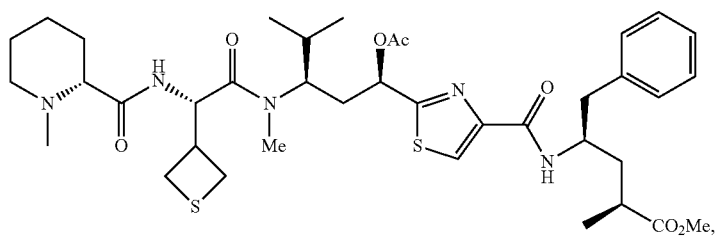
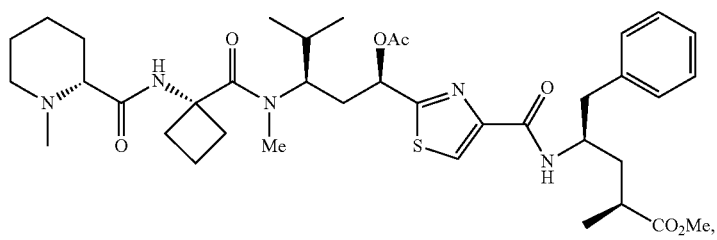
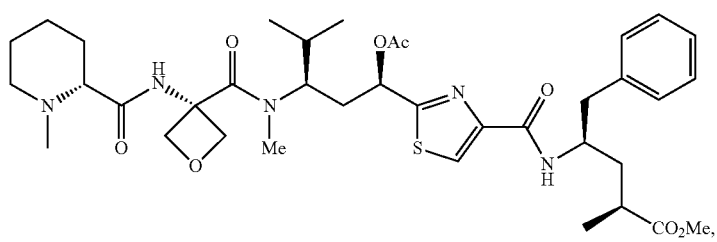
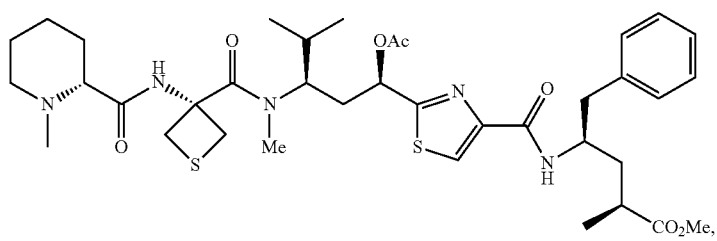

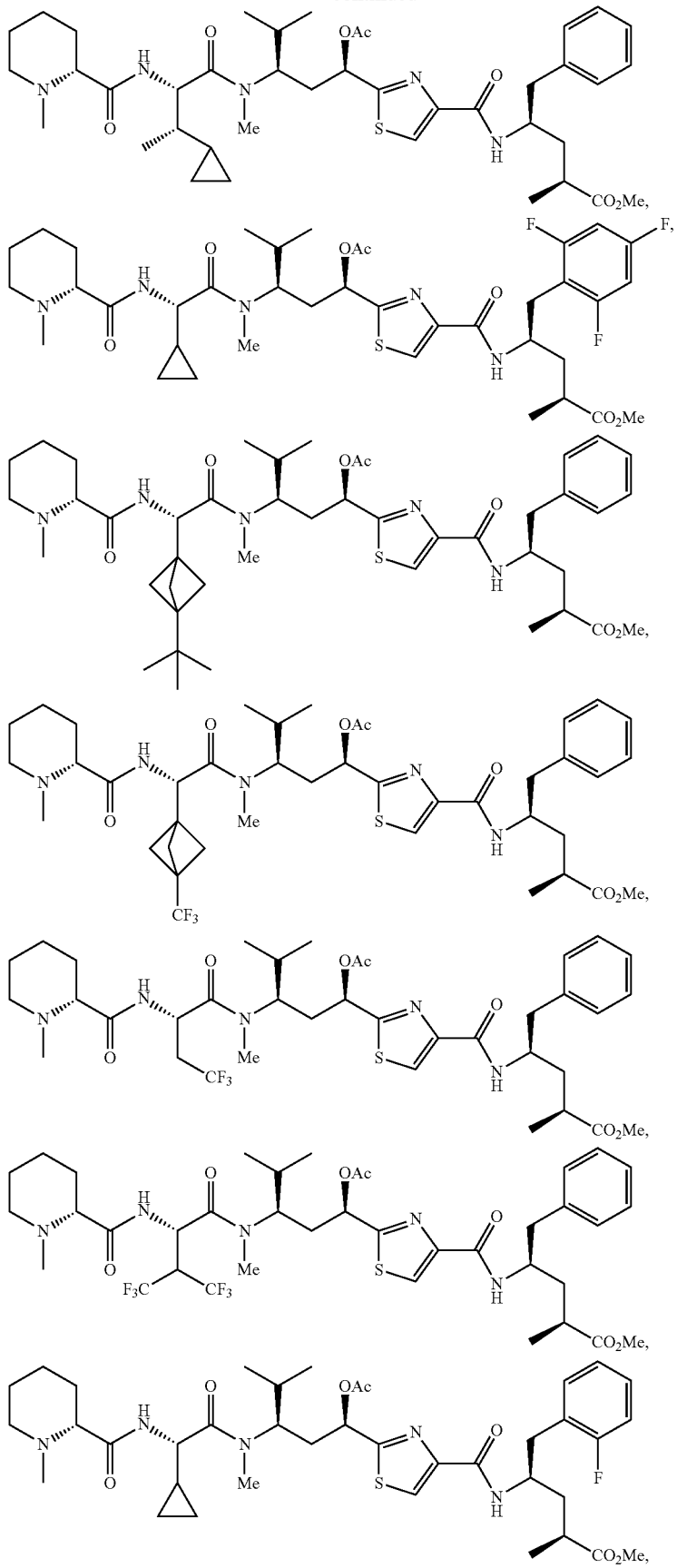

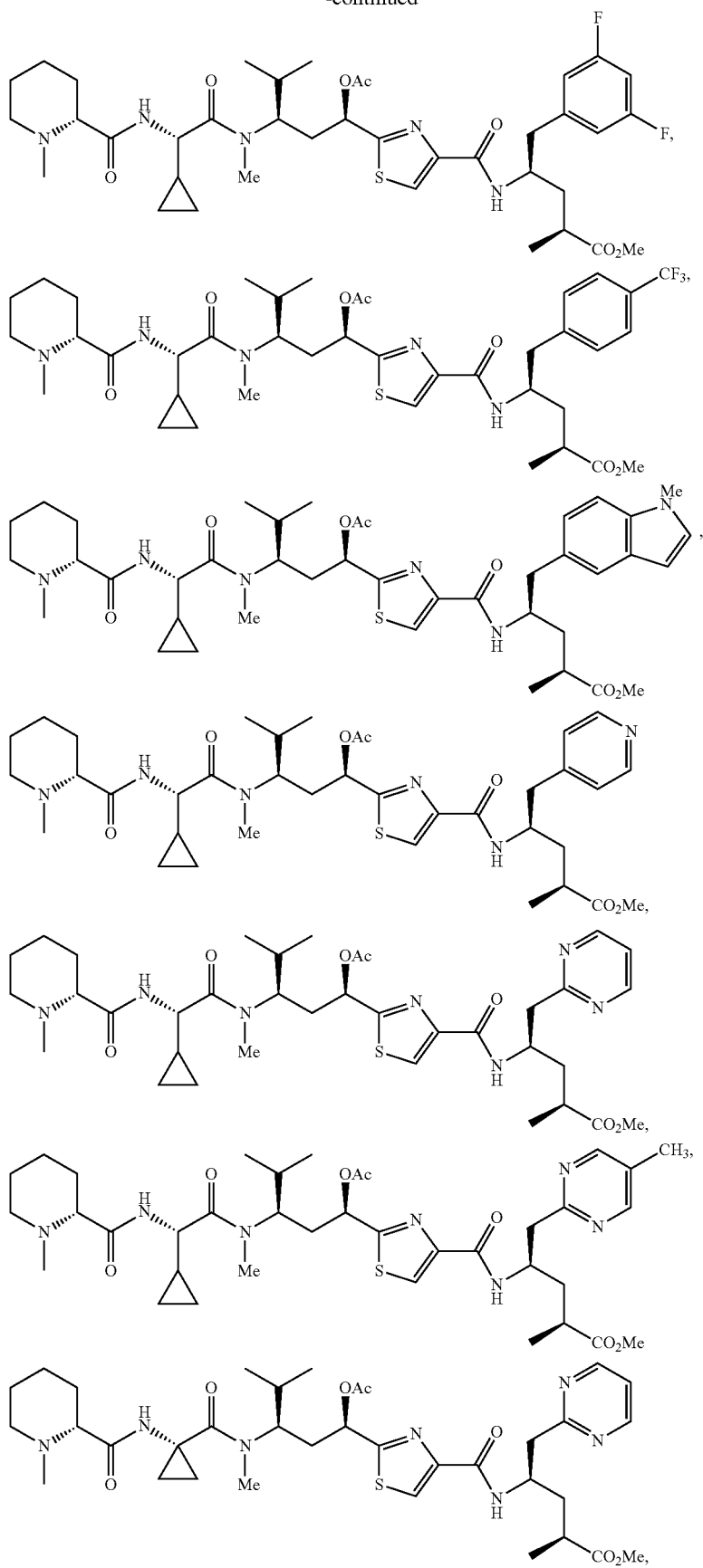

-continued
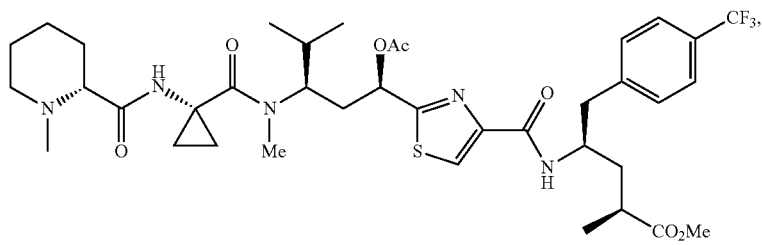
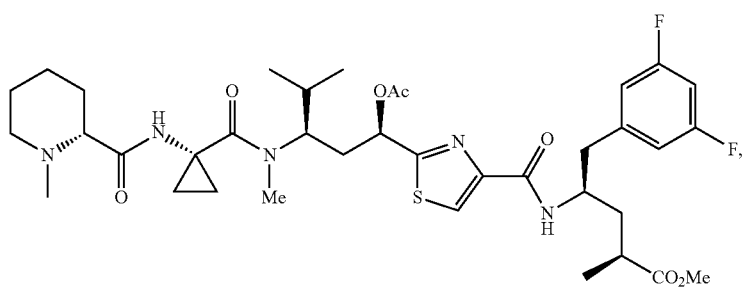
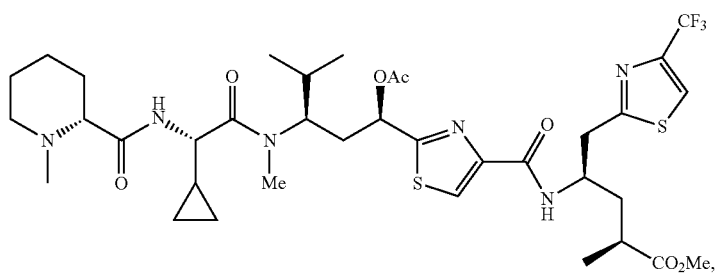
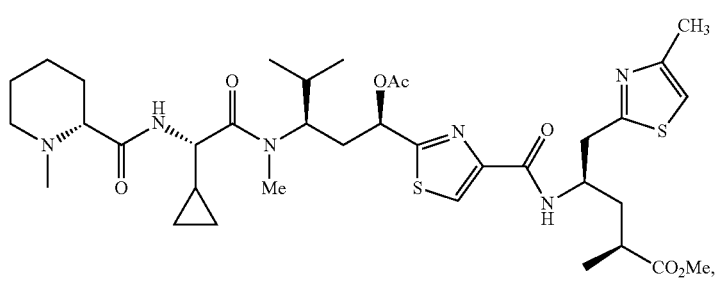
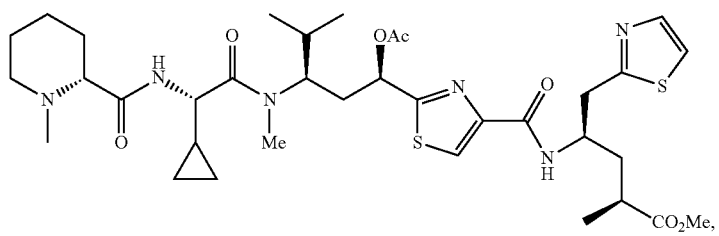
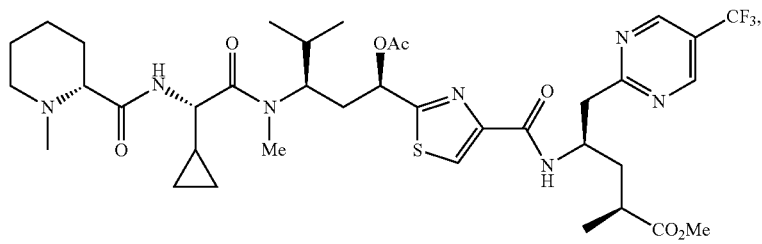

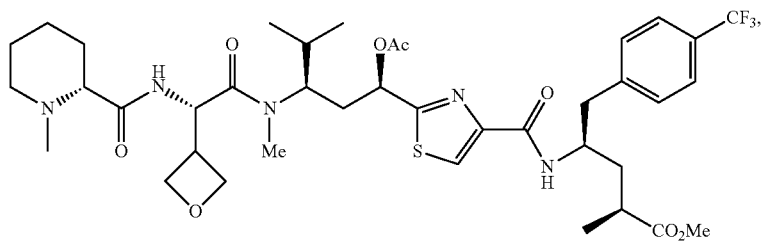
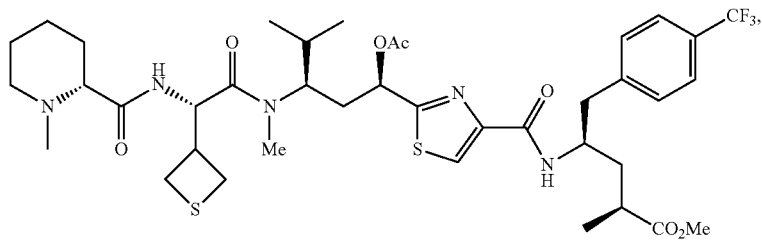
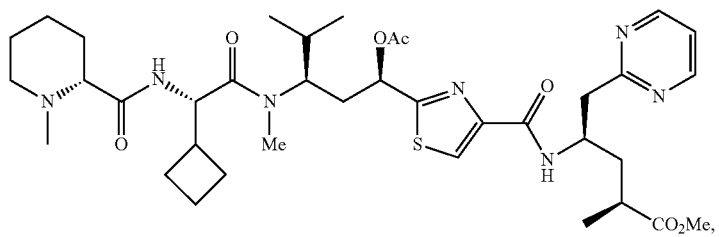
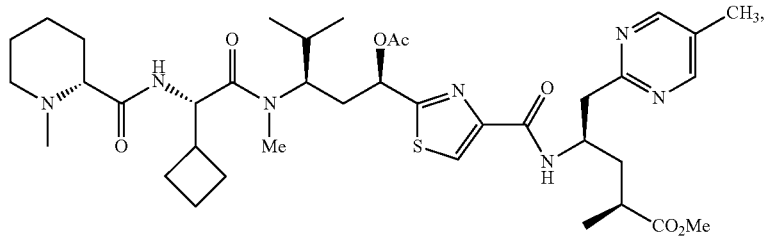
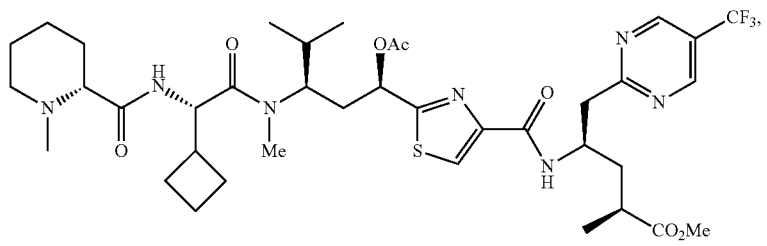
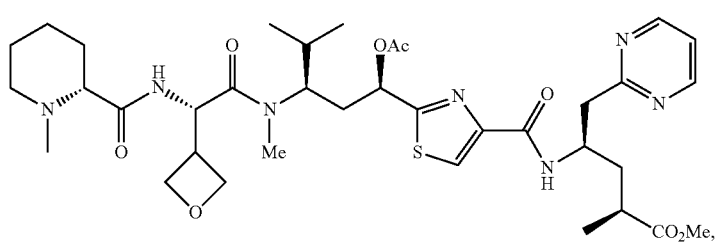
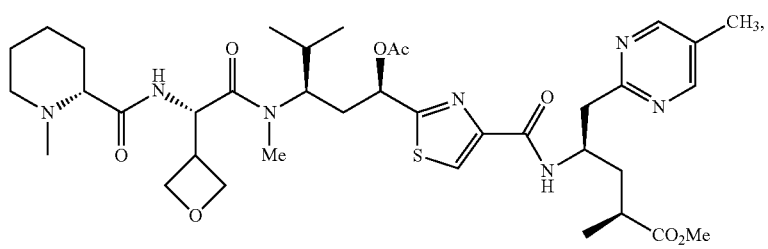

-continued
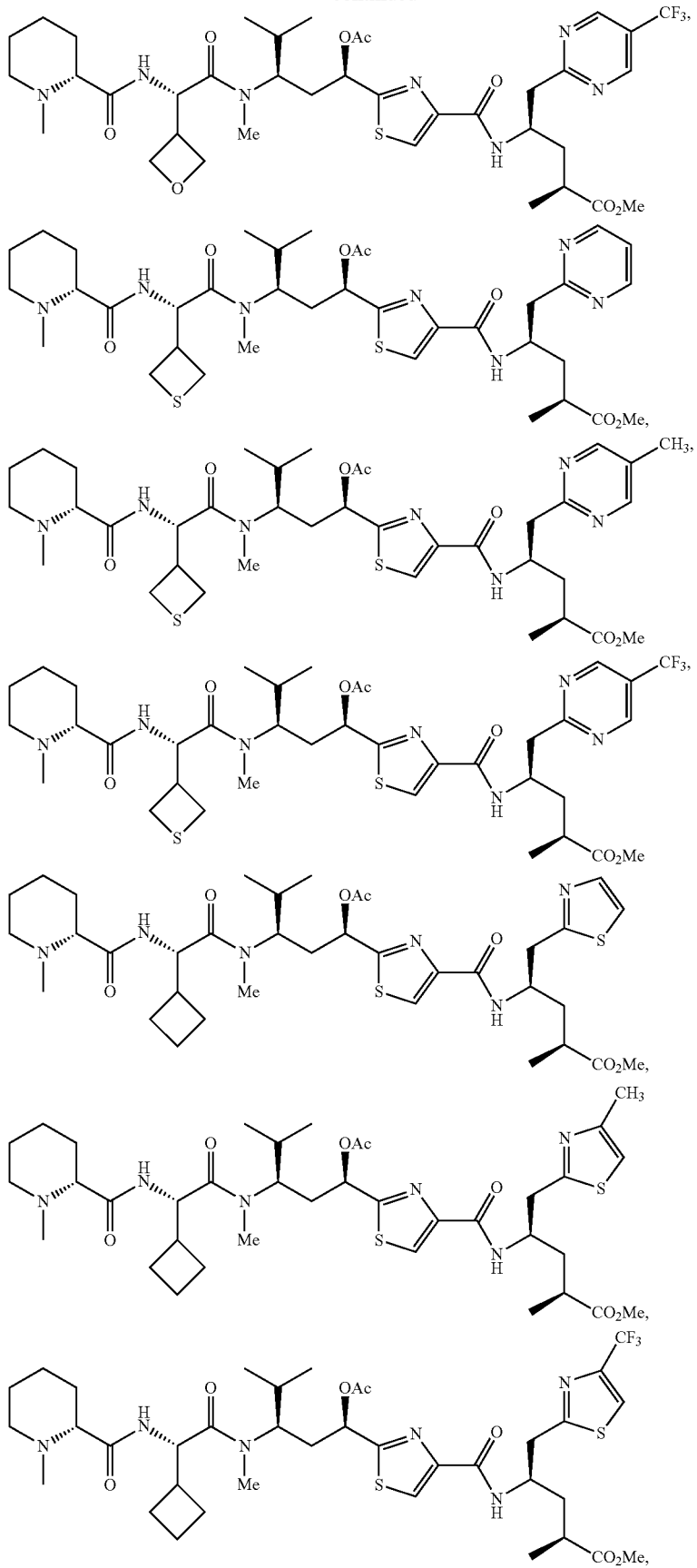

-continued
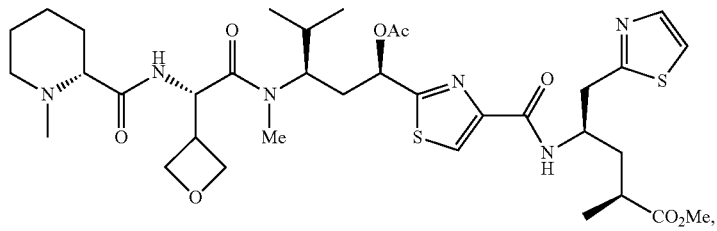
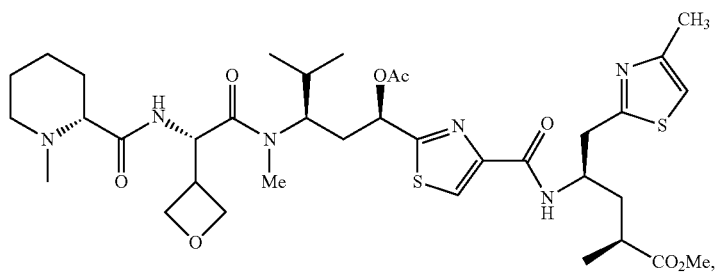
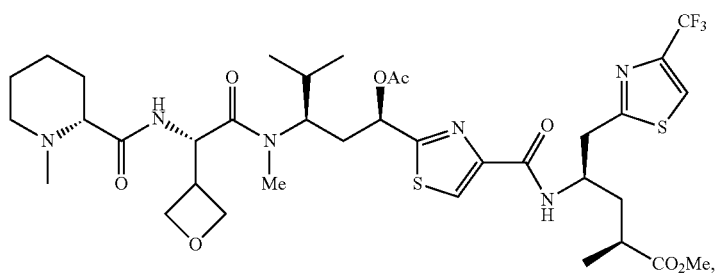
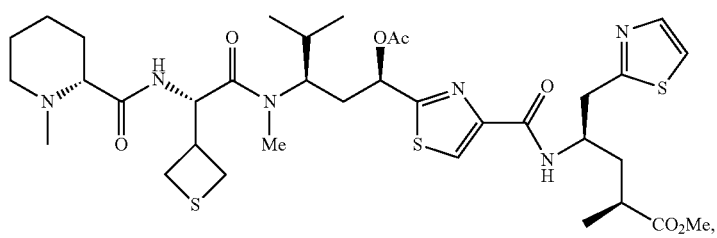
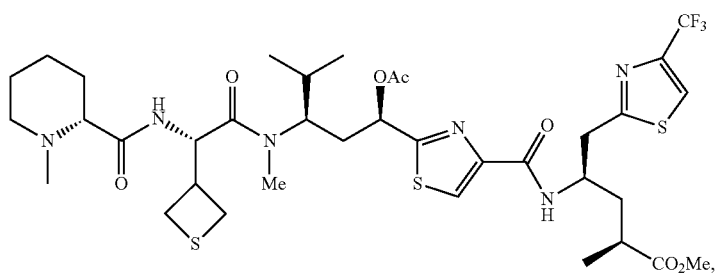
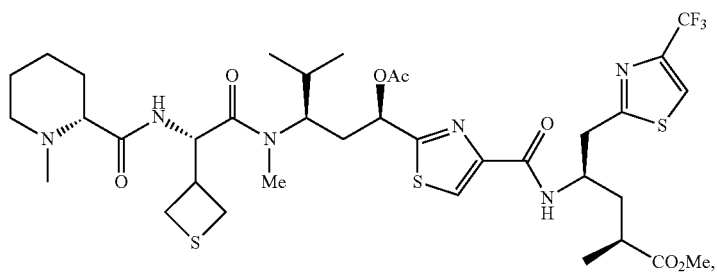

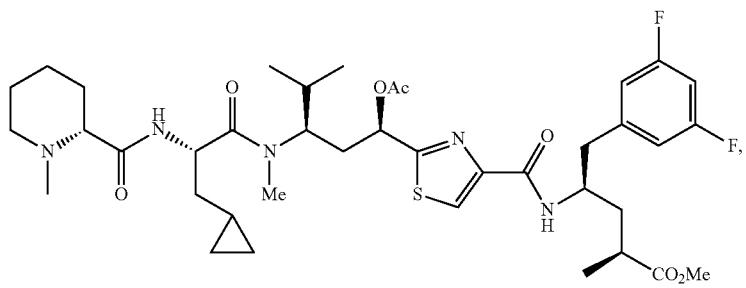
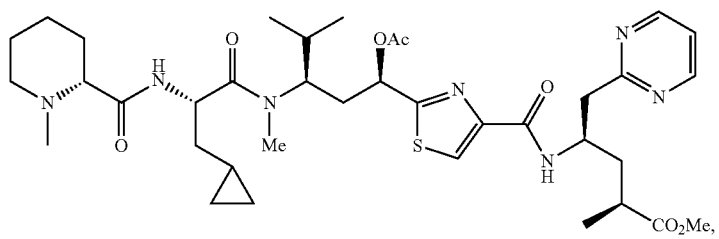
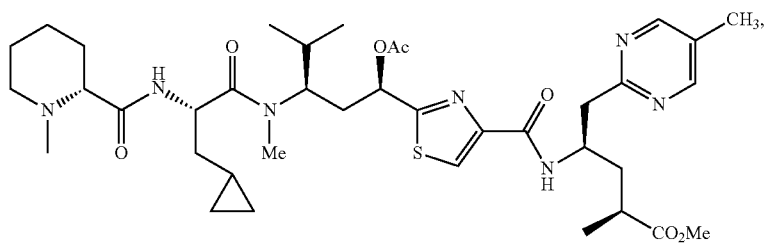
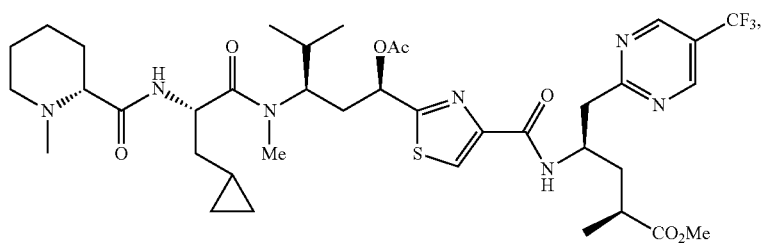
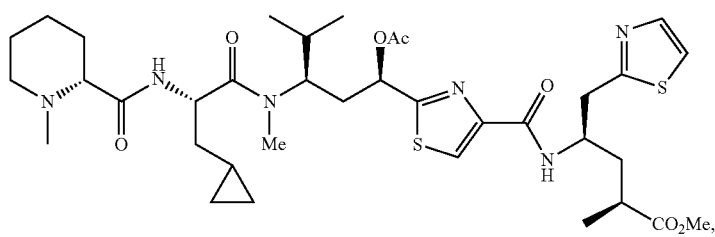
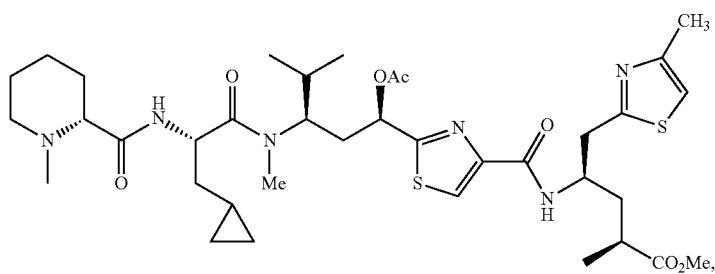

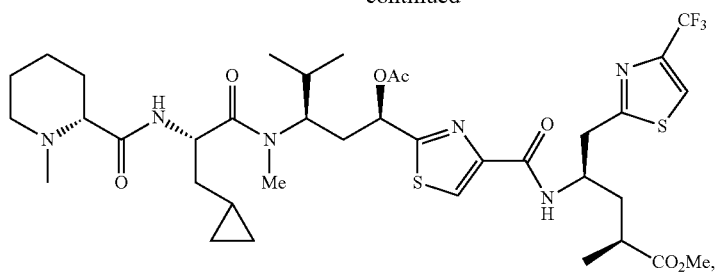
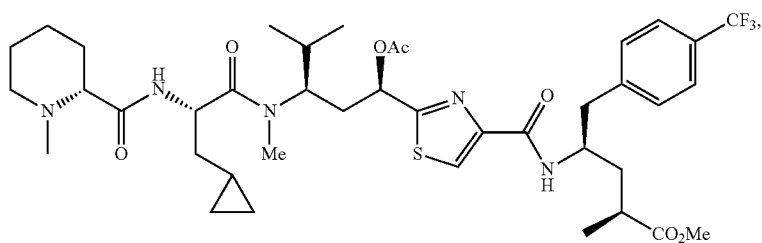
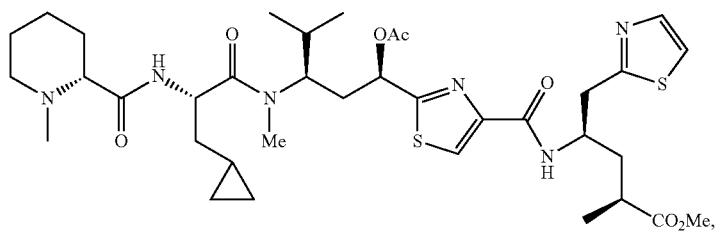
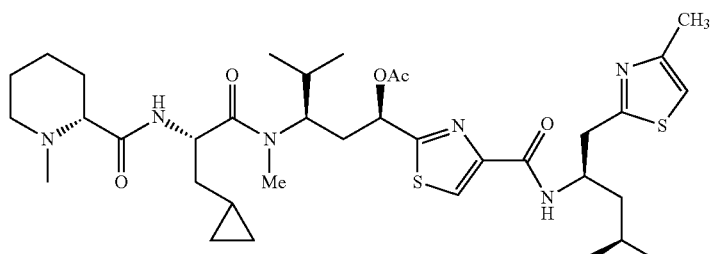
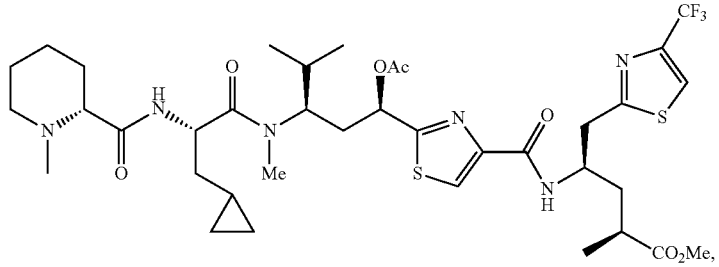
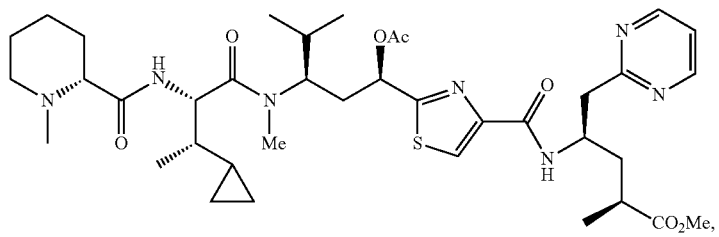

-continued
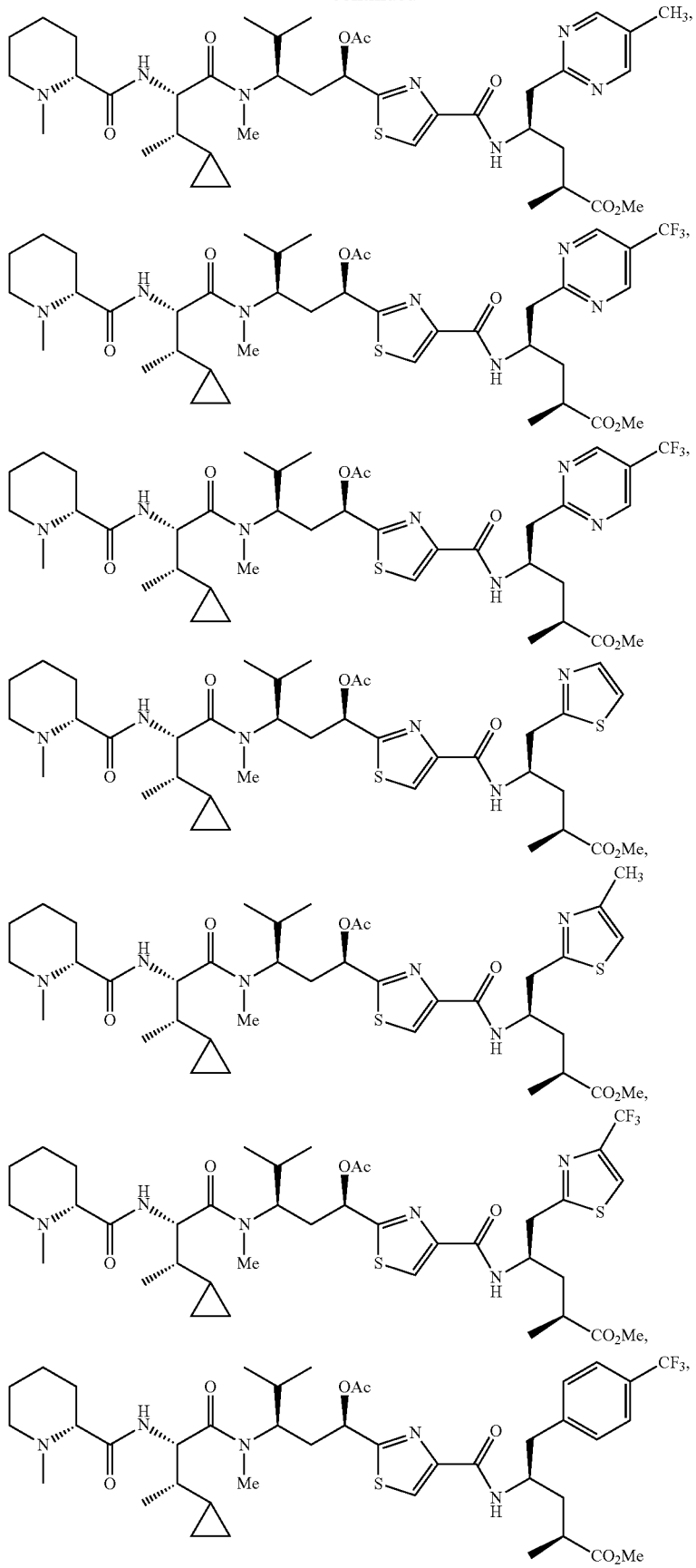

-continued
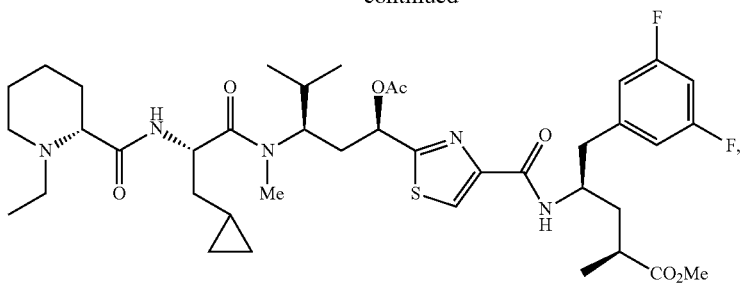
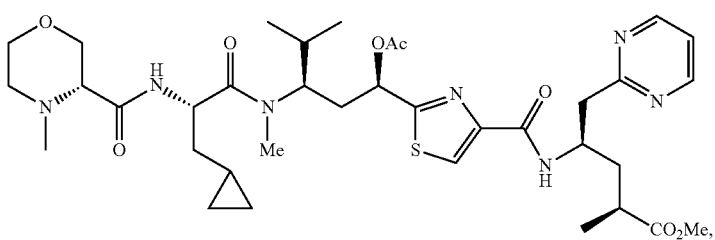
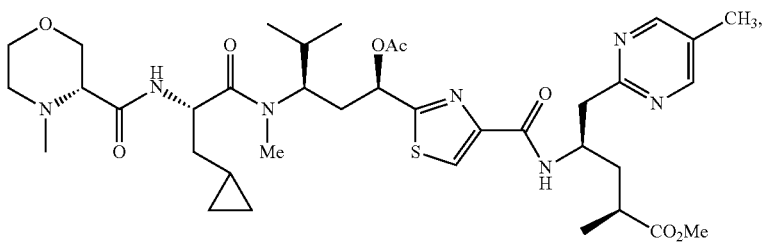
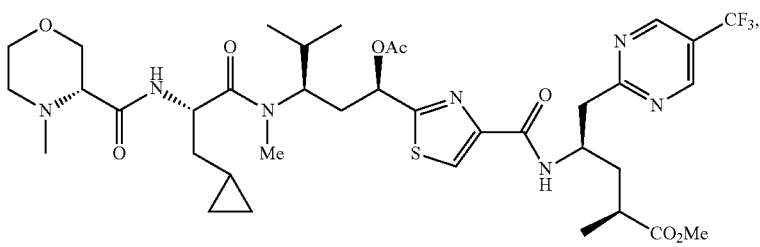
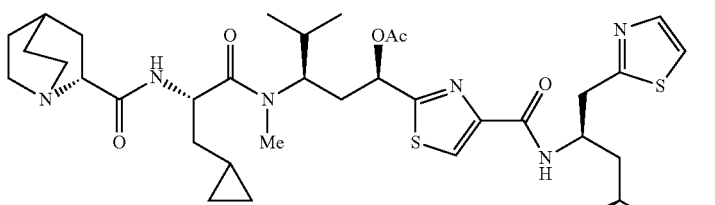
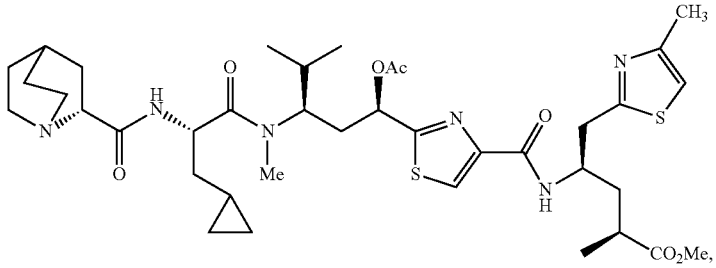

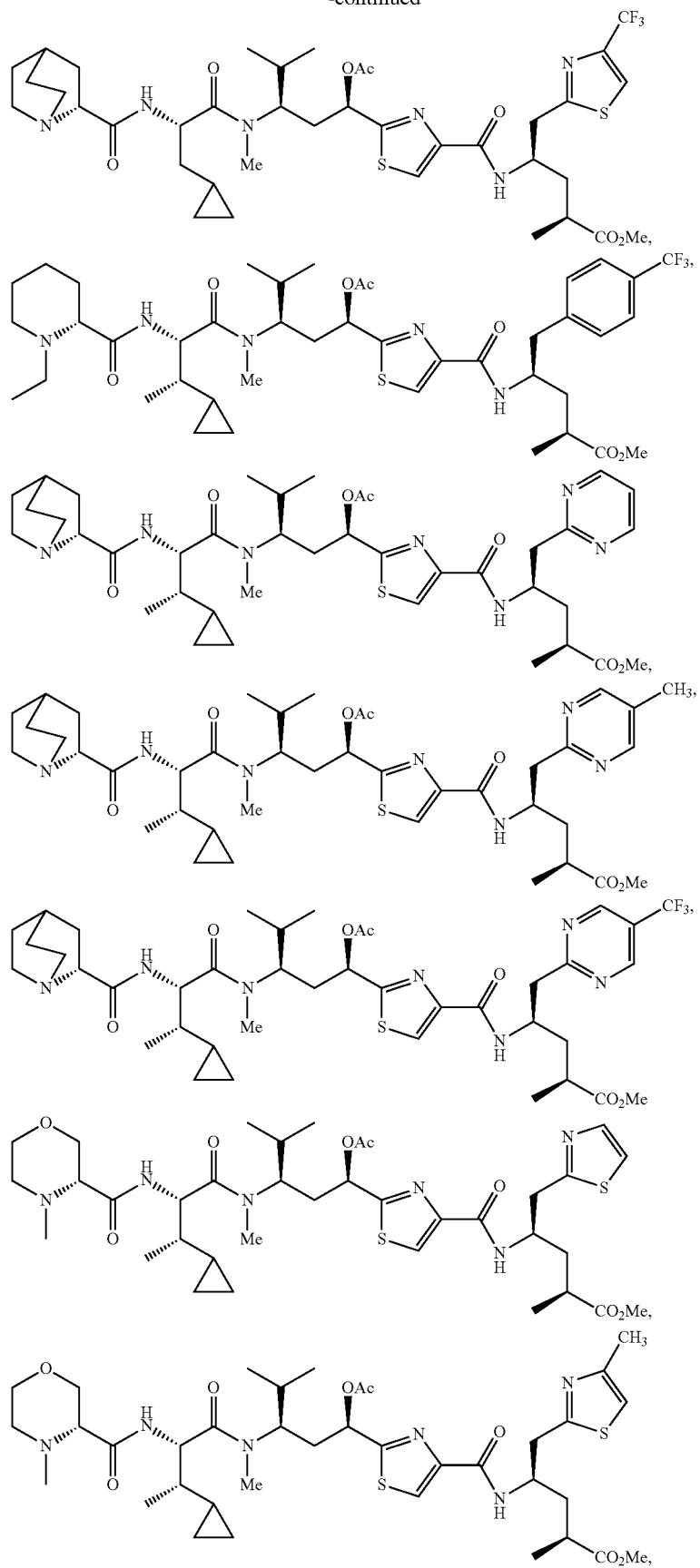

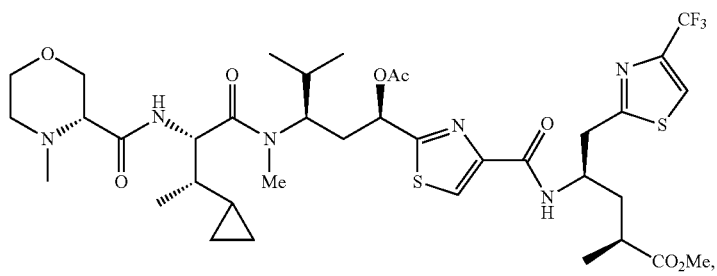
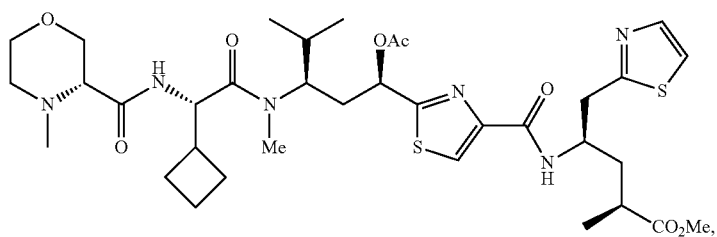
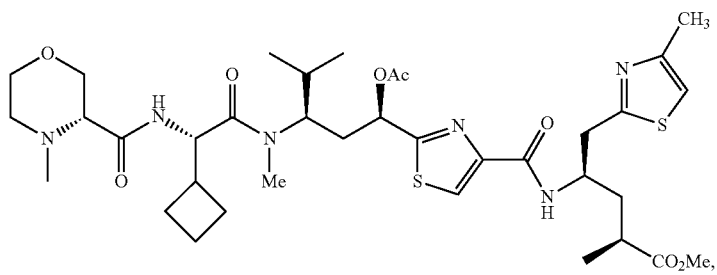
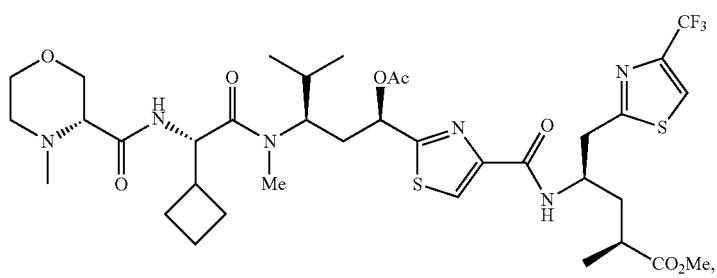
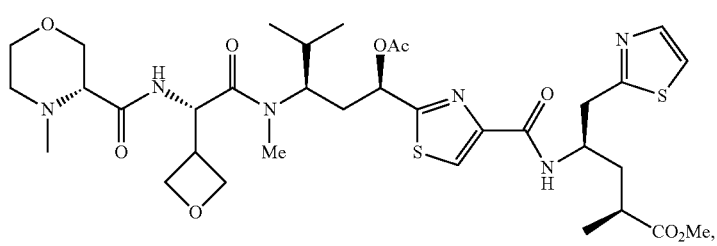
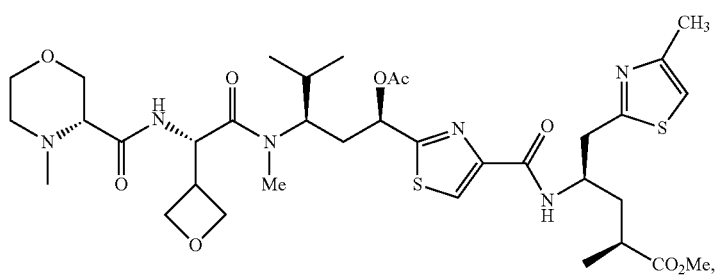

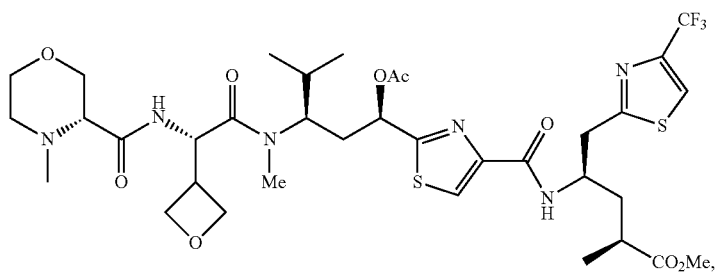
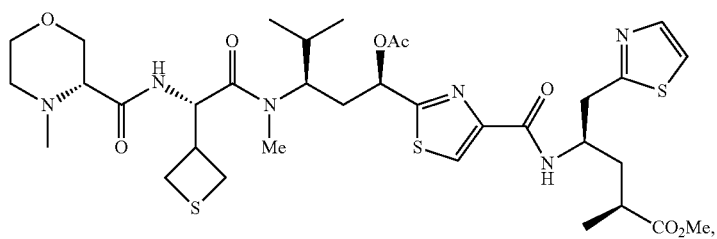
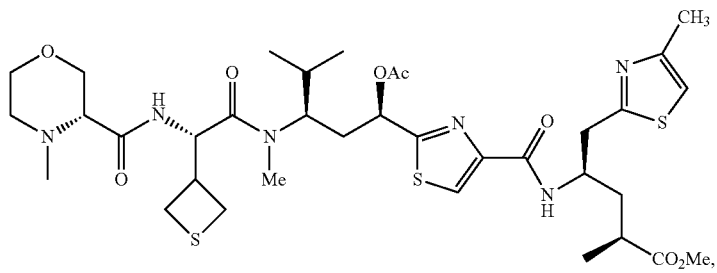
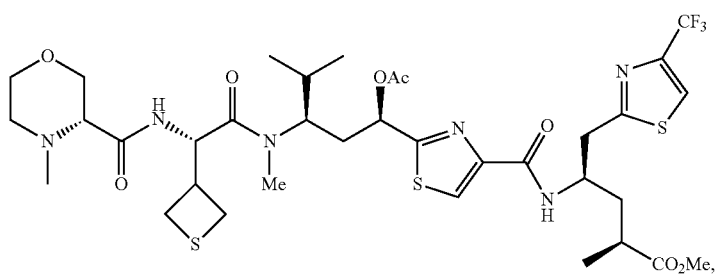
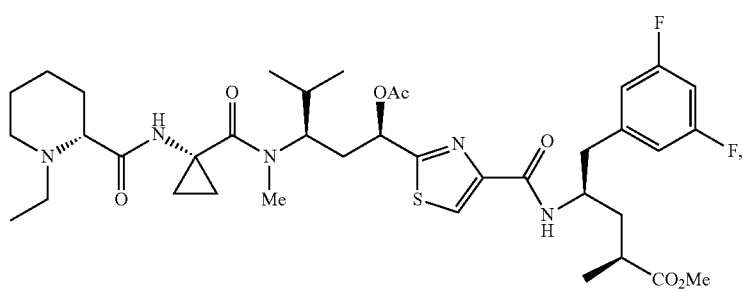
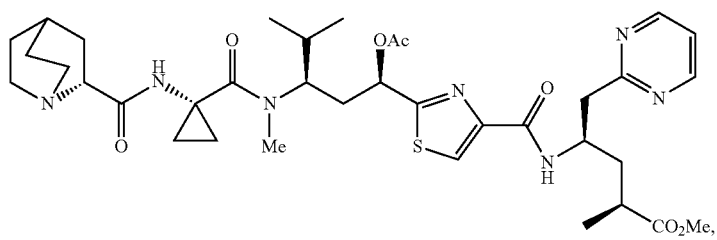

-continued
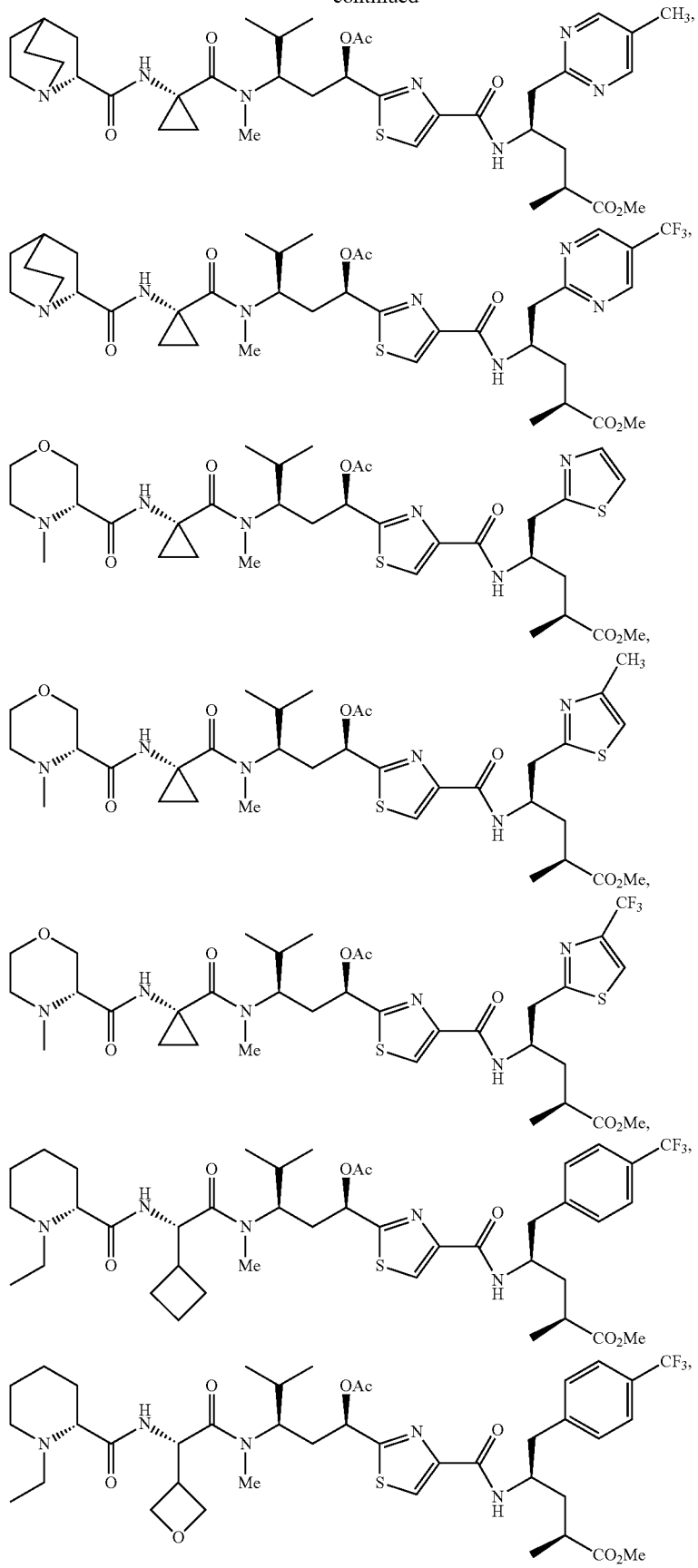

-continued
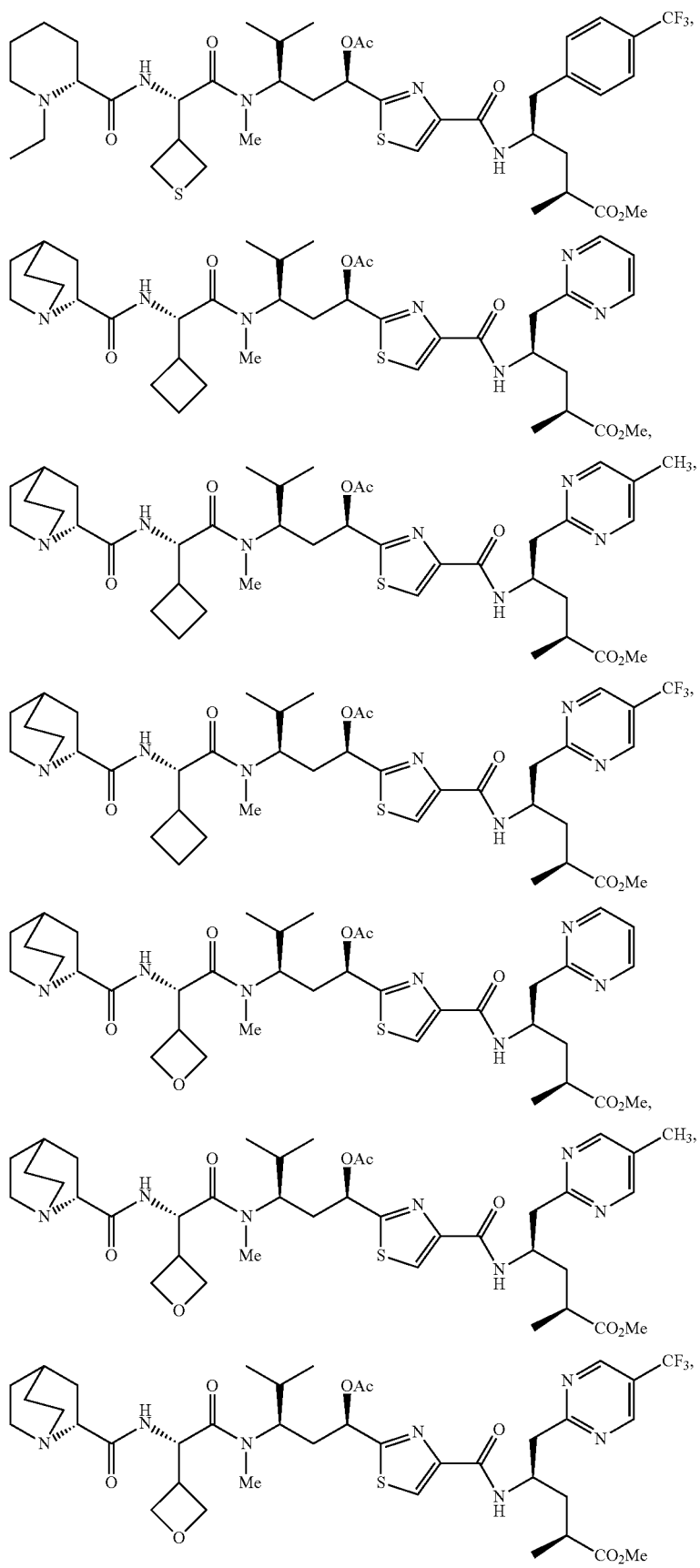

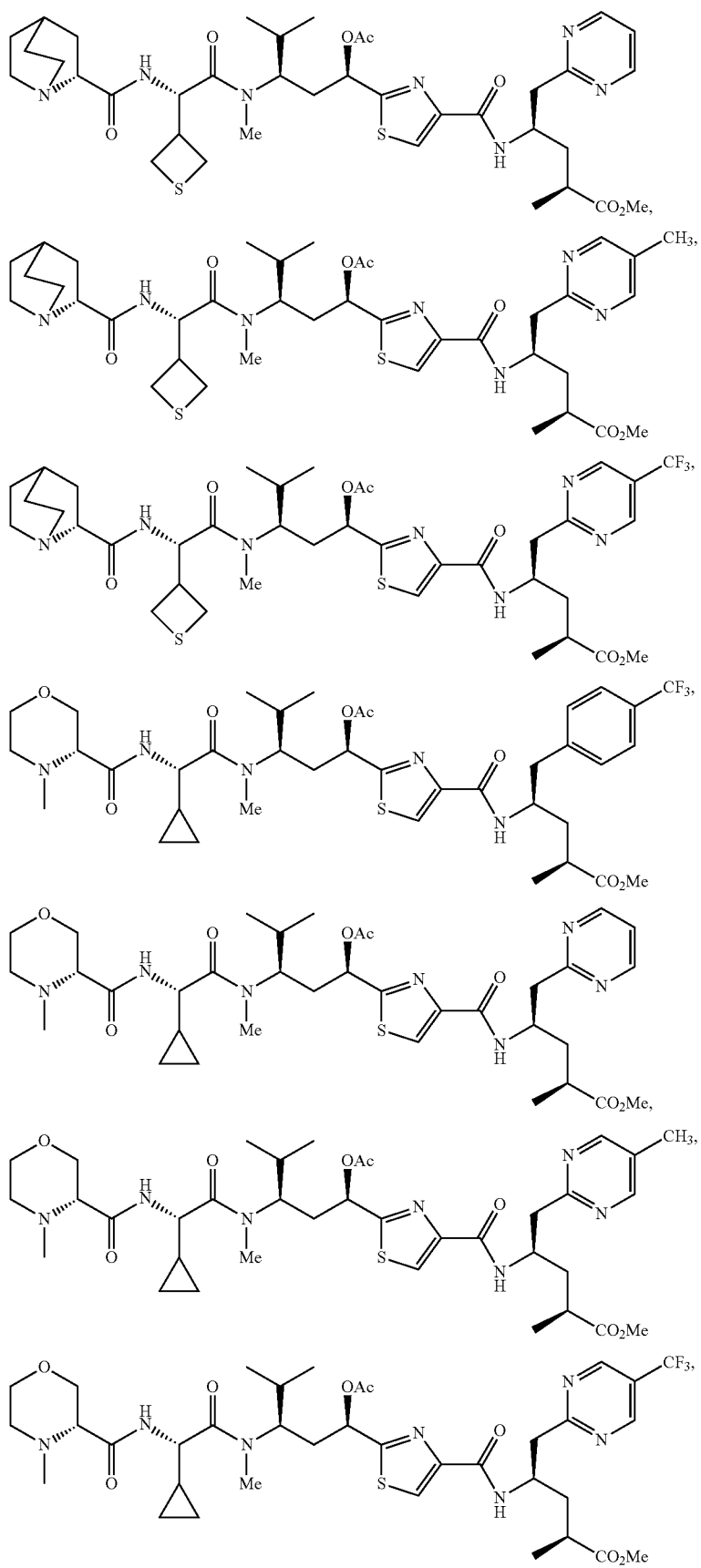

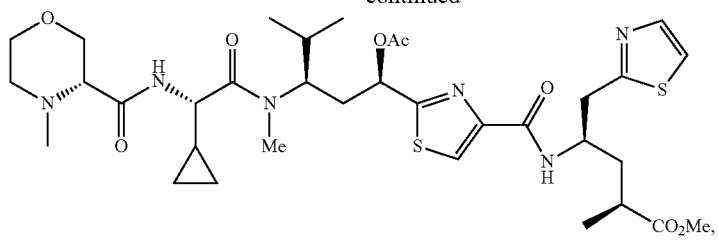
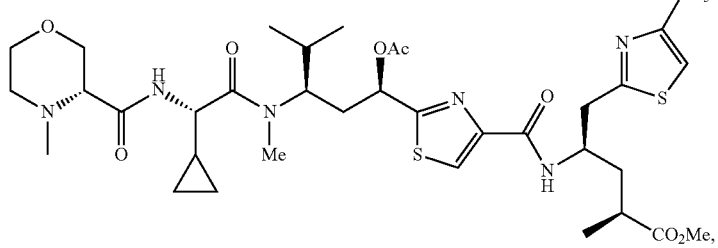
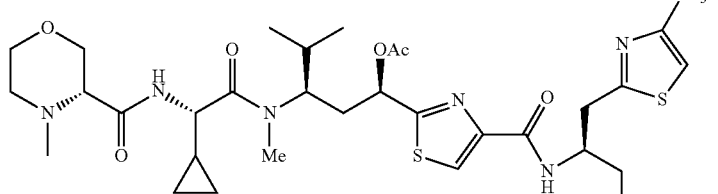
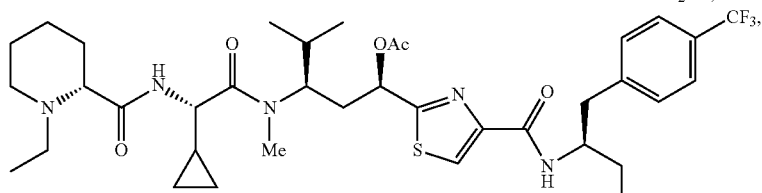
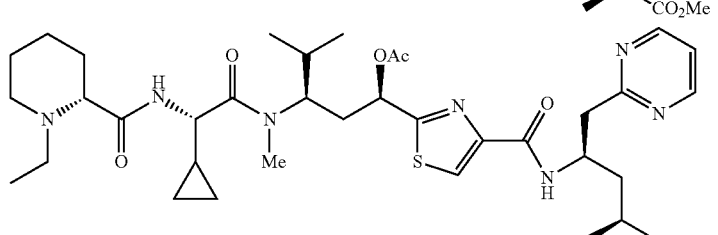
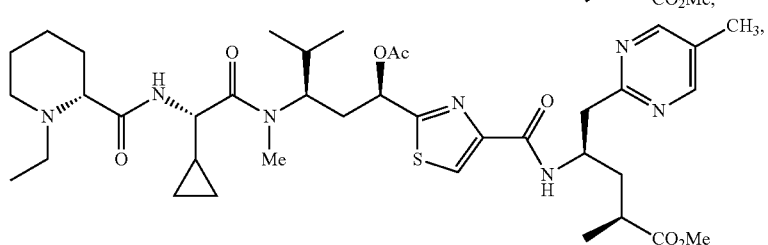
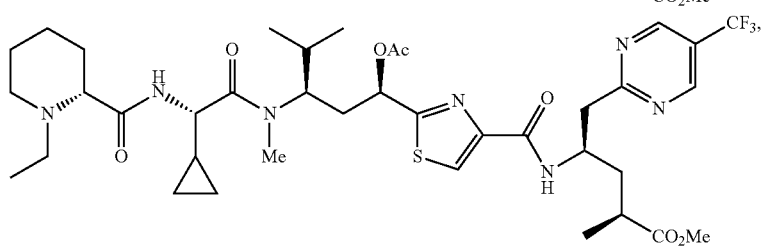

-continued
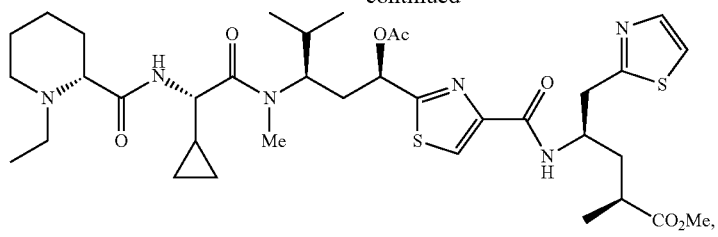

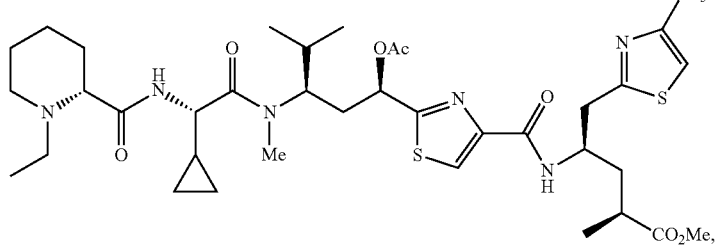
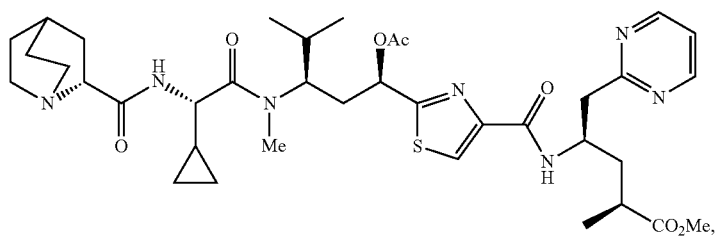
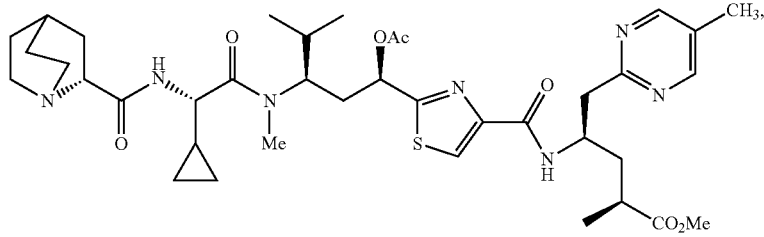
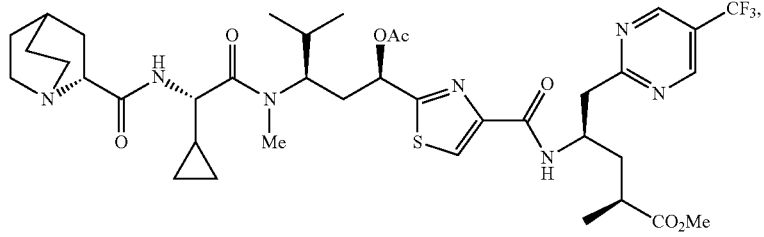
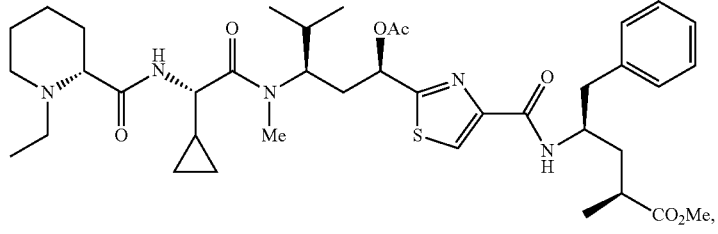

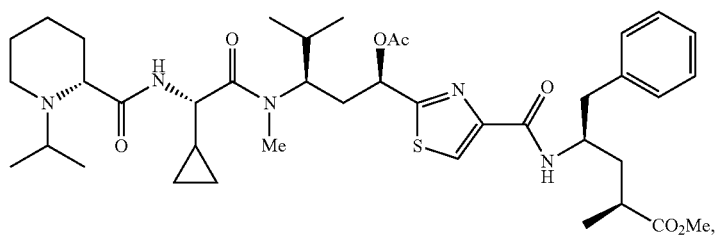
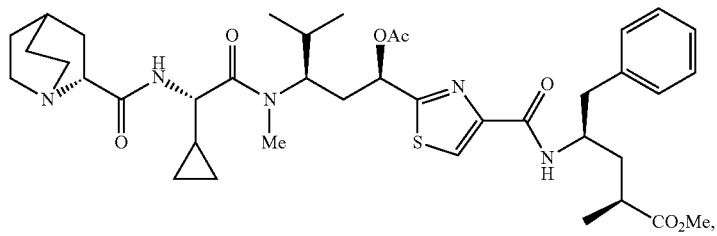
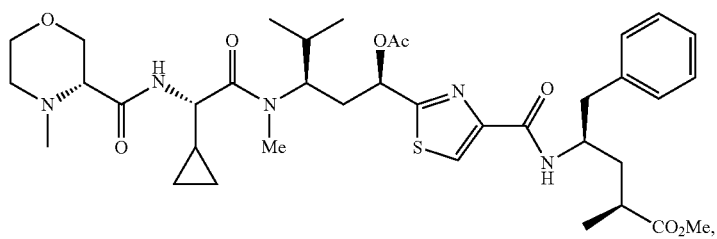
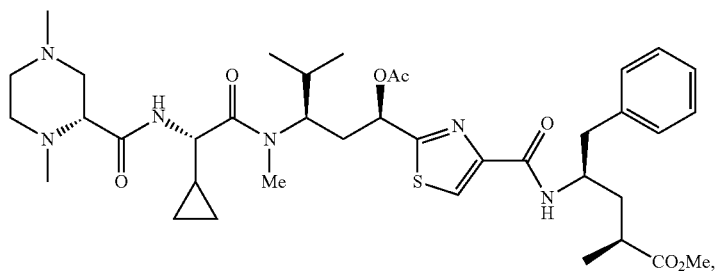
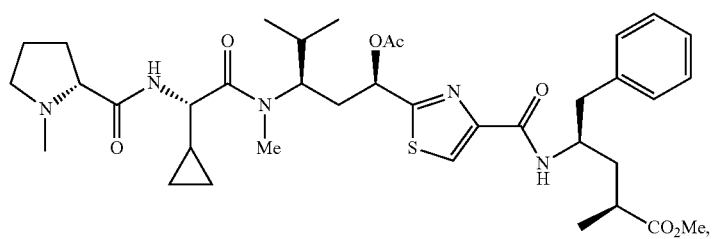
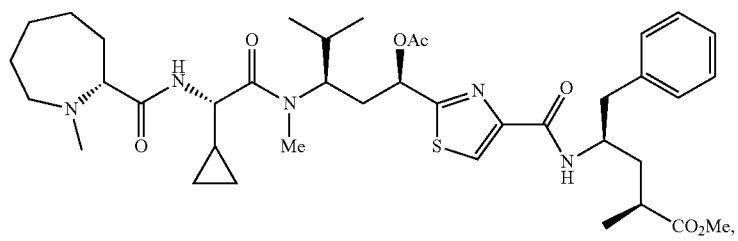
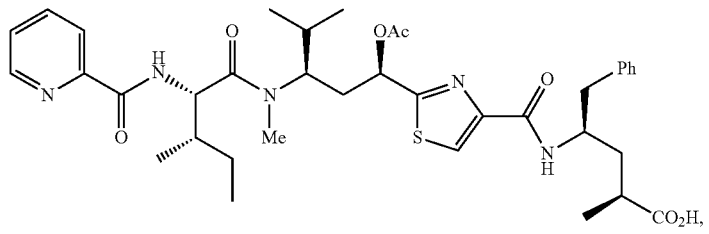

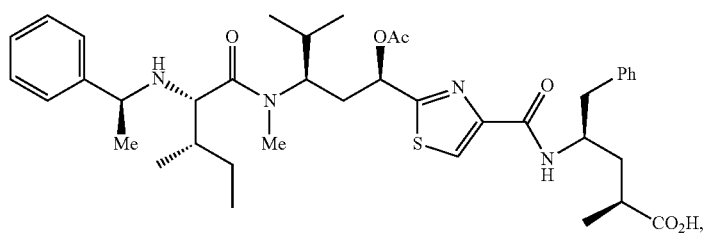
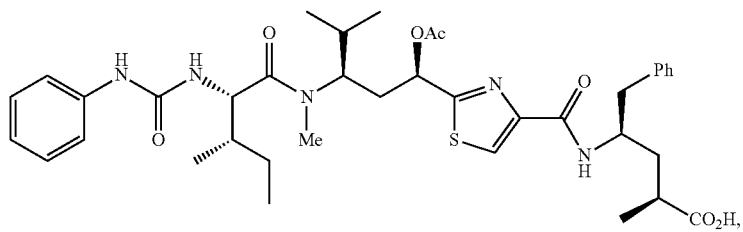
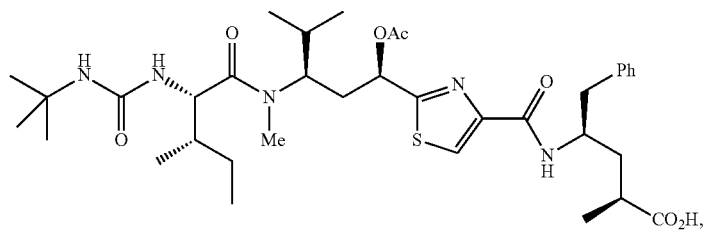
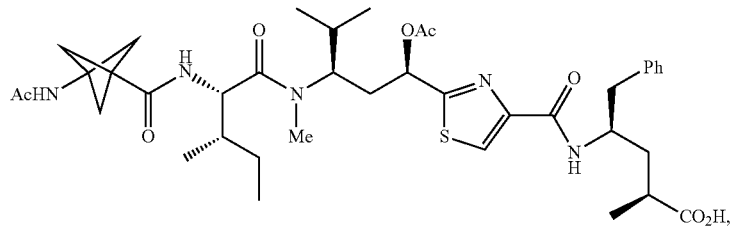
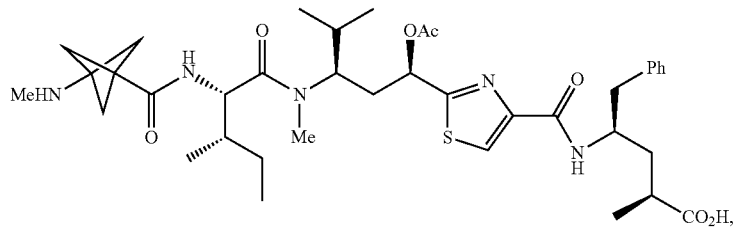
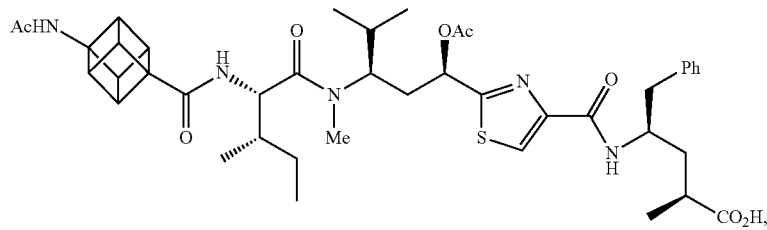
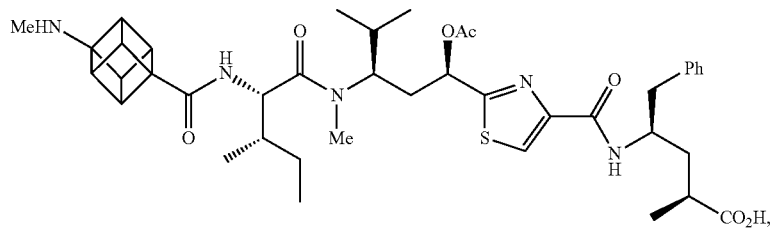

-continued
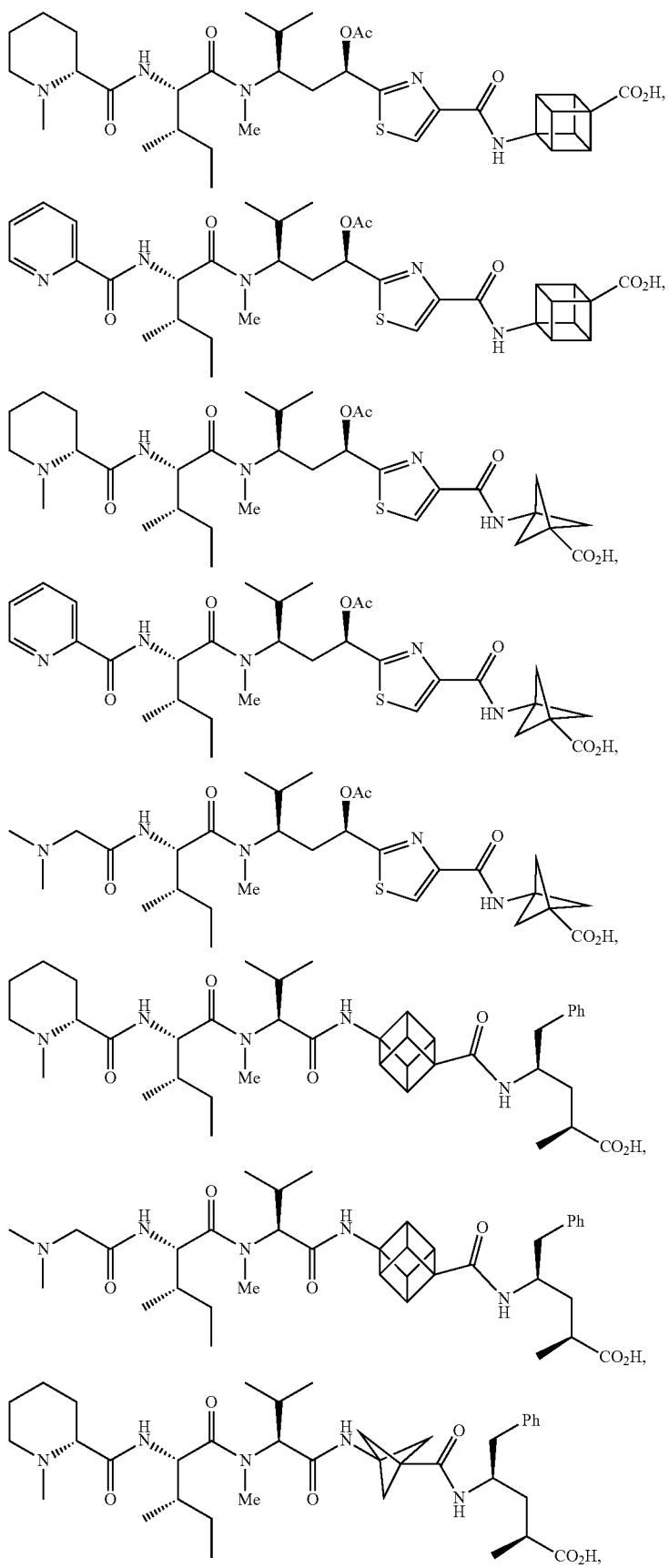

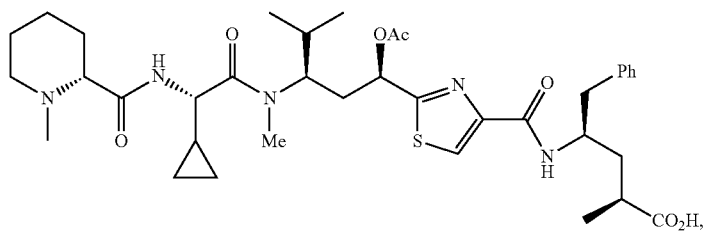
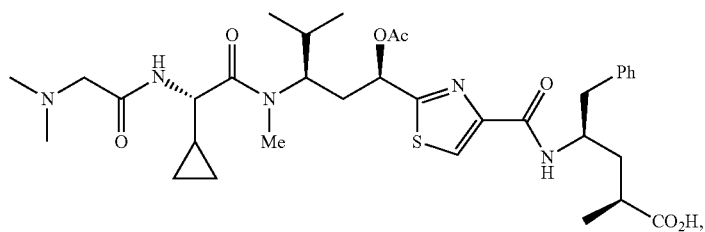
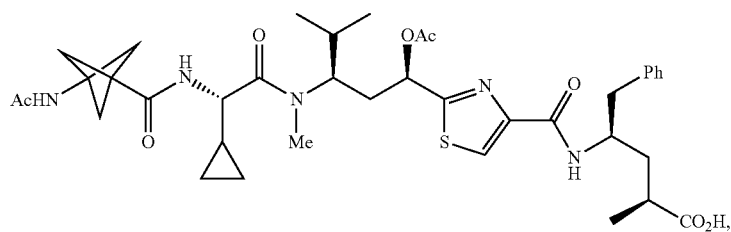
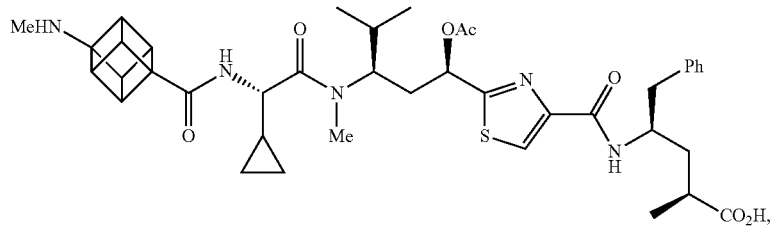
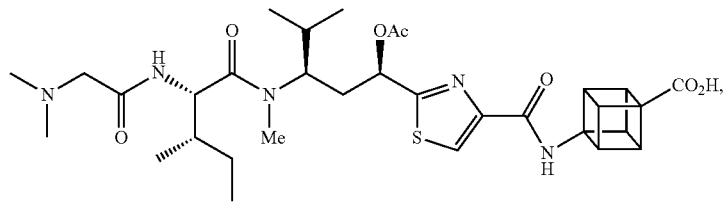
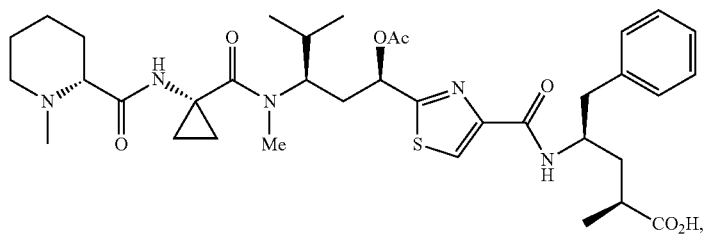
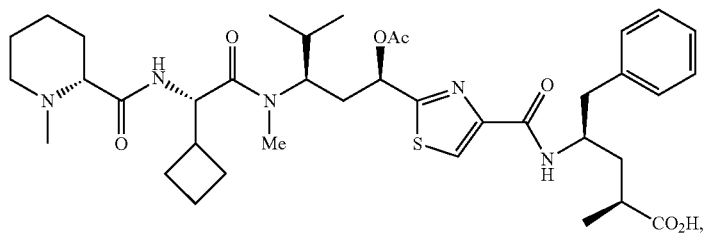

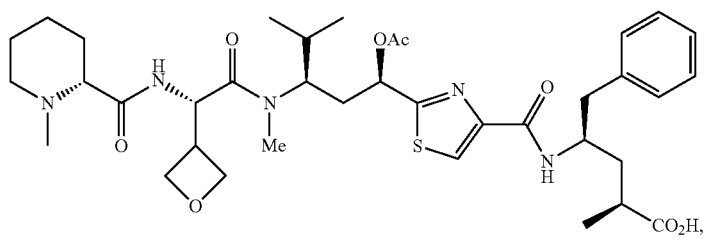
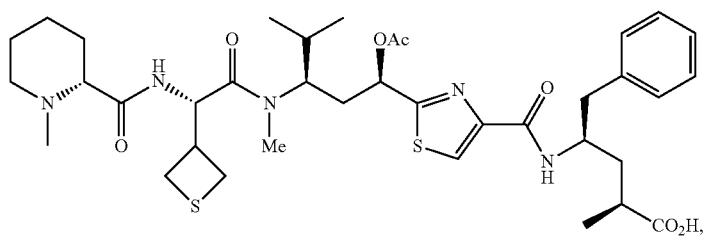
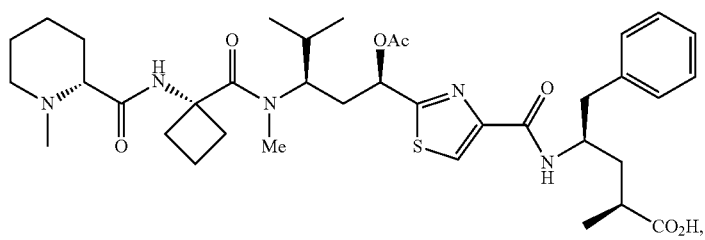
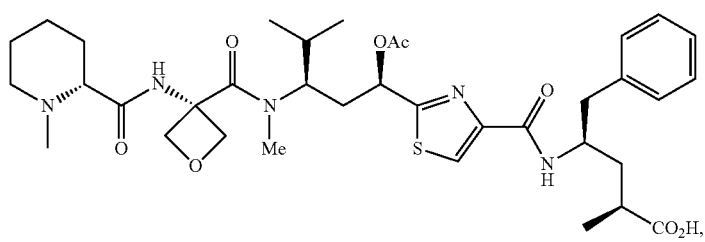
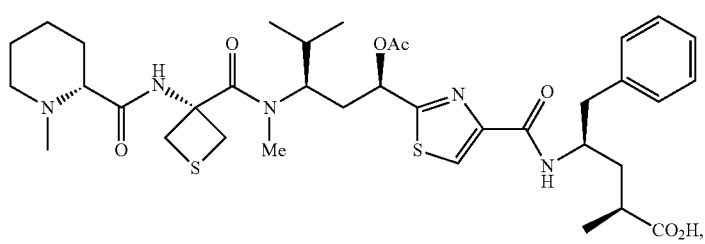
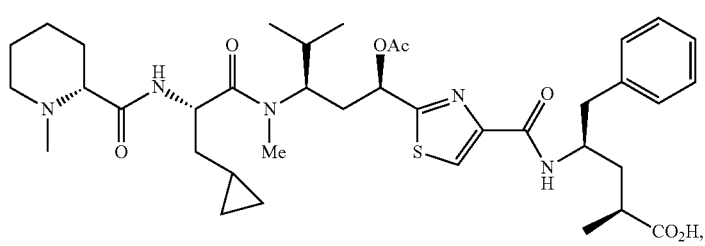
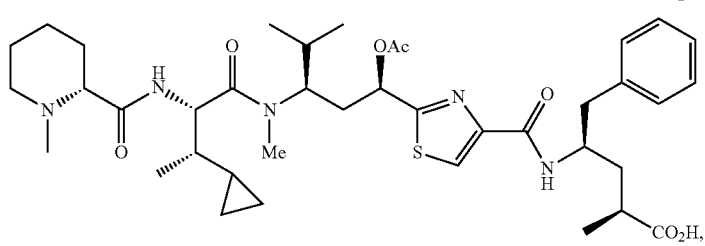

-continued
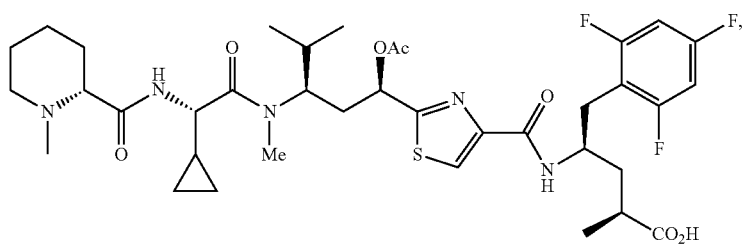
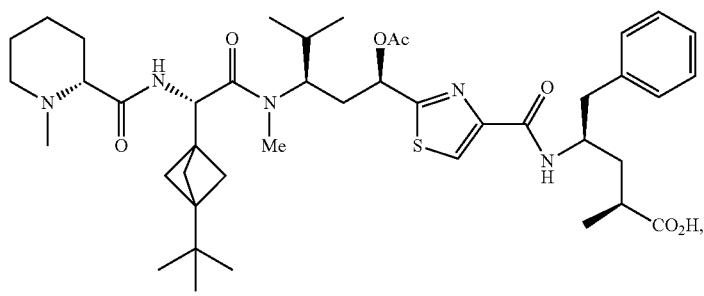
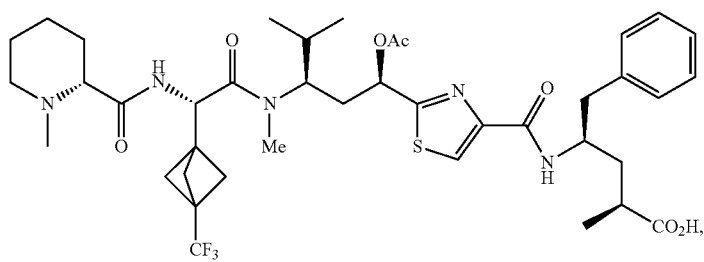
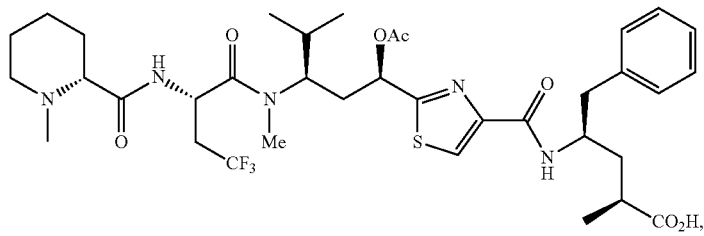
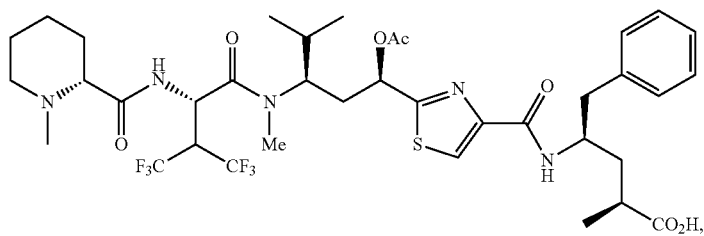
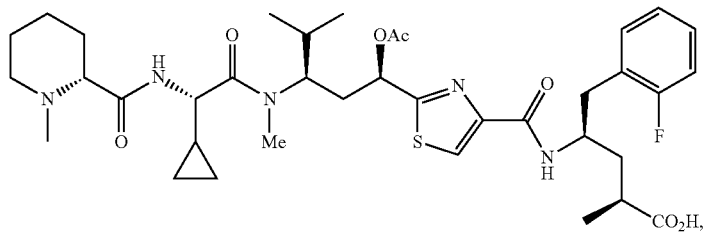

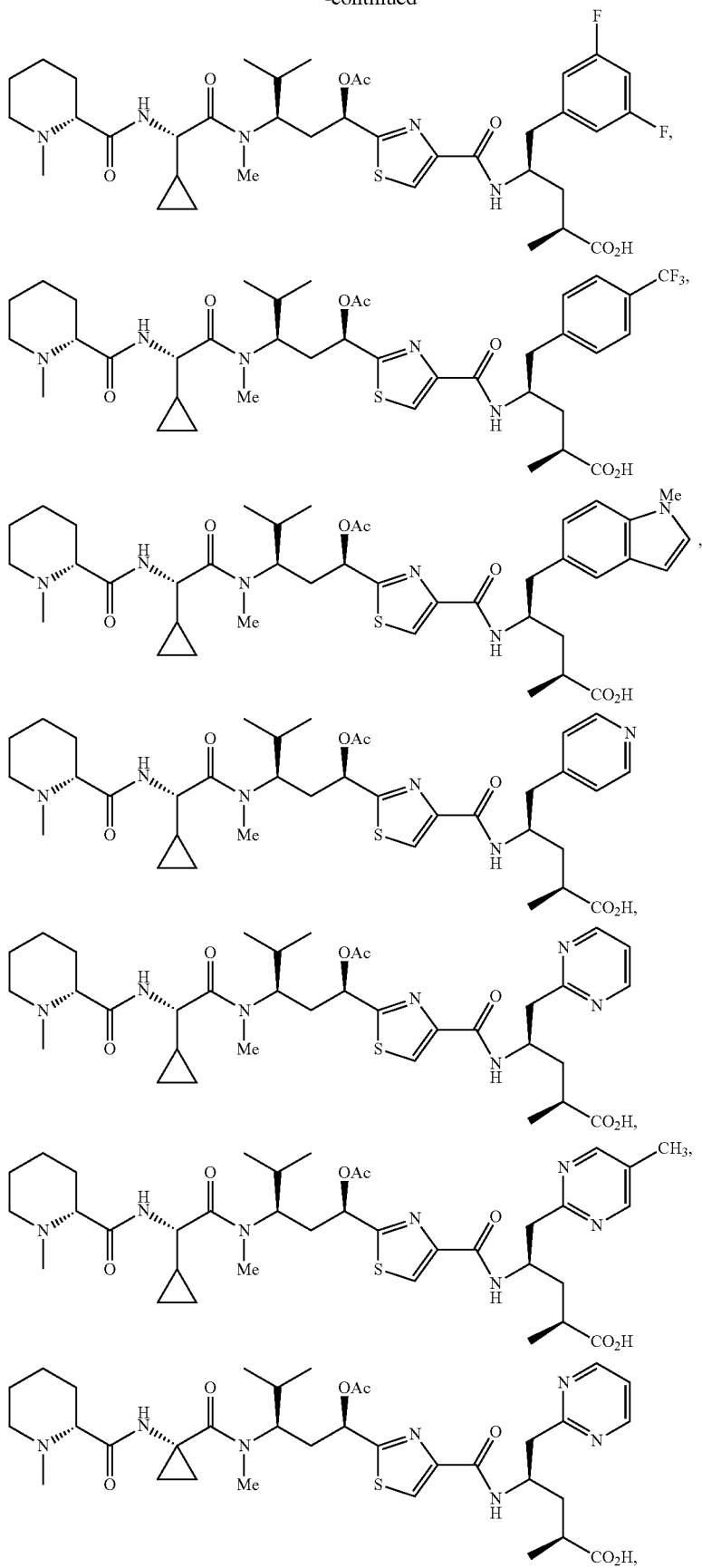

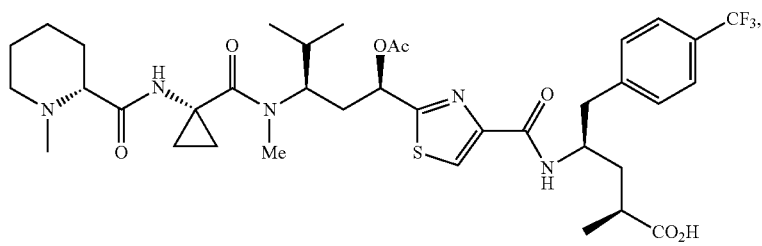
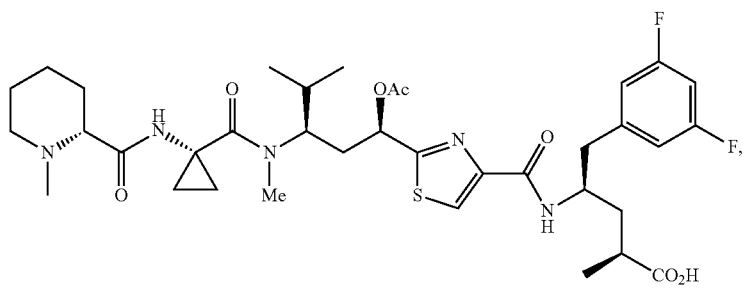
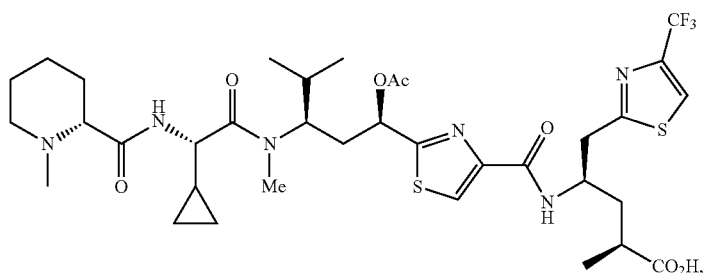
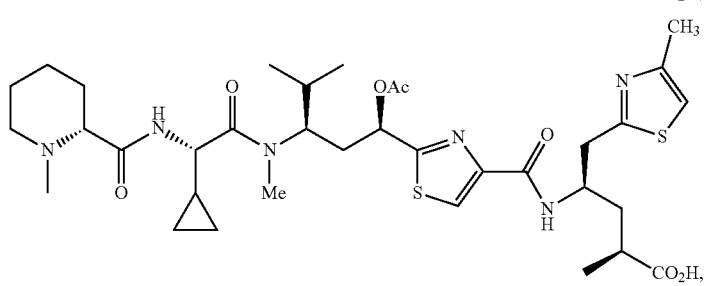
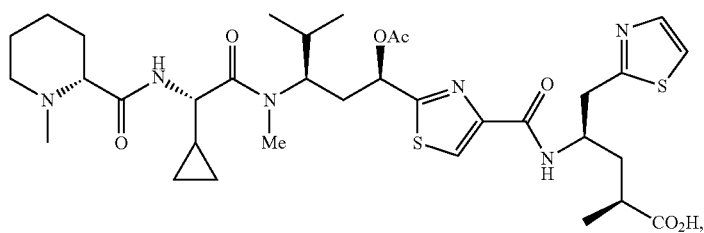
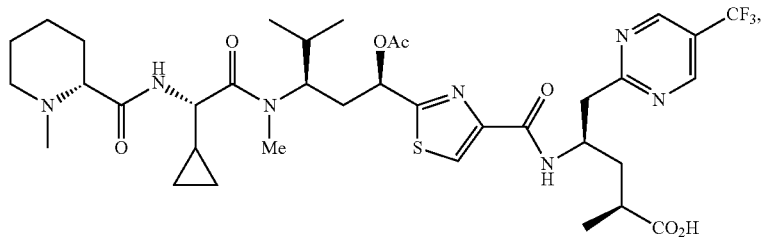

-continued
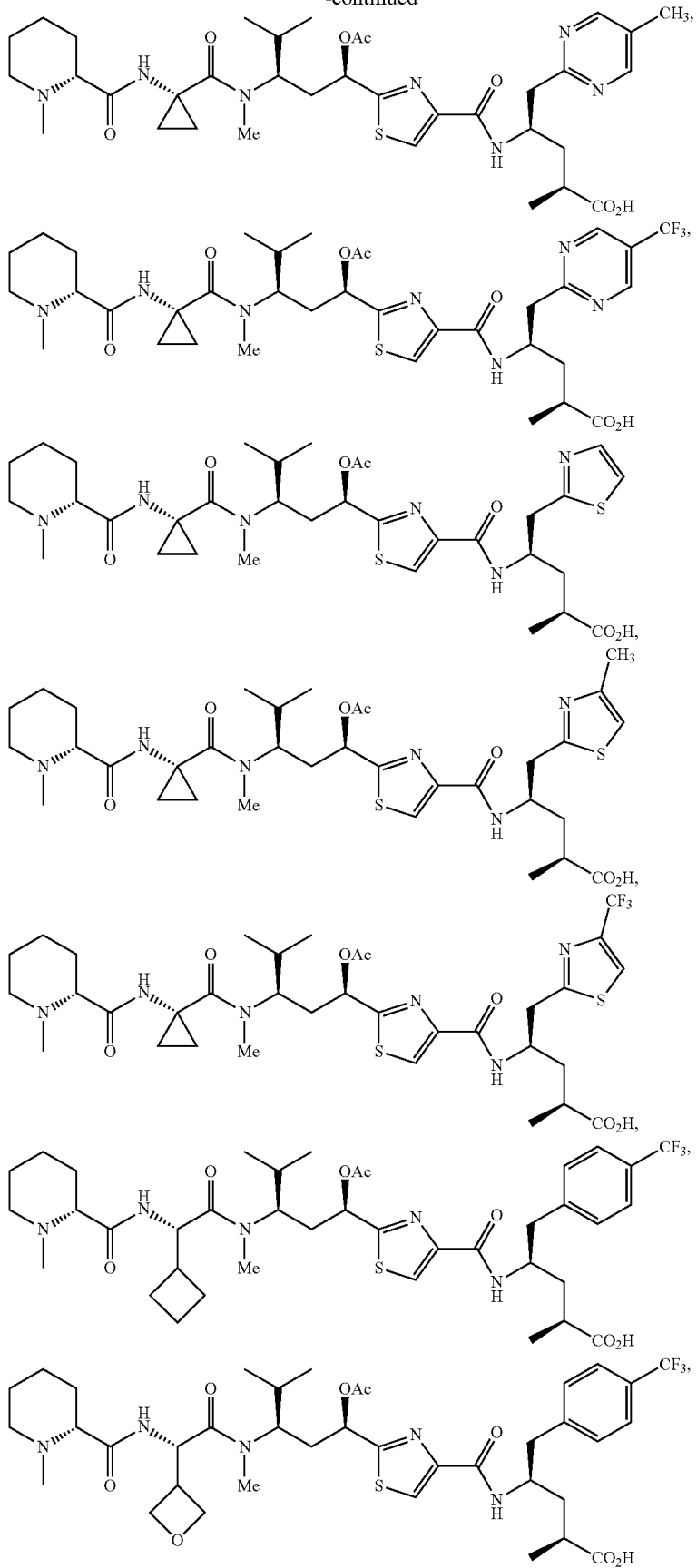

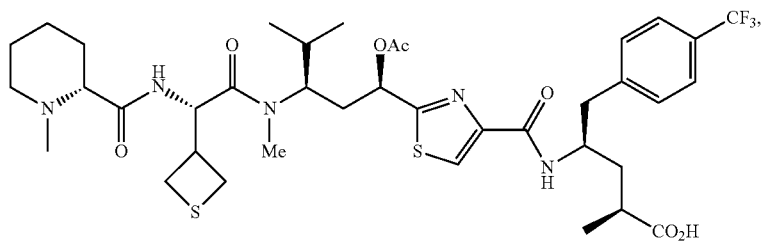
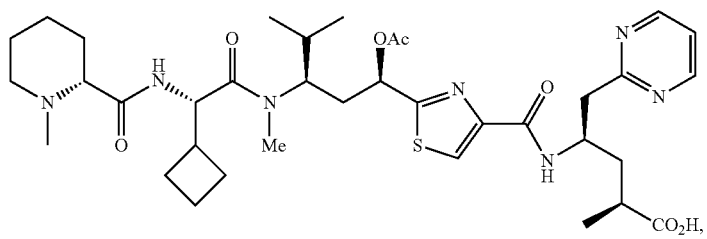
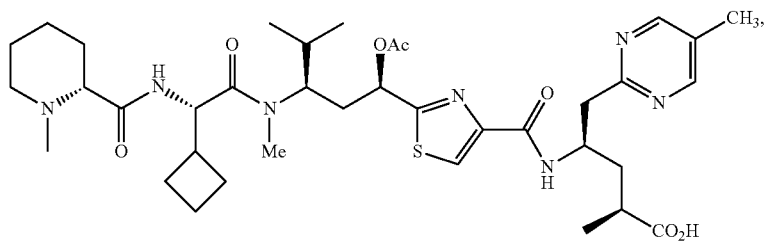
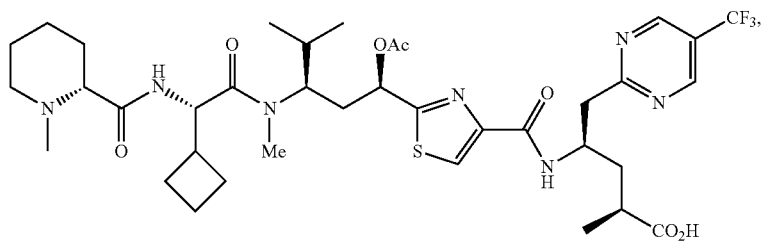
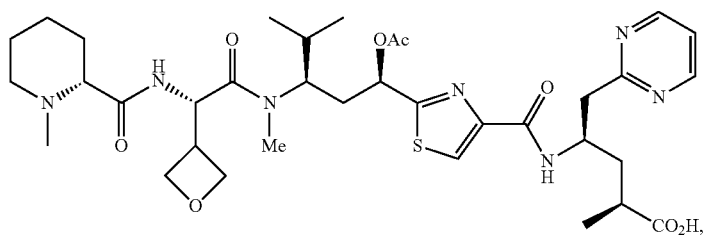
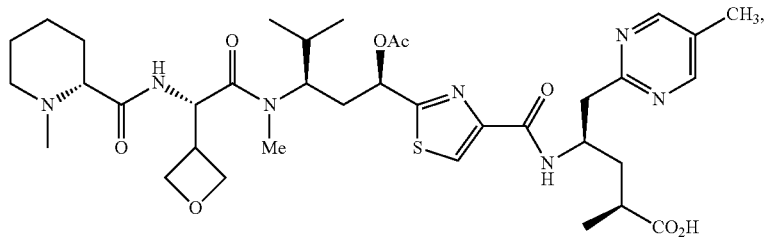
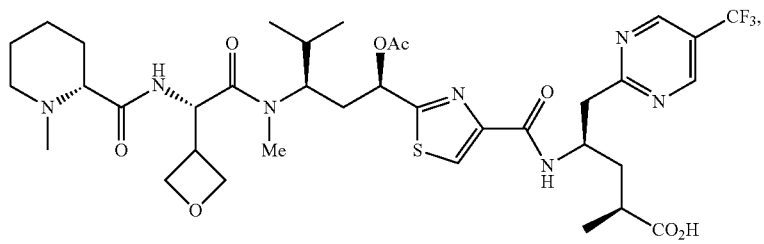

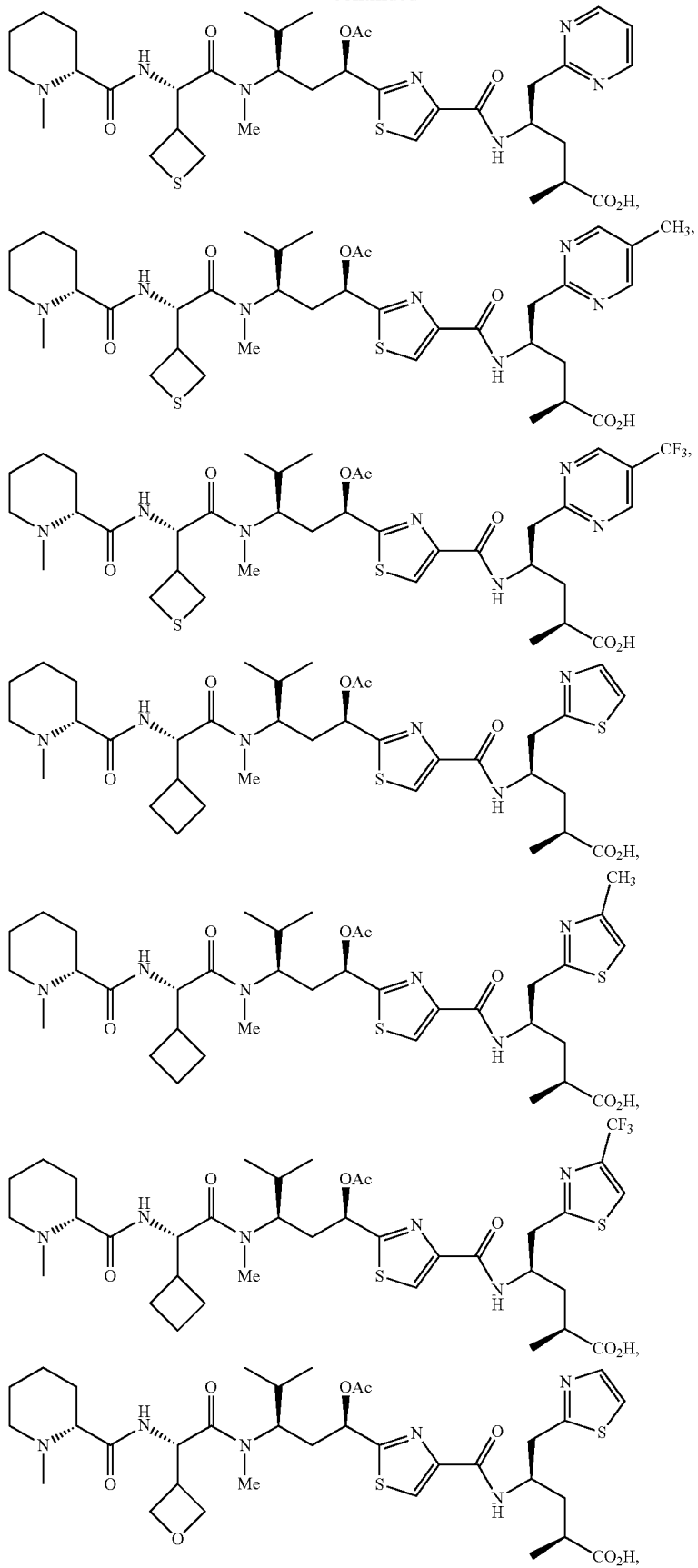

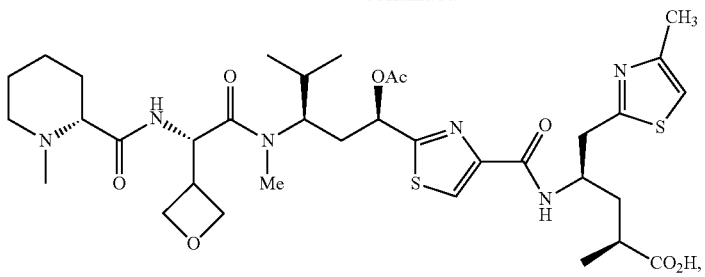
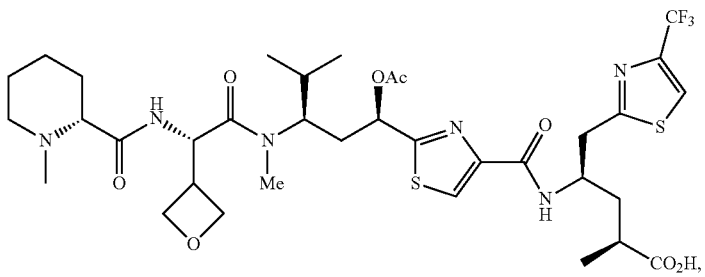
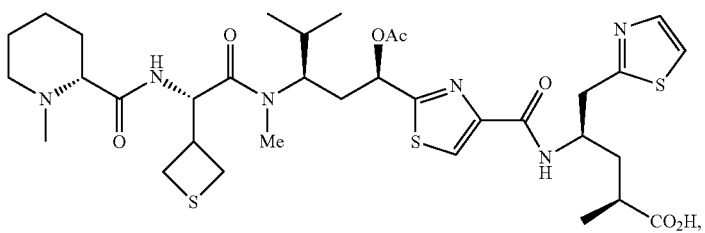
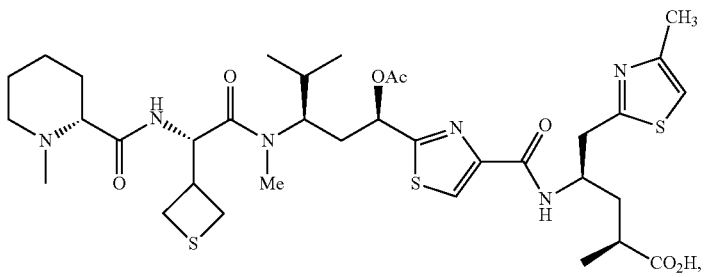
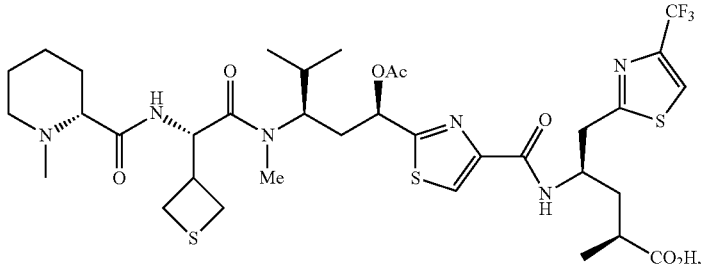
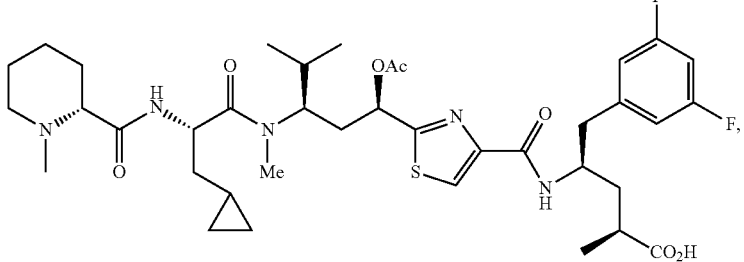

-continued
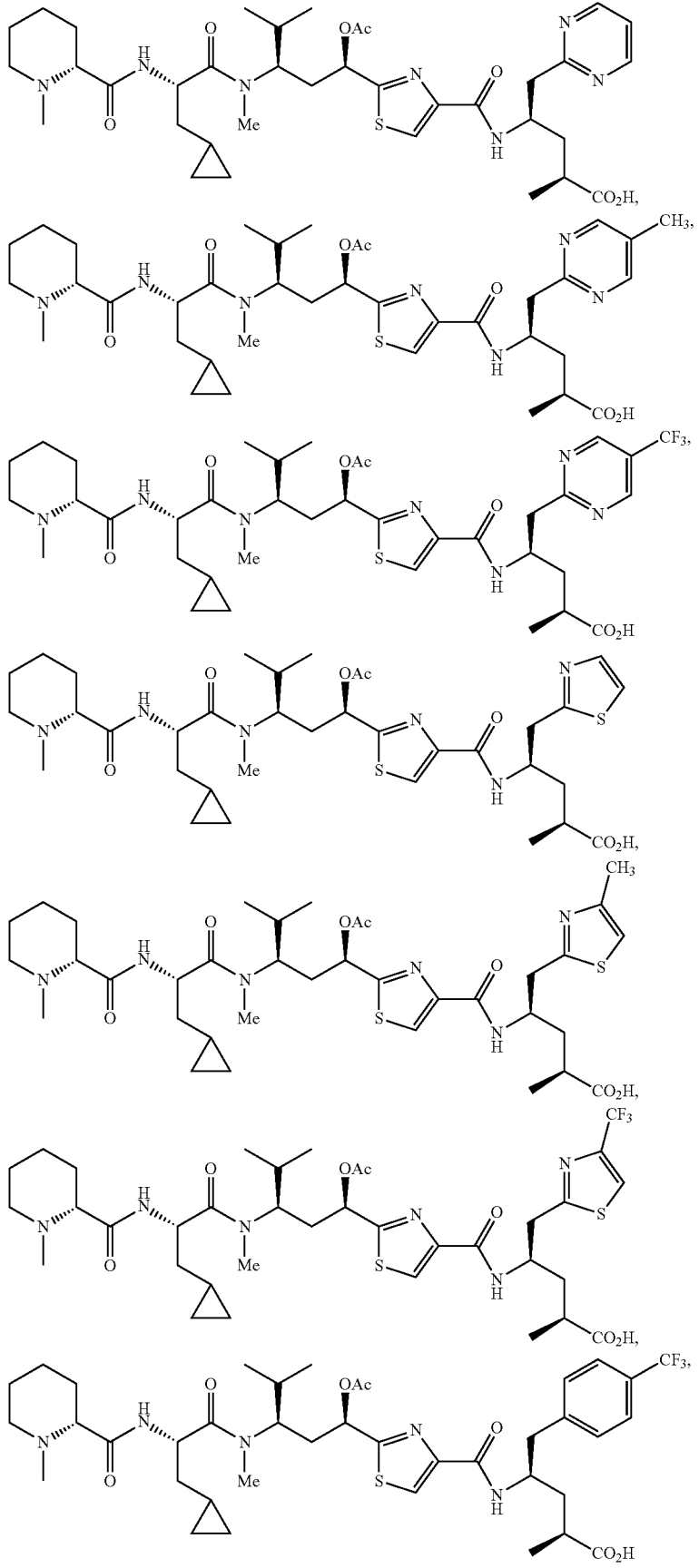

-continued
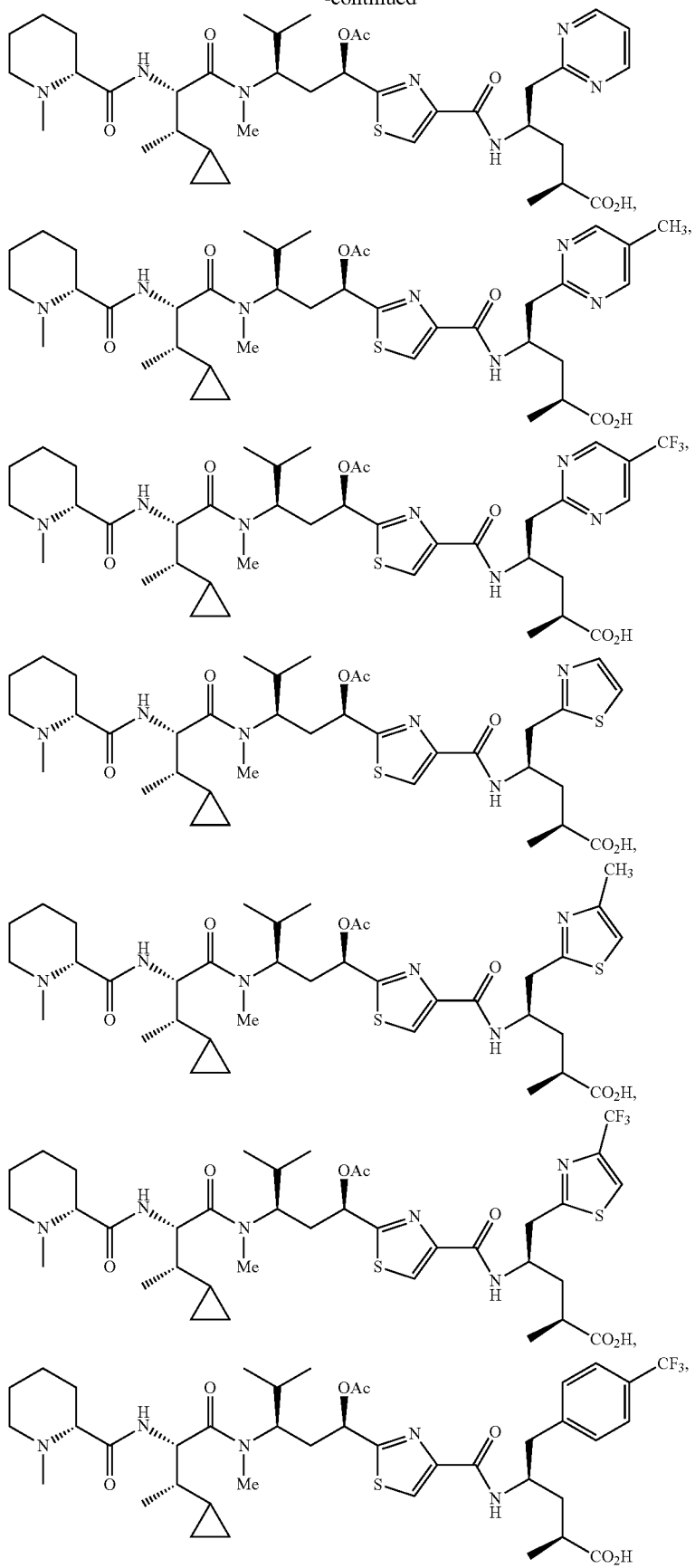

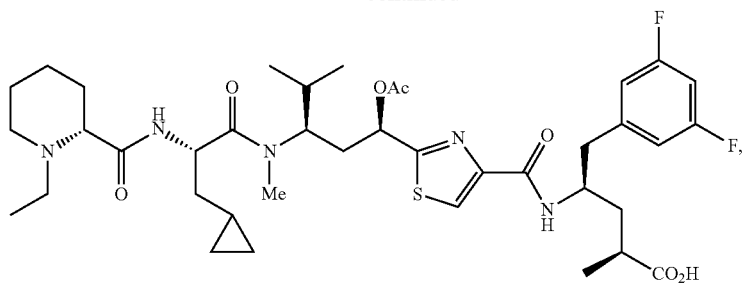
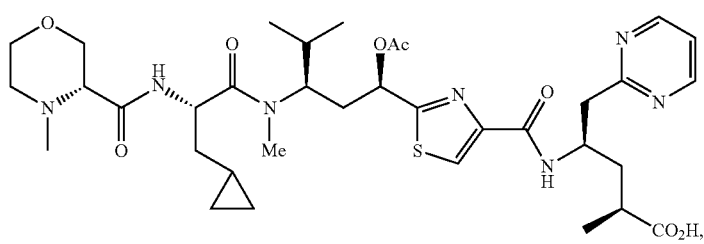
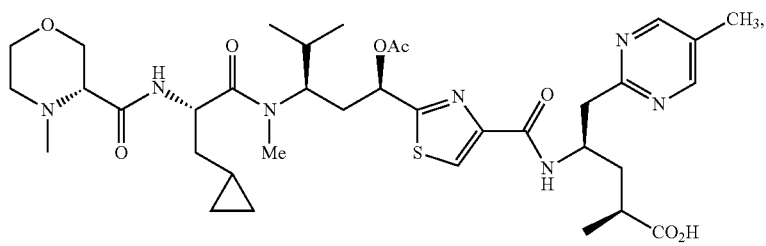
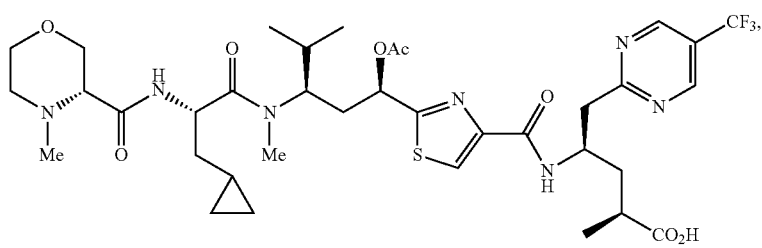 [SMILES: CC(=O)O[C@H](C[C@H](C(C)C)N(C)C(=O)[C@H](CC1CC1)NC(=O)[C@H]1COCCN1C)c1nc(C(=O)N[C@@H](Cc2ncc(C(F)(F)F)cn2)C[C@H](C)C(=O)O)cs1]
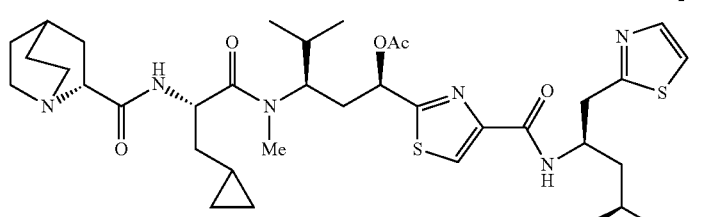
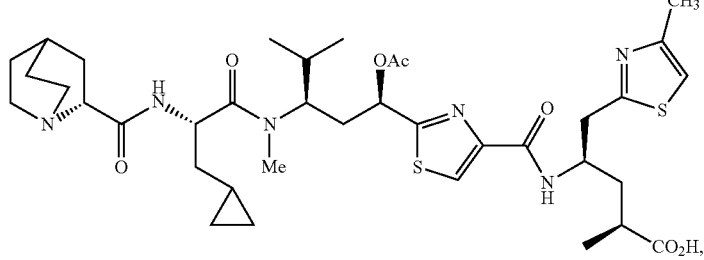

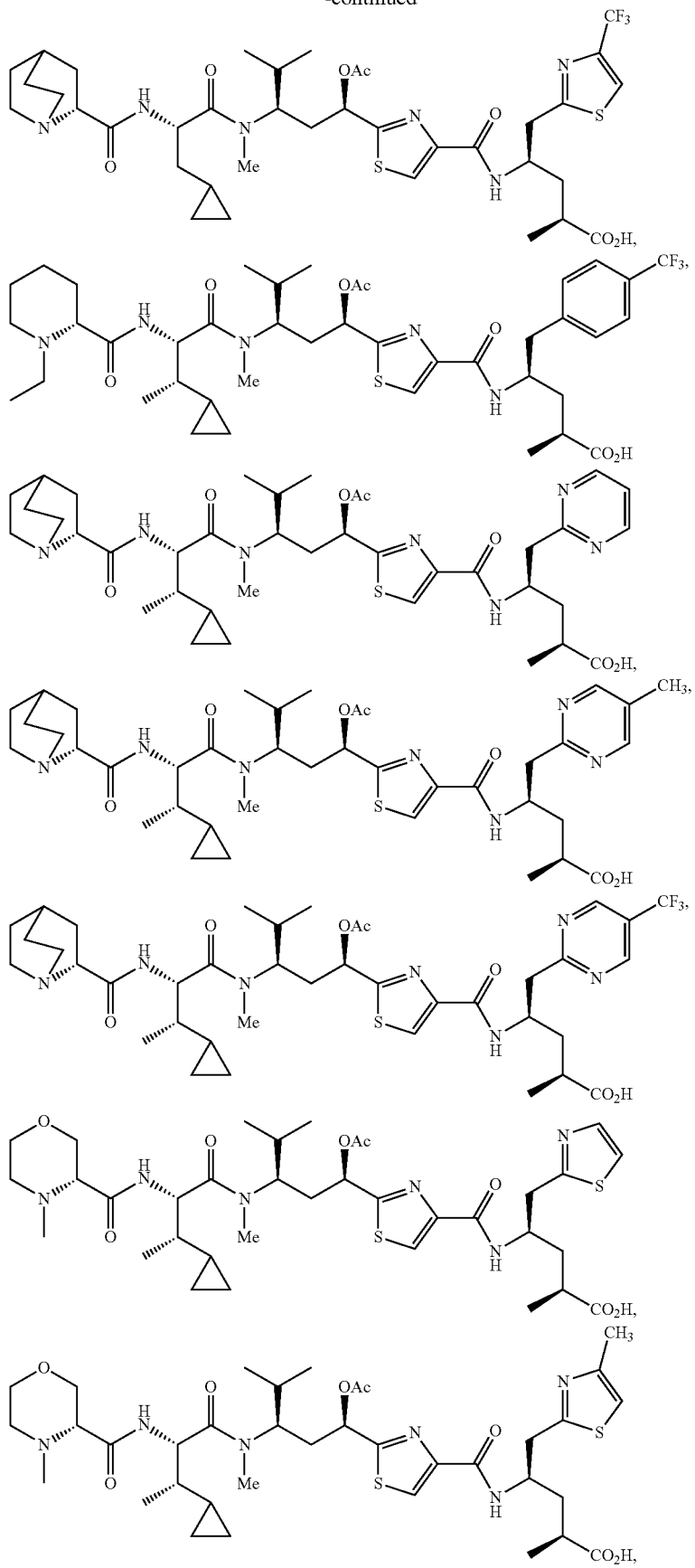

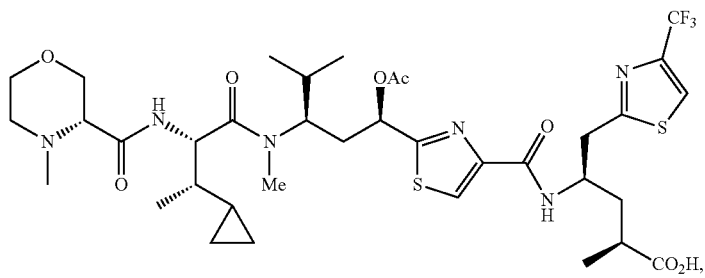
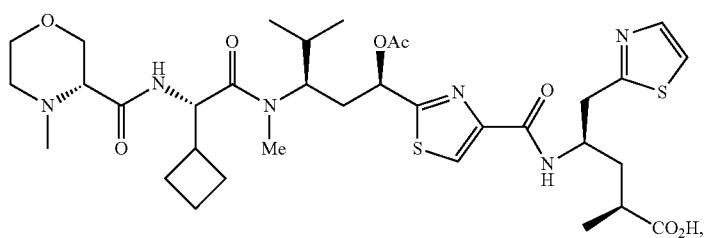
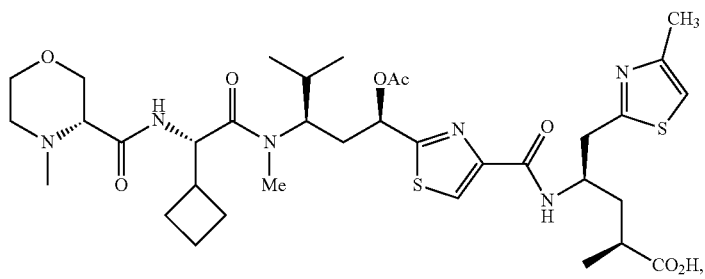
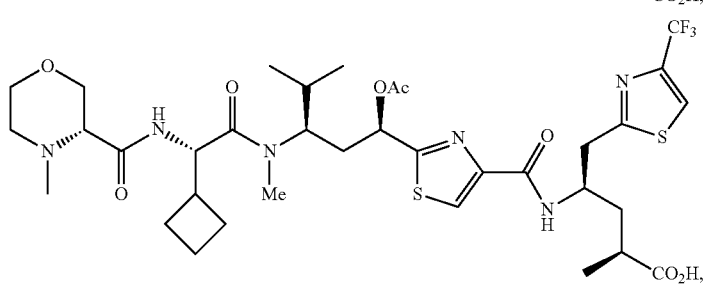
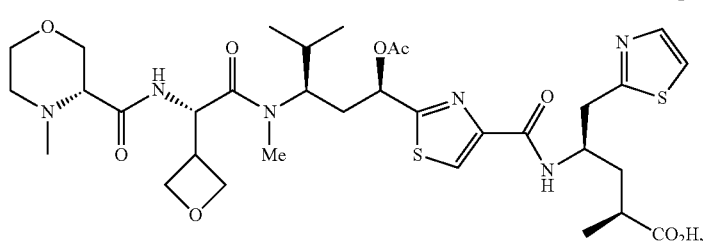
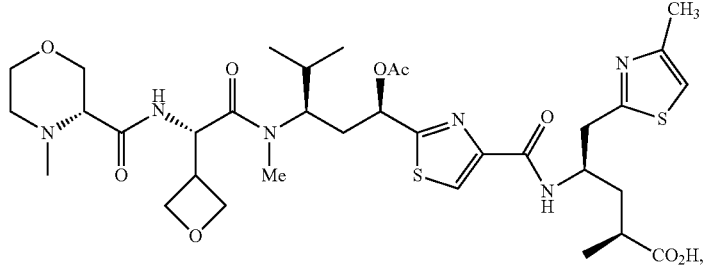

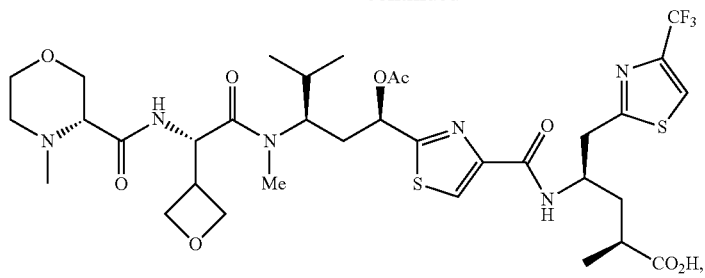
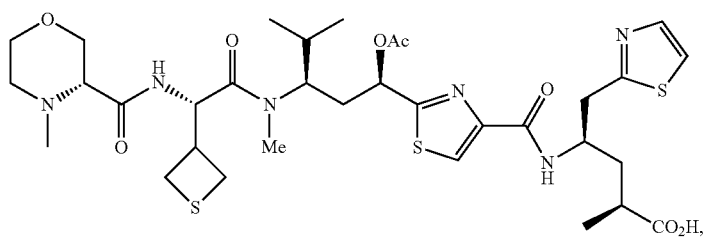
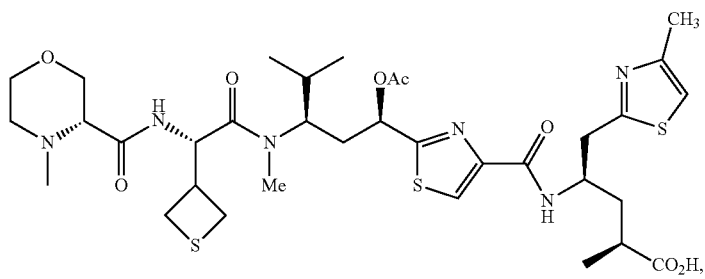
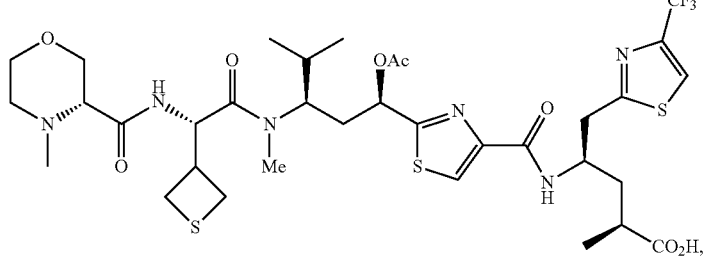
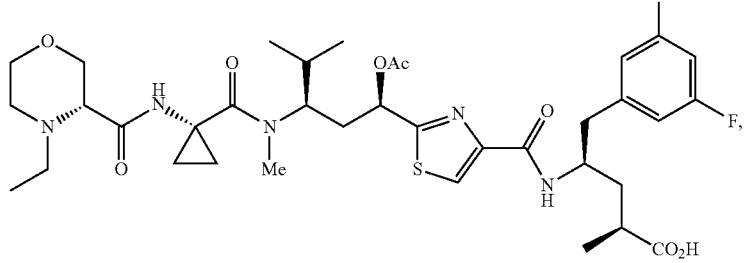
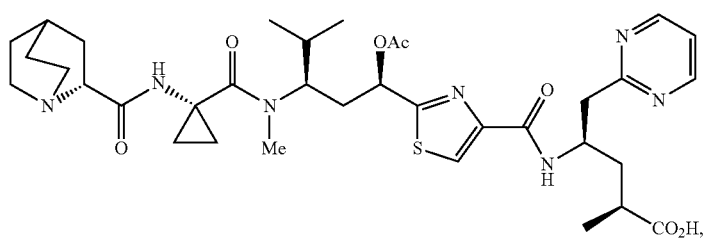

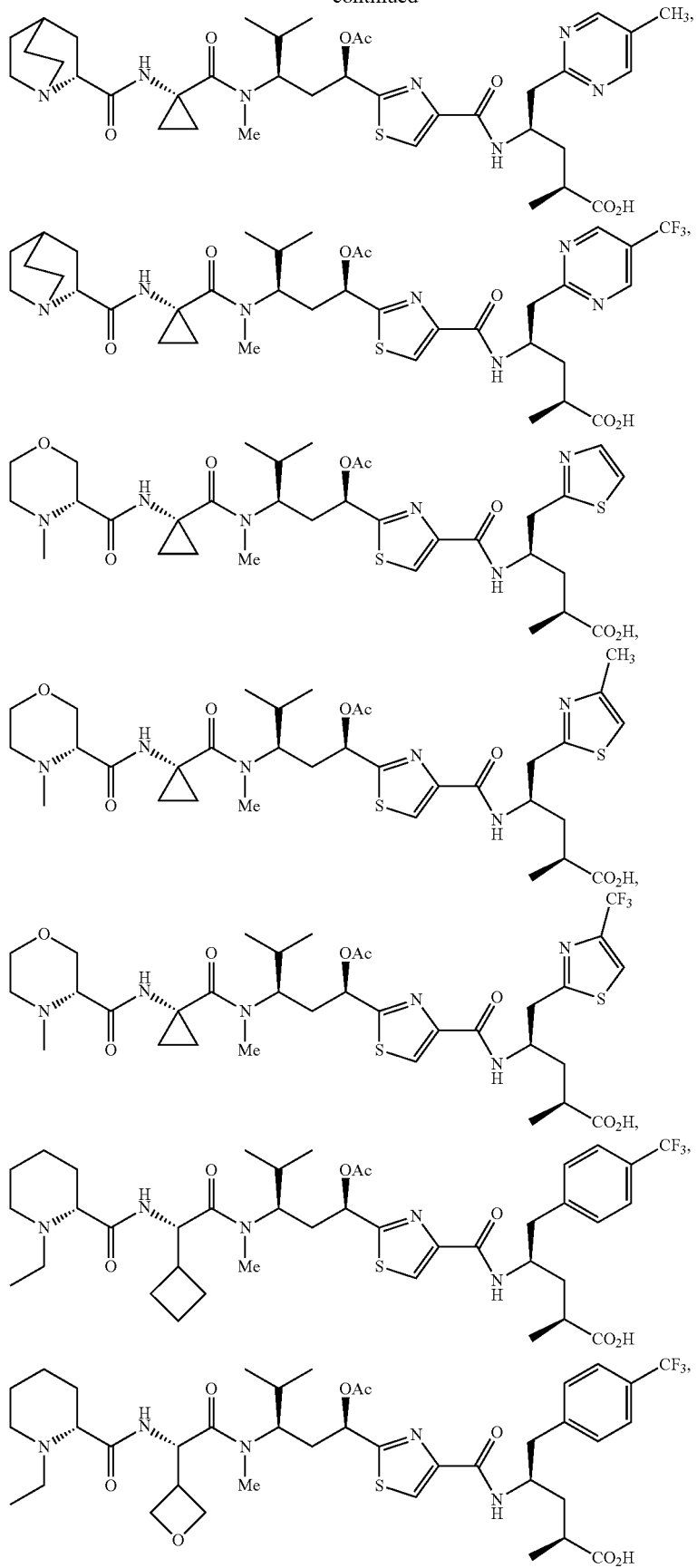

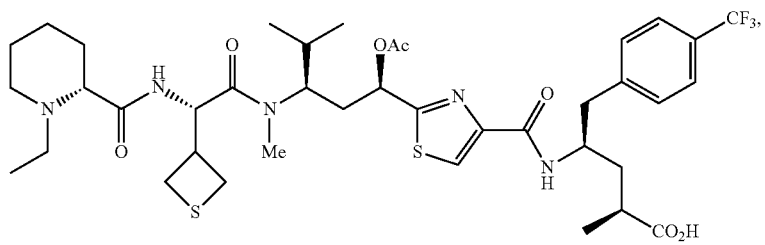
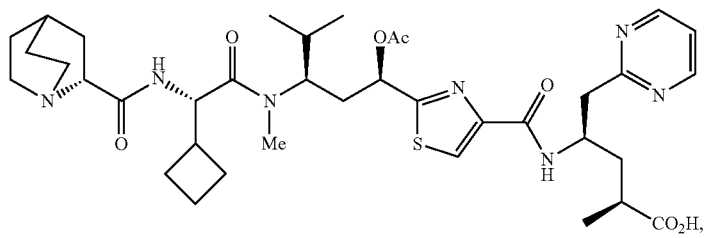
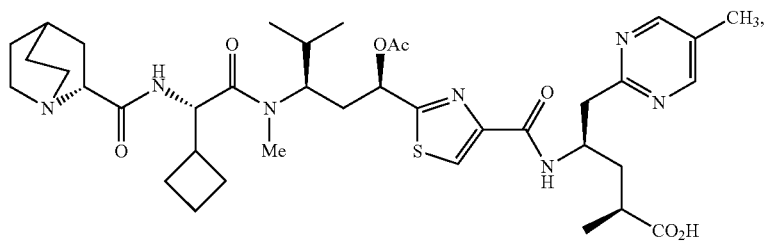
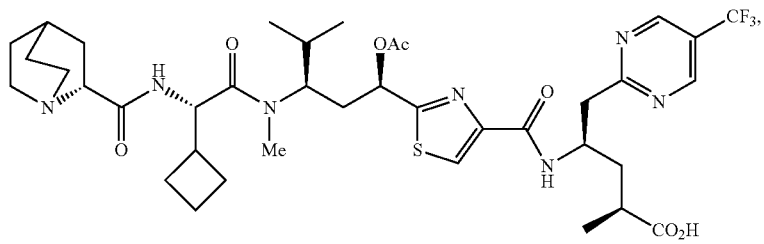
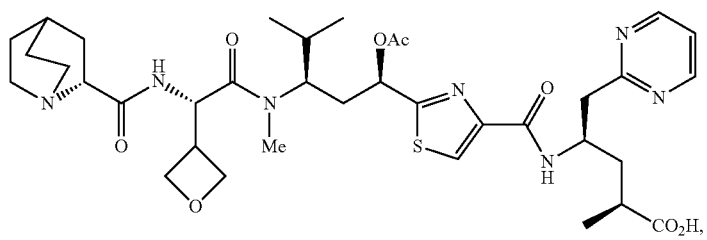
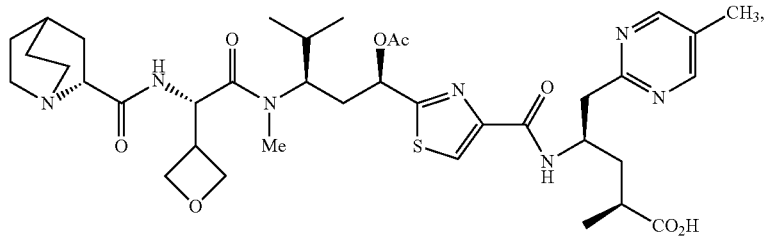
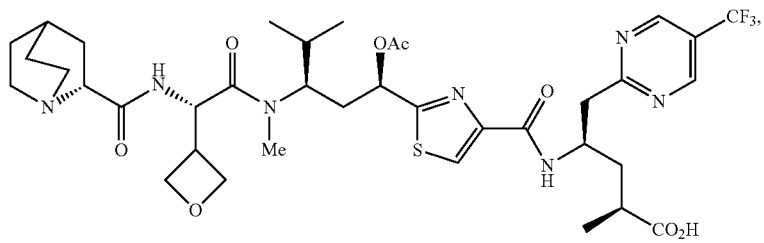

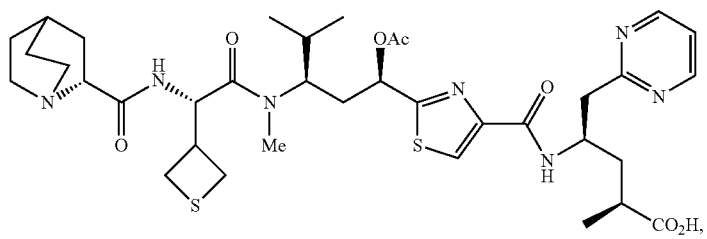
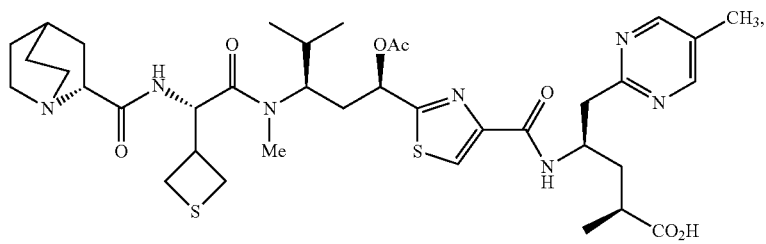
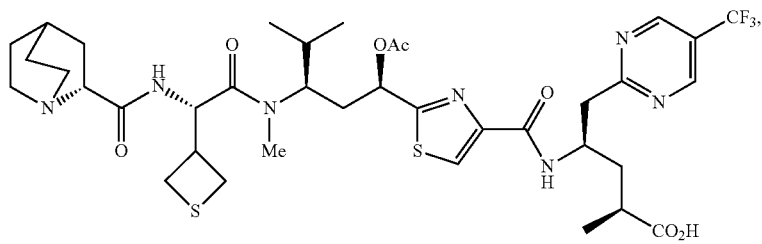
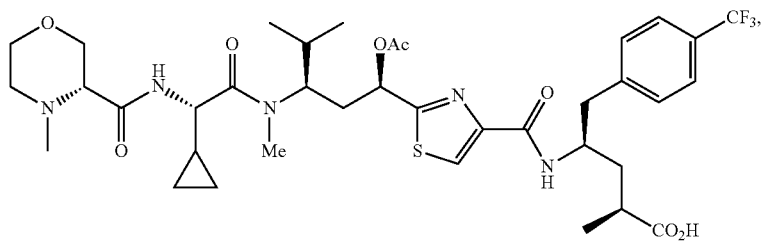
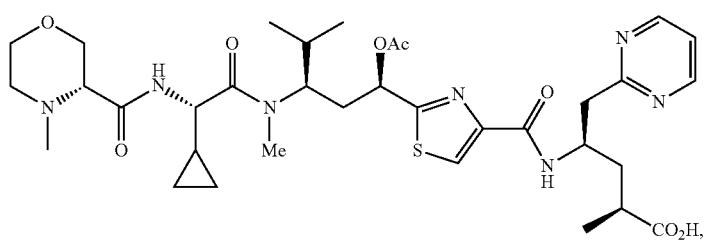
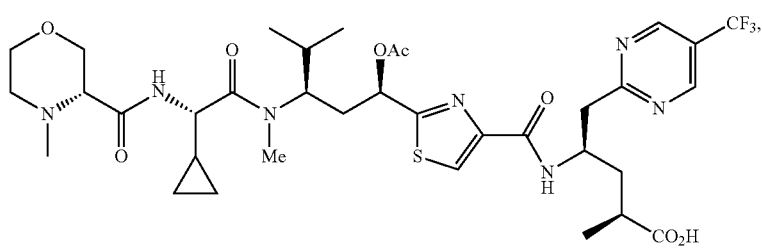

-continued
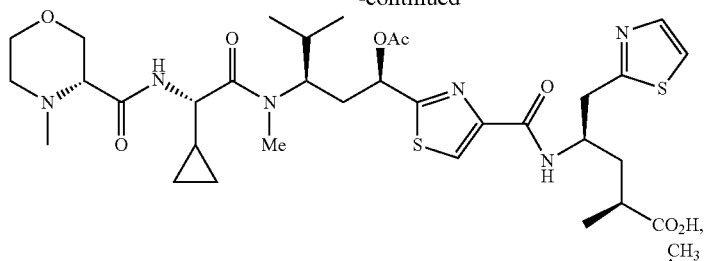
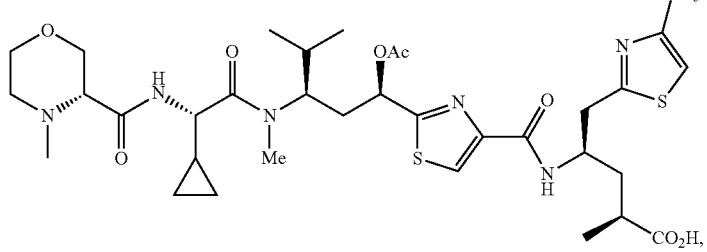
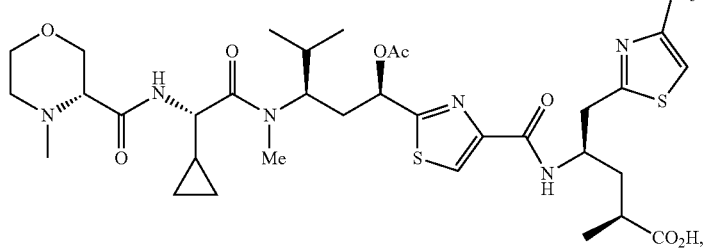
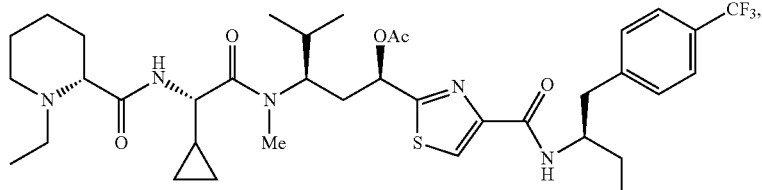
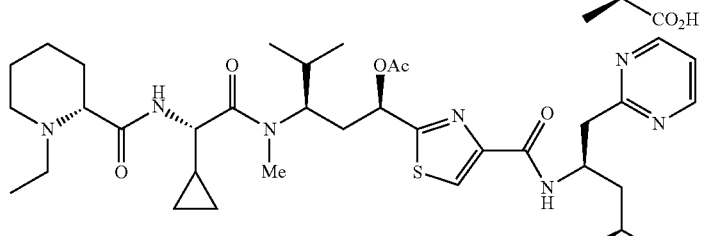
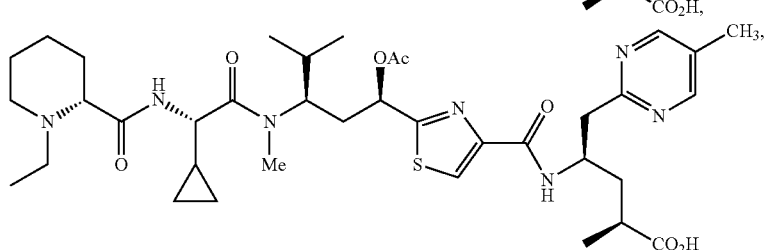
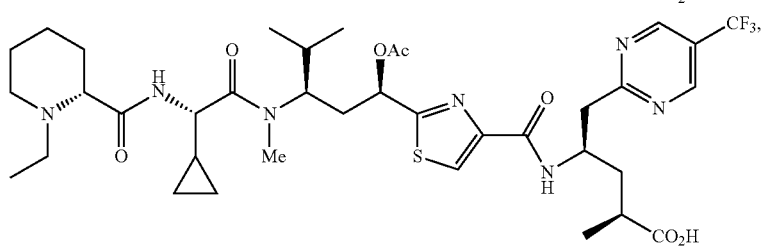

-continued
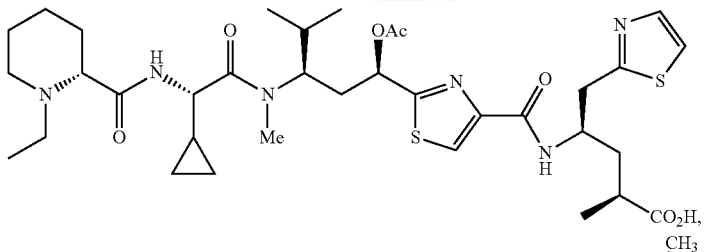
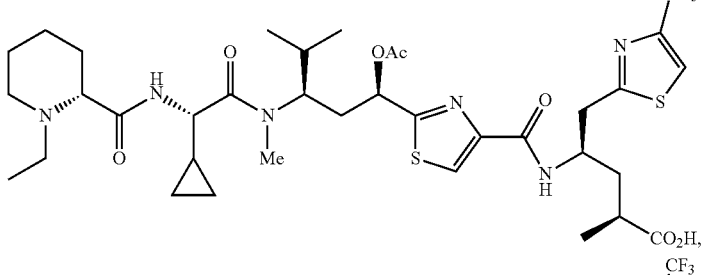
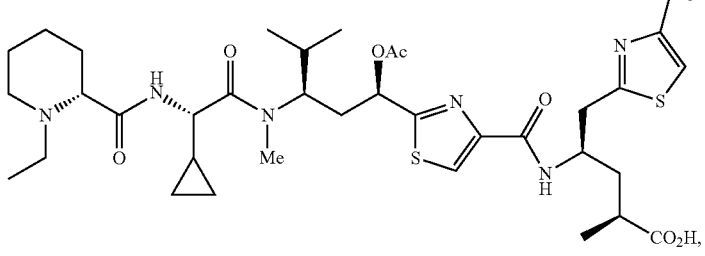
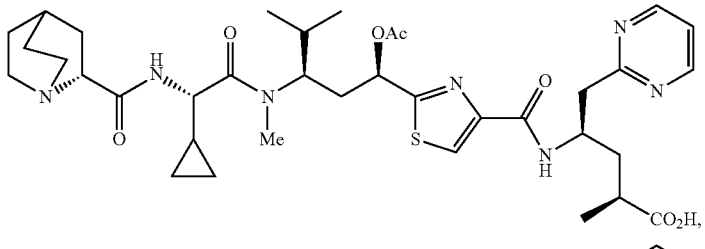
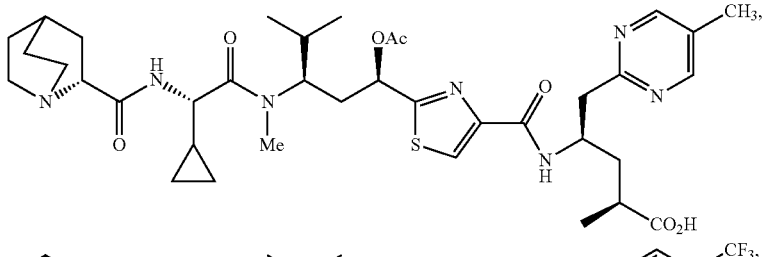
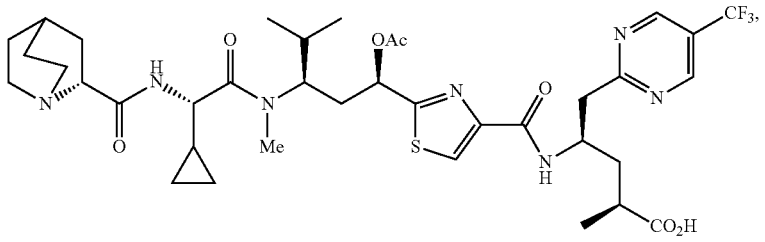
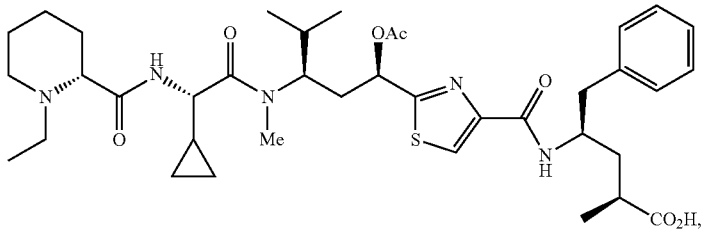

-continued
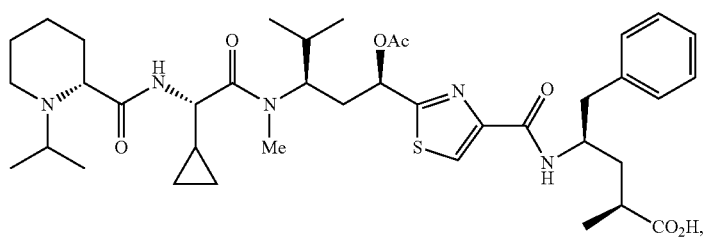
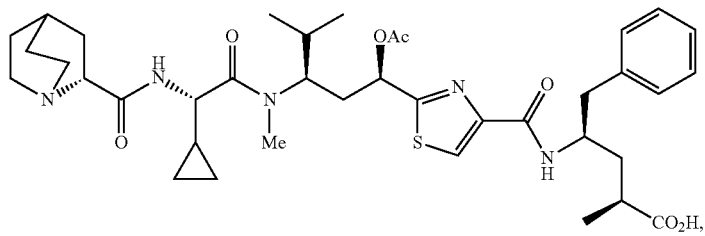
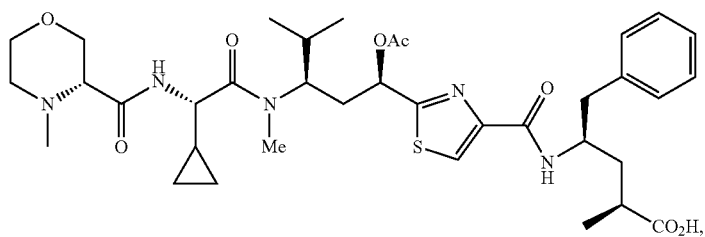
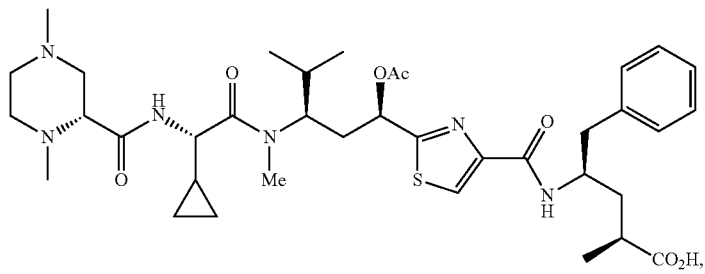
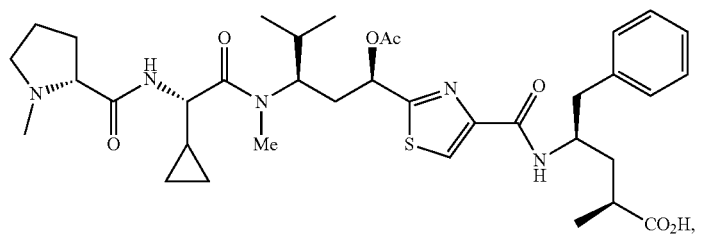
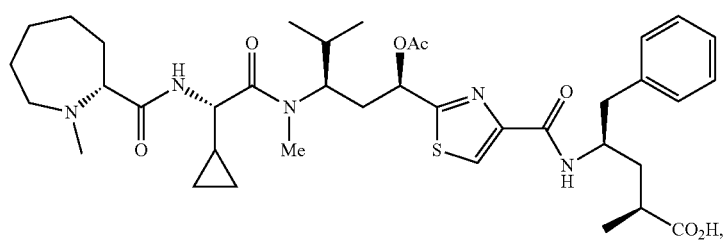
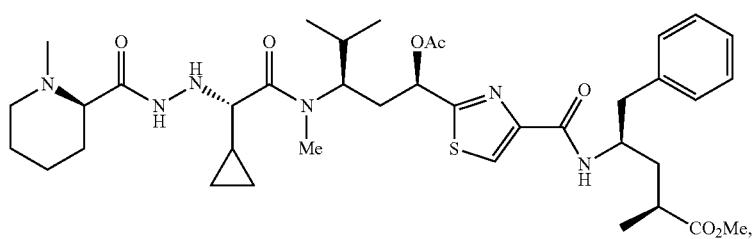

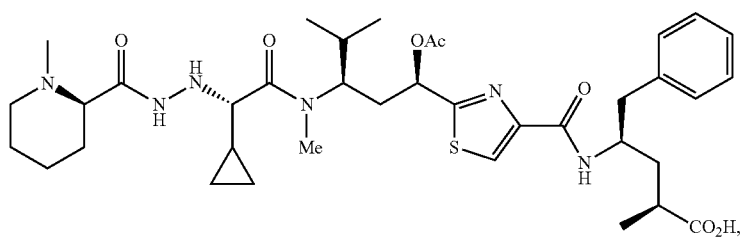
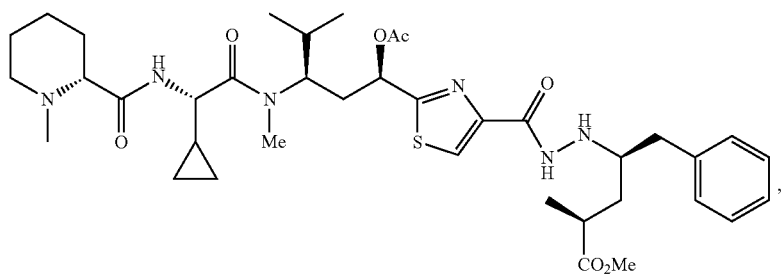
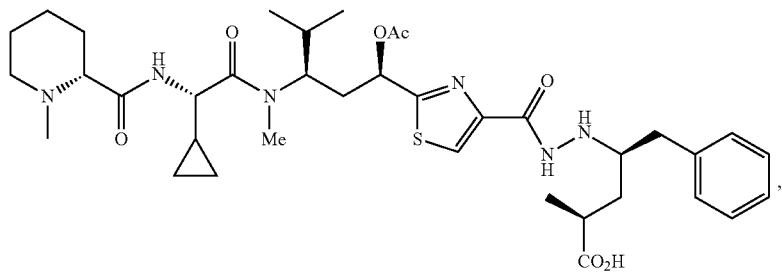
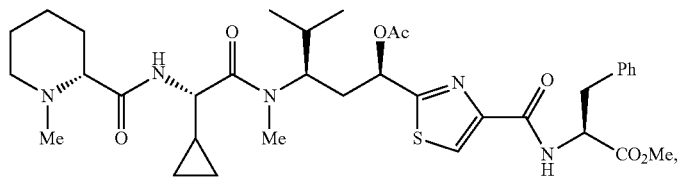
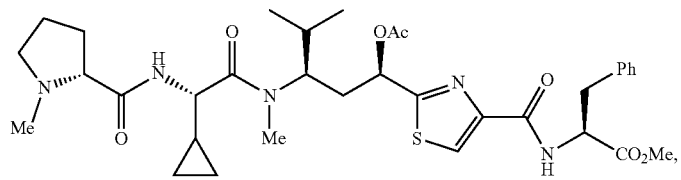
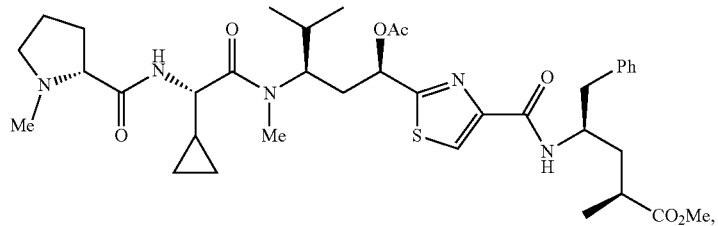
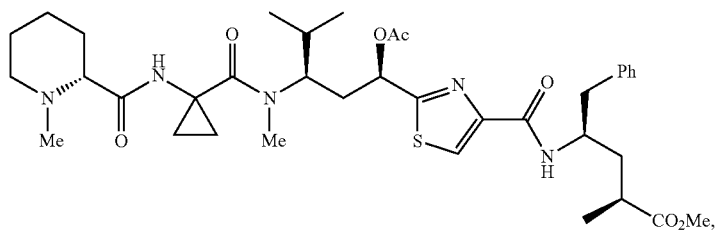

-continued
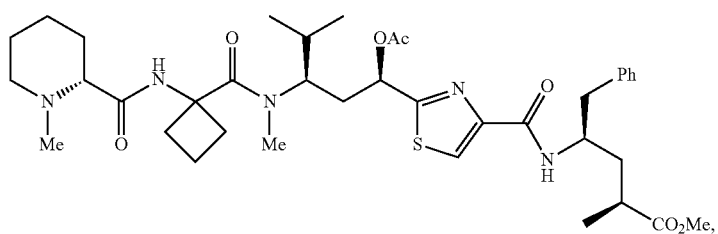
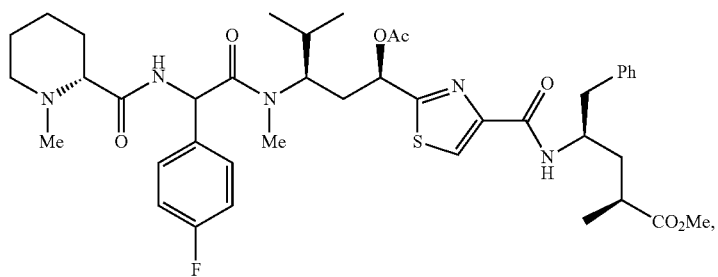
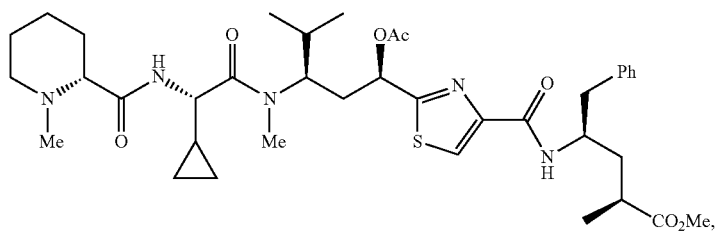
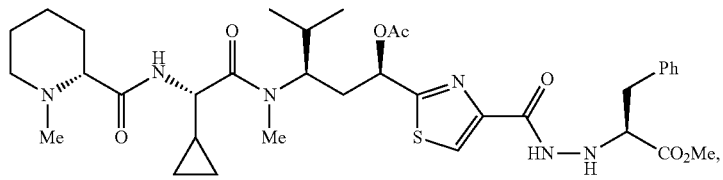
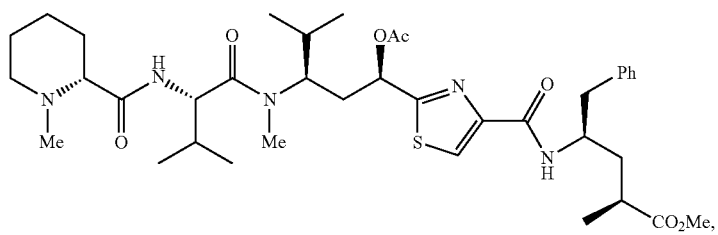
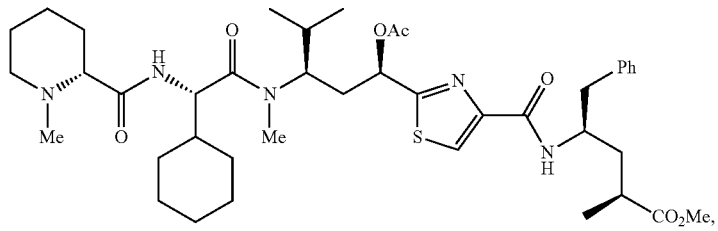
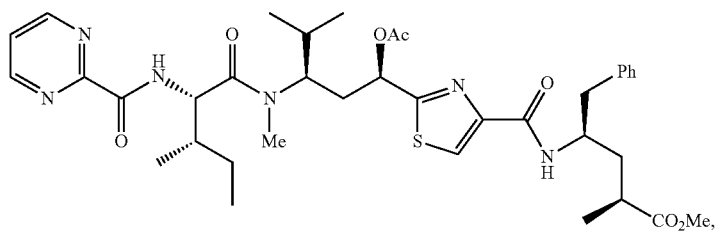

-continued
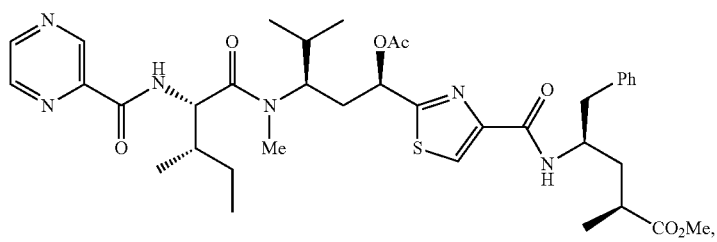
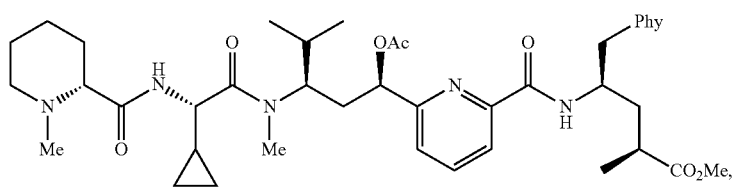
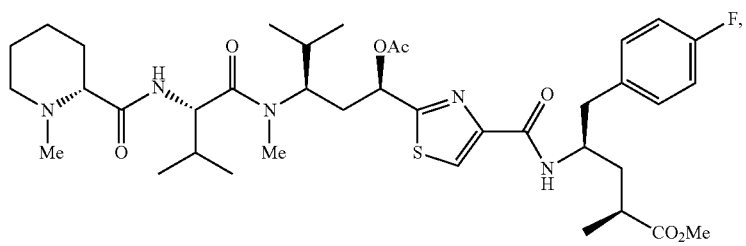
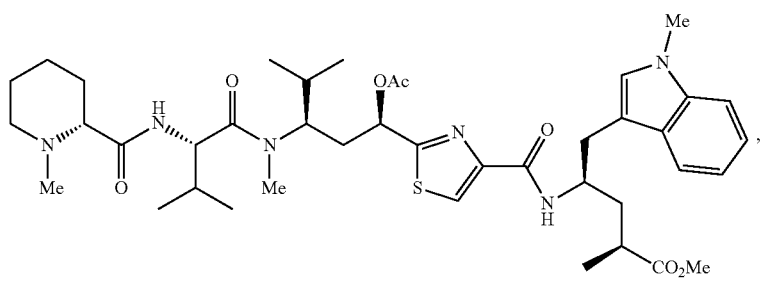
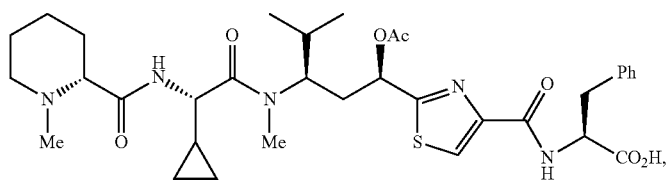
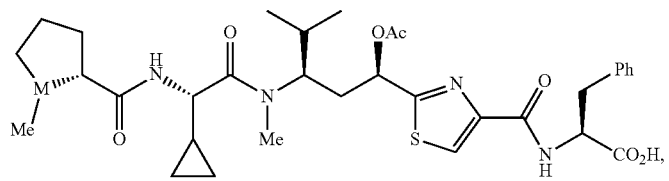
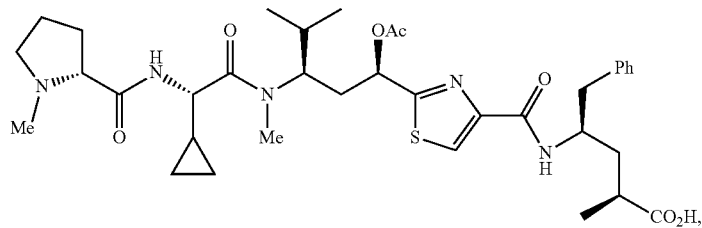

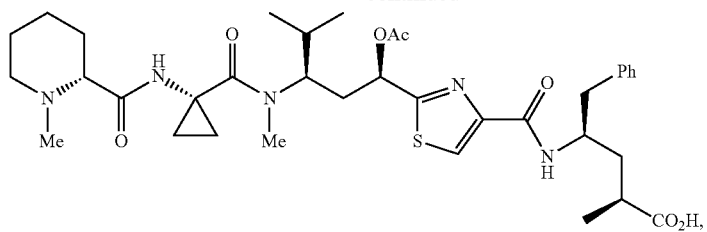
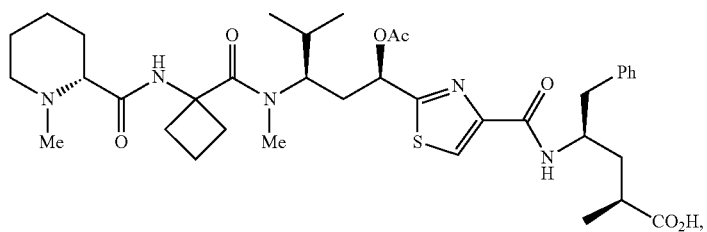
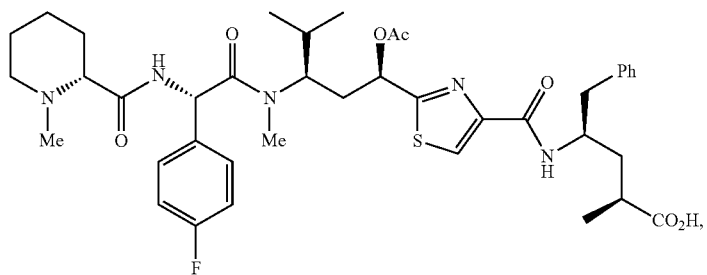
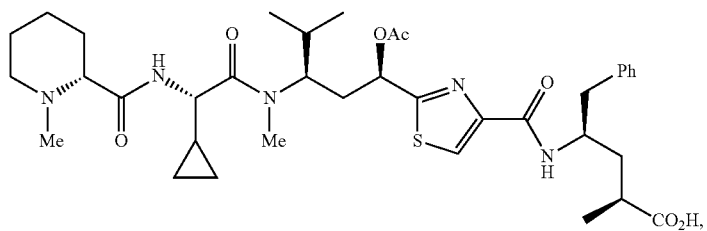
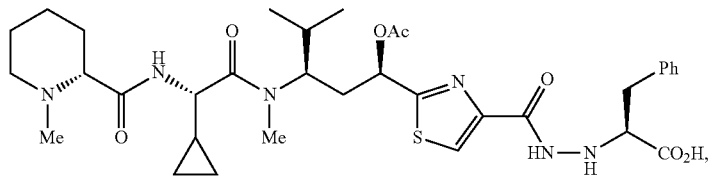
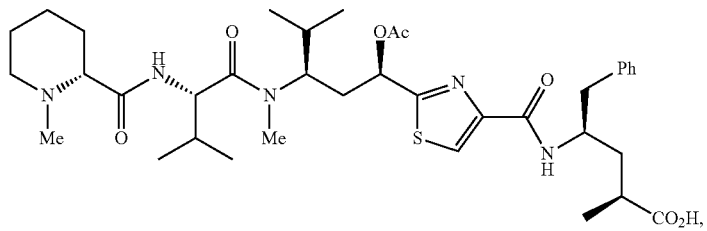
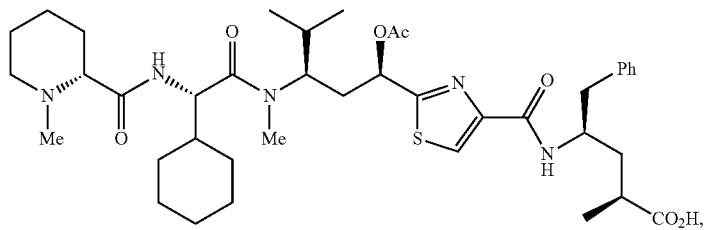

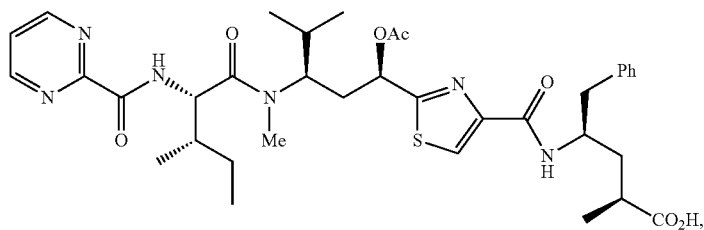
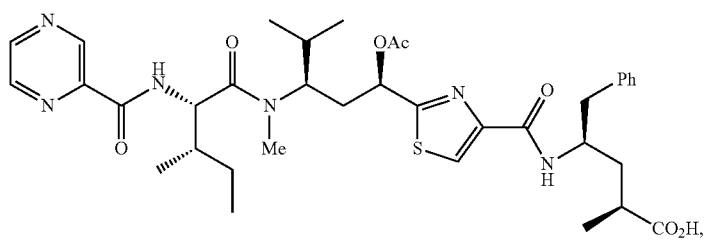
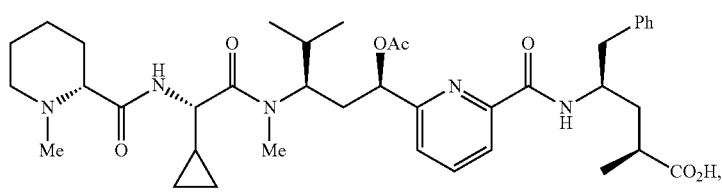
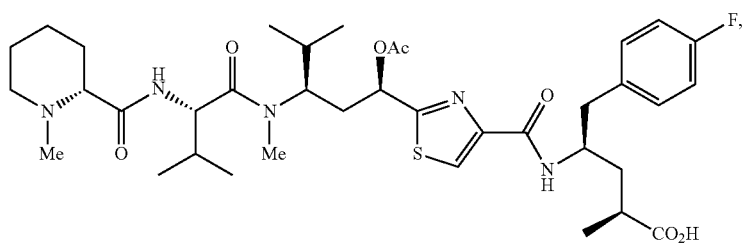
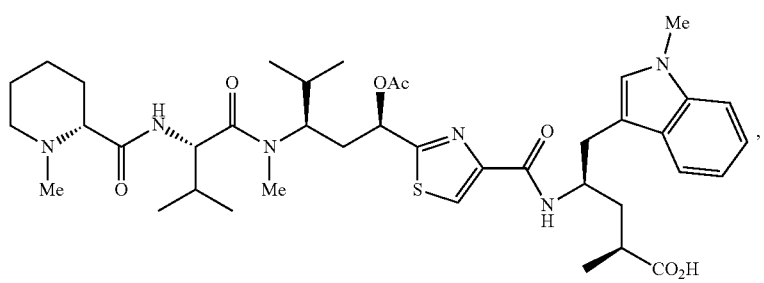
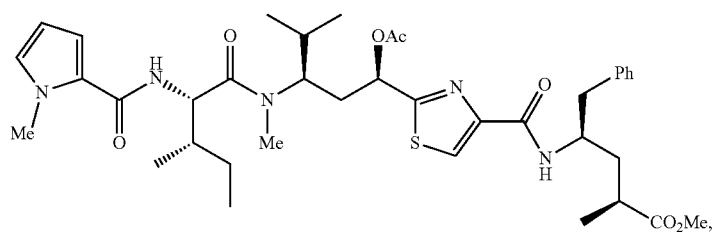
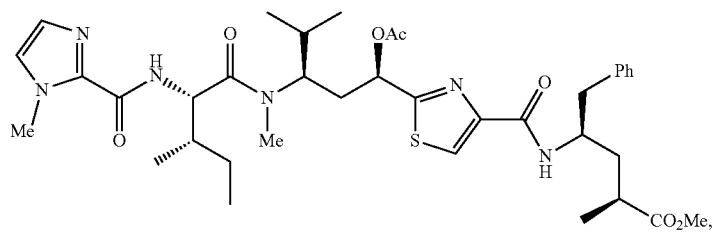

-continued
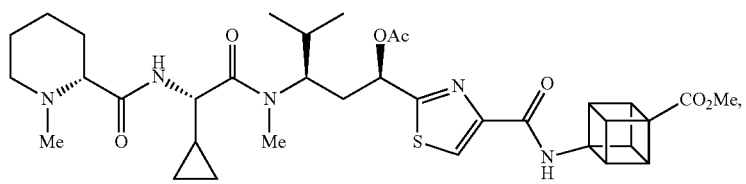
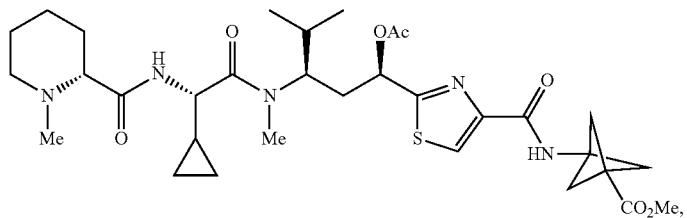
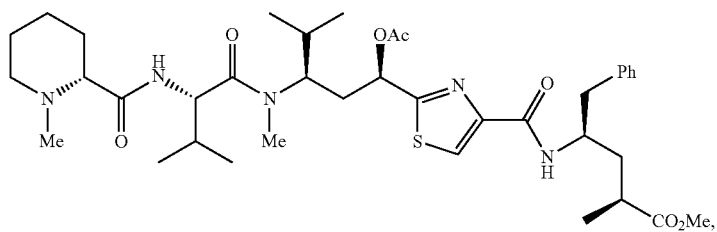
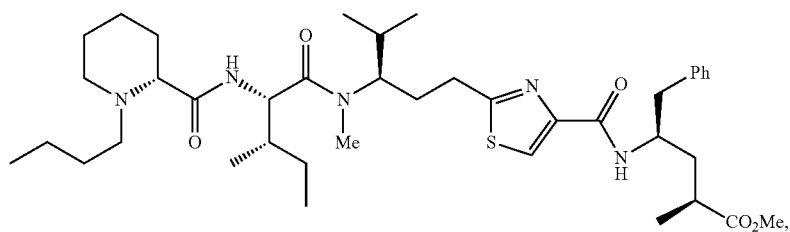
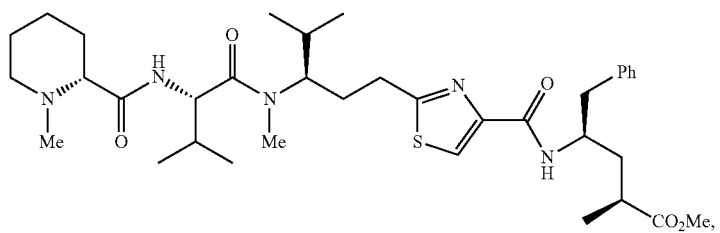
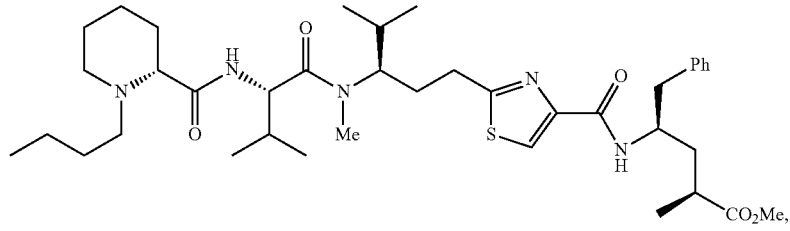
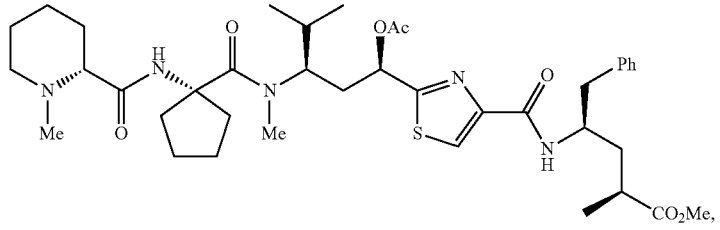

-continued
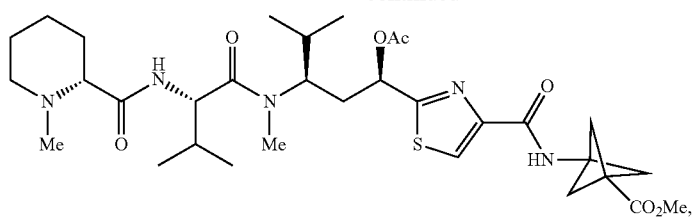
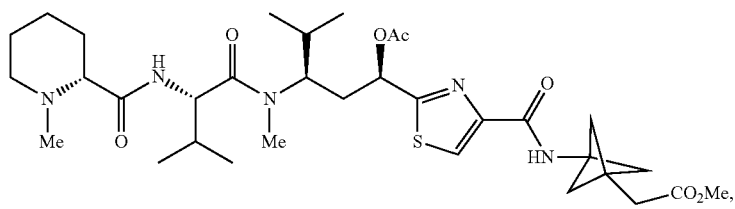
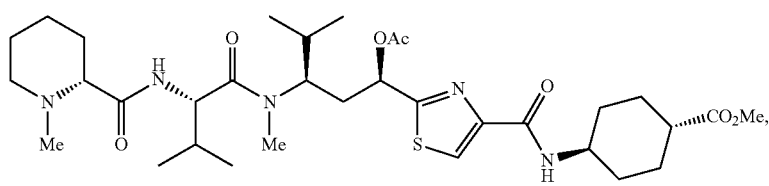
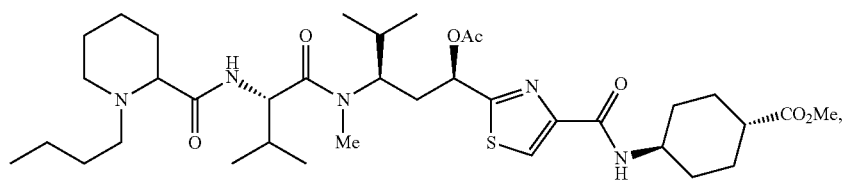
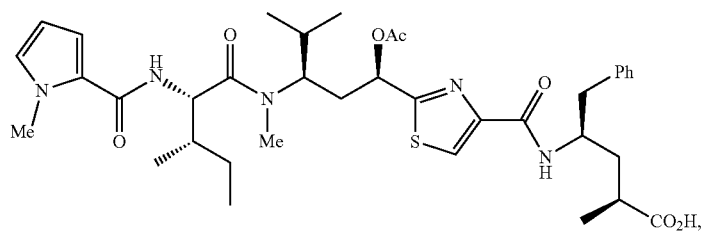
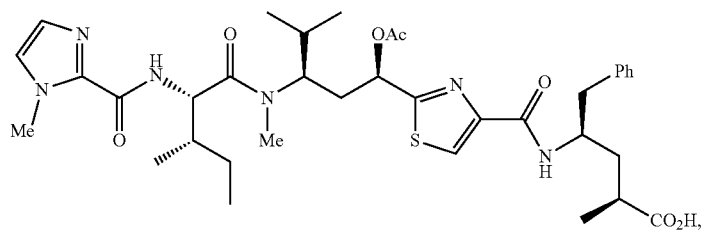
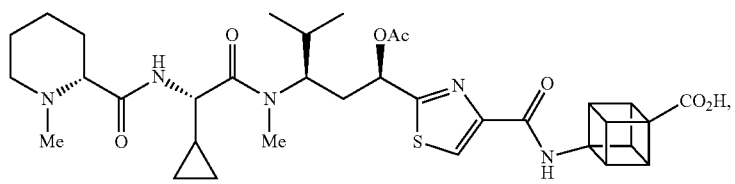
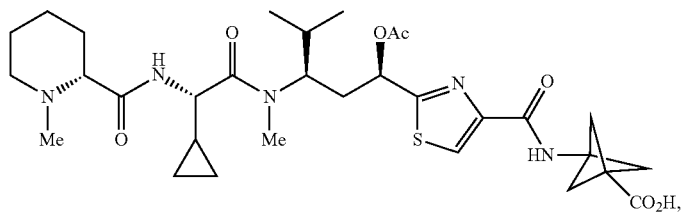

-continued
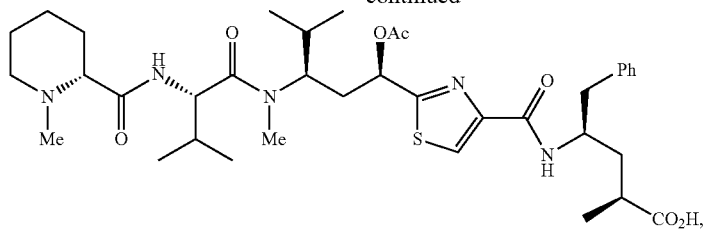
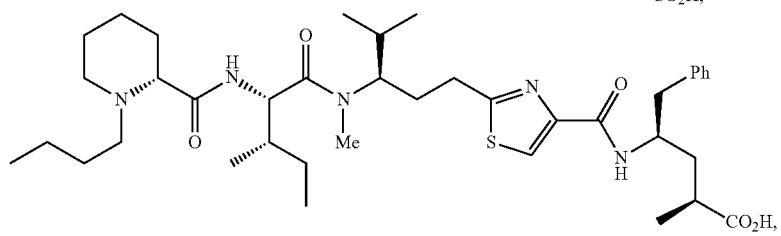
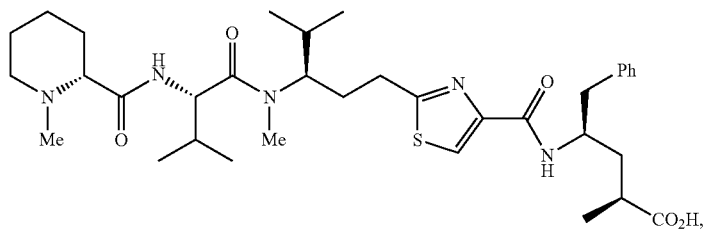
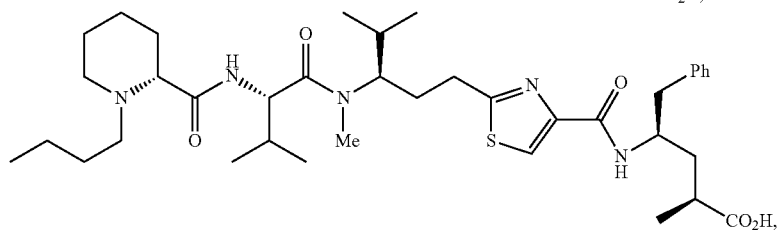
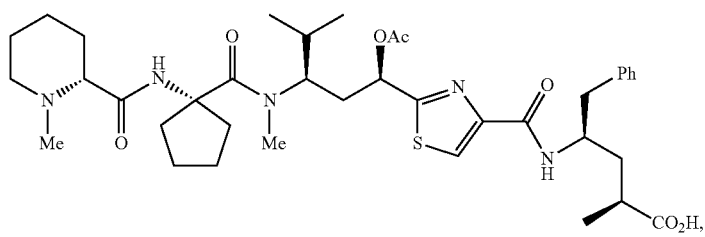
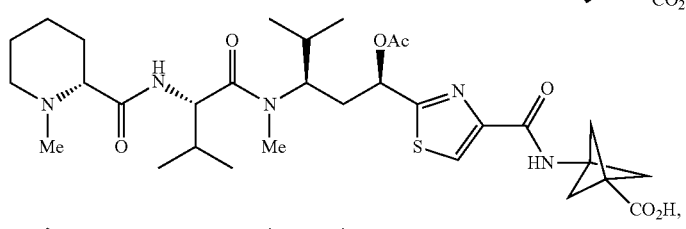
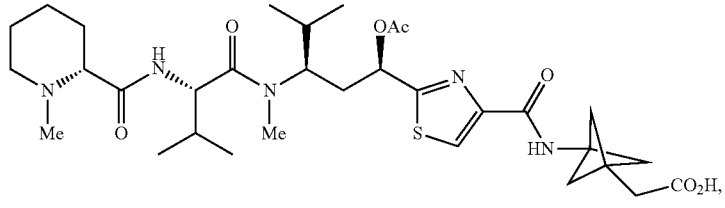
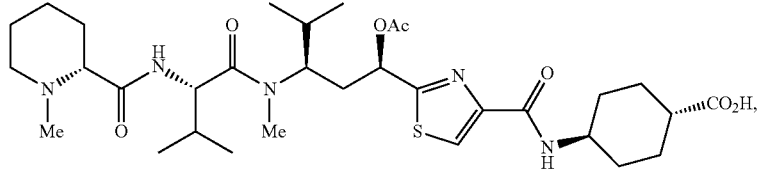

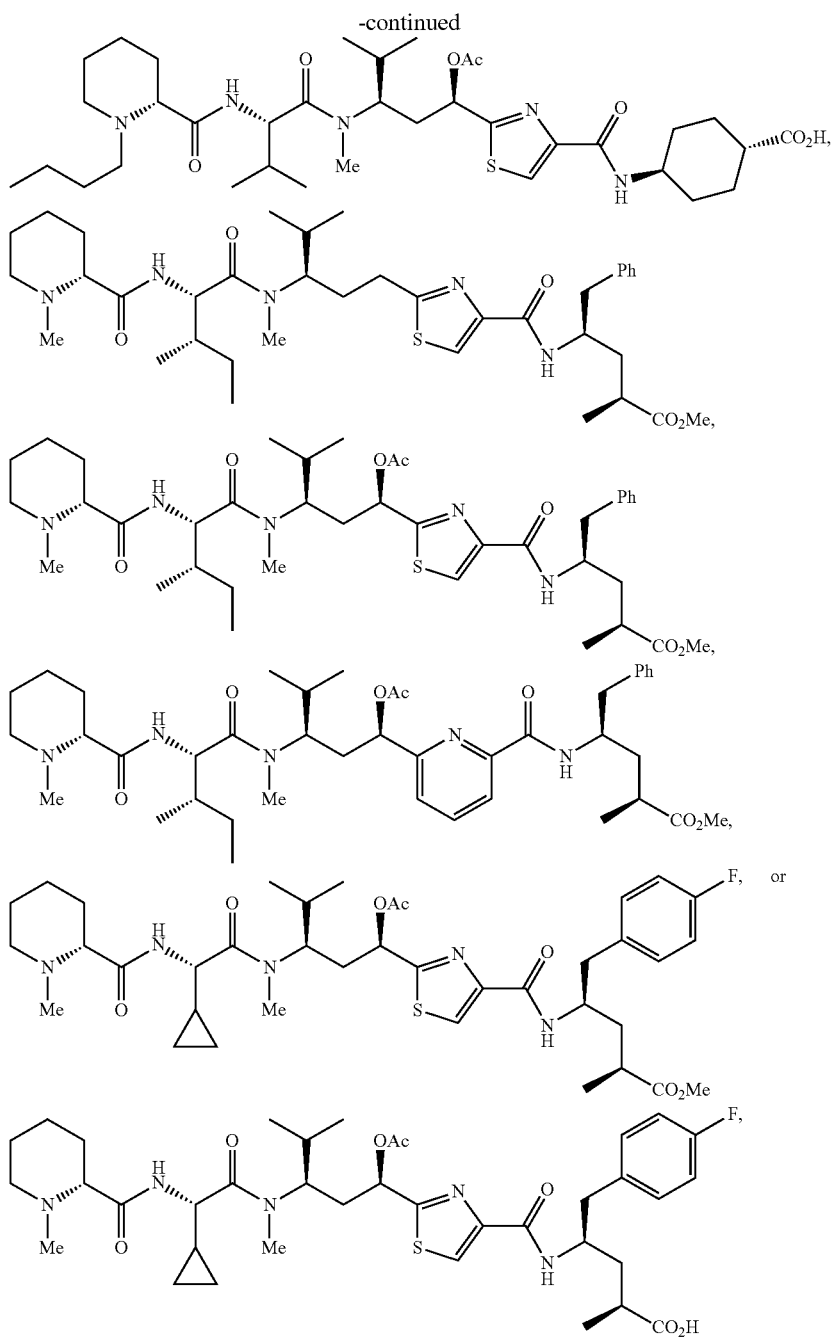
or a pharmaceutically acceptable salt thereof.
In some aspects, the present disclosure provides compounds of the formula:
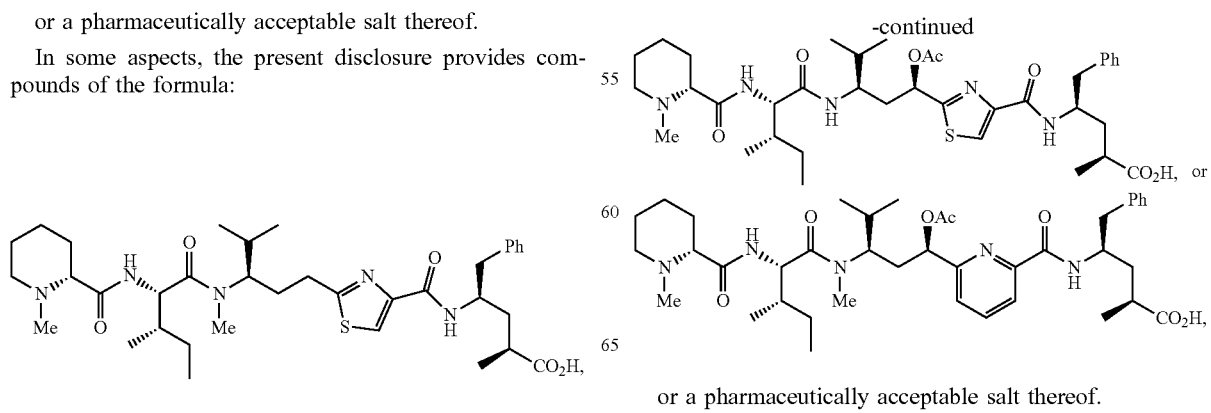
or a pharmaceutically acceptable salt thereof.

In yet another aspect, the present disclosure provides a pharmaceutical composition comprising a compound of the present disclosure and an excipient. In some embodiments, the composition is formulated for administration: orally, intraadiposally, intraarterially, intraarticularly, intracranially, intradermally, intralesionally, intramuscularly, intranasally, intraocularly, intrapericardially, intraperitoneally, intrapleurally, intraprostatically, intrarectally, intrathecally, intratracheally, intratumorally, intraumbilically, intravaginally, intravenously, intravesicularlly, intravitreally, liposomally, locally, mucosally, parenterally, rectally, subconjunctivally, subcutaneously, sublingually, topically, transbuccally, transdermally, vaginally, in cremes, in lipid compositions, via a catheter, via a lavage, via continuous infusion, via infusion, via inhalation, via injection, via local delivery, or via localized perfusion.

In still another aspect, the present disclosure provides a method of treating a disease or disorder in a patient in need thereof comprising administering to the patient a therapeutically effective amount of a compound or composition of the present disclosure. In some embodiments, the disease or disorder is cancer. In some embodiments, the cancer is a carcinoma, sarcoma, lymphoma, leukemia, melanoma, mesothelioma, multiple myeloma, or seminoma. In some embodiments, the cancer is of the bladder, blood, bone, brain, breast, central nervous system, cervix, colon, endometrium, esophagus, gall bladder, gastrointestinal tract, genitalia, genitourinary tract, head, kidney, larynx, liver, lung, muscle tissue, neck, oral or nasal mucosa, ovary, pancreas, prostate, skin, spleen, small intestine, large intestine, stomach, testicle, or thyroid. In some embodiments, the method further comprises administering a second therapy. In some embodiments, the second therapy is surgery, a second chemotherapeutic, radiotherapy, or immunotherapy. In some embodiments, the patient is a mammal. In some embodiments, the patient is a human. In some embodiments, the compound is administered once. In other embodiments, the compound is administered two or more times.

In yet another aspect, the present disclosure provides an antibody-drug conjugate comprising:

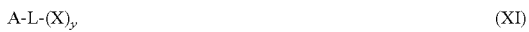

A-L-(X)$_y$     (XI)

wherein: A is an antibody; L is a covalent bond or a difunctional linker; X is a compound of the present disclosure; y is an integer selected from 1, 2, 3, 4, 5, 6, 7, 8, 9, 10, 11, 12, 13, 14, 15, 16, 17, 18, 19, or 20.

In still yet another aspect, the present disclosure provides a method of preparing a compound of the formula:

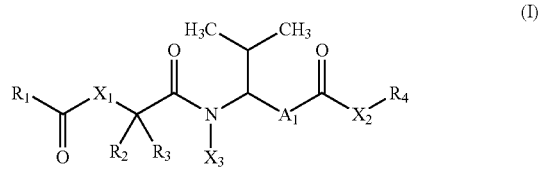

(I)

wherein: $R_1$ is heteroaryl$_{(C \leq 12)}$, heterocycloalkyl$_{(C \leq 12)}$, arylamino$_{(C \leq 12)}$, aralkylamino$_{(C \leq 12)}$, alkanediyl$_{(C \leq 12)}$-$Y_2$, fused cycloalkyl$_{(C \leq 12)}$-$Y_2$, or a substituted version of any of these groups; wherein $Y_2$ is amino, alkylamino$_{(C \leq 12)}$, dialkylamino$_{(C \leq 12)}$, amido$_{(C \leq 12)}$, substituted alkylamino$_{(C \leq 12)}$, substituted dialkylamino$_{(C \leq 12)}$, or substituted amido$_{(C \leq 12)}$; $R_2$ and $R_3$ are each independently selected from hydrogen, alkyl$_{(C \leq 12)}$, cycloalkyl$_{(C \leq 12)}$, fused cycloalkyl$_{(C \leq 12)}$, heterocycloalkyl$_{(C \leq 12)}$, -alkanediyl$_{(C \leq 12)}$-cycloalkyl$_{(C \leq 12)}$, or a substituted version of any of these groups; or $R_2$ and $R_3$ are taken together and are alkanediyl$_{(C \leq 12)}$, alkoxydiyl$_{(C \leq 12)}$, alkylthiodiyl$_{(C \leq 12)}$, or alkylaminodiyl$_{(C \leq 12)}$; $R_4$ is fused cycloalkylamino$_{(C \leq 12)}$, substituted fused cycloalkylamino$_{(C \leq 12)}$, or a structure of the formula:

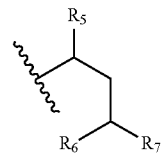

wherein: $R_5$ is aryl$_{(C \leq 12)}$, aralkyl$_{(C \leq 12)}$, heteroaryl$_{(C \leq 12)}$, heteroaralkyl$_{(C \leq 12)}$, or a substituted version of any of these groups; or is -alkanediyl$_{(C \leq 12)}$-arenediyl$_{(C \leq 12)}$-$Y_3$ or a substituted version of any of these groups; wherein: $Y_3$ is alkoxy$_{(C \leq 12)}$, aryloxy$_{(C \leq 12)}$, an oxygen linked antibody, —C(O)-alkoxy$_{(C \leq 12)}$, —C(O)-alkylamino$_{(C \leq 12)}$, —C(O)-dialkylamino$_{(C \leq 12)}$, —C(O)-aryloxy$_{(C \leq 12)}$, —C(O)-arylamino$_{(C \leq 12)}$, —C(O)—$Y_4$; or a substituted version of any of these groups; wherein: $Y_4$ is a nitrogen linked antibody or an oxygen linked antibody; $R_6$ is hydrogen, alkyl$_{(C \leq 8)}$, or substituted alkyl$_{(C \leq 8)}$; $R_7$ is —C(O)—$Y_5$; wherein $Y_5$ is amino, hydroxy, alkoxy$_{(C \leq 12)}$, substituted alkoxy$_{(C \leq 12)}$, alkylamino$_{(C \leq 12)}$, substituted alkylamino$_{(C \leq 12)}$, dialkylamino$_{(C \leq 12)}$, substituted dialkylamino$_{(C \leq 12)}$, an oxygen linked antibody, or a nitrogen linked antibody; $X_1$ is selected from —N$Y_6$$R_8$— or —N$Y_6$$R_9$N$R_{10}$—; $X_2$ is —O—, —S—, —N$R_8$—, or —N$R_9$N$R_{10}$—, wherein: $Y_6$ is hydrogen or a monovalent amino protecting group; and $R_8$, $R_9$, and $R_{10}$ are each independently selected from hydrogen, alkyl$_{(C \leq 12)}$, substituted alkyl$_{(C \leq 12)}$, cycloalkyl$_{(C \leq 12)}$, or substituted cycloalkyl$_{(C \leq 12)}$; $X_3$ is hydrogen, alkyl$_{(C \leq 12)}$, or substituted alkyl$_{(C \leq 12)}$; and $A_1$ is —C(O)N$R_3$-fused cycloalkanediyl$_{(C \leq 12)}$, -alkanediyl$_{(C \leq 12)}$-heteroarenediyl$_{(C \leq 12)}$, -alkanediyl$_{(C \leq 12)}$-heteroarenediyl$_{(C \leq 12)}$, wherein the alkanediyl is substituted with an amido$_{(C \leq 8)}$ or acyloxy$_{(C \leq 8)}$ group, or a substituted version of any of these groups, wherein: $R_{13}$ is hydrogen, alkyl$_{(C \leq 12)}$, substituted alkyl$_{(C \leq 12)}$, cycloalkyl$_{(C \leq 12)}$, or substituted cycloalkyl$_{(C \leq 12)}$; provided that $X_3$ is not hydrogen, methyl, hydroxymethyl, or acetoxymethyl, when $R_2$ or $R_3$ is sec-butyl, $R_5$ is benzyl, $R_7$ is —CO$_2$H, and $R_1$ is 2-N-methylpiperidinyl; comprising reacting a compound of the formula:

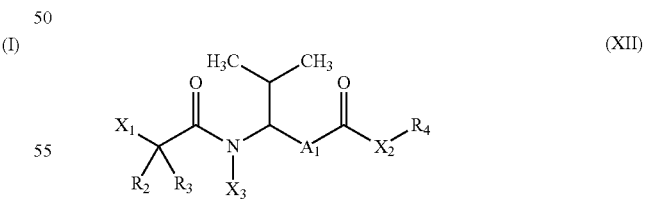

(XII)

wherein: $R_2$ and $R_3$ are each independently selected from hydrogen, alkyl$_{(C \leq 12)}$, cycloalkyl$_{(C \leq 12)}$, fused cycloalkyl$_{(C \leq 12)}$, heterocycloalkyl$_{(C \leq 12)}$, -alkanediyl$_{(C \leq 12)}$-cycloalkyl$_{(C \leq 12)}$, or a substituted version of any of these groups; or $R_2$ and $R_3$ are taken together and are alkanediyl$_{(C \leq 12)}$, alkoxydiyl$_{(C \leq 12)}$, alkylthiodiyl$_{(C \leq 12)}$, or alkylaminodiyl$_{(C \leq 12)}$; $R_4$ is fused cycloalkylamino$_{(C \leq 12)}$, substituted fused cycloalkylamino$_{(C \leq 12)}$, or a structure of the formula:

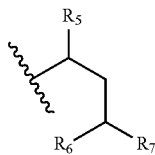

wherein: $R_5$ is aryl$_{(C \leq 12)}$, aralkyl$_{(C \leq 12)}$, heteroaryl$_{(C \leq 12)}$, heteroaralkyl$_{(C \leq 12)}$, or a substituted version of any of these groups; or is -alkanediyl$_{(C \leq 6)}$-arenediyl$_{(C \leq 12)}$-$Y_3$ or a substituted version of any of these groups; wherein: $Y_3$ is alkoxy$_{(C \leq 12)}$, aryloxy$_{(C \leq 12)}$, an oxygen linked antibody, —C(O)-alkoxy$_{(C \leq 12)}$, —C(O)-alkylamino$_{(C \leq 12)}$, —C(O)-dialkylamino$_{(C \leq 12)}$, —C(O)-aryloxy$_{(C \leq 12)}$, —C(O)-arylamino$_{(C \leq 12)}$, —C(O)—$Y_4$; or a substituted version of any of these groups; wherein: $Y_4$ is a nitrogen linked antibody or an oxygen linked antibody; $R_6$ is hydrogen, alkyl$_{(C \leq 8)}$, or substituted alkyl$_{(C \leq 8)}$; $R_7$ is —C(O)—$Y_5$; wherein $Y_5$ is amino, hydroxy, alkoxy$_{(C \leq 12)}$, substituted alkoxy$_{(C \leq 12)}$, alkylamino$_{(C \leq 12)}$, substituted alkylamino$_{(C \leq 12)}$, dialkylamino$_{(C \leq 12)}$, substituted dialkylamino$_{(C \leq 12)}$, an oxygen linked antibody, or a nitrogen linked antibody; $X_1$ is selected from —NR$_8$— or —NR$_9$NR$_{10}$—; $X_2$ is —O—, —S—, —NR$_9$—, or —NR$_9$NR$_{10}$—, wherein: $R_8$, $R_9$, and $R_{10}$ are each independently selected from hydrogen, alkyl$_{(C \leq 12)}$, substituted alkyl$_{(C \leq 12)}$, cycloalkyl$_{(C \leq 12)}$, or substituted cycloalkyl$_{(C \leq 12)}$; $X_3$ is hydrogen, alkyl$_{(C \leq 12)}$, or substituted alkyl$_{(C \leq 12)}$; and $A_1$ is —C(O)NR$_{13}$-fused cycloalkanediyl$_{(C \leq 12)}$, -alkanediyl$_{(C \leq 12)}$-heteroarenediyl$_{(C \leq 12)}$, -alkanediyl$_{(C \leq 12)}$-heteroarenediyl$_{(C \leq 12)}$, wherein the alkanediyl is substituted with an amido$_{(C \leq 8)}$ or acyloxy$_{(C \leq 8)}$ group, or a substituted version of any of these groups, wherein: $R_{13}$ is hydrogen, alkyl$_{(C \leq 12)}$, substituted alkyl$_{(C \leq 12)}$, cycloalkyl$_{(C \leq 12)}$, or substituted cycloalkyl$_{(C \leq 12)}$; provided that $X_3$ is not hydrogen, methyl, or hydroxymethyl when $R_2$ or $R_3$ is sec-butyl; with a compound of the formula:

$$R_1—Z \quad (XIII)$$

$R_1$ is heteroaryl$_{(C \leq 12)}$, heterocycloalkyl$_{(C \leq 12)}$, arylamino$_{(C \leq 12)}$, aralkylamino$_{(C \leq 12)}$, alkanediyl$_{(C \leq 12)}$-$Y_2$, fused cycloalkyl$_{(C \leq 12)}$-$Y_2$, or a substituted version of any of these groups, wherein $Y_2$ is amino, alkylamino$_{(C \leq 12)}$, dialkylamino$_{(C \leq 12)}$, amido$_{(C \leq 12)}$, substituted alkylamino$_{(C \leq 12)}$, substituted dialkylamino$_{(C \leq 12)}$, or substituted amido$_{(C \leq 12)}$; and Z is an isocyanate, —C(O)-activating agent, —C(O)-aryloxy$_{(C \leq 12)}$, or —C(O)-substituted aryloxy$_{(C \leq 12)}$; in the presence of a base. In some embodiments, the method further comprises one or more deprotection steps. In some embodiments, the method further comprises protecting one or more hydroxyl groups with an acyl$_{(C \leq 12)}$ or a substituted acyl$_{(C \leq 12)}$ group. In some embodiments, the method further comprises removing the monovalent amino protecting group in the presence of a base. In some embodiments, the base is pyridine, triethylamine, or diisopropylethylamine. In some embodiments, the method further comprises purifying the compound.

It is contemplated that any method or composition described herein can be implemented with respect to any other method or composition described herein. For example, a compound synthesized by one method may be used in the preparation of a final compound according to a different method.

The use of the word "a" or "an" when used in conjunction with the term "comprising" in the claims and/or the specification may mean "one," but it is also consistent with the meaning of "one or more," "at least one," and "one or more than one." The word "about" means plus or minus 5% of the stated number.

Other objects, features and advantages of the present disclosure will become apparent from the following detailed description. It should be understood, however, that the detailed description and the specific examples, while indicating specific embodiments of the disclosure, are given by way of illustration only, since various changes and modifications within the spirit and scope of the disclosure will become apparent to those skilled in the art from this detailed description.

BRIEF DESCRIPTION OF THE FIGURES

The following drawings form part of the present specification and are included to further demonstrate certain aspects of the present invention. The invention may be better understood by reference to one or more of these drawings in combination with the detailed description.

FIGS. 9-25—In vitro testing results for tubulysin analogs of the present disclosure.

DESCRIPTION OF ILLUSTRATIVE EMBODIMENTS

Figure 1:
FIG. 1—Molecular structures of naturally occurring tubulysins A, B, C, G, I; D, E, F, H; U, V; pretubulysin D (PTb-D43) and N$^{14}$-desacetoxytubulysin H (Tb1).
Figure 1:
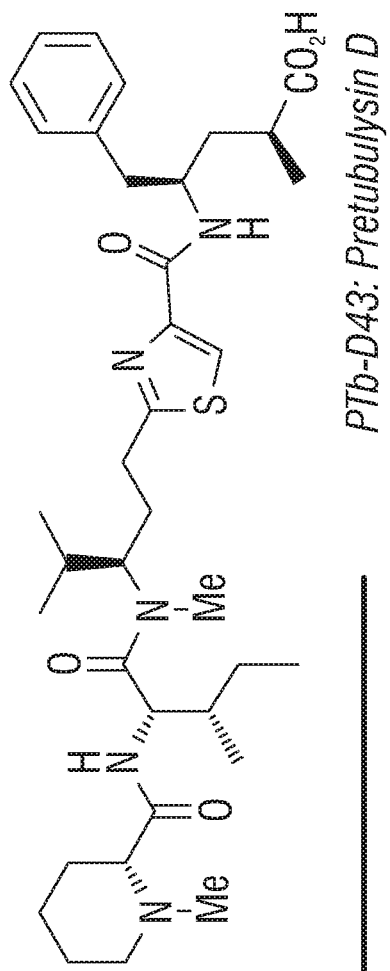
Figure 1:
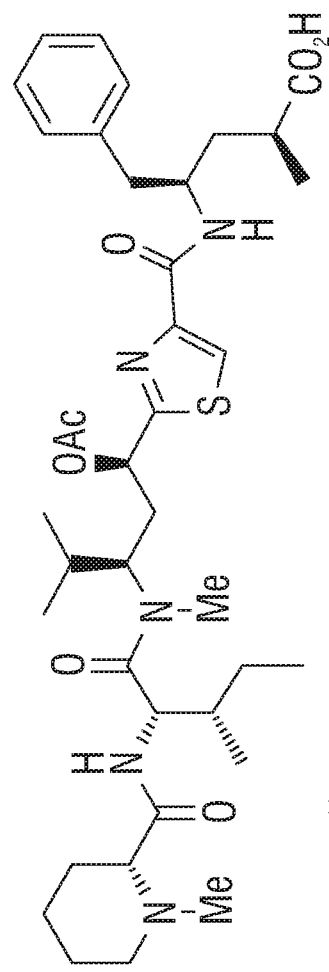

The present disclosure relates to new analogs of tubulysin useful for the treatment of cancer or a hyperproliferative disease. In some embodiments, the side chain of the isoleucine in the formula has been replaced with a group containing a three or four membered ring. In some embodiments, this group is a cyclopropyl or a cyclobutyl group.

I. COMPOUNDS AND FORMULATIONS THEREOF

A. Compounds

In one aspect, the present disclosure provides compounds of the formula:

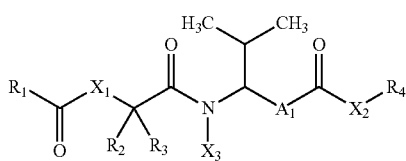

(I)

wherein: $R_1$ is heteroaryl$_{(C≤12)}$, heterocycloalkyl$_{(C≤12)}$, arylamino$_{(C≤12)}$, aralkylamino$_{(C≤12)}$, alkanediyl$_{(C≤12)}$-$Y_2$, fused cycloalkyl$_{(C≤12)}$-$Y_2$, or a substituted version of any of these groups, wherein $Y_2$ is amino, alkylamino$_{(C≤12)}$, dialkylamino$_{(C≤12)}$, amido$_{(C≤12)}$, substituted alkylamino$_{(C≤12)}$, substituted dialkylamino$_{(C≤12)}$, or substituted amido$_{(C≤12)}$; $R_2$ and $R_3$ are each independently selected from hydrogen, alkyl$_{(C≤12)}$, cycloalkyl$_{(C≤12)}$, fused cycloalkyl$_{(C≤12)}$, aryl$_{(C≤12)}$, heterocycloalkyl$_{(C≤12)}$, -alkanediyl$_{(C≤12)}$-cycloalkyl$_{(C≤12)}$, or a substituted version of any of these groups; or $R_2$ and $R_3$ are taken together and are alkanediyl$_{(C≤12)}$, alkoxydiyl$_{(C≤12)}$, alkylthiodiyl$_{(C≤12)}$, or alkylaminodiyl$_{(C≤12)}$; $R_4$ is cycloalkyl$_{(C≤12)}$, fused cycloalkyl$_{(C≤12)}$, aralkyl$_{(C≤12)}$, substituted cycloalkyl$_{(C≤12)}$, substituted fused cycloalkyl$_{(C≤12)}$, substituted aralkyl$_{(C≤12)}$, fused cycloalkylamino$_{(C≤12)}$, substituted fused cycloalkylamino$_{(C≤12)}$, or a structure of the formula:

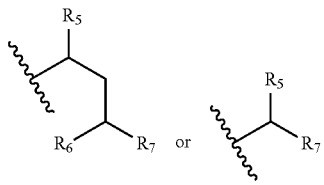

wherein: $R_5$ is aryl$_{(C≤12)}$, aralkyl$_{(C≤12)}$, heteroaryl$_{(C≤12)}$, heteroaralkyl$_{(C≤12)}$, or a substituted version of any of these groups; or is -alkanediyl$_{(C≤8)}$-arenediyl$_{(C≤12)}$-$Y_3$ or a substituted version of any of these groups; wherein: $Y_3$ is alkoxy$_{(C≤12)}$, aryloxy$_{(C≤12)}$, an oxygen linked antibody, —C(O)-alkoxy$_{(C≤12)}$, —C(O)-alkylamino$_{(C≤12)}$, —C(O)-dialkylamino$_{(C≤12)}$, —C(O)-aryloxy$_{(C≤12)}$, —C(O)-arylamino$_{(C≤12)}$, —C(O)—$Y_4$; or a substituted version of any of these groups; wherein: $Y_4$ is a nitrogen linked antibody or an oxygen linked antibody; $R_6$ is hydrogen, alkyl$_{(C≤8)}$, or substituted alkyl$_{(C≤8)}$; $R_7$ is —C(O)—$Y_5$; wherein $Y_5$ is amino, hydroxy, alkoxy$_{(C≤12)}$, substituted alkoxy$_{(C≤12)}$, alkylamino$_{(C≤12)}$, substituted alkylamino$_{(C≤12)}$, dialkylamino$_{(C≤12)}$, substituted dialkylamino$_{(C≤12)}$, an oxygen linked antibody, or a nitrogen linked antibody; $X_1$ and $X_2$ are each independently selected from a covalent bond, —O—, —S—, —$NR_8$—, or —$NR_9NR_{10}$—, wherein: $R_8$, $R_9$, and $R_{10}$ are each independently selected from hydrogen, alkyl$_{(C≤12)}$, substituted alkyl$_{(C≤12)}$, cycloalkyl$_{(C≤12)}$, or substituted cycloalkyl$_{(C≤12)}$; $X_3$ is hydrogen, alkyl$_{(C≤12)}$, or substituted alkyl$_{(C≤12)}$; and $A_1$ is —C(O)$NR_3$-fused cycloalkanediyl$_{(C≤12)}$, -alkanediyl$_{(C≤12)}$-heteroarenediyl$_{(C≤12)}$, -alkanediyl$_{(C≤12)}$-heteroarenediyl$_{(C≤12)}$, wherein the alkanediyl is substituted with an amido$_{(C≤8)}$ or acyloxy$_{(C≤8)}$ group, or a substituted version of any of these groups; wherein: $R_{13}$ is hydrogen, alkyl$_{(C≤12)}$, substituted alkyl$_{(C≤12)}$, cycloalkyl$_{(C≤12)}$, or substituted cycloalkyl$_{(C≤12)}$; provided that $X_3$ is not hydrogen, methyl, hydroxymethyl, or acetoxymethyl, when $R_2$ or $R_3$ is sec-butyl, $R_5$ is benzyl, $R_7$ is —$CO_2H$, and $R_1$ is 2-N-methylpiperidinyl; or a pharmaceutically acceptable salt thereof.

Additionally, the compounds provided by the present disclosure are shown, for example, above in the summary of the invention section and in the examples and claims below. They may be made using the methods outlined in the Examples section. The tubulysin analogs described herein can be synthesized according to the methods described, for example, in the Examples section below. These methods can be further modified and optimized using the principles and techniques of organic chemistry as applied by a person skilled in the art. Such principles and techniques are taught, for example, in *March's Advanced Organic Chemistry: Reactions, Mechanisms, and Structure* (2007), which is incorporated by reference herein.

The tubulysin analogs described herein may contain one or more asymmetrically-substituted carbon or nitrogen atoms, and may be isolated in optically active or racemic form. Thus, all chiral, diastereomeric, racemic form, epimeric form, and all geometric isomeric forms of a chemical formula are intended, unless the specific stereochemistry or isomeric form is specifically indicated. Compounds may occur as racemates and racemic mixtures, single enantiomers, diastereomeric mixtures and individual diastereomers. In some embodiments, a single diastereomer is obtained. The chiral centers of the compounds of the present invention can have the S or the R configuration.

Chemical formulas used to represent the tubulysin analogs described herein will typically only show one of possibly several different tautomers. For example, many types of ketone groups are known to exist in equilibrium with corresponding enol groups. Similarly, many types of imine groups exist in equilibrium with enamine groups. Regardless of which tautomer is depicted for a given compound, and regardless of which one is most prevalent, all tautomers of a given chemical formula are intended.

The tubulysin analogs described herein may also have the advantage that they may be more efficacious than, be less toxic than, be longer acting than, be more potent than, produce fewer side effects than, be more easily absorbed than, and/or have a better pharmacokinetic profile (e.g., higher oral bioavailability and/or lower clearance) than, and/or have other useful pharmacological, physical, or chemical properties over, compounds known in the prior art, whether for use in the indications stated herein or otherwise.

In addition, atoms making up the tubulysin analogs described herein are intended to include all isotopic forms of such atoms. Isotopes, as used herein, include those atoms having the same atomic number but different mass numbers. By way of general example and without limitation, isotopes of hydrogen include tritium and deuterium, and isotopes of carbon include $^{13}C$ and $^{14}C$.

The tubulysin analogs described herein may also exist in prodrug form. Since prodrugs are known to enhance numerous desirable qualities of pharmaceuticals (e.g., solubility, bioavailability, manufacturing, etc.), the compounds employed in some methods of the disclosure may, if desired, be delivered in prodrug form. Thus, the invention contemplates prodrugs of compounds of the present invention as well as methods of delivering prodrugs. Prodrugs of the tubulysin analogs described herein may be prepared by modifying functional groups present in the compound in such a way that the modifications are cleaved, either in routine manipulation or in vivo, to the parent compound. Accordingly, prodrugs include, for example, compounds described herein in which a hydroxy, amino, or carboxy group is bonded to any group that, when the prodrug is administered to a subject, cleaves to form a hydroxy, amino, or carboxylic acid, respectively.

It should be recognized that the particular anion or cation forming a part of any salt form of a compound provided herein is not critical, so long as the salt, as a whole, is pharmacologically acceptable. Additional examples of pharmaceutically acceptable salts and their methods of preparation and use are presented in *Handbook of Pharmaceutical Salts: Properties, and Use* (2002), which is incorporated herein by reference.

Those skilled in the art of organic chemistry will appreciate that many organic compounds can form complexes with solvents in which they are reacted or from which they are precipitated or crystallized. These complexes are known as "solvates." For example, a complex with water is known as a "hydrate." Solvates of the tubulysin analogs described herein are within the scope of the invention. It will also be appreciated by those skilled in organic chemistry that many organic compounds can exist in more than one crystalline form. For example, crystalline form may vary from solvate to solvate. Thus, all crystalline forms of the tubulysin analogs described herein are within the scope of the present disclosure.

B. Formulations

In some embodiments of the present disclosure, the compounds are included a pharmaceutical formulation. Materials for use in the preparation of microspheres and/or microcapsules are, e.g., biodegradable/bioerodible polymers such as polygalactin, poly-(isobutyl cyanoacrylate), poly(2-hydroxyethyl-L-glutamine) and, poly(lactic acid). Biocompatible carriers that may be used when formulating a controlled release parenteral formulation are carbohydrates (e.g., dextrans), proteins (e.g., albumin), lipoproteins, or antibodies. Materials for use in implants can be non-biodegradable (e.g., polydimethyl siloxane) or biodegradable (e.g., poly(caprolactone), poly(lactic acid), poly(glycolic acid) or poly(ortho esters) or combinations thereof).

Formulations for oral use include tablets containing the active ingredient(s) (e.g., the tubulysin analogs described herein) in a mixture with non-toxic pharmaceutically acceptable excipients. Such formulations are known to the skilled artisan. Excipients may be, for example, inert diluents or fillers (e.g., sucrose, sorbitol, sugar, mannitol, microcrystalline cellulose, starches including potato starch, calcium carbonate, sodium chloride, lactose, calcium phosphate, calcium sulfate, or sodium phosphate); granulating and disintegrating agents (e.g., cellulose derivatives including microcrystalline cellulose, starches including potato starch, croscarmellose sodium, alginates, or alginic acid); binding agents (e.g., sucrose, glucose, sorbitol, acacia, alginic acid, sodium alginate, gelatin, starch, pregelatinized starch, microcrystalline cellulose, magnesium aluminum silicate, carboxymethylcellulose sodium, methylcellulose, hydroxypropyl methylcellulose, ethylcellulose, polyvinylpyrrolidone, or polyethylene glycol); and lubricating agents, glidants, and antiadhesives (e.g., magnesium stearate, zinc stearate, stearic acid, silicas, hydrogenated vegetable oils, or talc). Other pharmaceutically acceptable excipients can be colorants, flavoring agents, plasticizers, humectants, buffering agents, and the like.

The tablets may be uncoated or they may be coated by known techniques, optionally to delay disintegration and absorption in the gastrointestinal tract and thereby providing a sustained action over a longer period. The coating may be adapted to release the active drug in a predetermined pattern (e.g., in order to achieve a controlled release formulation) or it may be adapted not to release the active drug until after passage of the stomach (enteric coating). The coating may be a sugar coating, a film coating (e.g., based on hydroxypropyl methylcellulose, methylcellulose, methyl hydroxyethylcellulose, hydroxypropylcellulose, carboxymethylcellulose, acrylate copolymers, polyethylene glycols and/or polyvinylpyrrolidone), or an enteric coating (e.g., based on methacrylic acid copolymer, cellulose acetate phthalate, hydroxypropyl methylcellulose phthalate, hydroxypropyl methylcellulose acetate succinate, polyvinyl acetate phthalate, shellac, and/or ethylcellulose). Furthermore, a time delay material, such as, e.g., glyceryl monostearate or glyceryl distearate may be employed.

II. HYPERPROLIFERATIVE DISEASES

A. Cancer and Other Hyperproliferative Disease

While hyperproliferative diseases can be associated with any disease which causes a cell to begin to reproduce uncontrollably, the prototypical example is cancer. One of the key elements of cancer is that the cell's normal apoptotic cycle is interrupted and thus agents that interrupt the growth of the cells are important as therapeutic agents for treating these diseases. In this disclosure, the tubulysin analogs described herein may be used to lead to decreased cell counts and as such can potentially be used to treat a variety of types of cancer lines. In some aspects, it is anticipated that the tubulysin analogs described herein may be used to treat virtually any malignancy.

Cancer cells that may be treated with the compounds of the present disclosure include but are not limited to cells from the bladder, blood, bone, bone marrow, brain, breast, colon, esophagus, gastrointestine, gum, head, kidney, liver, lung, nasopharynx, neck, ovary, prostate, skin, stomach, pancreas, testis, tongue, cervix, or uterus. In addition, the cancer may specifically be of the following histological type, though it is not limited to these: neoplasm, malignant; carcinoma; carcinoma, undifferentiated; giant and spindle cell carcinoma; small cell carcinoma; papillary carcinoma; squamous cell carcinoma; lymphoepithelial carcinoma; basal cell carcinoma; pilomatrix carcinoma; transitional cell carcinoma; papillary transitional cell carcinoma; adenocarcinoma; gastrinoma, malignant; cholangiocarcinoma; hepatocellular carcinoma; combined hepatocellular carcinoma and cholangiocarcinoma; trabecular adenocarcinoma; adenoid cystic carcinoma; adenocarcinoma in adenomatous polyp; adenocarcinoma, familial polyposis coli; solid carcinoma; carcinoid tumor, malignant; branchiolo-alveolar adenocarcinoma; papillary adenocarcinoma; chromophobe carcinoma; acidophil carcinoma; oxyphilic adenocarcinoma; basophil carcinoma; clear cell adenocarcinoma; granular cell carcinoma; follicular adenocarcinoma; papillary and follicular adenocarcinoma; nonencapsulating sclerosing carcinoma; adrenal cortical carcinoma; endometroid carcinoma; skin appendage carcinoma; apocrine adenocarcinoma; sebaceous adenocarcinoma; ceruminous adenocarcinoma; mucoepidermoid carcinoma; cystadenocarcinoma; papillary cystadenocarcinoma; papillary serous cystadenocarcinoma; mucinous cystadenocarcinoma; mucinous adenocarcinoma; signet ring cell carcinoma; infiltrating duct carcinoma; medullary carcinoma; lobular carcinoma; inflammatory carcinoma; Paget's disease, mammary; acinar cell carcinoma; adenosquamous carcinoma; adenocarcinoma w/squamous metaplasia; thymoma, malignant; ovarian stromal tumor, malignant; thecoma, malignant; granulosa cell tumor, malignant; androblastoma, malignant; sertoli cell carcinoma; Leydig cell tumor, malignant; lipid cell tumor, malignant; paraganglioma, malignant; extramammary paraganglioma, malignant; pheochromocytoma; glomangiosarcoma; malignant melanoma; amelanotic melanoma: superficial spreading melanoma; malignant melanoma in giant pigmented nevus; epithelioid cell melanoma; blue nevus, malignant; sarcoma; fibrosarcoma; fibrous histiocytoma, malignant; myxosarcoma; liposarcoma; leiomyosarcoma; rhabdomyosarcoma; embryonal rhabdomyosarcoma; alveolar rhabdomyosarcoma; stromal sarcoma; mixed tumor, malignant; Mullerian mixed tumor; nephroblastoma; hepatoblastoma; carcinosarcoma; mesenchymoma, malignant; Brenner tumor, malignant; phyllodes tumor, malignant; synovial sarcoma; mesothelioma, malignant; dysgerminoma; embryonal carcinoma; teratoma, malignant; struma ovarii, malignant; choriocarcinoma; mesonephroma, malignant; hemangiosarcoma; hemangioendothelioma, malignant; Kaposi's sarcoma; hemangiopericytoma, malignant; lymphangiosarcoma; osteosarcoma; juxtacortical osteosarcoma; chondrosarcoma; chondroblastoma, malignant; mesenchymal chondrosarcoma; giant cell tumor of bone: Ewing's sarcoma; odontogenic tumor, malignant; ameloblastic odontosarcoma; ameloblastoma, malignant; ameloblastic fibrosarcoma; pinealoma, malignant; chordoma; glioma, malignant; ependymoma; astrocytoma; protoplasmic astrocytoma; fibrillary astrocytoma; astroblastoma; glioblastoma; oligodendroglioma; oligodendroblastoma; primitive neuroectodermal; cerebellar sarcoma; ganglioneuroblastoma; neuroblastoma; retinoblastoma; olfactory neurogenic tumor; meningioma, malignant; neurofibrosarcoma; neurilemmoma, malignant; granular cell tumor, malignant; malignant lymphoma; Hodgkin's disease; paragranuloma; malignant lymphoma, small lymphocytic; malignant lymphoma, large cell, diffuse; malignant lymphoma, follicular; mycosis fungoides; other specified non-Hodgkin's lymphomas; malignant histiocytosis; multiple myeloma; mast cell sarcoma; immunoproliferative small intestinal disease; leukemia; lymphoid leukemia; plasma cell leukemia; erythroleukemia; lymphosarcoma cell leukemia; myeloid leukemia; basophilic leukemia; eosinophilic leukemia; monocytic leukemia; mast cell leukemia; megakaryoblastic leukemia; myeloid sarcoma; and hairy cell leukemia. In certain aspects, the tumor may comprise an osteosarcoma, angiosarcoma, rhabdosarcoma, leiomyosarcoma, Ewing sarcoma, glioblastoma, neuroblastoma, or leukemia.

III. CELL TARGETING MOIETIES

In some aspects, the present disclosure provides compounds conjugated directly or through linkers to a cell targeting moiety. In some embodiments, the conjugation of the compound to a cell targeting moiety increases the efficacy of the compound in treating a disease or disorder. Cell targeting moieties according to the embodiments may be, for example, an antibody, a growth factor, a hormone, a peptide, an aptamer, a small molecule such as a hormone, an imaging agent, or cofactor, or a cytokine. For instance, a cell targeting moiety according the embodiments may bind to a liver cancer cell such as a Hep3B cell. It has been demonstrated that the gp240 antigen is expressed in a variety of melanomas but not in normal tissues. Thus, in some embodiments, the compounds of the present disclosure may be used in conjugates with an antibody for a specific antigen that is expressed by a cancer cell but not in normal tissues.

In certain additional embodiments, it is envisioned that cancer cell targeting moieties bind to multiple types of cancer cells. For example, the 8H9 monoclonal antibody and the single chain antibodies derived therefrom bind to a glycoprotein that is expressed on breast cancers, sarcomas and neuroblastomas (Onda et al., 2004). Another example is the cell targeting agents described in U.S. Patent Publication No. 2004/005647 and in Winthrop et al., 2003 that bind to MUC-1, an antigen that is expressed on a variety cancer types. Thus, it will be understood that in certain embodiments, cell targeting constructs according the embodiments may be targeted against a plurality of cancer or tumor types.

Additionally, certain cell surface molecules are highly expressed in tumor cells, including hormone receptors such as human chorionic gonadotropin receptor and gonadotropin releasing hormone receptor (Nechushtan et al., 1997). Therefore, the corresponding hormones may be used as the cell-specific targeting moieties in cancer therapy. Additionally, the cell targeting moiety that may be used include a cofactor, a sugar, a drug molecule, an imaging agent, or a fluorescent dye. Many cancerous cells are known to over express folate receptors and thus folic acid or other folate derivatives may be used as conjugates to trigger cell-specific interaction between the conjugates of the present disclosure and a cell (Campbell, et al., 1991; Weitman, et al., 1992).

Since a large number of cell surface receptors have been identified in hematopoietic cells of various lineages, ligands or antibodies specific for these receptors may be used as cell-specific targeting moieties. IL2 may also be used as a cell-specific targeting moiety in a chimeric protein to target IL2R+ cells. Alternatively, other molecules such as B7-1, B7-2 and CD40 may be used to specifically target activated T cells (The Leucocyte Antigen Facts Book, 1993, Barclay et al. (eds.), Academic Press). Furthermore, B cells express CD19, CD40 and IL4 receptor and may be targeted by moieties that bind these receptors, such as CD40 ligand, IL4, IL5, IL6 and CD28. The elimination of immune cells such as T cells and B cells is particularly useful in the treatment of lymphoid tumors.

Other cytokines that may be used to target specific cell subsets include the interleukins (IL1 through IL15), granulocyte-colony stimulating factor, macrophage-colony stimulating factor, granulocyte-macrophage colony stimulating factor, leukemia inhibitory factor, tumor necrosis factor, transforming growth factor, epidermal growth factor, insulin-like growth factors, and/or fibroblast growth factor (Thompson (ed.), 1994, The Cytokine Handbook, Academic Press, San Diego). In some aspects, the targeting polypeptide is a cytokine that binds to the Fn14 receptor, such as TWEAK (see, e.g., Winkles, 2008; Zhou et al., 2011 and Burkly et al., 2007, incorporated herein by reference).

A skilled artisan recognizes that there are a variety of known cytokines, including hematopoietins (four-helix bundles) (such as EPO (erythropoietin), IL-2 (T-cell growth factor), IL-3 (multicolony CSF), IL-4 (BCGF-1, BSF-1), IL-5 (BCGF-2), IL-6 IL-4 (IFN-β2, BSF-2, BCDF), IL-7, IL-8, IL-9, IL-11, IL-13 (P600), G-CSF, IL-15 (T-cell growth factor), GM-CSF (granulocyte macrophage colony stimulating factor), OSM (OM, oncostatin M), and LIF (leukemia inhibitory factor)); interferons (such as IFN-γ, IFN-α, and IFN-β); immunoglobin superfamily (such as B7.1 (CD80), and B7.2 (B70, CD86)); TNF family (such as TNF-α (cachectin), TNF-β (lymphotoxin, LT, LT-α), LT-β, CD40 ligand (CD40L), Fas ligand (FasL), CD27 ligand (CD27L), CD30 ligand (CD30L), and 4-1BBL)); and those unassigned to a particular family (such as TGF-β, IL 1α, IL-1β, IL-1 RA, IL-10 (cytokine synthesis inhibitor F), IL-12 (NK cell stimulatory factor), MIF, IL-16, IL-17 (mCTLA-8), and/or IL-18 (IGIF, interferon-γ inducing factor)). Furthermore, the Fc portion of the heavy chain of an antibody may be used to target Fc receptor-expressing cells such as the use of the Fc portion of an IgE antibody to target mast cells and basophils.

Furthermore, in some aspects, the cell-targeting moiety may be a peptide sequence or a cyclic peptide. Examples, cell- and tissue-targeting peptides that may be used according to the embodiments are provided, for instance, in U.S. Pat. Nos. 6,232,287; 6,528,481; 7,452,964; 7,671,010; 7,781,565; 8,507,445; and 8,450,278, each of which is incorporated herein by reference.

Thus, in some embodiments, cell targeting moieties are antibodies or avimers. Antibodies and avimers can be generated against virtually any cell surface marker thus, providing a method for targeted to delivery of GrB to virtually any cell population of interest. Methods for generating antibodies that may be used as cell targeting moieties are detailed below. Methods for generating avimers that bind to a given cell surface marker are detailed in U.S. Patent Publications Nos. 2006/0234299 and 2006/0223114, each incorporated herein by reference.

IV. THERAPIES

A. Pharmaceutical Formulations and Routes of Administration

Where clinical applications are contemplated, it will be necessary to prepare pharmaceutical compositions in a form appropriate for the intended application. In some embodiments, such formulation with the compounds of the present disclosure is contemplated. Generally, this will entail preparing compositions that are essentially free of pyrogens, as well as other impurities that could be harmful to humans or animals.

One will generally desire to employ appropriate salts and buffers to render delivery vectors stable and allow for uptake by target cells. Buffers also will be employed when recombinant cells are introduced into a patient. Aqueous compositions of the present invention comprise an effective amount of the vector to cells, dissolved or dispersed in a pharmaceutically acceptable carrier or aqueous medium. Such compositions also are referred to as inocula. The phrase "pharmaceutically or pharmacologically acceptable" refers to molecular entities and compositions that do not produce adverse, allergic, or other untoward reactions when administered to an animal or a human. As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the vectors or cells of the present invention, its use in therapeutic compositions is contemplated. Supplementary active ingredients also can be incorporated into the compositions.

The active compositions of the present invention may include classic pharmaceutical preparations. Administration of these compositions according to the present invention will be via any common route so long as the target tissue is available via that route. Such routes include oral, nasal, buccal, rectal, vaginal or topical route. Alternatively, administration may be by orthotopic, intradermal, subcutaneous, intramuscular, intratumoral, intraperitoneal, or intravenous injection. Such compositions would normally be administered as pharmaceutically acceptable compositions, described supra.

The active compounds may also be administered parenterally or intraperitoneally. Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

For oral administration the tubulysin analogs described herein may be incorporated with excipients and used in the form of non-ingestible mouthwashes and dentifrices. A mouthwash may be prepared incorporating the active ingredient in the required amount in an appropriate solvent, such as a sodium borate solution (Dobell's Solution). Alternatively, the active ingredient may be incorporated into an antiseptic wash containing sodium borate, glycerin and potassium bicarbonate. The active ingredient may also be dispersed in dentifrices, including: gels, pastes, powders and slurries. The active ingredient may be added in a therapeutically effective amount to a paste dentifrice that may include water, binders, abrasives, flavoring agents, foaming agents, and humectants.

The compositions of the present disclosure may be formulated in a neutral or salt form. Pharmaceutically-acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

Upon formulation, solutions will be administered in a manner compatible with the dosage formulation and in such amount as is therapeutically effective. The formulations are easily administered in a variety of dosage forms such as injectable solutions, drug release capsules and the like. For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion, (see for example, "Remington's Pharmaceutical Sciences," 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

B. Methods of Treatment

In particular, the compositions that may be used in treating microbial infections and cancer in a subject (e.g., a human subject) are disclosed herein. The compositions described above are preferably administered to a mammal (e.g., rodent, human, non-human primates, canine, bovine, ovine, equine, feline, etc.) in an effective amount, that is, an amount capable of producing a desirable result in a treated subject (e.g., causing apoptosis of cancerous cells or killing bacterial cells). Toxicity and therapeutic efficacy of the compositions utilized in methods of the invention can be determined by standard pharmaceutical procedures. As is well known in the medical and veterinary arts, dosage for any one animal depends on many factors, including the subject's size, body surface area, body weight, age, the particular composition to be administered, time and route of administration, general health, the clinical symptoms of the infection or cancer and other drugs being administered concurrently. A composition as described herein is typically administered at a dosage that inhibits the growth or proliferation of a bacterial cell, inhibits the growth of a biofilm, or induces death of cancerous cells (e.g., induces apoptosis of a cancer cell), as assayed by identifying a reduction in hematological parameters (complete blood count—CBC), or cancer cell growth or proliferation. In some embodiments, amounts of the tubulysin analogs used to inhibit bacterial growth or induce apoptosis of the cancer cells is calculated to be from about 0.01 mg to about 10,000 mg/day. In some embodiments, the amount is from about 1 mg to about 1,000 mg/day. In some embodiments, these dosings may be reduced or increased based upon the biological factors of a particular patient such as increased or decreased metabolic breakdown of the drug or decreased uptake by the digestive tract if administered orally. Additionally, the derivatives of tubulysin may be more efficacious and thus a smaller dose is required to achieve a similar effect. Such a dose is typically administered once a day for a few weeks or until sufficient reducing in cancer cells has been achieved.

The therapeutic methods of the invention (which include prophylactic treatment) in general include administration of a therapeutically effective amount of the compositions described herein to a subject in need thereof, including a mammal, particularly a human. Such treatment will be suitably administered to subjects, particularly humans, suffering from, having, susceptible to, or at risk for a disease, disorder, or symptom thereof. Determination of those subjects "at risk" can be made by any objective or subjective determination by a diagnostic test or opinion of a subject or health care provider (e.g., genetic test, enzyme or protein marker, marker (as defined herein), family history, and the like).

In one embodiment, the invention provides a method of monitoring treatment progress. The method includes the step of determining a level of changes in hematological parameters and/or cancer stem cell (CSC) analysis with cell surface proteins as diagnostic markers (which can include, for example, but are not limited to CD34, CD38, CD90, and CD117) or diagnostic measurement (e.g., screen, assay) in a subject suffering from or susceptible to a disorder or symptoms thereof associated with cancer (e.g., leukemia) in which the subject has been administered a therapeutic amount of a composition as described herein. The level of marker determined in the method can be compared to known levels of marker in either healthy normal controls or in other afflicted patients to establish the subject's disease status. In preferred embodiments, a second level of marker in the subject is determined at a time point later than the determination of the first level, and the two levels are compared to monitor the course of disease or the efficacy of the therapy. In certain preferred embodiments, a pre-treatment level of marker in the subject is determined prior to beginning treatment according to the methods described herein; this pre-treatment level of marker can then be compared to the level of marker in the subject after the treatment commences, to determine the efficacy of the treatment.

C. Combination Therapies

It is envisioned that the tubulysin analogs described herein may be used in combination therapies with an additional antimicrobial agent such as an antibiotic or a compound which mitigates one or more of the side effects experienced by the patient.

Furthermore, it is very common in the field of cancer therapy to combine therapeutic modalities. The following is a general discussion of therapies that may be used in conjunction with the therapies of the present disclosure.

To treat cancers using the methods and compositions of the present disclosure, one would generally contact a tumor cell or subject with a compound and at least one other therapy. These therapies would be provided in a combined amount effective to achieve a reduction in one or more disease parameter. This process may involve contacting the cells/subjects with the both agents/therapies at the same time, e.g., using a single composition or pharmacological formulation that includes both agents, or by contacting the cell/subject with two distinct compositions or formulations, at the same time, wherein one composition includes the compound and the other includes the other agent.

Alternatively, the tubulysin analogs described herein may precede or follow the other treatment by intervals ranging from minutes to weeks. One would generally ensure that a significant period of time did not expire between the time of each delivery, such that the therapies would still be able to exert an advantageously combined effect on the cell/subject. In such instances, it is contemplated that one would contact the cell with both modalities within about 12-24 hours of each other, within about 6-12 hours of each other, or with a delay time of only about 1-2 hours. In some situations, it may be desirable to extend the time period for treatment significantly: however, where several days (2, 3, 4, 5, 6 or 7) to several weeks (1, 2, 3, 4, 5, 6, 7 or 8) lapse between the respective administrations.

It also is conceivable that more than one administration of either the compound or the other therapy will be desired. Various combinations may be employed, where a compound of the present disclosure is "A," and the other therapy is "B," as exemplified below:

| | | | | | | |
|---|---|---|---|---|---|---|
| A/B/A | B/A/B | B/B/A | A/A/B | B/A/A | A/B/B | B/B/B/A B/B/A/B |
| A/A/B/B | A/B/A/B | A/B/B/A | B/B/A/A | B/A/B/A | B/A/A/B | B/B/B/A |
| A/A/A/B | B/A/A/A | A/B/A/A | A/A/B/A | A/B/B/B | B/A/B/B | B/B/A/B |

Other combinations are also contemplated. The following is a general discussion of cancer therapies that may be used combination with the compounds of the present disclosure.

1. Chemotherapy

The term "chemotherapy" refers to the use of drugs to treat cancer. A "chemotherapeutic agent" is used to connote a compound or composition that is administered in the treatment of cancer. These agents or drugs are categorized by their mode of activity within a cell, for example, whether and at what stage they affect the cell cycle. Alternatively, an agent may be characterized based on its ability to directly cross-link DNA, to intercalate into DNA, or to induce chromosomal and mitotic aberrations by affecting nucleic acid synthesis. Most chemotherapeutic agents fall into the following categories: alkylating agents, antimetabolites, antitumor antibiotics, mitotic inhibitors, and nitrosoureas.

Examples of chemotherapeutic agents include alkylating agents such as thiotepa and cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); a camptothecin (including the synthetic analogue topotecan): bryostatin: callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CBl-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin γ1 and calicheamicin ω1; dynemicin, including dynemicin A uncialamycin and derivatives thereof; bisphosphonates, such as clodronate; an esperamicin; as well as neocarzinostatin chromophore and related chromoprotein enediyne antiobiotic chromophores, aclacinomysins, actinomycin, authrarnycin, azaserine, bleomycins, cactinomycin, carabicin, carminomycin, carzinophilin, chromomycinis, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalarnycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine: androgens such as calusterone, dromostanolone propionate, epitiostanol, mepitiostane, testolactone; anti-adrenals such as aminoglutethimide, mitotane, trilostane; folic acid replenisher such as folinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK polysaccharide complex); razoxane; rhizoxin: sizofiran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol: mitolactol; pipobroman; gacytosine; arabinoside ("Ara-C"); cyclophosphamide; thiotepa; taxoids, e.g., paclitaxel and docetaxel; chlorambucil; gemcitabine; 6-thioguanine; mercaptopurine; methotrexate; platinum coordination complexes such as cisplatin, oxaliplatin and carboplatin; vinblastine; platinum; etoposide (VP-16); ifosfamide; mitoxantrone; vincristine; vinorelbine; novantrone; teniposide; edatrexate; daunomycin; aminopterin; xeloda; ibandronate; irinotecan (e.g., CPT-11); topoisomerase inhibitor RFS 2000; difluorometlhylornithine (DMFO); retinoids such as retinoic acid; capecitabine; cisplatin (CDDP), carboplatin, procarbazine, mechlorethamine, cyclophosphamide, camptothecin, ifosfamide, melphalan, chlorambucil, busulfan, nitrosurea, dactinomycin, daunorubicin, doxorubicin, bleomycin, plicomycin, mitomycin, etoposide (VP16), tamoxifen, raloxifene, estrogen receptor binding agents, taxol, paclitaxel, docetaxel, gemcitabien, navelbine, farnesyl-protein tansferase inhibitors, transplatinum, 5-fluorouracil, vincristin, vinblastin and methotrexate and pharmaceutically acceptable salts, acids or derivatives of any of the above.

2. Radiotherapy

Radiotherapy, also called radiation therapy, is the treatment of cancer and other diseases with ionizing radiation. Ionizing radiation deposits energy that injures or destroys cells in the area being treated by damaging their genetic material, making it impossible for these cells to continue to grow. Although radiation damages both cancer cells and normal cells, the latter are able to repair themselves and function properly.

Radiation therapy used according to the present invention may include, but is not limited to, the use of γ-rays, X-rays, and/or the directed delivery of radioisotopes to tumor cells. Other forms of DNA damaging factors are also contemplated such as microwaves and UV-irradiation. It is most likely that all of these factors induce a broad range of damage on DNA, on the precursors of DNA, on the replication and repair of DNA, and on the assembly and maintenance of chromosomes. Dosage ranges for X-rays range from daily doses of 50 to 200 roentgens for prolonged periods of time (3 to 4 wk), to single doses of 2000 to 6000 roentgens. Dosage ranges for radioisotopes vary widely, and depend on the half-life of the isotope, the strength and type of radiation emitted, and the uptake by the neoplastic cells.

Radiotherapy may comprise the use of radiolabeled antibodies to deliver doses of radiation directly to the cancer site (radioimmunotherapy). Antibodies are highly specific proteins that are made by the body in response to the presence of antigens (substances recognized as foreign by the immune system). Some tumor cells contain specific antigens that trigger the production of tumor-specific antibodies. Large quantities of these antibodies can be made in the laboratory and attached to radioactive substances (a process known as radiolabeling). Once injected into the body, the antibodies actively seek out the cancer cells, which are destroyed by the cell-killing (cytotoxic) action of the radiation. This approach can minimize the risk of radiation damage to healthy cells.

Conformal radiotherapy uses the same radiotherapy machine, a linear accelerator, as the normal radiotherapy treatment but metal blocks are placed in the path of the x-ray beam to alter its shape to match that of the cancer. This ensures that a higher radiation dose is given to the tumor. Healthy surrounding cells and nearby structures receive a lower dose of radiation, so the possibility of side effects is reduced. A device called a multi-leaf collimator has been developed and may be used as an alternative to the metal blocks. The multi-leaf collimator consists of a number of metal sheets which are fixed to the linear accelerator. Each layer can be adjusted so that the radiotherapy beams can be shaped to the treatment area without the need for metal blocks. Precise positioning of the radiotherapy machine is very important for conformal radiotherapy treatment and a special scanning machine may be used to check the position of internal organs at the beginning of each treatment.

High-resolution intensity modulated radiotherapy also uses a multi-leaf collimator. During this treatment the layers of the multi-leaf collimator are moved while the treatment is being given. This method is likely to achieve even more precise shaping of the treatment beams and allows the dose of radiotherapy to be constant over the whole treatment area.

Although research studies have shown that conformal radiotherapy and intensity modulated radiotherapy may reduce the side effects of radiotherapy treatment, it is possible that shaping the treatment area so precisely could stop microscopic cancer cells just outside the treatment area being destroyed. This means that the risk of the cancer coming back in the future may be higher with these specialized radiotherapy techniques.

Scientists also are looking for ways to increase the effectiveness of radiation therapy. Two types of investigational drugs are being studied for their effect on cells undergoing radiation. Radiosensitizers make the tumor cells more likely to be damaged, and radioprotectors protect normal tissues from the effects of radiation. Hyperthermia, the use of heat, is also being studied for its effectiveness in sensitizing tissue to radiation.

3. Immunotherapy

In the context of cancer treatment, immunotherapeutics, generally, rely on the use of immune effector cells and molecules to target and destroy cancer cells. Trastuzumab (Herceptin™) is such an example. The immune effector may be, for example, an antibody specific for some marker on the surface of a tumor cell. The antibody alone may serve as an effector of therapy or it may recruit other cells to actually affect cell killing. The antibody also may be conjugated to a drug or toxin (chemotherapeutic, radionuclide, ricin A chain, cholera toxin, pertussis toxin, etc.) and serve merely as a targeting agent. Alternatively, the effector may be a lymphocyte carrying a surface molecule that interacts, either directly or indirectly, with a tumor cell target. Various effector cells include cytotoxic T cells and NK cells. The combination of therapeutic modalities, i.e., direct cytotoxic activity and inhibition or reduction of ErbB2 would provide therapeutic benefit in the treatment of ErbB2 overexpressing cancers.

In one aspect of immunotherapy, the tumor cell must bear some marker that is amenable to targeting, i.e., is not present on the majority of other cells. Many tumor markers exist and any of these may be suitable for targeting in the context of the present invention. Common tumor markers include carcinoembryonic antigen, prostate specific antigen, urinary tumor associated antigen, fetal antigen, tyrosinase (p97), gp68, TAG-72, HMFG, Sialyl Lewis Antigen, MucA, MucB, PLAP, estrogen receptor, laminin receptor, erb B and p155. An alternative aspect of immunotherapy is to combine anticancer effects with immune stimulatory effects. Immune stimulating molecules also exist including: cytokines such as IL-2, IL-4, IL-12, GM-CSF, γ-IFN, chemokines such as MIP-1, MCP-1, IL-8 and growth factors such as FLT3 ligand. Combining immune stimulating molecules, either as proteins or using gene delivery in combination with a tumor suppressor has been shown to enhance anti-tumor effects (Ju et al., 2000). Moreover, antibodies against any of these compounds may be used to target the anti-cancer agents discussed herein.

Examples of immunotherapies currently under investigation or in use are immune adjuvants e.g., *Mycobacterium bovis*, *Plasmodium falciparum*, dinitrochlorobenzene and aromatic compounds (U.S. Pat. Nos. 5,801,005 and 5,739,169; Hui and Hashimoto, 1998; Christodoulides et al., 1998), cytokine therapy, e.g., interferons α, β, and γ; IL-1, GM-CSF and TNF (Bukowski et al., 1998; Davidson et al., 1998; Hellstrand et al., 1998) gene therapy, e.g., TNF, IL-1, IL-2, p53 (Qin et al., 1998; Austin-Ward and Villaseca, 1998; U.S. Pat. Nos. 5,830,880 and 5,846,945) and monoclonal antibodies, e.g., anti-ganglioside GM2, anti-HER-2, anti-p185 (Pietras et al., 1998: Hanibuchi et al., 1998; U.S. Pat. No. 5,824,311). It is contemplated that one or more anti-cancer therapies may be employed with the gene silencing therapies described herein.

In active immunotherapy, an antigenic peptide, polypeptide or protein, or an autologous or allogenic tumor cell composition or "vaccine" is administered, generally with a distinct bacterial adjuvant (Ravindranath and Morton, 1991; Morton et al., 1992; Mitchell et al., 1990; Mitchell et al., 1993).

In adoptive immunotherapy, the patient's circulating lymphocytes, or tumor infiltrated lymphocytes, are isolated in vitro, activated by lymphokines such as IL-2 or transduced with genes for tumor necrosis, and readministered (Rosenberg et al., 1988; 1989).

4. Surgery

Approximately 60% of persons with cancer will undergo surgery of some type, which includes preventative, diagnostic or staging, curative, and palliative surgery. Curative surgery is a cancer treatment that may be used in conjunction with other therapies, such as the treatment of the present invention, chemotherapy, radiotherapy, hormonal therapy, gene therapy, immunotherapy and/or alternative therapies.

Curative surgery includes resection in which all or part of cancerous tissue is physically removed, excised, and/or destroyed. Tumor resection refers to physical removal of at least part of a tumor. In addition to tumor resection, treatment by surgery includes laser surgery, cryosurgery, electrosurgery, and microscopically controlled surgery (Mohs' surgery). It is further contemplated that the present invention may be used in conjunction with removal of superficial cancers, precancers, or incidental amounts of normal tissue.

Upon excision of part or all of cancerous cells, tissue, or tumor, a cavity may be formed in the body. Treatment may be accomplished by perfusion, direct injection or local application of the area with an additional anti-cancer therapy. Such treatment may be repeated, for example, every 1, 2, 3, 4, 5, 6, or 7 days, or every 1, 2, 3, 4, and 5 weeks or every 1, 2, 3, 4, 5, 6, 7, 8, 9, 10, 11, or 12 months. These treatments may be of varying dosages as well.

In some particular embodiments, after removal of the tumor, an adjuvant treatment with a compound of the present disclosure is believe to be particularly efficacious in reducing the reoccurrence of the tumor. Additionally, the compounds of the present disclosure can also be used in a neoadjuvant setting.

5. Other Agents

It is contemplated that other agents may be used with the present disclosure. These additional agents include immunomodulatory agents, agents that affect the upregulation of cell surface receptors and GAP junctions, cytostatic and differentiation agents, inhibitors of cell adhesion, agents that increase the sensitivity of the hyperproliferative cells to apoptotic inducers, or other biological agents. Immunomodulatory agents include tumor necrosis factor; interferon alpha, beta, and gamma; IL-2 and other cytokines; F42K and other cytokine analogs; or MIP-1, MIP-13, MCP-1, RANTES, and other chemokines. It is further contemplated that the upregulation of cell surface receptors or their ligands such as Fas/Fas ligand, DR4 or DR5/TRAIL (Apo-2 ligand) would potentiate the apoptotic inducing abilities of the present invention by establishment of an autocrine or paracrine effect on hyperproliferative cells. Increases intercellular signaling by elevating the number of GAP junctions would increase the anti-hyperproliferative effects on the neighboring hyperproliferative cell population. In other embodiments, cytostatic or differentiation agents may be used in combination with the present invention to improve the anti-hyperproliferative efficacy of the treatments. Inhibitors of cell adhesion are contemplated to improve the efficacy of the present invention. Examples of cell adhesion inhibitors are focal adhesion kinase (FAKs) inhibitors and Lovastatin. It is further contemplated that other agents that increase the sensitivity of a hyperproliferative cell to apoptosis, such as the antibody c225, could be used in combination with the present invention to improve the treatment efficacy.

There have been many advances in the therapy of cancer following the introduction of cytotoxic chemotherapeutic drugs. However, one of the consequences of chemotherapy is the development/acquisition of drug-resistant phenotypes and the development of multiple drug resistance. The development of drug resistance remains a major obstacle in the treatment of such tumors and therefore, there is an obvious need for alternative approaches such as gene therapy.

Another form of therapy for use in conjunction with chemotherapy, radiation therapy or biological therapy includes hyperthermia, which is a procedure in which a patient's tissue is exposed to high temperatures (up to 106° F.). External or internal heating devices may be involved in the application of local, regional, or whole-body hyperthermia. Local hyperthermia involves the application of heat to a small area, such as a tumor. Heat may be generated externally with high-frequency waves targeting a tumor from a device outside the body. Internal heat may involve a sterile probe, including thin, heated wires or hollow tubes filled with warm water, implanted microwave antennae, or radiofrequency electrodes.

A patient's organ or a limb is heated for regional therapy, which is accomplished using devices that produce high energy, such as magnets. Alternatively, some of the patient's blood may be removed and heated before being perfused into an area that will be internally heated. Whole-body heating may also be implemented in cases where cancer has spread throughout the body. Warm-water blankets, hot wax, inductive coils, and thermal chambers may be used for this purpose.

The skilled artisan is directed to "Remington's Pharmaceutical Sciences" 15th Edition, chapter 33, in particular pages 624-652. Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

It also should be pointed out that any of the foregoing therapies may prove useful by themselves in treating cancer.

V. SYNTHETIC METHODS

In some aspects, the compounds of this disclosure can be synthesized using the methods of organic chemistry as described in this application. These methods can be further modified and optimized using the principles and techniques of organic chemistry as applied by a person skilled in the art. Such principles and techniques are taught, for example, in March's Advanced Organic Chemistry: Reactions, Mechanisms, and Structure (2007), which is incorporated by reference herein.

A. Process Scale-Up

The synthetic methods described herein can be further modified and optimized for preparative, pilot- or large-scale production, either batch of continuous, using the principles and techniques of process chemistry as applied by a person skilled in the art. Such principles and techniques are taught, for example, in *Practical Process Research & Development* (2000), which is incorporated by reference herein. The synthetic method described herein may be used to produce preparative scale amounts of the tubulysin analogs described herein.

B. Chemical Definitions

When used in the context of a chemical group: "hydrogen" means —H; "hydroxy" means —OH; "oxo" means =O; "carbonyl" means —C(=O)—; "carboxy" means —C(=O)OH (also written as —COOH or —CO$_2$H); "halo" means independently —F, —Cl, —Br or —I; "amino" means —NH$_2$; "hydroxyamino" means —NHOH; "nitro" means —NO$_2$; imino means =NH; "cyano" means —CN; "isocyanate" means —N=C=O; "azido" means —N$_3$; in a monovalent context "phosphate" means —OP(O)(OH)$_2$ or a deprotonated form thereof; in a divalent context "phosphate" means —OP(O)(OH)O— or a deprotonated form thereof; "mercapto" means —SH; and "thio" means =S; "sulfo" means —SO$_3$H, "sulfonyl" means —S(O)$_2$—; and "sulfinyl" means —S(O)—.

In the context of chemical formulas, the symbol "-" means a single bond, "=" means a double bond, and "≡" means triple bond. The symbol "----" represents an optional bond, which if present is either single or double. The symbol "===" represents a single bond or a double bond. Thus, for example, the formula includes

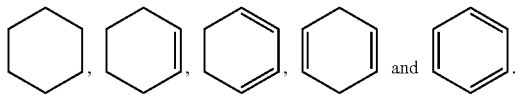

And it is understood that no one such ring atom forms part of more than one double bond. Furthermore, it is noted that the covalent bond symbol "-", when connecting one or two stereogenic atoms, does not indicate any preferred stereochemistry. Instead, it covers all stereoisomers as well as mixtures thereof. The symbol " ~~ ", when drawn perpendicularly across a bond (e.g.,

for methyl) indicates a point of attachment of the group. It is noted that the point of attachment is typically only identified in this manner for larger groups in order to assist the reader in unambiguously identifying a point of attachment. The symbol "◀" means a single bond where the group attached to the thick end of the wedge is "out of the page." The symbol "⦀⦀⦀" means a single bond where the group attached to the thick end of the wedge is "into the page". The symbol " ~~ " means a single bond where the geometry around a double bond (e.g., either E or Z) is undefined. Both options, as well as combinations thereof are therefore intended. Any undefined valency on an atom of a structure shown in this application implicitly represents a hydrogen atom bonded to that atom. A bold dot on a carbon atom indicates that the hydrogen attached to that carbon is oriented out of the plane of the paper.

When a group "R" is depicted as a "floating group" on a ring system, for example, in the formula:

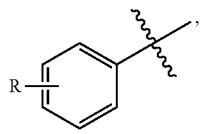

then R may replace any hydrogen atom attached to any of the ring atoms, including a depicted, implied, or expressly defined hydrogen, so long as a stable structure is formed. When a group "R" is depicted as a "floating group" on a fused ring system, as for example in the formula:

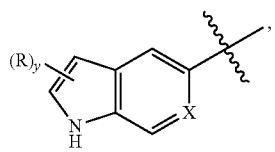

then R may replace any hydrogen attached to any of the ring atoms of either of the fused rings unless specified otherwise. Replaceable hydrogens include depicted hydrogens (e.g., the hydrogen attached to the nitrogen in the formula above), implied hydrogens (e.g., a hydrogen of the formula above that is not shown but understood to be present), expressly defined hydrogens, and optional hydrogens whose presence depends on the identity of a ring atom (e.g., a hydrogen attached to group X, when X equals —CH—), so long as a stable structure is formed. In the example depicted, R may reside on either the 5-membered or the 6-membered ring of the fused ring system. In the formula above, the subscript letter "y" immediately following the group "R" enclosed in parentheses, represents a numeric variable. Unless specified otherwise, this variable can be 0, 1, 2, or any integer greater than 2, only limited by the maximum number of replaceable hydrogen atoms of the ring or ring system.

For the groups and classes below, the following parenthetical subscripts further define the group/class as follows: "(Cn)" defines the exact number (n) of carbon atoms in the group/class. "(C≤n)" defines the maximum number (n) of carbon atoms that can be in the group/class, with the minimum number as small as possible for the group in question, e.g., it is understood that the minimum number of carbon atoms in the group "alkenyl$_{(C≤8)}$" or the class "alkene$_{(C≤8)}$" is two. For example, "alkoxy$_{(C≤10)}$" designates those alkoxy groups having from 1 to 10 carbon atoms. (Cn-n') defines both the minimum (n) and maximum number (n') of carbon atoms in the group. Similarly, "alkyl$_{(C2-10)}$" designates those alkyl groups having from 2 to 10 carbon atoms.

The term "saturated" as used herein means the compound or group so modified has no carbon-carbon double and no carbon-carbon triple bonds, except as noted below. In the case of substituted versions of saturated groups, one or more carbon oxygen double bond or a carbon nitrogen double bond may be present. And when such a bond is present, then carbon-carbon double bonds that may occur as part of keto-enol tautomerism or imine/enamine tautomerism are not precluded.

The term "aliphatic" when used without the "substituted" modifier signifies that the compound/group so modified is an acyclic or cyclic, but non-aromatic hydrocarbon compound or group. In aliphatic compounds/groups, the carbon atoms can be joined together in straight chains, branched chains, or non-aromatic rings (alicyclic). Aliphatic compounds/groups can be saturated, that is joined by single bonds (alkanes/ alkyl), or unsaturated, with one or more double bonds (alkenes/alkenyl) or with one or more triple bonds (alkynes/ alkynyl).

The term "alkyl" when used without the "substituted" modifier refers to a monovalent saturated aliphatic group with a carbon atom as the point of attachment, a linear or branched acyclic structure, and no atoms other than carbon and hydrogen. The groups —CH₃ (Me), —CH₂CH₃ (Et), —CH₂CH₂CH₃ (n-Pr or propyl), —CH(CH₃)₂ (i-Pr, $^i$Pr or isopropyl), —CH₂CH₂CH₂CH₃ (n-Bu), —CH(CH₃) CH₂CH₃ (sec-butyl), —CH₂CH(CH₃)₂ (isobutyl), —C(CH₃)₃ (tert-butyl, t-butyl, t-Bu or $^t$Bu), and —CH₂C (CH₃)₃ (neo-pentyl) are non-limiting examples of alkyl groups. The term "alkanediyl" when used without the "substituted" modifier refers to a divalent saturated aliphatic group, with one or two saturated carbon atom(s) as the point(s) of attachment, a linear or branched acyclic structure, no carbon-carbon double or triple bonds, and no atoms other than carbon and hydrogen. The groups, —CH₂— (methylene), —CH₂CH₂—, —CH₂C(CH₃)₂CH₂—, and —CH₂CH₂CH₂—, are non-limiting examples of alkanediyl groups. The term "alkylidene" when used without the "substituted" modifier refers to the divalent group =CRR' in which R and R' are independently hydrogen or alkyl. Non-limiting examples of alkylidene groups include: =CH₂, =CH(CH₂CH₃), and =C(CH₃)₂. An "alkane" refers to the compound H—R, wherein R is alkyl as this term is defined above. When any of these terms is used with the "substituted" modifier one or more hydrogen atom has been independently replaced by —OH, —F, —Cl, —Br, —I, —NH₂, —NO₂, —CO₂H, —CO₂CH₃, —CN, —SH, —OCH₃, —OCH₂CH₃, —C(O)CH₃, —NHCH₃, —NHCH₂CH₃, —N(CH₃)₂, —C(O)NH₂, —OC(O)CH₃, or —S(O)₂NH₂. The following groups are non-limiting examples of substituted alkyl groups: —CH₂OH, —CH₂Cl, —CF₃, —CH₂CN, —CH₂C(O)OH, —CH₂C(O)OCH₃, —CH₂C(O)NH₂, —CH₂C(O)CH₃, —CH₂OCH₃, —CH₂OC(O)CH₃, —CH₂NH₂, —CH₂N(CH₃)₂, and —CH₂CH₂Cl. The term "haloalkyl" is a subset of substituted alkyl, in which one or more hydrogen atoms has been substituted with a halo group and no other atoms aside from carbon, hydrogen and halogen are present. The group, —CH₂Cl is a non-limiting example of a haloalkyl. The term "fluoroalkyl" is a subset of substituted alkyl, in which one or more hydrogen has been substituted with a fluoro group and no other atoms aside from carbon, hydrogen and fluorine are present. The groups, —CH₂F, —CF₃, and —CH₂CF₃ are non-limiting examples of fluoroalkyl groups.

The term "cycloalkyl" when used without the "substituted" modifier refers to a monovalent saturated aliphatic group with a carbon atom as the point of attachment, said carbon atom forms part of one or more non-aromatic ring structures, a cyclo or cyclic structure, no carbon-carbon double or triple bonds, and no atoms other than carbon and hydrogen. Non-limiting examples of cycloalkyl groups include: —CH(CH₂)₂ (cyclopropyl), cyclobutyl, cyclopentyl, or cyclohexyl. The term "cycloalkanediyl" when used without the "substituted" modifier refers to a divalent saturated aliphatic group with one or two carbon atom as the point(s) of attachment, said carbon atom(s) forms part of one or more non-aromatic ring structures, a cyclo or cyclic structure, no carbon-carbon double or triple bonds, and no atoms other than carbon and hydrogen.

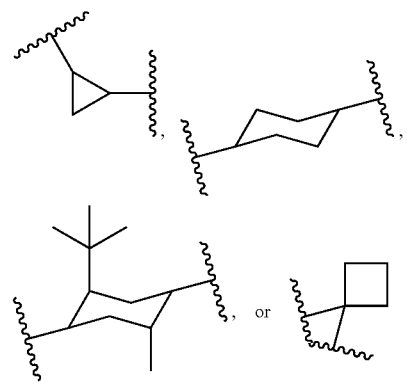

are non-limiting examples of cycloalkanediyl groups. A "cycloalkane" refers to the compound H—R, wherein R is cycloalkyl as this term is defined above. When any of these terms is used with the "substituted" modifier one or more hydrogen atom has been independently replaced by —OH, —F, —Cl, —Br, —I, —NH₂, —NO₂, —CO₂H, —CO₂CH₃, —CN, —SH, —OCH₃, —OCH₂CH₃, —C(O)CH₃, —NHCH₃, —NHCH₂CH₃, —N(CH₃)₂, —C(O)NH₂, —OC (O)CH₃, or —S(O)₂NH₂. The following groups are non-limiting examples of substituted cycloalkyl groups: —C(OH)(CH₂)₂,

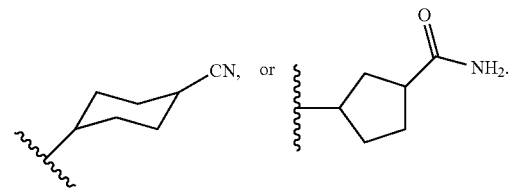 [SMILES: *C1CCC(C#N)CC1 ; "or" ; *C1CCC(C(N)=O)C1]

The term "fused cycloalkyl" when used without the "substituted" modifier refers to a monovalent saturated aliphatic group with a carbon atom as the point of attachment, a bicycle or bicyclic structure or a structure which contains multiple fused rings in a 3 dimensional arrangement or a multiring structure which contain one or more highly strained bonds, no carbon-carbon double or triple bonds, and no atoms other than carbon and hydrogen. Non-limiting examples of fused cycloalkyl groups include:

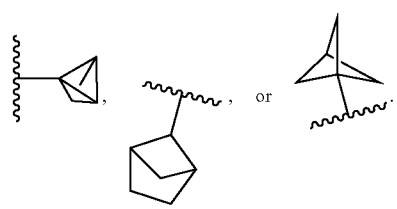

The term "fused cycloalkanediyl" when used without the "substituted" modifier refers to a divalent saturated aliphatic group with one or two carbon atom as the point(s) of attachment, a bicycle or bicyclic structure or a structure which contains multiple fused rings in a 3 dimensional arrangement or a multiring structure which contain one or more highly strained bonds, no carbon-carbon double or triple bonds, and no atoms other than carbon and hydrogen.

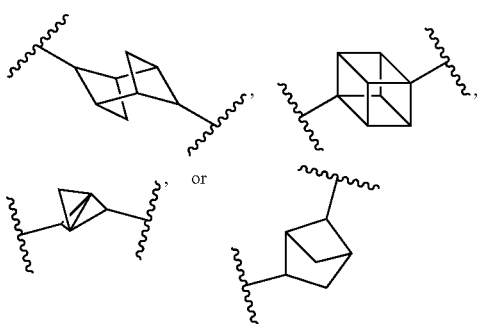

are non-limiting examples of fused cycloalkanediyl groups. A "fused cycloalkane" refers to the compound H—R, wherein R is fused cycloalkyl as this term is defined above. Some non-limiting examples of fused cycloalkanes include cubane and propellane. When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$. The following groups are non-limiting examples of substituted fused cycloalkyl groups:

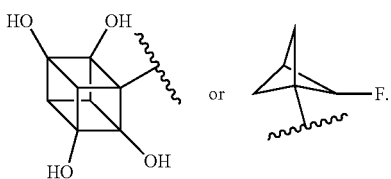 [SMILES: *C12C3C4(O)C5C(C41O)C2(O)C53O ; *C12CC(C1)C2F]

The term "alkenyl" when used without the "substituted" modifier refers to a monovalent unsaturated aliphatic group with a carbon atom as the point of attachment, a linear or branched, acyclic structure, at least one nonaromatic carbon-carbon double bond, no carbon-carbon triple bonds, and no atoms other than carbon and hydrogen. Non-limiting examples of alkenyl groups include: —CH=CH$_2$ (vinyl), —CH=CHCH$_3$, —CH=CHCH$_2$CH$_3$, —CH$_2$CH=CH$_2$ (allyl), —CH$_2$CH=CHCH$_3$, and —CH=CHCH=CH$_2$. The term "alkenediyl" when used without the "substituted" modifier refers to a divalent unsaturated aliphatic group, with two carbon atoms as points of attachment, a linear or branched, cyclo, cyclic or acyclic structure, at least one nonaromatic carbon-carbon double bond, no carbon-carbon triple bonds, and no atoms other than carbon and hydrogen. The groups, —CH=CH—, —CH=C(CH$_3$)CH$_2$—, and —CH=CHCH$_2$—, are non-limiting examples of alkenediyl groups. It is noted that while the alkenediyl group is aliphatic, once connected at both ends, this group is not precluded from forming part of an aromatic structure. The terms "alkene" and refer to a compound having the formula H—R, wherein R is alkenyl as this term is defined above. A "terminal alkene" refers to an alkene having just one carbon-carbon double bond, wherein that bond forms a vinyl group at one end of the molecule. When any of these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$. The groups, —CH=CHF, —CH=CHCl and —CH=CHBr, are non-limiting examples of substituted alkenyl groups.

The term "cycloalkenyl" when used without the "substituted" modifier refers to a monovalent unsaturated aliphatic group with a carbon atom as the point of attachment, said carbon atom forms part of one or more non-aromatic ring structures, a cyclo or cyclic structure, at least one non-aromatic carbon-carbon double bond, no carbon-carbon triple bonds, and no atoms other than carbon and hydrogen. In some non-limiting examples of cycloalkenyl groups include

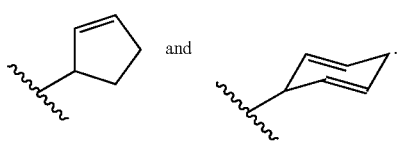 [SMILES: *C1C=CCC1 ; *C1C=CCC=C1]

The term "cycloalkenediyl" when used without the "substituted" modifier refers to a divalent unsaturated aliphatic group with one or two carbon atom(s) as the point(s) of attachment, said carbon atom(s) forms part of one or more non-aromatic ring structures, a cyclo or cyclic structure, at least one non-aromatic carbon-carbon double bond, no carbon-carbon triple bonds, and no atoms other than carbon and hydrogen.

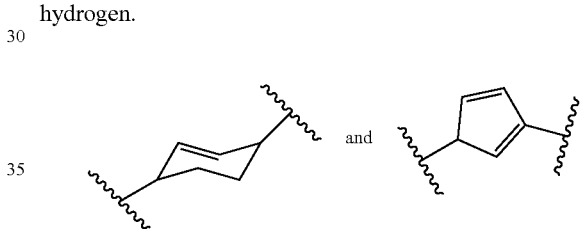

are non-limiting examples of cycloalkenediyl. It is noted that while the cycloalkenediyl group is aliphatic, once connected at both ends, this group is not precluded from forming part of an aromatic structure. The terms "cycloalkene" and refer to a compound having the formula H—R, wherein R is cycloalkenyl as this term is defined above. The term "olefin" is synonymous with the terms "alkene" or a "cycloalkane" as those terms are defined above. When any of these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$. In some non-limiting examples of substituted cycloalkenyl include

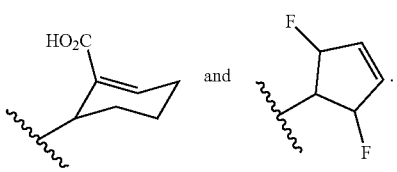 [SMILES: *C1CCCC=C1C(=O)O ; *C1C(F)C=CC1F]

The term "alkynyl" when used without the "substituted" modifier refers to a monovalent unsaturated aliphatic group with a carbon atom as the point of attachment, a linear or branched, acyclic structure, at least one carbon-carbon triple bond, and no atoms other than carbon and hydrogen. As used herein, the term alkynyl does not preclude the presence of one or more non-aromatic carbon-carbon double bonds. The groups, —C≡CH, —C≡CCH₃, and —CH₂C≡CCH₃, are non-limiting examples of alkynyl groups. An "alkyne" refers to the compound H—R, wherein R is alkynyl. When any of these terms are used with the "substituted" modifier one or more hydrogen atom has been independently replaced by —OH, —F, —Cl, —Br, —I, —NH₂, —NO₂, —CO₂H, —CO₂CH₃, —CN, —SH, —OCH₃, —OCH₂CH₃, —C(O)CH₃, —NHCH₃, —NHCH₂CH₃, —N(CH₃)₂, —C(O)NH₂, —OC(O)CH₃, or —S(O)₂NH₂.

The term "aryl" when used without the "substituted" modifier refers to a monovalent unsaturated aromatic group with an aromatic carbon atom as the point of attachment, said carbon atom forming part of a one or more six-membered aromatic ring structure, wherein the ring atoms are all carbon, and wherein the group consists of no atoms other than carbon and hydrogen. If more than one ring is present, the rings may be fused or unfused. As used herein, the term does not preclude the presence of one or more alkyl or aralkyl groups (carbon number limitation permitting) attached to the first aromatic ring or any additional aromatic ring present. Non-limiting examples of aryl groups include phenyl (Ph), methylphenyl, (dimethyl)phenyl, —C₆H₄CH₂CH₃ (ethylphenyl), naphthyl, and a monovalent group derived from biphenyl. The term "arenediyl" when used without the "substituted" modifier refers to a divalent aromatic group with two aromatic carbon atoms as points of attachment, said carbon atoms forming part of one or more six-membered aromatic ring structure(s) wherein the ring atoms are all carbon, and wherein the monovalent group consists of no atoms other than carbon and hydrogen. As used herein, the term does not preclude the presence of one or more alkyl, aryl or aralkyl groups (carbon number limitation permitting) attached to the first aromatic ring or any additional aromatic ring present. If more than one ring is present, the rings may be fused or unfused. Unfused rings may be connected via one or more of the following: a covalent bond, alkanediyl, or alkenediyl groups (carbon number limitation permitting). Non-limiting examples of arenediyl groups include:

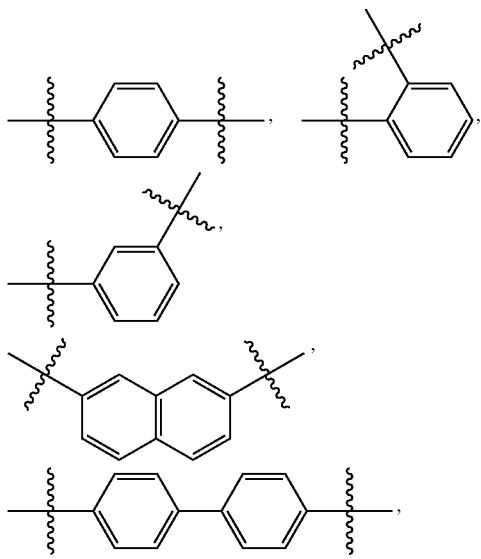

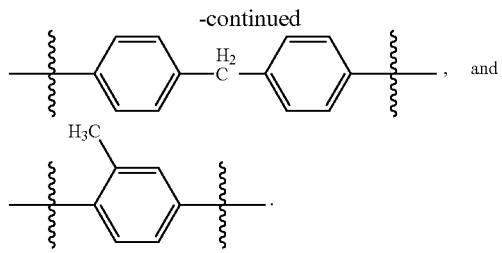

An "arene" refers to the compound H—R, wherein R is aryl as that term is defined above. Benzene and toluene are non-limiting examples of arenes. When any of these terms are used with the "substituted" modifier one or more hydrogen atom has been independently replaced by —OH, —F, —Cl, —Br, —I, —NH₂, —NO₂. —CO₂H, —CO₂CH₃, —CN, —SH, —OCH₃, —OCH₂CH₃, —C(O)CH₃, —NHCH₃, —NHCH₂CH₃, —N(CH₃)₂, —C(O)NH₂, —OC(O)CH₃, or —S(O)₂NH₂.

The term "aralkyl" when used without the "substituted" modifier refers to the monovalent group -alkanediyl-aryl, in which the terms alkanediyl and aryl are each used in a manner consistent with the definitions provided above. Non-limiting examples of aralkyls are: phenylmethyl (benzyl, Bn) and 2-phenyl-ethyl. When the term aralkyl is used with the "substituted" modifier one or more hydrogen atom from the alkanediyl and/or the aryl group has been independently replaced by —OH, —F, —Cl, —Br, —I, —NH₂, —NO₂, —CO₂H, —CO₂CH₃, —CN, —SH, —OCH₃, —OCH₂CH₃, —C(O)CH₃, —NHCH₃, —NHCH₂CH₃, —N(CH₃)₂, —C(O)NH₂. —OC(O)CH₃, or —S(O)₂NH₂. Non-limiting examples of substituted aralkyls are: (3-chlorophenyl)-methyl, and 2-chloro-2-phenyl-eth-1-yl.

The term "heteroaryl" when used without the "substituted" modifier refers to a monovalent aromatic group with an aromatic carbon atom or nitrogen atom as the point of attachment, said carbon atom or nitrogen atom forming part of one or more aromatic ring structures wherein at least one of the ring atoms is nitrogen, oxygen or sulfur, and wherein the heteroaryl group consists of no atoms other than carbon, hydrogen, aromatic nitrogen, aromatic oxygen and aromatic sulfur. If more than one ring is present, the rings may be fused or unfused. As used herein, the term does not preclude the presence of one or more alkyl, aryl, and/or aralkyl groups (carbon number limitation permitting) attached to the aromatic ring or aromatic ring system. Non-limiting examples of heteroaryl groups include furanyl, imidazolyl, indolyl, indazolyl, isoxazolyl, methylpyridinyl, oxazolyl, phenylpyridinyl, pyridinyl, pyrrolyl, pyrimidinyl, pyrazinyl, quinolyl, quinazolyl, quinoxalinyl, triazinyl, tetrazolyl, thiazolyl, thienyl, and triazolyl. The term "N-heteroaryl" refers to a heteroaryl group with a nitrogen atom as the point of attachment. The term "heteroarenediyl" when used without the "substituted" modifier refers to an divalent aromatic group, with two aromatic carbon atoms, two aromatic nitrogen atoms, or one aromatic carbon atom and one aromatic nitrogen atom as the two points of attachment, said atoms forming part of one or more aromatic ring structure(s) wherein at least one of the ring atoms is nitrogen, oxygen or sulfur, and wherein the divalent group consists of no atoms other than carbon, hydrogen, aromatic nitrogen, aromatic oxygen and aromatic sulfur. If more than one ring is present, the rings may be fused or unfused. Unfused rings may be connected via one or more of the following: a covalent bond, alkanediyl, or alkenediyl groups (carbon number limitation permitting). As used herein, the term does not preclude the presence of one or more alkyl, aryl, and/or aralkyl groups (carbon number limitation permitting) attached to the aromatic ring or aromatic ring system. Non-limiting examples of heteroarenediyl groups include:

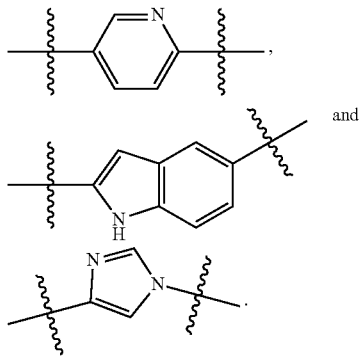

and

A "heteroarene" refers to the compound H—R, wherein R is heteroaryl. Pyridine and quinoline are non-limiting examples of heteroarenes. When these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$. —OC(O)CH$_3$, or —S(O)$_2$NH$_2$.

The term "heteroaralkyl" when used without the "substituted" modifier refers to the monovalent group -alkanediyl-heteroaryl, in which the terms alkanediyl and heteroaryl are each used in a manner consistent with the definitions provided above. Non-limiting examples of heteroaralkyls are: 2-pyridylmethyl and 2-indazolyl-ethyl. When the term heteroaralkyl is used with the "substituted" modifier one or more hydrogen atom from the alkanediyl and/or the heteroaryl group has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$. —N(CH$_3$)$_2$, —C(O)NH$_2$, —OC(O)CH$_3$, or —S(O)$_2$NH$_2$. Non-limiting examples of substituted heteroaralkyls are: (3-chloroquinolyl)-methyl, and 2-chloro-2-thienyl-eth-1-yl.

The term "heterocycloalkyl" when used without the "substituted" modifier refers to a monovalent non-aromatic group with a carbon atom or nitrogen atom as the point of attachment, said carbon atom or nitrogen atom forming part of one or more non-aromatic ring structures wherein at least one of the ring atoms is nitrogen, oxygen or sulfur, and wherein the heterocycloalkyl group consists of no atoms other than carbon, hydrogen, nitrogen, oxygen and sulfur. If more than one ring is present, the rings may be fused or unfused. As used herein, the term does not preclude the presence of one or more alkyl groups (carbon number limitation permitting) attached to the ring or ring system. Also, the term does not preclude the presence of one or more double bonds in the ring or ring system, provided that the resulting group remains non-aromatic. Non-limiting examples of heterocycloalkyl groups include aziridinyl, azetidinyl, pyrrolidinyl, piperidinyl, piperazinyl, morpholinyl, thiomorpholinyl, tetrahydrofuranyl, tetrahydrothiofuranyl, tetrahydropyranyl, pyranyl, oxiranyl, and oxetanyl. The term "N-heterocycloalkyl" refers to a heterocycloalkyl group with a nitrogen atom as the point of attachment. The term "heterocycloalkanediyl" when used without the "sub-stituted" modifier refers to an divalent cyclic group, with two carbon atoms, two nitrogen atoms, or one carbon atom and one nitrogen atom as the two points of attachment, said atoms forming part of one or more ring structure(s) wherein at least one of the ring atoms is nitrogen, oxygen or sulfur, and wherein the divalent group consists of no atoms other than carbon, hydrogen, nitrogen, oxygen and sulfur. If more than one ring is present, the rings may be fused or unfused. Unfused rings may be connected via one or more of the following: a covalent bond, alkanediyl, or alkenediyl groups (carbon number limitation permitting). As used herein, the term does not preclude the presence of one or more alkyl groups (carbon number limitation permitting) attached to the ring or ring system. Also, the term does not preclude the presence of one or more double bonds in the ring or ring system, provided that the resulting group remains non-aromatic. Non-limiting examples of heterocycloalkanediyl groups include:

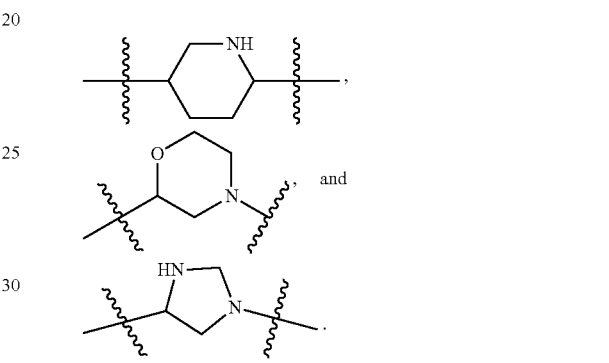

and

When these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, —S(O)$_2$NH$_2$, or —C(O)OC(CH$_3$)$_3$ (tert-butyloxycarbonyl, BOC).

The term "acyl" when used without the "substituted" modifier refers to the group —C(O)R, in which R is a hydrogen, alkyl, cycloalkyl, aryl, aralkyl or heteroaryl, as those terms are defined above. The groups, —CHO, —C(O)CH$_3$ (acetyl, Ac), —C(O)CH$_2$CH$_3$, —C(O)CH$_2$CH$_2$CH$_3$, —C(O)CH(CH$_3$)$_2$, —C(O)CH(CH$_2$)$_2$, —C(O)C$_6$H$_5$, —C(O)C$_6$H$_4$CH$_3$, —C(O)CH$_2$C$_6$H$_5$, —C(O)(imidazolyl) are non-limiting examples of acyl groups. A "thioacyl" is defined in an analogous manner, except that the oxygen atom of the group —C(O)R has been replaced with a sulfur atom, —C(S)R. The term "aldehyde" corresponds to an alkane, as defined above, wherein at least one of the hydrogen atoms has been replaced with a —CHO group. When any of these terms are used with the "substituted" modifier one or more hydrogen atom (including a hydrogen atom directly attached the carbonyl or thiocarbonyl group, if any) has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$. The groups, —C(O)CH$_2$CF$_3$, —CO$_2$H (carboxyl), —CO$_2$CH$_3$ (methylcarboxyl), —CO$_2$CH$_2$CH$_3$, —C(O)NH$_2$ (carbamoyl), and —CON(CH$_3$)$_2$, are non-limiting examples of substituted acyl groups.

The term "alkylamino" when used without the "substituted" modifier refers to the group —NHR, in which R is an alkyl, as that term is defined above. Non-limiting examples of alkylamino groups include: —NHCH₃ and —NHCH₂CH₃. The term "dialkylamino" when used without the "substituted" modifier refers to the group —NRR', in which R and R' can each independently be the same or different alkyl groups, or R and R' can be taken together to represent an alkanediyl. Non-limiting examples of dialkylamino groups include: —N(CH₃)₂, —N(CH₃)(CH₂CH₃), and N-pyrrolidinyl. The terms "alkoxyamino", "cycloalkylamino", "alkenylamino", "cycloalkenylamino", "alkynylamino", "arylamino", "aralkylamino", "heteroarylamino", "heterocycloalkylamino" and "alkylsulfonylamino" when used without the "substituted" modifier, refers to groups, defined as —NHR, in which R is alkoxy, cycloalkyl, alkenyl, cycloalkenyl, alkynyl, aryl, aralkyl, heteroaryl, heterocycloalkyl, and alkylsulfonyl, respectively. A non-limiting example of an arylamino group is —NHC₆H₅. The term "amido" (acylamino), when used without the "substituted" modifier, refers to the group —NHR, in which R is acyl, as that term is defined above. A non-limiting example of an amido group is —NHC(O)CH₃. The term "alkylimino" when used without the "substituted" modifier refers to the divalent group =NR, in which R is an alkyl, as that term is defined above. The term "alkylaminodiyl" refers to the divalent group —NH-alkanediyl-, —NH-alkanediyl-NH—, or -alkanediyl-NH-alkanediyl-. When any of these terms is used with the "substituted" modifier one or more hydrogen atom has been independently replaced by —OH, —F, —Cl, —Br, —I, —NH₂, —NO₂, —CO₂H, —CO₂CH₃, —CN, —SH, —OCH₃, —OCH₂CH₃, —C(O)CH₃, —NHCH₃, —NHCH₂CH₃, —N(CH₃)₂, —C(O)NH₂, —OC(O)CH₃, or —S(O)₂NH₂. The groups —NHC(O)OCH₃ and —NHC(O)NHCH₃ are non-limiting examples of substituted amido groups.

The term "alkoxy" when used without the "substituted" modifier refers to the group —OR, in which R is an alkyl, as that term is defined above. Non-limiting examples include: —OCH₃ (methoxy), —OCH₂CH₃ (ethoxy), —OCH₂CH₂CH₃, —OCH(CH₃)₂ (isopropoxy), and —OC(CH₃)₃ (tert-butoxy). The terms "cycloalkoxy". "alkenyloxy", "alkynyloxy", "aryloxy", "aralkoxy", "heteroaryloxy", "heterocycloalkoxy", and "acyloxy", when used without the "substituted" modifier, refers to groups, defined as —OR, in which R is cycloalkyl, alkenyl, alkynyl, aryl, aralkyl, heteroaryl, heterocycloalkyl, and acyl, respectively. The term "alkoxydiyl" refers to the divalent group —O-alkanediyl-, —O-alkanediyl-O—, or -alkanediyl-O-alkanediyl-. The term "alkylthio" and "acylthio" when used without the "substituted" modifier refers to the group —SR, in which R is an alkyl and acyl, respectively. The term "alkylthiodiyl" refers to the divalent group —S-alkanediyl-, —S-alkanediyl-S—, or -alkanediyl-S-alkanediyl-. The term "alcohol" corresponds to an alkane, as defined above, wherein at least one of the hydrogen atoms has been replaced with a hydroxy group. The term "ether" corresponds to an alkane or cycloalkane, as defined above, wherein at least one of the hydrogen atoms has been replaced with an alkoxy or cycloalkoxy group. When any of these terms is used with the "substituted" modifier one or more hydrogen atom has been independently replaced by —OH, —F, —Cl, —Br, —I, —NH₂, —NO₂, —CO₂H, —CO₂CH₃, —CN, —SH, —OCH₃, —OCH₂CH₃, —C(O)CH₃, —NHCH₃, —NHCH₂CH₃. —N(CH₃)₂, —C(O)NH₂, —OC(O)CH₃, or —S(O)₂NH₂.

As indicated above in some aspects the cell-targeting moiety is an antibody. As used herein, the term "antibody" is intended to include immunoglobulins and fragments thereof which are specifically reactive to the designated protein or peptide, or fragments thereof. Suitable antibodies include, but are not limited to, human antibodies, primatized antibodies, de-immunized antibodies, chimeric antibodies, bi-specific antibodies, humanized antibodies, conjugated antibodies (i.e., antibodies conjugated or fused to other proteins, radiolabels, cytotoxins), Small Modular ImmunoPharmaceuticals ("SMIPs™"), single chain antibodies, cameloid antibodies, antibody-like molecules (e.g., anticalins), and antibody fragments. As used herein, the term "antibodies" also includes intact monoclonal antibodies, polyclonal antibodies, single domain antibodies (e.g., shark single domain antibodies (e.g., IgNAR or fragments thereof)), multispecific antibodies (e.g., bi-specific antibodies) formed from at least two intact antibodies, and antibody fragments so long as they exhibit the desired biological activity. Antibody polypeptides for use herein may be of any type (e.g., IgG, IgM, IgA, IgD and IgE). Generally, IgG and/or IgM are preferred because they are the most common antibodies in the physiological situation and because they are most easily made in a laboratory setting. As used herein the term antibody also encompasses an antibody fragment such as a portion of an intact antibody, such as, for example, the antigen-binding or variable region of an antibody. Examples of antibody fragments include Fab, Fab', F(ab')₂, Fc and Fv fragments; triabodies; tetrabodies; linear antibodies; single-chain antibody molecules; and multi specific antibodies formed from antibody fragments. The term "antibody fragment" also includes any synthetic or genetically engineered protein that acts like an antibody by binding to a specific antigen to form a complex. For example, antibody fragments include isolated fragments, "Fv" fragments, consisting of the variable regions of the heavy and light chains, recombinant single chain polypeptide molecules in which light and heavy chain variable regions are connected by a peptide linker ("ScFv proteins"), and minimal recognition units consisting of the amino acid residues that mimic the hypervariable region. An oxygen linked antibody is an antibody which has a chemical function group such that the linkage between the antibody and the linker or compound is joined via an oxygen atom. Similarly, a nitrogen linked antibody is an antibody which has a chemical function group such that the linkage between the antibody and the linker or compound is joined via an nitrogen atom.

A "base" in the context of this application is a compound which has a lone pair of electron that can accept a proton. Non-limiting examples of a base can include triethylamine, a metal hydroxide, a metal alkoxide, a metal hydride, or a metal alkane. An alkyllithium or organolithium is a compound of the formula alkyl$_{(C≤12)}$-Li. A nitrogenous base is an alkylamine, dialkylamino, trialkylamine, nitrogen containing heterocycloalkane or heteroarene wherein the base can accept a proton to form a positively charged species. For example, but not limited to, a nitrogenous base could be 4,4-dimethylpyridine, pyridine, 1,8-diazabicyclo[5.4.0]undec-7-ene, diisopropylethylamine, or triethylamine. A metal alkoxide is an alkoxy group wherein the oxygen atom, which was the point of connectivity, has an extra electron and thus a negative charge which is charged balanced by the metal ion. For example, a metal alkoxide could be a sodium tert-butoxide or potassium methoxide.

A "linker" in the context of this application is divalent chemical group which may be used to join one or more molecules to the compound of the instant disclosure. In some embodiments, the linker contains a reactive functional group, such as a carboxyl, an amide, a amine, a hydroxy, a mercapto, an aldehyde, or a ketone on each end that be used to join one or more molecules to the compounds of the instant disclosure. In some non-limiting examples, —CH₂CH₂CH₂CH₂—, —C(O)CH₂CH₂CH₂—, —OCH₂CH₂NH—, —NHCH₂CH₂NH—, and —(OCH₂CH₂)$_n$—, wherein n is between 1-1000, are linkers.

An "amine protecting group" is well understood in the art. An amine protecting group is a group which prevents the reactivity of the amine group during a reaction which modifies some other portion of the molecule and can be easily removed to generate the desired amine. Amine protecting groups can be found at least in Greene and Wuts, 1999, which is incorporated herein by reference. Some non-limiting examples of amino protecting groups include formyl, acetyl, propionyl, pivaloyl, t-butylacetyl, 2-chloroacetyl, 2-bromoacetyl, trifluoroacetyl, trichloroacetyl, o-nitrophenoxyacetyl, α-chlorobutyryl, benzoyl, 4-chlorobenzoyl, 4-bromobenzoyl, 4-nitrobenzoyl, and the like; sulfonyl groups such as benzenesulfonyl, p-toluenesulfonyl and the like; alkoxy- or aryloxycarbonyl groups (which form urethanes with the protected amine) such as benzyloxycarbonyl (Cbz), p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 3,5-dimethoxybenzyloxycarbonyl, 2,4-dimethoxybenzyloxycarbonyl, 4-methoxybenzyloxycarbonyl, 2-nitro-4,5-dimethoxybenzyloxycarbonyl, 3,4,5-trimethoxybenzyloxycarbonyl, 1-(p-biphenylyl)-1-methylethoxycarbonyl, α,α-dimethyl-3,5-dimethoxybenzyloxycarbonyl, benzhydryloxycarbonyl, t-butyloxycarbonyl (Boc), diisopropylmethoxycarbonyl, isopropyloxycarbonyl, ethoxycarbonyl, methoxycarbonyl, allyloxycarbonyl (Alloc), 2,2,2-trichloroethoxycarbonyl, 2-trimethylsilylethyloxycarbonyl (Teoc), phenoxycarbonyl, 4-nitrophenoxycarbonyl, fluorenyl-9-methoxycarbonyl (Fmoc), cyclopentyloxycarbonyl, adamantyloxycarbonyl, cyclohexyloxycarbonyl, phenylthiocarbonyl and the like; aralkyl groups such as benzyl, triphenylmethyl, benzyloxymethyl and the like; and silyl groups such as trimethylsilyl and the like. Additionally, the "amine protecting group" can be a divalent protecting group such that both hydrogen atoms on a primary amine are replaced with a single protecting group. In such a situation the amine protecting group can be phthalimide (phth) or a substituted derivative thereof wherein the term "substituted" is as defined above. In some embodiments, the halogenated phthalimide derivative may be tetrachlorophthalimide (TCphth).

A "hydroxyl protecting group" is well understood in the art. A hydroxyl protecting group is a group which prevents the reactivity of the hydroxyl group during a reaction which modifies some other portion of the molecule and can be easily removed to generate the desired hydroxyl. Hydroxyl protecting groups can be found at least in Greene and Wuts, 1999, which is incorporated herein by reference. Some non-limiting examples of hydroxyl protecting groups include acyl groups such as formyl, acetyl, propionyl, pivaloyl, t-butylacetyl, 2-chloroacetyl, 2-bromoacetyl, trifluoroacetyl, trichloroacetyl, o-nitrophenoxyacetyl, α-chlorobutyryl, benzoyl, 4-chlorobenzoyl, 4-bromobenzoyl, 4-nitrobenzoyl, and the like; sulfonyl groups such as benzenesulfonyl, p-toluenesulfonyl and the like; acyloxy groups such as benzyloxycarbonyl (Cbz), p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 3,5-dimethoxybenzyloxycarbonyl, 2,4-dimethoxybenzyloxycarbonyl, 4-methoxybenzyloxycarbonyl, 2-nitro-4,5-dimethoxybenzyloxycarbonyl, 3,4,5-trimethoxybenzyloxycarbonyl, 1-(p-biphenylyl)-1-methylethoxycarbonyl, α,α-dimethyl-3,5-dimethoxybenzyloxycarbonyl, benzhydryloxycarbonyl, t-butyloxycarbonyl (Boc), diisopropylmethoxycarbonyl, isopropyloxycarbonyl, ethoxycarbonyl, methoxycarbonyl, allyloxycarbonyl (Alloc), 2,2,2-trichloroethoxycarbonyl, 2-trimethylsilylethyloxycarbonyl (Teoc), phenoxycarbonyl, 4-nitrophenoxycarbonyl, fluorenyl-9-methoxycarbonyl (Fmoc), cyclopentyloxycarbonyl, adamantyloxycarbonyl, cyclohexyloxycarbonyl, phenylthiocarbonyl and the like; aralkyl groups such as benzyl, triphenylmethyl, benzyloxymethyl and the like; and silyl groups such as trimethylsilyl and the like.

A "thiol protecting group" is well understood in the art. A thiol protecting group is a group which prevents the reactivity of the mercapto group during a reaction which modifies some other portion of the molecule and can be easily removed to generate the desired mercapto group. Thiol protecting groups can be found at least in Greene and Wuts, 1999, which is incorporated herein by reference. Some non-limiting examples of thiol protecting groups include acyl groups such as formyl, acetyl, propionyl, pivaloyl, t-butylacetyl, 2-chloroacetyl, 2-bromoacetyl, trifluoroacetyl, trichloroacetyl, o-nitrophenoxyacetyl, α-chlorobutyryl, benzoyl, 4-chlorobenzoyl, 4-bromobenzoyl, 4-nitrobenzoyl, and the like; sulfonyl groups such as benzenesulfonyl, p-toluenesulfonyl and the like; acyloxy groups such as benzyloxycarbonyl (Cbz), p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 3,5-dimethoxybenzyloxycarbonyl, 2,4-dimethoxybenzyloxycarbonyl, 4-methoxybenzyloxycarbonyl, 2-nitro-4,5-dimethoxybenzyloxycarbonyl, 3,4,5-trimethoxybenzyloxycarbonyl, 1-(p-biphenylyl)-1-methylethoxycarbonyl, α,α-dimethyl-3,5-dimethoxybenzyloxycarbonyl, benzhydryloxycarbonyl, t-butyloxycarbonyl (Boc), diisopropylmethoxycarbonyl, isopropyloxycarbonyl, ethoxycarbonyl, methoxycarbonyl, allyloxycarbonyl (Alloc), 2,2,2-trichloroethoxycarbonyl, 2-trimethylsilylethyloxycarbonyl (Teoc), phenoxycarbonyl, 4-nitrophenoxycarbonyl, fluorenyl-9-methoxycarbonyl (Fmoc), cyclopentyloxycarbonyl, adamantyloxycarbonyl, cyclohexyloxycarbonyl, phenylthiocarbonyl and the like; aralkyl groups such as benzyl, triphenylmethyl, benzyloxymethyl and the like; and silyl groups such as trimethylsilyl and the like.

A "stereoisomer" or "optical isomer" is an isomer of a given compound in which the same atoms are bonded to the same other atoms, but where the configuration of those atoms in three dimensions differs. "Enantiomers" are stereoisomers of a given compound that are mirror images of each other, like left and right hands. "Diastereomers" are stereoisomers of a given compound that are not enantiomers. Chiral molecules contain a chiral center, also referred to as a stereocenter or stereogenic center, which is any point, though not necessarily an atom, in a molecule bearing groups such that an interchanging of any two groups leads to a stereoisomer. In organic compounds, the chiral center is typically a carbon, phosphorus or sulfur atom, though it is also possible for other atoms to be stereocenters in organic and inorganic compounds. A molecule can have multiple stereocenters, giving it many stereoisomers. In compounds whose stereoisomerism is due to tetrahedral stereogenic centers (e.g., tetrahedral carbon), the total number of hypothetically possible stereoisomers will not exceed $2^n$, where n is the number of tetrahedral stereocenters. Molecules with symmetry frequently have fewer than the maximum possible number of stereoisomers. A 50:50 mixture of enantiomers is referred to as a racemic mixture. Alternatively, a mixture of enantiomers can be enantiomerically enriched so that one enantiomer is present in an amount greater than 50%. Typically, enantiomers and/or diastereomers can be resolved or separated using techniques known in the art. It is contemplated that that for any stereocenter or axis of chirality for which stereochemistry has not been defined, that stereocenter or axis of chirality can be present in its R form, S form, or as a mixture of the R and S forms, including racemic and non-racemic mixtures. As used herein, the phrase "substantially free from other stereoisomers" means that the composition contains ≤15%, more preferably ≤10%, even more preferably ≤5%, or most preferably ≤1% of another stereoisomer(s).

VI. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1—Synthesis of Tubulysin Analogs

Figure 3:
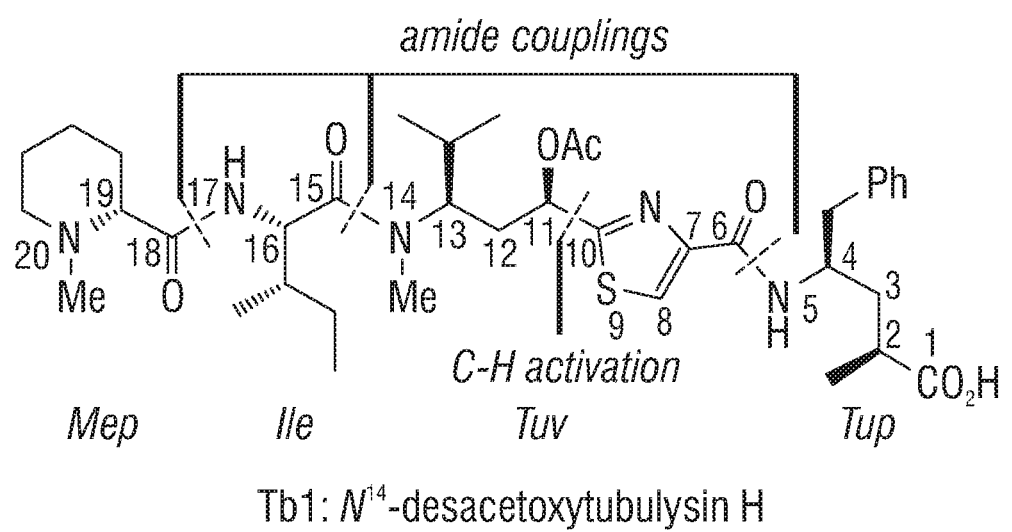
FIG. 3—A: Retrosynthetic analysis and strategy for the synthesis of N$^{14}$-desacetoxytubulysin H (Tb1); B: C—H activation step to form the C10-C11 bond. Mep=N-methyl-(D)-pipecolic acid; Ile=L-isoleucine; Tuv=tubuvaline: Tup=tubuphenylalanine FIG. 4—72 hour killing assay of tubulysin analogs in MES SA.
Figure 3:
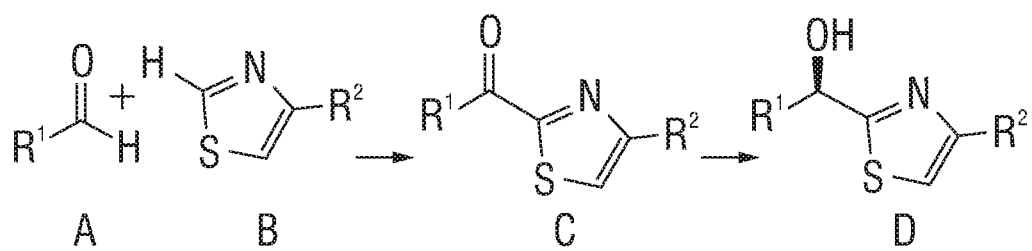
Figure 4:
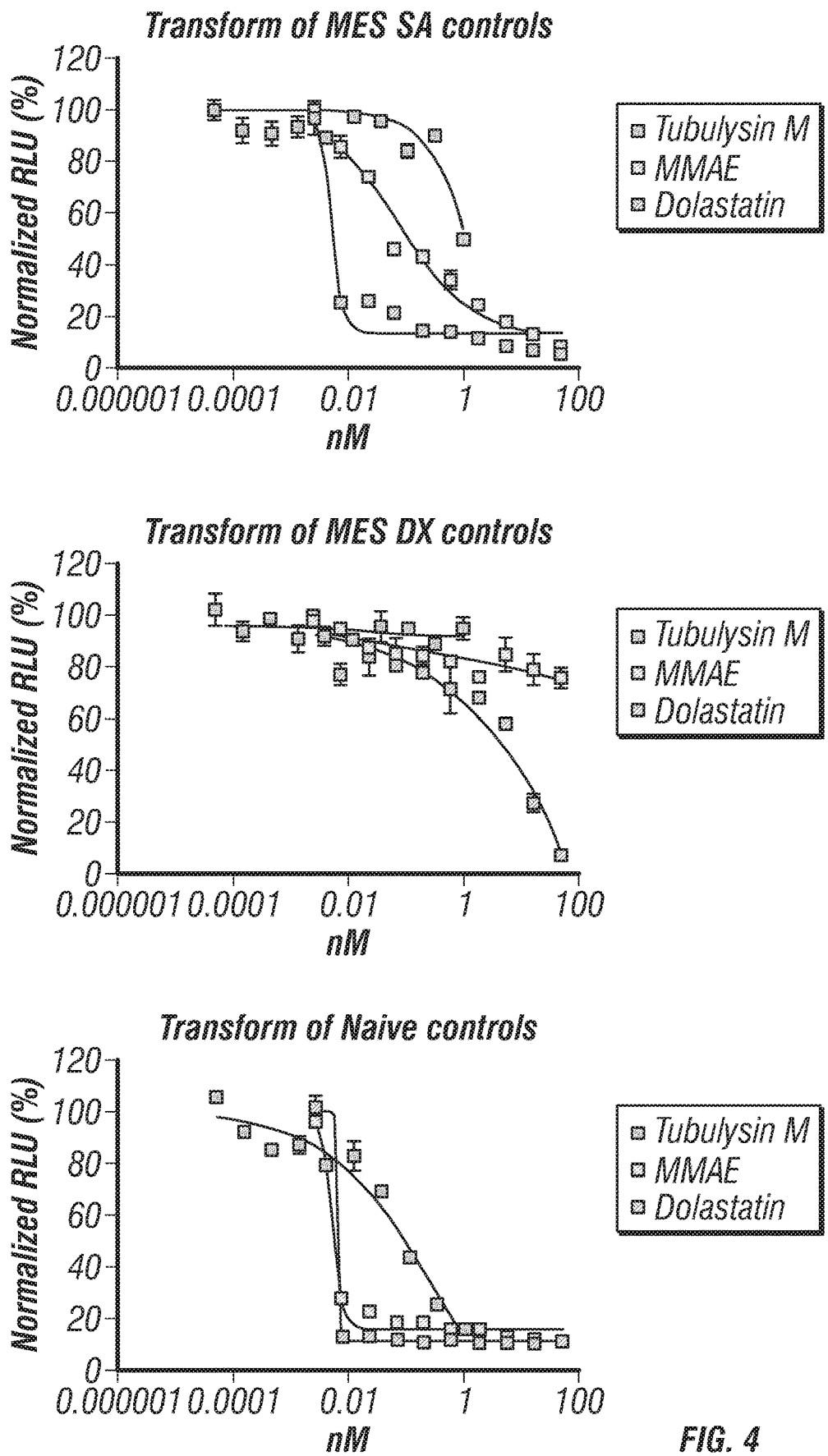
Figure 4:
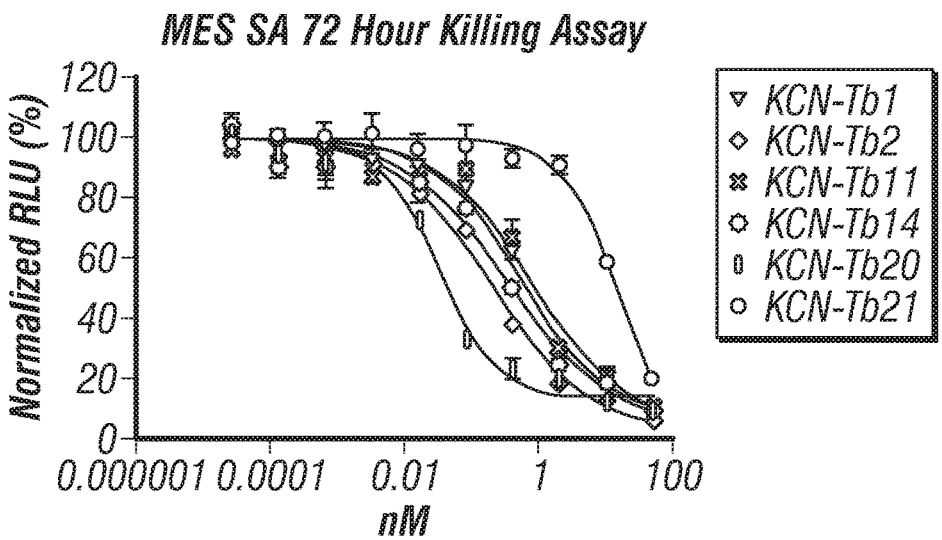
Figure 4:
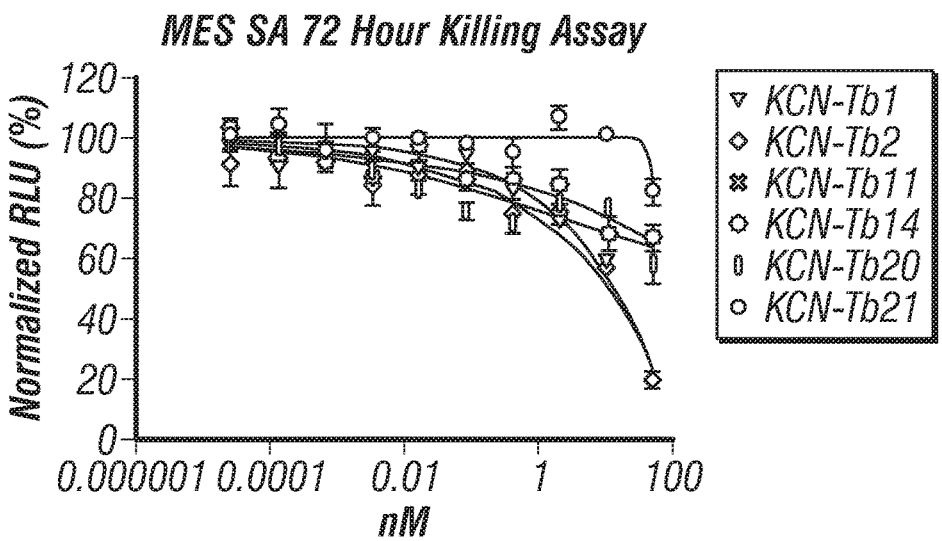
Figure 4:
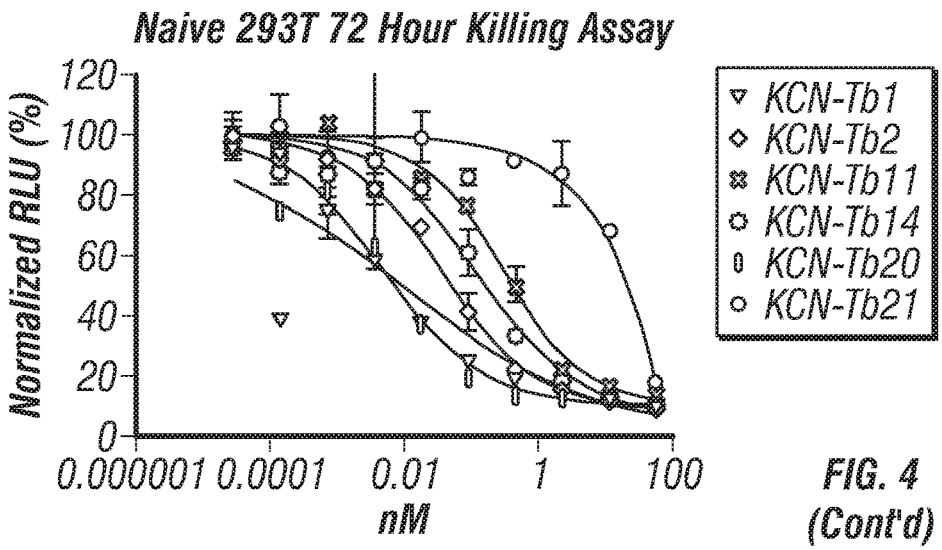
Figure 5:
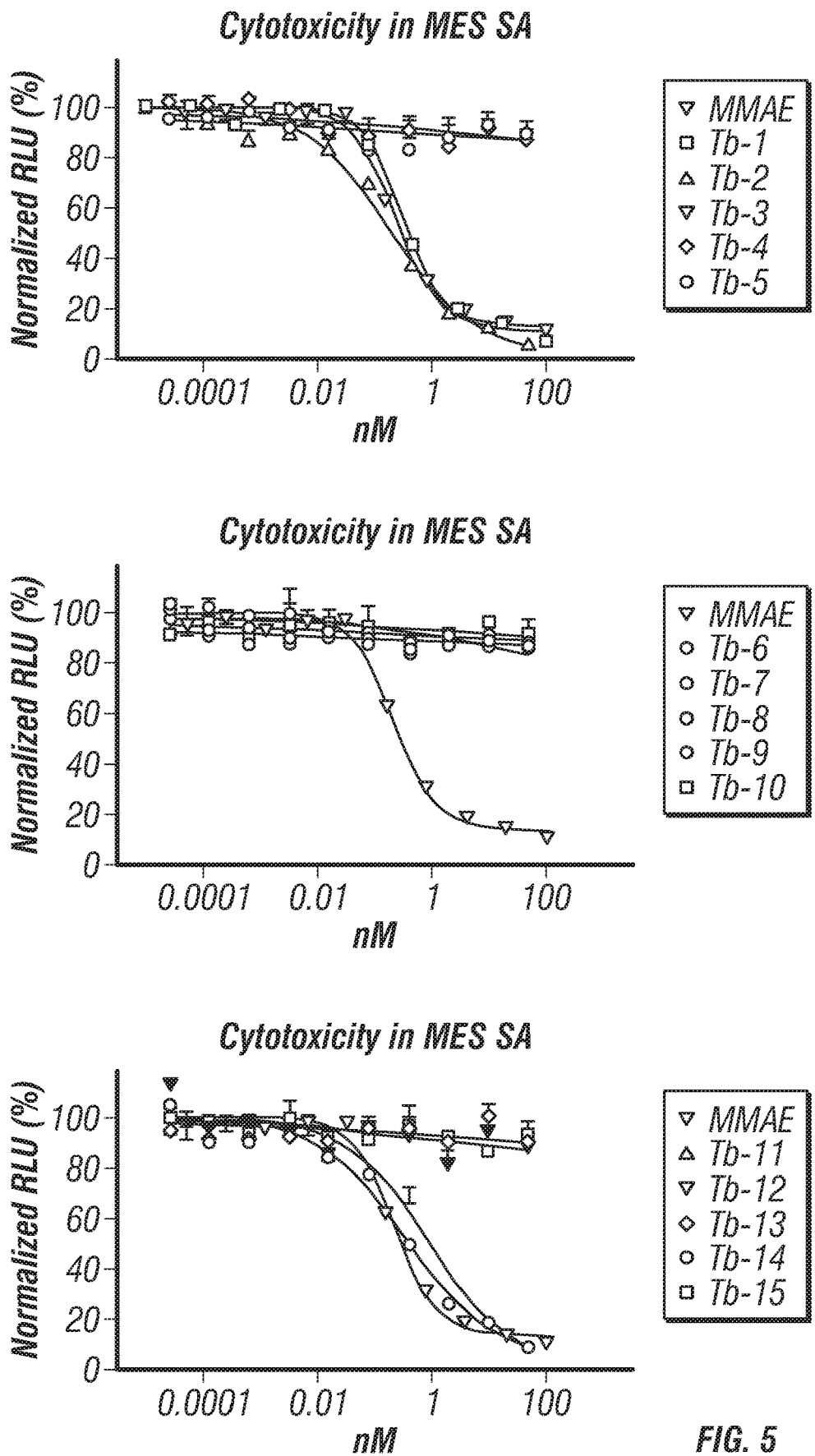
FIG. 5—Cytotoxicity assay for tubulysin analogs in MES SA.
Figure 5:
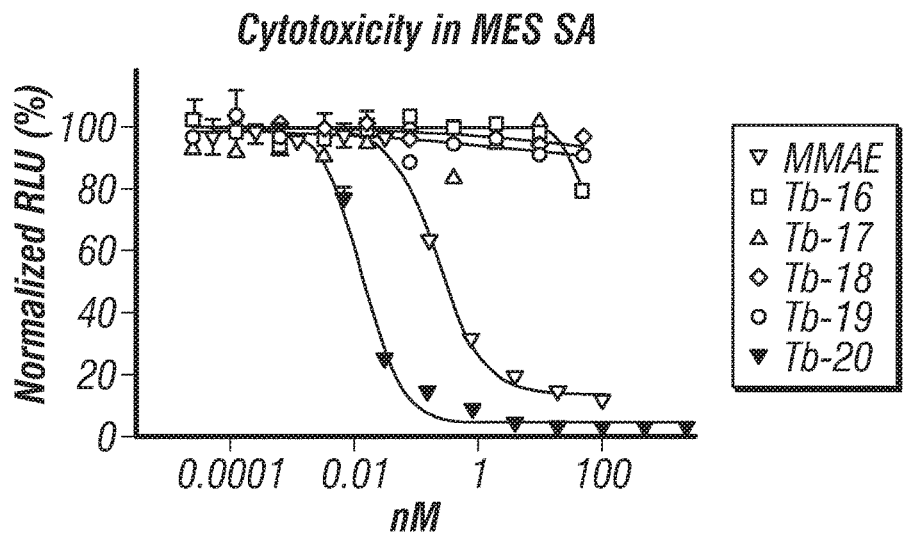
Figure 5:
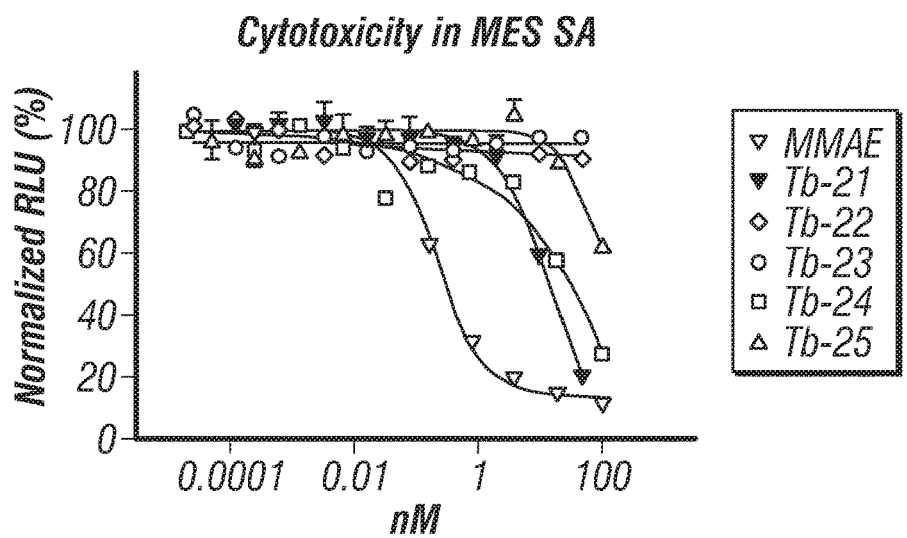
Figure 5:
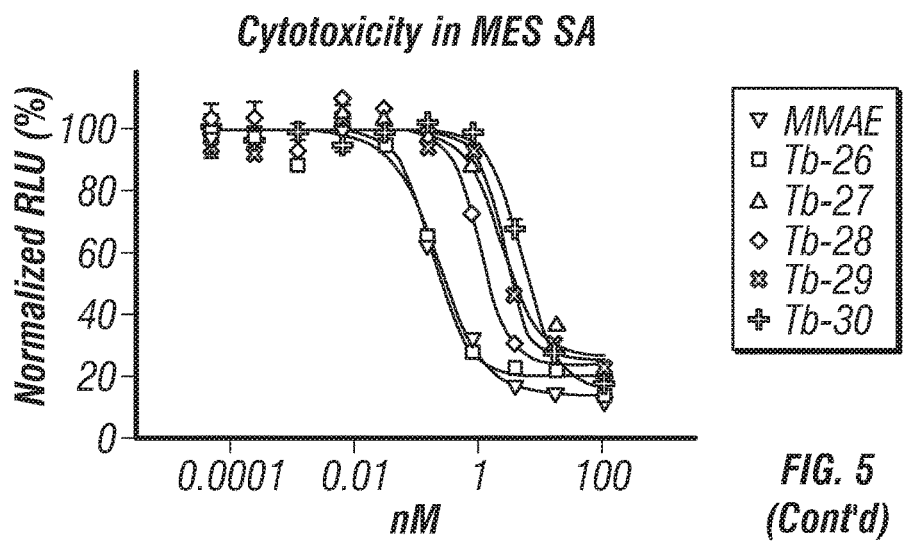
Figure 5:
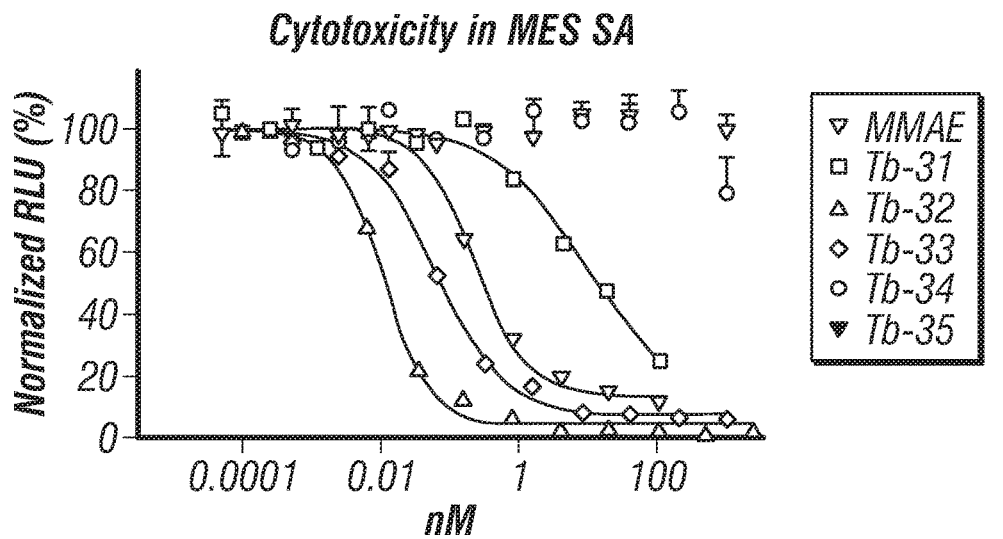
Figure 5:
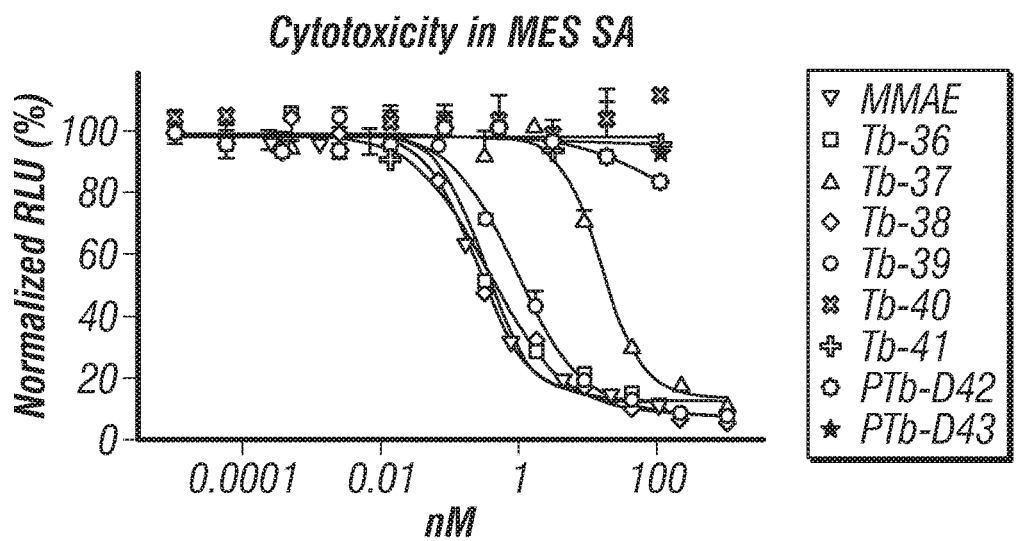
Figure 6A:
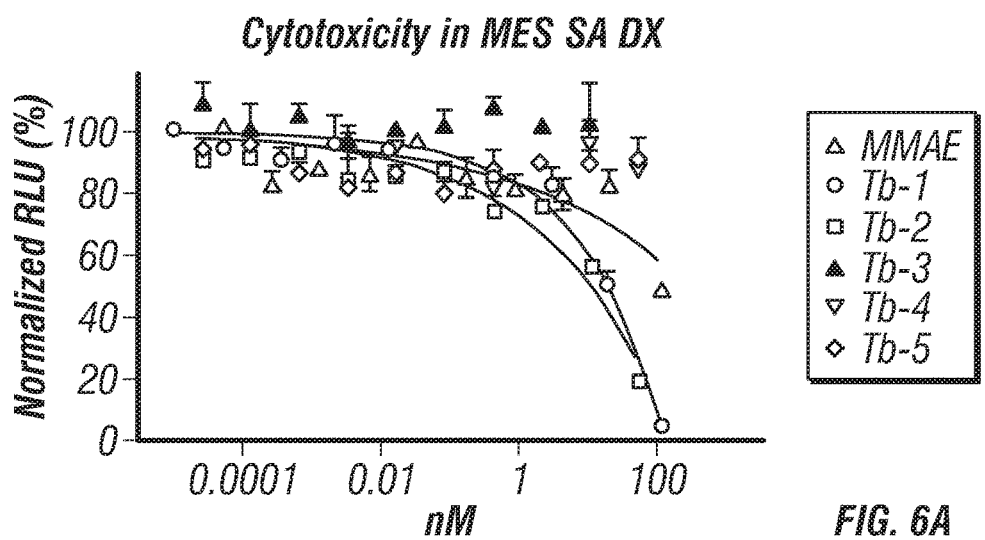
FIGS. 6A & 6B—Cytotoxicity assay for tubulysin analogs in MES SA Dx.
Figure 6A:
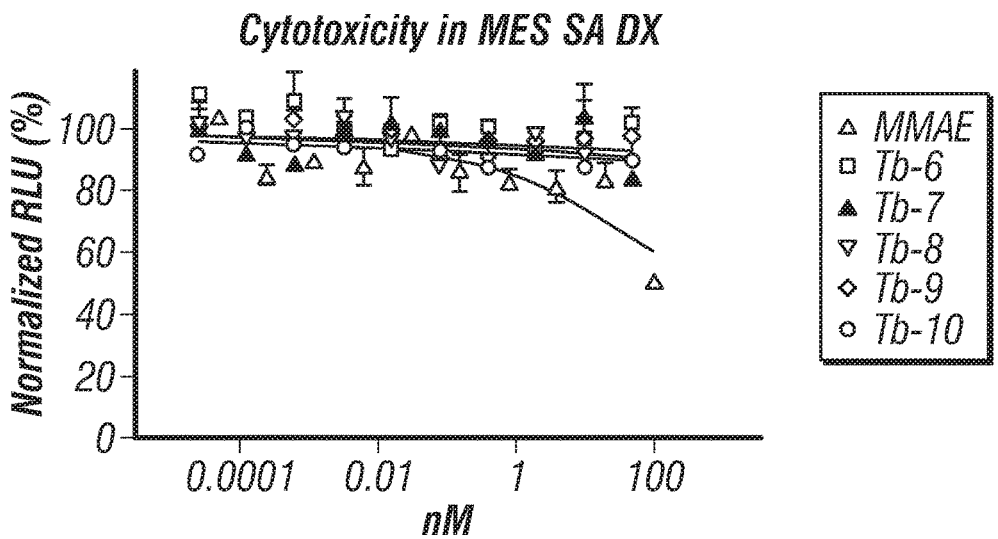
Figure 6A:
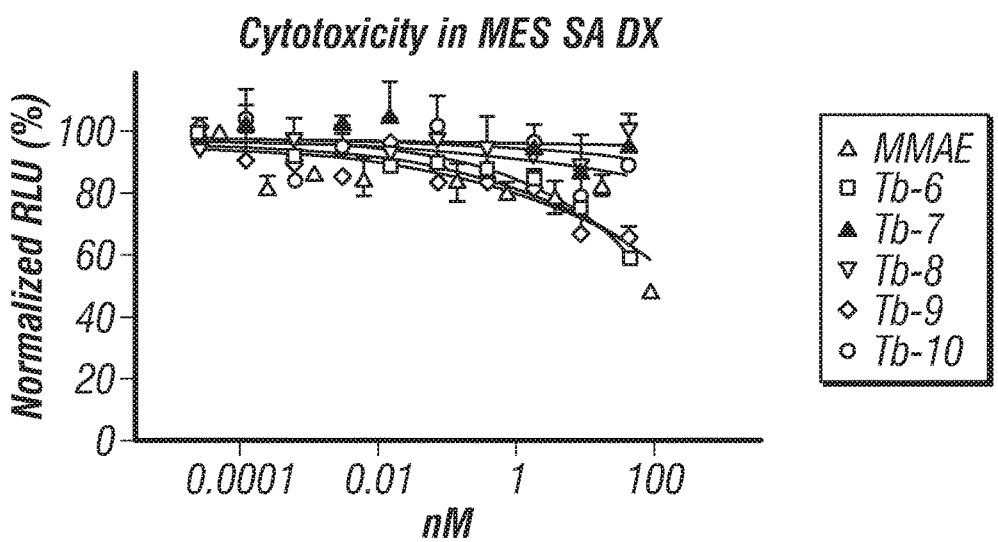
Figure 6A:
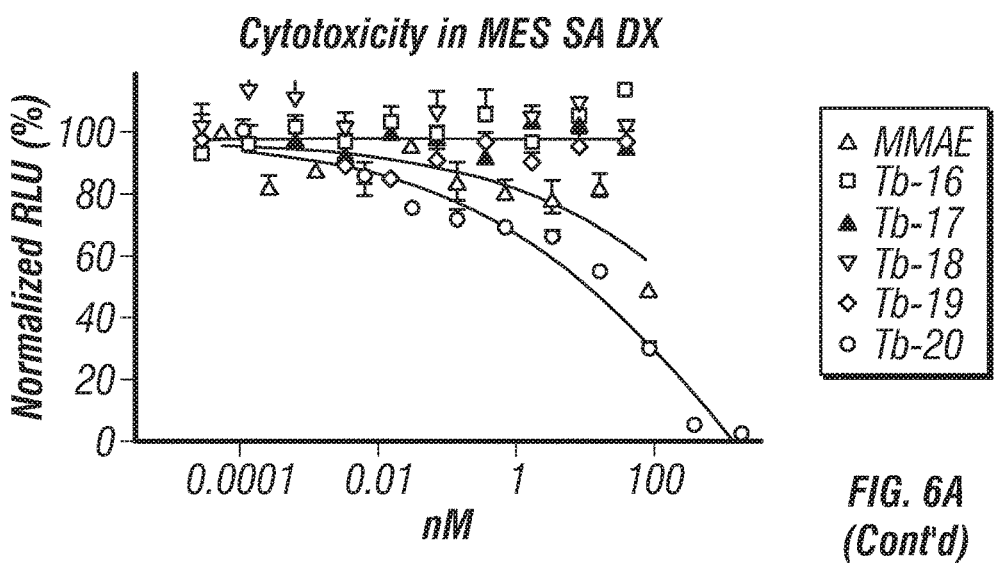
Figure 6B:
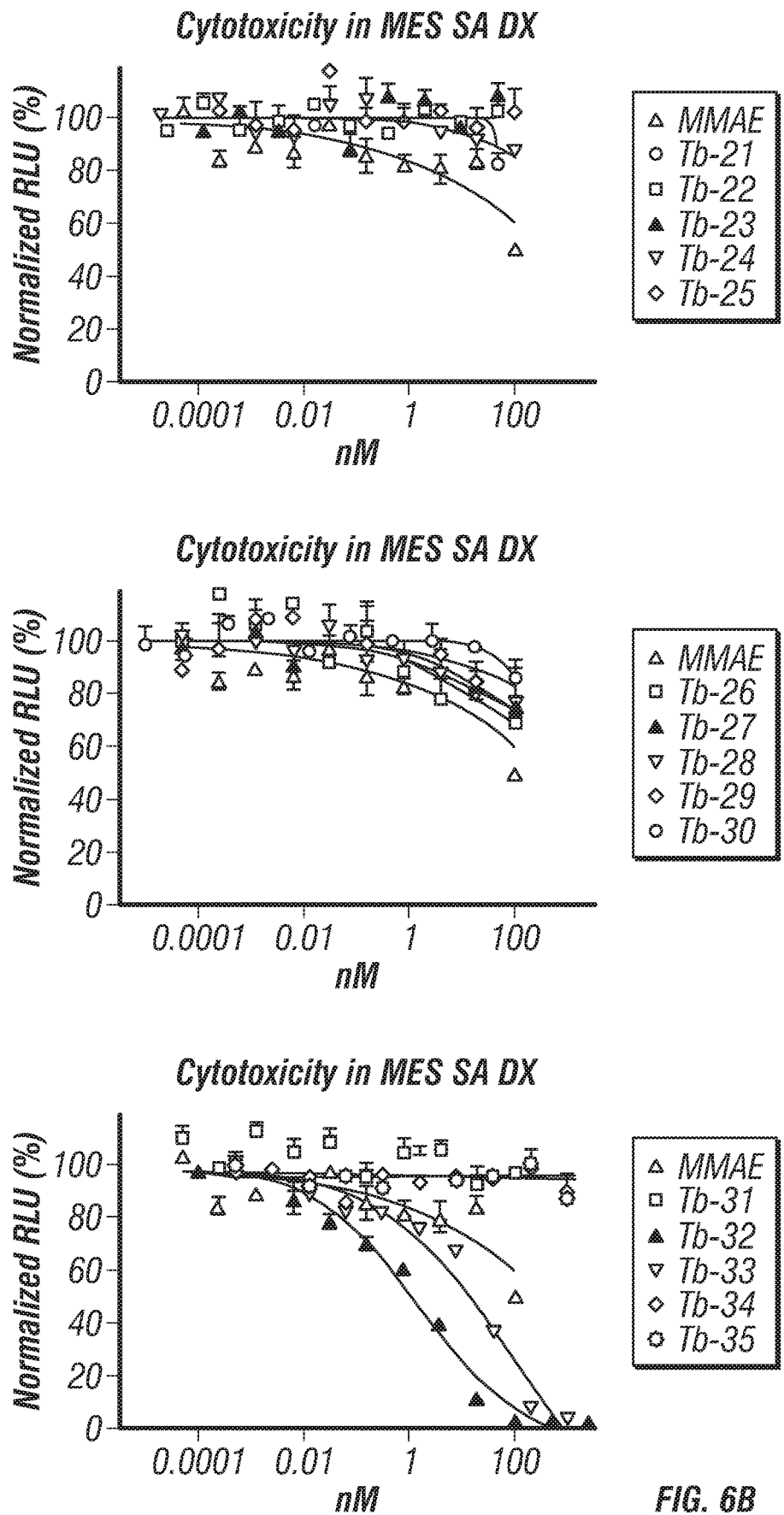
Figure 6B:
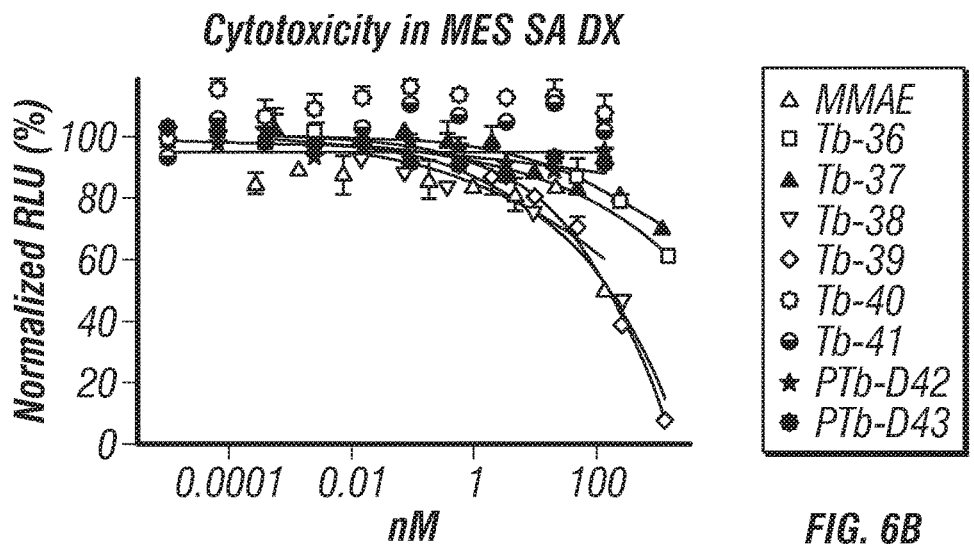
Figure 7A:
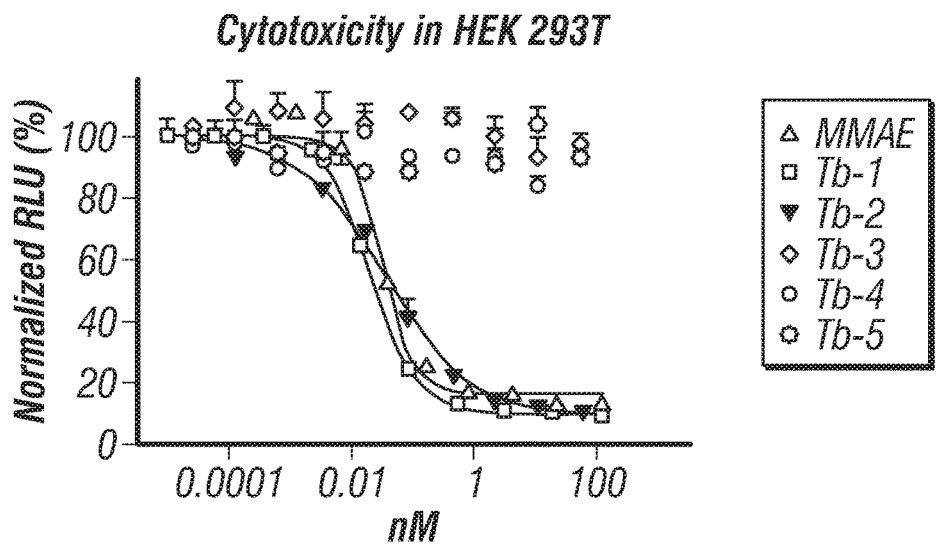
FIGS. 7A & 7B—Cytotoxicity assay for tubulysin analogs in HEK 293T.
Figure 7A:
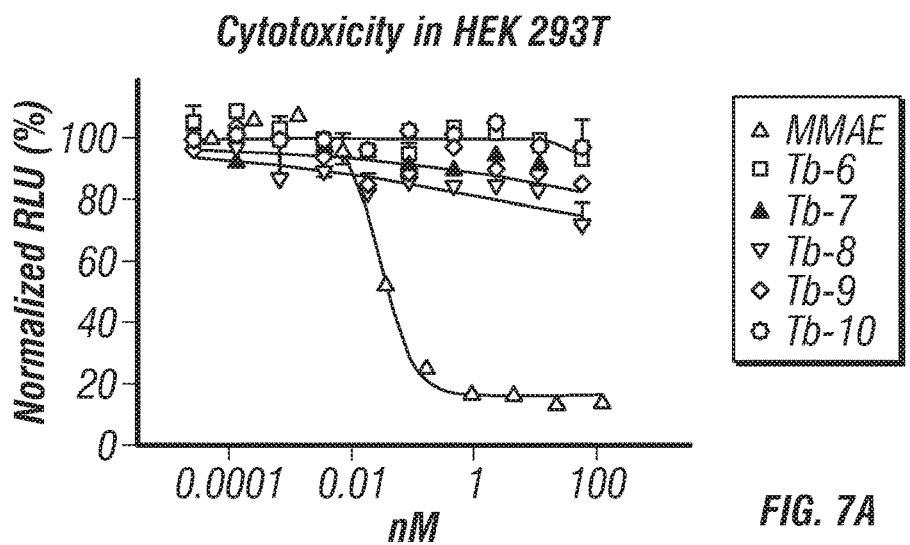
Figure 7A:
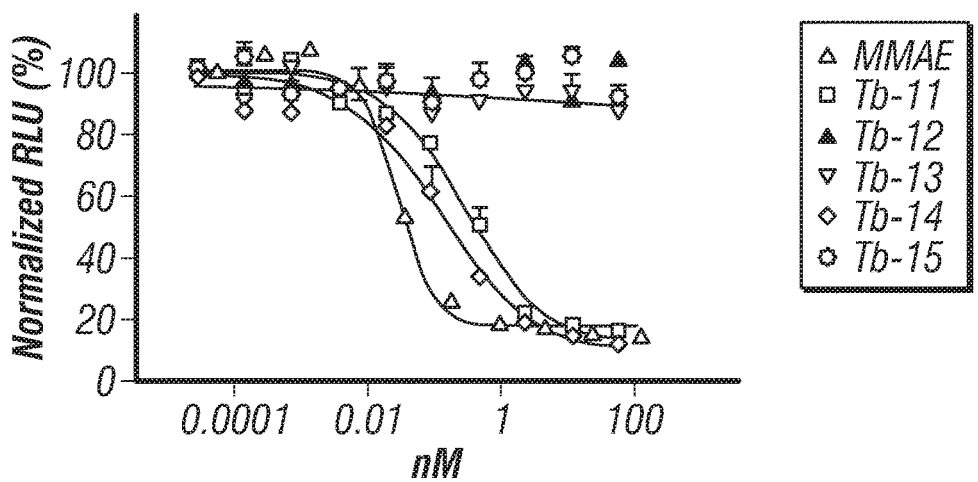
Figure 7A:
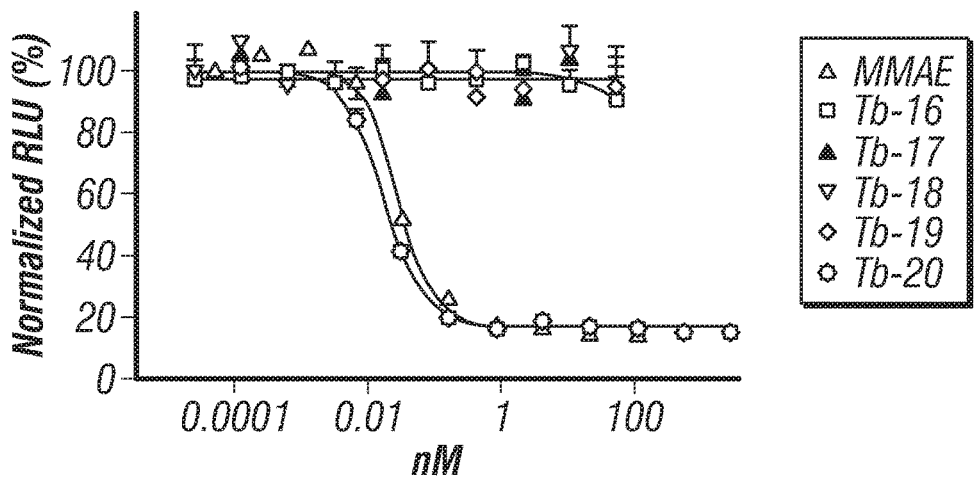
Figure 7A:
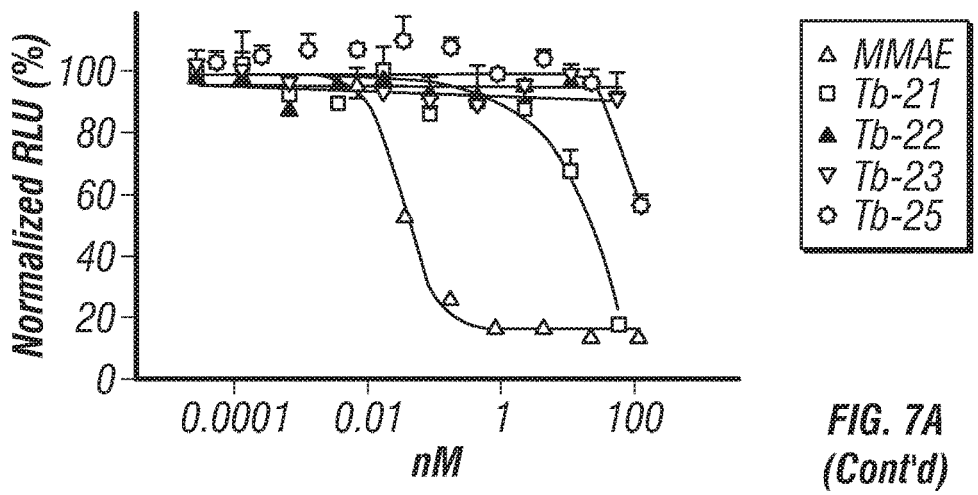
Figure 7B:
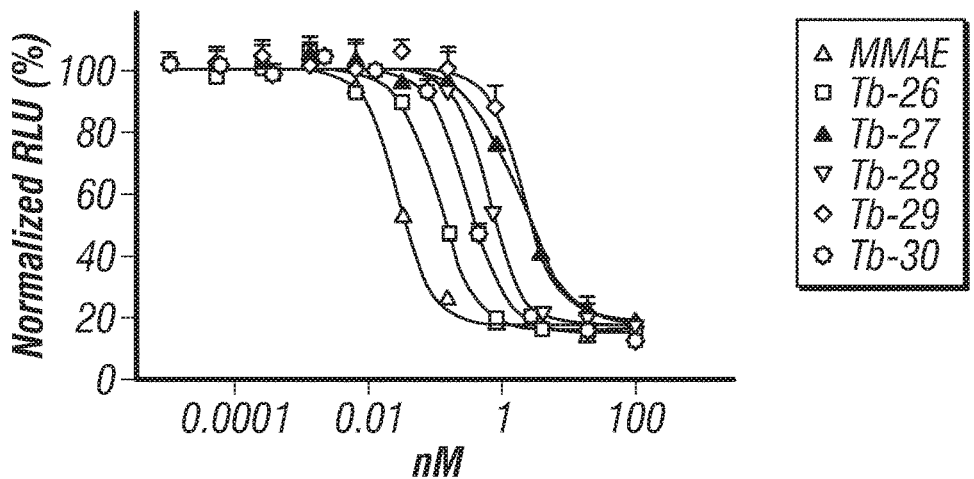
Figure 7B:
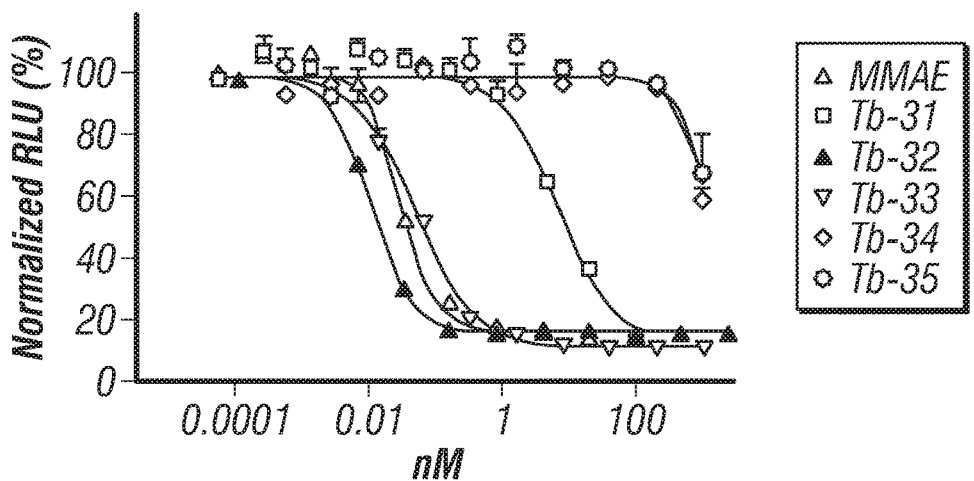
Figure 7B:
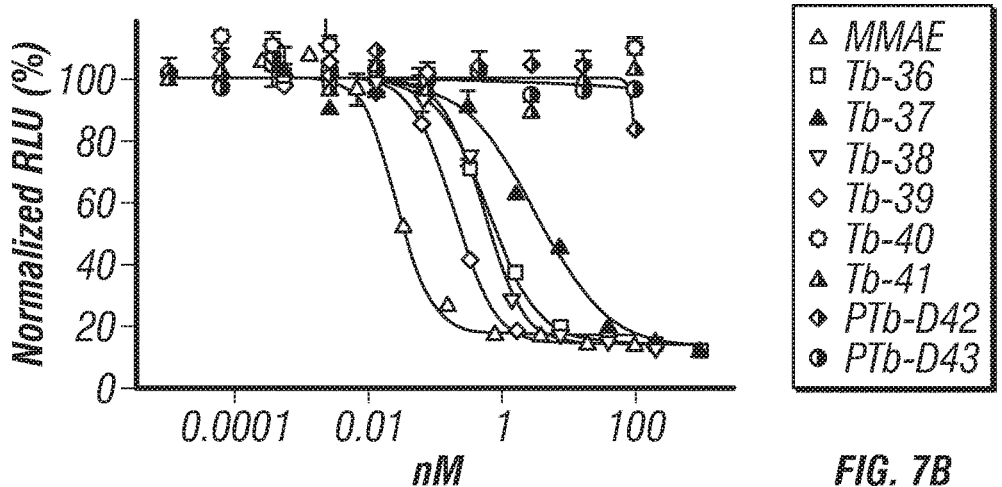
Figure 8A:
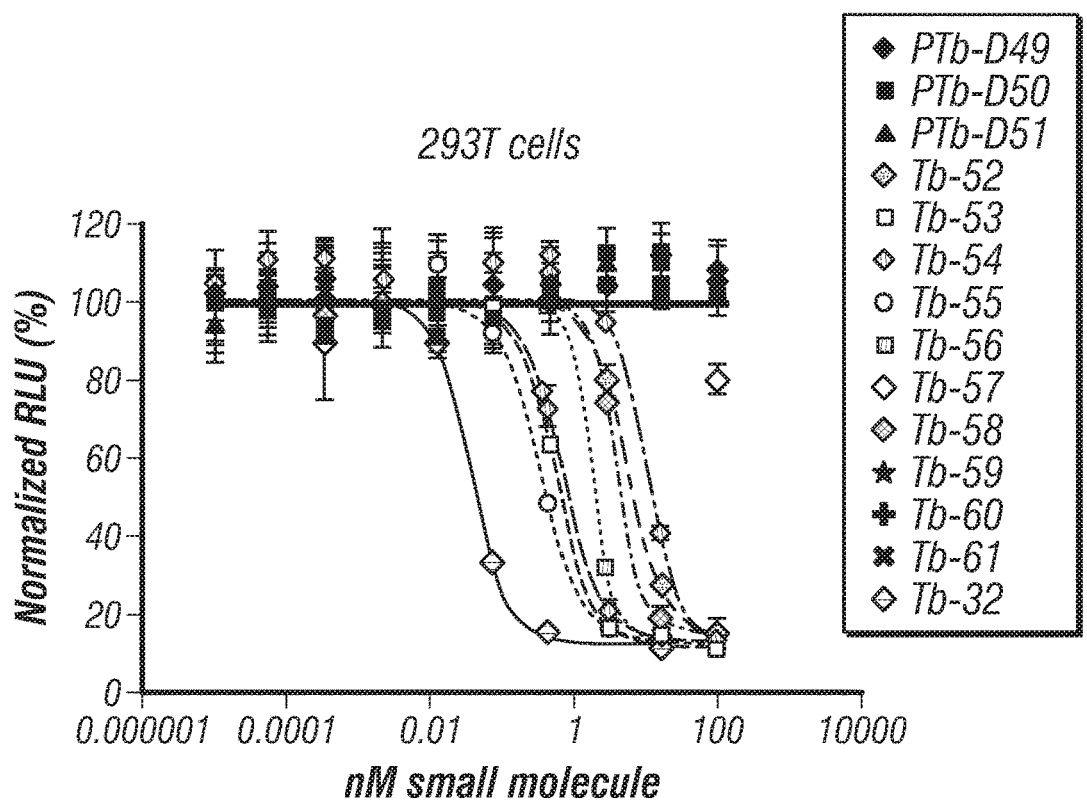
FIGS. 8A-8C—Cytotoxicity assay for tubulysin analos Tb-D49-D51 and Tb52-Tb63 in HEK 293T (FIG. 8A), MES SA (FIG. 8B), and MES SA Dx (FIG. 8C).
Figure 8B:
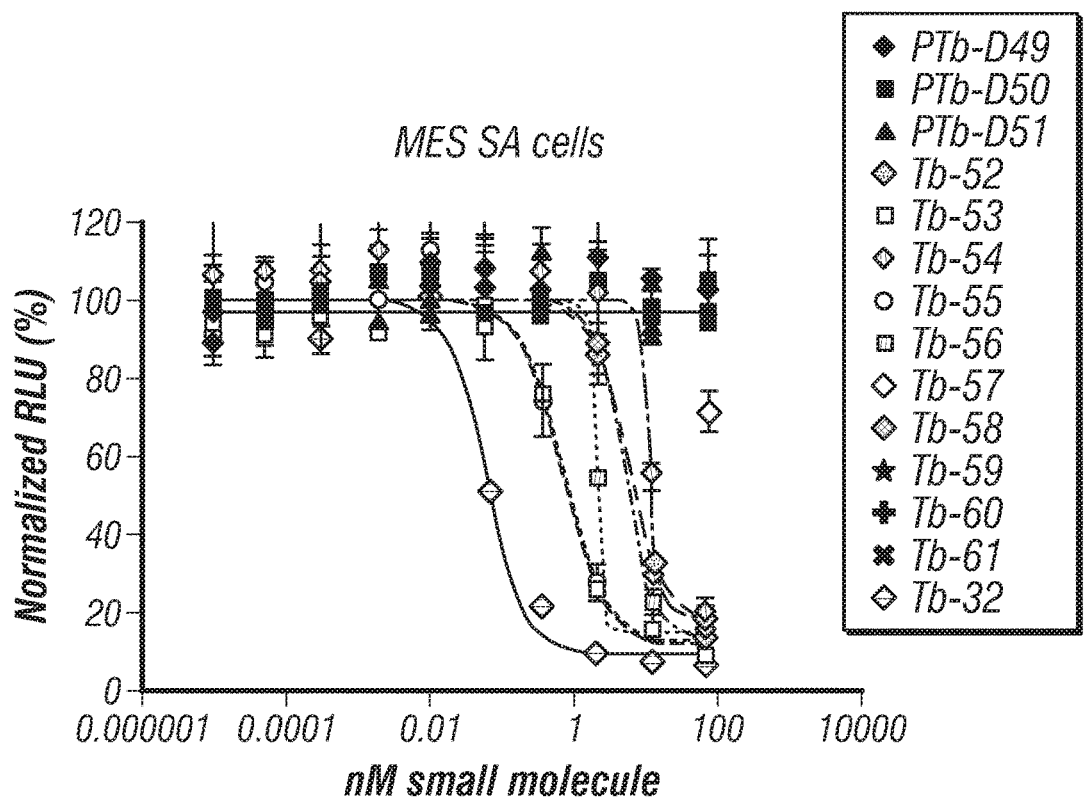
Figure 8C:
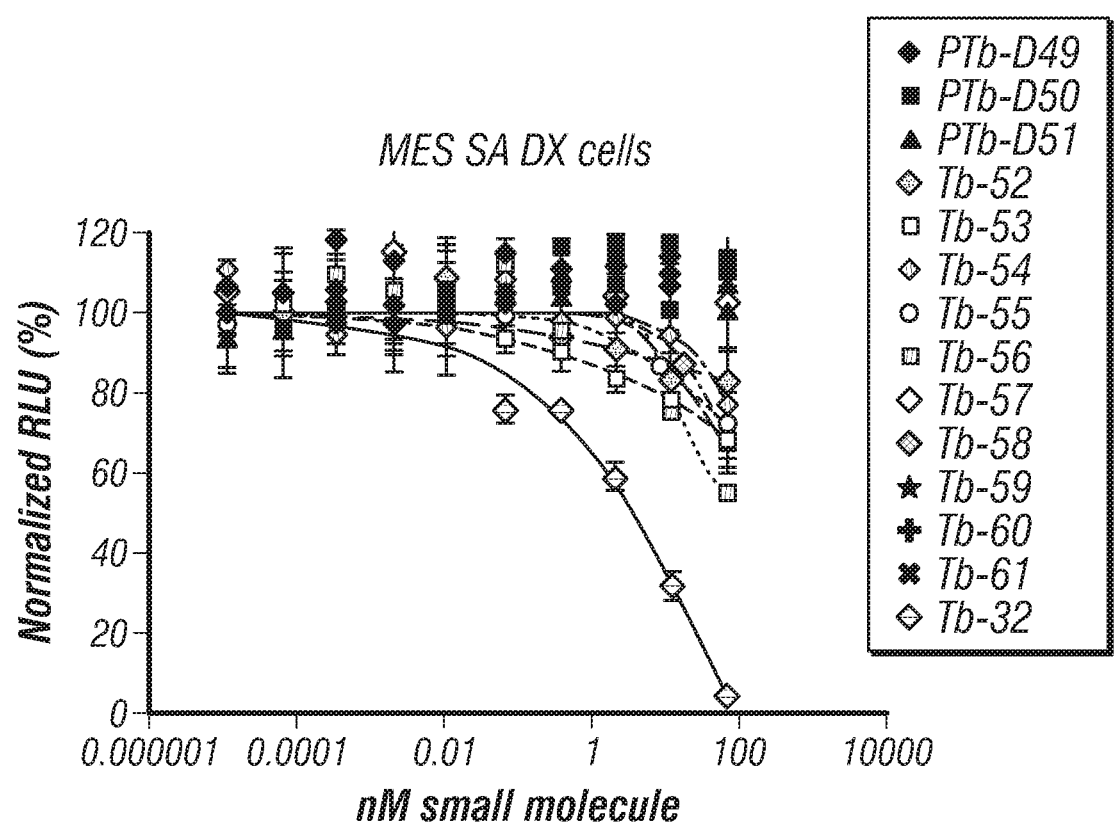

The peptide nature of the tubulysin structure clearly points to a synthetic strategy based on the three amide bond coupling shown in FIG. 3 as exemplified for the $N^{14}$-desacetoxytubulysin H (Tb1) case. Thus, three amide bond disconnections lead to fragments Mep (N-methyl-D-pipecolic acid), Ile (L-isoluecine), Tuv (tubuvaline), and Tup (tubuphenylalanine) as indicated in FIG. 3a. The most interesting disconnection of the tubulysin molecule, however, is that based on the C—H activation coupling (C10-C11 bond) of an aldehyde (A) with a thiazole system (B) to afford a thiazolyl ketone (C) whose asymmetric reduction would lead to a thiazolyl alcohol (D) corresponding to the desired structural motif of the target molecule (FIG. 3B).

Scheme 1 summarizes the streamlined total synthesis of $N^{14}$-desacetoxytubulysin H (Tb1) starting from the known and readily available aldehyde 1 (prepared from (S)-Boc-valine in multigram quantities) (Sohtome, et al., 2010; In, et al., 2007). Thus, a brief optimization study of the C—H activation-based coupling of aldehyde 1 with a suitable thiazolyl moiety (2, 2a-f, Scheme 1b) led to the finding that thiazolyl acetate 2 performed the best as a substrate suitable for this reaction, furnishing, under the previously reported condition |PhI(OCOCF$_3$)$_2$, TMSN$_3$| (Matcha, et al., 2014; Khemnar, et al., 2014; Chatgilialoglu, et al., 1999; Yeung, et al., 2011) coupling product ketone 3 in 81% yield. Reduction of thiazolyl ketone 3 with (S)—CBS in the presence of BH$_3$.SMe$_2$ (Corey, et al., 1987; Deloux and Srebnik, 1993; Corey and Helal, 1998) then produced alcohol 4 in 82% yield as a single diastereoisomer after chromatographic purification. Elaboration of hydroxy compound 4 to acetoxy carboxylic acid 5 was achieved through a sequence involving deacetylation (K$_2$CO$_3$, MeOH), selective oxidation of the primary alcohol (TEMPO, BAIB; then NaClO$_2$) and acetylation (Ac$_2$O, py) of the resulting secondary alcohol, in 66% overall yield. Coupling of carboxylic acid 5 and aminoester 6 (Shankar, et al., 2011) in the presence of i-BuOCOCl and Et$_3$N led to amide 7 (91% yield). The Boc group was cleaved from the latter compound (TFA) and the resulting amine was coupled with acid fluoride 8 (Wipf and Wang, 2007) to afford peptide 9 (i-Pr$_2$NEt, 92%) as shown in Scheme 1a. Removal of the Fmoc protecting group from 9 [N(CH$_2$CH$_2$NH$_2$)$_3$], followed by coupling of the so generated amine with N-methyl-(D)-pipecolic acid (10) provided tubulysin H methyl ester (Tb2, 62% overall yield), whose conversion to $N^{14}$-desacetoxytubulysin H (Tb1) required sequential treatment with Me$_3$SnOH (Nicolaou, et al., 2005) (cleavage of both methyl ester and acetate) and reacetylation (Ac$_2$O, py)/aqueous work-up (56% overall yield) as shown in Scheme 1a.

-continued
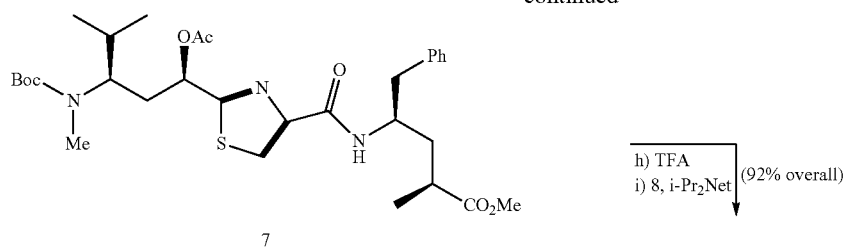
7
h) TFA
i) 8, i-Pr$_2$NEt (92% overall)
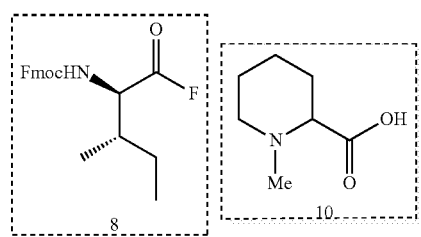
8      10
j) N(CH$_2$CH$_2$NH$_2$)$_3$
k) 10, HATU, Et$_3$N
(62% overall)
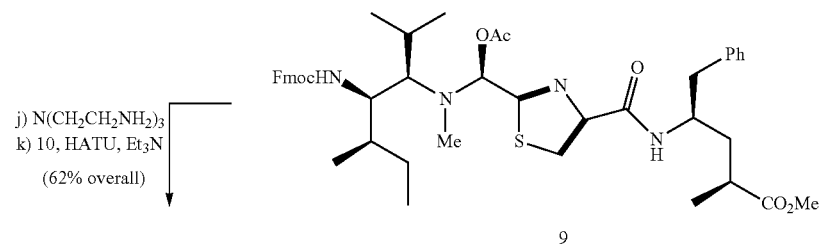
9
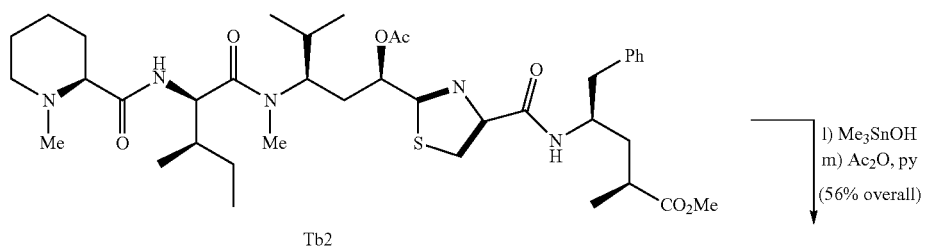
Tb2
l) Me$_3$SnOH
m) Ac$_2$O, py
(56% overall)
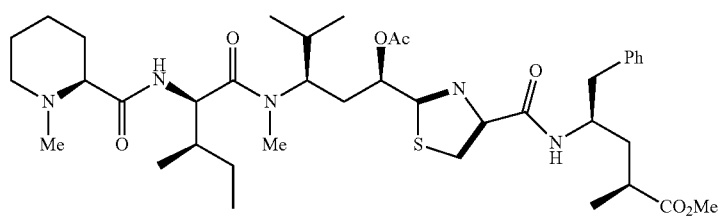
Tb1: N$^{14}$-desacetoxytubulysin H b. C-H activation step

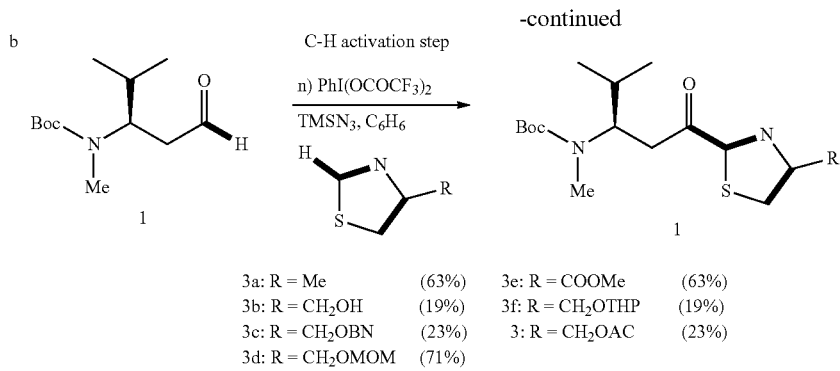

| 3a: R = Me | (63%) | 3e: R = COOMe | (63%) |
| 3b: R = CH₂OH | (19%) | 3f: R = CH₂OTHP | (19%) |
| 3c: R = CH₂OBN | (23%) | 3: R = CH₂OAC | (23%) |
| 3d: R = CH₂OMOM | (71%) | | |

Reagents and conditions: a. (a) 1 (2.0 equiv), 2 (1.0 equiv), TMSN₃ (2.0 equiv), PIFA (2.0 equiv), benzene, 23° C., 16 h; then 1 (2.0 equiv), TMSN₃ (2.0 equiv), TMSN₃ (2.0 equiv), PIFA (2.0 equiv), 23° C., 12 h, 81% b) (S)-CBS (0.2 equiv), BH₃•SMe₂ (1.0 equiv), 0→23° C., 18 h, 82%; c) K₂CO₃ (4.0 equiv), MeOH, 23° C., 3 h, 93%; (d) TEMPO (0.1 equiv), BAIB (1.0 equiv), CH₂Cl₁, 23° C., 16 h, 96%; (e) NaClO₂ (5.0 equiv), NaH₂PO₄•H₂O (12 equiv), 2-methyl-2-butene (7.5 equiv), t-BuOH, THF, H₂O, 23° C., 12 h; (f) Ac₂O (3.2 equiv), py (3.5 equiv), CH₂Cl₂, 0→23° C., 15 h, 74% for the two steps; (g) i-BuOCOCl (2.0 equiv), Et₃N (4.0 equiv), THF, -20° C., 30 min; then 6 (2.1 equiv), -20→20° C., 24 h, 91% or 6 (1.5 equiv), HATU (3.0 equiv), Et₃N (6.0 equiv), DMF, 0→23° C., 18 h, 74%; (h) TFA (45 equiv), CH₂Cl₂, 0→23° C., 3 h: (i) 8 (4.0 equiv), i-Pr₂NEt (6.0 equiv), DMF, 0→23° C., 18 h, 92% for the two steps; (j) N(CH₂CH₂NH₂)₃ (16 equiv), CH₂Cl₂, 0→23° C., 3 h; (k) 10 (3.0 equiv), HATU (3.0 equiv), Et₃N (6.0 equiv), DMF, 0→23° C., 24 h, 62% for the two steps; (l) Me₃SnOH (20 equiv), 1,2-dichloroethane, reflux, 12 H; (m) Ac₂O (Ac₂O) (4.0 equiv), py, 0→23° C., 12 H, 56% for the two steps; b. Screening of thiazole subsrates for C-H/C-H coupling; (n) 1 (2.0 equiv), 2 (1.0 equiv), TMSN₃ (2.0 equiv), PIFA (2.0 equiv), benzene, 23° C., 16 h; then 1 (2.0 equiv), TMSN₃ (2.0 equiv), 23° C., 12 h, 12-81% yield. THF = tetrahydrofuran; TFA = trifluoroacetic acid; TMS = trimethylsilyl; PIFA = phenyliodine(III) bis(trifluoroacetate); TEMPO = 2,2,6,6-tetramethyl-1-piperidinyloxy; BAIB = bis(acetoxy)iodo benzene; DMF = dimethylformamide; HATU = 1-[bis(dimethyl amino)methylene]-1H-1,2,3-triazolo[4,5-b]pyridinium 3-oxid hexafluorophosphate; (S)-CBS = (S)-(-)-methyl-CBS-oxazaborolidine; Boc = tert-butylloxycarbonyl; Fmoc = fluorenylmethyloxycarbonyl; py = pyridine; Ac = acetyl; TBS = tert-butyldimethylsilyl; THP = tetrahydropyran-2-yl; Bn = benzyl; MOM = methoxymethyl.

Scheme 2 summarizes the total synthesis of pretubulysin D (PTb-D43) starting from the known aldehyde 1 (Sohtome, et al., 2010; In, et al., 2007). Reduction of aldehyde 1 with NaBH₄ followed by bromination of the resulting alcohol using CBr₄ and PPh₃ furnished bromide 11 in 86% overall yield. Coupling of thiazole TBS-ether 12 with bromide 11 in the presence of n-BuLi gave product 13 in 76% yield. Elaboration of compound 13 to carboxylic acid 14 was achieved through desilylation (TBAF) and oxidation of the resulting alcohol (DMP; then NaClO₂) in 92% overall yield. Coupling of carboxylic acid 14 with aminoester 6 (Shankar, et al., 2011) in the presence of HATU and Et₃N led to amide 15 (81% yield). Boc group removal from the later compound (TFA) followed by coupling of the resulting amine with acid fluoride 8 (Wipf and Wang, 2007), furnished peptide 16 (i-Pr₂NEt, 94%) as shown in Scheme 2. Removal of the Fmoc protecting group from 16 [N(CH₂CH₂NH₂)₃] and coupling of the resulting amine with N-methyl-(D)-pipecolic acid (10) provided pretubulysin D analogue (PTb-D42, 72% overall yield), whose conversion to pretubulysin D (PTb-D43) was accomplished with Me₃SnOH (Nicolaou, et al., 2005) (82% yield) or LiOH (90% yield) as shown in Scheme 2.

Scheme 2. Total synthesis of pretubulysin D (PTb-D43) and its methyl ester (PTb-D42).

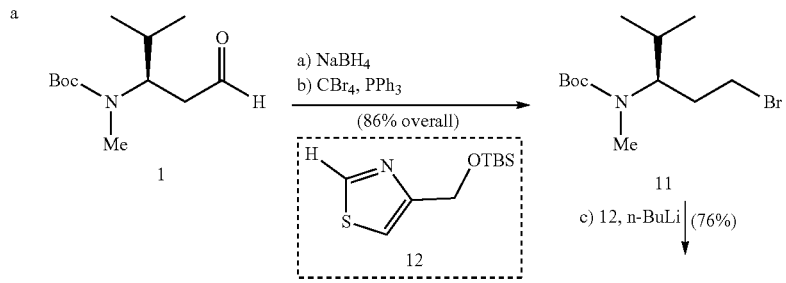

-continued
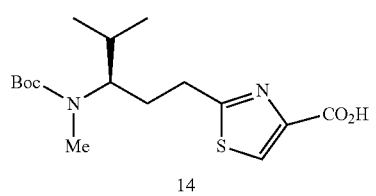
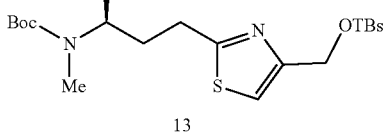
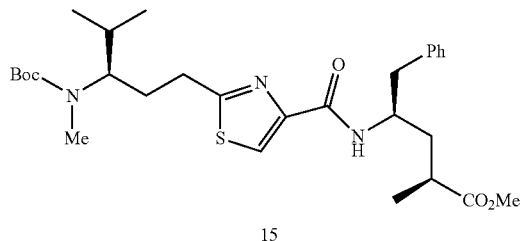
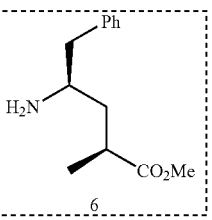
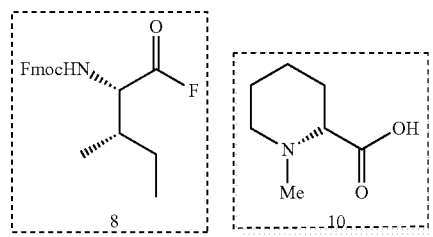
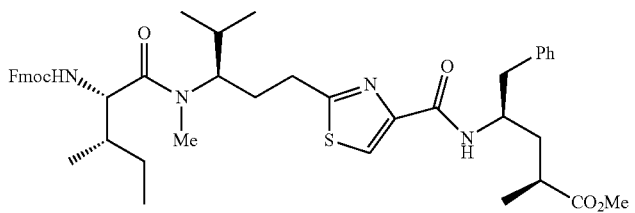
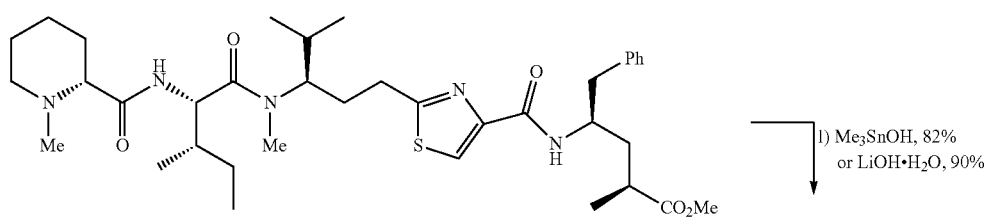

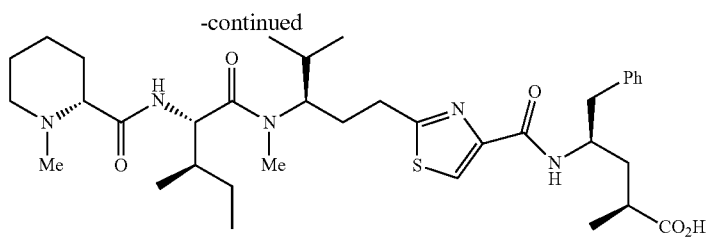

PTb-D43: pretubulysin D

Reagents and conditions: a. (a) NaBH₄ (1.5 equiv). MeOH, 0→23° C., 1 h, 92%; (b) CBr₄ (2.0 equiv), PPh₃ (2.0 equiv), 0→10° C., 1 h, 80%; (c) 12 (1.1 equiv), n-BuLi (1.2 equiv; 2.6M in hexane), THF, −78→0° C., 3 h, 76%; (d) TBAF (2.0 equiv; 1M in THF), THF, 0° C., 1 h, 94%; (e) DMP (1.5 equiv), CH₂Cl₂, 23° C., 1 h, 90%; (f) NaClO₂ (5.4 equiv), NaH₂PO₄•H₂O (12 equiv), 2-methyl-2-butene (7.5 equiv), t-BuOH, THF, H₂O, 23° C., 1 h; 92%; (g) 6 (1.5 equiv), HATU (3.0 equiv), Et₃N (6.0 equiv), DMF, 0→23° C., 18 h, 81%; (h) TFA (45 equiv), CH₂Cl₂, 23° C., 2 h; (i) 8 (4.1 equiv), i-Pr₂NEt (6.2 equiv), DMF, 0→23° C., 18 h. 94% for the two steps; (j) N(CH₂CH₂NH₂)₃ (16 equiv), CH₂Cl₂, 0→23° C., 2 h; (k) 10 (3.0 equiv), HATU (3.0 equiv), Et₃N (6.0 equiv), DMF, 0→23° C., 24 h, 72% for the two steps; (l) Me₃SnOH (20 equiv), 1,2-dichloroethane, reflux, 12 h, 82% or LiOH•H₂O (5.0 equiv), THF, H₂O, 23° C., 24 h, 90%. TBAF = tetra-n-butylammonium fluoride; DMP = Dess-Martin periodinane.

With a practical and efficient synthesis of tripeptide Fmoc derivative 9 (see Scheme 1) available, attention was turned to its application to the construction of designed tubulysin analogues Tb3-Tb10, Tb34, Tb35 (for structures, see FIG. 2A) with varying aminoacid residues at the "left side" (Mep) of the molecule. The required building blocks (17-26, Scheme 3) for these analogues were prepared as described. Removal of the Fmoc protecting group from 9 [N(CH₂CH₂NH₂)₃], followed by coupling of the resulting amine with carboxylic acids 20-25, ester 17 and isocyanates 18, 19 and 26 furnished the corresponding tetrapeptides, whose appropriate functional group manipulations led to the targeted tubulysin analogues (Tb3-Tb10, Tb34 and Tb35) in yields ranging from 46-90% as summarized in Scheme 3.

Scheme 3. Synthesis of N¹⁴-Desacetoxytubulysin H Analogues Tb3-Tb10, Tb34 and Tb35

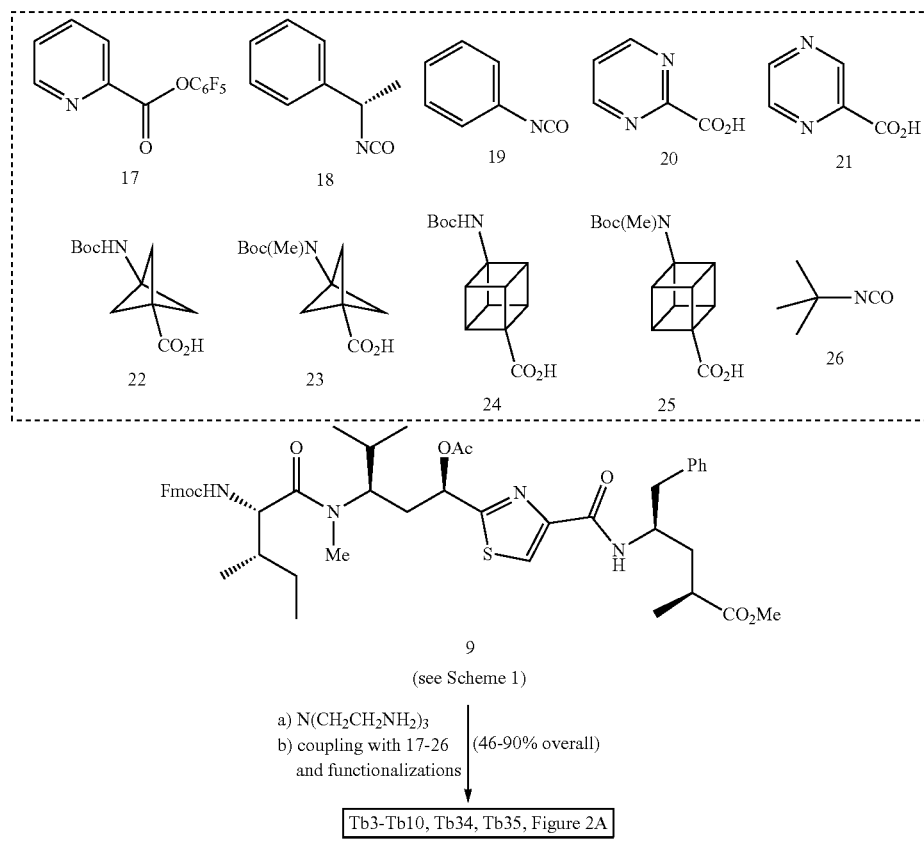

Reagents and conditions: (a) N(CH₂CH₂NH₂)₃ (16 equiv), CH₂Cl₂, 0→23° C., 3 h; (b) 17 (6.0 equiv), DMF, 0→23° C., 24 h, 58% for the two steps for Tb3; or 18 or 19 or 26 (6.0 equiv), i-Pr₂NEt (6.0 equiv), CH₂Cl₂, 0→23° C., 24 h, 80% for the two steps for Tb4, 74% for the two steps for Tb5, 83% for the two steps for Tb6; or 22 or 24 or 23 and 25 (1.5 equiv), HATU (1.3 equiv), HOAt (1.3 equiv), i-Pr₂NEt (3.0 equiv), DMF 0→23° C., 24 h, 48% for the two steps for Boc-protected Tb7, 52% for the two steps for Boc-protected Tb9, 46% for the two steps for Boc-protected Tb8 and 52% for the two steps for Boc-protected Tb10; then TFA (30 equiv), CH₂Cl₂, 0→23° C., 12 h, 90% for Tb8, 66% for Tb10; then Ac₂O (10 equiv), py, 0→23° C., 12 h, 56% for the two steps for Tb7, 55% for the two steps for Tb9; or 20 or 21 (3.0 equiv), HATU (3.0 equiv), Et₃N (6.0 equiv), DMF, 0→23° C., 24 h, 79% for the two steps for Tb34, 77% for the two steps for Tb35.

Tubulysin analogues Tb11-Tb16 (for structures, see FIG. 2A) in which the "right end" aminoacid (Tup) was replaced with varying aminoacid residues were synthesized through three sequential peptide coupling reactions from unnatural aminoacid derivative 5 (see Scheme 1) and building blocks 17, 27 and 28 (Scheme 4, synthesized as described in Example 3) as summarized in Scheme 4. Thus, coupling of 5 with either cubane (29) (Nicolaou, et al., 2015; Wlochal, et al., 2014; Falkiner, et al., 2013; Ingalsbe, et al., 2010; Stepan, et al., 2012; Patzel, et al., 2004) or bicyclopentane-methylester amine (30), (Nicolaou, et al., 2015; Wlochal, et al., 2014; Falkiner, et al., 2013; Ingalsbe, et al., 2010; Stepan, et al., 2012; Patzel, et al., 2004) respectively (see Example 3 for further details), in the presence of HATU and HOAt furnished dipeptides 31 (55% yield) and 32 (54% yield). Exposure of the so formed dipeptides to TFA resulted in removal of the Boc group to afford the corresponding amines, whose coupling with acid fluoride 8 in the presence of i-Pr$_2$NEt in DMF led to the formation of tripeptides 33 (76% overall yield) and 34 (71% overall yield). Finally, removal of the Fmoc group from 33 and 34 [N(CH$_2$CH$_2$NH$_2$)$_3$] followed by coupling of the resulting amines with pentafluorophenyl esters 17, 27 and 28 gave tubulysin analogues Tb11-Tb16 (58-73% overall yields) as shown in Scheme 4.

Scheme 5 summaries the synthesis of analogues Tb17-Tb19 possessing the cubane and [1.1.1] bicyclopentane rigid functionalities instead of the thiazole moiety. Thus, aminoesters 29 (Nicolaou, et al., 2015; Wlochal, et al., 2014; Falkiner, et al., 2013; Ingalsbe, et al., 2010; Stepan, et al., 2012; Patzel, et al., 2004) and 30 (Nicolaou, et al., 2015; Wlochal, et al., 2014; Falkiner, et al., 2013; Ingalsbe, et al., 2010; Stepan, et al., 2012; Patzel, et al., 2004) were coupled with the four remaining amino acid residues 35, 6, 8 and N-methyl-(D)-pipecolinic acid (10) and N,N-dimethylglycine 36 to furnish the desired $N^{14}$-desacetoxytubulysin derivatives Tb17, Tb18 and Tb19 in 75%, 58% and 72% overall yields, respectively, as depicted in Scheme 5.

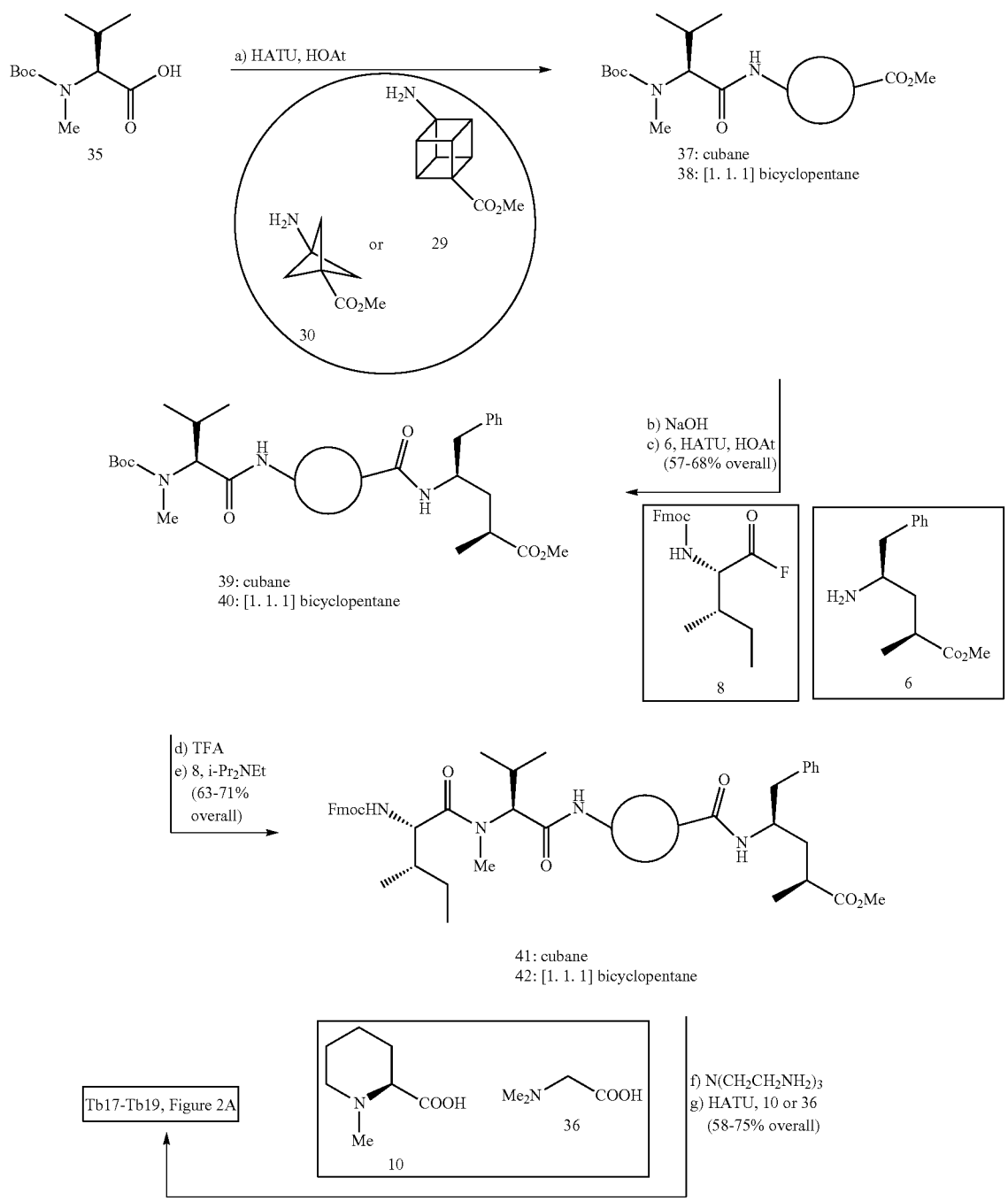

Reagents and conditions: (a) 29 or 30 (1.2 equiv), HATU (1.5 equiv), HOAt (0.1 equiv), Et₃N (8.0 equiv), DMF, 0→23° C., 4 h; (b) 1M NaOH (aq) (2.3 equiv), THF, 23° C., 11 h; (c) 6 (1.0 equiv), HATU (1.2 equiv), HOAt (0.1 equiv), Et₃N (6.5 equiv), DMF, 0→23° C., 15 h, 57% for the three steps for 39, 68% for the three steps for 40; (d) TFA (45 equiv), CH₂Cl, 23° C., 12 h; (e) 8 (3.0 equiv), i-Pr₂NEt (6.0 equiv), DMF, 0→23° C., 24 h, 63% for the two steps for 41, 71% for the two steps for 42; (f) N(CH₂CH₂NH₂)₃ (16 equiv), CH₂Cl, 0→23° C., 3 h; (g) N-methyl-D-pipecolinic acid (10, 6.0 equiv) or N,N-dimethylglycine (36, 6.0 equiv), HATU (6.0 equiv), Et₃N (6.5 equiv), DMF 0→23° C., 12 h, 75% for the two steps for Tb17, 58% for the two steps for Tb18 and 72% for the two steps for Tb19.

Scheme 6 summarizes the synthesis of tubulysin analogues Tb20-Tb23, Tb26-Tb30, Tb32 and Tb33, which incorporate varying combinations of structural motifs in the place of N-Me-pipecolinic acid and the isoleucine residues. Their synthesis began with removal of the Boc group of dipeptide 7 (see Scheme 1), which was coupled with Fmoc-protected acid fluorides 43-48 [prepared from their amino-acid counterparts (43a-48a) (Wipf and Wang, 2007) by sequential exposure to FmocCl and DAST (76-95% yield for the two steps), see Scheme 6 (top)] to give tripeptides 49-54 (72-92% yield for the two steps) as shown in Scheme 6 (see Example 3 for further detail). Cleavage of the Fmoc group [N(CH₂CH₂NH₂)₃] from these intermediates followed by coupling with building blocks 10, 22, 25, 36 and 55 and further standard elaborations of the resulting products led to tubulysin analogues Tb20-Tb23, Tb26-Tb30, Tb32 and Tb33 (39-91% overall yields).

Scheme 6. Synthesis of Tubulysin Analogues Tb20-Tb23, Tb26-Tb30, Tb32 and Tb33

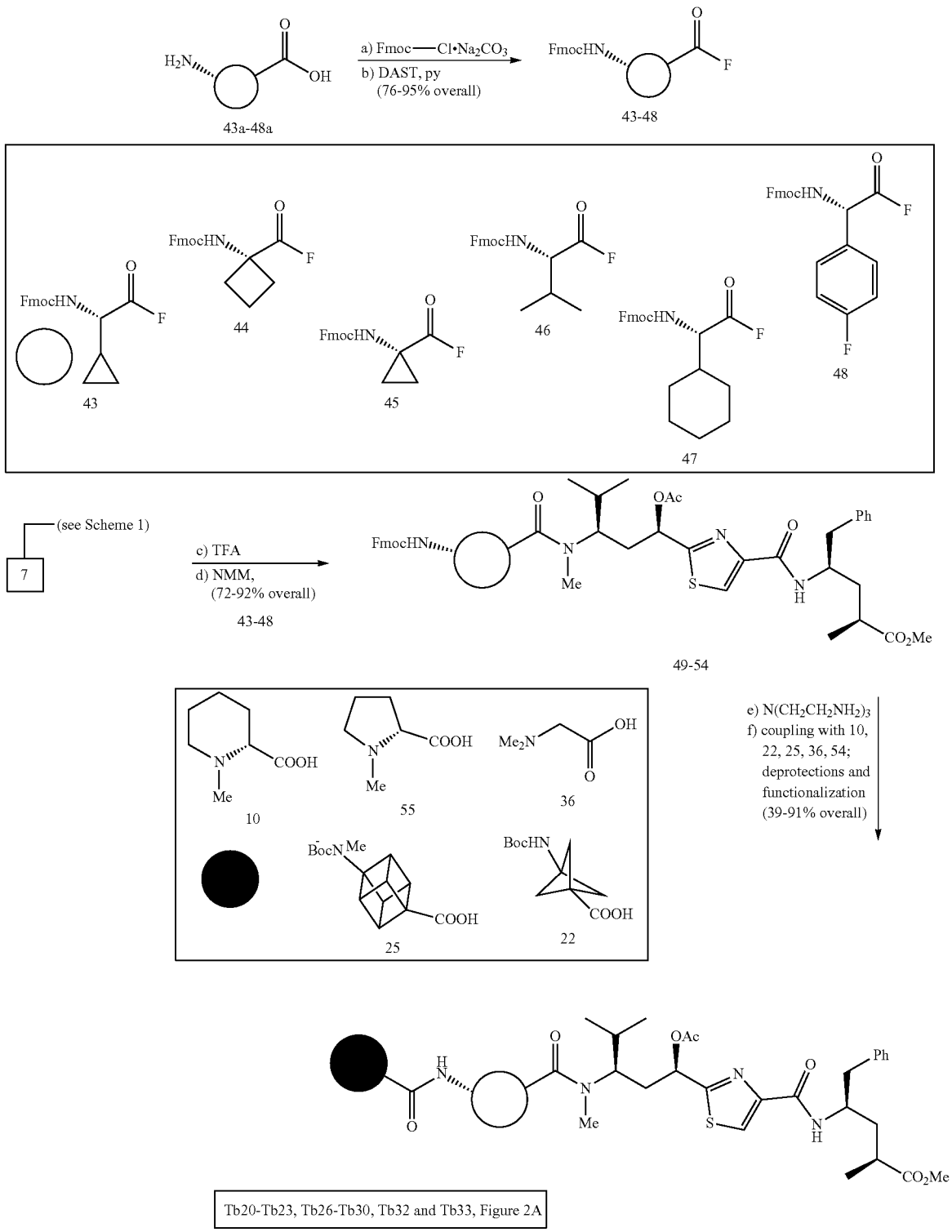

Figure 2A:
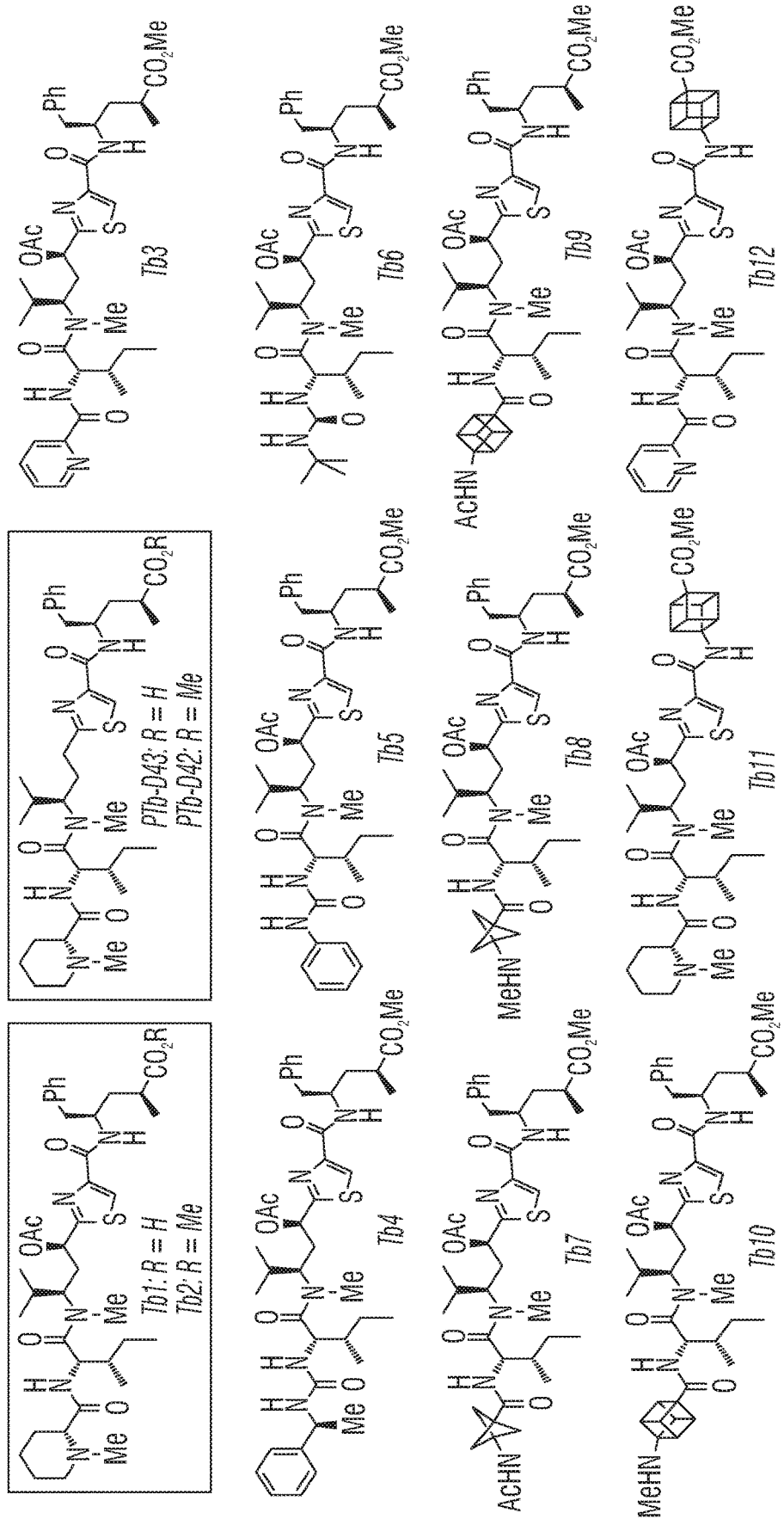
FIG. 2—A: Molecular structures of N$^{14}$-desacetoxytubulysin H (Tb1), pretubulysin D (PTb-D43), and designed analogues (Tb2-Tb41 and PTb-D42). B: Molecular structures of Tubulysin Analogs (Tb44-Tb48, PTb-D49-PTb-D51 and Tb52-Tb61).
Figure 2A:
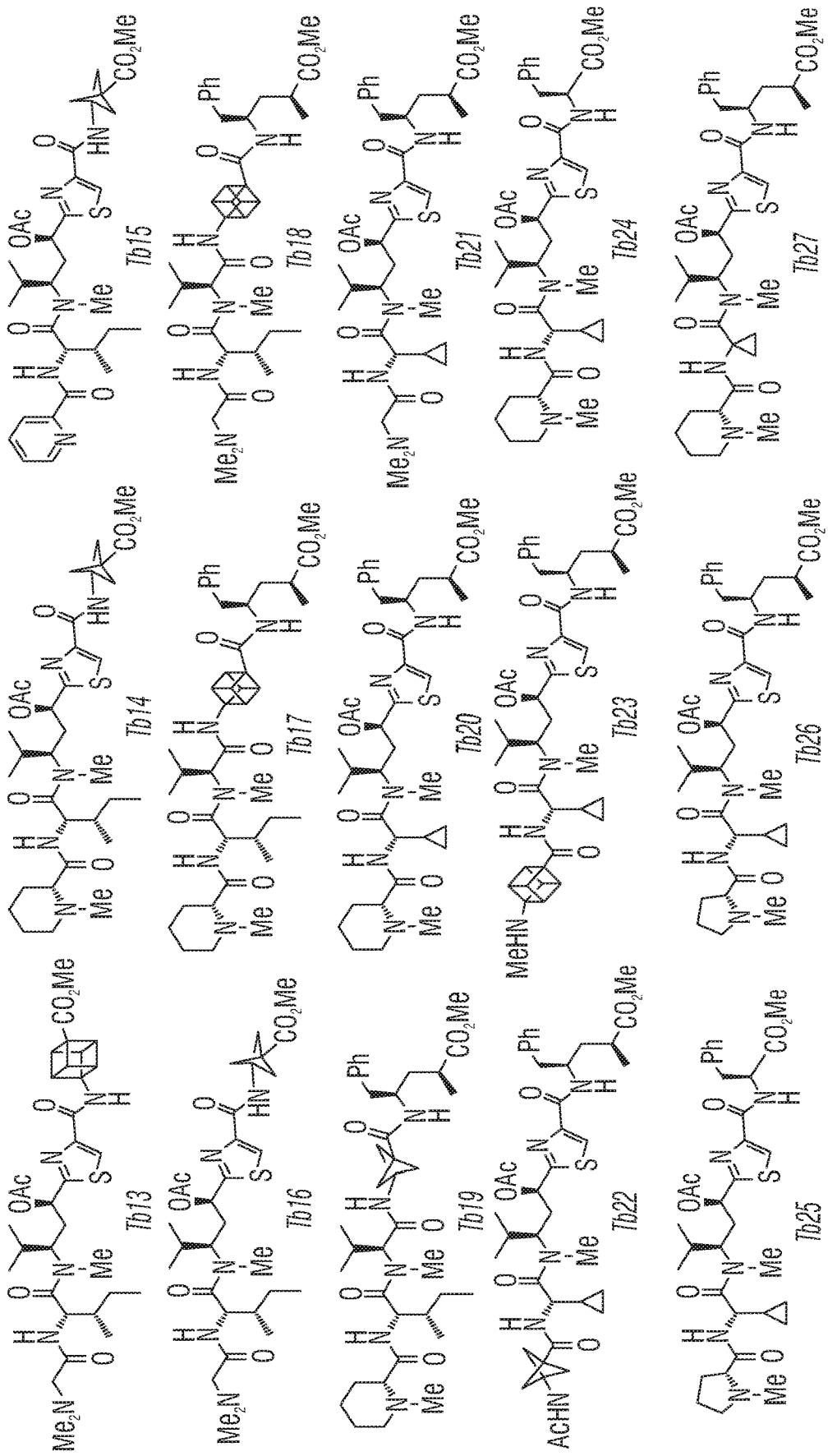
Figure 2A:
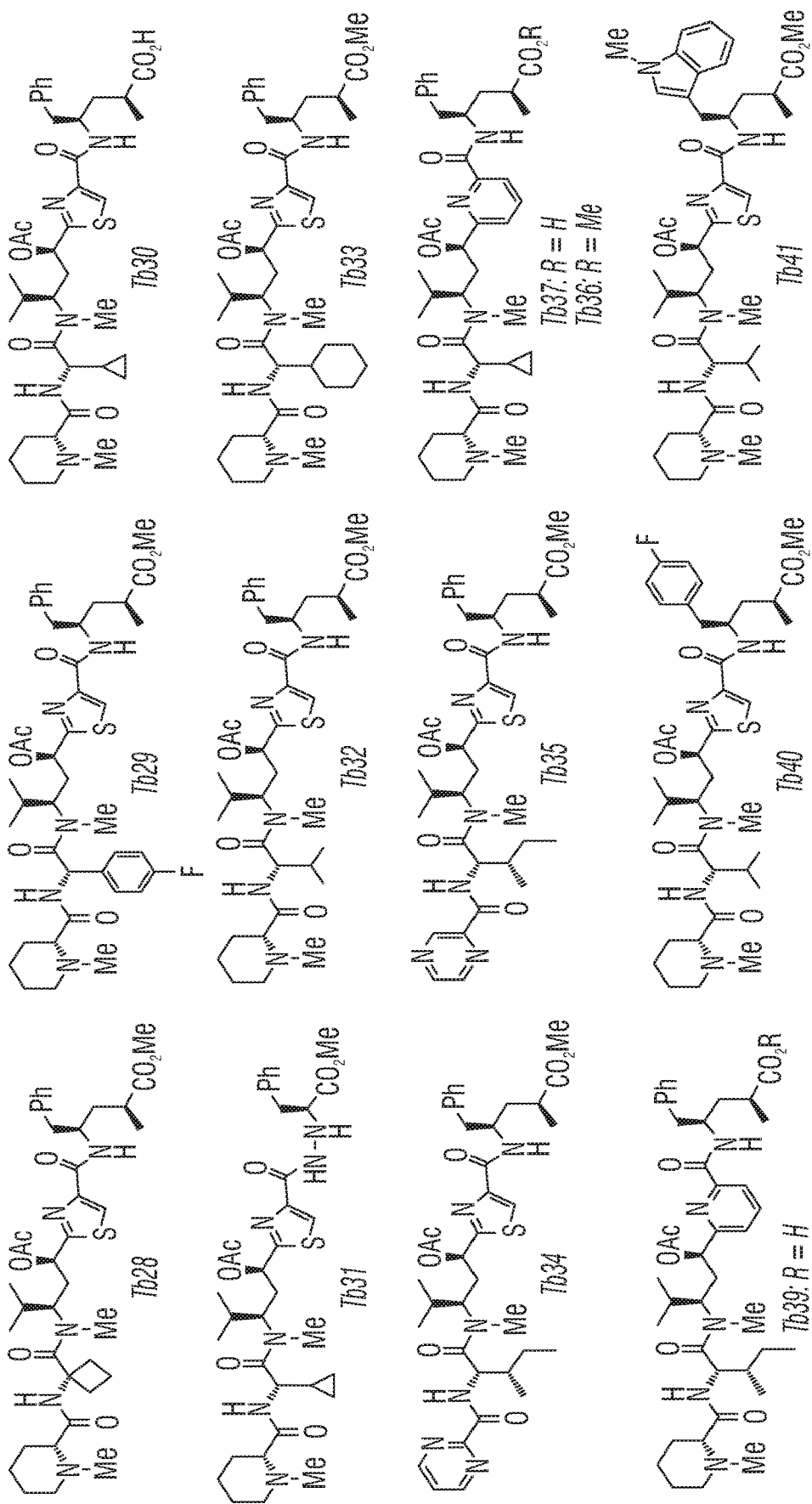

Tb20-Tb23, Tb26-Tb30, Tb32 and Tb33, Figure 2A

Reagents and conditions: (a) Fmoc-Cl (1.1 equiv), Na$_2$CO$_3$ (2.5 equiv), H$_2$O, 1,4-dioxane, 23° C., 6 h; (b) DAST (1.2 equiv), py (1.0 equiv), CH$_2$Cl$_2$, 23° C., 1 h, 76-95% for 43-48 for the two steps; (c) TFA (45 equiv), CH$_2$Cl$_2$, 23° C., 12 h; (d) 43-48 (4.0 equiv), NMM (8.0 equiv), DMF, 23° C., 18 h, 72-92% for the two steps; (e) N(CH$_2$CH$_2$NH$_2$)$_3$ (16 equiv), CH$_2$Cl$_2$ 0→23° C., 3 h; (f) N-methyl-(D)-pipecolinic acid (10) (2.0 equiv) or N,N-dimethylglycine (36, 1.5 equiv) or 22 (1.5 equiv) or 25 (1.5 equiv) or 55 (1.5 equiv), HATU (1.3 equiv), HOAt (1.3 equiv), NMM (3.0 equiv), DMF, 23° C., 24 h, 49% for the two steps for Tb20; then Me$_3$SnOH (20 equiv), 1,2-dichloroethane, reflux, 12 h; then Ac$_2$O (4.0 equiv), py, 0→23° C., 12 h, 54% for the two steps for Tb30; 39% for the two steps for Tb21, 49% for the two steps for Boc-protected Tb22; then TFA (30. equiv), CH$_2$Cl$_2$, 23° C., 12 h; then Ac$_2$O (10 equiv), py, 23° C., 6 h, 91% for the two steps for Tb22; 47% for the two steps for Boc-protected Tb23; then TFA (30 equiv), CH$_2$Cl$_2$, 23° C., 12 h, 73% for Tb23; 85% for the two steps for Tb26, 76-81% for the two steps for Tb27-Tb29, 75-80% for two steps for Tb32-Tb33. DAST = diethylaminosulfur trifluoride; NMM = N-methylmorpholine.

Tubulysin analogues Tb24 and Tb25 (for structures, see FIG. 2A) in which the "right end" aminoacid residue (Tup), isoleucine (Ile), and "left end" (Mep) have been replaced with 56, 43 and 10 or 55, respectively (Scheme 7). Thus, coupling of 5 with 56 in the presence of HATU furnished dipeptide 57 (93% yield). Exposure of the so formed dipeptide to TFA resulted in removal of the Boc group to afford the corresponding amine, whose coupling with acid fluoride 43 in the presence of i-Pr$_2$NEt in DMF led to the formation of tripeptide 58 (85% overall yield). Finally, removal of the Fmoc group from 58 [N(CH$_2$CH$_2$NH$_2$)$_3$] followed by coupling of the resulting amine with N-methyl-(D)-pipecolinic acid (10) or 55 under HATU conditions furnished tubulysin analogues Tb24 (82% yield) and Tb25 (97% yield) as shown in Scheme 7.

Tubulysin analogue Tb31, in which the "right side" amide linking was replaced by a hydrazide bond was synthesized from aminoacid derivative 5 (Scheme 1) through the sequence shown in Scheme 8. Thus, 5 was converted to its methyl ester (59, TMSCHN$_2$, 73% yield) and thence to dipeptide 60 by first removing the Boc group (TFA) and then coupling of the resulting amine with acid fluoride fragment 43 (i-Pr$_2$NEt, 75% overall yield). The latter was treated with [N(CH$_2$CH$_2$NH$_2$)$_3$] to cleave the Fmoc group and the resulting amine was coupled with N-methyl-(D)-pipecolinic acid (10, HATU, Et$_3$N, 82% overall yield) to furnish tripeptide 61. Tripeptide 61 was converted to its carboxylic acid counterpart (62, Me$_3$SnOH (Nicolaou, et al., 2005); Ac$_2$O-py, 75% overall yield). This compound was then transferred to its pentafluorophenyl ester C$_6$F$_5$OH, DIC) and the latter was coupled with hydrazine derivative 63 (Viret, et al., 1987) in the presence of i-Pr$_2$NEt to afford tubulysin analogue Tb31 (73% overall yield).

Scheme 7. Synthesis of Tubulysin Analogues Tb24 and Tb25

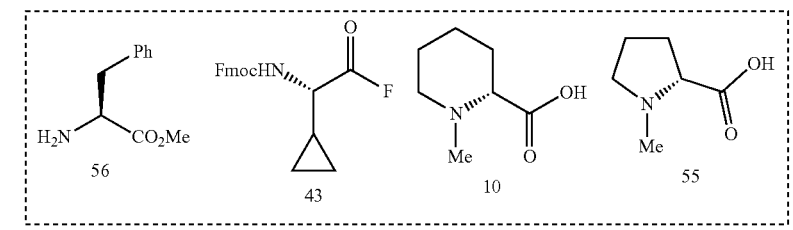

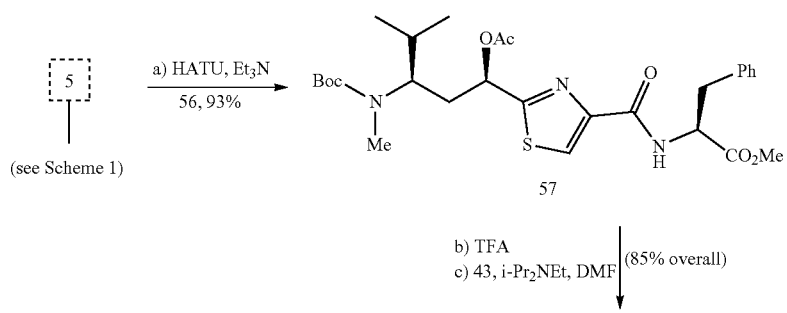

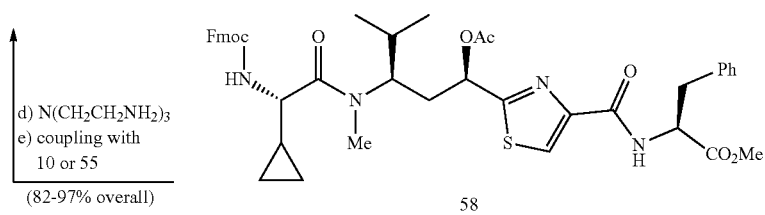

Reagents and conditions: (a) 56 (1.5 equiv), HATU (3.0 equiv), Et$_3$N (6.0 equiv), DMF, 23° C., 18 h, 93%; b) TFA (45 equiv), CH$_2$Cl$_2$, 0→23° C., 6 h; (c) 43 (4.0 equiv) i-Pr$_2$NEt 5.0 equiv), DMF, 0→23° C., 18 h, 85% for the two steps; (d) N(CH$_2$CH$_2$NH$_2$)$_3$ (16 equiv), CH$_2$Cl$_2$, 0→23° C., 3 h; (e) N-methyl-(D)-pipecolinic acid (10) (2.0 equiv) or (55) (2.0 equiv), HATU (1.5 equiv), Et$_3$N (3.0 equiv), DMF, 0→23° C., 24 h, 82% for the two steps for Tb24, 97% for the two steps for Tb25.

Scheme 8. Synthesis of Hydrazide Tubulysin Analogue Tb31

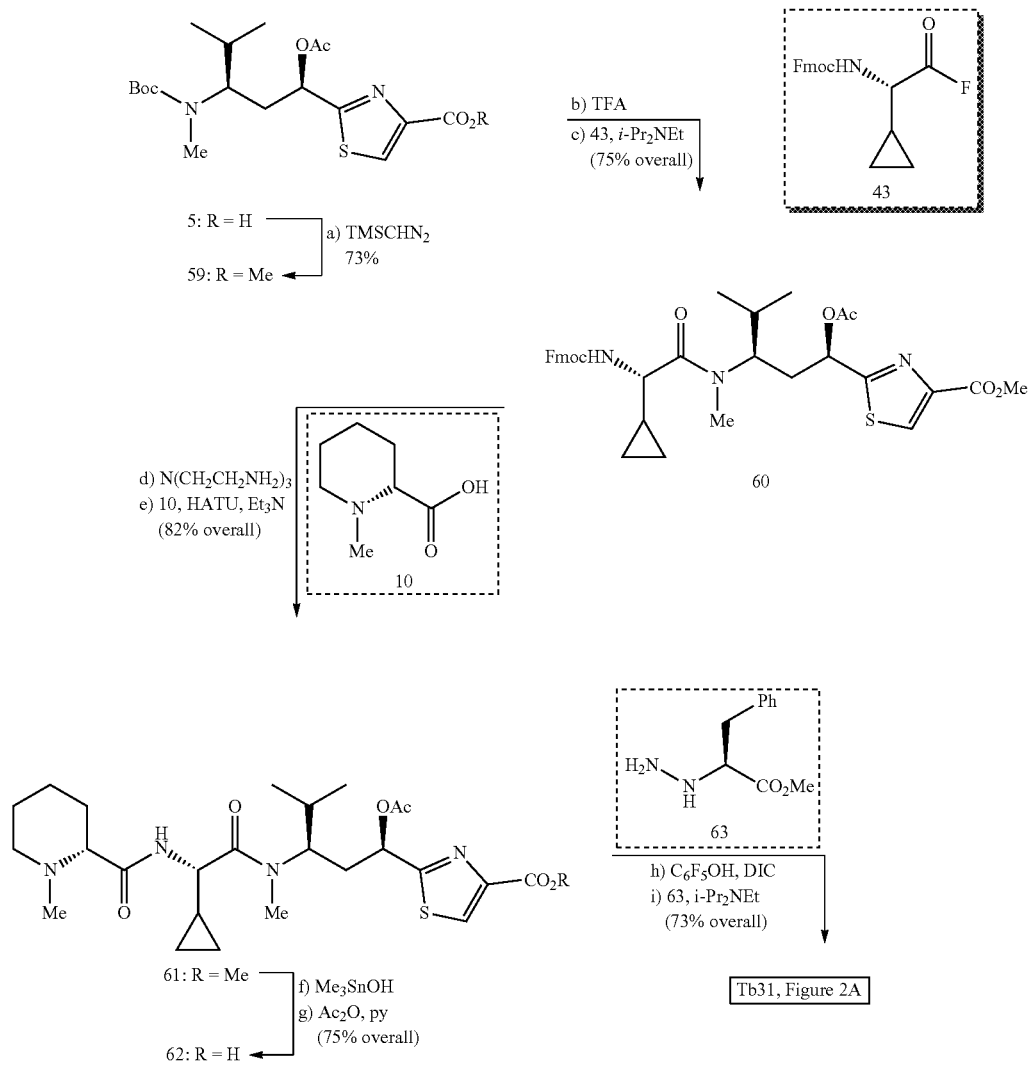

Reagents and conditions: (a) TMSCHN$_2$ (2M in Et$_3$O, 1.2 equiv), toluene : methanol (3:2), 23° C., 30 min, 73%; (b) TFA (45 equiv), CH$_2$Cl$_2$, 0→23° C., 12 h; (c) 43 (4.0 equiv), i-Pr$_2$NEt (6.0 equiv), DMF, 0→23° C., 18 h, 75% for the two steps; (d) N(CH$_2$CH$_2$NH$_2$)$_3$ (16 equiv), CH$_2$Cl$_2$, 0→23° C., 3 h; (e) 10 (1.5 equiv), Et$_3$N (3.0 equiv), DMF, 0→23° C. 24 h, 82% for the two steps; (f) Me$_3$SnOH (10 equiv), 1,2-dichloroethane, reflux, 12 h; (g) Ac$_2$O (4.0 equiv), py, 0→23° C., 12 h, 75% for the two steps; (h) C$_6$F$_5$OH (1.5 equiv), DIC (1.2 equiv), CH$_2$Cl$_2$, 0→23° C., 24 h; (i) 63 (1.2 equiv), i-Pr$_2$NEt (3.0 equiv), DMF, 23° C., 20 h, 73% for the two steps. DIC = N,N'-diisopropyl carbodiimide.

Scheme 9. Synthesis of Tubulysin Analogues Tb36-Tb3

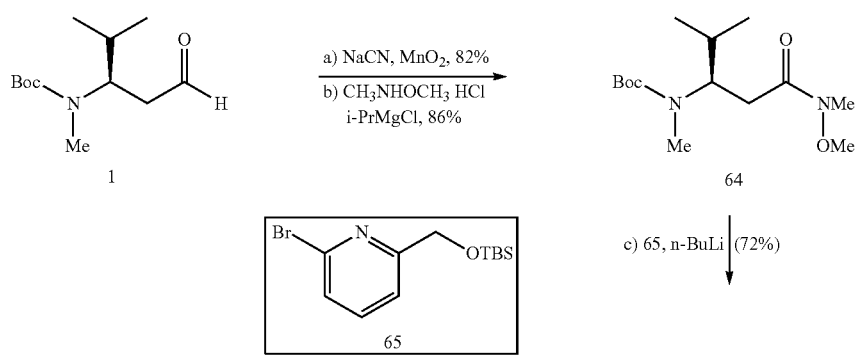

179 180
-continued
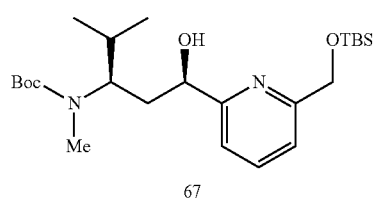
67
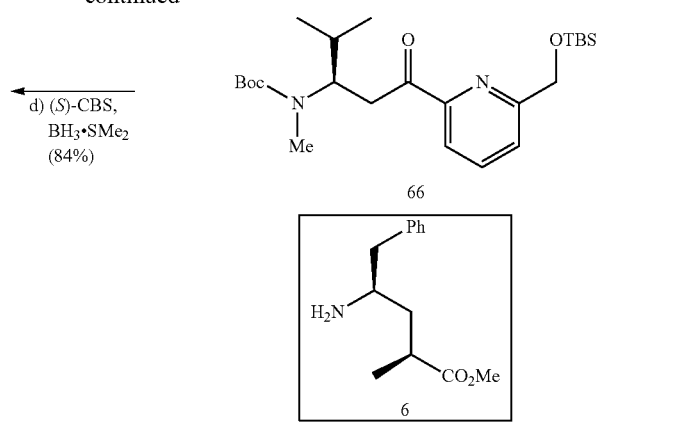
d) (S)-CBS, BH₃·SMe₂ (84%)
66
e) Ac₂O, py
f) TBAF
g) DMP
h) NaClO₂ (93% overall)
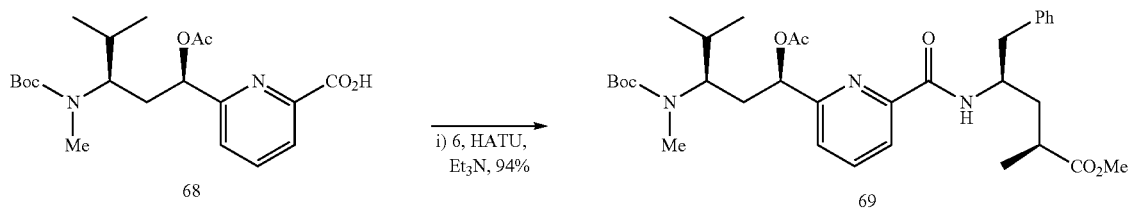
68
i) 6, HATU, Et₃N, 94%
69
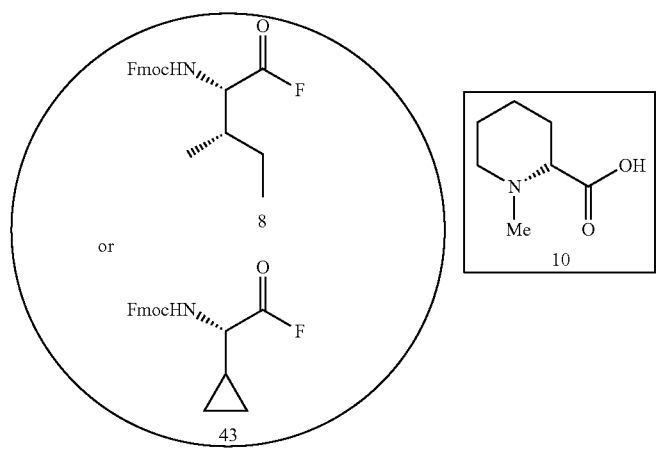
j) TFA
k) 8, 43, i-Pr₂NEt (90-96% overall)
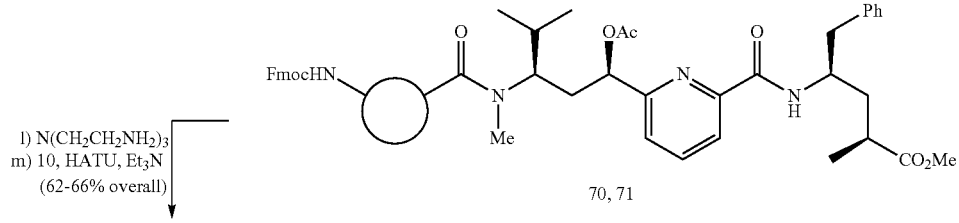
70, 71
l) N(CH₂CH₂NH₂)₃
m) 10, HATU, Et₃N
(62-66% overall)

-continued

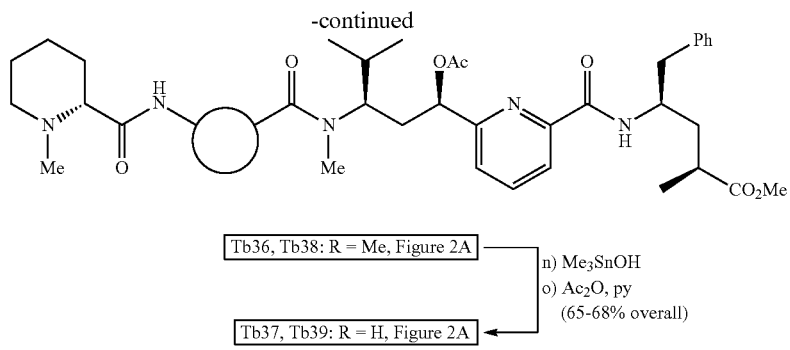

| Tb36, Tb38: R = Me, Figure 2A |
| Tb37, Tb39: R = H, Figure 2A | n) Me₃SnOH
o) Ac₂O, py
   (65-68% overall)

Reagents and conditions: (a) NaCN (2.0 equiv), MnO₂ (17 equiv), MeOH, 0→23° C., 24 h, 82%; (b) CH₃NHOCH₃•HCl (2.1 equiv), i-PrMgCl (4.0 equiv), THF, -20 → 0° C., 3 h, 86%; (c) n-BuLi (2.5 mol in hexanes, 1.44 equiv), 65 (1.2 equiv), THF, -78→ -50° C., 3 h, 72%; (d) (S)-CBS (0.1 equiv), BH₃•SMe₂ (1.0 equiv), 0→23° C., 24 h, 84%; (e) Ac₂O (3.0 equiv), Et₃N (4 equiv), 0→23° C., 2 h, 93%; (f) TBAF (1M soln. in THF, 2.0 equiv), THF, 0→23° C., 30 min, 96%; (g) DMP (1.5 equiv), CH₂Cl₂, 23° C., 1 h, 89%; (h) NaClO₂ (5.4 equiv), NaH₂PO₄•H₂O (12 equiv), 2-methyl-2-butene (7.5 equiv), t-BuOH, THF, H₂O, 23° C., 1 h, 95%; (i) 6 (1.5 equiv), HATU (3.0 equiv) Et₃N (6.0 equiv), DMF, 0→23° C., 24 h, 94%; (j) TFA (45 equiv), CH₂Cl₂ 0→23° C., 2 h; (k) 8 or 43 (4.0 equiv), i-Pr₂NEt (6.0 equiv) DMF, 0→23° C., 18 h, 96% for the two steps for 70, 90% for the two steps for 71; (l) N(CH₂CH₂NH₂)₃ (16 equiv), CH₂Cl₂, 0→23° C., 3 h; (m) 10 (1.5 equiv), HATU (1.5 equiv, Et₃N (3.0 equiv), DMF, 0→23° C., 24 h, 62% for the two steps for Tb36, 66% for the two steps for Tb38; (n) Me₃SnOH (20 equiv), 1,2-dichloroethane, reflux, 12 h; (o) Ac₂O (4.0 equiv), py, 0→23° C., 12 h, 65% for the two steps for Tb37, 68% for the two steps for Tb39.

Scheme 9 depicts the synthesis of tubulysin analogues Tb36-Tb39 in which the thiazole moiety was replaced with a pyridine structural motif (within the Tuv aminoacid unit) and a number of varying isoleucine substitutes. Aldehyde 1 (Sohtome, et al., 2010; In, et al., 2007) was converted to Weinreb amide 64 through a sequence involving methyl ester formation (NaCN, MnO2, MeOH, 82% yield) followed by reaction with MeNHOCH₃HCl and i-PrMgCl (86% yield). Coupling of 64 with the lithioderivative of bromopyridine 65 (see Example 3 for preparation) furnished ketone 66 (72% yield), whose asymmetric reduction with (S)—CBS and BH₃.SMe₂ led to hydroxy compound 67 (84% yield). The latter compound was elaborated to acetoxy carboxylic acid 68 through a sequence involving acetylation (Ac₂O, py), desilylation (TBAF) and oxidation (DMP; NaClO₂) in 93% overall yield. Coupling of 68 with amino methyl ester 6 gave dipeptide 69 (94% yield), whose Boc group cleavage (TFA) led to the corresponding secondary amine which was coupled with acid fluoride fragments 8 and 43 to afford tripeptides 70 and 71, respectively (90-96% overall yield). Removal of the Fmoc [N(CH₂CH₂NH₂)₃] from the latter intermediates D-pipecolinic acid (10) under HATU conditions furnished tubulysin analogues Tb36 and Tb38 (62-66% yield), respectively. The latter were converted to their carboxylic acid counterparts Tb37 and Tb39, respectively, through the sequential action of Me₃SnOH (Nicolaou, et al., 2005) (cleavage of methyl ester and acetate moieties) and Ac₂O, py (reacetylation of hydroxy group) in 65-68% overall yield as shown in Scheme 9.

Tubulysin analogues Tb40 and Tb41 (for structures, see FIG. 2A) in which the "right end" aminoacid residue (Tup) and isoleucine have been replaced with structural motifs represented by 75 or 76 and 46, respectively, as shown in Scheme 10. Thus, removal of the Boc group from 59 (TFA) followed by coupling of the resulting amine with 46 in the presence of i-Pr₂NEt in DMF led to the formation of dipeptide 72 (73% overall yield). The latter was treated with [N(CH₂CH₂NH₂)₃] to cleave the Fmoc group and the resulting amine was coupled with N-methyl-(D)-pipecolinic acid (10, HATU, Et₃N, 78% overall yield) to furnish tripeptide 73. Tripeptide 73 was then converted to its carboxylic acid counterpart (74, Me₃SnOH; Ac₂O-py, 74% overall yield). Finally, coupling of 74 with 75 or 76 under HATU conditions furnished tubulysin analogues Tb40 (75% yield) and Tb41 (76% yield) as shown in Scheme 10 (see Example 3 for more details).

Scheme 10. Synthesis of Tubulysin Analogue Tb40 and Tb41

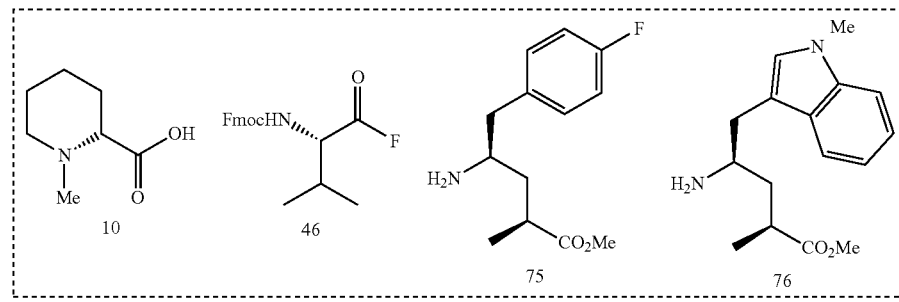

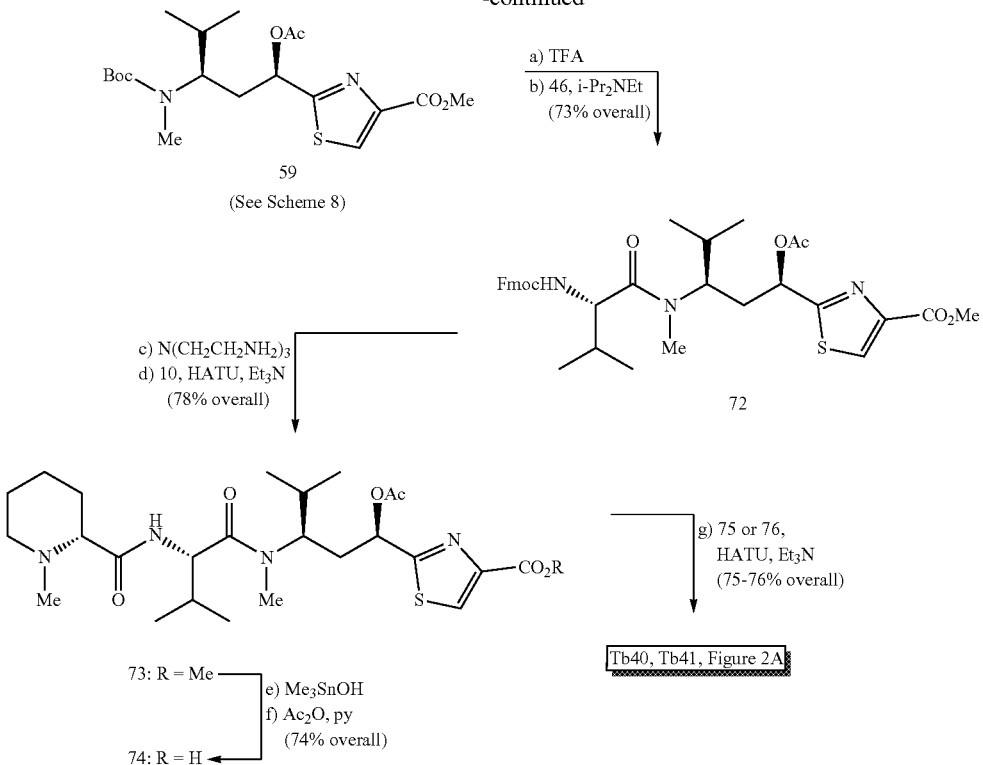

Reagents and conditions: (a) TFA (45 equiv), CH$_2$Cl$_2$, 0→23° C., 12 h; (b) 46 (4.0 equiv), i-Pr$_2$NEt (6.0 equiv), DMF, 0→23° C., 18 h, 73% for the two steps; (c) N(CH$_2$CH$_2$NH$_2$)$_3$ (16 equiv), CH$_2$Cl, 0→23° C., 3 h; (d) 10 (1.5 equiv), HATU (1.5 equiv), Et$_3$N (3.0 equiv) DMF, 0→23° C., 24 h, 78% for the two steps; (e) Me$_3$SnOH (20 equiv), 1,2-dichloroethane, reflux, 12 h; (f) Ac$_2$O (4.0 equiv), py, 0→23° C., 12 h, 74% for the two steps; (g) 75 or 76 (1.2 equiv), HATU (1.2 equiv), Et$_3$N (2.4 equiv), DMF, 23° C., 18 h, 75% for the two steps for Tb40, 76% for the two steps for Tb41.

With inspiration of the earlier syntheses of tubulysin analogs and their promising activity, additional tubulysin analogs (Tb44-Tb48, PTb-D49-PTb-D51 and Tb52-Tb61) have been synthesized and tested against several cancer cell lines.

Scheme 11 summarizes the streamlined total synthesis of tubulysin U (Tb54), its methyl ester (Tb53) and tubulysin V (77) starting from the known and readily available aldehyde 78. Thus, C—H activation-based coupling of aldehyde 78 with a suitable thiazolyl moiety 2 led to furnishing, under the previously reported condition [PhI(OCOCF$_3$)$_2$, TMSN$_3$] (Matcha et al., 2013; Khemnar et al., 2014; Chatgilialoglu et al., 1999; Yeung et al., 2011) coupling product ketone 79 in 56% yield. Reduction of thiazolyl ketone 79 with (S)—CBS in the presence of BH$_3$.SMe$_2$ (Corey, et al., 1987; Deloux and Srebnik, 1993; Corey and Helal, 1998) then produced alcohol 80 in 83% yield as a single diastereoisomer after chromatographic purification. Elaboration of hydroxy compound 80 to acetoxy carboxylic acid 81 was achieved through a sequence involving deacetylation (K$_2$CO$_3$, MeOH), selective oxidation of the primary alcohol (TEMPO, BAIB; then NaClO$_2$) and acetylation (Ac$_2$O, py) of the resulting secondary alcohol, in 82% overall yield. Coupling of carboxylic acid 81 and aminoester 6 (Shankar et al., 2013) in the presence of HATU and Et$_3$N led to amide 82 (94% yield). The Boc group was cleaved from the latter compound (TFA) and the resulting amine was coupled with acid fluoride 8 (Wipf et al., 2007) to afford peptide 83 (i-Pr$_2$NEt, 92%) as shown in Scheme 11. Removal of the Fmoc protecting group from 83 [N(CH$_2$CH$_2$NH$_2$)$_3$], followed by coupling of the so generated amine with N-methyl-(D)-pipecolic acid (10) provided tubulysin U methyl ester (Tb53, 85% overall yield), whose conversion to tubulysin U (Tb54) via tubulysin V (77) required sequential treatment with Me$_3$SnOH (Nicolaou et al., 2005) (cleavage of both methyl ester and acetate) and reacetylation (Ac$_2$O, py)/aqueous work-up (74% overall yield) as shown in Scheme 11.

Scheme 12 summarizes the synthesis of N$^{14}$-desacetoxy-tubulysin analogs Tb44 and Tb45 starting from the known and readily available aldehyde 1 (prepared from (S)-Boc-valine in multigram quantities) (Sohtome et al., 2010; in et al., 2007). Thus, C—H activation-based coupling of aldehyde 1 with a suitable thiazolyl moiety 2 led to furnishing, under the previously reported condition [PhI(OCOCF$_3$)$_2$, TMSN$_3$](Matcha et al., 2013; Khemnar et al., 2014; Chatgilialoglu et al., 1999; Yeung et al., 2011) coupling product ketone 3 in 81% yield. Reduction of thiazolyl ketone 3 with (S)—CBS in the presence of BH$_3$.SMe$_2$ then produced alcohol 4 in 82% yield as a single diastereoisomer after chromatographic purification. Elaboration of hydroxy compound 4 to acetoxy carboxylic acid 5 was achieved through a sequence involving deacetylation (K$_2$CO$_3$, MeOH), selective oxidation of the primary alcohol (TEMPO, BAIB; then NaClO$_2$) and acetylation (Ac$_2$O, py) of the resulting secondary alcohol, in 66% overall yield. Coupling of carboxylic acid 5 and aminoester 6 (Shankar et al., 2013) in the presence of i-BuOCOCl and Et$_3$N led to amide 7 (91% yield). The Boc group was cleaved from the latter compound (TFA) and the resulting amine was coupled with acid fluoride 8 (Wipf et al., 2007) to afford peptide 9 (i-Pr$_2$NEt, 92%) as shown in Scheme 12. Removal of the Fmoc protecting group from 9 [N(CH$_2$CH$_2$NH$_2$)$_3$], followed by coupling of the so generated amine with N-Me-2-pyrrole carboxylic acid (84) or N-Me-2-imidazole carboxylic acid (85) provided analogs Tb44 and Tb45, (74% each, overall yield), respectively.
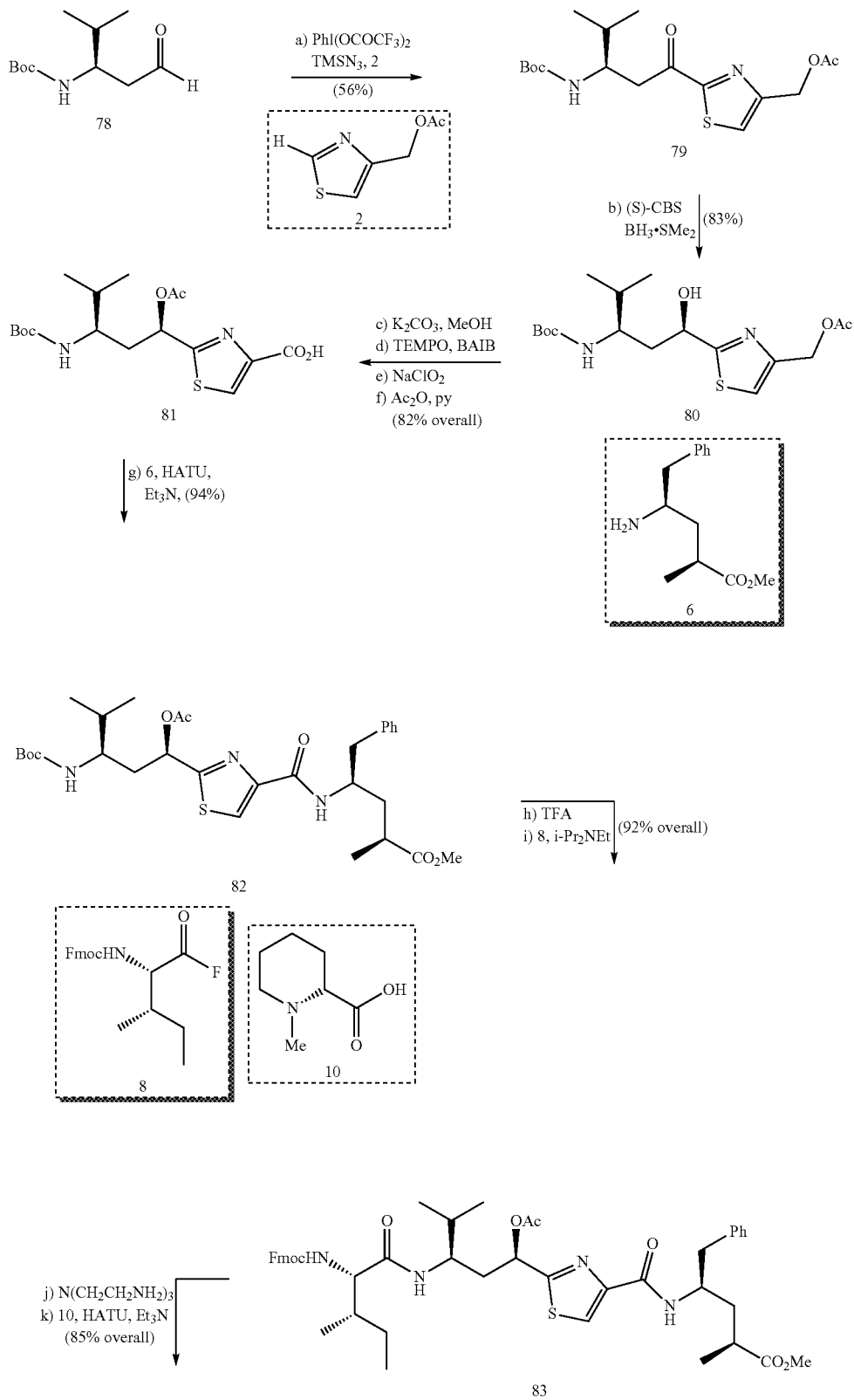

-continued

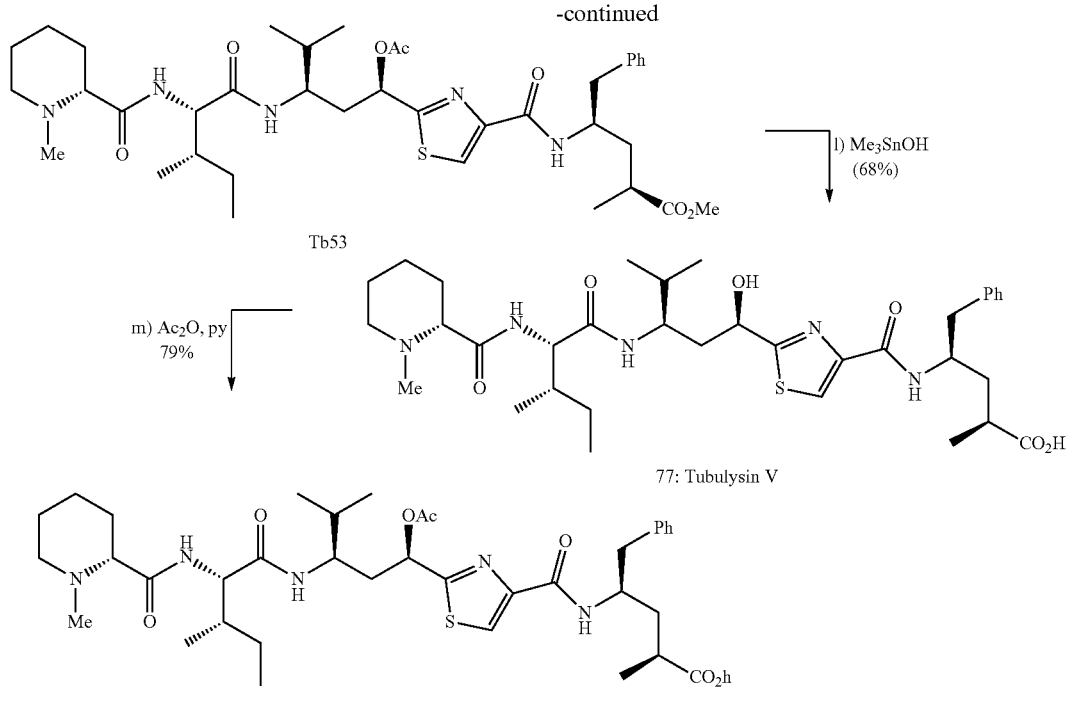

Tb53

77: Tubulysin V

Tb54: Tubulysin U

Reagents and conditions: (a) 78 (2.0 equiv), 2 (1.0 equiv), TMSN₃ (2.0 equiv), PIFA (2.0 equiv), benzene, 23° C., 16 h; then 77 (2.0 equiv), TMSN₃ (2.0 equiv), PIFA (2.0 equiv), 23° C., 12 h, 56%; (b) (S)-CBS (0.2 equiv), BH₃•SMe₂ (1.0 equiv), 0→23° C., 18 h, 83%; (c) K₂CO₃ (4.0 equiv), MeOH, 23° C., 3 h, 95%; (d) TEMPO (0.1 equiv), BAIB (1.0 equiv) CH₂Cl₂, 23° C., 16 h, 98%; (e) NaClO₂ (5.0 equiv), NaH₂PO₂•H₂O (12 equiv), 2-methyl-2-butene (7.5 equiv), t-BuOH, THF, H₂O, 23° C., 12 h; (f) Ac₂O (3.2 equiv), py (3.5 equiv), CH₂Cl₂, 0→23° C., 15 h, 78% for the two steps; (g) 6 (1.5 equiv), HATU (3.0 equiv), Et₃N (6.0 equiv), DMF, 0→23° C., 18 h, 94%; (h) TFA (45 equiv), CHCl₂, 0→23° C., 3 h; (i) 8 (4.0 equiv), i-Pr₂NEt (6.0 equiv), DMF, 0→23° C., 18 h, 92% for the two steps; (j) N(CH₂CH₂NH₂)₃ (16 equiv), CH₂Cl₂, 0→23° C., 3 h; (k) 10 (3.0 equiv), HATU (3.0 equiv), Et₃N (6.0 equiv), DMF, 0→23° C., 24 G, 85% for the two steps; (l) Me₃SnOH (20 equiv), 1,2-dichloroethane, reflux, 12 h, 68%; (m) Ac₂O (4.0 equiv), py, 0→23° C., 12 h, 79%; TMS = trimethylsilyl; PIFA = phenyliodine(III) bis(trifluoroacetate); (S)-CBS = (S)-(-)-methyl-CBS-oxazaborolidine; TEMPO = 2,2,6,6-tetramethyl-1-piperidinyloxy; BAIB = bis(acetoxy)iodo benzene; Ac = acetyl; py = pyridine; THF = tetrahydrofuran; HATU = 1-[bis(dimethyl amino)methylene]-1H-1,2,3-triazolo[4,5-b]pyridinium 3-oxid hexafluorophosphate; DMF = dimethylformamide; TFA = trifluoroacetic acid; Boc = tert-butylloxycarbonyl; Fmoc = fluorenylmethyloxycarbonyl.

Scheme 12. Synthesis of Tubulysin Analogs Tb44 and Tb45

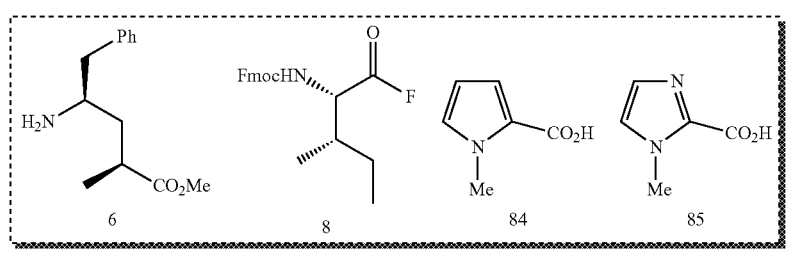

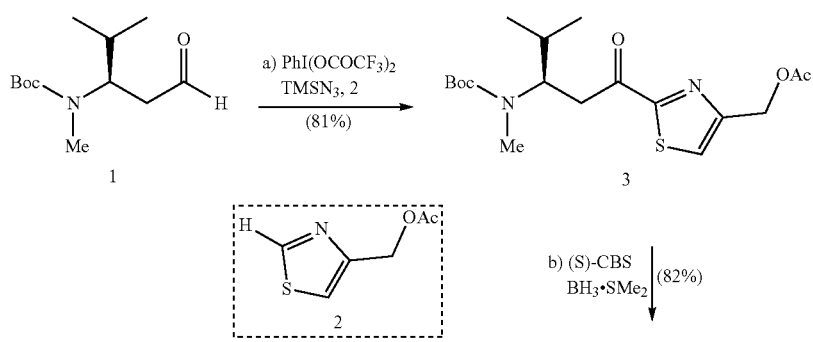

-continued

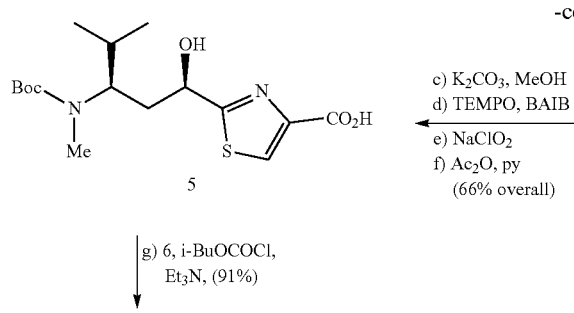
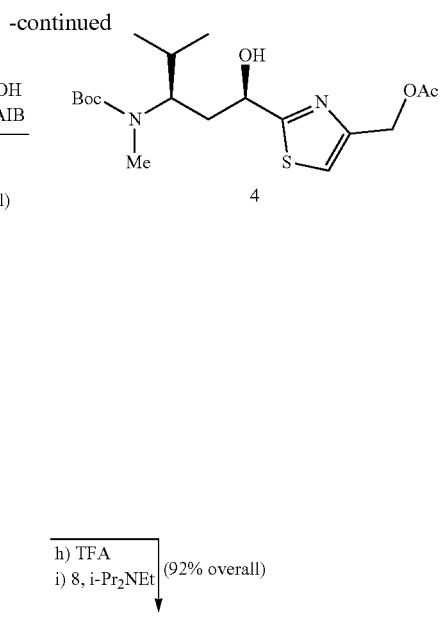

Reagents and conditions: (a) 1 (2.0 equiv), 2 (1.0 equiv), TMSN$_3$ (2.0 equiv), PIFA (2.0 equiv), benzene, 23° C., 16 h; then 1 (2.0 equiv), TMSN$_3$ (2.0 equiv, PIFA (2.0 equiv), 23° C., 12 h, 81%; (b) (S)-CBS (0.2 equiv), BH$_3$•SMe$_2$ (1.0 equiv), 0→23° C., 18 h, 82%; (c) K$_2$CO$_3$ (4.0 equiv), MeOH, 23° C., 3 h, 93%; (d) TEMPO (0.1 equiv), BAIB (1.0 equiv), CH$_2$Cl$_2$ 23° C., 16 h, 96%; (e) NaClO$_2$ (5.0 equiv), NaH$_2$PO$_4$•H$_2$O (12 equiv), 2-methyl-2-butene (7.5 equiv), t-BuOH, THF, H$_2$O, 23° C., 12 h; (f) Ac$_2$O (3.2 equiv), py (3.5 equiv), CH$_2$Cl$_2$, 0→23° C., 15 h, 74% for the two steps; (g) i-BuOCOCl (2.0 equiv), Et$_3$N (4.0 equiv), THF, -20° C., 30 min; then 6 (2.1 equiv), -20→23° C., 24 h, 91% or 6 (1.5 equiv), HATU (3.0 equiv), Et$_3$N (6.0 equiv), DMF, 0→23° C., 18 h, 74%; (h) TFA (45 equiv), CH$_2$Cl$_2$, 0→23° C., 3 h; (i) 8 (4.0 equiv), i-Pr$_2$NEt (6.0 equiv), DMF, 0→23° C., 18 h, 92% for the two steps; (j) N(CH$_2$CH$_2$NH$_2$)$_3$ (16 equiv), CH$_2$Cl$_2$, 0→23° C., 3 h; (k) 84 or 85 (3.0 equiv), HATU (3.0 equiv), Et$_3$N (6.0 equiv), DMF, 0→23° C., 18 h, 74% for the two steps for Tb44, 74% for the two steps for Tb45.

Tubulysin analogs Tb46, Tb47 and Tb57 (for structures, see FIG. 2B) in which the "right side" amide linking were replaced by various amino acid residues such as 29, 30 and 75 was synthesized from aminoacid derivative 5 (see Scheme 12) through the sequence shown in Scheme 13. Thus, 5 was converted to its methyl ester (59, TMSCHN$_2$, 73% yield) and thence to dipeptide 60 by first removing the Boc group (TFA) and then coupling of the resulting amine with acid fluoride fragment 43 (i-Pr$_2$NEt, 75% overall yield). The latter was treated with [N(CH$_2$CH$_2$NH$_2$)$_3$] to cleave the Fmoc group and the resulting amine was coupled with N-methyl-(D)-pipecolinic acid (10, HATU, Et$_3$N, 82% overall yield) to furnish tripeptide 61. Tripeptide 61 was converted to its carboxylic acid counterpart (62, Me$_3$SnOH; Ac$_2$O-py, 75% overall yield). Finally, coupling of 62 with 29, 30 or 75 under HATU conditions furnished tubulysin analogues Tb46 (70% yield) Tb47 (72% yield) and Tb57 (75% yield) as shown in Scheme 13 (see Example 3 for more details).

Scheme 14 summarizes the synthesis of tubulysin analogs (Tb48 in which previously reported analog Tb32 converted to its acid counterpart) and Tb52. Their synthesis began with removal of the Boc group of dipeptide 7 (see Scheme 12), which were coupled with Fmoc-protected acid fluorides 46 or 88 to give tripeptides 52 or 89 (88 and 56% yield for the two steps) respectively, as shown in Scheme 14. Cleavage of the Fmoc group [N(CH$_2$CH$_2$NH$_2$)$_3$] from these intermediates followed by coupling with N-methyl-(D)-pipecolinic acid 10, led to tubulysin analogs Tb32 (81% overall yields) and Tb52 (69% yield for the two steps). Conversion of Tb32 to its acid counterpart Tb48 required sequential treatment with Me$_3$SnOH (Nicolaou et al., 2005) (cleavage of both methyl ester and acetate) and reacetylation (Ac$_2$O, py)/aqueous work-up (50% overall yield) as shown in Scheme 14.

Scheme 13. Synthesis of Tubulysin Analogs Tb46, Tb47, and Tb57

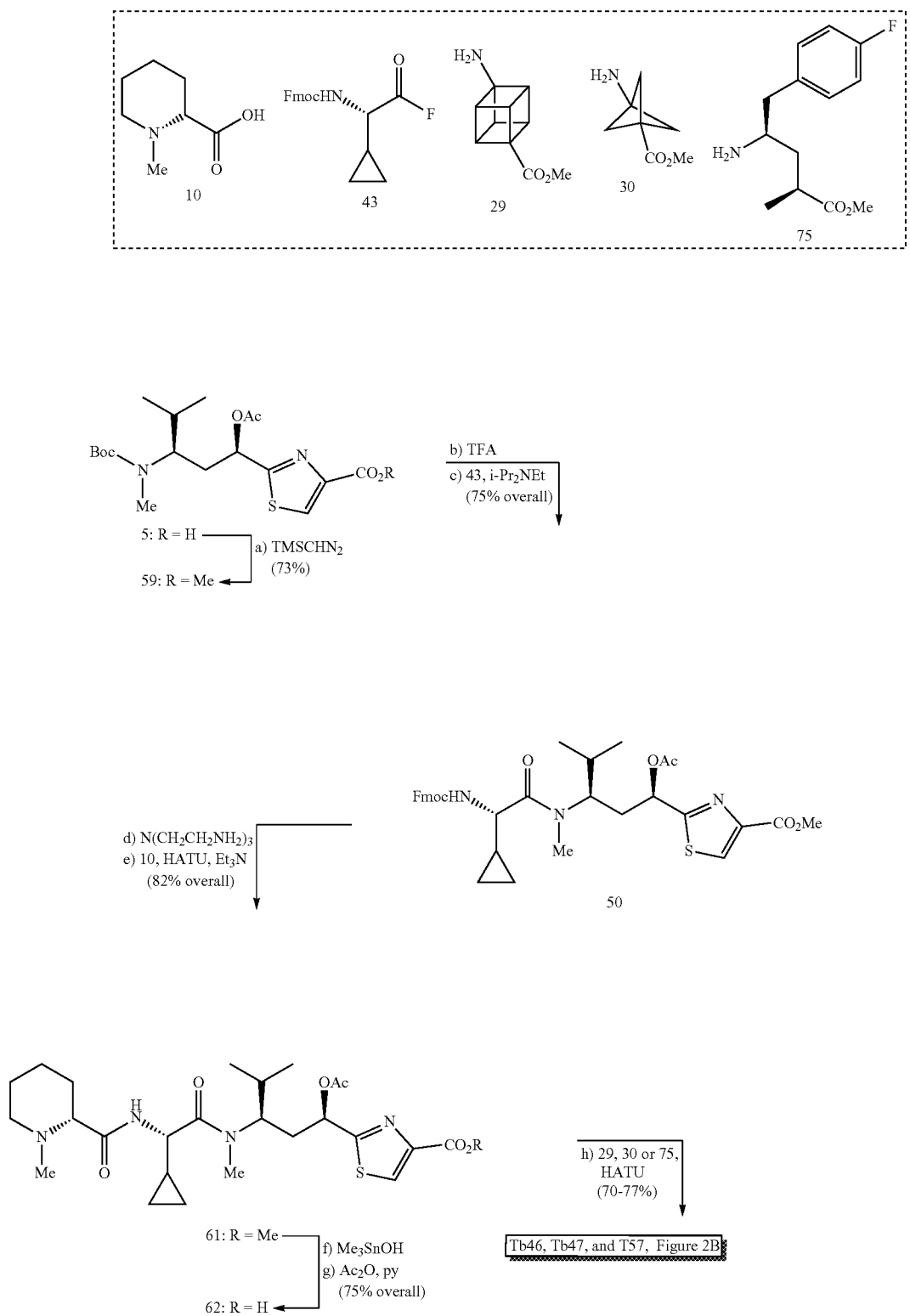

Reagents and conditions: (a) TMSCHN$_2$ (2M in Et$_2$O, 1.2 equiv), toluene : methanol (3:2), 23° C., 30 min, 73%; (b) TFA (45 equiv), CH$_2$Cl$_2$, 0→23° C., 12 h; (c) 43 (4.0 equiv), i-Pr$_2$NEt (6.0 equiv), DMF, 0→23° C., 18 h, 75% for the two steps; (d) N(CH$_2$CH$_2$NH$_2$)$_3$ (16 equiv), CH$_2$Cl$_2$, 0→23° C., 3 h; (e) 10 (1.5 equiv), HATU (1.5 equiv), Et$_3$N (3.0 equiv), DMF, 0→23° C., 24 h, 82% for the two steps; (f) Me$_3$SnOH (20 equiv), 1,2-dichloroethane, reflux, 12 h; (g) Ac$_2$O (4.0 equiv), py, 0→23° C., 12 h, 75% for the two steps; (h) 29 or 30 or 75 (5.0 equiv), HATU (5.0 equiv), Et$_3$N (10 equiv), DMF, 0→23° C., 16 h, 70% for the two steps for Tb46, 72% for the two steps for Tb47 and 75% for the two steps for Tb57.

Scheme 14. Synthesis of Tubulysin Analogs Tb32 and its acid counterpart Tb48 and Tb52

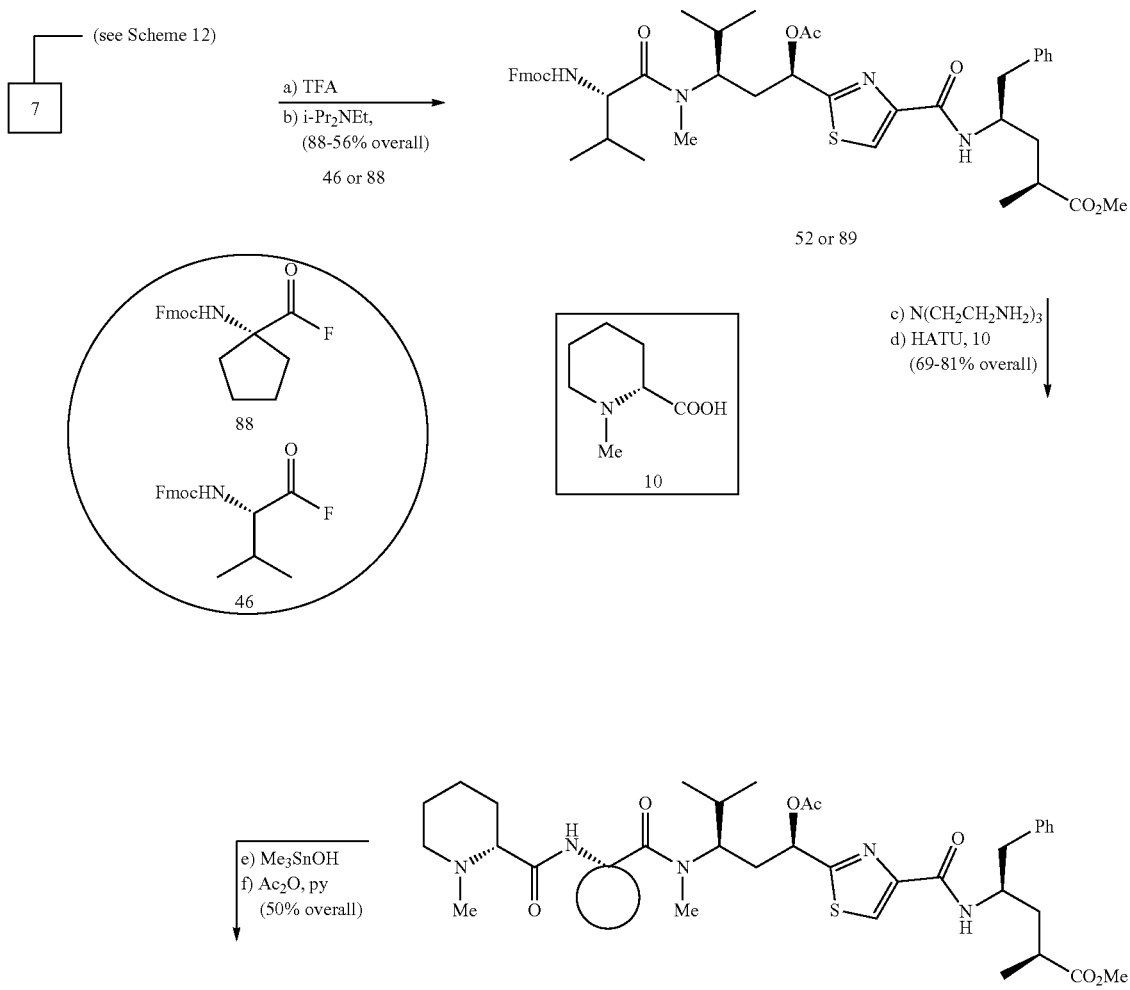

Figure 2B:
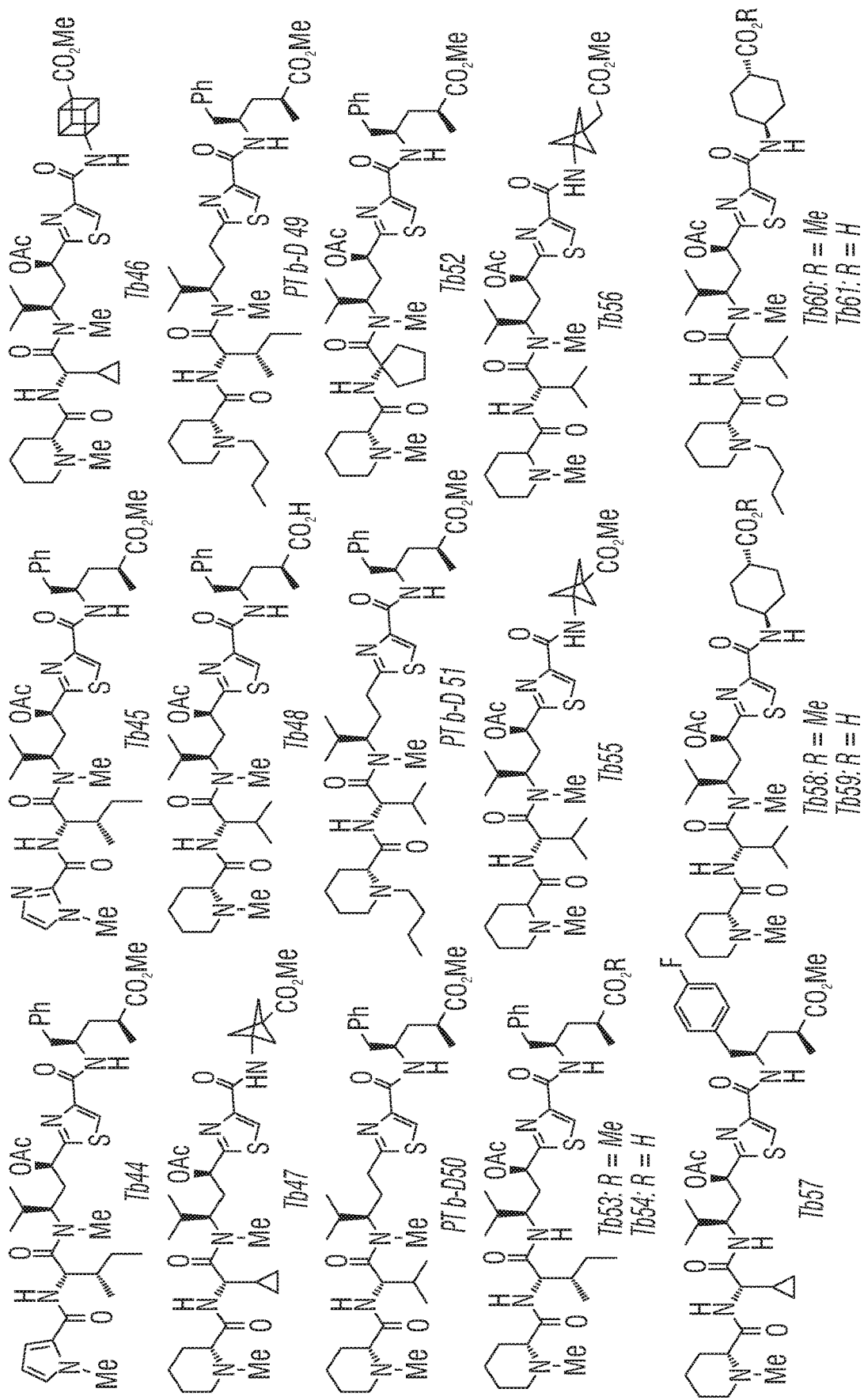

| Tb48, Figure 2B | Tb32 and Tb52, Figure 2A and Figure 2B |

Reagents and conditions: (a) TFA (45 equiv), CH₂Cl₂, 23° C., 12 h; (b) 46 (4.0 equiv) or 88 (4.0 equiv), i-Pr₂NEt (6.0 equiv), DMF, 0→23° C., 18 h, 88% for the two steps for 52; 56% for the two steps for 89; (c) N(CH₂CH₂NH₂)₃ (16 equiv), CH₂Cl₂, 0→23° C., 2 h; (d) N-methyl-(D)-pipecolinic acid (10) (2.0 equiv), HATU (1.3 equiv), Et₃N (3.0 equiv), DMF, 0→23° C., 24 h, 81% for the two steps for Tb32; 69% for the two steps for Tb53; (e) Tb32, Me₃SnOH (20 equiv), 1,2-dichloroethane, reflux, 12 h; (f) Ac₂O (4.0 equiv), py, 0→23° C., 12 h, 50% for the two steps.

Exploration of the pretubulysin by synthesizing its analogs (PTb-D49-PTb-D51) which incorporate varying combinations of structural motifs in place of N-Me-pipecolinic acid and the isoleucine residues (Scheme 15). Reduction of the known aldehyde 1 with NaBH₄ followed by bromination of the resulting alcohol using CBr₄ and PPh₃ furnished bromide 11 in 86% overall yield. Coupling of thiazole TBS-ether 12 with bromide 11 in the presence of n-BuLi gave product 13 in 76% yield. Elaboration of compound 13 to carboxylic acid 14 was achieved through desilylation (TBAF) and oxidation of the resulting alcohol (DMP; then NaClO₂) in 92% overall yield. Coupling of carboxylic acid 14 with aminoester 6 (Shankar et al., 2013) in the presence of HATU and Et₃N led to amide 15 (81% yield). Boc group removal from the later compound (TFA) followed by coupling of the resulting amine with acid fluoride 8 or 46 furnished peptide 16 or 86 (i-Pr₂NEt, 94-95% yield), respectively, as shown in Scheme 15. Removal of the Fmoc protecting group from 16 [N(CH₂CH₂NH₂)₃] and coupling of the resulting amine with N-methyl-(D)-pipecolic acid (10) provided pretubulysin D analogue (PTb-D49, 82% overall yield). And removal of the Fmoc protecting group from 86 [N(CH₂CH₂NH₂)₃] and coupling of the resulting amine with either N-methyl-(D)-pipecolic acid (10) or amino acid (87) provided pretubulysin D analogue (PTb-D50, 81% overall yield) or (PTb-D51, 76% overall yield) respectively as shown in Scheme 15.

Scheme 15. Synthesis of Pretubulysin Analogs PTb-D49-PTb-D51
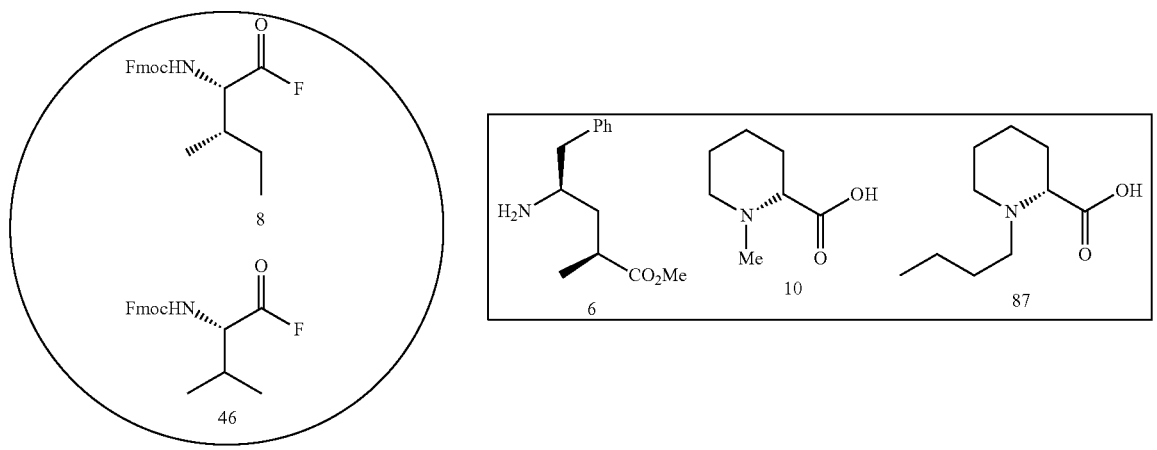
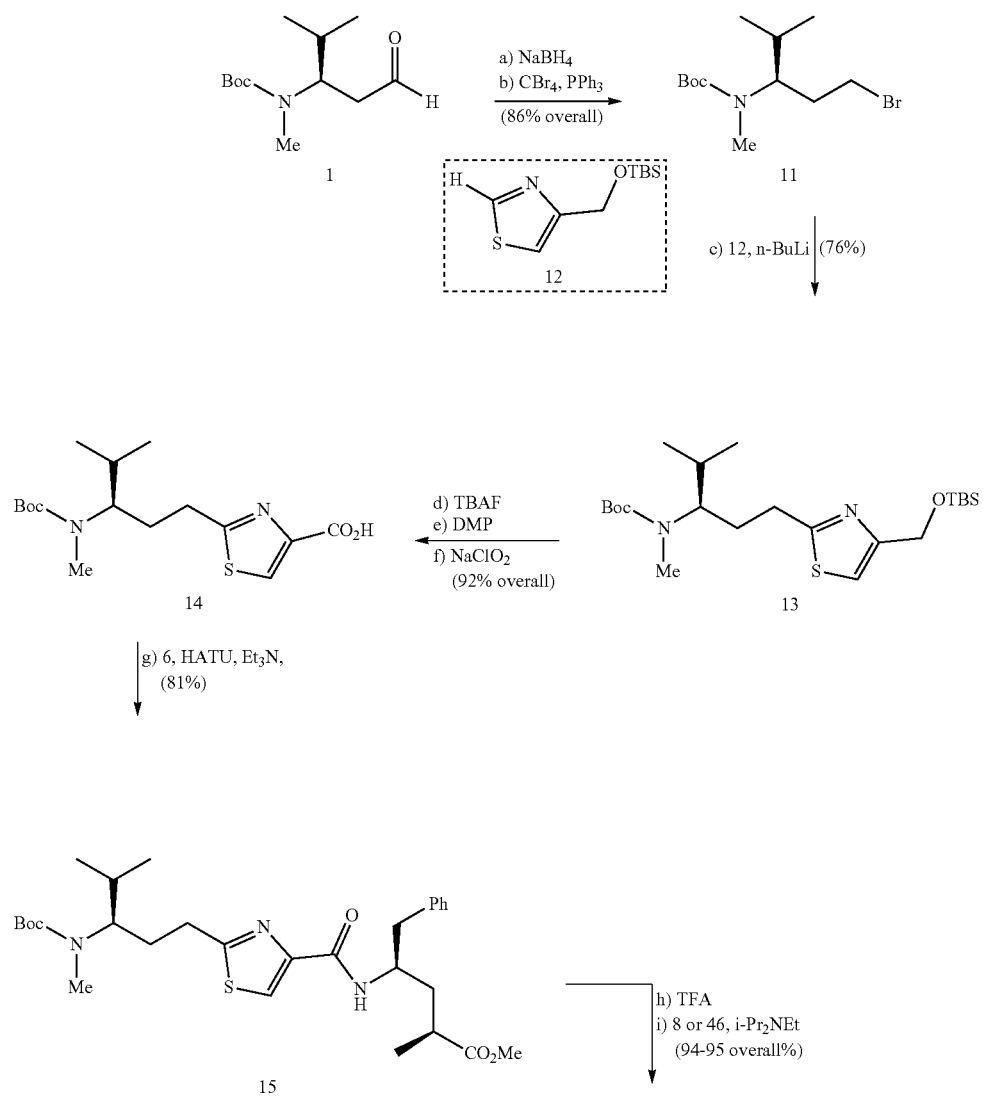

j) N(CH₂CH₂NH₂)₃
k) 10 or 87, HATU (76-82% overall)

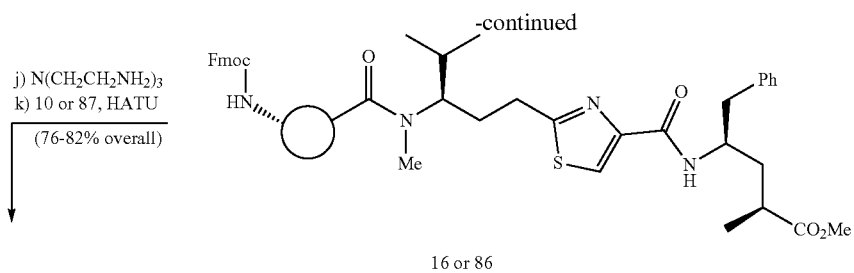

16 or 86

PTb-D49-PTb-D51, Figure 2B

Reagents and conditions: (a) NaBH₄ (1.5 equiv), MeOH, 0→23° C., 1 h, 92%; (b) CBr₄ (2.0 equiv), PPh₃ (2.0 equiv), 0→10° C., 1 h, 80%; (c) 12 (1.1 equiv), n-BuLi (1.2 equiv; 2.6 M in hexane), THF, -78→0° C., 3 h, 76%; (d) TBAF (2.0 equiv; 1 M in THF), THF, 0° C., 1 h, 94%; (e) DMP (1.5 equiv), CH₂Cl₂, 23° C.,1 h, 90%; (f) NaClO₂ (5.4 equiv), NaH₂PO₄·H₂O (12 equiv), 2-methyl-2-butene (7.5 equiv), t-BuOH, THF, H₂O, 23° C., 1 h; 92%; (g) 6 (1.5 equiv), HATU (3.0 equiv), Et₃N (6.0 equiv), DMF, 0→23° C., 18 h, 81%; (h) TFA (45 equiv), CH₂Cl₂, 23° C., 2 h; (i) 8 or 46 (4.1 equiv), i-Pr₂NEt (6.2 equiv), DMF, 0→23° C., 18 h, 94% for the two steps for 16, 95% for the two steps for 86; (j) N(CH₂CH₂NH₂)₃ (16 equiv), CH₂Cl₂, 0→23° C., 2 h; (k) N-methyl-D-pipecolinic acid (10, 3.0 equiv) or 87 (3.0 equiv), HATU (3.0 equiv), Et₃N (6.0 equiv), DMF, 0→23° C., 24 h 82% for the two steps for PTb-D49, 81% for the two steps for PTb-D50 and 76% for the two steps for PTb-D51.

Scheme 16. Synthesis of Tubulysin Analogs Tb55 and Tb56

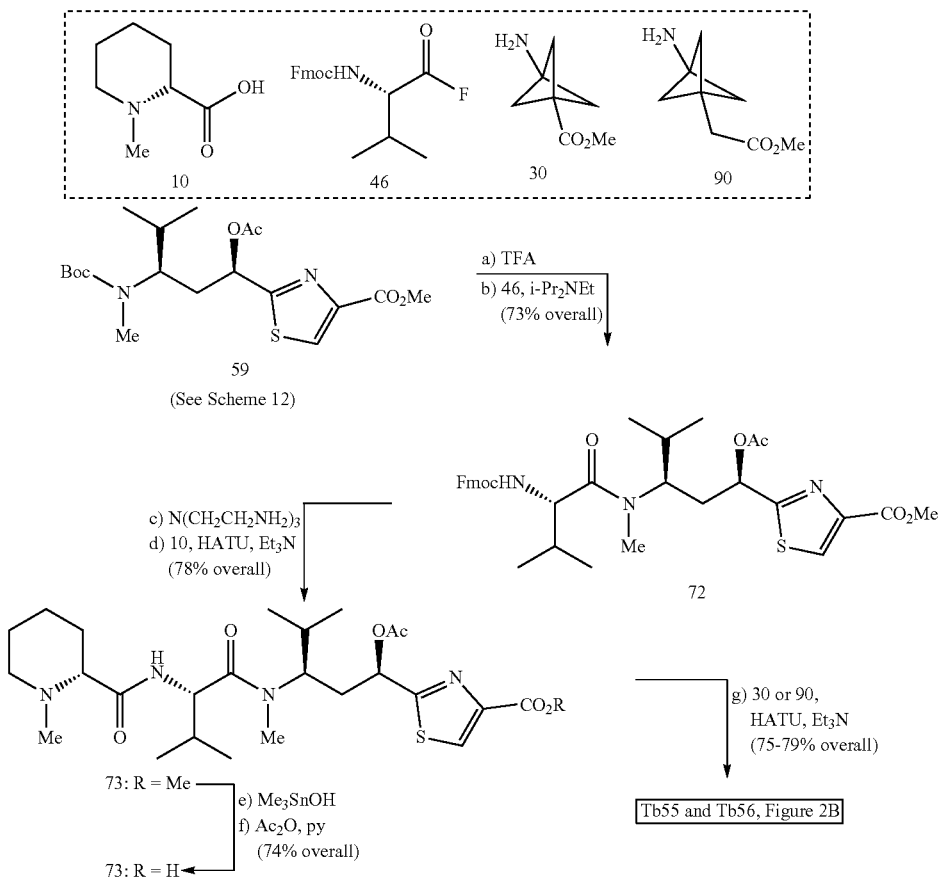

Reagents and conditions: (a) TFA (45 equiv), CH₂Cl₂, 0→23° C., 12 h; (b) 46 (4.0 equiv), i-Pr₂NEt (6.0 equiv), DMF, 0→23° C., 18 h, 73% for the two steps; (c) N(CH₂CH₂NH₂)₃ (16 equiv), CH₂Cl₂, 0→23° C., 3 h; (d) 10 (1.5 equiv), HATU (1.5 equiv), Et₃N (3.0 equiv), DMF, 0→23° C., 24 h, 78% for the two steps; (e) Me₃SnOH (20 equiv), 1,2-dichloroethane, reflux, 12 h; (f) Ac₂O (4.0 equiv), py, 0→23° C., 12 h, 74% for the two steps; (g) 30 or 90 (1.2 equiv), HATU (1.2 equiv), Et₃N (2.4 equiv), DMF, 0→23° C., 18 h, 75% for the two steps for Tb55 and 79% for the two steps for Tb56.

Tubulysin analogues Tb55 and Tb56 (for structures, see FIG. 2B) in which the "right end" aminoacid residue (Tup) and isoleucine have been replaced with structural motifs represented by 30 or 90 and 46, respectively, as shown in Scheme 16. Thus, removal of the Boc group from 59 (TFA) followed by coupling of the resulting amine with 46 in the presence of i-Pr₂NEt in DMF led to the formation of dipeptide 72 (73% overall yield). The latter was treated with [N(CH₂CH₂NH₂)₃] to cleave the Fmoc group and the resulting amine was coupled with N-methyl-(D)-pipecolinic acid (10, HATU, Et₃N, 78% overall yield) to furnish tripeptide 73. Tripeptide 73 was then converted to its carboxylic acid counterpart (74, Me₃SnOH; Ac₂O-py, 74% overall yield). Finally, coupling of 74 with 30 or 90 under HATU conditions furnished tubulysin analogues Tb55 (75% yield) and Tb56 (79% yield) as shown in Scheme 16.

Tubulysin analogues Tb58-Tb61 (for structures, see FIG. 2B) in which the "right end" aminoacid residue (Tup), isoleucine (Ile), and "left end" (Mep) have been replaced with 91, 46 and 10 or 87, respectively (Scheme 17). Thus, coupling of 5 with 91 in the presence of HATU furnished dipeptide 92 (84% yield). Exposure of the so formed dipeptide to TFA resulted in removal of the Boc group to afford the corresponding amine, whose coupling with acid fluoride 46 in the presence of i-Pr₂NEt in DMF led to the formation of tripeptide 93 (92% overall yield). Finally, removal of the Fmoc group from 93 [N(CH₂CH₂NH₂)₃] followed by coupling of the resulting amine with N-methyl-(D)-pipecolinic acid (10) or 87 under HATU conditions furnished tubulysin analogues Tb58 (72% yield) and Tb60 (77% yield) as shown in Scheme 17 (see Example 3 for further details). The latter were converted to their carboxylic acid counterparts Tb59 and Tb60, respectively, through the sequential action of Me₃SnOH (Nicolaou et al., 2005) (cleavage of methyl ester and acetate moieties) and Ac₂O, py (reacetylation of hydroxy group) in 68-74% overall yield as shown in Scheme 17.

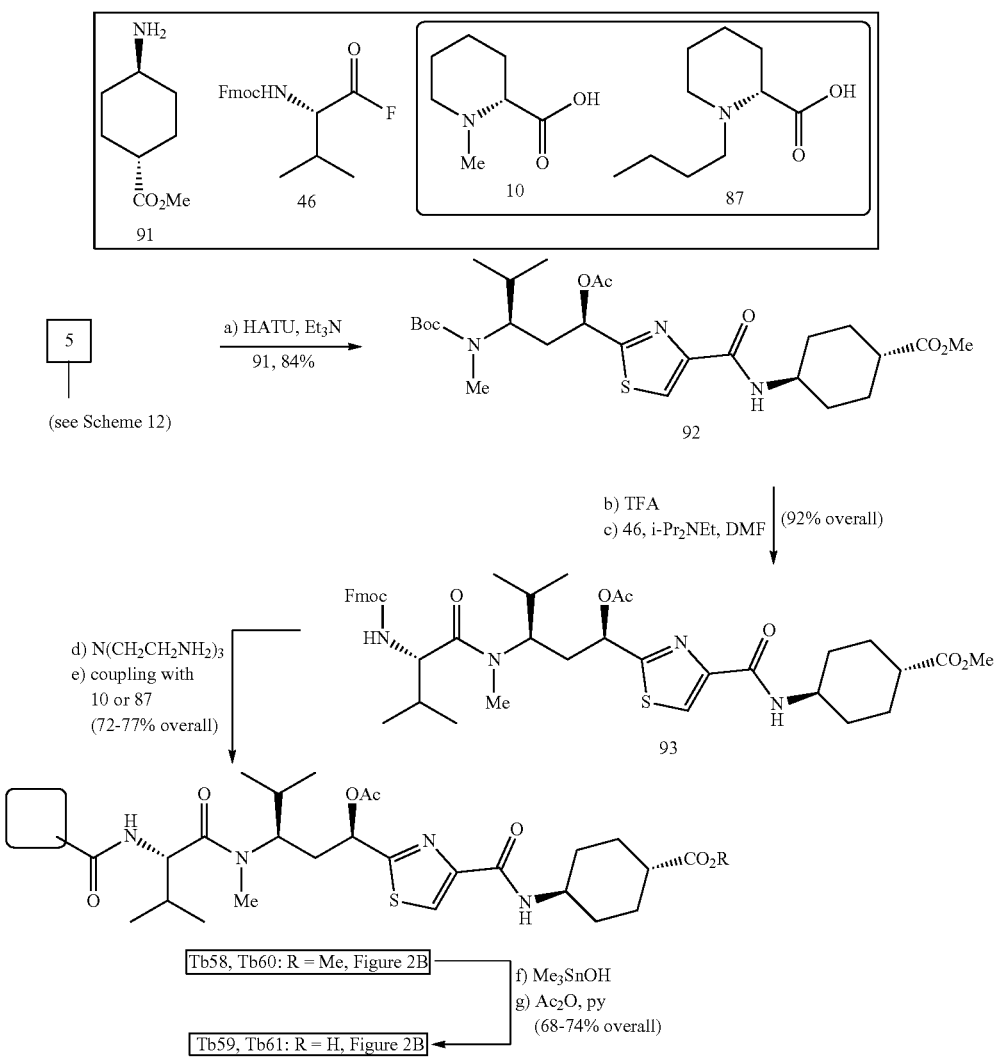

Scheme 17. Synthesis of Tubulysin Analogs Tb58-Tb61

Reagents and conditions: (a) 91 (1.5 equiv), HATU (3.0 equiv), Et₃N (6.0 equiv), DMF, 23° C., 18 h, 84%; b) TFA (45 equiv), CH₂Cl₂, 0→23° C., 1 h; (c) 46 (4.0 equiv), i-Pr₂NE (5.0 equiv), DMF, 0→23° C., 18 h, 92% for the two steps; (d) N(CH₂CH₂NH₂)₃ (16 equiv), CH₂Cl₂, 0→23° C., 2 h; (e) N-methyl-(D)-pipecolinic acid (10) (2.0 equiv), or (87) (2.0 equiv), HATU (1.5 equiv), Et₃N (3.0 equiv), DMF, 0→23° C., 24 h, 72% for the two steps for Tb58, 77% for the two steps for Tb60; (f) Me₃SnOH (20 equiv), 1,2-dichloroethane, reflux, 12 h; (g) Ac₂O (4.0 equiv), py, 0→23° C., 12 h, 68% for the two steps for Tb59, 74% for the two steps for Tb61.

Example 2—General Methods and Materials

All reactions were carried out under an argon atmosphere with dry solvent under anhydrous conditions, unless otherwise noted. Methylene chloride ($CH_2Cl_2$), 1,2-dichloroethane ($C_2H_4Cl_2$) tetrahydrofuran (THF), toluene, methanol (MeOH), dimethylformamide (DMF), diisopropylethylamine, and triethylamine were dried prior to use by passage through an activated alumina column unless otherwise noted (Pangborn et al., 1996). Anhydrous acetone, ethyl acetate, and 1,2-dichloro-ethane were purchased from commercial suppliers and stored under argon. Reagents were purchased at the highest commercial quality and used without further purification, unless otherwise noted. Yields refer to chromatographically and spectroscopically ($^1H$ NMR) homogenous material, unless otherwise stated.

Reactions were monitored by thin-layer chromatography (TLC) carried out on S-2 0.25 mm E. Merck silica gel plates (60F-254) and were visualized using UV light and an ethanolic solution of phosphomolybdic acid and cerium sulfate or an aqueous solution of potassium permanganate. Flash column chromatography using E. Merck silica gel (60, particle size 0.040-0.063 mm) was performed as described by Still (Still et al., 1978). NMR spectra were recorded on a Bruker DRX-600 equipped with a 5 mm DCH cryoprobe and calibrated using residual undeuterated solvent for $^1H$ NMR [$\delta_H$=7.26 ($CDCl_3$) and 3.31 ($CD_3OD$) ppm] and $^{13}C$ deuterated solvent for $^{13}C$ NMR [$\delta_C$=77.00 ($CDCl_3$) and 49.00 ($CD_3OD$) ppm] as an internal reference at 298 K (Fulmer et al., 2010). The following abbreviations were used to designate the multiplicities: s=singlet, d=doublet, t=triplet, q=quartet, m=multiplet, b=broad, ap=apparent.

ATR-Infrared (IR) spectra were recorded on a Perkin-Elmer 100 series FT-IR spectrometer. High-resolution mass spectra (HRMS) were recorded on an Agilent LC/MSD/TOIF mass spectrometer using ESI (electrospray ionization) or a Shimadzu Ion Trap-TOF using ESI. Optical rotations were recorded on a POLARTRONIC M100 polarimeter at 589 nm, and are reported in units of $10^{-1}$ (deg $cm^2$ $g^{-1}$).

Example 3—Compound Characterization

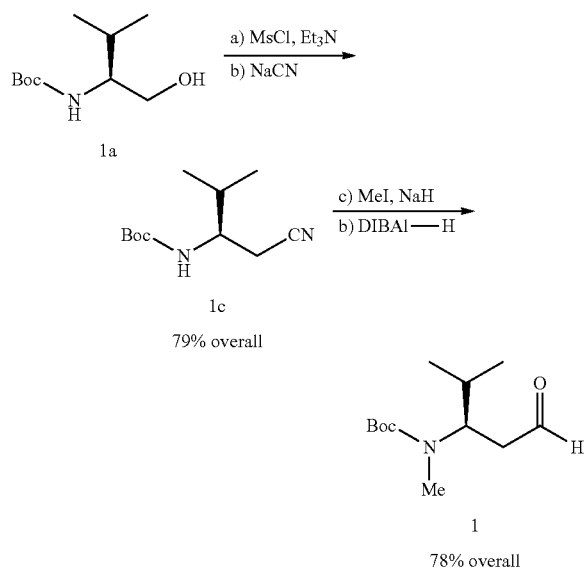

79% overall

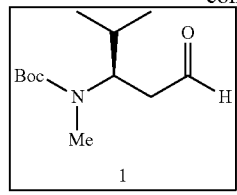

tert-Butyl-(R)-methyl(4-methyl-1-oxopentan-3-yl) carbamate (1)

Aldehyde 1 was synthesized according to a procedure previously reported in the literature (Sohtone, et al., 2010: In, et al., 2007).

To a stirred solution of 1a (5.0 g, 24.6 mmol) in $CH_2Cl_2$ (60 mL) at 0° C. was added $Et_3N$ (6.84 mL, 49.2 mmol) followed by methansulfonyl chloride (2.85 mL, 37.0 mmol). The reaction mixture was allowed to warm to 25° C. and stirred for an additional 30 min. Then the reaction mixture was quenched with a saturated aqueous solution of $NH_4Cl$ (20 mL), and the two phases were separated. The aqueous layer was extracted with $CH_2Cl_2$ (3×20 mL), and the combined organic layer was dried with anhydrous $Na_2SO_4$ and concentrated under reduced pressure to give mesylate 1b. To a stirred solution of mesylate 1b in DMSO (60 mL) at 25° C. was added NaCN (3.6 g, 74.0 mmol). The reaction mixture was heated to 45° C. and stirred for 12 h. The reaction mixture was then allowed to cool to 25° C., diluted with EtOAc (30 mL) and poured into water (30 ml). The aqueous layer was extracted with EtOAc (3×30 mL) and the combined organic layer was washed with brine (3×20 mL). The organic layer was dried with anhydrous $Na_2SO_4$ and concentrated under reduced pressure. The obtained residue was purified by flash column chromatography (silica gel, 10→30% EtOAc in hexanes) to afford pure cyanide 1c (4.1 g, 79% for the two steps) as a yellowish solid. 1c: $R_f$=0.36 (silica gel, 20% EtOAc in hexanes).

To a stirred solution of NaH (60% dispersion in mineral oil, 1.3 g, 37.55 mmol) in DMF (5 mL) at 0° C. was drop wise added solution of 1c (4.0 g, 18.8 mmol) in DMF (30 mL). After stirring for 30 min at the same temperature, methyl iodide (3.5 mL, 56.3 mmol) was added. The reaction mixture was allowed to slowly warm to 25° C. and stirred for an additional 2 h. Then the reaction mixture was quenched with a saturated aqueous solution of $NH_4Cl$ (20 mL). The aqueous layer was extracted with EtOAc (3×30 mL) and the combined organic layer was dried with anhydrous $Na_2SO_4$ and concentrated under reduced pressure. The obtained residue was purified by flash column chromatography (silica gel, 10→30% EtOAc in hexanes) to afford pure cyanide 1d (3.4 g, 80%) as a white solid. 1d: $R_f$=0.37 (silica gel, 20% EtOAc in hexanes).

To a stirred solution of 1d (3.4 g, 15.0 mmol) in $CH_2Cl_2$ (20 mL) at −50° C. was added DIBAl-H (1M in toluene, 50.0 mL, 60.0 mmol). After stirring for 1 h at the same temperature, the reaction mixture was quenched with MeOH (10 mL) and saturated aqueous solution of Na/K tartarate. The reaction mixture was allowed to warm to 25° C. and stirred for an additional 2 h. The reaction mixture was then concentrated under reduce pressure to remove toluene and the aqueous layer was extracted with EtOAc (3×30 mL). The combined organic layer was dried with anhydrous sodium sulfate and concentrated under reduced pressure. The obtained residue was purified by flash column chromatography (silica gel, 10→30% EtOAc in hexanes) to afford pure aldehyde 1 (2.6 g, 76%) as a colorless oil. 1: $R_f$=0.4 (silica gel, 25% EtOAc in hexanes). $^1$H NMR: (CDCl$_3$, 600 MHz) δ=9.76-9.52 (m, 1H), 4.26 (td, J=10.6, 4.2 Hz, 1H), 2.66 (s, 3H), 2.61-2.37 (m, 2H), 1.74 (dq, J=10.3, 6.6 Hz, 1H), 1.40 (d, J=16.1 Hz, 9H), 0.90 (dd, J=11.7, 6.6 Hz, 3H), 0.84 (dd, J=6.7, 2.2 Hz, 3H); $^{13}$C NMR: (CDCl$_3$, 150 MHz) δ=201.4, 156.0, 79.5, 56.6, 44.8, 30.3, 29.0, 28.3, 19.9, 19.4, 19.2; Diagnostic signals of minor rotamer: $^{13}$C NMR: (CDCl$_3$, 150 MHz) δ=200.6, 155.6, 79.9, 57.8, 30.8, 28.8, 28.3, 20.0, 19.2.

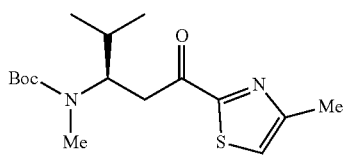

3a tert-Butyl(R)-methyl(4-methyl-1-(4-methylthiazol-2-yl)-1-oxopentan-3-yl)carbamate (3a)

To a stirred solution of aldehyde 1 (115 mg, 0.50 mmol) and 4-methylthiazole 2a (25 mg, 0.25 mmol) in anhydrous benzene (1.0 mL) at 25° C. were added portion-wise over 15 min TMSN$_3$ (0.066 mL, 0.50 mmol) followed by phenyliodinebis(trifluoroacetate) (PIFA, 216 mg, 0.50 mmol). After stirring for 12 h at 25° C., the reaction mixture was cooled to 0° C. and quenched with Et$_3$N (0.2 mL). The solvent was removed under reduced pressure and the obtained residue was purified by flash column chromatography (silica gel, 10→30% EtOAc in hexanes) to produce ketone 3a (52 mg, 63% yield) as a colorless oil. 3a: $R_f$=0.5 (silica gel, 20% EtOAc in hexanes); $[α]_D^{22}$=−4.5 (c=1.0, CHCl$_3$); FT-IR (neat) $\tilde{v}_{max}$: 2964, 2925, 1687, 1434, 1365, 1304, 1170, 1149, 994, 949, 870, 771 cm$^{-1}$; $^1$H NMR: (CDCl$_3$, 600 MHz) δ=7.24-7.18 (m, 1H), 4.40-4.15 (m, 1H), 3.56-3.06 (m, 2H), 2.73 (d, J=6.3 Hz, 3H), 2.52 (d, J=2.1 Hz, 3H), 1.9 (s, 1H), 1.34 (d, J=27.7 Hz, 9H), 1.03 (t, J=6.1 Hz, 3H), 0.89 (d, J=6.6 Hz, 3H); $^{13}$C NMR: (CDCl$_3$, 150 MHz) δ=192.1, 165.9, 155.8, 155.1, 121.4, 79.3, 59.9, 59.1, 40.0, 31.2, 28.2, 20.3, 19.6, 17.2; Diagnostic signals of minor rotamer: $^{13}$C NMR: (CDCl$_3$, 150 MHz) δ=192.3, 155.0, 121.2, 79.0, 39.6, 30.9, 30.1, 28.3, 20.2, 19.5, 17.2; HRMS calcd for C$_{16}$H$_{26}$N$_2$O$_3$S [M+Na$^+$] 349.1562. found 349.1556.

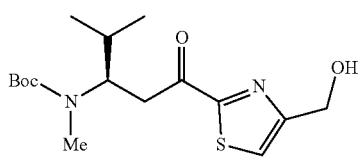

3b tert-Butyl(R)-(1-(4-(hydroxymethyl)thiazol-2-yl)-4-methyl-1-oxopentan-3-yl)(methyl)carbamate (3b)

To a stirred solution of aldehyde 1 (100 mg, 0.43 mmol) and thiazol-4-ylmethanol 2b (25 mg, 0.22 mmol) in anhydrous benzene (1.0 mL) at 25° C. were added portion-wise over 15 min TMSN$_3$ (0.06 mL, 0.43 mmol) followed by phenyliodinebis(trifluoroacetate) (PIFA, 186 mg, 0.43 mmol). Within 10 min the reaction was stopped, the solvent was removed under reduced pressure and the obtained residue was purified by flash column chromatography (silica gel, 10→60% EtOAc in hexanes) to produce ketone 3b (14 mg, 19% yield) as a white amorphous solid. 3b: $R_f$=0.4 (silica gel, 50% EtOAc in hexanes); $[α]_D^{22}$=−2.8 (c=1.0, CHCl$_3$); FT-IR (neat) $\tilde{v}_{max}$: 3424, 2965, 2924, 1685, 1440, 1389, 1366, 1307, 1168, 1148, 1066, 1046, 993, 950, 870, 772 cm$^{-1}$; $^1$H NMR: (CDCl$_3$, 600 MHz) δ=7.52 (d, J=30.6 Hz, 1H), 4.96-4.75 (m, 2H), 4.57-4.01 (m, 1H), 3.65-2.96 (m, 2H), 2.72 (d, J=19.3 Hz, 3H), 2.01-1.76 (m, 1H), 1.56 (brs, 1H), 1.32 (d, J=19.3 Hz, 9H), 1.03 (d, J=6.6 Hz, 3H), 0.88 (dd, J=10.8, 6.6 Hz, 3H); $^{13}$C NMR: (CDCl$_3$, 150 MHz) δ=192.2, 167.0, 158.5, 155.9, 122.1, 79.5, 61.0, 59.1, 40.7, 39.8, 31.2, 28.3, 20.4, 19.7; Diagnostic signals of minor rotamer: $^{13}$C NMR: (CDCl$_3$, 150 MHz) δ=192.3, 166.6, 158.3, 155.8, 121.8, 118.9, 79.2, 61.0, 60.4, 29.8, 29.7, 28.2, 20.1, 19.5, 19.3; HRMS calcd for C$_{16}$H$_{26}$N$_2$O$_4$S [M+Na$^+$] 365.1511. found 365.1494.

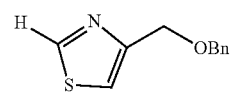

2c 4-((Benzyloxy)methyl)thiazole (2c)

To a stirred solution of thiazol-4-yl-methanol (50 mg, 0.43 mmol) in DMF (1.0 mL) at 0° C. was added NaH (60% dispersion in mineral oil, 26 mg, 0.65 mmol) followed by BnBr (0.077 ml, 0.65 mmol). The reaction mixture was allowed to warm to 25° C. and stirred for an additional 1 h. Then the reaction mixture was quenched with water (10 mL), and the two phases were separated. The aqueous layer was extracted with EtOAc (3×10 mL), and the combined organic layer was dried with anhydrous sodium sulfate and concentrated under reduced pressure. The obtained residue was purified by flash column chromatography (silica gel, 10→40% EtOAc in hexanes) to afford pure compound 2c (78 mg, 88%) as a colorless liquid. 2c: $R_f$=0.45 (silica gel, 30% EtAOc in hexanes); FT-IR (neat) $\tilde{v}_{max}$: 2859, 1454, 1417, 1361, 1093, 1072, 875, 817, 735, 697 cm$^{-1}$; $^1$H NMR: (CDCl$_3$, 600 MHz) δ=8.79 (q, J=1.5 Hz, 1H), 7.46-7.26 (m, 6H), 4.75 (d, J=0.9 Hz, 2H), 4.66 (s, 2H); $^{13}$C NMR: (CDCl$_3$, 150 MHz) δ=154.8, 152.8, 137.8, 128.3, 127.7, 127.6, 115.5, 72.7, 67.8. HRMS calcd for C$_{11}$H$_{11}$NOS [M+H$^+$] 206.0640. found 206.0635.

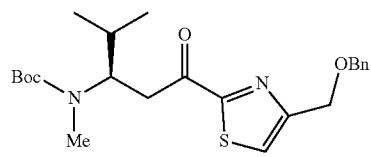

3c tert-butyl (R)-(1-(4-((benzyloxy)methyl)thiazol-2-yl)-4-methyl-1-oxopentan-3-yl)(methyl)carbamate (3c)

To a stirred solution of aldehyde 1 (56 mg, 0.24 mmol) and 4-((benzyloxy)methyl)thiazole 2c (25 mg, 0.12 mmol)

in anhydrous benzene (1.0 mL) at 25° C. were added portion-wise over 15 min TMSN$_3$ (0.03 mL, 0.24 mmol) followed by phenyliodinebis(trifluoroacetate) (PIFA, 104 mg, 0.24 mmol). The reaction mixture was stirred for an additional 1 h at same temperature. The solvent was removed under reduced pressure and the obtained residue was purified by flash column chromatography (silica gel, 10-50% EtOAc in hexanes) to produce ketone 3c (12 mg, 23% yield) as a yellowish oil. 3c: R$_f$=0.4 (silica gel, 30% EtOAc in hexanes); [α]$_D^{22}$=−1.4 (c=1.0, CHCl$_3$); FT-IR (neat) $\tilde{v}_{max}$: 2962, 2923, 2852, 2108, 1686, 1452, 1387, 1364, 1305, 1259, 1169, 1140, 1108, 994, 949, 871, 740, 898 cm$^{-1}$; $^1$H NMR: (CD$_3$OD, 600 MHz) δ=7.85 (d, J=23.3 Hz, 1H), 7.43-7.26 (m, 5H), 4.73 (d, J=3.4 Hz, 2H), 4.67 (d, J=3.5 Hz, 2H), 4.28 (td, J=10.5, 3.6 Hz, 1H), 3.51 (td, J=14.0, 3.8 Hz, 1H), 3.21-3.03 (m, 1H), 2.72 (d, J=6.4 Hz, 3H), 1.98-1.81 (m, 1H), 1.28 (d, J=67.9 Hz, 9H), 1.06 (t, J=6.9 Hz, 3H), 0.87 (dd, J=9.2, 6.6 Hz, 3H); $^{13}$C NMR: (CD$_3$OD, 150 MHz) δ=193.5, 167.8, 157.8, 139.3, 129.4, 129.0, 125.2, 81.1, 73.8, 68.6, 61.8, 60.7, 40.7, 32.2, 28.5, 20.5, 20.1; Diagnostic signals of minor rotamer: $^{13}$C NMR: (CD$_3$OD, 150 MHz) δ=193.7, 167.9, 157.8, 129.6, 128.8, 125.2, 80.7, 73.7, 40.3, 32.0, 28.6, 20.5, 19.9; HRMS calcd for C$_{23}$H$_{32}$N$_2$O$_4$S [M+Na$^+$] 455.1980. found 455.1958.

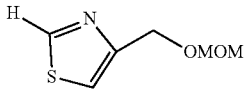

4-((methoxymethoxy)methyl)thiazole (2d)

To a stirred solution of thiazol-4-yl-methanol (50 mg, 0.434 mmol) in THF/DMF (1:1, 2.0 mL) at 0° C. was added NaH (60% dispersion in mineral oil, 18 mg, 0.455 mmol) followed by MOMCl (0.034 ml, 0.45 mmol). The reaction mixture was allowed to warm to 25° C. and stirred for an additional 2 h. Then the reaction mixture was quenched with water (5 mL) and the two phases were separated. The aqueous layer was extracted with EtOAc (3×10 mL), the combined organic layer was dried with anhydrous Na$_2$SO$_4$ and concentrated under reduced pressure. The obtained residue was purified by flash column chromatography (silica gel, 10→50% EtOAc in hexanes) to afford pure compound 2d (65 mg, 94%) as a colorless oil. 2d: R$_f$=0.3 (silica gel, 35% EtAOc in hexanes); FT-IR (neat) $\tilde{v}_{max}$: 2930, 1417, 1149, 1101, 1041, 949, 918, 875, 820 cm$^{-1}$; $^1$H NMR: (CDCl$_3$, 600 MHz) δ=8.71 (dq, J=7.4, 2.6, 2.1 Hz, 1H), 7.22 (dt, J=5.3, 2.6 Hz, 1H), 4.79-4.56 (m, 4H), 3.43-3.19 (m, 3H); $^{13}$C NMR: (CDCl$_3$, 150 MHz) δ=154.2, 152.9, 115.5, 95.7, 64.6, 55.1. HRMS calcd for C$_6$H$_9$NO$_2$S [M+H$^+$] 160.0432. found 160.0425.

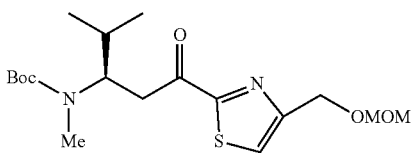

tert-Butyl(R)-(1-(4-((methoxymethoxy)methyl)thi-azol-2-yl)-4-methyl-1-oxopentan-3-yl)(methyl) carbamate (3d)

To a stirred solution of aldehyde 1 (72 mg, 0.31 mmol) and compound 2d (25 mg, 0.16 mmol) in anhydrous benzene (1.0 mL) at 25° C. were added portion-wise over 15 min TMSN$_3$ (0.04 mL, 0.31 mmol) followed by phenyliodinebis (trifluoroacetate) (PIFA, 135 mg, 0.31 mmol). After stirring for 16 h at 25° C., TLC analysis indicated complete consumption of aldehyde 1, while unreacted thiazole compound 2d was still present in the reaction mixture. Consequently, more aldehyde 1 (72 mg, 0.31 mmol), TMSN$_3$ (0.04 mL, 0.31 mmol) and PIFA (135 g, 0.31 mmol) were added portion-wise over 15 min at 25° C. and stirring was continued for an additional 12 h. The reaction mixture was cooled to 0° C. and quenched with Et$_3$N (0.2 mL). The solvent was removed under reduced pressure and the resulting residue was purified by flash column chromatography (silica gel, 10→50% EtOAc in hexanes) to produce ketone 3d (43 mg, 71% yield) as a colorless oil. 3d: R$_f$=0.4 (silica gel, 30% EtOAc in hexanes); [α]$_D^{22}$=−2.4 (c=1.0, CHCl$_3$); FT-IR (neat) $\tilde{v}_{max}$: 2963, 2924, 2110, 1688, 1443, 1366, 1150, 1050, 772 cm$^{-1}$; $^1$H NMR: (CDCl$_3$, 600 MHz) δ=7.57 (d, J=19.8 Hz, 1H), 4.77 (d, J=2.2 Hz, 4H), 4.27 (dt, J=10.4, 5.2 Hz, 1H), 3.43 (s, 3H), 3.38-2.97 (m, 2H), 2.72 (d, J=6.8 Hz, 3H), 1.99-1.77 (m, 1H), 1.33 (d, J=30.9 Hz, 9H), 1.01 (t, J=6.7 Hz, 3H), 0.88 (d, J=6.6 Hz, 3H); $^{13}$C NMR: (CDCl$_3$, 150 MHz) δ=192.1, 166.7, 155.8, 155.5, 123.2 96.1, 79.3, 64.8, 58.9, 55.5, 39.8, 31.1, 29.8, 28.2, 20.2, 19.6; Diagnostic signals of minor rotamer: $^{13}$C NMR: (CDCl$_3$, 150 MHz) δ=192.3, 166.8, 155.8, 155.7, 123.1, 96.1, 79.0, 64.9, 59.8, 39.7, 30.8, 29.7, 28.3, 20.1, 19.5; HRMS calcd for C$_{17}$H$_{30}$N$_2$O$_5$S [M+Na$^+$] 409.1773. found 409.1769.

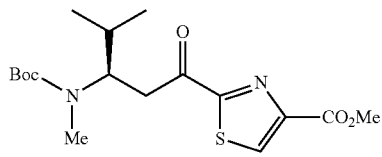

Methyl(R)-2-(3-((tert-butoxycarbonyl)(methyl) amino)-4-methylpentanoyl)thiazole-4-carboxylate (3e)

To a stirred solution of aldehyde 1 (80 mg, 0.35 mmol) and methyl thiazole-4-carboxylate 2e (25 mg, 0.17 mmol) in anhydrous benzene (1.0 mL) at 25° C. were added portion-wise over 15 min TMSN$_3$ (0.05 mL, 0.35 mmol) followed by phenyliodinebis(trifluoroacetate) (PIFA, 150 mg, 0.35 mmol). After stirring for 16 h at 25° C., TLC analysis indicated complete consumption of aldehyde 1, while unreacted methyl thiazole-4-carboxylate 2e was still present in the reaction mixture. Consequently, more aldehyde 1 (80 mg, 0.35 mmol), TMSN$_3$ (0.046 mL, 0.35 mmol) and PIFA (150 mg, 0.35 mmol) were added portion-wise over 15 min at 25° C. and stirring was continued for an additional 12 h. The reaction mixture was cooled to 0° C. and quenched with Et$_3$N (0.2 mL). The solvent was removed under reduced pressure and the resulting residue was purified by flash column chromatography (silica gel, 10→40% EtOAc in hexanes) to produce ketone 3e (7.7 mg, 12% yield) as a colorless oil. 3e: R$_f$=0.35 (silica gel, 25% EtOAc in hexanes); [α]$_D^{22}$=−12.0 (c=1.0, CHCl$_3$); FT-IR (neat) $\tilde{v}_{max}$: 2960, 2921, 2851, 1743, 1690, 1460, 1366, 1335, 1248, 1218, 1145, 995, 770 cm$^{-1}$; $^1$H NMR: (CDCl$_3$, 600 MHz) δ=8.42 (d, J=13.4 Hz, 1H), 4.27 (s, 1H), 3.97 (d, J=4.3 Hz, 3H), 3.66-3.08 (m, 2H), 2.72 (d, J=1.7 Hz, 3H), 1.88 (dt, J=16.5, 7.6 Hz, 1H), 1.34 (d, J=15.0 Hz, 9H), 1.03 (dd, J=16.7, 6.6 Hz, 3H), 0.89 (dd, J=6.7, 2.6 Hz, 3H); $^{13}$C NMR: (CDCl$_3$, 150 MHz) J=192.0, 167.2, 161.2, 155.8, 148.3, 133.4, 79.5, 59.7, 58.8, 52.6, 39.8, 31.1, 28.2, 20.2, 19.6; HRMS calcd for C$_{17}$H$_{26}$N$_2$O$_5$S [M+Na$^+$] 393.1460. found 393.1448.

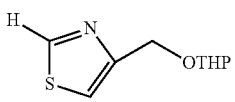

2f 4-(((Tetrahydro-2H-pyran-2-yl)oxy)methyl)thiazole (2f)

To a stirred solution of thiazol-4-yl-methanol (50 mg, 0.43 mmol) and 3,4-dihydro-2H-pyran (0.043 mL, 0.48 mmol) in CH$_2$Cl$_2$ (4 mL) at 0° C. was added TsOH (8.0 mg, 0.043 mmol). The reaction mixture was allowed to warm to 25° C. and stirred for an additional 3 h. Then the reaction mixture was quenched with water (10 mL) and the two phases were separated. The aqueous layer was extracted with CH$_2$Cl$_2$ (3×20 mL), and the combined organic layer were dried with anhydrous sodium sulfate and concentrated under reduced pressure. The obtained residue was purified by flash column chromatography (silica gel, 10→50% EtOAc in hexanes) to afford compound 2f (73 mg, 84%) as a colorless oil. 2f: R$_f$=0.3 (silica gel, 30% EtAOc in hexanes); FT-IR (neat) $\tilde{v}_{max}$: 2940, 1200, 1118, 1068, 1033, 947, 905, 872, 814 cm$^{-1}$; $^1$H NMR: (CDCl$_3$, 600 MHz) δ=8.76 (d, J=2.1 Hz, 1H), 7.27 (d, J=2.0 Hz, 1H), 4.91 (d, J=12.7 Hz, 1H), 4.75 (t, J=3.6 Hz, 1H), 4.68 (d, J=12.7 Hz, 1H), 3.89 (ddd, J=11.4, 8.6, 2.9 Hz, 1H), 3.63-3.42 (m, 1H), 1.90-1.46 (m, 6H); $^{13}$C NMR: (CDCl$_3$, 150 MHz) (5=154.8, 152.9, 115.4, 98.1, 64.7, 62.0, 30.4, 25.3, 19.2. HRMS calcd for C$_9$H$_{13}$NO$_2$S [M+Na$^+$] 222.0565. found 222.0559.

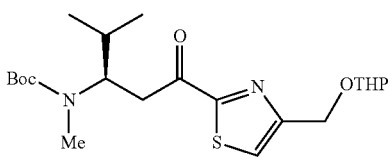

3f tert-Butyl-methyl((3R)-4-methyl-1-oxo-1-(4-(((tetrahydro-2H-pyran-2-yl)oxy)methyl)thiazol-2-yl)pentan-3-yl)carbamate (31)

To a stirred solution of aldehyde 1 (57 mg, 0.25 mmol) and compound 2f (25 mg, 0.12 mmol) in anhydrous benzene (1.0 mL) at 25° C. were added portion-wise over 15 min TMSN$_3$ (0.03 mL, 0.251 mmol) followed by phenyliodinebis(trifluoroacetate) (PIFA, 108 mg, 0.25 mmol). After stirring for 10 h at 25° C., the reaction mixture was cooled to 0° C. and quenched with Et$_3$N (0.2 mL). The solvent was removed under reduced pressure and the obtained residue was purified by flash column chromatography (silica gel, 10→30% EtOAc in hexanes) to produce ketone 3f (29 mg, 55% yield) as a colorless oil. 3f: R$_f$=0.5 (silica gel, 20% EtOAc in hexanes); [α]$_D^{22}$=−1.2 (c=1.0, CHCl$_3$); FT-IR (neat) $\tilde{v}_{max}$: 2961, 2925, 2107, 1690, 1443, 1388, 1365, 1260, 1139, 1037, 949, 871, 772 cm$^{-1}$; $^1$H NMR: (CDCl$_3$, 600 MHz) δ=7.57 (d, J=18.8 Hz, 1H), 4.93 (dd, J=13.2, 1.2 Hz, 1H), 4.79 (q, J=3.5 Hz, 1H), 4.71 (dt, J=13.0, 3.5 Hz, 1H), 4.31-4.16 (m, 1H), 3.96-3.82 (m, 1H), 3.57 (dt, J=11.3, 4.3 Hz, 1H), 3.32 (td, J=12.7, 10.9, 4.8 Hz, 1H), 2.72 (d, J=7.2 Hz, 3H), 1.95-1.52 (m, 8H), 1.33 (dd, J=30.0, 2.5 Hz, 9H), 1.02 (t, J=6.1 Hz, 3H), 0.88 (d, J=6.7 Hz, 3H); $^{13}$C NMR: (CDCl$_3$, 150 MHz) δ=192.1, 166.6, 156.4, 155.8, 122.8, 98.3, 79.4, 64.9, 62.1, 59.9, 39.9, 31.2, 30.4, 29.7, 28.2, 25.4, 20.3, 19.6, 19.2; Diagnostic signals of minor rotamer; $^{13}$C NMR: (CDCl$_3$, 150 MHz) δ=192.3, 166.7, 156.4, 155.8, 122.8, 98.2, 79.5, 64.8, 62.1, 59.1, 39.9, 30.9, 30.4, 28.3, 20.2, 19.6, 19.2; HRMS calcd for C$_{21}$H$_{34}$N$_2$O$_5$S [M+Na$^+$] 449.2086. found 449.2093.

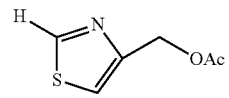

2

Thiazol-4-ylmethyl acetate (2)

To a stirred solution of thiazol-4-yl-methanol (1.0 g, 8.7 mmol), Et$_3$N (4.8 mL, 34.4 mmol) and DMAP (0.106 g, 0.87 mmol) in CH$_2$Cl$_2$ (15 mL) at 0° C. was added acetic anhydride (2.46 mL, 26.05 mmol). The reaction mixture was allowed to warm to 25° C. and stirred for an additional 1 h. Then the reaction mixture was quenched with water (10 mL) and the two phases were separated. The aqueous layer was extracted with CH$_2$Cl$_2$ (3×20 mL), the combined organic layer was dried with anhydrous Na$_2$SO$_4$ and concentrated under reduced pressure. The obtained residue was purified by flash column chromatography (silica gel, 10→40% EtOAc in hexanes) to afford pure acetate 2 (1.35 g, 99%) as a colorless liquid. 2: R$_f$=0.45 (silica gel, 40% EtAOc in hexanes); FT-IR (neat) $\tilde{v}_{max}$: 3111, 2954, 1732, 1523, 1440, 1416, 1376, 1330, 1226, 1138, 1027, 971, 932, 876, 821, 738 cm$^{-1}$; $^1$H NMR: (CDCl$_3$, 600 MHz) δ=8.74 (s, 1H), 7.29 (s, 1H), 5.19 (s, 2H), 2.03 (s, 3H) ppm; $^{13}$C NMR: (CDCl$_3$, 150 MHz) δ=170.3, 153.1, 151.8, 117.2, 61.2, 20.6 ppm; HRMS calcd for C$_6$H$_7$NO$_2$S [M+Na$^+$] 180.0090. found 180.0089.

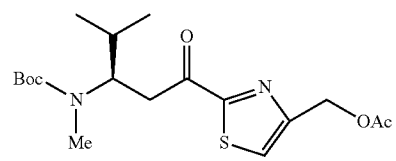

3

(R)-(2-(3-((tert-Butoxycarbonyl)(methyl)amino)-4-methylpentanoyl)thiazol-4-yl)methyl acetate (3)

To a stirred solution of aldehyde 1 (1.46 g, 6.36 mmol) and thiazole 2 (0.5 g, 3.18 mmol) in anhydrous benzene (23 mL) at 25° C. were added portion-wise over 15 min TMSN$_3$ (0.84 mL, 6.36 mmol) followed by phenyliodinebis(trifluoroacetate) (PIFA, 2.7 g, 6.36 mmol). After stirring for 16 h at 25° C., TLC analysis indicated complete consumption of aldehyde 1, while unreacted thiazole 2 was still present in the reaction mixture. Consequently, more aldehyde 1 (1.46 g, 6.36 mmol), TMSN$_3$ (0.84 mL, 6.36 mmol) and PIFA (2.7 g, 6.36 mmol) were added portion-wise over 15 min at 25° C. and stirring was continued for an additional 12 h. The reaction mixture was cooled to 0° C. and quenched with Et$_3$N (7.0 mL). The solvent was removed under reduced pressure and the resulting residue was purified by flash column chromatography (silica gel, 10→25% EtOAc in hexanes) to produce ketone 3 (0.99 g, 81% yield) as a colorless oil. 3: $R_f$=0.65 (silica gel, 40% EtOAc in hexanes); $[\alpha]_D^{22}$=+2.7 (c=1.0, CH$_2$Cl$_2$); FT-IR (neat) $\tilde{\nu}_{max}$: 2969, 2930, 2878, 2108, 1745, 1687, 1442, 1388, 1365, 1306, 1223, 1148, 1031, 995, 872, 772 cm$^{-1}$; $^1$H NMR analysis at ambient temperature indicated a ca. 1.7:1 mixture of rotamers. Major rotamer: $^1$H NMR: (CDCl$_3$, 600 MHz) δ=7.61 (s, 1H), 5.26 (s, 2H), 4.27-4.23 (m, 1H), 3.51 (dd, J=14.4, 3.6 Hz, 1H), 3.32-3.26 (m, 1H), 2.72 (s, 3H), 2.13 (s, 3H), 1.90-1.85 (m, 1H), 1.30 (s, 9H), 1.02 (d, J=6.6 Hz, 3H), 0.88 (d, J=Hz, 3H) ppm; $^{13}$C NMR: (CDCl$_3$, 150 MHz) δ=192.3, 170.6, 167.1, 155.9, 153.4, 124.8, 79.5, 61.7, 60.1, 40.0, 31.3, 28.4, 21.0, 20.4, 19.7 ppm; Diagnostic signals of the Minor rotamer: $^1$H NMR: (CDCl$_3$, 600 MHz) δ=7.58 (s, 1H), 5.26 (s, 3H), 4.27-4.23 (m, 1H), 3.32-3.29 (m, 1H), 3.10 (dd, 1H, J=13.8, 10.8 Hz), 2.72 (s, 3H), 1.90-1.85 (m, 1H), 1.35 (s, 6H), 1.01 (d, 3H, J=6.0 Hz), 0.88 (d, 3H, J=6.0 Hz) ppm; $^{13}$C NMR: (CDCl$_3$, 150 MHz) δ=192.1, 170.6, 162.0, 155.8, 153.2, 124.6, 79.2, 61.6, 59.2, 39.6, 31.0, 28.3, 20.9, 20.3, 19.6; HRMS calcd for C$_{18}$H$_{28}$N$_2$O$_5$S [M+Na$^+$] 407.1611. found 407.1594.

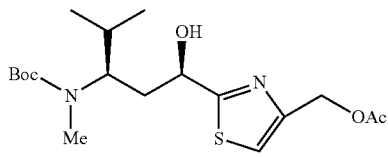

(2-((1R,3R)-3-((tert-Butoxycarbonyl) (methyl) amino)-1-hydroxy-4-methylpentyl)thiazol-4-yl) methyl acetate (4)

To an ice-cooled stirred solution of (S)—CBS catalyst (1.0 M in THF, 0.36 mL, 0.36 mmol) in THF (13.5 mL) was added BH$_3$.SMe$_2$ (2.0 M in THF, 0.91 mL, 1.82 mmol) and stirring was continued for 10 min at 0° C. Then, a solution of ketone 3 (0.7 g, 1.82 mmol) in THF (5.6 mL) was added dropwise to the reaction mixture and stirring was continued for 18 h while the temperature gradually increased to 25° C. The reaction was quenched with MeOH (10 mL) and the solvent was removed under reduced pressure. The resulting residue was purified using flash column chromatography (silica gel, 10→30% EtOAc in hexanes) to furnish alcohol 4 (0.58 g, 82% yield) as a colorless oil. 6: $R_f$=0.57 (silica gel, 40% EtOAc in hexanes); $[\alpha]_D^{22}$=−2.65 (c=2.0, CH$_2$Cl$_2$); FT-IR (neat) $\tilde{\nu}_{max}$: 3383, 2968, 2932, 1742, 1686, 1657, 1480, 1446, 1388, 1366, 1350, 1311, 1223, 1154, 1051, 1029, 982, 952, 866, 775 cm$^{-1}$; $^1$H NMR: (CDCl$_3$, 600 MHz) δ=7.22 (s, 3H), 5.15 (dd, J=24, 12 Hz, 2H), 5.04 (s, 1H), 4.69 (d, J=10.8 Hz, 1H), 2.73 (s, 3H), 2.09 (s, 3H), 2.07-2.02 (m, 1H), 1.93-1.88 (m, 1H), 1.76-1.71 (m, 1H), 1.46 (s, 9H), 0.94 (d, J=6.6 Hz, 3H), 0.89 (d, J=6.6 Hz, 3H) ppm; $^{13}$C NMR: (CDCl$_3$, 150 MHz) δ=175.9, 170.8, 158.6, 150.6, 117.8, 80.7, 69.2, 61.9, 57.9, 37.9, 29.8, 28.6, 28.5, 28.4, 28.3, 21.1, 20.3, 20.2 ppm; HRMS calcd for C$_{18}$H$_{30}$N$_2$O$_5$S [M+Na$^+$] 387.1948. found 387.1934.

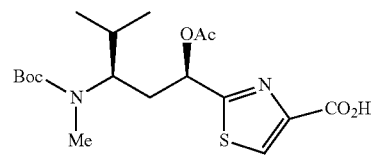

2-((1R,3R)-1-Acetoxy-3-((tert-butoxycarbonyl) (methyl)amino)-4-methylpentyl)thiazole-4-carboxylic Acid (5)

To a stirred solution of alcohol 4 (0.6 g, 1.55 mmol) in methanol (160 mL) at 25° C. was added K$_2$CO$_3$ (0.86 g, 6.2 mmol). The reaction mixture was stirred for 3 h at the same temperature and then quenched with saturated aqueous NH$_4$Cl solution (10 mL). The organic solvent was evaporated under reduced pressure and the remaining aqueous phase was extracted with EtOAc (3×25 mL). The combined organic layer was washed with brine (10 mL) and dried over Na$_2$SO$_4$. The solvent was evaporated and the obtained residue was purified using flash column chromatography (silica gel, 30→70% EtOAc in hexanes) to furnish the corresponding diol 5a (0.49 g, 1.44 mmol, 93% yield) as a colorless oil: $R_f$=0.24 (silica gel, 50% EtOAc in hexanes); $[\alpha]_D^{22}$=−10.3 (c=2.0, CH$_2$Cl$_2$); FT-IR (neat) $\tilde{\nu}_{max}$: 3365, 2968, 2931, 2874, 1655, 1478, 1446, 1391, 1365, 1350, 1310, 1256, 1151, 1062, 954, 866, 736 cm$^{-1}$; $^1$H NMR: (CDCl$_3$, 600 MHz) δ=7.11 (s, 1H), 5.07 (s, 1H), 4.70-4.66 (m, 2H), 3.92 (t, J=10.8 Hz, 1H), 3.57 (bs, 1H), 2.72 (s, 3H), 2.03-1.99 (m, 1H), 1.87 (t, J=12 Hz, 1H), 1.72-1.68 (m, 1H), 1.45 (s, 9H), 0.92 (d, J=6 Hz, 3H), 0.88 (d, J=6.6 Hz, 3H) ppm; $^{13}$C NMR: (CDCl$_3$, 150 MHz) δ=176.2, 158.5, 155.7, 114.7, 80.6, 60.6, 57.9, 38.0, 29.8, 28.6, 28.5, 28.3, 20.2 ppm; HRMS calcd for C$_{16}$H$_{28}$N$_2$O$_4$S [M+H$^+$] 345.1843. found 345.1830.

To a stirred solution of the diol 5a (0.6 g, 1.74 mmol) in CH$_2$Cl$_2$ (17.4 mL) at 25° C. was added TEMPO (0.26 g, 0.17 mmol) followed by bis(acetoxy)iodobenzene (BAIB, 0.56 g, 1.74 mmol). After stirring for 16 h at the same temperature, TLC analysis indicated the disappearance of starting material. The reaction mixture was quenched with aqueous Na$_2$S$_2$O$_3$ solution (10 mL), and extracted with CH$_2$Cl$_2$ (3×30 mL). The combined organic phase was washed with saturated aqueous NaHCO$_3$ solution (10 mL) and dried over Na$_2$SO$_4$. The solvent was evaporated under reduced pressure and the resulting crude aldehyde was purified by flash column chromatography (silica gel, 10→30% EtOAc in hexanes) to give the corresponding hydroxy-aldehyde 5b (0.57 g, 1.67 mmol, 96% yield) as a colorless oil: $R_f$=0.38 (silica gel, 30% EtOAc in hexanes); $[\alpha]_D^{22}$=−13.3 (c=1.0, CH$_2$Cl$_2$); FT-IR (neat) $\tilde{\nu}_{max}$: 3374, 3093, 2969, 2931, 2874, 1692, 1655, 1484, 1448, 1393, 1365, 1349, 1311, 1258, 1154, 1134, 1077, 968, 866, 765, 750 cm$^{-1}$; $^1$H NMR analysis at ambient temperature revealed a ca. 7:1 mixture of rotamers. Major rotamer: $^1$H NMR: (CDCl$_3$, 600 MHz) δ=9.96 (s, 1H), 8.14 (s, 1H), 5.22 (s, 1H), 4.71 (dd, J=10.8, 1.8 Hz, 1H), 3.97-3.92 (m, 1H), 2.74 (s, 3H), 2.15-2.11 (m, 1H), 1.94-1.89 (m, 1H), 1.78-1.72 (m, 1H), 1.47 (s, 9H), 0.94 (d, J=6 Hz, 3H), 0.91 (d, J=6 Hz, 3H) ppm; $^{13}$C NMR:

(CDCl$_3$, 150 MHz) δ=184.6, 177.3, 158.7, 154.9, 129.3, 80.9, 69.1, 57.9, 37.7, 29.8, 28.5, 28.3, 20.2 ppm; Diagnostic signals of the minor rotamer: $^1$H NMR: (CDCl$_3$, 600 MHz) δ=9.9 (s, 1H), 8.14 (s, 1H), 2.77 (s, 3H), 1.51 (s, 9H); $^{13}$C NMR: (CDCl$_3$, 150 MHz) δ=28.6, 20.3. HRMS calcd for C$_{16}$H$_{26}$N$_2$O$_1$S [M+Na$^+$] 365.1505. found 365.1501.

To a stirred solution of the aldehyde 5b (0.5 g, 1.46 mmol) in t-BuOH (35 mL) at 25° C. were consecutively added a solution of 2-methyl-2-butene (1.1 mL, 10.9 mmol) in THF (5.5 mL), followed by a solution of NaClO$_2$ (0.7 g, 7.84 mmol) and NaH$_2$PO$_4$.H$_2$O (2.4 g, 17.7 mmol) in H$_2$O (18 mL) and stirring was continued for 12 h at 25° C. The reaction mixture was then diluted with aqueous HCl (1N, 40 mL) and the resulting solution was extracted with ethyl acetate (3×100 mL). The combined organic layers were dried over Na$_2$SO$_4$ and evaporated under reduced pressure to furnish the desired acid 5c (0.52 g, 1.46 mmol, quantitative) which was used in the next step without further purification.

To an ice-cooled stirred solution of the crude acid 5c (0.52 g, 1.46 mmol) and pyridine (0.4 mL, 4.6 mmol) in CH$_2$Cl$_2$ (15 mL) was added acetic anhydride (0.42 mL, 4.4 mmol) dropwise. The reaction mixture was stirred for 15 h while allowing the temperature to slowly rise to 25° C. The solvent was evaporated under reduced pressure and the obtained residue was purified by flash column chromatography (silica gel, 5% MeOH in CH$_2$Cl$_2$ with 1% AcOH) to give acid 5 (0.43 g, 74% yield) as a colorless oil. 5: [α]$_D^{22}$=+5.1 (c=1.0, CHCl$_3$); FT-IR (neat) ν$_{max}$: 2971, 2931, 1713, 1689, 1369, 1217, 1156, 1043, 731; R$_f$=0.3 (silica gel, 10% MeOH in CH$_2$Cl$_2$); $^1$H NMR: (CDCl$_3$, 600 MHz) δ=8.24 (d, J=6.2 Hz, 1H), 5.88 (dd, J=11.5, 3.0 Hz, 1H), 4.08 (td, J=11.4, 3.7 Hz, 1H), 2.69 (s, 3H), 2.32 (ddd, J=15.1, 11.5, 3.7 Hz, 1H), 2.16 (d, J=2.3 Hz, 3H), 2.14 (t, J=3.0 Hz, 1H), 1.77-1.63 (m, 1H), 1.43 (d, J=3.2 Hz, 9H), 0.97 (dd, J=6.6, 1.8 Hz, 3H), 0.88-0.83 (m, 3H); $^{13}$C NMR: (CDCl$_3$, 150 MHz) δ=177.1, 170.2, 164.4, 156.4, 146.2, 129.1, 79.6, 69.4, 56.4, 34.7, 30.4, 29.7, 28.4, 20.8, 20.0, 19.6 ppm; Diagnostic signals of minor rotamer; $^{13}$C NMR: (CDCl$_3$, 150 MHz) δ=171.8, 169.6, 164.0, 156.5, 146.4, 129.5, 80.1, 70.4, 21.0, 19.7, 14.1. HRMS calcd for C$_{18}$H$_{29}$N$_2$O$_6$S [M+H$^+$] 401.1746. found 401.1752.

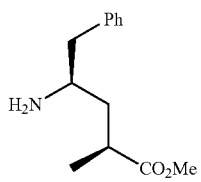

6

Methyl (2S,4R)-4-amino-2-methyl-5-phenylpentanoate (6)

Compound 6 was synthesized in two steps. At First, methyl (2S,4R)-4-(((S)-tert-butylsulfinyl)amino)-2-methyl-5-phenylpentanoate was generated according to a procedure previously reported in the literature (Shankar, et al., 2013). Consequently, an ice-cooled stirred solution of the obtained sulfinimine in MeOH (0.1 M) was treated with 4(M) HCl in dioxane (10.0 equiv) and the reaction mixture was stirred for 12 h while warming up to ambient temperature. Evaporation of the volatile components under reduced pressure and trituration of resulting crude product with ether provided 6 as its HCl salt (40% for the two steps) as a white solid. The spectral data of 6 matched with those previously reported in the literature (Peltier, et al., 2006).

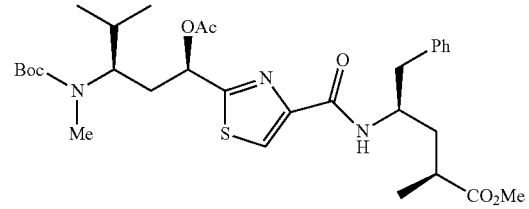

7

Methyl (2S,4R)-4-(2-((1R,3R)-1-acetoxy-3-((tert-butoxycarbonyl)(methyl)amino)-4-methylpentyl) thia-zole4-carboxamido)-2-methyl-5-phenylpentano-ate (7)

To a stirred solution of 5 (0.2 g, 0.49 mmol) and Et$_3$N (0.27 mL, 1.96 mmol) in THF (10 mL), at −20° C., was added dropwise isobutyl chloroformate (0.11 ml, 0.88 mmol) and stirring was continued at the same temperature for 30 minutes. A pre-cooled (−20° C.) solution of 6 (0.23 g, 1.04 mmol) in THF (4.6 ml) was then cannulated to the above reaction mixture and stirring was continued for 24 h while allowing the temperature to slowly rise to 25° C. The reaction mixture was diluted with ethyl acetate (50 mL) and the resulting solution was washed with brine (5 mL), dried over Na$_2$SO$_4$ and concentrated. The obtained residue was purified by flash column chromatography (silica gel, 2→40% EtOAc in hexanes) to furnish 7 (0.27 g, 0.45 mmol, 91% yield) as a light yellow amorphous solid.

Alternatively, to a stirred solution of 5 (100 mg, 0.25 mmol) in dry DMF (2.0 ml) at 0° C. were added HATU (285 mg, 0.75 mmol) followed by Et$_3$N (0.2 ml, 1.5 mmol) and the resulting mixture was stirred for 5 min at the same temperature. A solution of 6 (83 mg, 0.375 mmol) in dry DMF (0.5 ml) was then added and the stirring was continue for 24 h while allowing the temperature to slowly rise to 25° C. The reaction mixture was diluted with H$_2$O (5 mL) and the resulting solution was extracted with EtOAc (3×20 mL). The combined organic extracts were washed with brine (5 mL), dried over Na$_2$SO$_4$ and evaporated under reduced pressure. The obtained residue was purified by flash column chromatography (silica gel, 10→50% EtOAc in hexanes) to furnish 7 (111 mg, 74%) as a light yellow amorphous solid.

7: R$_f$=0.52 (silica gel, 50% EtOAc in hexanes); [α]$_D^{22}$=+11.5 (c=2.0, CH$_2$Cl$_2$); FT-IR (neat): 3394, 2970, 2931, 1736, 1686, 1541, 1492, 1367, 1255, 1220, 1157, 1086, 1046, 934, 785 cm$^{-1}$. $^1$H NMR analysis at ambient temperature indicated a ca. 7:1 mixture of rotamers. Major rotamer: $^1$H NMR: (CDCl$_3$, 600 MHz) δ=8.05 (s, 1H), 7.33-7.25 (m, 5H), 7.15 (d, 1H, J=8.4 Hz), 5.98-5.83 (m, 1H), 4.45 (s, 1H), 4.12 (t, 1H, J=12 Hz), 3.67 (s, 3H), 3.00-2.90 (m, 2H), 2.76 (s, 3H), 2.66-2.63 (m, 1H), 2.36-2.31 (m, 1H), 2.20 (s, 3H), 2.08-2.03 (m, 2H), 1.78-1.61 (m, 2H), 1.48 (s, 9H), 1.19 (d, 3H, J=6.6 Hz), 1.04-1.01 (m, 3H), 0.93-0.91 (m, 3H) ppm; $^{13}$C NMR: (CDCl$_3$, 150 MHz) δ=176.7, 170.2, 169.5, 160.5, 156.3, 150.0, 137.6, 129.6, 128.4, 126.6, 123.4, 79.5, 70.8, 69.3, 56.5, 51.8, 48.4, 41.2, 37.8, 36.5, 35.1, 30.5, 28.4, 20.9, 20.1, 19.7, 17.8 ppm; Diagnostic signals of minor rotamer: $^1$H NMR: (CDCl$_3$, 600 MHz) δ=2.70 (s, 3H), 2.21 (s, 3H). $^{13}$C NMR: (CDCl$_3$, 150 MHz) δ=176.6, 170.2, 160.4, 150.2, 137.7, 129.5, 128.4, 126.5, 123.2, 79.9, 51.8, 48.5, 41.4, 37.9, 35.6, 30.6, 28.5, 28.4, 21.1, 20.4, 19.8, 17.9 ppm; HRMS calcd for $C_{31}H_{15}N_3NaO_7S$ [M+Na$^+$] 626.2870. found 626.2867.

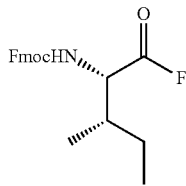

(9H-Fluoren-9-yl)methyl ((2S,3S)-1-fluoro-3-methyl-1-oxopentan-2-yl)carbamate (8)

Compound 8 was synthesized according to a procedure previously reported in the literature (Wipf and Wang, 2007). $[\alpha]_D^{22}$=+12.6 (c=0.1, CHCl$_3$); FT-IR (neat) $\tilde{v}_{max}$: 3322, 2967, 1842, 1699, 1516, 1450, 1332, 1252, 1080, 1035, 758, 737; $^1$H NMR: (CDCl$_3$, 600 MHz) δ=7.78 (d, J=7.5 Hz, 2H), 7.64-7.53 (m, 2H), 7.41 (t, J=7.2 Hz, 2H), 7.33 (t, J=7.5 Hz, 2H), 5.21 (d, J=8.9 Hz, 1H), 4.50 (dd, J=38.6, 5.9 Hz, 3H), 4.24 (t, J=6.8 Hz, 1H), 1.98 (dt, J=12.0, 5.7 Hz, 1H), 1.58-1.35 (m, 1H), 1.27 (dt, J=13.5, 6.9 Hz, 1H), 1.09-0.78 (m, 6H); $^{13}$C NMR: (CDCl$_3$, 150 MHz) δ=163.6, 161.1, 155.9, 143.5, 141.3, 127.8, 127.1, 124.9, 120.0, 67.3, 57.7, 57.3, 47.1, 37.1, 25.0, 15.5, 11.4.

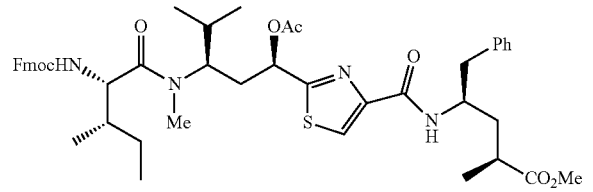

Methyl(2S,4R)-4-(2-((5S,8R,10R)-5-((S)-sec-butyl)-1-(9H-fluoren-9-yl)-8-isopropyl-7-methyl-3,6,12-trioxo-2,11-dioxa-4,7-diazatridecan-10-yl)thiazole-4-carboxamido)-2-methyl-5-phenylpenta-noate (9)

To an ice-cooled stirred solution of 7 (0.1 g, 0.16 mmol) in CH$_2$Cl$_2$ (4 mL) was added trifluoroacetic acid (0.55 mL, 7.2 mmol) and the reaction mixture was stirred for 3 h while warming up to 25° C. Evaporation of the volatile components under reduced pressure furnished the crude TFA-ammonium salt (96 mg, 0.16 mmol, quantitative), which was used for the following step without further purification.

To a stirred, ice-cooled solution of crude ammonium salt from the previous step and i-Pr$_2$NEt (0.17 mL, 0.99 mmol) in DMF (0.68 mL) was added dropwise a solution of Fmoc-Ile-F$^4$ (8, 0.23 g, 0.66 mmol) in DMF (0.3 mL) and stirring was continued for 18 h at 25° C. The reaction mixture was diluted with ethyl acetate (10 mL), washed with saturated aqueous NaHCO$_3$ solution (10 mL) and brine (10 mL), dried over Na$_2$SO$_4$ and concentrated under reduced pressure. The obtained residue was purified by flash column chromatography (silica gel, 20%→40% EtOAc in hexanes) to provide 9 (0.12 g, 0.15 mmol, 92% yield) as a white amorphous solid. 9: R$_f$=0.43 (silica gel, 50% EtOAc in hexanes); $[\alpha]_D^{22}$=+4.5 (c=1.0, CH$_2$Cl$_2$); FT-IR (neat) $\tilde{v}_{max}$: 3394, 3288, 3063, 2964, 2876, 1718, 1639, 1539, 1494, 1450, 1409, 1370, 1219, 1081, 1032, 935, 852, 804 cm$^{-1}$; $^1$H NMR: (CDCl$_3$, 600 MHz) δ=8.00 (s, 1H), 7.74 (d, J=7.6 Hz, 2H), 7.56 (dd, J=7.5, 4.1 Hz, 2H), 7.38 (t, J=7.5 Hz, 2H), 7.27 (dt, J=14.4, 7.4 Hz, 5H), 7.22-7.16 (m, 3H), 7.08 (d, J=9.3 Hz, 1H), 5.62 (dd, J=11.5, 2.5 Hz, 1H), 5.42 (d, J=9.6 Hz, 1H), 4.53 (dd, J=9.8, 6.8 Hz, 1H), 4.40-4.27 (m, 3H), 4.19 (t, J=7.2 Hz, 1H), 3.61 (s, 3H), 2.97 (s, 3H), 2.94 (dd, J=14.0, 6.1 Hz, 1H), 2.87 (dd, J=13.8, 6.6 Hz, 1H), 2.63-2.53 (m, 1H), 2.31 (ddd, J=14.9, 11.4, 3.1 Hz, 1H), 2.16 (s, 3H), 2.07-1.91 (m, 2H), 1.74 (td, J=6.5, 3.2 Hz, 3H), 1.59 (ddt, J=14.0, 8.9, 4.1 Hz, 2H), 1.14 (d, J=7.1 Hz, 3H), 1.01 (d, J=6.5 Hz, 3H), 0.97 (d, J=6.7 Hz, 3H), 0.91 (t, J=7.4 Hz, 3H), 0.80 ppm (d, J=6.6 Hz, 3H) ppm; $^{13}$C NMR: (CDCl$_3$, 150 MHz) δ=176.9, 173.9, 170.4, 170.3, 160.6, 156.7, 150.3, 144.3, 144.1, 141.7, 141.6, 137.8, 129.9, 128.7, 128.0, 127.4, 126.9, 125.5, 125.4, 123.8, 120.3, 69.9, 67.4, 56.1, 52.1, 48.6, 47.5, 41.4, 38.0, 37.7, 36.8, 35.0, 30.3, 30.0, 24.2, 21.1, 20.4, 19.9, 18.0, 16.3, 11.6 ppm; HRMS calcd for $C_{47}H_{58}N_4NaO_8S$ [M+Na$^+$] 861.3863. found 861.3837.

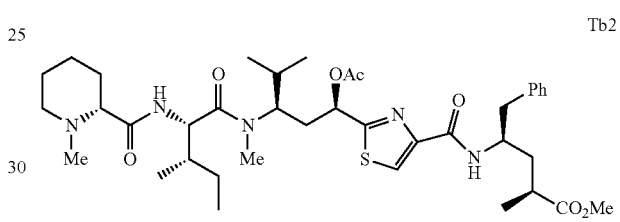

Methyl (2S,4R)-4-(2-((1R,3R)-1-acetoxy-3-((2S,3S)—N,3-dimethyl-2-((R)-1-methylpiperidine-2-carbo-xamido)pentanamido)-4-methylpentyl)thiazole-4-carboxamido)-2-methyl-5-phenylpentanoate (Tb2)

To an ice-cooled stirred solution of Fmoc-derivative 9 (50 mg, 0.059 mmol) in CH$_2$Cl$_2$ (1.49 mL) was added tris(2-aminoethyl)amine (0.14 mL, 0.98 mmol). The reaction mixture was stirred for 3 h at 25° C. and then diluted with ethyl acetate (20 mL). The solution was washed with saturated aqueous NaHCO$_3$ solution (10 mL) and brine (10 mL), dried over Na$_2$SO$_4$, and concentrated. The crude amine so obtained (0.036 g, 0.059 mmol, quantitative) was used for the next step without further purification.

To an ice-cooled stirred solution of N-methyl-(D)-pipecolinic acid 10 (25 mg, 0.175 mmol) in DMF (2.0 ml) at 0° C. was added HATU (67 mg, 0.175 mmol) followed by above obtained crude amine (36 mg, 0.058 mmol) and Et$_3$N (0.049 ml, 0.350 mmol) and the reaction mixture was stirred at 25° C. for 24 h. The reaction mixture was diluted with H$_2$O (5 mL) and the resulting solution was extracted with EtOAc (3×10 mL). The combined organic extracts were washed with saturated aqueous NaHCO$_3$ solution (5 mL) and brine (5 mL), dried over Na$_2$SO$_4$ and evaporated under reduced pressure. The obtained residue was purified by flash column chromatography (silica gel, 5→10% MeOH in CH$_2$Cl$_2$) to furnish Tb2 (0.027 g, 62% yield) as a white amorphous solid. Tb2: $[\alpha]_D^{22}$=−6.6 (c=0.33, MeOH); R$_f$=0.71 (silica gel, 5% MeOH in CH$_2$Cl$_2$); FT-IR (neat) $\tilde{v}_{max}$: 3389, 2919, 2850, 1736, 1639, 1540, 1492, 1463, 1410, 1371, 1218, 1115, 1083, 1036 cm$^{-1}$; $^1$H NMR: (CD$_3$OD, 600 MHz) δ=8.08 (s, 1H), 7.26-7.22 (m, 4H), 7.18-7.16 (m, 1H), 5.70 (dd, J=6.12 Hz, 1H), 4.75 (d, J=8.4 Hz, 1H), 4.50-4.47 (m, 1H), 4.38-4.33 (m, 1H), 3.58 (s, 3H), 3.11 (s, 3H), 2.97-2.89 (m, 3H), 2.88-2.84 (m, 2H), 2.63-2.58 (m, 1H), 2.25-2.23 (m, 1H), 2.21 (s, 3H), 2.15 (s, 3H), 2.11-2.08 (m, 1H), 2.00-1.95 (m, 1H), 1.89-1.81 (m, 2H), 1.79-1.73 (m, 2H), 1.68-1.52 (m, 5H), 1.20-1.17 (m, 1H), 1.14 (d, J=7.2 Hz, 3H), 1.03 (d, J=6.6 Hz, 3H), 0.98 (d, J=7.2 Hz, 3H), 0.92 (t, J=7.2 Hz, 3H), 0.81 (d, J=6.6 Hz, 3H) ppm; $^{13}$C NMR: (CD$_3$OD, 150 MHz) δ=177.8, 174.8, 174.7, 171.3, 162.2, 150.3, 139.0, 130.0, 128.9, 127.0, 124.7, 70.8, 70.0, 56.1, 54.4, 51.8, 49.8, 44.2, 41.9, 38.4, 37.3, 37.2, 35.2, 31.1, 30.3, 25.6, 25.1, 23.8, 20.4, 20.0, 19.8, 17.6, 15.9, 10.7 ppm; HRMS calcd for C$_{39}$H$_{59}$N$_5$O$_7$S [M+H$^+$] 742.4208. found 742.4222.

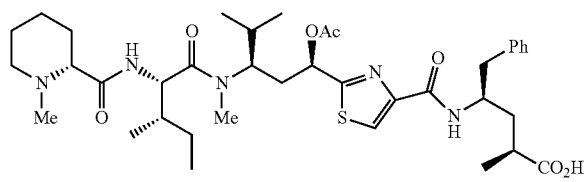

N$^{14}$-Desacetoxytubulysin H (Tb1)

N$^{14}$-Desacetoxytubulysin H (Tb1)

To a stirred solution of methyl ester Tb2 (20 mg, 0.027 mmol) in 1,2-dichloroethane (1 mL) was added Me$_3$SnOH (97 mg, 0.54 mmol) at 25° C. The reaction mixture was refluxed for 12 h and the solvent was removed under reduced pressure. The resulting hydroxyl acid (20 mg, 0.027 mmol, quantitative) was used in the following step without further purification.

To an ice-cooled stirred solution of the above obtained hydroxyl acid (20 mg, 0.027 mmol) in pyridine (0.2 mL) was added dropwise Ac$_2$O (0.01 ml, 0.1 mmol). The reaction mixture was stirred at 25° C. for 12 h and then the solvent was removed under reduced pressure. The crude reaction mixture was purified by flash column chromatography (silica gel, 5→10% MeOH/CH$_2$Cl$_2$) to furnish N$^{14}$-desacetoxytubulysin H (Tb1, 11 mg, 56% yield) as an amorphous colorless solid. Tb1: R$_f$=0.42 (silica gel 5% MeOH in CH$_2$Cl$_2$); The spectral data of Tb1 matched those previously reported.[8] $^1$H NMR: (CD$_3$OD, 600 MHz) δ=8.08 (s, 1H), 7.27-7.22 (m, 4H), 7.14-7.12 (m, 1H), 5.71 (dd, J=10.8, 2.4 Hz, 1H), 4.72 (d, J=7.8 Hz, 1H), 4.41-4.33 (m, 2H), 3.10 (s, 3H), 2.98-2.87 (m, 4H), 2.53 (bs, 1H), 2.36 (s, 3H), 2.42-2.25 (m, 3H), 2.15 (s, 3H), 2.03-1.98 (m, 1H), 1.89-1.57 (m, 9H), 1.42-1.36 (m, 1H), 1.21-1.13 (m, 1H), 1.16 (d, J=7.2 Hz, 3H), 1.02 (d, J=6.0 Hz, 3H), 0.98 (d, J=6.6 Hz, 3H) ppm; $^{13}$C NMR: (CD$_3$OD, 150 MHz) δ=181.3, 175.0, 173.6, 171.9, 171.6, 162.9, 151.1, 139.8, 130.6, 129.4, 127.5, 125.1, 71.3, 69.8, 56.6, 55.3, 51.1, 44.3, 42.1, 39.4, 38.8, 37.7, 35.7, 31.2, 31.1, 30.8, 25.6, 25.6, 23.8, 20.9, 20.6, 20.4, 18.9, 16.4, 11.3 ppm. HRMS calcd for C$_{38}$H$_{57}$N$_5$O$_7$S [M+H$^+$] 728.4051. found 728.4035.

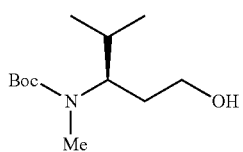

11a tert-Butyl (R)-(1-hydroxy-4-methylpentan-3-yl)(methyl)carbamate (11a)

To a stirred solution of 1 (1.0 g, 4.36 mmol) in MeOH (10 mL) at 0° C. was added NaBH$_4$ (250 mg, 6.55 mmol). The reaction mixture was allowed to warm to 25° C. and stirred for an additional 1 h. Then the reaction mixture was quenched with water (2 mL). The reaction mixture was concentrated under reduce pressure to remove MeOH and the aqueous layer was extracted with EtOAc (3×20 mL). The combined organic layer was dried with anhydrous Na$_2$SO$_4$ and concentrated under reduced pressure. The obtained residue was purified by flash column chromatography (silica gel. 10-50% EtOAc in hexanes) to afford pure alcohol 11a (0.92 g, 92%) as a colorless oil. 11a: R$_f$=0.3 (silica gel, 25% EtOAc in hexanes); [α]$_D^{22}$=−22.4 (c=1.0, CHCl$_3$); FT-IR (neat) $\tilde{v}_{max}$: 3444, 2964, 1665, 1398, 1365, 1254, 1150, 1049, 871, 772 cm$^{-1}$; $^1$H NMR: (CDCl$_3$, 600 MHz) δ=3.78 (ddd, J=11.8, 10.4, 3.2 Hz, 1H), 3.53 (tdd, J=10.9, 5.1, 2.4 Hz, 1H), 3.48-3.39 (m, 1H), 3.31 (tt, J=11.3, 3.4 Hz, 1H), 2.60 (d, J=29.6 Hz, 3H), 1.89 (dddd, J=14.3, 11.1, 5.2, 3.3 Hz, 1H), 1.63 (dp, J=10.3, 6.5 Hz, 1H), 1.49-1.37 (m, 9H), 1.31 (ddt, J=14.8, 12.1, 2.9 Hz, 1H), 0.91 (dd, J=12.8, 6.6 Hz, 3H), 0.82 (dd, J=13.7, 6.6 Hz, 3H); $^{13}$C NMR: (CDCl$_3$, 150 MHz) δ=157.9, 79.9, 58.9, 57.4, 31.7, 29.9, 28.4, 28.4, 20.2, 20.1 ppm; Diagnostic signals of minor rotamer; $^{13}$C NMR: (CDCl$_3$, 150 MHz) δ=156.2, 80.0, 79.9, 59.7, 59.0, 32.2, 30.5, 27.9, 20.0; HRMS calcd for C$_{12}$H$_{25}$NNaO$_3$ [M+Na$^+$] 254.1732. found 254.1738.

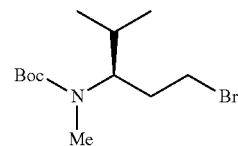

11 tert-Butyl (R)-(1-bromo-4-methylpentan-3-yl)(methyl)carbamate (11)

To a stirred solution of 11a (300 mg, 1.29 mmol) in benzene (4 mL) at 0° C. were added CBr$_4$ (860 mg, 2.59 mmol), followed by PPh$_3$ (680 mg, 2.59 mmol). The reaction mixture was allowed to warm to 20° C. and stirred for an additional 1 h. The reaction mixture was filtered through a pad of celite and washed with hexane. The solvent was removed under reduced pressure and the obtained residue was purified by flash column chromatography (silica gel, 10→20% EtOAc in hexanes) to afford pure bromo compound 11 (304 mg, 80%) as a colorless oil. 11: R$_f$=0.5 (silica gel, 20% EtOAc in hexanes); [α]$_D^{22}$=+29.7 (c=1.0, CHCl$_3$); FT-IR (neat) $\tilde{v}_{max}$: 2967, 1686, 1388, 1365, 1255, 1154, 1136, 873, 770 cm$^{-1}$; $^1$H NMR: (CDCl$_3$, 600 MHz) δ=3.73 (t, J=12.3 Hz, 1H), 3.41-3.14 (m, 2H), 2.65 (d, J=8.7 Hz, 3H), 2.19-2.01 (m, 1H), 2.00-1.88 (m, 1H), 1.70 (brs, 1H), 1.44 (d, J=9.4 Hz, 9H), 0.92 (dd, J=6.6, 4.8 Hz, 3H), 0.83 (dd, J=9.2, 6.6 Hz, 3H); $^{13}$C NMR: (CDCl$_3$, 150 MHz) δ=156.3, 79.6, 60.6, 33.5, 30.4, 30.1, 28.4, 20.0, 19.8, 19.5 ppm; Diagnostic signals of minor rotamer; $^{13}$C NMR: (CDCl$_3$, 150 MHz) δ=79.2, 33.2, 30.3, 30.2, 20.1; HRMS data could not be obtained for this compound.

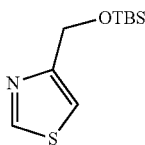

4-(((tert-Butyldimethylsilyl)oxy)methyl)thiazole (12)

To a stirred solution of thiazol-4-ylmethanol (500 mg, 4.34 mmol) in CH$_2$Cl$_2$ (4 mL) at 0° C. was added imidazole (363 mg, 5.34 mmol), followed by TBSCl (806 mg, 5.34 mmol). The reaction mixture was allowed to warm to 25° C. and stirred for an additional 30 min. The reaction mixture was diluted with H$_2$O (5 mL) and the resulting solution was extracted with CH$_2$Cl$_2$ (3×10 mL). The combined organic extracts were washed with brine (5 mL), dried over Na$_2$SO$_4$ and evaporated under reduced pressure. The obtained residue was purified by flash column chromatography (silica gel, 5→10% EtOAc in hexanes) to afford pure compound 12 (990 mg, 99%) as a colorless oil. 12: R$_f$=0.6 (silica gel, 10% EtOAc in hexanes); FT-IR (neat) $\tilde{v}_{max}$: 2954, 2929, 2857, 1524, 1462, 1416, 1254, 1131, 1096, 835, 776; $^1$H NMR: (CDCl$_3$, 600 MHz) δ=8.76 (d, J=2.1 Hz, 1H), 7.24 (dt, J=2.4, 1.3 Hz, 1H), 4.92 (d, J=1.5 Hz, 2H), 0.95 (s, 9H), 0.12 (s, 6H); $^{13}$C NMR: (CDCl$_3$, 150 MHz) δ=158.3, 152.7, 113.5, 62.3, 25.9, 18.4, −5.4; HRMS calcd for C$_{10}$H$_{19}$NOSSi [M+H$^+$] 230.1035. found 230.1022.

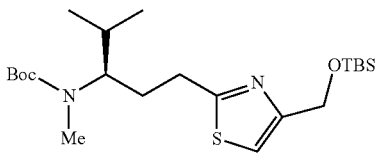

tert-Butyl(R)-(1-(4-(((tert-butyldimethylsilyl)oxy)methyl)thiazol-2-yl)-4-methylpentan-3-yl) (methyl) carbamate (13)

To a stirred solution of thiazol compound 12 (0.934 g, 4.08 mmol) in THF (12.0 mL) at −78° C. was carefully added n-BuLi (2M in hexane, 2.04 mL, 4.08 mmol). After stirring for 30 min at the same temperature, a solution of bromo compound 11 (1.0 g, 3.40 mmol) in THF (2.0 mL) was added. The reaction mixture was allowed to slowly warm to 0° C., stirred for an additional 1 h followed by 2 h at 25° C., and quenched with a saturated aqueous solution of NH$_4$Cl (10 mL). The two phases were separated, the aqueous layer was extracted with EtOAc (3×20 mL), and the combined organic extracts were dried over Na$_2$SO$_4$ and evaporated under reduced pressure. The obtained residue was purified by flash column chromatography (silica gel, 10→30% EtOAc in hexanes) to afford pure compound 13 (1.4 g, 76%) as a colorless oil. 13: R$_f$=0.4 (silica gel, 20% EtOAc in hexanes); [α]$_D^{22}$=−11.2 (c=1.0, CHCl$_3$); FT-IR (neat) $\tilde{v}_{max}$: 2928, 1692, 1472, 1365, 1254, 1137, 1091, 873, 777 cm$^{-1}$; $^1$H NMR: (CDCl$_3$, 600 MHz) δ=7.08-6.92 (m, 1H), 4.82 (t, J=1.4 Hz, 2H), 2.88 (dddd, J=20.9, 15.3, 6.9, 3.2 Hz, 2H), 2.67 (d, J=29.3 Hz, 3H), 2.10 (m, 1H), 1.84-1.55 (m, 3H), 1.44 (d, J=20.3 Hz, 9H), 1.02 (d, J=6.6 Hz, 3H), 1.01-0.90 (m, 9H), 0.85 (d, J=6.6 Hz, 3H), 0.11 (s, 6H); $^{13}$C NMR: (CDCl$_3$, 150 MHz) δ=170.9, 156.9, 156.6, 112.4, 79.4, 62.3, 30.6, 30.4, 30.0, 28.5, 25.9, 20.3, 20.1, 19.9, 19.6, 18.4, −5.4 ppm; Diagnostic signals of minor rotamer: $^{13}$C NMR: (CDCl$_3$, 150 MHz) δ=170.5, 156.8, 156.5, 79.1, 62.3, 30.8; HRMS calcd for C$_{22}$H$_{43}$N$_2$O$_3$SSi [M+H$^+$]443.2764. found 443.2760.

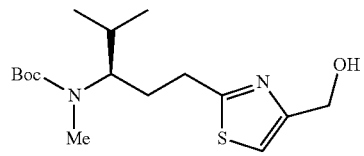

tert-Butyl (R)-(1-(4-(hydroxymethyl)thiazol-2-yl)-4-methylpentan-3-yl)(methyl)carbamate (14a)

To a stirred solution of compound 13 (125 mg, 0.28 mmol) in THF (4 mL) at 0° C. was added TBAF (1M in THF, 0.56 mL, 0.56 mmol). The reaction mixture was allowed to warm to 25° C. and stirred for an additional 30 min. The reaction mixture was diluted with H$_2$O (10 mL) and the resulting solution was extracted with EtOAc (3×10 mL). The combined organic extracts were washed with brine (5 mL), dried over Na$_2$SO$_4$ and evaporated under reduced pressure. The obtained residue was purified by flash column chromatography (silica gel, 30→80% EtOAc in hexanes) to afford pure alcohol 14a (87 mg, 94%) as a colorless oil. 14a: R$_f$=0.2 (silica gel, 50% EtOAc in hexanes); [α]$_D^{22}$=−10.2 (c=1.0, CHCl$_3$); FT-IR (neat) $\tilde{v}_{max}$: 3414, 2966, 1686, 1390, 1365, 1157, 1141, 1046, 869, 770 cm$^{-1}$; $^1$H NMR: (CDCl$_3$, 600 MHz) δ=7.01 (d, J=8.6 Hz, 1H), 4.70 (d, J=4.7 Hz, 2H), 3.64 (s, 1H), 3.37 (d, J=11.9 Hz, 1H), 2.96-2.76 (m 1H), 2.64 (d, J=9.7 Hz, 3H), 2.08 (dtd, J=16.5, 6.8, 3.3 Hz, 1H), 1.85-1.56 (m, 2H), 1.42 (d, J=17.1 Hz, 9H), 0.92 (dd, J=6.6, 2.3 Hz, 3H), 0.82 (dd, J=6.6, 2.3 Hz, 3H); $^{13}$C NMR: (CDCl$_3$, 150 MHz) δ=171.5, 156.6, 155.9, 113.7, 79.4, 60.7, 30.5, 30.3, 29.9, 28.4, 20.2, 20.2, 19.9, 19.6 ppm; Diagnostic signals of minor rotamer: $^{13}$C NMR: (CDCl$_3$, 150 MHz) δ=171.2, 156.5, 156.0, 79.1, 30.7, 30.4; HRMS calcd for C$_{16}$H$_{28}$N$_2$O$_3$S [M+Na$^+$] 351.1718. found 351.1707.

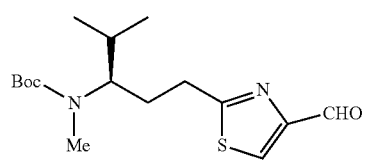

tert-Butyl (R)-(1-(4-formylthiazol-2-yl)-4-methyl-pentan-3-yl)(methyl)carbamate (14b)

To a stirred solution of alcohol 14a (85 mg, 0.26 mmol) in CH$_2$Cl$_2$ (4 mL) at 25° C. was added DMP (165 mg, 0.388 mmol) and stirring was continue for 15 min. The reaction mixture was diluted with H$_2$O (10 mL) and the resulting solution was extracted with CH$_2$Cl$_2$ (3×10 mL). The combined organic extracts were washed with saturated aqueous solution of NaHCO$_3$:Na$_2$S$_2$O$_3$ (1:1, 5 mL), dried over Na₂SO₄ and evaporated under reduced pressure. The obtained residue was purified by flash column chromatography (silica gel, 10→40% EtOAc in hexanes) to afford aldehyde 14b (76 mg, 90%) as a colorless oil. 14b: Rf=0.4 (silica gel, 30% EtOAc in hexanes); $[\alpha]_D^{22}$=−12.4 (c=1.0, CHCl₃); FT-IR (neat) $\nu_{max}$: 2966, 2750, 1685, 1483, 1389, 1365, 1141, 871, 770 cm⁻¹; ¹H NMR: (CDCl₃, 600 MHz) δ=9.97 (d, J=8.5 Hz, 1H), 8.04 (d, J=8.8 Hz, 1H), 3.66 (s, 1H), 3.07-2.86 (m, 2H), 2.66 (d, J=26.1 Hz, 3H), 2.30-2.05 (m, 1H), 1.96-1.59 (m, 2H), 1.42 (d, J=25.5 Hz, 9H), 0.95 (dd, J=6.6, 1.9 Hz, 3H), 0.84 (dd, J=6.6, 2.4 Hz, 3H); ¹³C NMR: (CDCl₃, 150 MHz) δ=184.4, 172.4, 156.5, 154.7, 127.8, 79.2, 60.2, 30.5, 30.5, 30.4, 29.6, 20.1, 19.9, 19.6 ppm; Diagnostic signals of minor rotamer: ¹³C NMR: (CDCl₃, 150 MHz) δ=172.1, 156.4, 154.8, 127.6, 79.5, 30.7, 20.2; HRMS calcd for C₁₆H₂₆N₂O₃S [M+Na⁺] 349.1562. found 349.1543.

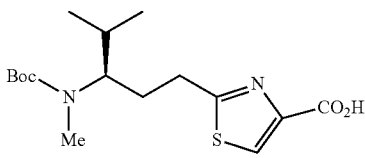

14

(R)-2-(3-((tert-Butoxycarbonyl)(methyl)amino)-4-methylpentyl)thiazole-4-carboxylic Acid (14)

To a stirred solution of aldehyde 14b (75 mg, 0.230 mmol) in t-BuOH (4 mL) at 25° C. were consecutively added a solution of 2-methyl-2-butene (0.18 mL, 1.725 mmol) in THF (1.0 mL), followed by a solution of NaClO₂ (112 mg, 1.24 mmol) and NaH₂PO₄·H₂O (440 mg, 2.817 mmol) in H₂O (1.5 mL) and stirring was continued for 1 h at 25° C. The reaction mixture was then diluted with aqueous HCl (1N, 1 mL) and the resulting solution was extracted with ethyl acetate (3×10 mL). The combined organic layers were dried over Na₂SO₄ and evaporated under reduced pressure. The obtained residue was purified by flash column chromatography (silica gel, 3→18% MeOH in CH₂Cl₂) to afford pure acid 14 (73 mg, 92%) as a colorless oil. 14: Rf=0.3 (silica gel, 10% MeOH in CH₂Cl₂); $[\alpha]_D^{22}$=−5.8 (c=1.0, CHCl₃); FT-IR (neat) $\nu_{max}$: 2965, 2924, 1686, 1483, 1390, 1366, 1156, 868, 771, 713 cm⁻¹; ¹H NMR: (CDCl₃, 600 MHz) δ=8.14 (d, J=13.9 Hz, 1H), 3.66 (s, 1H), 2.96 (td, J=8.2, 4.2 Hz, 2H), 2.66 (d, J=17.7 Hz, 3H), 2.26-2.00 (m, 1H), 1.84 (dp, J=19.7, 7.6 Hz, 2H), 1.43 (d, J=19.4 Hz, 9H), 1.04-0.91 (m, 3H), 0.84 (dd, J=6.7, 2.5 Hz, 3H); ¹³C NMR: (CDCl₃, 150 MHz) δ=171.6, 164.0, 156.6, 146.1, 128.0, 79.4, 69.5, 60.0, 31.1, 30.6, 29.8, 28.4, 20.1, 19.6 ppm; Diagnostic signals of minor rotamer; ¹³C NMR: (CDCl₃, 150 MHz) δ=79.8, 30.7, 30.5, 30.3, 20.3, 19.9; HRMS calcd for C₁₆H₂₆N₂O₄S [M+Na⁺] 365.1511. found 365.1505.

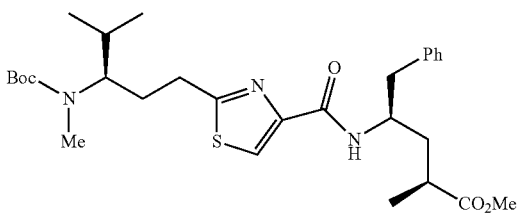

15

Methyl(2S,4R)-4-(2-((R)-3-((tert-butoxycarbonyl)(methyl)amino)-4-methylpentyl)thiazole-4-carboxamido)-2-methyl-5-phenylpentanoate (15)

To a stirred solution of 14 (85 mg, 0.25 mmol) in dry DMF (2.0 mL) at 0° C. were added HATU (283 mg, 0.75 mmol) followed by Et₃N (0.2 mL, 1.5 mmol) and the resulting mixture was stirred for 5 min at the same temperature. A solution of 6 (82 mg, 0.37 mmol) in dry DMF (0.5 mL) was then added and the stirring was continue for 24 h while allowing the temperature to slowly rise to 25° C. The reaction mixture was diluted with H₂O (5 mL) and the resulting solution was extracted with EtOAc (3×10 mL). The combined organic extracts were washed with brine (5 mL), dried over Na₂SO₄ and evaporated under reduced pressure. The obtained residue was purified by flash column chromatography (silica gel, 10→50% EtOAc in hexanes) to afford pure dipeptide 15 (109 mg, 81%) as a colorless oil. 15: Rf=0.5 (silica gel, 50% EtOAc in hexanes); $[\alpha]_D^{22}$=−17.0 (c=1.0, CHCl₃); FT-IR (neat) $\nu_{max}$: 2967, 2925, 1735, 1684, 1540, 1493, 1454, 1365, 1257, 1143, 776, 746, 700 cm⁻¹; ¹H NMR: (CDCl₃, 600 MHz) δ=7.93 (s, 1H), 7.34-7.12 (m, 6H), 4.38 (dt, J=9.4, 5.5 Hz, 1H), 3.87 (s, 1H), 3.63 (d, J=2.4 Hz, 3H), 3.04-2.79 (m, 4H), 2.66 (d, J=20.6 Hz, 3H), 2.62-2.52 (m, 1H), 2.22-2.07 (m, 1H), 2.01 (ddd, J=13.6, 9.4, 3.8 Hz, 1H), 1.76-1.74 (m, 1H), 1.58 (tdd, J=14.5, 9.9, 4.4 Hz, 1H), 1.50-1.54 (m, 1H), 1.43 (d, J=43.8 Hz, 9H), 1.15 (d, J=7.1 Hz, 3H), 0.96 (dd, J=8.4, 6.6 Hz, 3H), 0.86 (t, J=6.5 Hz, 3H); ¹³C NMR: (CDCl₃, 150 MHz) δ=176.6, 170.5, 170.7, 156.5, 149.6, 137.7, 129.5, 128.3, 126.4, 122.2, 79.5, 60.3, 51.7, 48.4, 41.3, 37.9, 36.4, 30.6, 30.3, 29.7, 29.3, 28.5, 20.3, 19.9, 17.7; HRMS calcd for C₂₉H₄₃N₃O₅S [M+Na⁺]=568.2821. found 568.2803.

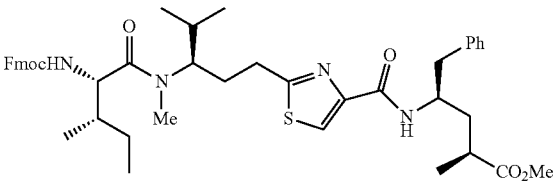

16

Methyl(2S,4R)-4-(2-((R)-3-((2S,3S)-2-((((9H-fluoren-9-yl)methoxy)carbonyl)amino)-N,3-dimethylpentanamido)-4-methylpentyl)thiazole-4-carboxamido)-2-methyl-5-phenylpentanoate (16)

To an ice-cooled stirred solution of 15 (80 mg, 0.15 mmol) in CH₂Cl₂ (4 mL) was added trifluoroacetic acid (0.5 mL, 6.63 mmol) and the reaction mixture was stirred for 2 h while warming up to 25° C. Evaporation of the volatile components under reduced pressure furnished the crude TFA-ammonium salt (77 mg, quantitative), which was used for the following step without further purification.

To a stirred, ice-cooled solution of crude ammonium salt from the previous step and i-Pr₂NEt (0.19 mL, 1.083 mmol) in DMF (1.0 mL) was added dropwise a solution of Fmoc-Ile-F⁸ (8, 255 mg, 0.722 mmol) in DMF (0.3 mL) and stirring was continued for 18 h at 25° C. The reaction mixture was diluted with ethyl acetate (10 mL), washed with saturated aqueous NaHCO₃ solution (10 mL) and brine (10 mL), dried over Na₂SO₄ and concentrated under reduced pressure. The obtained residue was purified by flash column chromatography (silica gel, 10→50% EtOAc in hexanes) to afford pure tripeptide 16 (107 mg, 94%) as a white amorphous solid. 16: $R_f$=0.4 (silica gel, 50% EtOAc in hexanes); $[α]_D^{22}$=−12.2 (c=1.0, CHCl$_3$); FT-IR (neat) $\tilde{v}_{max}$: 3295, 2962, 2924, 1717, 1637, 1540, 1495, 1451, 1249, 1227, 1083, 1032, 758, 742, 700 cm$^{-1}$; $^1$H NMR: (CDCl$_3$, 600 MHz) δ=7.89 (s, 1H), 7.76 (d, J=7.5 Hz, 2H), 7.59 (dd, J=7.5, 4.3 Hz, 2H), 7.39 (t, J=7.5 Hz, 2H), 7.33-7.17 (m, 9H), 5.49 (d, J=9.5 Hz, 1H), 4.57 (dd, J=9.5, 6.9 Hz, 1H), 4.38 (qd, J=10.7, 7.2 Hz, 3H), 4.22 (t, J=7.1 Hz, 1H), 3.62 (d, J=14.0 Hz, 3H), 2.98 (m, 3H), 2.93-2.74 (m, 4H), 2.68-2.56 (m, 1H), 2.08 (dddd, J=46.8, 13.8, 10.0, 5.5 Hz, 2H), 1.91-1.56 (m, 6H), 1.17 (d, J=7.1 Hz, 3H), 1.03-0.96 (m, 6H), 0.90 (t, J=7.4 Hz, 3H), 0.81 (d, J=6.6 Hz, 3H); $^{13}$C NMR: (CDCl$_3$, 150 MHz) δ=176.6, 173.3, 169.5, 160.6, 156.4, 149.8, 143.9, 141.3, 137.8, 129.5, 128.3, 127.7, 127.0, 126.4, 125.1, 122.6, 119.9, 67.1, 55.8, 51.7, 48.6, 47.2, 41.2, 38.1, 37.8, 36.5, 31.3, 30.7, 29.7, 27.4, 23.9, 20.4, 20.1, 19.6, 17.8, 16.0, 11.3; HRMS calcd for C$_{45}$H$_{56}$N$_4$O$_6$S [M+Na$^+$] 803.3818. found 803.3804.

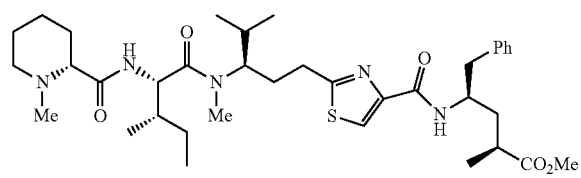

Ptb-D42

Methyl(2S,4R)-4-(2-((R)-3-((2S,3S)—N,3-dimethyl-2-((R)-1-methylpiperidine-2-carboxamido) pentanamido)-4-methylpentyl)thiazole-4-carboxamido)-2-methyl-5-phenylpentanoate (PTb-D42)

To an ice-cooled stirred solution of Fmoc-derivative 16 (100 mg, 0.13 mmol) in CH$_2$Cl$_2$ (4 mL) was added tris(2-aminoethyl)amine (0.3 mL, 2.1 mmol). The reaction mixture was stirred for 2 h at 25° C. and then diluted with ethyl acetate (20 mL). The solution was washed with saturated aqueous NaHCO$_3$ solution (10 mL) and brine (10 mL), dried over Na$_2$SO$_4$, and concentrated. The crude amine so obtained (72 mg, quantitative) was used for the next step without further purification.

To an ice-cooled stirred solution of N-methyl-(D)-pipecolinic acid 10 (57 mg, 0.4 mmol) in DMF (2.0 ml) at 0° C. was added HATU (151 mg, 0.4 mmol) followed by the above obtained crude amine (72 mg, 0.13 mmol) and Et$_3$N (0.11 mL, 0.8 mmol) and the reaction mixture was stirred at 25° C. for 24 h. The reaction mixture was diluted with H$_2$O (5 mL) and the resulting solution was extracted with EtOAc (3×10 mL). The combined organic extracts were washed with saturated aqueous NaHCO$_3$ solution (5 mL) and brine (5 mL), dried over Na$_2$SO$_4$ and evaporated under reduced pressure. The obtained residue was purified by flash column chromatography (silica gel, 3→18% MeOH in CH$_2$Cl$_2$) to afford analog PTb-D42 (63 mg, 72%) as a white amorphous solid. PTb-D42: $R_f$=0.4 (silica gel, 10% MeOH in CH$_2$Cl$_2$); $[α]_D^{22}$=+9.4 (c=1.0, CHCl$_3$); FT-IR (neat) $\tilde{v}_{max}$: 3301, 2925, 2854, 1735, 1635, 1542, 1497, 1198, 700 cm$^{-1}$; $^1$H NMR: (CDCl$_3$, 600 MHz) δ=7.87 (s, 1H), 7.39 (d, J=9.4 Hz, 1H), 7.30-7.16 (m, 5H), 7.07 (s, 1H), 4.79 (t, J=8.6 Hz, 1H), 4.39 (ddq, J=9.6, 7.0, 3.8, 3.0 Hz, 2H), 3.64 (s, 3H), 3.01 (s, 3H), 2.98 (dd, J=13.8, 6.7 Hz, 1H), 2.89 (dd, J=13.7, 6.4 Hz, 2H), 2.85-2.78 (m, 2H), 2.61 (dqd, J=8.8, 6.9, 4.3 Hz, 1H), 2.49 (d, J=11.3 Hz, 1H), 2.24 (s, 3H), 2.14-1.96 (m, 3H), 1.82-1.78 (m, 4H), 1.75-1.45 (m, 6H), 1.23-1.11 (m, 5H), 0.99 (d, J=6.8 Hz, 3H), 0.98-0.94 (m, 3H), 0.89 (t, J=7.4 Hz, 3H), 0.78 (d, J=6.6 Hz, 3H); $^{13}$C NMR: (CDCl$_3$, 150 MHz) δ=176.6, 174.3, 173.2, 169.5, 160.7, 149.9, 137.8, 129.5, 128.3, 126.4, 122.2, 69.7, 62.8, 58.5, 55.4, 53.1, 51.7, 48.6, 44.9, 41.2, 38.2, 37.2, 36.5, 29.6, 30.4, 30.2, 30.0, 29.4, 25.1, 24.6, 23.3, 20.1, 17.9, 16.0, 11.0; HRMS calcd for C$_{37}$H$_{58}$N$_5$O$_5$S [M+H$^+$] 684.4159. found 684.4142.

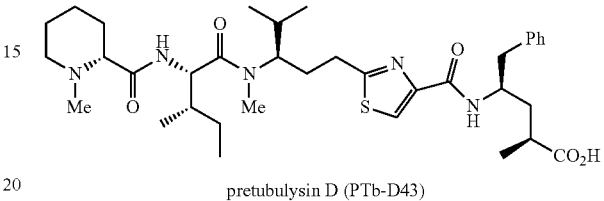

pretubulysin D (PTb-D43)

Pretubulysin D (PTb-D43)

To a stirred solution of methyl ester PTb-D42 (10 mg, 0.014 mmol) in 1,2-dichloroethane (1 mL) was added Me$_3$SnOH (53.0 mg, 0.29 mmol) at 25° C. The reaction mixture was refluxed for 12 h, filtered through a pad of celite and washed with CH$_2$Cl$_2$. The solvent was removed under reduced pressure and the obtained residue was purified by flash column chromatography (silica gel, 3→18% MeOH in CH$_2$Cl$_2$) to afford pretubulysin D PTb-D43 (8 mg, 82%) as a colorless oil.

Alternatively, to a stirred solution of PTb-D42 (10 mg, 0.014 mmol) in THF:H$_2$O (5:1, 0.5 mL) at 25° C. was added a solution of LiOH—H$_2$O (3.0 mg, 0.073 mmol) in H$_2$O (0.1 mL) and the resulting mixture was stirred for 24 h at the same temperature. The reaction mixture was diluted with H$_2$O (5 mL) and the resulting solution was extracted with EtOAc (3×10 mL). The combined organic extracts were dried over Na$_2$SO$_4$ and evaporated under reduced pressure. The obtained residue was purified by flash column chromatography (silica gel, 3→18% MeOH in CH$_2$Cl$_2$) to afford pretubulysin D PTb-D43 (8.8 mg, 90%) as a colorless oil. PTb-D43: $R_f$=0.37 (silica gel, 10% MeOH in CH$_2$Cl$_{12}$); $[α]_D^{22}$=+9.4 (c=1.0, CHCl$_3$); FT-IR (neat) $\tilde{v}_{max}$: 3286, 2959, 2924, 2853, 1635, 1544, 1497, 1463, 1086, 751 cm$^{-1}$; $^1$H NMR: (CDCl$_3$, 600 MHz) δ=$^1$H NMR (600 MHz, Chloroform-d) δ 8.14 (d, J=8.2 Hz, 1H), 7.86 (s, 1H), 7.33-7.11 (m, 6H), 4.81 (t, J=8.4 Hz, 1H), 4.32 (dd, J=9.2, 4.6 Hz, 1H), 3.17 (dd, J=13.8, 8.3 Hz, 1H), 3.00 (s, 3H), 2.98-2.90 (m, 2H), 2.82-2.57 (m, 4H), 2.31 (s, 3H), 2.09 (ddd, J=15.5, 8.6, 3.1 Hz, 2H), 1.94-1.53 (m, 10H), 1.43 (s, 1H), 1.19 (s, 1H), 1.18 (d, J=6.9 Hz, 3H), 1.09-1.01 (m, 2H), 0.96 (d, J=6.5 Hz, 3H), 0.93 (d, J=6.8 Hz, 3H), 0.86 (m, 1H), 0.83-0.73 (m, 6H); $^{13}$C NMR: (CDCl$_3$, 150 MHz) δ=173.3, 168.5, 161.8, 149.5, 138.3, 129.4, 129.3, 128.5, 128.3, 126.3, 122.4, 70.0, 55.4, 53.4, 50.1, 44.1, 40.1, 39.5, 37.7, 36.7, 31.3, 30.6, 30.0, 29.7, 29.0, 24.5, 23.1, 20.8, 20.0, 19.6, 17.8, 16.5, 15.7, 11.0;

HRMS calcd for C$_{36}$H$_{56}$N$_5$O$_5$S [M+H$^+$] 670.4002. found 670.4004.

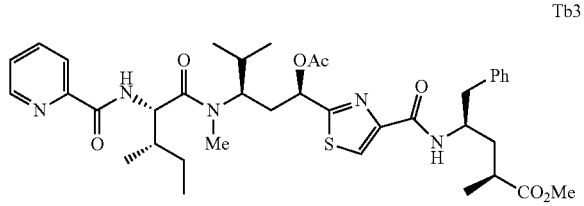 [SMILES: CC[C@H](C)[C@H](NC(=O)c1ccccn1)C(=O)N(C)[C@H](C[C@@H](OC(C)=O)c1nc(C(=O)N[C@@H](Cc2ccccc2)C[C@H](C)C(=O)OC)cs1)C(C)C]

Tb3

(2S,4R)-Methyl 4-(2-((1R,3R)-1-acetoxy-3-((2S,3S)—N,3-dimethyl-2-(picolinamido)pentanamido)-4-methylpentyl)thi-azole-4-carboxamido)-2-methyl-5-phenylpentanoate (Tb3)

To a stirred solution of Fmoc-protected amine 9 (20 mg, 0.024 mmol) in CH$_2$Cl$_2$ (0.6 mL) was added tris(2-aminoethyl)amine (60 µL, 0.39 mmol) and the reaction mixture was stirred at 25° C. for 3 h. The reaction mixture was then diluted with EtOAc (20 mL) and washed with saturated aqueous NaHCO$_3$ (5 mL) and brine (5 mL). The organic layer was dried over Na$_2$SO$_4$ and concentrated under reduced pressure to furnish the corresponding amine (~15 mg, quantitative yield), which was used in the following step without further purification.

To a stirred solution of picolinic acid (18 mg, 0.14 mmol) in dry DMF (0.7 mL) were added DCC (40 mg, 0.19 mmol) and pentafluorophenol (30 mg, 0.16 mmol) and the reaction mixture was stirred at 25° C. for 24 h. The reaction mixture was then filtered and the resulting clear solution of the pentafluorophenyl ester 17 was added to the above synthesized amine (15 mg) and stirred at 25° C. for 24 h. The reaction mixture was diluted with toluene (20 mL) and evaporated under reduced pressure. The resulting residue was purified using preparative thin-layer chromatography (silica gel, first elution 3% MeOH in CH$_2$Cl$_2$, followed by second elution 50% EtOAc in hexanes) to furnish Tb3 (10 mg, 58%) as a colorless oil. Tb3: R$_f$=0.03 (silica gel, 50% EtOAc in hexanes); [α]$_D^{22}$=+2.0 (c=0.5, CH$_2$Cl$_2$); FT-IR (neat) $\tilde{v}_{max}$: 3710, 3681, 3382, 2967, 2937, 2924, 2874, 2845, 2826, 1735, 1671, 1644, 1591, 1569, 1541, 1513, 1456, 1436, 1411, 1371, 1346, 1321, 1258, 1222, 1170, 1142, 1054, 1033, 1015, 933, 914, 874, 851, 819, 797, 781, 750, 702, 662, 638, 624, 610 cm$^{-1}$; $^1$H NMR: (CDCl$_3$, 600 MHz) δ=8.55 (d, J=14.0 Hz, 1H), 8.55 (s, 1H), 8.13 (d, J=7.8 Hz, 1H), 8.00 (s, 1H), 7.81 (td, J=7.7, 1.7 Hz, 1H), 7.40 (ddd, J=7.6, 4.8, 1.1 Hz, 1H), 7.30-7.25 (m, 2H), 7.20 (d, J=6.6, 5.1 Hz, 3H), 7.11 (d, J=9.2 Hz, 1H), 5.66 (dd, J=11.3, 2.5 Hz, 1H), 4.99 (dd, J=9.7, 7.0 Hz, 1H), 4.54 (s, 1H), 4.39 (qd, J=9.9, 6.3 Hz, 1H), 3.62 (s, 3H), 3.05 (s, 3H), 2.95 (dd, J=13.8, 5.8 Hz, 1H), 2.87 (dd, J=13.8, 6.7 Hz, 1H), 2.60 (dtt, J=14.1, 7.1, 3.5 Hz, 1H), 2.31 (ddd, J=14.6, 11.4, 3.0 Hz, 1H), 2.17 (s, 3H), 2.09-1.88 (m, 4H), 1.74 (dq, J=14.7, 8.2, 7.4 Hz, 1H), 1.72-1.55 (m, 3H), 1.15 (d, J=7.1 Hz, 3H), 1.02 (d, J=6.7 Hz, 3H), 0.98 (d, J=6.6 Hz, 3H), 0.90 (t, J=7.4 Hz, 3H), 0.75 ppm (d, J=6.6 Hz, 3H); $^{13}$C NMR: (CDCl$_3$, 150 MHz) δ=176.8, 173.3, 170.3, 170.3, 164.3, 160.6, 150.2, 149.7, 148.6, 137.8, 137.4, 129.8, 128.6, 126.8, 126.4, 123.6, 122.4, 69.8, 56.0, 54.2, 52.0, 48.5, 41.3, 37.9, 37.7, 36.7, 35.0, 30.2, 29.9, 24.3, 21.1, 20.3, 19.7, 17.9, 16.4, 11.5 ppm; HRMS calcd for C$_{35}$H$_{51}$N$_5$O$_7$S [M+Na$^+$] 744.3401. found 744.3380.

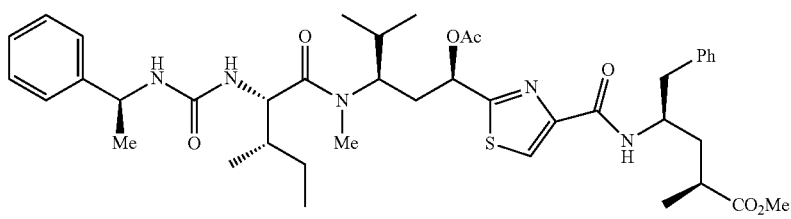

Tb4

(2S,4R)-Methyl 4-(2-((2S,6S,9R,11R)-6-((S)-sec-butyl)-9-isopropyl-8-methyl-4,7,13-trioxo-2-phenyl-12-oxa-3,5,8-tri-azatetradecan-11-yl)thiazole-4-carboxamido)-2-methyl-5-phenylpentanoate (Tb4)

To a stirred solution of Fmoc-protected amine 9 (18 mg, 0.021 mmol) in CH$_2$Cl$_2$ (0.5 mL) was added tris(2-aminoethyl)amine (0.055 mL, 0.35 mmol) and the mixture was stirred at 25° C. for 3 h. The reaction mixture was diluted with EtOAc (20 mL) and washed with saturated aqueous NaHCO$_3$ (5 mL) and brine (5 mL). The resulting residue was diluted in CH$_2$Cl$_2$ (0.53 mL), i-Pr$_2$NEt (0.022 mL, 0.128 mmol) and (S)-(1-isocyanatoethyl)benzene 18 (0.018 mL, 0.128 mmol) were added and the mixture was stirred for 24 h at 25° C. The reaction solution was directly applied to thin-layer chromatography (silica gel, 50% EtOAc in hexanes) to provide Tb4 (13 mg, 80%) as a white amorphous solid. Tb4: R$_f$=0.22 (silica gel, 50% EtOAc in hexanes); [α]$_D^{22}$=−15.6 (c=0.5, CH$_2$Cl$_2$); FT-IR (neat) $\tilde{v}_{max}$: 3369, 3319, 3028, 2966, 2929, 2876, 1738, 1641, 1614, 1543, 1493, 1454, 1411, 1371, 1339, 1220, 1170, 1128, 1084, 1046, 999, 933, 853, 806, 781, 752, 701, 638, 601 cm$^{-1}$; $^1$H NMR: (CDCl$_3$, 600 MHz) δ=8.00 (s, 1H), 7.32 (d, J=4.4 Hz, 4H), 7.29-7.18 (m, 6H), 7.09 (d, J=9.2 Hz, 1H), 5.61 (dd, J=11.3, 2.6 Hz, 1H), 5.51 (s, 1H), 5.07 (s, 1H), 4.91 (t, J=6.9 Hz, 1H), 4.62 (s, 1H), 4.49 (t, J=11.0 Hz, 1H), 4.39 (ddt, J=9.6, 7.1, 3.4 Hz, 1H), 3.60 (s, 3H), 3.03 (s, 3H), 2.94 (dd, J=13.8, 5.8 Hz, 1H), 2.86 (dd, J=13.7, 6.7 Hz, 1H), 2.59 (dqd, J=14.0, 7.1, 4.2 Hz, 1H), 2.27 (ddd, J=17.2, 10.2, 4.5 Hz, 1H), 2.05 (s, 3H), 2.00 (ddd, J=18.3, 8.3, 3.8 Hz, 2H), 1.78-1.70 (m, 1H), 1.71-1.63 (m, 2H), 1.64-1.51 (m, 2H), 1.41 (d, J=6.8 Hz, 3H), 1.14 (d, J=7.1 Hz, 3H), 0.95 (d, J=6.5 Hz, 3H), 0.92 (d, J=6.7 Hz, 3H), 0.86 (t, J=7.4 Hz, 3H), 0.81 ppm (d, J=6.6 Hz, 3H); $^{13}$C NMR: (CDCl$_3$, 150 MHz) δ=176.9, 175.7, 170.3, 170.2, 160.5, 157.6, 150.2, 144.4, 137.7, 129.8, 128.8, 128.6, 127.3, 126.8, 126.2, 123.6, 69.9, 55.3, 54.4, 52.0, 49.9, 48.5, 41.2, 37.9, 37.1, 36.7, 35.0, 30.2, 29.9, 24.6, 23.3, 20.9, 20.2, 19.8, 17.9, 16.1, 11.2 ppm; HRMS calcd for C$_{41}$H$_{57}$N$_5$O$_7$S [M+Na$^+$] 786.3871. found 786.3868.

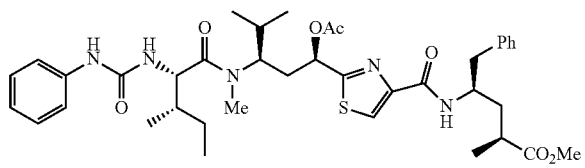

(2S,4R)-Methyl 4-(2-((1R,3R)-1-acetoxy-3-((2S, 3S)—N,3-dimethyl-2-(3-phenylureido)pentanamido)-4-methylpentyl)thiazole-4-carboxamido)-2-methyl-5-phenylpentanoate (Tb5)

According to the procedure described for the synthesis of Tb4, analog Tb5 was obtained as a colorless liquid (12.9 mg, 74%). Tb5: $R_f$=0.19 (silica gel, 50% EtOAc in hexanes); $[\alpha]_D^{22}$=−21.6 (c=0.5, $CH_2Cl_2$); FT-IR (neat) $\tilde{v}_{max}$: 3351, 2967, 2937, 2924, 2875, 2845, 2827, 1736, 1692, 1642, 1614, 1543, 1498, 1442, 1412, 1371, 1346, 1311, 1217, 1175, 1137, 1105, 1053, 1033, 1016, 911, 852, 804, 782, 732, 697, 645, 610 cm$^{-1}$; $^1$H NMR: (CDCl$_3$, 600 MHz) δ=8.01 (s, 1H), 7.58 (s, 1H), 7.40 (d, J=7.9 Hz, 2H), 7.28-7.24 (m, 6H), 7.22-7.18 (m, 4H), 7.09 (d, J=9.2 Hz, 1H), 7.01 (t, J=7.4 Hz, 1H), 6.46 (s, 1H), 5.67 (dd, J=11.7, 2.4 Hz, 1H), 4.78 (d, J=8.5 Hz, 1H), 4.62-4.49 (m, 1H), 4.40 (td, J=5.9, 3.3 Hz, 1H), 3.61 (s, 3H), 3.13 (s, 3H), 2.95 (dd, J=13.8, 5.8 Hz, 1H), 2.87 (dd, J=13.8, 6.6 Hz, 1H), 2.60 (dqd, J=14.1, 7.2, 4.3 Hz, 1H), 2.36 (ddd, J=14.4, 11.6, 2.8 Hz, 1H), 2.06 (s, 3H), 2.10-1.93 (m, 1H), 1.79 (tt, J=17.1, 6.4 Hz, 2H), 1.72-1.63 (m, 1H), 1.61 (ddd, J=14.2, 9.6, 4.5 Hz, 1H), 1.15 (d, J=7.1 Hz, 4H), 0.99 (d, J=6.5 Hz, 3H), 0.92 (d, J=7.2 Hz, 3H), 0.91 (t, J=7.6 Hz, 3H), 0.79 ppm (d, J=6.6 Hz, 3H); $^{13}$C NMR: (CDCl$_3$, 150 MHz) δ=176.9, 176.12 170.1, 170.0, 160.5, 155.7, 150.2, 139.3, 137.7, 129.8, 129.2, 128.6, 126.8, 123.7, 123.2, 120.1, 120.0, 69.9, 56.4, 54.6, 52.0, 48.5, 41.2, 37.8, 37.1, 36.7, 34.9, 30.2, 29.9, 24.7, 20.8, 20.1, 19.7, 17.9, 16.1, 11.0 ppm; HRMS calcd for $C_{39}H_{53}N_5O_7S$ [M+Na$^+$] 758.3558. found 758.3537.

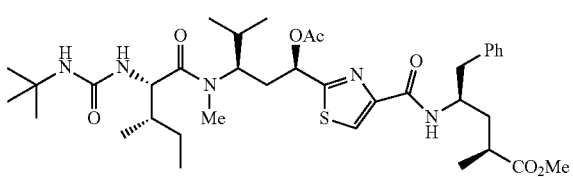

Methyl (2S,4R)-4-(2-((6S,9R,1R)-6-((S)-sec-butyl)-9-isopropyl-2,2,8-trimethyl-4,7,13-trioxo-12-oxa-3,5,8-triazatetradecan-11-yl)thiazole-4-carboxamido)-2-methyl-5-phenylpentanoate (Tb6)

According to the procedure described for the synthesis of Tb6, analog Tb6 was obtained as a colorless liquid (6.0 mg, 83%). Tb6: $R_f$=0.25 (silica gel, 50% EtOAc in hexanes); $[\alpha]_D^{22}$=−15.5 (c=0.5, $CH_2Cl_2$); FT-IR (neat) $\tilde{v}_{max}$: 3359, 2951, 2930, 2929, 2924, 2870, 2841, 2823, 1736, 1700, 1641, 1611, 1543, 1496, 1440, 1411, 1371, 1341, 1311, 1212, 1169, 1130, 1115, 1043, 1032, 1010, 910, 848, 801, 778, 722, 691, 644, 601 cm$^{-1}$; $^1$H NMR: (CDCl$_3$, 600 MHz) δ=8.00 (s, 1H), 7.28-7.24 (m, 2H), 7.19 (d, J=7.6 Hz, 3H), 7.09 (d, J=9.1 Hz, 1H), 5.63 (d, J=10.3 Hz, 1H), 5.28 (s, 2H), 4.57 (d, J=7.5 Hz, 1H), 4.51 (t, J=9.9 Hz, 1H), 4.39 (q, J=9.7 Hz, 1H), 3.61 (s, 3H), 3.04 (s, 3H), 2.94 (dd, J=13.7, 5.8 Hz, 1H), 2.86 (dd, J=13.7, 6.7 Hz, 1H), 2.59 (dq, J=15.7, 7.1 Hz, 1H), 2.29 (t, J=13.2 Hz, 1H), 2.14 (s, 3H), 2.05-1.96 (m, 2H), 1.75 (dq, J=12.8, 6.5 Hz, 2H), 1.69-1.56 (m, 3H), 1.28 (s, 9H), 1.14 (d, J=7.1 Hz, 3H), 0.99 (d, J=6.4 Hz, 3H), 0.94 (d, J=6.6 Hz, 3H), 0.88 (t, J=7.2 Hz, 3H), 0.83 ppm (d, J=6.5 Hz, 5H) $^{13}$C NMR: (CDCl$_3$, 150 MHz) δ=176.6, 175.9, 170.1, 170.0, 160.3, 157.3, 150.0, 137.5, 129.6, 128.4, 126.5, 123.4, 69.6, 55.7, 54.3, 51.8, 50.2, 48.3, 41.0, 37.6, 36.8, 36.5, 34.8, 29.9, 29.7, 29.5, 24.5, 20.8, 20.1, 19.5, 17.7, 15.9, 14.2, 11.0 ppm; HRMS calcd for $C_{37}H_{57}N_5O_7S$ [M+Na$^+$] 738.3871. found 738.3857.

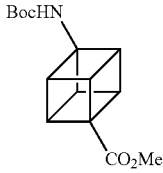

Methyl (1r,2R,3r,4s,5S,6s,7R,8S)-4-((tert-butoxycarbonyl)amino)cubane-1-carboxylate (24a) (Nicolaou, et al., 2015; Wlochal, et al., 2014; Falkiner, et al., 2013; Ingalsbe, et al., 2010)

To a stirred solution of 4-methoxycarbonyl-cubane-1-carboxylic acid (Nicolaou, et al., 2015; Wlochal, et al., 2014; Falkiner, et al., 2013; Ingalsbe, et al., 2010) (1.3 g, 6.3 mmol) in t-BuOH (25 mL) were added Et$_3$N (3.5 mL, 25.2 mmol) and DPPA (2.04 mL, 9.45 mmol) at 25° C. Stirring continued for 1 hour, after which the reaction mixture was heated to reflux for 12 h. The solvent was removed under reduced pressure and EtOAc (100 mL) was added to the dry residue. The solution was washed with brine (3×30 mL), dried with anhydrous Na$_2$SO$_4$, filtered and concentrated under reduced pressure. The obtained residue was purified by flash column chromatography (silica gel, 10→20% EtOAc in hexanes) to provide protected amino acid 24a (1.26 g, 72% yield) as an amorphous white solid. 24a: $R_f$=0.29 (silica gel, 25% EtOAc in hexanes); FT-IR (neat) $\tilde{v}_{max}$: 3397, 3243, 3122, 3011, 2974, 2950, 2928, 2849, 2360, 2333, 1726, 1713, 1692, 1504, 1439, 1364, 1314, 1269, 1252, 1206, 1164, 1088, 1054, 1022 cm$^{-1}$; $^1$H NMR (CDCl$_3$, 600 MHz) δ=5.13 (brs, 1H), 4.09 (brs, 6H), 3.69 (s, 3H), 1.44 (s, 9H) ppm; $^{13}$C NMR: (CDCl$_3$, 150 MHz) δ=172.8, 154.0, 80.0, 66.4, 56.1, 51.6, 50.2, 44.7, 28.4 ppm; HRMS calcd for $C_{15}H_{19}NO_4$ [M-C$_4$H$_7$] 222.0688. found 222.0753.

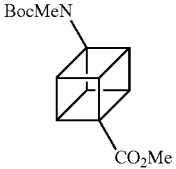

Methyl (1r,2R,3R,4s,5s,6S,7S,8r)-4-((tert-butoxycarbonyl)amino)cubane-1-carboxylate (25a)

To a stirred solution of 4-(tertiary-butoxycarbonyl-amino)-cubane-1-carboxylate methyl ester (290 mg, 1.05 mmol) in dry THF (10 mL) was added dropwise NaHMDS (1.0M in THF, 1.47 mL, 1.47 mmol) at −78° C. The solution was stirred at −78° C. for 30 minutes. Then MeI (0.195 mL, 2.1 mmol) was added dropwise into the above solution and stirring continued at −78° C. for 15 minutes. The solution was allowed to slowly warm up to 25° C. and stirred for 18 hours. The reaction was quenched with saturated NH$_4$Cl solution. The solvent was removed under reduced pressure and EtOAc (50 mL) was added to the residue. The solution was washed with brine (2×20 mL), dried with anhydrous Na$_2$SO$_4$ and concentrated under reduced pressure. The obtained residue was purified by flash column chromatography (10-30% EtOAc in hexanes) to give 25a (220 mg, 73% yield) as white solid. 25a: R$_f$=0.44 (silica gel, 25% EtOAc in hexanes); FT-IR (neat) $v_{max}$: 2998, 2981, 2968, 2955, 2926, 2363, 1716, 1450, 1427, 1366, 1351, 1318, 1249, 1219, 1204, 1191, 1169, 1152, 1088, 1039 cm$^{-1}$; $^1$H NMR (600 MHz, CDCl$_3$) δ=4.10-4.05 (m, 6H), 3.69 (s, 3H), 2.86 (s, 3H), 1.43 (s, 9H) ppm; $^{13}$C NMR: (CDCl$_3$, 150 MHz) δ=172.8, 155.1, 79.9, 71.6, 55.7, 51.6, 50.5, 44.1, 30.9, 28.5 ppm; HRMS calcd for C$_{16}$H$_{21}$NO$_4$ [M-C$_4$H$_7$] 236.0845. found 236.0910.

22a

Methyl 3-((tert-butoxycarbonyl)amino)bicyclo[1.1.1]pentane-1-carboxylate (22a) (Stepan, et al., 2012; Patzel, et al., 2004)

To a stirred solution of 3-methoxycarbonyl-bicyclo[1.1.1]pentane-1-carboxylic acid (85 mg, 0.5 mmol) in r-BuOH (2.0 mL) was added Et$_3$N (0.028 mL, 2.0 mmol) and DPPA (0.162 mL, 0.75 mmol) at 25° C. The solution was stirred at 25° C. for 1 hour and then heated to reflux for 22 h. The solvent was removed under reduced pressure and EtOAc (40 mL) was added to the residue. The solution was washed with brine (2×20 mL), dried with anhydrous Na$_2$SO$_4$ and concentrated under reduced pressure. The obtained residue was purified by flash column chromatography (10→20% EtOAc in hexanes) to give 22a (105 mg, 87% yield) as white solid. 22a: R$_f$=0.46 (silica gel, 25% EtOAc in hexanes); $^1$H NMR (600 MHz, CDCl$_3$) δ=5.03 (brs, 1H), 3.66 (s, 3H), 2.27 (s, 6H), 1.43 (s, 9H) ppm; $^{13}$C NMR: (CDCl$_3$, 150 MHz) δ=170.3, 154.9, 79.9, 54.3, 51.8, 45.7, 35.3, 28.4 ppm; HRMS calcd for C$_{12}$H$_{19}$NO$_4$ [M-C$_4$H$_7$] 186.0688. found 186.0754.

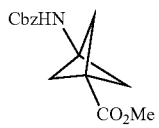

23a

Methyl 3-(((benzyloxy)carbonyl)amino)bicyclo[1.1.1]pentane-1-carboxylate (23a)

To a stirred solution of 3-methoxycarbonyl-bicyclo[1.1.1]pentane-1-carboxylic acid (300 mg, 1.76 mmol) in toluene (9.0 mL) was added Et$_3$N (0.73 mL, 5.28 mmol) and DPPA (0.76 mL, 3.52 mmol) at 25° C. The solution was stirred at 25° C. for 30 minutes, then heated to reflux for 3 h. The solution was cooled to 25° C. and benzyl alcohol (0.550 mL, 5.28 mmol) was added. The solution was stirred at 25° C. for 15 minutes and then heated to reflux for 4 h. The solvent was removed under reduced pressure and EtOAc (100 mL) was added to the residue. The solution was washed with brine (3×30 mL), dried with anhydrous Na$_2$SO$_4$ and concentrated under reduced pressure. The obtained residue was purified by flash column chromatography (10→20% EtOAc in hexanes) to give 23a (305 mg, 63% yield) as white solid. 23a: R$_f$=0.21 (silica gel, 25% EtOAc in hexanes); FT-IR (neat) $v_{max}$: 3336, 2995, 2953, 2920, 2885, 2851, 1718, 1525, 1506, 1455, 1437, 1399, 1354, 1287, 1245, 1206, 1184, 1155, 1090, 1060, 1025, 915 cm$^{-1}$; $^1$H NMR (600 MHz, CDCl$_3$) δ=7.37-7.31 (m, 5H), 5.25 (br HRMS, 1H), 5.08 (s, 2H), 3.68 (s, 3H), 2.32 (s, 6H) ppm; $^{13}$C NMR: (CDCl$_3$, 150 MHz) δ=170.0, 155.1, 136.2, 128.5, 128.2, 128.1, 66.6, 54.2, 51.8, 45.6, 35.2 ppm; HRMS calcd for C$_{15}$H$_{17}$NO$_4$ [M+H$^+$] 276.1158. found 276.1225.

General Procedure for the Synthesis of Cubane and Propellane Carboxylic Acids 22-25:

To a stirred solution of the corresponding methyl carboxylate (0.5 mmol) in THF (3.8 mL) at 25° C. was added dropwise a solution of NaOH (0.024 g, 0.6 mmol) in MeOH (0.4 mL) dropwise and the reaction mixture was stirred at the same temperature for 12 h. The solvent was removed under reduced pressure and the obtained residue was dissolved in H$_2$O (5 mL). The two layers were separated, and the aqueous layer was extracted with EtOAc (3×30 mL). The combined organic layers were dried with anhydrous Na$_2$SO$_4$. The solvent was evaporated to give the corresponding carboxylic acid as white solids. The crude carboxylic acids were used for the next reaction without further purification.

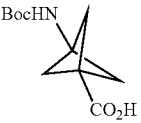

22

3-((tert-Butoxycarbonyl)amino)bicyclo[1.1.1]pentane-1-carboxylic Acid (22)

According to the general procedure described for the synthesis of propaellane carboxylic acids, carboxylic acid 22 was obtained as white solid (118.2 mg, 98%).

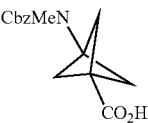

23c

3-(((Benzyloxy)carbonyl)(methyl)amino)bicyclo[1.1.1]pentane-1-carboxylic Acid (23c)

According to the general procedure described for the synthesis of propaellane carboxylic acids, carboxylic acid 23c was obtained as white solid (140.3 mg, 97%).

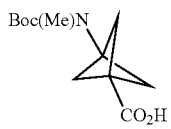

23

3-((tert-Butoxycarbonyl)(methyl)amino)bicyclo[1.1.1]pentane-1-carboxylic Acid (23)

To a stirred solution of 23c (116 mg, 0.42 mmol) and (Boc)$_2$O (120 mg, 0.54 mmol) in MeOH (5.9 mL) was added Pd/C (23.2 mg, 20 wt %) at 25° C. and the reaction mixture was stirred at the same temperature for 12 h. The reaction was filtered through a pad of celite and washed with MeOH. The solvent was removed under reduced pressure and the obtained residue was purified by flash column chromatography (silica gel, 5% MeOH in CH$_2$Cl$_2$ with 1% AcOH) to give 23 (81.2 mg, 80%) as a white solid. R$_f$=0.44 (silica gel, 5% MeOH in CH$_2$Cl$_2$ with 1% AcOH); FT-IR (neat) $\hat{v}_{max}$: 3032, 2672, 2341, 2109, 1771, 1585, 1497, 1330, 1281, 1083, 992 cm$^{-1}$; $^1$H NMR: (CD$_3$OD, 600 MHz) δ=2.82 (s, 3H), 2.32 (s, 6H), 1.49 (s, 9H) ppm. $^{13}$C NMR: (CD$_3$OD, 150 MHz) δ=173.6, 157.1, 81.5, 54.8, 51.6, 35.6, 31.8, 28.8.

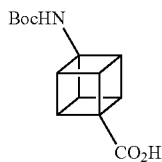

24

4-((tert-Butoxycarbonyl)amino)cubane-1-carboxylic Acid (24)

According to the general procedure described for the synthesis of propaellane carboxylic acids, carboxylic acid 24 was obtained as white solid (130.3 mg, 99%).

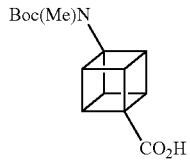

25

4-((tert-Butoxycarbonyl)(methyl)amino)cubane-1-carboxylic Acid (25)

According to the general procedure described for the synthesis of propaellane carboxylic acids, carboxylic acid 25 was obtained as white solid (135.8 mg, 98%).

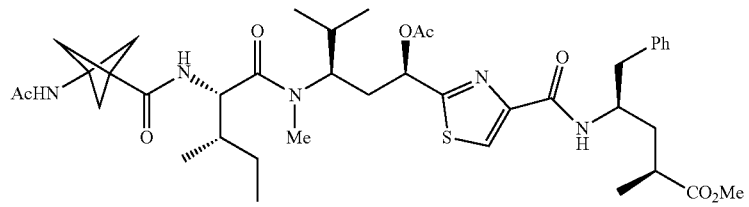

Tb7

Methyl (2S,4R)-4-(2-((1R,3R)-3-((2S,3S)-2-(3-acetamidobicyclo[1.1.1]pentane-1-carboxamido)-N,3-dimethylpentanamido)-1-acetoxy-4-methylpentyl)thiazole-4-carboxamido)-2-methyl-5-phenyl-pentanoate (Tb7)

According the procedure described for the synthesis of Tb2, Fmoc removal [N(CH$_2$CH$_2$NH$_2$)$_3$] from 9 followed by coupling (acid 22:amine 9a:HATU:Et$_3$N/3:1:3:6), Boc-Tb7 was obtained as colorless liquid (15.6 mg, 48% for the two steps). Boc-Tb7: R$_f$=0.45 (silica gel, 5% MeOH in CH$_2$Cl$_2$ with 1% NH$_4$OH).

To an ice-cooled stirred solution of Boc-Tb7 (15.6 mg, 0.018 mmol) in CH$_2$Cl$_2$ (0.47 mL) was added trifluoroacetic acid (0.045 mL, 0.56 mmol) and the reaction mixture was stirred for 12 h while warming up to 25° C. Evaporation of the volatile components under reduced pressure furnished the crude TFA-ammonium salt (13.71 mg, 0.018 mmol, quantitative), which was used for the following step without further purification.

To an ice-cooled stirred solution of crude ammonium salt from the previous step (13.71 mg, 0.018 mmol) in pyridine (0.18 mL) was added acetic anhydride (0.018 mL, 0.18 mmol) dropwise. The reaction mixture was stirred for 12 h while allowing the temperature to rise to 25° C. The solvent was evaporated under reduced pressure by azeotroping with toluene (0.5 mL) and the obtained residue was purified using flash column chromatography (silica gel, 5% MeOH in CH$_2$Cl$_2$) to give Tb7 (8.1 mg, 56%) as colorless liquid. Tb7: R$_f$=0.48 (silica gel. 5% MeOH in CH$_2$Cl$_2$); FT-IR $v_{max}$ (film in MeOH): 2384, 2345, 2158, 1780, 1762, 1689, 1666, 1589, 1553, 1516, 1482, 1429, 1395, 1327, 1280, 1248, 1181, 983 cm$^{-1}$; [α]$_D^{23}$ −23.6 (c=1.0, MeOH); $^1$H NMR: (CD$_3$OD, 600 MHz) δ=8.1 (s, 1H), 7.75 (d, 1H, J=9 Hz), 7.28-7.24 (m, 4H), 7.20-7.18 (m, 1H), 5.71 (dd, 1H, J=11.4 Hz), 4.78-4.75 (m, 1H), 4.47 (bs, 1H), 4.39-4.35 (m, 1H), 3.61 (s, 3H), 3.1 (s, 3H), 2.94-2.86 (m, 2H), 2.65-2.59 (m, 1H), 2.41-2.36 (m, 1H), 2.29 (s, 6H), 2.28-2.23 (m, 1H), 2.17 (s, 3H), 2.02-1.93 (m, 2H), 1.90 (s, 3H), 1.89-1.83 (m, 1H), 1.78-1.73 (m, 1H), 1.60-1.56 (m, 1H), 1.16 (d, 3H, J=7.2 Hz), 1.05 (d, 3H, J=6.6 Hz), 0.96-0.93 (m, 6H), 0.81 (d, 3H, J=6.6 Hz) ppm; $^{13}$C NMR: (CD$_3$OD, 150 MHz) δ=178.3, 175.1, 173.8, 171.8, 171.8, 171.7, 162.7, 150.8, 139.5, 130.4, 129.3, 127.4, 125.2, 71.2, 55.3, 54.6, 52.2, 50.2, 49.8, 46.0, 42.3, 38.8, 38.4, 37.7, 37.0, 35.6, 31.1, 25.6, 22.8, 20.9, 20.5, 19.9, 18.1, 16.3, 11.1 ppm; HRMS calcd for $C_{40}H_{57}N_5O_8S$ [M+Na$^+$] 790.3820. found 790.3788.

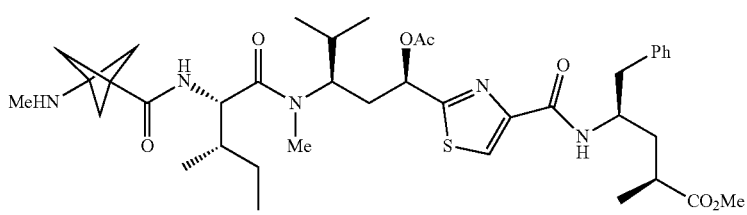

Tb8

Methyl(2S,4R)-4-(2-((1R,3R)-1-acetoxy-3-((2S,3S)—N,3-dimethyl-2-(3-(methylamino)-bicyclo[1.1.1] pentane-1-carboxamido)pentanamido)-4-methylpentyl)thiazole-4-carboxamido)-2-methyl,5-phenyl-pentanoate-phenylpentanoate (Tb8)

According the procedure described for the synthesis of Tb2, Fmoc removal [N(CH$_2$CH$_2$NH$_2$)$_3$] from 9 followed by coupling (acid 23:amine9a:HATU:Et$_3$N/3:1:3:6), Boc-Tb8 was obtained as white foam (8.7 mg, 46%, for the two steps). Boc-Tb8: R$_f$=0.47 (silica gel, 5% MeOH in CH$_2$Cl$_2$).

To an ice-cooled stirred solution of Boc-Tb8 (15.6 mg, 0.018 mmol) in CH$_2$Cl$_2$ (0.47 mL) was added trifluoroacetic acid (0.045 mL, 0.56 mmol) and the reaction mixture was stirred for 12 h while warming up to 25° C. Evaporation of the volatile components under reduced pressure furnished the crude TFA-ammonium salt. To the resulting crude was added Et$_2$O (5 mL) and the solvent was removed under reduced pressure. The resulting crude was purified by flash column chromatography (silica gel, 10% MeOH in CH$_2$Cl$_2$ with 1% NH$_4$OH) to furnish Tb8 as colorless liquid (6.9 mg, 90%). Tb8: R$_f$=0.32 (silica gel, 10% MeOH in CH$_2$Cl$_2$ with 1% NH$_4$OH); FT-IR $v_{max}$ (film in MeOH): 3002, 2600, 2334, 2159, 1768, 1707, 1688, 1660, 1591, 1550, 1509, 1478, 1439, 1392, 1329, 1251, 1184, 1001 cm$^{-1}$; [α]$_D^{23}$ −34.3 (c 0.69, MeOH); $^1$H NMR: (CD$_3$OD, 600 MHz) δ=8.1 (s, 1H), 7.29-7.24 (m, 4H), 7.21-7.18 (m, 1H), 5.72-5.70 (m, 1H), 4.77 (d, 1H, J=9 Hz), 4.48 (bs, 1H), 4.39-4.35 (m, 1H), 3.61 (s, 3H), 3.1 (s, 3H), 2.94-2.86 (m, 2H), 2.64-2.59 (m, 1H), 2.42-2.37 (m, 1H), 2.35 (s, 3H), 2.28-2.24 (m, 1H), 2.17 (s, 3H), 2.05 (s, 6H), 2.02-1.93 (m, 3H), 1.89-1.84 (m, 1H), 1.78-1.73 (m, 1H), 1.61-1.57 (m, 1H), 1.16 (d, 3H, J=6.6 Hz), 1.05 (d, 3H, J=6.6 Hz), 0.96-0.93 (m, 6H), 0.82 (d, 3H, J=6.6 Hz) ppm; $^{13}$C NMR: (CD$_3$OD, 150 MHz) δ=178.2, 175.1, 175.1, 172.8, 171.8, 162.7, 150.8, 139.5, 130.4, 129.3, 127.4, 125.2, 71.2, 55.3, 53.3, 52.2, 52.0, 50.2, 49.6, 42.3, 38.8, 37.7, 37.0, 36.2, 35.6, 31.2, 31.1, 31.1, 25.6, 20.9, 20.5, 19.9, 18.1, 16.3, 11.1 ppm; HRMS calcd for $C_{39}H_{57}N_5O_7S$ [M+Na$^+$]762.3871. found 762.3847.

Methyl(2S,4R)-4-(2-((R,3R)-3-((2S,3S)-2-(4-acetamidocubane-1-carboxamido)-N,3-dimethylpentanamido)-1-acetoxy-4-methylpentyl)thiazole-4-carboxamido)-2-methyl-5-phenylpentanoate (Tb9)

According the procedure described for the synthesis of Tb7, analog Tb9 was obtained as colorless liquid (9.7 mg, 52% for the four steps). Tb9: R$_f$=0.52 (silica gel, 10% MeOH in CH$_2$Cl$_2$ with 1% NH$_4$OH); FT-IR $v_{max}$ (film in MeOH): 3013, 2671, 2345, 2159, 2105, 1776, 1709, 1678, 1586, 1552, 1513, 1482, 1466, 1425, 1384, 1309, 1247, 1184, 984 cm$^{-1}$; [α]$_D^{22}$=−19.0 (c 0.2, MeOH); $^1$H NMR: (CD$_3$OD, 600 MHz) δ=8.09 (s, 1H), 7.68 (d, 1H, J=9 Hz), 7.28-7.24 (m, 4H), 7.20-7.18 (m, 1H), 5.71 (d, 1H, J=10.2 Hz), 4.81-4.78 (m, 1H), 4.60 (s, 2H), 4.46 (bs, 1H), 4.39-4.34 (m, 1H), 4.10-4.07 (m, 4H), 3.61 (s, 3H), 3.12 (s, 3H), 2.94-2.86 (m, 2H), 2.63-2.60 (m, 1H), 2.41-2.34 (m, 2H), 2.29-2.24 (m, 1H), 2.17 (s, 3H), 2.01-1.98 (m, 1H), 1.96 (s, 3H), 1.90-1.84 (m, 1H), 1.78-1.73 (m, 1H), 1.63-1.58 (m, 2H), 1.16 (d, 3H, J=6.6 Hz), 1.04 (d, 3H, J=6.6 Hz), 0.97-0.93 (m, 6H), 0.82 (d, 3H, J=6.6 Hz) ppm; $^{13}$C NMR: (CD$_3$OD, 150 MHz) δ=178.3, 175.3, 174.5, 172.7, 171.8, 162.7, 150.8, 139.4, 130.4, 129.4, 129.3, 127.4, 125.2, 71.2, 67.9, 58.8, 55.1, 52.2, 50.9, 50.2, 49.8, 46.2, 42.3, 38.8, 37.7, 37.1, 35.6, 31.1, 25.6, 22.4, 20.8, 20.5, 20.1, 18.1, 16.3, 11.1 ppm; HRMS calcd for $C_{43}H_{57}N_5O_8S$ [M+Na$^+$] 826.3820. found 826.3815.

Tb9

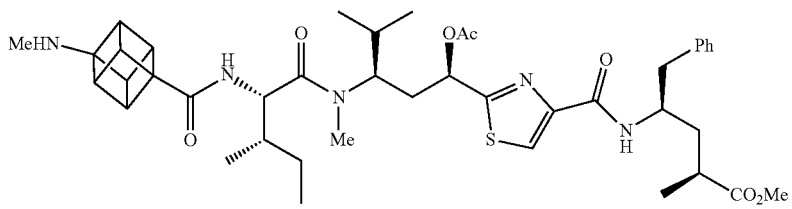

Tb10

Methyl(2S,4R)-4-(2-((1R,3R)-1-acetoxy-3-((2S,3S)—N,3-dimethyl-2-(4-(methylamino)cubane-1-carboxamido)pentanamido)-4-methylpentyl)thiazole-4-carboxamido)-2-methyl-5-phenylpentanoate (Tb10)

According the procedure described for the synthesis of Tb8, analog Tb10 was obtained as colorless liquid (14 mg, 56% for the three steps). Tb10: $R_f$=0.42 (silica gel, 5% MeOH in CH$_2$Cl$_2$); FT-IR $v_{max}$ (film in MeOH): 2671, 2337, 2158, 2113, 1999, 1786, 1760, 1712, 1660, 1593, 1572, 1549, 1525, 1480, 1442, 1429, 1390, 1284, 1249, 1159, 1105, 1006 cm$^{-1}$; $[\alpha]_D^{22}$=−16.8 (c 1.0, MeOH); $^1$H NMR: (CD$_3$OD, 600 MHz) δ=8.08 (s, 1H), 7.25-7.21 (m, 4H), 7.18-7.15 (m, 1H), 5.71-5.69 (m, 1H), 4.77 (d, 1H, J=9 Hz), 4.40 (bs, 1H), 4.36-4.31 (m, 1H), 4.29-4.27 (m, 2H), 4.19-4.17 (m, 2H), 3.58 (s, 3H), 3.50-3.47 (m, 2H), 3.12 (s, 3H), 2.99-2.91 (m, 1H), 2.90-2.84 (m, 2H), 2.68 (s, 3H), 2.40-2.35 (m, 1H), 2.28-2.25 (m, 1H), 2.18 (s, 3H), 1.99-1.90 (m, 2H), 1.89-1.85 (m, 1H), 1.75-1.70 (m, 1H), 1.62-1.56 (m, 1H), 1.18-1.16 (m, 3H), 1.14 (d, 3H, J=7.2 Hz), 1.03 (d, 3H, J=6.6 Hz), 0.96 (d, 3H, J=6.6 Hz), 0.94-0.91 (m, 3H), 0.81 (d, 3H, J=6.6 Hz) ppm; $^{13}$C NMR: (CD$_3$OD, 150 MHz) δ=178.2, 175.2, 173.1, 171.7, 162.7, 160.7, 150.8, 139.5, 130.4, 129.3, 127.4, 125.2, 71.3, 71.2, 66.9, 59.3, 55.3, 52.2, 50.2, 47.6, 46.1, 42.2, 38.8, 37.7, 37.2, 35.6, 31.1, 27.8, 25.6, 20.8, 20.5, 20.1, 18.1, 16.2, 15.4, 11.1 ppm; HRMS calcd for C$_{42}$H$_{57}$N$_5$O$_7$S [M+Na$^+$] 798.3871. found 798.3840.

Tb34

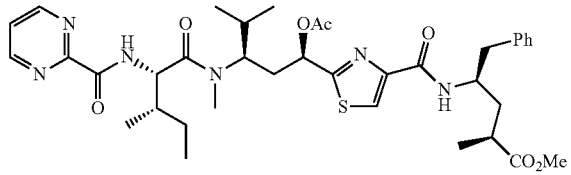

(2S,4R)-methyl 4-(2-((1R,3R)-1-acetoxy-3-((2S,3S)—N,3-dimethyl-2-(pyrimidine-2-carboxamido)pentanamido)-4-methylpentyl)thiazole-4-carboxamido)-2-methyl-5-phenylpentanoate (Tb34)

According to the procedure described for the synthesis of Tb2, analog Tb34 was obtained as an off-white amorphous solid (57 mg, 79% for the two steps). Tb34: $[\alpha]_D^{22}$=−20.3 (c=1.1, MeOH); $R_f$=0.43 (silica gel, MeOH:CH$_2$Cl$_2$:NH$_3$=5:100:0.1); FT-IR (neat) $v_{max}$: 3380, 2966, 2932, 2878, 1731, 1643, 1570, 1544, 1534, 1495, 1458, 1410, 1373, 1222, 1085, 1046, 1003, 935, 843, 740, 702 cm$^{-1}$; $^1$H NMR (CD$_3$OD, 600 MHz) δ 8.95 (d, J=4.7 Hz, 2H), 8.09 (s, 1H), 7.65 (t, J=4.8 Hz, 1H), 7.27-7.21 (m, 4H), 7.17 (ddd, J=8.5, 4.4, 2.0 Hz, 1H), 5.74 (dd, J=11.1, 2.5 Hz, 1H), 5.05 (d, J=7.0 Hz, 1H), 4.50 (m, 1H), 4.36 (m, 1H), 3.59 (s, 3H), 3.16 (s, 3H), 2.95-2.83 (m, 2H), 2.65-2.57 (m, 1H), 2.39 (m, 1H), 2.32-2.24 (m, 1H), 2.16 (s, 3H), 2.04-1.94 (m, 2H), 1.91-1.82 (m, 1H), 1.75 (m, 1H), 1.71-1.64 (m, 1H), 1.31 (dd, J=15.0, 7.7 Hz, 1H), 1.20 (m, 1H), 1.14 (dd, J=7.0, 2.8 Hz, 3H), 1.07 (d, J=6.8 Hz, 3H), 1.02 (d, J=6.6 Hz, 3H), 0.95 (t, J=7.4 Hz, 3H), 0.78 (d, J=6.6 Hz, 3H) ppm. $^{13}$C NMR: (CD$_3$OD, 150 MHz) δ=176.8, 176.3, 172.6, 169.8, 169.7, 162.0, 160.7, 157.1, 156.2, 148.8, 137.5, 128.5, 127.4, 125.5, 123.2, 122.7, 69.2, 53.9, 50.3, 48.3, 40.4, 36.8, 36.3, 35.7, 33.6, 29.0, 23.2, 18.8, 18.5, 18.0, 16.1, 15.7, 14.6, 9.5 ppm; HRMS calcd for C$_{37}$H$_{50}$N$_6$O$_7$S [M+Na]$^+$ 745.3354. found 745.3347.

Tb35

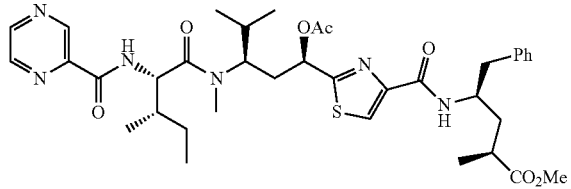

(2S,4R)-methyl 4-(2-((1R,3R)-1-acetoxy-3-((2S,3S)—N,3-dimethyl-2-(pyrazine-2-carboxamido)pentanamido)-4-methylpentyl)thiazole-4-carboxamido)-2-methyl-5-phenylpentanoate (Tb35)

According to the procedure described for the synthesis of Tb2, analog Tb35 was obtained as an off-white amorphous solid (56 mg, 77% for the two steps): $[\alpha]_D^{22}$=−21.0 (c=1.45, MeOH); $R_f$=0.50 (silica gel, MeOH:CH$_2$Cl$_2$:NH$_3$=5:100:0.1); FT-IR (neat) $v_{max}$: 3387, 2965, 2929, 2876, 1735, 1645, 1579, 1541, 1516, 1494, 1464, 1399, 1371, 1258, 1221, 1168, 1082, 1046, 1020, 933, 865, 778, 748, 701 cm$^{-1}$; $^1$H NMR (CD$_3$OD, 600 MHz) δ 9.25 (d, J=1.3 Hz, 1H), 8.81 (d, J=2.4 Hz, 1H), 8.68 (dd, J=2.3, 1.5 Hz, 1H), 8.09 (s, 1H), 7.28-7.20 (m, 4H), 7.17 (m, 1H), 5.73 (dd, J=11.1, 2.6 Hz, 1H), 5.04 (d, J=7.0 Hz, 1H), 4.48 (m, 1H), 4.37 (m, 1H), 3.54 (s, 3H), 3.16 (s, 3H), 2.95-2.83 (m, 2H), 2.61 (m, 1H), 2.43-2.35 (m, 1H), 2.28 (t, J=13.2 Hz, 1H), 2.16 (s, 3H), 2.01 (m, 2H), 1.91-1.81 (m, 1H), 1.74 (m, 1H), 1.70-1.62 (m, 1H), 1.31 (dd, J=16.4, 9.1 Hz, 1H), 1.23-1.15 (m, 1H), 1.14 (d, J=7.1 Hz, 3H), 1.06 (d, J=6.8 Hz, 3H), 1.03-0.98 (m, 3H), 0.94 (t, J=7.4 Hz, 3H), 0.78 (d, J=6.6 Hz, 3H) ppm. $^{13}$C NMR: (CD$_3$OD, 150 MHz) δ=176.8, 176.3, 172.6, 169.74, 169.66, 162.6, 160.7, 148.8, 147.0, 143.6, 142.8, 137.5, 128.4, 127.4, 125.5, 123.2, 69.1, 53.5, 50.2, 48.2, 40.4, 36.8, 36.3, 35.7, 33.6, 29.0, 23.1, 18.8, 18.5, 18.0, 16.1, 15.7, 14.6, 9.5 ppm; HRMS calcd for C$_{37}$H$_{50}$N$_6$O$_7$S [M+Na]$^+$ 745.3354. found 745.3345.

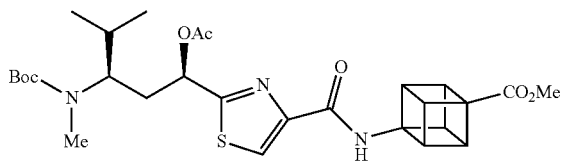

Methyl 4-(2-((1R,3R)-1-acetoxy-3-((tert-butoxycarbonyl)(methyl)-amino)-4-methylpentyl)thiazole-4-carboxamido)cubane-1-carb-oxylate (31)

To a stirred solution of carbamate 24a (50 mg, 0.180 mmol) in $CH_2Cl_2$ (4.0 mL) was added TFA (0.5 mL, 6.2 mmol) and the mixture was stirred at 25° C. for 4 h. The reaction mixture was diluted with toluene (30 mL) and evaporated under reduced pressure to furnish crude amine 29 (~32 mg, quantitative), which was used in the next step without further purification.

To a stirred solution of acid 5 (56 mg, 0.139 mmol) in dry DMF (0.25 mL) were added i-$Pr_2$NEt (0.1 mL, 0.55 mmol), HATU (68 mg, 0.180 mmol) and HOAt (25 mg, 0.180 mmol) at 25° C. and the reaction mixture was stirred for 30 min at 25° C. A solution of the previously synthesized cubane amine 29 (32 mg) in dry DMF (0.23 mL) was then added and stirring was continued at the same temperature for 24 h. The reaction mixture was diluted with $H_2O$ (5 mL) and the resulting solution was extracted with diethyl ether (3×20 mL). The combined organic extracts were washed with brine (5 mL), dried over $Na_2SO_4$ and evaporated under reduced pressure. The resulting residue was purified using flash column chromatography (silica gel, 10→50% EtOAc in hexanes) to produce 31 (43 mg, 55%) as an amorphous light yellow solid. 31: $R_f$=0.54 (silica gel, 50% EtOAc in hexanes); $[\alpha]_D^{22}$=−3.2 (c=0.5, $CH_2Cl_2$); FT-IR (neat) $\tilde{v}_{max}$: 3382, 3299, 2967, 2937, 2924, 2874, 2845, 2826, 1735, 1671, 1644, 1591, 1569, 1541, 1513, 1456, 1436, 1411, 1371, 1346, 1321, 1258, 1222, 1170, 1142, 1054, 1033, 1015, 933, 914, 874, 851, 819, 797, 781, 750, 702, 662, 638, 624, 610 $cm^{-1}$; $^1$H NMR analysis at 23° C. indicated a ca. 7:3 mixture of rotamers. Major rotamer: $^1$H NMR: ($CDCl_3$, 600 MHz) δ=8.00 (s, 1H), 7.73 (s, 1H), 5.80 (dd, J=11.5, 2.8 Hz, 1H), 4.28-4.22 (m, 3H), 4.20 (q, J=5.0, 4.2 Hz, 3H), 4.10-4.03 (m, 1H), 3.70 (s, 3H), 2.68 (s, 3H), 2.30 (ddd, J=15.0, 11.6, 3.8 Hz, 1H), 2.13 (s, 3H), 1.99 (t, J=13.2 Hz, 1H), 1.77-1.63 (m, 1H), 1.42 (s, 10H), 0.97 (d, J=6.8 Hz, 3H), 0.85 ppm (d, J=6.6 Hz, 3H); $^{13}$C NMR: ($CDCl_3$, 150 MHz) δ=172.9, 170.8, 170.4, 160.4, 156.4, 150.0, 123.8, 79.7, 69.4, 66.7, 56.1, 51.8, 50.6, 45.4, 35.2, 30.7, 28.6, 21.1, 20.2, 19.8 ppm; Minor rotamer: $^1$H NMR: ($CDCl_3$, 600 MHz) δ=8.00 (s, 1H), 7.90 (s, 1H), 5.91 (dd, J=8.8, 3.6 Hz, 1H), 4.28-4.22 (m, 3H), 4.20 (q, J=5.0, 4.2 Hz, 3H), 4.13-3.98 (m, 1H), 3.70 (s, 3H), 2.63 (s, 3H), 2.21 (ddd, J=14.8, 8.7, 2.7 Hz, 1H), 2.14 (s, 3H), 1.99 (t, J=13.2 Hz, 1H), 1.74-1.64 (m, 1H), 1.43 (s, 10H), 0.96 (d, J=7.4 Hz, 3H), 0.85 ppm (d, J=6.6 Hz, 3H); $^{13}$C NMR: ($CDCl_3$, 150 MHz) δ=172.9, 170.5, 169.6, 160.4, 156, 1, 150.0, 123.6, 80.1, 70.8, 66.7, 56.1, 51.8, 50.6, 45.5, 35.2, 30.7, 28.7, 21.2, 20.5, 20.0 ppm; HRMS calcd for $C_{28}H_{37}N_3NaO_7S$ [M+Na$^+$] 582.2244. found 582.2238.

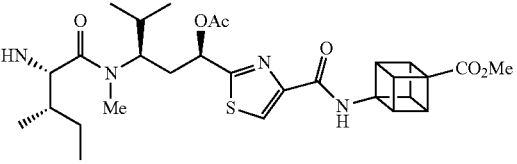

Methyl 4-(2-((5S,8R,10R)-5-((S)-sec-butyl)-1-(9H-fluoren-9-yl)-8-isopropyl-7-methyl-3,6,12-trioxo-2,11-dioxa-4,7-diazatri-decan-10-yl)thiazole-4-carboxamido)cubane-1-carboxylate (33)

According to the procedure described for the synthesis of 9, compound 33 was obtained as an amorphous light yellow solid (43 mg, 76% for the two steps). 33: $R_f$=0.37 (silica gel, 50% EtOAc in hexanes); $[\alpha]_D^{22}$=−21.6° (c=0.5, $CH_2Cl_2$); FT-IR (neat) $\tilde{v}_{max}$: 3694, 3681, 3382, 2967, 2937, 2924, 2874, 2845, 2826, 1735, 1671, 1644, 1591, 1569, 1541, 1513, 1456, 1436, 1411, 1371, 1346, 1321, 1258, 1222, 1170, 1142, 1054, 1033, 1015, 933, 914, 874, 851, 819, 797, 781, 750, 702, 662, 638, 624, 610 $cm^{-1}$; $^1$H NMR: ($CDCl_3$, 600 MHz) δ=8.01 (s, 1H), 7.79 (s, 1H), 7.74 (d, J=7.5 Hz, 2H), 7.55 (dd, J=7.3, 3.5 Hz, 2H), 7.37 (t, J=7.4 Hz, 2H), 7.28 (t, J=7.4 Hz, 2H), 5.66 (dd, J=10.7, 2.6 Hz, 1H), 5.38 (d, J=9.8 Hz, 1H), 4.54 (s, 1H), 4.54-4.48 (m, 1H), 4.40-4.35 (m, 1H), 4.32 (dd, J=10.5, 7.4 Hz, 1H), 4.28-4.23 (m, 3H), 4.23-4.18 (m, 3H), 4.21-4.16 (m, 1H), 3.70 (s, 3H), 2.97 (s, 3H), 2.32 (ddd, J=14.5, 11.0, 2.9 Hz, 1H), 2.15 (s, 3H), 1.80-1.68 (m, 2H), 1.67-1.48 (m, 3H), 1.01 (d, J=6.5 Hz, 3H), 0.96 (d, J=6.7 Hz, 3H), 0.91 (t, J=7.3 Hz, 3H), 0.79 ppm (d, J=6.5 Hz, 3H): $^{13}$C NMR: ($CDCl_3$, 150 MHz) δ=173.8, 172.9, 170.4, 170.2, 160.3, 156.6, 149.9, 144.1, 144.0, 141.5, 141.5, 127.9, 127.3, 125.3, 125.3, 123.9, 120.2, 169.8, 67.2, 66.7, 56.1, 55.9, 51.8, 50.6, 50.5, 47.4, 45.4, 37.6, 35.2, 30.4, 24.2, 21.0, 20.3, 19.8, 16.2, 14.4, 11.4 ppm: HRMS calcd for $C_{44}H_{50}N_4NaO_8S$ [M+Na$^+$] 817.3242. found 817.3212.

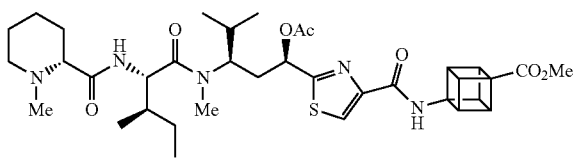

Methyl 4-(2-((1R,3R)-1-acetoxy-3-((2S,3S)—N,3-dimethyl-2-((R)-1-methylpiperidine-2-carboxamido)-pentanamido)-4-methylpentyl)thiazole-4-carboxamido)cubane-1-carboxylate (Tb11)

According to the procedure described for the synthesis of Tb3, analogue Tb11 was obtained as a colorless oil (11.2 mg, 63% for the two steps). Tb11: $R_f$=0.03 (silica gel, 50% EtOAc in hexanes); $[\alpha]_D^{22}$=+5.6 (c=0.5, $CH_2Cl_2$); FT-IR (neat) $\tilde{v}_{max}$: 3710, 3694, 3681, 2967, 2937, 2924, 2874, 2845, 2826, 1735, 1671, 1644, 1591, 1569, 1541, 1513, 1456, 1436, 1411, 1371, 1346, 1321, 1258, 1222, 1170, 1142, 1054, 1033, 1015, 933, 914, 874, 851, 819, 797, 781, 750, 702, 662, 638, 624, 610 $cm^{-1}$; $^1$H NMR: ($CDCl_3$, 600

MHz) δ=8.01 (s, 1H), 7.86 (s, 1H), 7.03 (s, 1H), 5.68 (dd, J=10.5, 3.3 Hz, 1H), 4.74 (t, J=7.6 Hz, 1H), 4.58 (s, 1H), 4.30-4.23 (m, 3H), 4.20 (dd, J=5.9, 4.2 Hz, 3H), 3.70 (s, 3H), 3.01 (s, 3H), 2.87 (dd, J=13.1, 5.8 Hz, 1H), 2.51-2.41 (m, 1H), 2.30 (ddd, J=14.6, 10.7, 3.5 Hz, 1H), 2.21 (s, 3H), 2.14 (s, 3H), 2.09-1.93 (m, 2H), 1.78 (m, 3H), 1.68-1.54 (m, 3H), 1.48 (d, J=13.5 Hz, 1H), 1.38-1.28 (m, 1H), 1.15 (dd, J=23.1, 10.3 Hz, 2H), 1.00 (d, J=6.5 Hz, 3H), 0.94 (d, J=6.9 Hz, 3H), 0.89 (t, J=7.4 Hz, 3H), 0.77 ppm (d, J=6.6 Hz, 3H); $^{13}$C NMR: (CDCl$_3$, 150 MHz) δ=174.5, 173.7, 172.9, 170.4, 170.2, 160.4, 149.9, 123.8, 70.0, 66.7, 56.1, 55.6, 53.1, 50.6, 45.4, 37.2, 35.5, 32.2, 31.2, 30.7, 30.4, 29.9, 25.3, 24.8, 23.5, 21.1, 20.2, 19.9, 16.1, 14.3, 11.1 ppm; HRMS calcd for C$_{36}$H$_{52}$N$_5$O$_7$S [M+H$^+$] 698.3582. found 698.3591.

Tb12

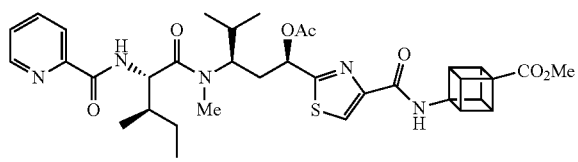

Methyl 4-(2-((1R,3R)-1-acetoxy-3-((2S,3S)—N,3-dimethyl-2-(picolinamido)pentanamido)-4-methylpentyl)thiazole-4-carboxamido)cubane-1-carboxylate (Tb12)

According to the procedure described for the synthesis of Tb3, analogue Tb12 was obtained as a colorless oil (12.5 mg, 73% for the two steps). Tb12: R$_f$=0.04 (silica gel, 50% EtOAc in hexanes); [α]$_D^{22}$=−4.4 (c=0.5, CH$_2$Cl$_2$); FT-IR (neat) $\tilde{v}_{max}$: 3680, 3381, 3299, 3279, 2967, 2936, 2875, 2845, 1752, 1721, 1646, 1591, 1570, 1515, 1485, 1466, 1435, 1410, 1371, 1310, 1216, 1136, 1092, 1052, 1033, 1017, 999, 921, 872, 841, 819, 800, 771, 732, 695, 645, 622 cm$^{-1}$; $^1$H NMR: (CDCl$_3$, 600 MHz) δ=8.54 (s, 1H), 8.54 (d, J=15.1 Hz, 1H), 8.12 (d, J=7.8 Hz, 1H), 8.01 (s, 1H), 7.86 (s, 1H), 7.81 (td, J=7.7, 1.7 Hz, 1H), 7.40 (ddd, J=7.6, 4.8, 1.1 Hz, 1H), 5.71 (dd, J=10.6, 3.3 Hz, 1H), 4.97 (dd, J=9.7, 7.2 Hz, 1H), 4.58 (s, 1H), 4.27 (dd, J=6.2, 3.9 Hz, 3H), 4.21 (dd, J=6.2, 3.9 Hz, 3H), 3.70 (s, 3H), 3.05 (s, 3H), 2.31 (ddd, J=14.4, 10.7, 3.5 Hz, 1H), 2.16 (s, 3H), 2.10-2.02 (m, 1H), 1.92 (ddt, J=9.9, 6.9, 3.5 Hz, 1H), 1.74 (dp, J=16.5, 6.6 Hz, 3H), 1.64 (dtt, J=15.0, 7.4, 3.7 Hz, 1H), 1.21-1.12 (m, 3H), 1.00 (d, J=6.7 Hz, 3H), 0.98 (d, J=6.6 Hz, 3H), 0.90 (t, J=7.4 Hz, 3H), 0.74 ppm (d, J=6.6 Hz, 3H); $^{13}$C NMR: (CDCl$_3$, 150 MHz) δ=173.2, 172.9, 170.4, 170.3, 164.2, 160.4, 149.9, 149.6, 148.5, 137.4, 126.4, 123.8, 122.4, 69.9, 66.7, 56.1, 54.1, 51.8, 50.6, 50.5, 45.5, 37.3, 35.3, 30.5, 29.9, 24.4, 21.1, 20.3, 19.7, 16.3, 11.4 ppm; HRMS calcd for C$_{35}$H$_{44}$N$_5$O$_7$S [M+H$^+$] 678.2956. found 678.2946.

Tb13

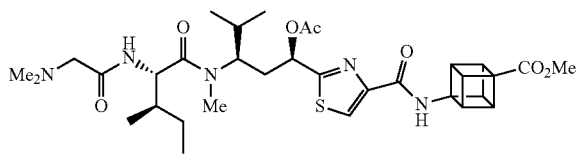

Methyl 4-(2-((6S,9R,11R)-6-((S)-sec-butyl)-9-isopropyl-2,8-dimethyl-4,7,13-trioxo-12-oxa-2,5,8-triaza-tetradecan-11-yl)thiazole-4-carboxamido)cubane-1-carboxylate (Tb13)

According to the procedure described for the synthesis of Tb3, analogue Tb13 was obtained as an amorphous yellow solid (16.9 mg, 64% for the two steps). Tb13: Rt=0.02 (silica gel, 50% EtOAc in hexanes); [α]$_D^{22}$=−6.4 (c=0.5, CH$_2$Cl$_2$); FT-IR (neat) $\tilde{v}_{max}$: 3680, 3381, 3299, 3279, 2967, 2936, 2875, 2845, 1752, 1721, 1646, 1591, 1570, 1515, 1485, 1466, 1435, 1410, 1371, 1310, 1216, 1136, 1092, 1052, 1033, 1017, 999, 921, 872, 841, 819, 800, 771, 732, 695, 645, 622 cm$^{-1}$; $^1$H NMR: 8.00 (s, 1H), 7.84 (s, 1H), 7.60 (d, J=9.1 Hz, 1H), 5.67 (dd, J=10.6, 3.2 Hz, 1H), 4.77 (dd, J=9.5, 7.6 Hz, 3H), 4.54 (s, 1H), 4.25 (dd, J=6.1, 3.9 Hz, 3H), 4.20 (dt, J=5.3, 3.7 Hz, 3H), 3.69 (s, 3H), 3.48-3.38 (m, 1H), 3.02 (d, J=10.0 Hz, 1H), 2.99 (s, 3H), 2.90 (d, J=16.0 Hz, 1H), 2.31-2.27 (m, 1H), 2.27 (s, 6H), 2.14 (s, 3H), 1.90 (dd, J=12.6, 3.3 Hz, 1H), 1.82-1.75 (m, 1H), 1.78-1.69 (m, 1H), 1.66 (dt, J=13.6, 3.7 Hz, 1H), 1.60-1.51 (m, 1H), 1.00 (d, J=6.6 Hz, 3H), 0.93 (d, J=6.8 Hz, 3H), 0.88 (t, J=7.4 Hz, 3H), 0.77 ppm (d, J=6.6 Hz, 3H); $^{13}$C NMR: (CDCl$_3$, 150 MHz) δ=173.4, 172.9, 170.4, 170.2, 160.4, 157.0, 149.9, 123.8, 69.9, 66.7, 63.0, 56.1, 53.4, 51.8, 50.6, 49.3, 46.0, 45.4, 37.3, 35.4, 34.2, 30.5, 25.8, 25.2, 24.5, 21.0, 20.2, 19.7, 16.1, 11.3 ppm; HRMS calcd for C$_{35}$H$_{44}$N$_5$O$_7$S [M+H$^+$] 658.3269. found 658.3269.

32

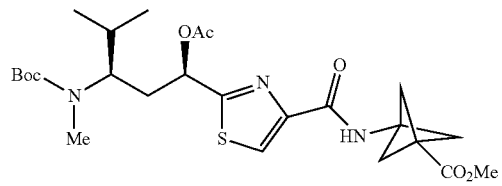

Methyl 3-(2-((1R,3R)-1-acetoxy-3-((tert-butoxycarbonyl)(methyl)-amino)-4-methylpentyl)thiazole-4-carb-oxamido)bicyclo[1.1]-pentane-1-carboxylate (32)

To a stirred solution of benzyl carbamate 23a (50 mg, 0.198 mmol) in MeOH (4.5 mL) under a nitrogen atmosphere was added 10% wt. palladium on charcoal (5 mg). The atmosphere was exchanged to hydrogen (1 atm) and the mixture was stirred at 25° C. for 4 h. After TLC analysis indicated complete liberation of the amine functionality, the mixture was filtered through a pad of Celite©, rinsed with MeOH (5 mL) and evaporated under reduced pressure to produce free amine 30 (~28 mg, quantitative yield), which was used in the next step without further purification.

To a stirred solution of 5 (57 mg, 0.141 mmol) in dry DMF (0.3 mL) were added i-Pr$_2$NEt (0.1 mL, 0.564 mmol), HATU (75 mg, 0.198 mmol) and HOAt (27 mg, 0.198 mmol) at 25° C. and the mixture was stirred for 30 min. A solution of the previously synthesized amine 30 (28 mg) in dry DMF (0.3 mL) was then added and the reaction mixture was stirred at 25° C. for 24 h. The reaction mixture was diluted with H$_2$O (5 mL) and the resulting solution was extracted with diethyl ether (3×20 mL). The combined organic extracts were washed with brine (5 mL), dried over Na$_2$SO$_4$ and evaporated under reduced pressure. The resulting residue was purified using flash column chromatography (silica gel, 10→50% EtOAc in hexanes) to provide 32 (40 mg, 54%) as an amorphous yellow solid. 32: $R_f$=0.60 (silica gel, 50% EtOAc in hexanes); $[\alpha]_D^{22}$=−1.4 (c=0.5, $CH_2Cl_2$); FT-IR (neat) $\tilde{v}_{max}$: 3680, 3381, 3299, 3279, 2967, 2936, 2875, 2845, 1752, 1721, 1646, 1591, 1570, 1515, 1485, 1466, 1435, 1410, 1371, 1310, 1216, 1136, 1092, 1052, 1033, 1017, 999, 921, 872, 841, 819, 800, 771, 732, 695, 645, 622 $cm^{-1}$; $^1$H NMR analysis at 23° C. revealed a ca. 2:1 mixture of rotamers. Major rotamer: $^1$H NMR: ($CDCl_3$, 600 MHz) δ=8.01 (s, 1H), 7.59 (s, 1H), 5.79 (dd, J=11.6, 2.6 Hz, 1H), 4.05 (t, J=9.4 Hz, 1H), 3.68 (s, 3H), 2.68 (s, 3H), 2.46 (s, 6H), 2.29 (ddd, J=15.0, 11.7, 3.6 Hz, 1H), 2.12 (s, 3H), 1.74-1.63 (m, 1H), 1.64-1.56 (m, 1H), 1.42 (s, 9H), 0.97 (d, J=6.8 Hz, 3H), 0.85 ppm (d, J=6.5 Hz, 3H); $^{13}$C NMR: ($CDCl_3$, 150 MHz) δ=170.8, 170.4, 170.1, 161.3, 156.4, 149.9, 123.9, 79.7, 69.4, 56.7, 54.8, 52.1, 45.9, 36.4, 35.2, 30.6, 28.6, 21.1, 20.2, 19.8 ppm; Minor rotamer: $^1$H NMR: ($CDCl_3$, 600 MHz) δ=8.01 (s, 1H), 7.81 (s, 1H), 5.91 (dd, J=8.5, 3.6 Hz, 1H), 4.05 (t, J=9.4 Hz, 1H), 3.68 (s, 3H), 2.61 (s, 3H), 2.46 (s, 6H), 2.20 (ddd, J=14.4, 8.7, 2.5 Hz, 1H), 2.14 (s, 3H), 1.75-1.64 (m, 1H), 1.64-1.55 (m, 1H), 1.43 (s, 9H), 0.96 (d, J=8.1 Hz, 3H), 0.85 (d, J=6.5 Hz, 3H); $^{13}$C NMR: ($CDCl_3$, 150 MHz) h=170.4, 170.2, 169.6, 161.4, 156.5, 150.1, 80.1, 70.9, 56.7, 54.8, 52.1, 45.9, 36.4, 35.2, 30.6, 28.7, 21.2, 20.5, 20.0 ppm; HRMS calcd for $C_{25}H_{37}N_3O_7S$ [M+Na$^+$] 546.2244. found 546.2235.

34

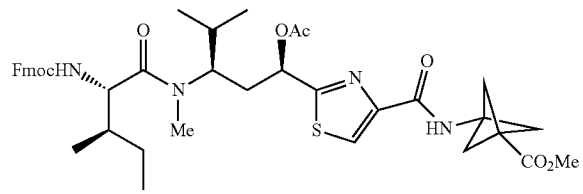

Methyl 3-(2-((5S,8R,10R)-5-((S)-sec-butyl)-1-(9H-fluoren-9-yl)-8-isopropyl-7-methyl-3,6,12-trioxo-2,11-dioxa-4,7-diaza-tridecan-10-yl)thiazole-4-carboxamido)bicyclo[1.1.1]pentane-1-carboxylate (34)

According to the procedure described for the synthesis of 9, compound 34 was obtained as an amorphous light yellow solid (41 mg, 71% for the two steps). 34: $R_f$=0.42 (silica gel, 50% EtOAc in hexanes); $[\alpha]_D^{22}$=−4.0 (c=1, $CH_2Cl_2$); FT-IR (neat) $\tilde{v}_{max}$: 3680, 3381, 3299, 3279, 2967, 2936, 2875, 2845, 1752, 1721, 1646, 1591, 1570, 1515, 1485, 1466, 1435, 1410, 1371, 1310, 1216, 1136, 1092, 1052, 1033, 1017, 999, 921, 872, 841, 819, 800, 771, 732, 695, 645, 622 $cm^{-1}$; $^1$H NMR: ($CDCl_3$, 600 MHz) δ=8.02 (s, 1H), 7.74 (d, J=7.5 Hz, 2H), 7.59 (s, 1H), 7.55 (dd, J=7.1, 4.1 Hz, 2H), 7.37 (t, J=7.4 Hz, 2H), 7.28 (t, J=7.5 Hz, 2H), 5.64 (d, J=9.4 Hz, 1H), 5.39 (d, J=9.6 Hz, 1H), 4.55-4.46 (m, 1H), 4.50 (s, 1H), 4.41-4.27 (m, 2H), 4.18 (t, J=7.2 Hz, 1H), 3.69 (s, 3H), 2.97 (s, 3H), 2.47 (s, 6H), 2.35-2.29 (m, 1H), 2.15 (s, 3H), 2.06 (m, 1H), 1.79-1.70 (m, 2H), 1.65-1.48 (m, 2H), 1.00 (d, J=6.6 Hz, 3H), 0.97 (d, J=6.7 Hz, 3H), 0.92 (t, J=7.3 Hz, 3H), 0.79 ppm (d, J=6.5 Hz, 3H); $^{13}$C NMR: ($CDCl_3$, 150 MHz) δ=173.8, 170.3, 170.3, 170.1, 161.3, 156.6, 150.0, 144.1, 144.0, 141.5, 141.5, 127.9 127.3, 125.3, 125.3, 124.0, 120.2, 69.6, 67.2, 56.0, 56.0, 54.8, 52.1, 47.4, 45.9, 37.6, 36.4, 34.9, 30.2, 29.9, 24.1, 21.0, 20.3, 19.8, 16.2, 11.4 ppm; HRMS calcd for $C_{47}H_{58}N_4NaO_8S$ [M+Na$^+$] 861.3868. found 861.3867.

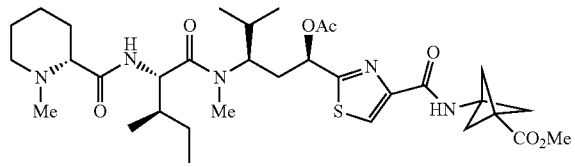

Methyl 3-(2-((1R,3R)-1-acetoxy-3-((2S,3S)—N,3-dimethyl-2-((R)-1-methylpiperidine-2-carboxamido)-pentanamido)-4-methylpentyl)thiazole-4-carboxamido)bicyclo[1.1.1]pentane-1-carboxylate (Tb14)

According to the procedure described for the synthesis of Tb3, analogue Tb14 was obtained as a colorless oil (10.3 mg, 59% for the two steps). Tb14: $R_f$=0.03 (silica gel, 50% EtOAc in hexanes); $[\alpha]_D^{22}$=+11.0 (c=0.5, $CH_2Cl_2$); FT-IR (neat) $\tilde{v}_{max}$: 3708, 3681, 3664, 3381, 3360, 3299, 3281, 2966, 2937, 2924, 2875, 2825, 1743, 1670, 1642, 1535, 1489, 1439, 1412, 1371, 1348, 1309, 1277, 1205, 1143, 1099, 1054, 1033, 1015, 936, 920, 851, 795, 732, 696, 663, 644, 623 $cm^{-1}$; $^1$H NMR: ($CDCl_3$, 600 MHz) δ=8.01 (s, 1H), 7.64 (s, 1H), 7.06 (s, 1H), 5.65 (dd, J=11.1, 2.8 Hz, 1H), 4.75 (t, J=8.2 Hz, 1H), 4.53 (s, 1H), 3.69 (s, 3H), 3.01 (s, 3H), 2.88-2.82 (m, 1H), 2.47 (s, 6H), 2.31 (ddd, J=14.8, 11.2, 3.3 Hz, 1H), 2.24-2.17 (m, 3H), 2.14 (s, 3H), 2.07-1.92 (m, 2H), 1.84-1.70 (m, 3H), 1.68-1.55 (m, 2H), 1.53-1.44 (m, 1H), 1.37-1.27 (m, 2H), 1.21-1.07 (m, 2H), 0.99 (d, J=6.5 Hz, 3H), 0.96 (d, J=6.8 Hz, 3H), 0.89 (t, J=7.4 Hz, 3H), 0.77 ppm (d, J=6.6 Hz, 3H); $^{13}$C NMR: ($CDCl_3$, 150 MHz) δ=174.5, 173.7, 170.4, 170.3, 170.1, 161.3, 150.1, 124.0, 124.0, 69.8, 55.6, 54.8, 53.1, 52.1, 52.1, 45.9, 45.2, 37.2, 36.4, 35.1, 30.7, 30.3, 30.2, 29.9, 25.3, 24.7, 23.5, 21.1, 20.3, 19.9, 16.2, 11.2 ppm; HRMS calcd for $C_{33}H_{52}N_5O_7S$ [M+H$^+$]662.3582. found 662.3572.

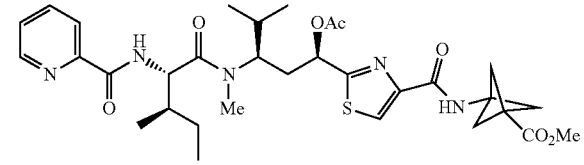

Methyl 3-(2-((1R,3R)-1-acetoxy-3-((2S,3S)—N,3-dimethyl-2-(picolinamido)pentanamido)-4-methylpentyl)thiazole-4-carboxamido)bicyclo[1.1.1]pentane-1-carboxylate (Tb15)

According to the procedure described for the synthesis of Tb3, analogue Tb15 (9.8 mg, 58% for the two steps) was obtained as a colorless oil. Tb15: $R_f$=0.05 (silica gel, 50% EtOAc in hexanes); $[\alpha]_D^{22}$=+1.6 (c=0.5, $CH_2Cl_2$); FT-IR (neat) $\tilde{v}_{max}$: 3708, 3681, 3664, 3381, 3360, 3299, 3281, 2966, 2937, 2924, 2875, 2825, 1743, 1670, 1642, 1535, 1489, 1439, 1412, 1371, 1348, 1309, 1277, 1205, 1143, 1099, 1054, 1033, 1015, 936, 920, 851, 795, 732, 696, 663, 644, 623 $cm^{-1}$; $^1$H NMR: ($CDCl_3$, 600 MHz) δ=8.55 (d, J=9.1 Hz, 1H), 8.54 (s, 1H), 8.12 (d, J=7.8 Hz, 1H), 8.02 (s, 1H), 7.81 (td, J=7.7, 1.6 Hz, 1H), 7.67 (s, 1H), 7.44-7.34 (m, 1H), 5.69 (dd, J=11.0, 2.9 Hz, 1H), 4.98 (dd, J=9.7, 7.0 Hz, 1H), 4.55 (s, 1H), 3.69 (s, 3H), 3.05 (s, 3H), 2.48 (s, 6H), 2.31 (ddd, J=14.6, 11.0, 3.3 Hz, 1H), 2.16 (s, 3H), 2.09-2.03 (m, 1H), 1.97-1.89 (m, 1H), 1.73 (ddt, J=19.9, 13.4, 6.7 Hz, 1H), 1.64 (ddp, J=14.9, 7.4, 4.4, 3.8 Hz, 1H), 1.21-1.12 (m, 1H), 1.01 (d, J=6.7 Hz, 3H), 0.97 (d, J=6.6 Hz, 3H), 0.90 (t, J=7.4 Hz, 3H), 0.74 ppm (d, J=6.6 Hz, 3H); $^{13}$C NMR: (CDCl$_3$, 150 MHz) δ=173.2, 170.3, 170.3, 170.2, 164.2, 161.3, 150.1, 149.7, 148.6, 137.4, 126.4, 124.0, 122.4, 69.8, 56.1, 54.9, 54.8, 54.1, 52.1, 45.9, 37.7, 36.4, 35.1, 30.3, 29.9, 24.3, 21.1, 20.3, 19.7, 16.4, 11.5 ppm; HRMS calcd for C$_{32}$H$_{44}$N$_5$O$_7$S [M+H$^+$] 642.2956. found 642.2970.

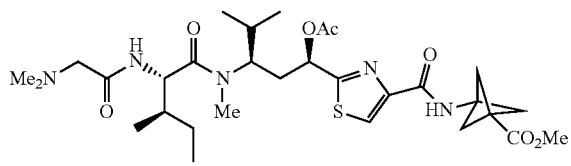

Methyl 3-(2-((6S,9R,11R)-6-((S sec-butyl)-9-isopropyl-2,8-dimethyl-4,7,13-trioxo-12-oxa-2,5,8-triazatetradecan-11-yl)thiazole-4-carboxamido)bicyclo[1.1.1]pentane-1-carboxylate (Tb16)

According to the procedure described for the synthesis of Tb3, analogue Tb16 was obtained as a colorless oil (12.5 mg, 69% for the two steps). Tb16: R$_f$=0.02 (silica gel, 50% EtOAc in hexanes); [α]$_D^{22}$=−3.4 (c=0.5, CH$_2$Cl$_2$); FT-IR (neat) $\tilde{v}_{max}$: 3708, 3681, 3664, 3381, 3360, 3299, 3281, 2966, 2937, 2924, 2875, 2825, 1743, 1670, 1642, 1535, 1489, 1439, 1412, 1371, 1348, 1309, 1277, 1205, 1143, 1099, 1054, 1033, 1015, 936, 920, 851, 795, 732, 696, 663, 644, 623 cm$^{-1}$; $^1$H NMR: (CDCl$_3$, 600 MHz) δ=8.01 (s, 1H), 7.67 (s, 1H), 7.64 (s, 1H), 5.65 (dd, J=11.1, 2.8 Hz, 1H), 4.77 (dd, J=9.3, 7.4 Hz, 1H), 4.49 (s, 1H), 1.11-1.06 (m, 1H), 3.68 (s, 3H), 3.15-3.02 (m, 1H), 3.00 (s, 3H), 3.00-2.91 (m, 1H), 2.47 (s, 6H), 2.32 (m, 7H), 2.13 (s, 3H), 2.10-2.02 (m, 1H), 1.81 (dtt, J=13.7, 9.7, 4.9 Hz, 1H), 1.77-1.71 (m, 1H), 1.57 (ddp, J=14.9, 7.4, 4.5, 3.8 Hz, 1H), 0.99 (d, J=6.6 Hz, 3H), 0.95 (d, J=6.7 Hz, 3H), 0.89 (t, J=7.4 Hz, 3H), 0.78 (d, J=6.6 Hz, 3H); $^{13}$C NMR: (CDCl$_3$, 150 MHz) δ=173.4, 170.3, 170.2, 170.1, 161.3, 150.0, 124.0 (2C), 69.8, 62.7, 56.2, 54.8, 53.6, 52.1, 45.9, 45.8, 37.2, 36.4, 35.1, 30.3, 29.9, 24.4, 21.0, 20.3, 19.8, 16.2, 11.4 ppm; HRMS calcd for C$_{35}$H$_{44}$N$_5$O$_7$S [M+H$^+$] 622.3269. found 622.3278.

Methyl (2S,4R)-4-(4-((S)-2-((tert-butoxycarbonyl)(methyl)amino)-3-methylbutanamido) cubane-1-carboxamido)-2-methyl-5-phenylpentanoate (39)

To a stirred solution of amino ester 29 (100 mg, 0.36 mmol) in dry DMF (2.5 mL) was added Et$_3$N (0.35 mL, 2.4 mmol) at 0° C., and stirring continued for 15 minutes. Protected amino acid 35 (70 mg, 0.3 mmol) and HOAt (4.0 mg, 0.03 mmol) were then added, followed by HATU (171.0 mg, 0.45 mmol) and the reaction mixture was stirred at 25° C. for 4 h. The solvent was removed under reduced pressure and EtOAc (100 mL) was added. The resulting solution was washed with brine (3×20 mL), dried with Na$_2$SO$_4$, filtered and concentrated under reduced pressure to furnish crude ester 37, which was used in the next step without further purification.

To a solution of crude ester 37 in THF (3.0 mL) was added 1N NaOH (aq, 0.72 mL), and the reaction mixture was stirred at 25° C. for 11 h. After completion of the saponification was established by TLC chromatography, the solution was neutralized to pH=3 with 1N HCl at 0° C. The solvent was removed under reduced pressure and EtOAc (100 mL) was added to the residue. The solution was washed with brine (2×10 mL), dried over Na$_2$SO$_4$, filtered, and concentrated to produce the desired carboxylic acid, which was used in the next step without further purification.

To a stirred solution of the crude carboxylic acid in dry DMF (1.6 mL) were consecutively added amino ester 6 (56 mg, 0.25 mmol), Et$_3$N (0.23 mL, 1.64 mmol), HOAt (2.8 mg, 0.02 mmol) and HATU (120 mg, 0.3 mmol) at 0° C. After stirring at ambient temperature for 15 h, the solvent was removed under reduced pressure and EtOAc (100 mL) was added to the residue. The resulting solution was washed with brine (3×20 mL), dried over Na$_2$SO$_4$, filtered, and concentrated. Purification by flash column chromatography (silica gel, 50% EtOAc in hexanes) provided tripeptide 39 (80.0 mg, 57% for the three steps) as a colorless amorphous solid. 39: R$_f$=0.23 (silica gel, 50% EtOAc in hexanes); [α]$_D^{22}$=−59.4 (c=0.35, CHCl$_3$); FT-IR (neat) $\tilde{v}_{max}$: 3302, 2966, 2926, 1736, 1659, 1525, 1455, 1366, 1318, 1153, 935, 840, 748, 701 cm$^{-1}$; $^1$H NMR (CDCl$_3$, 600 MHz) δ=7.33-7.26 (m, 2H), 7.21 (t, J=7.2 Hz, 1H), 7.15 (d, J=7.2 Hz, 2H), 6.68 (brs, 1H), 5.36 (brs, 1H), 4.22 (m, 1H), 4.02 (m, 6H), 3.67 (s, 3H), 2.90-2.74 (m, 6H), 2.57 (m, 1H), 2.25 (m, 1H), 1.91 (m, 1H), 1.57 (m, 1H), 1.47 (s, 9H), 1.15 (d, J=6.5 Hz, 3H), 0.95 (d, J=5.8 Hz, 3H), 0.86 (d, J=6.5 Hz, 3H) ppm; $^{13}$C NMR: (CDCl$_3$, 150 MHz) δ=177.0, 171.5, 170.2, 157.0, 137.5, 129.5, 128.4, 126.6, 80.4, 66.6, 64.3, 57.8, 51.8, 49.8, 48.0, 44.8, 40.8, 37.2, 36.3, 30.2, 28.4, 26.2, 19.9, 18.5, 17.4 ppm; HRMS calcd for C$_{33}$H$_{45}$N$_3$O$_6$ [M+Na$^+$] 602.3206. found 602.3183.

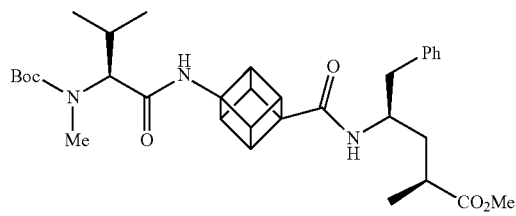

39

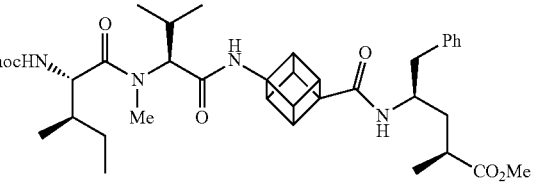

41

Methyl (2S,4R)-4-(4-((S)-2-((2S,3S)-2-((((9H-fluoren-9-yl)methoxy)carbonyl)amino)-N,3-dimethylpentanamido)-3-methylbutanamido)cubane-1-carboxamido)-2-methyl-5-phenylpentanoate (41)

To a stirred solution of Boc-carbamate 39 (25.0 mg, 0.043 mmol) in dry $CH_2Cl_2$ (5.0 mL) was added trifluoroacetic acid (1.0 mL), and stirring continued for 12 h at 25° C. The solvent was removed under reduced pressure and dry DMF (0.3 mL) was added to the residue. The resulting solution was cooled to 0° C., i-$Pr_2$NEt (33 mg, 0.26 mmol) was added and the reaction mixture was stirred at the same temperature for 15 minutes. A solution of acid fluoride 8 (46 mg, 0.13 mmol) in dry DMF (0.1 mL) was then added dropwise to the above mixture at 0° C. and stirring continued for 15 min at 0° C. and 24 h at 25° C. The reaction mixture was diluted with EtOAc (100 mL), and the resulting solution was washed with saturated aqueous $NaHCO_3$ (10 mL) and brine (10 mL), dried over $Na_2SO_4$, filtered and concentrated. The obtained residue was purified by flash column chromatography (silica gel. 50% EtOAc in hexanes) to furnish tetrapeptide 41 (22 mg, 63% yield for the two steps) as a colorless amorphous solid. 41: $R_f$ =0.32 (silica gel, 5% MeOH in $CH_2Cl_2$); $[\alpha]_D^{22}$=−48.6 (c=1.4, $CHCl_3$); FT-IR (neat) $\tilde{v}_{max}$: 3306, 2961, 2926, 2876, 2854, 2200, 1726, 1672, 1636, 1511, 1466, 1452, 1407, 1376, 1313, 1246, 1215, 1170, 1139, 1112, 1080, 1031 $cm^{-1}$; $^1$H NMR ($CDCl_3$, 600 MHz) δ=7.76 (d, J=7.4 Hz, 2H), 7.58 (d, J=6.3 Hz, 2H), 7.40 (t, J=7.1 Hz, 2H), 7.35-7.27 (m, 3H), 7.26-7.17 (m, 2H), 7.15 (d, J=7.3 Hz, 2H), 6.59 (s, 1H), 5.40 (d, J=9.3 Hz, 1H), 5.35 (d, J=8.5 Hz, 1H), 4.54 (m, 2H), 4.40 (dd, J=10.5, 7.3 Hz, 1H), 4.35 (dd, J=10.5, 7.3 Hz, 1H), 4.21 (t, J=6.7 Hz, 2H), 4.05-3.82 (m, 6H), 3.66 (s, 3H), 3.09 (s, 3H), 2.86-2.75 (m, 2H), 2.56 (d, J=6.9 Hz, 1H), 2.29 (td, J=12.6, 6.5 Hz, 1H), 1.91 (ddd, J=13.4, 9.0, 4.1 Hz, 1H), 1.79-1.70 (m, 2H), 1.61-1.50 (m, 2H), 1.43 (s, 1H), 1.15 (d, J=7.1 Hz, 3H), 0.98 (dd, J=15.3, 6.4 Hz, 3H), 0.93-0.85 (m, 6H), 0.81 (d, J=6.5 Hz, 3H) ppm; $^{13}$C NMR ($CDCl_3$, 150 MHz) δ=176.9, 173.7, 171.3, 169.0, 156.2, 143.8, 141.3, 137.5, 129.5, 128.4, 127.7, 127.0, 126.6, 125.1, 120.0, 67.0, 66.4, 57.8, 55.1, 51.8, 49.7, 48.0, 47.2, 44.8, 40.7, 37.9, 37.2, 36.3, 30.7, 29.7, 25.5, 24.2, 19.6, 18.4, 17.4, 15.4, 11.1 ppm; HRMS calcd for $C_{19}H_{58}N_4O_7$ [M+Na$^+$] 837.4204. found 837.4169.

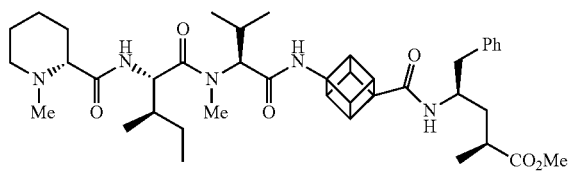

Tb17

Methyl (2S,4R)-4-(4-((S)-2-((2S,3S)—N,3-dimethyl-2-((R)-1-methylpiperidine-2-carboxamido)penta-namido)-3-methylbutanamido)cubane-1-carboxamido)-2-methyl-5-phenylpentanoate (Tb17)

To a stirred solution of Fmoc-tetrapeptide 41 (7.0 mg, 0.0086 mmol) in dry $CH_2Cl_2$ (0.5 mL) was added tris(2-aminoethyl)amine (22 μL, 0.14 mmol) at 0° C. and stirring continued for 3 h while the temperature gradually increased to 25° C. The reaction mixture was diluted with EtOAc (50 mL) and the resulting solution was washed with saturated aqueous $NaHCO_3$ (10 mL) and brine (10 mL), dried over $Na_2SO_4$, and concentrated. The resulting residue was diluted with DMF (0.2 mL) and cooled to 0° C. Then, $Et_3N$ (12.0 μL), N-methyl-(D)-pipecolinic acid 10 (7.4 mg, 0.05 mmol) and HATU (20 mg, 0.05 mmol) were consecutively added and stirring continued for 12 h at 25° C. The solvent was removed under reduced pressure and EtOAc (50 mL) was added to the residue. The solution was washed with brine (2×10 mL), dried over $Na_2SO_4$ and concentrated. The resulting residue was purified by preparative TLC (5% MeOH in $CH_2Cl_2$) to provide compound Tb17 (4.6 mg, 75% yield for the two steps) as a white amorphous solid. Tb17: $R_f$=0.27 (silica gel, 5% MeOH in $CH_2Cl_2$); $[\alpha]_D^{22}$=−35.2 (c=0.23, $CHCl_3$); FT-IR (neat) $\tilde{v}_{max}$: 3270, 2961, 2921, 2849, 1733, 1718, 1685, 1654, 1646, 1636, 1624, 1618, 1578, 1558, 1540, 1521, 1506, 1497, 1473, 1463, 1457, 1436, 1418 $cm^{-1}$; $^1$H NMR ($CDCl_3$, 600 MHz) δ=7.28 (d, J=7.4 Hz, 2H), 7.23-7.19 (m, 1H), 7.15 (d, J=7.5 Hz, 2H), 6.56 (brs, 1H), 5.34 (d, J=8.6 Hz, 1H), 4.71 (brs, 2H), 4.54 (s, 1H), 4.21 (dd, J=19.8, 15.7 Hz, 1H), 4.08-3.91 (m, 6H), 3.66 (s, 3H), 3.10 (dd, J=14.1, 6.9 Hz, 3H), 2.91 (s, 1H), 2.82 (d, J=6.4 Hz, 3H), 2.76 (s, 1H), 2.57 (dd, J=12.2, 7.8 Hz, 2H), 2.43 (s, 1H), 2.36-2.32 (m, 1H), 2.31-2.19 (m, 3H), 2.00 (s, 1H), 1.94-1.86 (m, 2H), 1.61-1.51 (m, 3H), 1.49-1.45 (m, 1H), 1.42 (t, J=7.3 Hz, 3H), 1.15 (d, J=7.1 Hz, 3H), 1.03-0.94 (m, 3H), 0.89 (m, 5H), 0.80 (d, J=6.6 Hz, 3H) ppm; $^{13}$C NMR: ($CDCl_3$, 150 MHz) δ=176.9, 171.5, 171.4, 169.2, 166.0, 137.6, 129.5, 128.4, 126.6, 70.6, 66.5, 57.8, 51.8, 49.7, 47.9, 45.8, 44.8, 42.1, 40.7, 37.2, 36.3, 33.4, 31.9, 29.7, 29.4, 26.5, 24.8, 22.7, 19.6, 17.4, 15.3, 14.1, 12.9, 10.7, 8.6 ppm; HRMS calcd for $C_{41}H_{59}N_5O_6$ [M+H$^+$] 718.4465. found 718.4534.

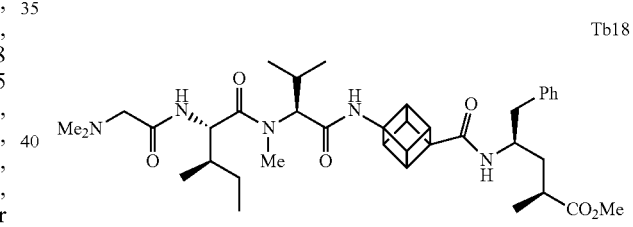

Tb18

Methyl (2S,4R)-4-(4-((S)-2-((2S,3S)-2-(2-(dimethylamino)acetamido)-N,3-dimethylpentanamido)-3-methylbutanamido)cubane-1-carboxamido)-2-methyl-5-phenylpentanoate (Tb18)

According to the procedure described for the synthesis of Tb17, analog Tb18 was obtained as a colorless oil (9.8 mg, 58% yield for the two steps). Tb18: $R_f$=0.20 (silica gel, 5% MeOH in $CH_2Cl_2$); $[\alpha]_D^{22}$=−63.5 (c=0.40, $CHCl_3$); FT-IR (neat) $\tilde{v}_{max}$ 2959, 2922, 2851, 2360, 2337, 1736, 1729, 1690, 1658, 1640, 1631, 1621, 1546, 1530, 1515, 1484, 1469, 1463, 1452, 1443, 1412, 1378, 1278, 1260, 1203, 1172, 1143, 845 $cm^{-1}$; $^1$H NMR: (600 MHz. $CDCl_3$) δ=9.99 (s, 1H), 7.90 (s, 1H), 7.28 (t, J=7.3 Hz, 2H), 7.23-7.18 (m, 1H), 7.14 (d, J=7.3 Hz, 2H), 6.83 (s, 1H), 5.39 (d, J=8.4 Hz, 1H), 4.77 (m, 1H), 4.53 (d, J=9.0 Hz, 1H), 4.20 (m, 1H), 3.99 (d, J=26.1 Hz, 6H), 3.65 (s, 3H), 3.19-3.09 (m, 3H), 2.94-2.86 (m, 1H), 2.82 (d, J=6.2 Hz, 2H), 2.68 (s, 3H), 2.57 (d, J=4.0 Hz, 1H), 2.44 (m, 2H), 2.29 (m, 2H), 2.01 (m, 1H), 1.93-1.88 (m, 1H), 1.57 (m, 1H), 1.40 (t, J=6.7 Hz, 3H), 1.15 (d, J=7.1 Hz, 3H), 0.99 (dd, J=26.7, 6.0 Hz, 3H), 0.93-0.86 (m, 5H), 0.83 ppm (d, J=13.4 Hz, 3H); $^{13}$C NMR: ($CDCl_3$, 150 MHz)

δ=176.9, 173.0, 171.4, 169.1, 168.0, 137.6, 129.5, 128.4, 126.6, 66.4, 57.8, 51.8, 49.6, 49.5, 48.0, 46.5, 44.8, 40.8, 37.2, 36.3, 31.9, 29.7, 29.4, 22.7, 19.5, 18.5, 17.4, 16.3, 15.3, 14.1, 11.0, 8.7 ppm; HRMS calcd for $C_{38}H_{55}N_5O_6$ [M+H$^+$] 678.4152. found 678.4165.

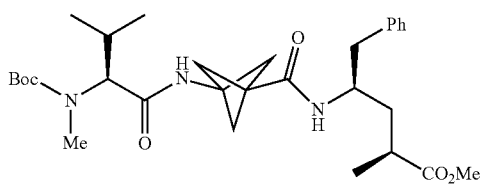

40

Methyl (2S,4R)-4-(3-((S)-2-((tert-butoxycarbonyl)(methyl)amino)-3-methylbutanamido)bicyclo [1.1.1] pentane-1-carboxamido)-2-methyl-5-phenylpentanoate (40)

According to the procedure described for the synthesis of 39, tripeptide 40 was obtained as a colorless amorphous solid (90 mg, 68% for the three steps). 40: Rt=0.25 (silica gel, 50% EtOAc in hexanes); $[\alpha]_D^{22}$=−50.0 (c=0.33, CHCl$_3$); FT-IR (neat) $\nu_{max}$: 3312, 2966, 2923, 1735, 1665, 1530, 1455, 1367, 1275, 1260, 1216, 1151, 1054, 1033, 1015, 939, 882, 764, 749, 702 cm$^{-1}$; $^1$H NMR (CDCl$_3$, 600 MHz) δ=7.28 (t, J=7.3 Hz, 2H), 7.22 (t, J=7.3 Hz, 1H), 7.12 (d, J=7.3 Hz, 2H), 6.55 (br, 1H), 5.38 (br, 1H), 4.15 (d, J=3.8 Hz, 1H), 3.90 (d, J=9.8 Hz, 1H), 3.66 (s, 3H), 2.87-2.71 (m, 6H), 2.54 (m, 1H), 2.20 (s, 7H), 1.89 (m, 1H), 1.58-1.53 (m, 1H), 1.47 (s, 9H), 1.15 (d, J=7.1 Hz, 3H), 0.93 (d, J=5.3 Hz, 3H), 0.85 (d, J=6.4 Hz, 3H) ppm; $^{13}$C NMR: (CDCl$_3$, 150 MHz) δ=176.8, 171.0, 168.6, 157.1, 137.4, 129.5, 128.4, 126.6, 80.5, 64.9, 53.6, 51.9, 48.3, 44.8, 40.5, 37.6, 37.1, 36.3, 30.3, 28.4, 25.9, 19.8, 18.5, 17.4 ppm; HRMS calcd for $C_{30}H_{45}N_3O_6$ [M+Na$^+$] 566.3206. found 566.3196.

42

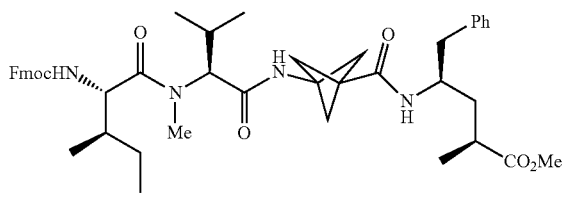

Methyl (2S,4R)-4-(3-((S)-2-((2S,3S)-2-((((9H-fluoren-9-yl)methoxy)carbonyl)amino)-N,3-dimethyl pentanamido)-3-methylbutanamido)bicyclo[1.1.1] pentane-1-carboxamido)-2-methyl-5-phenylpenta noate (42)

According to the procedure described for the synthesis of 41, tetrapeptide 42 was obtained as a colorless amorphous solid (23 mg, 71% for the two steps). 42: R$_f$=0.48 (silica gel, 5% MeOH in CH$_2$Cl$_2$); $[\alpha]_D^{22}$=−44.6 (c=0.94, CHCl$_3$); FT-IR (neat) $\nu_{max}$: 3243, 2961, 2920, 2881, 2854, 1726, 1645, 1538, 1452, 1372, 1296, 1242, 1211, 1170, 1134, 1085, 1036, 991, 924 cm$^{-1}$; $^1$H NMR (CDCl$_3$, 600 MHz) δ=7.76 (d, J=7.4 Hz, 2H), 7.57 (d, J=7.3 Hz, 2H), 7.40 (t, J=7.3 Hz, 2H), 7.30 (dt, J=20.6, 7.3 Hz, 3H), 7.22 (dd, J=15.3, 7.7 Hz, 2H), 7.12 (d, J=7.3 Hz, 2H), 6.40 (s, 1H), 5.39 (dd, J=17.7, 8.2 Hz, 2H), 4.55-4.50 (m, 1H), 4.44 (d, J=11.4 Hz, 1H), 4.40 (dd, J=10.7, 7.5 Hz, 1H), 4.35 (dd, J=10.5, 7.1 Hz, 1H), 4.20 (dd, J=12.1, 5.4 Hz, 1H), 4.14 (m, 1H), 3.67 (s, 3H), 3.05 (s, 3H), 2.80 (m, 2H), 2.57-2.49 (m, 1H), 2.29-2.22 (m, 1H), 2.18 (s, 6H), 1.89 (ddd, J=13.4, 8.9, 4.3 Hz, 1H), 1.76 (d, J=6.9 Hz, 1H), 1.57-1.51 (m, 2H), 1.41 (t, J=7.3 Hz, 3H), 1.14 (d, J=7.0 Hz, 3H), 0.95 (dd, J=13.3, 6.4 Hz, 3H), 0.92-0.87 (m, 5H), 0.79 (d, J=6.5 Hz, 3H) ppm; $^{13}$C NMR (CDCl$_3$, 150 MHz) δ=176.8, 173.8, 169.8, 168.4, 156.2, 143.8, 141.3, 137.4, 129.5, 128.4, 127.7, 127.0, 126.6, 125.1, 120.0, 67.0, 62.8, 53.6, 51.9, 48.3, 47.2, 45.8, 40.5, 38.0, 37.1, 36.3, 30.7, 29.7, 25.2, 24.3, 19.59, 18.3, 17.4, 15.3, 11.2, 8.6 ppm; HRMS calcd for $C_{46}H_{58}N_4O_7$ [M+Na$^+$] 801.4204. found 801.4203.

Tb19

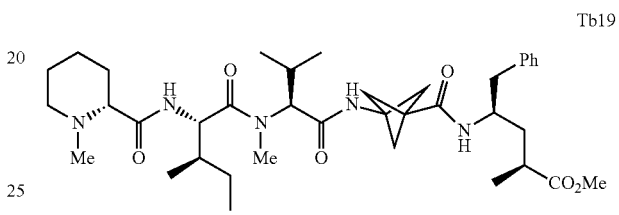

Methyl (2S,4R)-4-(3-((S)-2-((2S,3S)—N,3-dimethyl-2-((R)-1-methylpiperidine-2 carboxamido) pentan amido)-3-methylbutanamido)bicyclo[1.1.1] pentane-1-carboxamido)-2-methyl-5-phenylpentanoate (Tb19)

According to the procedure described for the synthesis of Tb14, final analogue Tb19 was obtained as a white amorphous solid (5 mg, 72% for the two steps). Tb19: R$_f$=0.34 (silica gel, 5% MeOH in CH$_2$Cl$_2$); $[\alpha]_D^{22}$=−44.8 (c=0.25, CHCl$_3$); FT-IR (neat) $\nu_{max}$: 3288, 2961, 2921, 2854, 1730, 1681, 1645, 1528, 1497, 1457, 1376, 1242, 1215, 1166, 1134, 1090, 1067 cm$^{-1}$; $^1$H NMR (CDCl$_3$, 600 MHz) δ=7.31-7.26 (m, 2H), 7.23-7.20 (m, 1H), 7.12 (d, J=7.2 Hz, 2H), 6.48 (brs, 1H), 5.38 (d, J=8.6 Hz, 1H), 4.66 (brs, 2H), 4.46 (d, J=8.8 Hz, 1H), 4.15 (dd, J=14.2, 5.3 Hz, 1H), 3.66 (s, 3H), 3.10 (m, 4H), 2.85 (s, 1H), 2.80 (m, 3H), 2.57-2.50 (m, 2H), 2.44-2.38 (m, 1H), 2.36-2.31 (m, 1H), 2.29-2.23 (m, 2H), 2.16 (s, 6H), 1.92-1.86 (m, 2H), 1.63 (m, 2H), 1.57-1.50 (m, 2H), 1.42 (t, J=7.3 Hz, 3H), 1.14 (d, J=7.1 Hz, 3H), 0.98-0.92 (m, 3H), 0.92-0.86 (m, 5H), 0.86-0.81 (m, 2H), 0.78 (d, J=6.6 Hz, 3H) ppm; $^{13}$C NMR (CDCl$_3$, 150 MHz) δ=176.8, 173.8, 170.0, 168.8, 168.4, 137.4, 129.5, 128.4, 126.6, 70.6, 62.7, 53.6, 51.9, 48.3, 45.8, 44.7, 40.5, 37.6, 37.1, 36.3, 31.9, 30.7, 29.7, 29.4, 26.5, 25.0, 22.7, 19.6, 18.3, 17.4, 15.3, 14.1, 10.8, 8.6 ppm; HRMS calcd for $C_{38}H_{59}N_5O_6$ [M+H$^+$] 682.4465. found 682.4553.

43a

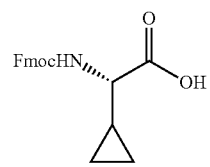

(S)-2-((((9H-fluoren-9-yl)methoxy)carbonyl)amino)-2-cyclopropylacetic Acid (43a)

To a stirred solution of Na$_2$CO$_3$ (2.3 g) in water (34 mL) was added (S)-2-amino-2-cyclopropylacetic acid (1.0 g, 8.68 mmol). The resulted solution was cooled to 0° C. and 1,4-dioxane (21.7 mL) was added dropwise at the same temperature. A solution of Fmoc-Cl (2.48 g, 9.59 mmol) in dioxane (21.7 mL) was added dropwise to the above reaction mixture over 10 min at 0° C. The reaction mixture was stirred at 0° C. for 2 h followed by 6 h at 25° C. The solvent was evaporated under reduced pressure and the resulted residue was dissolved in water (150 mL). The aqueous layer was extracted with EtOAc (4×150 mL). The aqueous layer was then acidified with 1(M) HCl to pH 2 and extracted with EtOAc (4×100 mL). The resulted organic layers were combined and washed with brine (100 mL), dried over Na$_2$SO$_4$, and evaporated to give a white solid. The solid was stirred with hexane (60 mL) for 1 h and then hexane was decanted. The white solid was dissolved in boiling ethyl acetate (50 mL). Then hexane (100 mL) was added dropwise to the above solution while warming gently. The solution was allowed to cool to room temperature and then kept at 0° C. for crystallization. The crystallized white solid was isolated by filtration, washed with hexane (2×50 mL), and vacuum dried to give 43a as a white solid (2.45 g, 84% yield). 43a: [α]$_D^{22}$=+15.7 (c 1.0, CH$_2$Cl$_2$); FT-IR (neat) $\tilde{v}_{max}$ 2669, 2335, 2159, 2106, 1785, 1689, 1550, 1489, 1463, 1433, 1369, 1296, 1253, 1172, 1128, 1001 cm$^{-1}$; $^1$H NMR: (CDCl$_3$, 600 MHz) δ=7.76 (d, 2H, J=7.2 Hz), 7.60-7.59 (m, 2H), 7.41-7.39 (m, 2H), 7.32-7.30 (m, 2H), 5.36 (d, 1H, J=6), 4.45-4.39 (m, 2H), 4.24-4.21 (m, 1H), 3.83-3.81 (m, 1H), 1.14-1.13 (m, 1H), 0.65-0.46 (m, 5H) ppm. $^{13}$C NMR: (CDCl$_3$, 150 MHz) δ=176.6, 156.2, 143.9, 143.8, 141.4, 127.9, 127.2, 125.2, 125.1, 120.1, 67.3, 57.4, 47.3, 13.9, 3.4 ppm; HRMS calcd for C$_2$OH$_{19}$NO$_4$ [M+Na$^+$] 360.1206. found 360.1193.

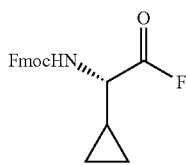

43

(9H-fluoren-9-yl)methyl (S)-(1-cyclopropyl-2-fluoro-2-oxoethyl)carbamate (43)

To a stirred solution of 43a (0.2 g, 0.59 mmol) and pyridine (0.048 mL, 0.59 mmol) in CH$_2$Cl$_2$ (3.55 mL) was added a solution of (diethylamino)sulfur trifluoride (0.095 mL, 0.71 mmol) in CH$_2$Cl$_2$ (0.6 mL) dropwise at 25° C. The reaction mixture was stirred for 1 h at 25° C. and then diluted with CH$_2$Cl$_2$ (30 mL). The solution was washed with ice-cold water (2×20 mL), dried over Na$_2$SO$_4$, concentrated, and recrystallized from CH$_2$Cl$_2$/hexanes to furnish the acyl fluoride 43 (0.17 g, 85% yield) as white solid. 43: [α]z=+13.5 (c 1.0, CH$_2$Cl$_2$); FT-IR (neat) $\tilde{v}_{max}$: 2668, 2345, 2109, 1775, 1627, 1581, 1482, 1364, 1213, 1132, 1001 cm$^{-1}$; $^1$H NMR: (CDCl$_3$, 600 MHz) δ=7.78 (d, 2H, J=7.2 Hz), 7.60-7.58 (m, 2H), 7.43-7.40 (m, 2H), 7.33 (t, 2H, J=7.2 Hz), 5.29-5.28 (m, 1H), 4.49-4.41 (m, 2H), 4.23 (t, 1H, J=6.6 Hz), 3.86-3.83 (m, 1H), 1.19-1.12 (m, 1H), 0.76-0.48 (m, 5H) ppm. $^{13}$C NMR: (CDCl$_3$, 150 MHz) δ=162.16 (d, J=370.5 Hz), 155.8, 143.7, 141.5, 127.9, 127.3, 125.1, 120.1, 67.5, 56.9 (d, J=60 Hz), 47.2, 12.8, 3.8 (d, J=28.5) ppm. HRMS data could not be obtained for this compound.

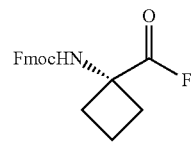

44

(9H-fluoren-9-yl)methyl (1-(fluorocarbonyl)cyclobutyl)carbamate (44)

According to the procedure described for compound 43, compound 44 was prepared as a white solid (430 mg, 76% yield). 44: $^1$H NMR (CDCl$_3$, 600 MHz) δ 7.77 (d, J=7.5 Hz, 2H), 7.63-7.52 (m, 2H), 7.40 (t, J=7.4 Hz, 2H), 7.32 (t, J=7.3 Hz, 2H), 5.48 (s, 1H), 4.50-4.33 (m, 2H), 4.28-4.16 (m, 1H), 2.69-2.51 (m, 2H), 2.48-2.26 (m, 2H), 2.11-1.95 (m, 2H) ppm. $^{13}$C NMR: (CDCl$_3$, 150 MHz) δ=163.1, 155.0, 143.6, 141.3, 127.7, 127.1, 124.9, 120.0, 66.9, 57.2, 47.1, 31.1, 15.1 ppm.

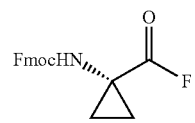

45

(9H-fluoren-9-yl)methyl (1-(fluorocarbonyl)cyclopropyl)carbamate (45)

According to the procedure described for compound 43, compound 45 was prepared as a white solid (440 mg, 90% yield). 45: $^1$H NMR (CDCl$_3$, 600 MHz) δ 7.83-7.70 (m, 2H), 7.64-7.51 (m, 2H), 7.46-7.37 (m, 2H), 7.34-7.28 (m, 2H), 5.55-5.35 (m, 1H), 4.65-4.40 (m, 2H), 4.30-4.15 (m, 1H), 1.80-1.58 (m, 2H), 1.45-1.25 (m, 2H) ppm; $^{13}$C NMR: (CDCl$_3$, 150 MHz) δ=163.4, 156.0, 143.6, 141.3, 127.8, 127.1, 124.9, 120.0, 67.2, 47.1, 32.6, 19.4, 19.0 ppm.

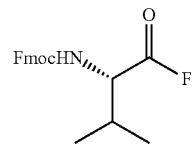

46

(9H-fluoren-9-yl)methyl (S)-(1-fluoro-3-methyl-1-oxobutan-2-yl)carbamate (46)

According to the procedure described for compound 43, compound 46 was prepared as a white solid (355 mg, 91% yield). 46: $^1$H NMR (CDCl$_3$, 600 MHz) δ 7.83-7.70 (d, J=6.8 Hz, 2H), 7.59 (s, 2H), 7.44-7.38 (m, 2H), 7.35-7.28 (m, 2H), 5.19 (s, 1H), 4.55-4.40 (m, 3H), 4.26-4.18 (m, 1H), 2.35-2.15 (m, 1H), 1.10-0.85 (m, 6H) ppm. $^{13}$C NMR:

(CDCl₃, 150 MHz) δ=162.3, 156.0, 143.5, 141.3, 127.8, 127.1, 124.9, 120.0, 67.3, 58.1, 47.1, 30.4, 18.8, 17.6 ppm.

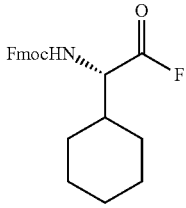

47

(9H-fluoren-9-yl)methyl (S)-(1-cyclohexyl-2-fluoro-2-oxoethyl)carbamate (47)

According to the procedure described for compound 43, compound 47 was prepared as a white solid (360 mg, 95% yield). 47: ¹H NMR (CDCl₃, 600 MHz) δ 7.77 (d, J=7.4 Hz, 2H), 7.59 (d, J=7.3 Hz, 2H), 7.44-7.38 (m, 2H), 7.33 (t, J=7.4 Hz, 2H), 5.14 (d, J=8.5 Hz, 1H), 4.58-4.43 (m, 3H), 4.23 (t, J=6.6 Hz, 1H), 1.96-1.84 (m, 1H), 1.83-1.77 (m, 2H), 1.76-1.61 (m, 3H), 1.34-1.23 (m, 2H), 1.19-1.05 (m, 3H) ppm. ¹³C NMR: (CDCl₃, 150 MHz) δ=162.3, 155.9, 143.5, 141.4, 127.8, 127.1, 125.0, 120.0, 67.2, 57.8, 47.2, 40.0, 29.2, 28.0, 25.8, 25.7, 25.6 ppm.

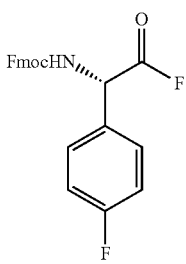

48

(9H-fluoren-9-yl)methyl (S)-(2-fluoro-1-(4-fluorophenyl)-2-oxoethyl)carbamate (48)

According to the procedure described for compound 43, compound 48 was prepared as a white solid (357 mg, 90% yield). 48: ¹H NMR (CDCl₃, 600 MHz) δ 7.77 (d, J=7.5 Hz, 2H), 7.62-7.51 (m, 2H), 7.45-7.33 (m, 4H), 7.31 (t, J=7.4 Hz, 2H), 7.16-7.01 (m, 2H), 5.60 (d, J=6.6 Hz, 1H), 5.50 (d, J=5.8 Hz, 1H), 4.65-4.38 (m, 2H), 4.22 (t, J=6.3 Hz, 1H) ppm. ¹³C NMR: (CDCl₃, 150 MHz) δ=168.7, 163.3, 160.9, 155.2, 143.4, 141.3, 129.4, 127.8, 127.1, 124.9, 120.1, 116.6, 67.4, 56.5, 47.0 ppm.

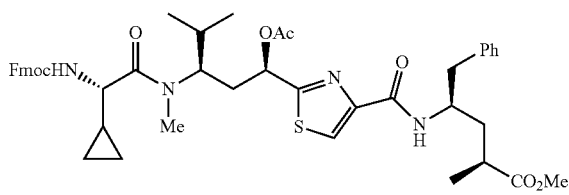

49

Methyl (2S,4R)-4-(2-((5S,8R,10R)-5-cyclopropyl-1-(9H-fluoren-9-yl)-8-isopropyl-7-methyl-3,6,12-trioxo-2,11-dioxa-4,7-diazatridecan-10-yl) thiazole-4-carboxamido)-2-methyl-5-phenylpentanoate (49)

To an iced-cooled stirred solution of 7 (0.18 g, 0.30 mmol) in CH₂Cl₂ (7.2 mL) was added trifluoroacetic acid (1.04 mL, 13.6 mmol) and the reaction mixture was stirred for 6 h while warming up to 25° C. Evaporation of the volatile components under reduced pressure furnished the crude TFA-ammonium salt (151.8 mg, 0.30 mmol, quantitative), which was used for the following step without further purification.

To a stirred, iced-cooled solution of crude ammonium salt from the previous step and N-methylmorpholine (0.27 mL, 2.41 mmol) in DMF (1.2 mL) was added dropwise a solution of acyl fluoride 43 (0.35 g, 1.02 mmol) in DMF (0.6 mL) and stirring was continued for 18 h at 25° C. The reaction mixture was diluted with ethyl acetate (120 mL), washed with saturated aqueous NaHCO₃ solution (10 mL), and brine (10 mL), dried over Na₂SO₄, and concentrated. The resulting residue was purified using flash column chromatography (60% EtOAc in hexanes) to give 49 (0.21 g, 83% yield for the two steps) as white foam. 49: R$_f$=0.36 (silica gel 60% EtOAc in hexanes); [α]$_D^{22}$=+55 (c 0.1, CH₂Cl₂); FT-IR (neat) $\tilde{\nu}_{max}$: 3395, 3301, 2966, 1719, 1646, 1536, 1492, 1450, 1410, 1370, 1300, 1219, 1104, 1081, 1041, 935, 759 cm⁻¹; ¹H NMR: (CDCl₃, 600 MHz) δ=8.02 (s, 1H), 7.76 (d, 2H, J=7.2 Hz), 7.60-7.58 (m, 2H), 7.40 (t, 2H, J=7.2 Hz), 7.32-7.27 (m, 4H), 7.23-7.21 (m, 3H), 7.09 (d, J=9.0 Hz, 1H), 5.71-5.67 (m, 2H), 4.57-4.53 (m, 1H), 4.45-4.38 (m, 1H), 4.37-4.31 (m, 3H), 4.22 (t, 1H, J=7.2 Hz), 3.63 (s, 3H), 2.99 (s, 3H), 2.98-2.94 (m, 1H), 2.91-2.87 (m, 1H), 2.64-2.58 (m, 1H), 2.39-2.34 (m, 1H), 2.18 (s, 3H), 2.1-2.0 (m, 3H), 1.82-1.76 (m, 2H), 1.65-1.59 (m, 3H), 1.17 (d, 4H, J=7.2 Hz), 1.05 (d, 3H, J=6.0 Hz), 0.86 (d, 3H, J=6.6 Hz), 0.67-0.63 (m, 1H), 0.58-0.54 (m, 1H), 0.49-0.43 (m, 3H) ppm; ¹³C NMR: (CDCl₃, 150 MHz) δ=176.7, 173.1, 170.2, 170.1, 160.4, 156.2, 150.1, 144.0, 143.9, 141.4, 137.6, 129.7, 128.5, 127.8, 127.2, 126.7, 125.3, 125.2, 123.6, 120.1, 69.3, 67.1, 60.5, 53.9, 51.9, 48.4, 47.3, 41.1, 37.8, 36.6, 34.9, 29.8, 21.2, 20.9, 20.1, 19.8, 17.8, 14.3, 14.2, 3.7, 2.2 ppm; HRMS calcd for C₄₆H₅₄N₄O₈S [M+Na⁺] 845.3555. found 845.3521.

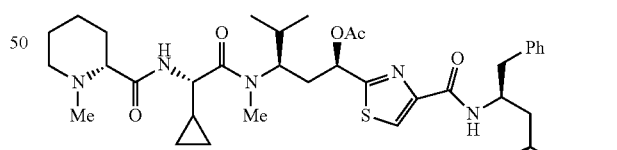

Tb20

Methyl (2S,4R)-4-(2-((1R,3R)-1-acetoxy-3-((S)-2-cyclopropyl-N-methyl-2-((R)-1-methylpiperidine-2-carboxamido)acetamido)-4-methylpentyl)thiazole-4-carboxamido)-2-methyl-5-phenylpentanoate (Tb20)

To an iced-cooled stirred solution of Fmoc-derivative 49 (0.050 g, 0.060 mmol) in CH₂Cl₂ (1.5 mL) was added tris(2-aminoethyl)amine (0.15 mL, 0.99 mmol). The reaction mixture was stirred for 3 h at 25° C. and then diluted with ethyl acetate (60 mL). The solution was washed with saturated aqueous NaHCO$_3$ solution (10 mL), and brine (10 mL), dried over Na$_2$SO$_4$, and concentrated. The crude amine so obtained (36.5 mg, 0.06 mmol, quantitative) was used for the next step without further purification.

To a stirred solution of N-methyl-(D)-pipecolinic acid (17.2 mg, 0.12 mmol) in DMF (0.3 mL) was added HATU (68.4 mg, 0.18 mmol), HOAt (24.5 mg, 0.18 mmol) and the mixture was stirred at 25° C. for 10 min. To the reaction mixture was added a solution of the above crude amine (36.5 mg, 0.06 mmol) and N-methylmorpholine (0.019 mL, 0.18 mmol) in DMF (0.3 mL) and the resulted yellow solution was stirred at 25° C. for 24 h. The reaction mixture was diluted with ethyl acetate (60 mL), washed with brine (10 mL), dried over Na$_2$SO$_4$ and concentrated. The resulting residue was purified using flash column chromatography (5% MeOH in CH$_2$Cl$_2$ with 0.5% NH$_4$OH) to give Tb20 (0.022 g, 49% yield for the two steps) as a colorless liquid. Tb20: R$_f$=0.41 (5% silica gel MeOH in CH$_2$Cl$_2$); FT-IR (neat) $\tilde{v}_{max}$: 3008, 2891, 2158, 1771, 1703, 1590 1523, 1484, 1469, 1396, 1384, 1319, 1250, 1108, 1063, 1006, 917 cm$^{-1}$; $[\alpha]_D^{22}$=+1.5 (c 0.2, MeOH); $^1$H NMR: (CD$_3$OD, 600 MHz) δ=8.10 (s, 1H), 7.28-7.25 (m, 4H), 7.21-7.18 (m, 1H), 5.80 (dd, J=11.4 Hz, 1H), 4.52-4.49 (m, 1H), 4.39-4.35 (m, 1H), 4.23 (d, J=9.0 Hz, 1H), 3.61 (s, 3H), 3.09 (s, 3H), 3.06-3.05 (m, 1H), 2.95-2.87 (m, 3H), 2.65-2.59 (m, 1H), 2.45-2.40 (m, 1H), 2.34 (s, 3H), 2.30-2.20 (m, 2H), 2.16 (s, 3H), 2.08-1.98 (m, 1H), 1.89-1.81 (m, 3H), 1.80-1.72 (m, 2H), 1.67-1.61 (m, 2H), 1.25-1.19 (m, 1H), 1.19 (d, J=6.6 Hz, 3H), 1.06 (d, J=6.6 Hz, 3H), 0.88 (d, J=7.2 Hz, 3H), 0.74-0.69 (m, 1H), 0.58-0.54 (m, 1H), 0.42-0.38 (m, 1H) ppm; $^{13}$C NMR: (CD$_3$OD, 150 MHz) δ=178.3, 174.9, 171.8, 171.7, 162.8, 150.8, 139.4, 130.5, 129.4, 129.3, 127.4, 125.2, 70.9, 70.1, 56.6, 55.0, 52.2, 50.2, 44.4, 42.3, 38.9, 37.7, 35.6, 31.3, 30.7, 25.9, 24.0, 20.9, 20.4, 20.3, 18.1, 14.3, 4.5, 3.6 ppm; HRMS calcd for C$_{38}$H$_{55}$N$_5$O$_7$S [M+H$^+$] 726.3895. found 726.3918.

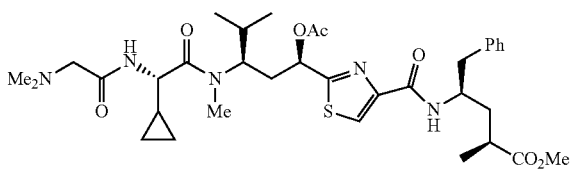

Tb21

Methyl (2S,4R)-4-(2-((6S,9R,11R)-6-cyclopropyl-9-isopropyl-2, 8-dimethyl-4,7,13-trioxo-12-oxa-2,5,8-triazatetradecan-11-yl)thiazole-4-carboxamido)-2-methyl-5-phenylpentanoate (Tb21)

According to the procedure described for the synthesis of Tb20, analog Tb21 was obtained as a colorless liquid (5.4 mg, 39% for the two steps). Tb21: R$_f$=0.39 (5% silica gel MeOH in CH$_2$Cl$_2$); $[\alpha]_D^{22}$=−14.4 (c 0.5, MeOH); FT-IR (neat) $\tilde{v}_{max}$:2669, 2374 2335, 2159, 2106, 1795, 1767, 1692, 1586, 1566, 1511, 1478, 1442, 1379, 1348, 1247 cm$^{-1}$; $^1$H NMR: (CD$_3$OD, 600 MHz) δ=8.1 (s, 1H), 7.28-7.24 (m, 4H), 7.21-7.18 (m, 1H), 5.81-5.78 (m, 1H), 4.52-4.49 (m, 1H), 4.39-4.35 (m, 1H), 3.61 (s, 3H), 3.10 (s, 3H), 2.95-2.86 (m, 3H), 2.65-2.59 (m, 1H), 2.45-2.40 (m, 1H), 2.37 (s, 3H), 2.27-2.25 (m, 1H), 2.16 (s, 3H), 2.02-1.98 (m, 1H), 1.90-1.86 (m, 1H), 1.78-1.73 (m, 1H), 1.21-1.19 (m, 1H), 1.16 (d, J=7.2 Hz, 3H), 1.06 (d, J=6.6 Hz, 3H), 0.87 (d, J=6.6 H, 3H), 0.72-0.69 (m, 1H), 0.64-0.60 (m, 1H), 0.58-0.54 (m, 1H), 0.43-0.39 (m, 1H) ppm; $^{13}$C NMR: (CD$_3$OD, 150 MHz) δ=178.2, 174.8, 171.9, 171.7, 162.7, 150.8, 139.4, 130.5, 130.4, 129.3, 127.4, 125.2, 70.8, 63.1, 57.5, 54.3, 52.2, 50.2, 49.5, 45.8, 42.3, 38.6, 37.7, 35.6, 30.7, 20.8, 20.4, 20.2, 18.1, 14.5, 4.4, 3.3 ppm; HRMS calcd for C$_{35}$H$_{51}$N$_5$O$_7$S [M+H$^+$] 686.3582. found 686.3599.

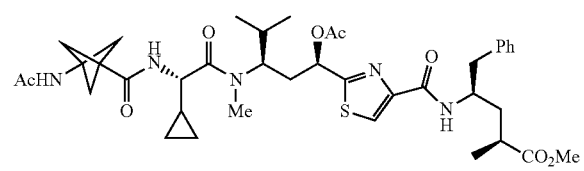

Tb22

Methyl (2S,4R)-4-(2-((1R,3R)-3-((S)-2-(3-acetamidobicyclo[1.1.1]pentane-1-carboxamido)-2-cyclopropyl-N-methylacetamido)-1-acetoxy-4-methylpentyl)thiazole-4-carboxamido)-2-methyl-5-phenylpentanoate (Tb22)

According to the procedure described for the synthesis of Tb20, compound Boc-Tb22 was obtained as a colorless liquid (17 mg, 49% for the two steps). According to the procedure described for the synthesis of Tb7 (deprotection of N-Boc followed by N—Ac protection), compound Tb22 was obtained as a colorless liquid (14.7 mg, 91%). Tb22: R$_f$=0.63 (5% silica gel MeOH in CH$_2$Cl$_2$); $[\alpha]_D^{22}$=−16.8 (c 2.0, MeOH); FT-IR (neat) $\tilde{v}_{max}$ 2998, 2675, 2159, 2116, 1776, 1707, 1692, 1586, 1509, 1462, 1423, 1394, 1331, 1278, 1242, 1182, 1066, 978 cm$^{-1}$; $^1$H NMR: (CD$_3$OD, 600 MHz) δ=8.11 (s, 1H), 7.28-7.25 (m, 4H), 7.21-7.18 (m, 1H), 5.80-5.78 (m, 1H), 4.51-4.48 (m, 1H), 4.39-4.37 (m, 1H), 4.19-4.17 (m, 1H), 3.61 (s, 3H), 3.06 (s, 3H), 2.95-2.86 (m, 2H), 2.65-2.59 (m, 1H), 2.45-2.39 (m, 1H), 2.31 (s, 6H), 2.16 (s, 3H), 2.02-1.98 (m, 1H), 1.91 (s, 3H), 1.89-1.84 (m, 1H), 1.78-1.73 (m, 1H), 1.29-1.23 (m, 1H), 1.17 (d, J=7.2 Hz, 3H), 1.07 (d, J=6.0 Hz, 3H), 0.87 (d, J=6.6 Hz, 3H), 0.77-0.68 (m, 1H), 0.65-0.60 (m, 1H), 0.55-0.50 (m, 1H) ppm; $^{13}$C NMR: (CD$_3$OD, 150 MHz) δ=178.3, 174.9, 173.8, 171.7, 171.5, 162.7, 150.8, 139.5, 130.4, 129.3, 127.4, 125.2, 70.8, 57.4, 55.5, 54.7, 52.2, 50.2, 45.9, 42.3, 38.8, 38.3, 37.7, 35.6, 30.7, 30.1, 22.8, 20.9, 20.4, 20.2, 18.1, 14.1, 4.6, 3.7 ppm; HRMS calcd for C$_{39}$H$_{53}$N$_5$O$_8$S [M+H$^+$] 774.3507. found 774.3475.

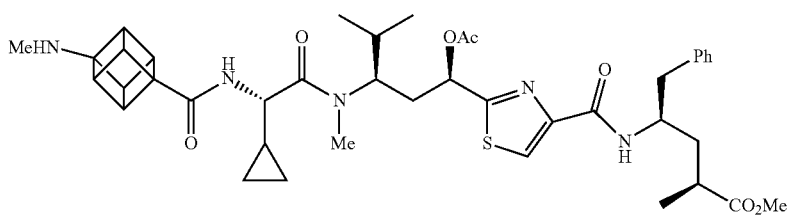

Tb23

Methyl (2S,4R)-4-(2-((1R,3R)-1-acetoxy-3-((S)-2-cyclopropyl-N-methyl-2-(4-(methylamino)cubane-1-carboxamido)acetamido)-4-methylpentyl)thiazole-4-carboxamido)-2-methyl-5-phenylpentanoate (Tb23)

According to the procedure described for the synthesis of Tb20, advanced intermediate Boc-Tb23 was obtained as a colorless liquid (8.1 mg, 47% for the two steps). According to the procedure described for the synthesis of Tb10 (deprotection of N-Boc), analog Tb23 was obtained as a colorless liquid (5.22 mg, 73%).

Tb23: $R_f$=0.52 (5% silica gel MeOH in $CH_2Cl_2$ with 0.5% $NH_4OH$); $[\alpha]_D^{22}$=−23 (c 0.1, MeOH); FT-IR (neat) $\tilde{v}_{max}$ 2675, 2352, 2159, 2109, 1788, 1707, 1588, 1525, 1482, 1466, 1445, 1427, 1329, 1249, 1003 cm$^{-1}$; $^1$H NMR: ($CD_3OD$, 600 MHz) δ=8.11 (s, 1H), 7.28-7.23 (m, 4H), 7.19-7.17 (m, 1H), 5.81-5.79 (m, 1H), 4.56-4.46 (m, 1H), 4.40-4.38 (m, 1H), 4.04-3.97 (m, 1H), 3.61 (s, 3H), 3.14-3.12 (m, 2H), 3.09 (s, 3H), 2.95-2.87 (m, 3H), 2.65-2.59 (m, 1H), 2.45-2.40 (m, 1H), 2.35 (s, 3H), 2.16 (s, 3H), 2.02-1.98 (m, 2H), 1.91-1.86 (m, 1H), 1.78-1.73 (m, 1H), 1.17 (d, J=7.2 Hz, 3H), 1.07 (d, J=6.0 Hz, 3H), 0.89 (d, J=6.0 Hz, 3H), 0.75-0.69 (m, 1H), 0.68-0.59 (m, 1H), 0.57-0.49 (m, 1H), 0.46-0.39 (m, 1H) ppm; $^{13}$C NMR: ($CD_3OD$, 150 MHz) δ=178.3, 171.8, 171.7, 163.1, 162.7, 150.8, 139.5, 130.5, 130.4, 129.3, 127.4, 125.3, 70.9, 69.8, 59.5, 55.3, 52.2, 50.2, 49.8, 44.9, 42.3, 38.9, 37.8, 35.7, 30.7, 30.2, 28.6, 20.9, 20.4, 20.3, 18.1, 14.3, 4.8, 3.8 ppm; HRMS calcd for $C_{41}H_{53}N_5O_7S$ [M+H$^+$] 760.3738. found 760.3729.

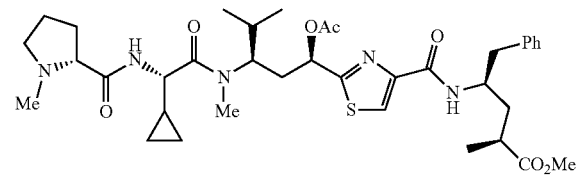

Tb26

(2S,4R)-Methyl 4-(2-((1R,3R)-1-acetoxy-3-((S)-2-cyclopropyl-N-methyl-2-((R)-1-methylpyrrolidine-2-carboxamido)acetamido)-4-methylpentyl)thiazole-4-carboxamido)-2methyl-5-phenylpentanoate (Tb26)

According to the procedure described for the synthesis of Tb20, Fmoc-group was removed through the action of tris(2-aminoethyl)amine, followed by coupling with (S)—N-methyl-pyrrolidine-2-carboxylic acid, furnishing ester Tb26 as an off-white amorphous solid (13 mg, 85% for the two steps). Tb26: =+7.64 (c=0.55, MeOH); $R_f$=0.46 (silica gel, MeOH:$CH_2Cl_2$:$NH_3$=7.5:100:0.5); FT-IR (neat) $\tilde{v}_{max}$: 3382, 3086, 2967, 2876, 2851, 2791, 1735, 1642, 1540, 1494, 1455, 1412, 1370, 1309, 1258, 1219, 1170, 1140, 1082, 1045, 1000, 933, 852, 830, 782, 746, 701 cm$^{-1}$; $^1$H NMR ($CD_3OD$, 600 MHz) δ 8.08 (s, 1H), 7.27-7.21 (m, 4H), 7.19-7.14 (m, 1H), 5.78 (dd, J=11.5, 2.6 Hz, 1H), 4.49 (m, 1H), 4.35 (d, J=8.6 Hz, 2H), 3.59 (s, 3H), 3.16-3.11 (m, 1H), 3.07 (s, 3H), 2.89 (m, 4H), 2.63-2.57 (m, 1H), 2.44-2.33 (m, 5H), 2.28-2.22 (m, 1H), 2.20-2.15 (m, 1H), 2.14 (s, 3H), 1.98 (m, 1H), 1.88-1.83 (m, 1H), 1.81-1.72 (m, 3H), 1.21 (m, 1H), 1.14 (d, J=7.1 Hz, 3H), 1.04 (d, J=6.5 Hz, 3H), 0.84 (d, J=6.6 Hz, 3H), 0.70-0.64 (m, 1H), 0.61-0.56 (m, 1H), 0.51 (dt, J=14.9, 4.9 Hz, 1H), 0.37 (dt, J=15.1, 4.9 Hz, 1H) ppm; $^{13}$C NMR: ($CD_3OD$, 150 MHz) δ=176.3, 174.1, 172.9, 169.74, 169.73, 160.7, 148.8, 137.5, 128.4, 127.4, 125.5, 123.2, 68.8, 67.9, 55.4, 52.1, 50.2, 48.3, 40.3, 39.6, 36.9, 35.7, 33.6, 29.7, 28.8, 22.8, 18.9, 18.4, 18.1, 16.1, 12.5, 2.3, 1.1 ppm; HRMS calcd for $C_{37}H_{53}N_5O_7S$ [M+H$^+$] 712.3738. found 712.3747.

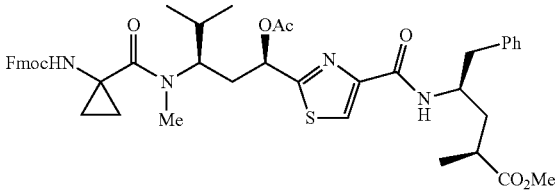

51

(2S,4R)-Methyl 4-(2-((1R,3R)-3-(1-(((9H-fluoren-9-yl)methoxy)carbonylamino)-N-methylcyclopropanecarboxamido)-1-acetoxy-4-methylpentyl)thiazole-4-carboxamido)-2-methyl-5-phenylpentano-ate (51)

According to the procedure described for the synthesis of compound 49, compound 51 was obtained as an off-white amorphous solid (46 mg, 72% for the two steps). 51: $[\alpha]_D^{22}$=−10.0 (c=0.72, MeOH); $R_f$=0.55 (silica gel, 50% EtOAc in hexanes); FT-IR (neat) $\tilde{v}_{max}$: 3332, 2966, 2303, 1729, 1651, 1542, 1492, 1450, 1402, 1369, 1329, 1223, 1170, 1082, 1033, 935, 782, 759, 741, 701 cm$^{-1}$; $^1$H NMR (600 MHz, $CD_3OD$) δ 8.05 (s, 1H), 7.78 (d, J=7.5 Hz, 2H), 7.62 (d, J=7.4 Hz, 2H), 7.37 (t, J=7.3 Hz, 2H), 7.28 (dd, J=13.3, 6.8 Hz, 2H), 7.25-7.19 (m, 4H), 7.18-7.12 (m, 1H), 5.69 (d, J=10.9 Hz, 1H), 4.40 (d, J=5.1 Hz, 1H), 4.33 (m, 2H), 4.22-4.17 (m, 1H), 3.58 (s, 3H), 3.05 (s, 3H), 2.86 (m, 2H), 2.56 (m, 1H), 2.37-2.31 (m, 1H), 2.30-2.23 (m, 1H), 2.09 (s, 3H), 1.94 (s, 2H), 1.72-1.64 (m, 1H), 1.38 (m, 1H), 1.17 (m, 1H), 1.10 (d, J=7.1 Hz, 3H), 1.08-1.03 (m, 1H), 0.99 (d, J=6.4 Hz, 3H), 0.93-0.83 (m, 2H), 0.78 (d, J=6.4 Hz, 3H) ppm; $^{13}$C NMR (150 MHz, $CD_3OD$) δ=176.3, 174.4, 171.2, 170.0, 160.7, 156.2, 148.8, 143.3, 140.7, 137.5, 128.4, 127.3, 126.8, 126.1, 125.4, 124.1, 123.1, 118.9, 68.7, 65.6, 50.2, 48.3, 40.3, 36.8, 35.7, 35.1, 33.7, 29.2, 28.8, 20.1, 18.9, 18.5, 18.2, 16.1, 12.6, 12.5 ppm; HRMS calcd for $C_{45}H_{52}N_4O_8S$ [M+Na$^+$]831.3398. found 831.3391.

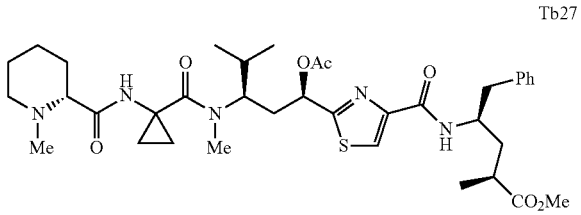 [SMILES: COC(=O)[C@@H](C)C[C@H](Cc1ccccc1)NC(=O)c1csc([C@@H](C[C@H](C(C)C)N(C)C(=O)C2(NC(=O)[C@H]3CCCCN3C)CC2)OC(C)=O)n1]

Tb27

(2S,4R)-Methyl 4-(2-((1R,3R)-1-acetoxy-4-methyl-3-(N-methyl-1-((R)-1-methylpiperidine-2-carboxamido)cyclopropanecarboxamido)pentyl)thiazole-4-carboxamido)-2-methyl-5-phenylpentanoate (Tb27)

According to the procedure described for the synthesis of Tb20, analog Tb27 was obtained as an off-white amorphous solid (46 mg 81% for the two steps). Tb27: $[\alpha]_D^{22}$=−1.45 (c=0.90, MeOH); $R_f$=0.29 (silica gel, 20% MeOH in EtOAc); FT-IR (neat) $\tilde{v}_{max}$: 3280, 2937, 2855, 2795, 1736, 1661, 1542, 1493, 1454, 1404, 1370, 1259, 1222, 1170, 1141, 1123, 1084, 1038, 1000, 935, 837, 783, 744, 701 cm$^{-1}$; $^1$H NMR (600 MHz, CD$_3$OD) δ 8.07 (s, 1H), 7.28-7.20 (m, 4H), 7.20-7.13 (m, 1H), 5.66 (dd, J=11.4, 2.5 Hz, 1H), 4.35 (m, 2H), 3.59 (s, 3H), 3.13 (s, 3H), 2.97 (d, J=11.6 Hz, 1H), 2.88 (ddd, J=30.4, 13.7, 7.0 Hz, 2H), 2.60 (ddd, J=10.9, 10.5, 7.1 Hz, 2H), 2.36 (ddd, J=15.1, 11.6, 3.8 Hz, 1H), 2.32-2.25 (m, 1H), 2.23 (s, 3H), 2.21-2.15 (m, 1H), 2.10 (s, 3H), 1.97 (ddd, J=13.7, 9.8, 3.7 Hz, 1H), 1.88-1.76 (m, 3H), 1.73 (ddd, J=14.3, 10.5, 4.0 Hz, 1H), 1.66 (t, J=11.7 Hz, 1H), 1.63-1.55 (m, 2H), 1.47 (ddd, J=10.3, 7.5, 5.2 Hz, 1H), 1.36-1.30 (m, 1H), 1.23 (ddd, J=10.3, 7.3, 5.4 Hz, 1H), 1.17-1.15 (m, 1H), 1.14 (d, J=5.5 Hz, 3H), 1.01 (d, J=6.6 Hz, 3H), 0.88-0.84 (m, 1H), 0.83 (d, J=6.6 Hz, 3H) ppm; $^{13}$C NMR: (150 MHz, CD$_3$OD) δ=176.3, 173.4, 170.6, 170.0, 169.9, 160.7, 148.8, 137.5, 128.4, 127.4, 125.4, 123.2, 68.5, 68.0, 54.6, 50.2, 48.3, 42.3, 40.3, 36.9, 35.7, 34.7, 33.6, 29.2, 29.0, 23.9, 22.1, 18.9, 18.42, 18.35, 16.1, 12.8, 12.4 ppm; HRMS calcd for $C_{37}H_{53}N_5O_7S$ [M+H$^+$] 712.3738. found 712.3753.

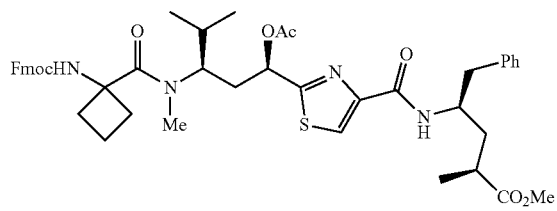

(2S,4R)-methyl-4-(2-((1R,3R)-3-(1-(((9H-fluoren-9-yl)methoxy)carbonylamino)-N-methyl cyclo butanecarboxamido)-1-acetoxy-4-methylpentyl)thiazole-4-carboxamido)-2-methyl-5-phenyl pentan oate (50)

According to the procedure described for the synthesis of compound 49, compound 50 was obtained as an off-white amorphous solid (52 mg, 77% for the two steps). 50: $[\alpha]_D^{22}$=−20.3 (c=0.31, MeOH); $R_f$=0.61 (silica gel. 50% EtOAc in hexanes); FT-IR (neat) $\tilde{v}_{max}$: 3346, 2923, 1728, 1660, 1542, 1494, 1451, 1397, 1223, 1085, 1046, 759, 741, 701 cm$^{-1}$; $^1$H NMR (600 MHz, CD$_3$OD) δ 8.05 (s, 1H), 7.79 (d, J=7.5 Hz, 2H), 7.64 (m, 2H), 7.38 (t, J=7.4 Hz, 2H), 7.32-7.26 (m, 2H), 7.25-7.19 (m, 3H), 7.18-7.13 (m, 1H), 5.76 (d, J=8.8 Hz, 1H), 4.37 (m, 2H), 4.31 (m, 1H), 4.23-4.18 (m, 1H), 3.57 (s, 3H), 2.94-2.78 (m, 6H), 2.63-2.51 (m, 2H), 2.37-2.28 (m, 2H), 2.16 (s, 3H), 2.10 (m, 1H), 2.01-1.90 (m, 5H), 1.82 (m, 1H), 1.67 (ddd, J=14.3, 10.5, 4.0 Hz, 1H), 1.08 (d, J=6.6 Hz, 3H), 1.00 (d, J=6.4 Hz, 3H), 0.79 (d, J=4.5 Hz, 3H) ppm; $^{13}$C NMR: (150 MHz, CD$_3$OD) δ=176.3, 174.4, 172.5, 170.0, 160.7, 154.5, 148.8, 143.3, 140.6, 137.5, 128.4, 127.3, 126.8, 126.1, 125.4, 124.1, 123.1, 118.9, 69.0, 65.5, 58.9, 50.2, 48.3, 40.3, 36.8, 35.7, 33.8, 30.5, 30.4, 29.0, 28.8, 20.1, 19.0, 18.6, 18.3, 16.1, 13.7 ppm; HRMS calcd for $C_{46}H_{54}N_4O_8S$ [M+Na$^+$] 845.3555. found 845.3536.

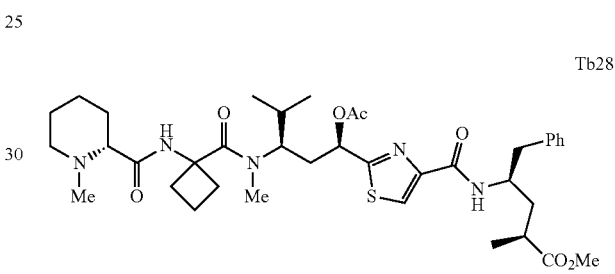

Tb28

(2S,4R)-Methyl 4-(2-((1R,3R)-1-acetoxy-4-methyl-3-(N-methyl-1-((R)-1-methylpiperidine-2-carboxamido)cyclobutanecarboxamido)pentyl)thiazole-4-carboxamido)-2-methyl-5-phenylpentanoate (Tb28)

According to the procedure described for the synthesis of Tb20, analog Tb28 was obtained as an off-white amorphous solid (36 mg, 83% for the two steps). Tb28: $[\alpha]_D^{22}$=−6.4 (c=0.55, MeOH); $R_f$=0.27 (silica gel, 20% MeOH in EtOAc); FT-IR (neat) $\tilde{v}_{max}$: 3279, 2937, 2854, 2794, 1735, 1657, 1541, 1493, 1455, 1398, 1370, 1308, 1262, 1221, 1170, 1141, 1117, 1085, 1048, 934, 785, 746, 701 cm$^{-1}$; $^1$H NMR (600 MHz, CD$_3$OD) δ 8.08 (s, 1H), 7.28-7.19 (m, 4H), 7.17 (m, 1H), 5.78-5.71 (m, 1H), 4.39-4.31 (m, 2H), 3.59 (s, 3H), 3.03-2.94 (m, 2H), 2.93-2.81 (m, 5H), 2.71 (d, J=10.2 Hz, 1H), 2.61 (m, 2H), 2.44-2.39 (m, 1H), 2.38-2.33 (m, 2H), 2.30 (s, 3H), 2.25-2.20 (m, 1H), 2.18 (s, 3H), 2.12 (m, 1H), 2.01-1.94 (m, 2H), 1.89-1.77 (m, 4H), 1.76-1.70 (m, 1H), 1.64 (m, 3H), 1.38-1.31 (m, 1H), 1.14 (d, J=7.1 Hz, 3H), 1.01 (d, J=6.6 Hz, 3H), 0.83 (d, J=6.6 Hz, 3H) ppm; $^{13}$C NMR: (150 MHz, CD$_3$OD) δ=176.3, 172.0, 171.4, 170.1, 170.0, 160.7, 148.8, 137.5, 128.5, 127.4, 125.5, 123.2, 68.8, 68.0, 59.2, 54.7, 50.2, 48.3, 42.3, 40.3, 36.9, 35.7, 33.7, 31.0, 30.8, 29.3, 28.8, 23.9, 22.1, 19.0, 18.6, 18.5, 16.1, 13.9 ppm; HRMS calcd for $C_{38}H_{55}N_5O_7S$ [M+H$^+$]726.3895. found 726.3924.

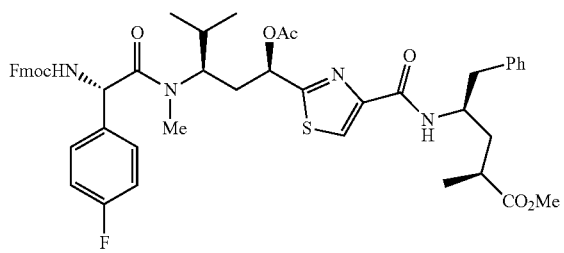

(2S,4R)-Methyl 4-(2-((5S,8R,10R)-1-(9H-fluoren-9-yl)-5-(4-fluorophenyl)-8-isopropyl-7-methyl-3,6,12-trioxo-2,11-dioxa-4,7-diazatridecan-10-yl)thiazole-4-carboxamido)-2-methyl-5-phenylpentanoate (54)

According to the procedure described for the synthesis of compound 49, compound 54 was obtained as an off-white amorphous solid (58 mg, 84% for the two steps). 54: $[\alpha]_D^{22}$=+19.9 (c=0.72, MeOH); $R_f$=0.49 (silica gel, 50% EtOAc in Hexanes); FT-IR (neat) $\tilde{v}_{max}$: 3398, 2966, 1727, 1650, 1604, 1539, 1508, 1493, 1451, 1408, 1370, 1222, 1162, 1080, 1044, 837, 760, 741, 702 cm$^{-1}$; $^1$H NMR (600 MHz, CD$_3$OD) δ 8.04 (s, 1H), 7.95-7.87 (m, 1H), 7.78 (d, J=7.3 Hz, 2H), 7.69-7.60 (m, 2H), 7.49 (dd, J=8.2, 5.1 Hz, 2H), 7.37 (t, J=7.4 Hz, 2H), 7.31-7.23 (m, 2H), 7.23-7.17 (m, 3H), 7.12 (dt, J=24.2, 7.8 Hz, 3H), 5.62 (m, 1H), 5.44 (d, J=10.6 Hz, 1H), 4.46 (m, 1H), 4.38-4.29 (m, 2H), 4.21 (m, 1H), 3.52 (s, 3H), 2.93-2.80 (m, 4H), 2.61-2.53 (m, 1H), 2.39-2.29 (m, 2H), 2.11 (s, 3H), 1.99-1.94 (m, 1H), 1.87-1.80 (m, 1H), 1.70 (ddd, J=14.2, 10.4, 4.0 Hz, 1H), 1.11 (d, J=7.1 Hz, 3H), 1.01 (d, J=6.4 Hz, 3H), 0.94-0.80 (m, 3H), 0.63 (m, 2H) ppm; $^{13}$C NMR: (150 MHz, CD$_3$OD) δ=176.3, 171.4, 170.0, 169.5, 162.2, 160.6, 155.8, 148.7, 143.2, 140.6, 137.4, 131.7, 129.9, 128.4, 127.3, 126.8, 126.2, 125.4, 124.2, 123.2, 118.9, 114.9, 69.0, 66.1, 55.4, 54.7, 50.2, 48.2, 40.3, 36.8, 35.7, 33.5, 29.2, 28.7, 19.0, 18.9, 18.5, 18.4, 16.1 ppm; HRMS calcd for C$_{49}$H$_{53}$FN$_4$O$_8$S [M+Na$^+$] 899.3460. found 899.3452.

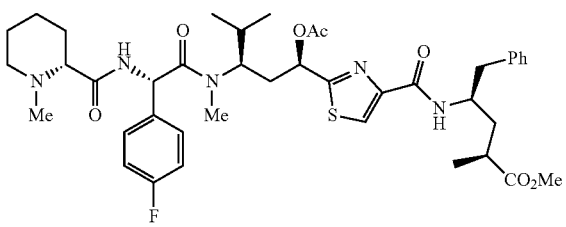

(2S,4R)-Methyl 4-(2-((1R,3R)-1-acetoxy-3-((S)-2-(4-fluorophenyl)-N-methyl-2-((R)-1-methyl piperidine-2-carboxamido)acetamido)-4-methylpentyl)thiazole-4-carboxamido)-2-methyl-5-phenylpentanoate (Tb29)

According to the procedure described for the synthesis of Tb20, analog Tb29 was obtained as an off-white amorphous solid (27 mg, 76% for the two steps). Tb29: $[\alpha]_D^{22}$=+53.9 (c=0.63, MeOH); $R_f$=0.56 (silica gel, 10% MeOH in EtOAc); FT-IR (neat) $\tilde{v}_{max}$: 3386, 2940, 1736, 1645, 1541, 1494, 1408, 1371, 1222, 1083, 1034, 838, 746, 702 cm$^{-1}$; $^1$H NMR (600 MHz, CD$_3$OD) δ 8.03 (s, 1H), 7.54-7.48 (m, 2H), 7.24-7.17 (m, 4H), 7.15 (m, 2H), 5.84 (s, 1H), 5.42 (d, J=10.9 Hz, 1H), 4.50 (m, 1H), 4.32 (m, 1H), 3.54 (s, 3H), 3.02-2.97 (m, 1H), 2.87 (s, 3H), 2.85-2.81 (m, 2H), 2.73 (m, 1H), 2.60-2.54 (m, 1H), 2.37-2.30 (m, 1H), 2.22 (m, 4H), 2.17 (s, 3H), 2.12-2.07 (m, 1H), 1.99-1.93 (m, 1H), 1.87-1.75 (m, 3H), 1.73-1.66 (m, 2H), 1.59 (dd, J=26.0, 11.5 Hz, 2H), 1.36-1.29 (m, 1H), 1.13 (d, J=7.1 Hz, 3H), 1.04 (d, J=6.5 Hz, 3H), 0.91 (d, J=6.5 Hz, 3H) ppm; $^{13}$C NMR: (150 MHz, CD$_3$OD) δ=176.3, 171.9, 170.8, 170.0, 169.4, 162.2, 160.6, 148.7, 137.4, 131.3, 129.9, 128.4, 127.3, 125.4, 123.2, 115.1, 69.0, 68.1, 54.6, 53.5, 50.2, 48.2, 47.6, 42.3, 40.3, 36.9, 35.7, 33.5, 29.1, 28.8, 23.8, 22.0, 18.9, 18.5, 18.3, 16.1 ppm; HRMS calcd for C$_{41}$H$_{54}$FN$_5$O$_7$S [M+H$^+$] 780.3801. found 780.3808.

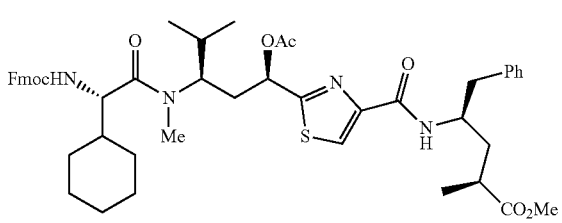

(2S,4R)-Methyl 4-(2-((5S,8R,10R)-5-cyclohexyl-1-(9H-fluoren-9-yl)-8-isopropyl-7-methyl-3,6,12-trioxo-2,11-dioxa-4,7-diazatridecan-10-yl)thiazole-4-carboxamido)-2-methyl-5-phenylpentanoate (53)

According to the procedure described for the synthesis of compound 49, compound 53 was obtained as an off-white amorphous solid (64 mg, 92% for the two steps). 53: $[\alpha]_D^{22}$=+8.1 (c=0.90, CHCl$_3$); $R_f$=0.44 (silica gel, 50% EtOAc in hexanes); FT-IR (neat) $v_{max}$: 3293, 2930, 2853, 2325, 1720, 1639, 1537, 1495, 1450, 1410, 1371, 1293, 1219, 1138, 1081, 1028, 758, 742, 701 cm$^{-1}$; $^1$H NMR (600 MHz, CDCl$_3$) δ 8.02 (s, 1H), 7.76 (d, J=7.5 Hz, 2H), 7.63-7.53 (m, 2H), 7.40 (t, J=7.3 Hz, 2H), 7.30 (m, 3H), 7.23 (m, 3H), 7.11 (d, J=9.1 Hz, 1H), 5.64 (d, J=10.9 Hz, 1H), 5.48 (d, J=9.4 Hz, 1H), 4.53 (m, 2H), 4.46-4.32 (m, 3H), 4.21 (m, 1H), 3.63 (s, 3H), 2.98 (s, 3H), 2.95 (m, 1H), 2.89 (m, 1H), 2.63 (m, 1H), 2.33 (dd, J=19.3, 7.2 Hz, 1H), 2.16 (s, 3H), 2.10-1.97 (m, 2H), 1.84-1.52 (m, 9H), 1.26 (m, 2H), 1.17 (d, J=7.0 Hz, 3H), 1.17-1.13 (m, 2H), 1.08-1.04 (m, 1H), 1.03 (d, J=6.5 Hz, 3H), 0.83 (d, J=6.4 Hz, 3H) ppm; $^{13}$C NMR: (150 MHz, CDCl$_3$) δ=176.6, 173.3, 169.9, 160.3, 156.3, 150.0, 143.9, 143.7, 141.3, 137.5, 129.6, 128.4, 127.6, 127.0, 126.5, 125.1, 123.4, 119.9, 69.5, 66.9, 55.8, 51.7, 48.2, 47.2, 41.0, 40.8, 37.7, 36.4, 34.6, 30.4, 30.0, 27.7, 26.1, 25.8, 20.8, 20.0, 19.6, 17.7 ppm; HRMS calcd for C$_{49}$H$_{60}$FN$_4$O$_8$S [M+Na$^+$] 887.4024. found 887.3991.

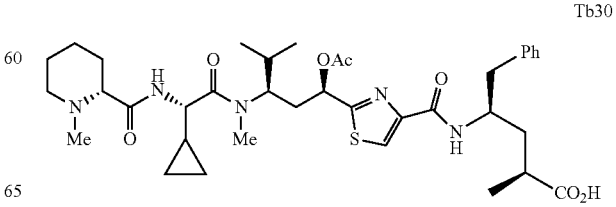

Tb30

(2S,4R)-4-(2-((1R,3R)-1-Acetoxy-3-((S)-2-cyclopropyl-N-methyl-2-((R)-1-methylpiperidine-2-carboxamido)acetamido)-4-methylpentyl)thiazole-4-carboxamido)-2-methyl-5-phenylpentanoic Acid (Tb30)

According to the procedure described for the synthesis of Tb1, analog Tb20 converted to analog Tb30 and was obtained as an colorless oil (12 mg, 54% for the two steps). Tb30: $R_f$=0.4 (10% MeOH in $CH_2Cl_2$); $[\alpha]_D^{22}$=−2.4 (c=0.1, $CHCl_3$); FT-IR (neat) $\tilde{v}_{max}$: 2921, 2851, 1727, 1555, 1463, 1379, 1267, 1095, 1017, 914, 730 cm$^{-1}$; $^1$H NMR: ($CD_3OD$, 600 MHz) δ=8.08 (s, 1H), 7.25-7.20 (m, 4H), 7.15 (tt, J=5.5, 3.0 Hz, 1H), 5.78 (dd, J=11.2, 2.7 Hz, 1H), 4.49-4.27 (m, 2H), 4.16 (d, J=9.1 Hz, 1H), 3.17-3.07 (m, 1H), 3.05 (s, 3H), 3.02-2.94 (m, 1H), 2.92 (dt, J=9.7, 5.3 Hz, 2H), 2.60-2.41 (m, 3H), 2.39 (s, 3H), 2.28 (t, J=13.8 Hz, 1H), 2.13 (s, 3H), 2.07-1.58 (m, 9H), 1.40 (qt, J=12.8, 3.8 Hz, 1H), 1.15-1.16 (m, 1H), 1.17 (dd, J=12.2, 7.7 Hz, 3H), 1.03 (d, J=6.5 Hz, 3H), 0.86 (d, J=6.6 Hz, 3H), 0.69 (tdd, J=8.5, 6.0, 4.5 Hz, 1H), 0.65-0.59 (m, 1H), 0.55 (dq, J=9.9, 4.9 Hz, 1H), 0.43-0.33 (m, 1H); $^{13}$C NMR: ($CDCl_3$, 150 MHz) δ=181.76, 174.87, 173.11, 171.72, 171.54, 162.73, 151.02, 139.70, 130.53, 129.28, 127.34, 125.04, 79.48, 70.89, 69.58, 56.50, 55.28, 51.15, 44.02, 41.92, 39.42, 39.10, 35.60, 30.90, 30.76, 25.44, 23.62, 20.86, 20.44, 20.31, 18.89, 14.16, 4.50, 3.60; HRMS calcd for $C_{37}H_{53}N_5O_7S$ [M+H$^+$] 712.3744. found 712.3767.

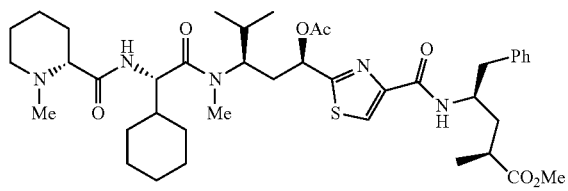

(2S,4R)-Methyl 4-(2-((1R,3R)-1-acetoxy-3-((S)-2-cyclohexyl-N-methyl-2-((R)-1-methylpiperidine-2-carboxamido)acetamido)-4-methylpentyl)thiazole-4-carboxamido)-2-methyl-5-phenylpentanoate (Tb33)

According to the procedure described for the synthesis of Tb20, analog Tb33 was obtained as an off-white amorphous solid (42 mg, 75% for the two steps). Tb33: $[\alpha]_D^{22}$=−6.55 (c=0.65, MeOH); $R_f$=0.21 (silica gel, 5% MeOH in $CH_2Cl_2$); FT-IR (neat) $\tilde{v}_{max}$: 3391, 2932, 2854, 1736, 1644, 1541, 1495, 1453, 1411, 1371, 1259, 1221, 1142, 1121, 1084, 1049, 1033, 781, 744, 702 cm$^{-1}$; $^1$H NMR (600 MHz, $CD_3OD$) δ 8.09 (s, 1H), 7.24 (m, 4H), 7.18 (t, J=6.6 Hz, 1H), 5.70 (d, J=11.0 Hz, 1H), 4.71 (d, J=7.6 Hz, 1H), 4.48 (m, 1H), 4.39-4.32 (m, 1H), 3.59 (s, 3H), 3.11 (s, 3H), 3.05 (d, J=10.8 Hz, 1H), 2.89 (m, 3H), 2.60 (ddd, J=17.1, 8.8, 5.4 Hz, 1H), 2.41-2.34 (m, 1H), 2.31 (s, 3H), 2.27-2.20 (m, 1H), 2.14 (s, 3H), 1.98 (ddd, J=13.5, 9.8, 3.4 Hz, 1H), 1.88-1.66 (m, 1H), 1.65-1.55 (m, 2H), 1.33 (m, 4H), 1.24-1.17 (m, 1H), 1.14 (d, J=7.1 Hz, 3H), 1.12-1.05 (m, 2H), 1.03 (d, J=6.5 Hz, 3H), 0.81 (d, J=6.5 Hz, 3H) ppm; $^{13}$C NMR: (150 MHz, $CD_3OD$) δ=176.3, 173.0, 172.3, 169.8, 169.7, 160.7, 148.8, 137.8, 128.5, 127.4, 125.5, 123.2, 69.3, 68.0, 54.5, 53.5, 50.3, 48.2, 42.4, 40.4, 39.1, 36.9, 35.7, 33.7, 29.4, 29.3, 29.0, 27.7, 25.24, 25.17, 25.0, 23.7, 21.9, 18.8, 18.5, 18.3, 16.1 ppm; HRMS calcd for $C_{41}H_{61}N_5O_7S$ [M+H$^+$] 768.4364. found 768.4379.

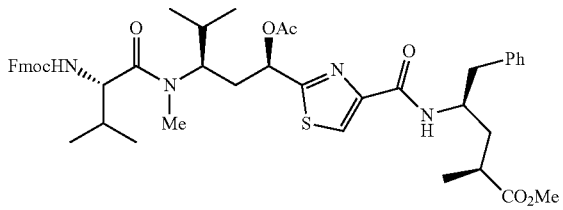

(2S,4R)-Methyl 4-(2-((5S,8R,10R)-1-(9H-fluoren-9-yl)-5,8-diisopropyl-7-methyl-3,6,12-trioxo-2,11-dioxa-4,7-diazatridecan-10-yl)thiazole-4-carboxamido)-2-methyl-5-phenylpentanoate (52)

According to the procedure described for the synthesis of compound 49, compound 52 was obtained as an off-white amorphous solid (61 mg, 88% for the two steps). 52: $[\alpha]_D^{22}$=+5.2 (c=1.10, $CHCl_3$); $R_f$=0.41 (silica gel. 50% EtOAc in hexanes); FT-IR (neat) $\tilde{v}_{max}$: 3396, 3304, 2965, 2875, 1721, 1647, 1537, 1495, 1451, 1410, 1370, 1296, 1220, 1172, 1140, 1105, 1082, 1029, 934, 851, 805, 757, 742, 702, 665 cm$^{-1}$; $^1$H NMR (600 MHz, $CDCl_3$) δ 8.02 (s, 1H), 7.76 (d, J=7.5 Hz, 2H), 7.59 (d, J=6.9 Hz, 2H), 7.40 (t, J=7.4 Hz, 2H), 7.34-7.26 (m, 4H), 7.24-7.20 (m, 3H), 7.10 (d, J=9.2 Hz, 1H), 5.65 (dd, J=11.3, 2.0 Hz, 1H), 5.49 (d, J=9.5 Hz, 1H), 4.53 (m, 1H), 4.45-4.33 (m, 3H), 4.22 (t, J=7.2 Hz, 1H), 3.63 (s, 3H), 2.98 (s, 3H), 2.97-2.93 (m, 1H), 2.89 (dd, J=13.8, 6.6 Hz, 1H), 2.62 (m, 1H), 2.33 (ddd, J=14.6, 11.5, 2.8 Hz, 1H), 2.18 (s, 3H), 2.12-2.06 (m, 1H), 2.05-1.98 (m, 2H), 1.81-1.75 (m, 1H), 1.63 (m, 2H), 1.17 (d, J=7.1 Hz, 3H), 1.03 (dd, J=6.5, 2.6 Hz, 6H), 0.95 (d, J=6.7 Hz, 4H), 0.83 (d, J=6.6 Hz, 3H). ppm; $^{13}$C NMR: (150 MHz, $CDCl_3$) δ=176.6, 173.4, 170.0, 160.3, 156.4, 150.0, 143.9, 143.8, 141.3, 137.5, 129.6, 128.4, 127.7, 127.0, 126.5, 125.1, 123.4, 120.0, 69.5, 67.0, 56.2, 51.7, 48.3, 47.2, 41.0, 37.6, 36.4, 34.7, 31.0, 30.0, 20.8, 20.1, 20.0, 19.6, 17.6, 17.1 ppm; HRMS calcd for $C_{46}H_{56}N_4O_8S$ [M+Na$^+$] 847.3711. found 847.3681.

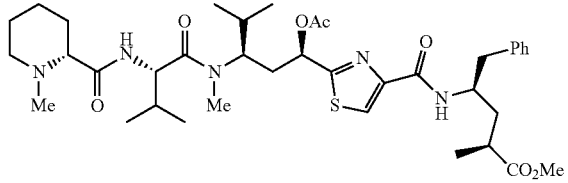

(2S,4R)-Methyl 4-(2-((1R,3R)-1-acetoxy-3-((S)—N,3-dimethyl-2-((R)-1-methylpiperidine-2-carboxamido)butanamido)-4-methylpentyl)thiazole-4-carboxamido)-2-methyl-5-phenylpentanoate (Tb32)

According to the procedure described for the synthesis of Tb20, analog Tb32 was obtained as an off-white amorphous solid (34 mg, 80% for the two steps). Tb32: $[\alpha]_D^{22}$=−6.02

(c=1.28, MeOH); $R_f$=0.51 (silica gel, 10% MeOH in CH$_2$Cl$_2$); FT-IR (neat) $\tilde{v}_{max}$: 3388, 2940, 2874, 2794, 1736, 1645, 1541, 1496, 1411, 1371, 1258, 1221, 1171, 1142, 1116, 1084, 1047, 1001, 933, 831, 782, 747, 702 cm$^{-1}$; H NMR (600 MHz, CD$_3$OD) δ 8.08 (s, 1H), 7.27-7.20 (m, 4H), 7.19-7.14 (m, 1H), 5.71 (dd, J=11.2, 2.4 Hz, 1H), 4.70 (d, J=7.4 Hz, 1H), 4.48 (m, 1H), 4.35 (dtd, J=10.6, 7.0, 3.7 Hz, 1H), 3.59 (s, 3H), 3.10 (s, 3H), 2.97 (d, J=11.3 Hz, 1H), 2.88 (ddd, J=30.1, 13.7, 7.0 Hz, 2H), 2.67 (d, J=10.3 Hz, 1H), 2.64-2.56 (m, 1H), 2.37 (ddd, J=14.4, 11.3, 2.9 Hz, 1H), 2.27-2.25 (m, 1H), 2.24 (s, 3H), 2.18-2.16 (m, 1H), 2.15 (s, 3H), 2.09 (td, J=13.7, 6.8 Hz, 1H), 1.98 (ddd, J=13.7, 9.8, 3.6 Hz, 1H), 1.79 (m, 4H), 1.68-1.66 (m, 1H), 1.58 (tdd, J=21.0, 11.8, 8.9 Hz, 2H), 1.32 (m, 1H), 1.14 (d, J=7.1 Hz, 3H), 1.02 (m, 6H), 0.98 (d, J=6.7 Hz, 3H), 0.81 (d, J=6.6 Hz, 3H) ppm; $^{13}$C NMR: (150 MHz, CD$_3$OD) δ=176.4, 173.3, 173.1, 169.9, 169.8, 160.8, 148.9, 137.6, 128.5, 127.5, 125.6, 123.3, 69.3, 68.5, 54.7, 54.1, 50.3, 48.3, 42.8, 40.5, 36.9, 35.8, 33.7, 29.62, 29.60, 29.1, 24.1, 22.3, 18.9, 18.6, 18.5, 18.3, 16.6, 16.2 ppm; HRMS calcd for C$_{38}$H$_{57}$N$_5$O$_7$S [M+H$^+$] 728.4051. found 728.4060.

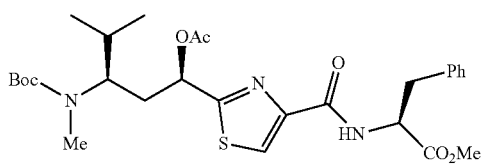

57

Methyl (2-((1R,3R)-1-acetoxy-3-((tert-butoxycarbonyl)(methyl)amino)-4-methylpentyl)thiazole-4-carbonyl)-L-phenylalaninate (57)

To a stirred solution of thiazole acid 5 (116 mg, 0.29 mmol) in dry DMF (1.9 mL) was added HATU (330 mg, 0.87 mmol) followed by a solution of L-phenylalanine methyl ester (94 mg, 0.44 mmol) and Et$_3$N (0.24 mL, 1.74 mmol), in DMF (1.0 mL) at 25° C., and the resulting mixture was stirred for 18 h at the same temperature. The reaction mixture was diluted with H$_2$O (50 mL) and the resulting solution was extracted with EtOAc (3×50 mL). The combined organic extracts were washed with brine (2×50 mL), dried over Na$_2$SO$_4$ and evaporated under reduced pressure. The obtained residue was purified by flash column chromatography (silica gel, 20%→40% EtOAc in hexanes) to furnish 57 (150 mg, 93%) as a light yellow amorphous solid. 57: $R_f$=0.55 (silica gel, 50% EtOAc in hexanes); $^1$H NMR analysis at ambient temperature indicated a ca. 2:1 mixture of rotamers. Major rotamer: $^1$H NMR: (CDCl$_3$, 600 MHz) δ=8.03 (s, 1H), 7.64 (d, J=8.3 Hz, 1H), 7.31-7.13 (m, 5H), 5.79 (d, J=11.6 Hz, 1H), 5.05-4.98 (m, 1H), 4.06 (dt, J=12.5, 7.7 Hz, 1H), 3.71 (s, 3H), 2.68 (s, 3H), 2.34-2.21 (m, 1H), 2.15 (s, 3H), 2.06-1.98 (m, 1H), 1.76-1.66 (m, 2H), 1.52-1.45 (m, 1H), 1.44 (s, 9H), 0.99 (d, J=7.02 Hz, 3H), 0.87 (d, J=7.02 Hz, 3H) ppm; $^{13}$C NMR: (CDCl$_3$, 150 MHz) δ=171.6, 170.4, 170.1, 160.3, 156.2, 149.1, 135.9, 129.2, 128.5, 127.0, 123.9, 79.4, 69.1, 56.3, 53.1, 52.3, 38.1, 34.5, 30.3, 28.3, 28.0, 20.8, 20.0, 19.5 ppm; Diagnostic signals of minor rotamer: $^1$H NMR: (CDCl$_3$, 600 MHz) δ=8.04 (s, 1H), 7.69 (d, J=8.2 Hz, 1H), 5.91 (dd, J=9.1, 3.1 Hz, 1H), 2.66 (s, 3H), 1.42 (s, 9H), 0.95 (d, J=6.5 Hz, 3H), 0.86 (d, J=7.1 Hz, 3H); $^{13}$C NMR: (CDCl$_3$, 150 MHz) δ=171.5, 169.9, 169.4, 160.3, 156.1, 149.3, 135.9, 129.2, 128.5, 127.0, 123.8, 79.6, 70.4, 56.3, 53.2, 52.3, 38.0, 34.7, 29.6, 28.3, 28.0, 20.9, 20.2, 19.7 ppm; HRMS calcd for C$_{28}$H$_{39}$N$_3$O$_7$S [M+Na$^+$] 584.2406. found 584.2401.

58

Methyl(2-((1R,3R)-3-((S)-2-((((9H-fluoren-9-yl)methoxy)carbonyl)amino)-2-cyclopropyl-N-methyl acetamido)-1-acetoxy-4-methylpentyl)thiazole-4-carbonyl)-L-phenylalaninate (58)

To an iced-cooled stirred solution of 57 (0.17 g, 0.27 mmol) in CH$_2$Cl$_2$ (4.5 mL) was added trifluoroacetic acid (1.5 mL) and the reaction mixture was stirred for 6 h while warming up to 25° C. Evaporation of the volatile components under reduced pressure furnished the crude TFA-ammonium salt (quantitative), which was used for the following step without further purification.

To a stirred, iced-cooled solution of the crude ammonium salt from the previous step and N,N-diisopropylethylamine (0.24 mL, 1.37 mmol) in DMF (2.7 mL) was added acyl fluoride 43 (0.37 g, 1.1 mmol) and stirring was continued for 18 h at 25° C. The reaction mixture was diluted with ethyl acetate (50 mL), washed with saturated aqueous NaHCO$_3$ solution (2×50 mL), and brine (2×50 mL), dried over Na$_2$SO$_4$, and concentrated. The obtained residue was purified using flash column chromatography (silica gel, 40→70% EtOAc in hexanes) to give 58 (0.18 g, 85% yield) as white foam. 58: $R_f$=0.36 (silica gel 50% EtOAc in hexanes); $[\alpha]_D^{22}$=+28.5 (c=1.0, CHCl$_3$); FT-IR $v_{max}$ (neat): 3312, 2960, 1743, 1717, 1646, 1537, 1494, 1450, 1411, 1369, 1221, 1104, 1081, 1042, 759, 741, 702 cm$^{-1}$; $^1$H NMR: (CDCl$_3$, 600 MHz) δ=8.07 (s, 1H), 7.81-7.51 (m, 5H), 7.43-7.11 (m, 8H), 5.88-5.79 (m, 1H), 5.72 (dd, J=11.4, 2.5 Hz, 1H), 5.06 (dd, J=6.4, 6.4 Hz, 1H), 4.62-4.53 (m, 1H), 4.38-4.29 (m, 3H), 4.23-4.16 (m, 1H), 3.72 (s, 3H), 3.28-3.18 (m, 2H), 2.96 (s, 3H), 2.41-2.33 (m, 1H), 2.17 (s, 3H), 2.14-2.05 (m, 1H), 1.84-1.70 (m, 1H), 1.25-1.14 (m, 1H), 1.09 (d, J=6.8 Hz, 3H), 0.96-0.90 (m, 1H), 0.87 (d, J=6.7 Hz, 3H), 0.69-0.62 (m, 1H), 0.61-0.52 (m, 1H), 0.52-0.43 (m, 2H) ppm; $^{13}$C NMR: (CDCl$_3$, 150 MHz) δ=172.8, 171.5, 169.9, 169.8, 160.0, 155.9, 149.0, 143.7, 143.6, 141.0, 135.7, 129.1, 128.3, 127.4, 126.8, 125.0, 123.9, 119.7, 69.0, 66.7, 55.4, 53.6, 52.9, 52.1, 46.9, 37.9, 34.1, 29.4, 29.1, 20.6, 19.8, 19.5, 13.8, 3.4, 1.9 ppm; HRMS calcd for C$_{43}$H$_{48}$N$_4$O$_8$S [M+Na$^+$] 803.3091. found 803.3086.

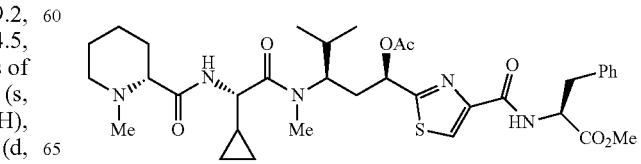

Methyl(2-((1R,3R)-1-acetoxy-3-((S)-2-cyclopropyl-N-methyl-2-((R)-1-methylpiperidine-2-carboxamido)acetamido)-4-methylpentyl)thiazole-4-carbonyl)-L-phenylalaninate (Tb24)

According to the procedure described for the synthesis of Tb2, analog Tb24 was obtained as an off-white amorphous solid (109 mg, 82% for the two steps). Tb24: $R_f$=0.51 (silica gel, 7% MeOH/2% NH$_4$OH/CH$_2$Cl$_2$); $[\alpha]_D^{22}$=+40.7° (c=1.0, CHCl$_3$); FT-IR (neat) $\tilde{\nu}_{max}$: 3396, 2937, 2855, 1744, 1670, 1643, 1541, 1494, 1412, 1370, 1219, 1082, 1048, 1033, 832, 751, 702 cm$^{-1}$; $^1$H NMR: (CDCl$_3$, 600 MHz) δ=7.98 (s, 1H), 7.56 (d, J=8.3 Hz, 1H), 7.23-7.16 (m, 4H), 7.12-7.08 (m, 2H), 5.64 (dd, J=11.5, 2.6 Hz, 1H), 4.97 (dt, J=8.5, 6.1 Hz, 1H), 4.49-4.44 (m, 1H), 4.35-4.25 (m, 1H), 3.67 (s, 3H), 3.23-3.08 (m, 2H), 2.91 (s, 3H), 2.90-2.81 (m, 1H), 2.27 (dd, J=11.6, 3.4 Hz, 1H), 2.22 (bs, 3H), 2.09 (s, 3H), 2.00 (t, J=14.4 Hz, 1H), 1.87-1.29 (m, 5H), 1.25-1.09 (m, 3H), 0.96 (d, J=6.5 Hz, 3H), 0.85-0.81 (m, 1H), 0.76 (d, J=6.6 Hz, 3H), 0.60 (dq, J=9.0, 5.1, 4.5 Hz, 1H), 0.54-0.43 (m, 1H), 0.35 (ddt, J=30.5, 9.7, 4.8 Hz, 2H) ppm; $^{13}$C NMR: (CDCl$_3$, 150 MHz) δ=173.7, 172.8, 171.7, 170.2, 170.0, 160.2, 149.2, 135.8, 129.3, 128.5, 127.1, 124.0, 69.7, 69.1, 55.2, 53.0, 52.3, 44.4, 38.6, 38.1, 34.4, 30.3, 29.7, 29.6, 29.2, 24.9, 23.2, 20.8, 19.9, 19.5, 13.7, 3.9, 2.5 ppm; HRMS calcd for C$_{35}$H$_{55}$N$_5$O$_7$S [M+H$^+$] 684.3431. found 684.3435.

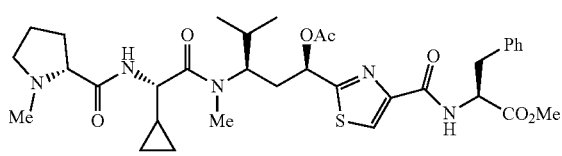

Methyl(2-((1R,3R)-1-acetoxy-3-((S)-2-cyclopropyl-N-methyl-2-((R)-1-methylpyrrolidine-2-carboxamido)acetamido)-4-methylpentyl)thiazole-4-carbonyl)-L-phenylalaninate (Tb25)

According to the procedure described for the synthesis of Tb2, analogue Tb25 was synthesized from methyl-(D)-proline as an off-white amorphous solid (58 mg, 97% yield). Tb25: $R_f$=0.54 (silica gel, 7% MeOH/2% NH$_4$OH in CH$_2$Cl$_2$); $[\alpha]_D^{22}$=+41.8 (c=1.0, CHCl$_3$); FT-IR (neat) $\tilde{\nu}_{max}$: 3350, 2962, 2875, 2790, 1745, 1669, 1645, 1540, 1495, 1412, 1369, 1218, 1082, 1046, 935, 830, 752, 702 cm$^{-1}$; $^1$H NMR: (CDCl$_3$, 600 MHz) δ=7.98 (s, 1H), 7.80 (d, J=9.0 Hz, 1H), 7.56 (d, J=8.2 Hz, 1H), 7.26-7.14 (m, 3H), 7.10 (d, J=7.4 Hz, 2H), 5.64 (dd, J=11.5, 2.6 Hz, 1H), 4.97 (dt, J=8.1, 6.2 Hz, 1H), 4.49-4.45 (m, 1H), 4.35 (t, J=8.5 Hz, 1H), 3.67 (s, 3H), 3.17 (dq, J=14.7, 7.9, 6.9 Hz, 2H), 3.05 (dt, J=9.1, 4.3 Hz, 1H), 2.91 (s, 3H), 2.34 (bs, 3H), 2.33-2.25 (m, 2H), 2.09 (s, 3H), 2.01 (t, J=13.0 Hz, 1H), 1.77-1.62 (m, 4H), 1.21-1.09 (m, 2H), 0.96 (d, J=6.5 Hz, 3H), 0.86-0.81 (m, 1H), 0.75 (d, J=6.5 Hz, 3H), 0.58 (tt, J=8.6, 4.8 Hz, 1H), 0.47 (tt, J=9.3, 4.4 Hz, 1H), 0.36-0.30 (m, 2H) ppm; $^{13}$C NMR: (CDCl$_3$, 150 MHz) δ=173.6, 172.9, 171.7, 170.2, 170.0, 160.2, 149.2, 135.8, 129.3, 128.5, 127.1, 124.0, 69.1, 68.6, 56.3, 55.2, 53.0, 52.3, 51.9, 41.1, 38.1, 34.3, 30.6, 29.7, 29.2, 23.9, 20.8, 19.9, 19.4, 13.6, 3.6, 2.1 ppm; HRMS calcd for C$_{34}$H$_{18}$N$_5$O$_7$S [M+H$^+$] 670.3274. found 670.3269.

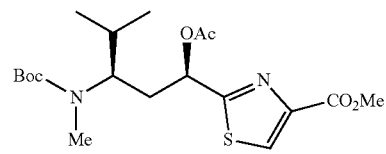

Methyl 2-((1R,3R)-1-acetoxy-3-((tert-butoxycarbonyl)(methyl)amino)-4-methylpentyl)thiazole-4-carboxylate (59)

To a stirred solution of carboxylic acid 5 (190 mg, 0.47 mmol) in toluene (1.8 mL) and MeOH (1.2 mL) at 25° C. was added TMSCHN$_2$ (2.0 M in Et$_2$O, 1.2 equiv, 0.29 mL, 0.57 mmol). The resulting mixture was stirred at 25° C. for 30 min and was then concentrated under reduced pressure. The obtained residue was purified by flash column chromatography (silica gel, 20%→50% EtOAc in hexanes) to produce the corresponding ester 59 as a colorless oil (142 mg, 73% yield). 59: $R_f$=0.65 (silica gel, 50% EtOAc in hexanes); $[\alpha]_D^{22}$=+12.1 (c=1.0, CHCl$_3$); FT-IR (neat): 3119, 2970, 1742, 1688, 1481, 1453, 1391, 1367, 1343, 1217, 1156, 1132, 1095, 1046, 952, 945, 868, 772, 673 cm$^{-1}$. $^1$H NMR analysis at ambient temperature indicated a ca. 3:1 mixture of rotamers. Major rotamer: $^1$H NMR: (CDCl$_3$, 600 MHz) δ=8.10 (s, 1H), 5.84 (dd, J=11.7, 2.2 Hz, 1H), 4.08-4.00 (m, 1H), 3.89 (s, 3H), 2.66 (s, 3H), 2.33-2.24 (m, 1H), 2.12-2.08 (m, 1H), 2.11 (s, 3H), 1.74-1.58 (m, 1H), 1.39 (s, 9H), 0.93 (d, J=6.6 Hz, 3H), 0.82 (d, J=6.7 Hz, 3H) ppm; $^{13}$C NMR: (CDCl$_3$, 150 MHz) δ=171.6, 170.1, 161.7, 156.3, 146.8, 127.8, 79.3, 70.1, 69.4, 56.3, 52.4, 34.7, 30.3, 28.3, 20.8, 20.0, 19.5 ppm; Diagnostic signals of minor rotamer: $^1$H NMR: (CDCl$_3$, 600 MHz) δ=8.12 (s, 1H), 5.91 (dd, J=9.9, 2.7 Hz, 1H), 1.38 (s, 9H), 0.88 (d, J=6.7 Hz, 3H), 0.86 (d, J=6.6 Hz, 1H), $^{13}$C NMR: (CDCl$_3$, 150 MHz) δ=170.3, 169.5, 161.6, 155.6, 146.9, 127.9, 79.6, 70.0, 69.3, 58.0, 51.3, 38.1, 32.8, 28.4, 21.0, 20.2, 19.8 ppm; HRMS calcd for C$_{19}$H$_{30}$N$_2$O$_6$S [M+Na$^+$] 437.1722. found 437.1720.

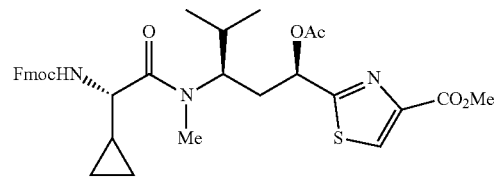

Methyl 2-((5S,8R,10R)-5-cyclopropyl-1-(9H-fluoren-9-yl)-8-isopropyl-7-methyl-3,6,12-trioxo-2,11-dioxa-4,7-diazatridecan-10-yl)thiazole-4-carboxylate (60)

According to the procedure described for the synthesis of 58, Fmoc-protected dipeptide 60 was synthesized after a Boc-cleavage/HATU-coupling sequence and isolated as a viscous yellow oil (160 mg, 75% for the two steps). 60: $R_f$=0.27 (silica gel, 50% EtOAc in hexanes); $[\alpha]_D^{22}$=+10.7 (c=1.0, CHCl$_3$); FT-IR $\nu_{max}$ (neat): 2963, 1719, 1639, 1499, 1450, 1370, 1324, 1218, 1103, 1043, 759, 742 cm$^{-1}$; $^1$H NMR: (CDCl$_3$, 600 MHz) δ=8.12 (s, 1H), 7.75 (d, J=7.6 Hz, 2H), 7.58 (dd, J=7.5, 4.3 Hz, 2H), 7.38 (t, J=7.5 Hz, 2H), 7.32-7.27 (m, 2H), 5.77 (dd, J=11.7, 2.7 Hz, 1H), 5.69 (d, J=8.5 Hz, 1H), 4.54 (dd, J=13.7, 8.3 Hz, 1H), 4.34 (d, J=7.3 Hz, 2H), 4.31 (t, J=8.0 Hz, 1H), 4.20 (t, J=7.0 Hz, 1H), 3.93 (s, 3H), 2.98 (s, 3H), 2.39 (ddd, J=15.0, 11.7, 3.3 Hz, 1H), 2.17 (s, 3H), 1.79-1.71 (m, 1H), 1.16-1.09 (m, 1H), 1.00 (d, J=6.5 Hz, 3H), 0.92-0.86 (m, 1H), 0.83 (d, J=6.6 Hz, 3H), 0.68-0.60 (m, 1H), 0.56-0.50 (m, 1H), 0.49-0.41 (m, 2H) ppm; $^{13}$C NMR: (CDCl$_3$, 150 MHz) δ=171.0, 169.1, 168.1, 159.6, 154.0, 144.8, 141.9, 139.2, 125.8, 125.6, 125.0, 123.1, 117.9, 67.3, 64.9, 53.5, 51.7, 50.5, 45.1, 32.3, 27.6, 27.4, 18.8, 18.0, 17.7, 12.0, 1.6, 0.0 ppm; HRMS calcd for C$_{34}$H$_{39}$N$_3$Na$_7$S [M+Na$^+$] 656.2406. found 656.2399.

61

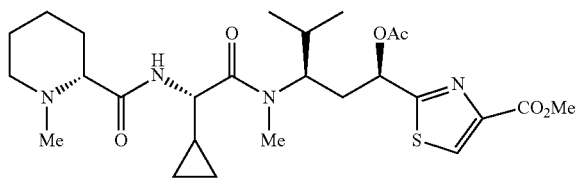

Methyl-2-((1R,3R)-1-acetoxy-3-((S)-2-cyclopropyl-N-methyl-2-((R)-1-methylpiperidine-2-carboxamido)acetamido)-4-methylpentyl)thiazole-4-carboxylate (61)

According to the procedure described for the synthesis of Tb2, Fmoc-group was removed through the action of tris (2-aminoethyl)amine, followed by coupling with N-methyl-(D)-pipecolinic acid (10), furnishing tripeptide 61 (109 mg, 82% for the two steps) as an off-white amorphous solid. 61: R$_f$=0.23 (silica gel, 7% MeOH in CH$_2$Cl$_2$); [α]$_D^{22}$=+39.2 (c=1.0, CHCl$_3$); FT-IR (neat) ν$_{max}$: 3378, 2941, 2794, 1740, 1643, 1496, 1412, 1371, 1325, 1218, 1099, 1047, 990, 935, 845, 756 cm$^{-1}$; $^1$H NMR: (CDCl$_3$, 600 MHz) δ=8.11 (s, 1H), 7.21 (d, J=8.6 Hz, 1H), 5.80 (d, J=11.4 Hz, 1H), 4.33 (t, J=8.6 Hz, 1H), 3.91 (s, 3H), 2.97 (s, 3H), 2.70-2.46 (m, 1H), 2.40-2.17 (m, 6H), 2.14 (s, 3H), 1.88-1.47 (m, 6H), 1.46-1.35 (m, 1H), 1.32-1.10 (m, 3H), 0.96 (d, J=6.8 Hz, 3H), 0.78 (d, J=6.4 Hz, 3H), 0.69-0.57 (m, 1H), 0.56-0.49 (m, 1H), 0.47-0.28 (m, 2H). ppm; $^{13}$C NMR: (CDCl$_3$, 150 MHz) δ=173.1, 172.7, 171.3, 170.0, 161.6, 146.7, 127.8, 69.4, 69.3, 55.4, 52.4, 52.3, 44.4, 39.7, 34.5, 30.2, 29.7, 24.9, 23.0, 22.9, 20.8, 19.9, 19.5, 13.5, 3.8, 2.4 ppm; HRMS calcd for C$_{26}$H$_{41}$N$_4$O$_6$S [M+H$^+$] 537.2747. found 537.2746.

62

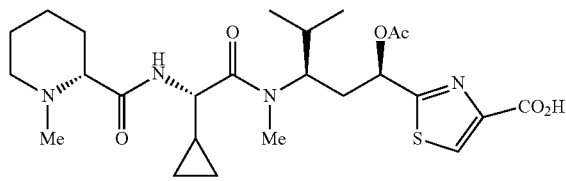

2-((1R,3R)-1-Acetoxy-3-((S)-2-cyclopropyl-N-methyl-2-((R)-1-methylpiperidine-2-carboxamido)-acetamido)-4-methylpentyl)thiazole-4-carboxylic Acid (62)

To a stirred solution of methyl ester 61 (105 mg, 0.2 mmol) in 1,2-dichloroethane (2.0 mL) was added Me$_3$SnOH (0.35 g, 2.0 mmol) at 25° C. The reaction mixture was refluxed for 12 h and the solvent was removed under reduced pressure. The obtained hydroxyl acid (quantitative) was used in the following step without further purification.

To an ice-cooled stirred solution of the above obtained hydroxyl acid (0.2 mmol) in pyridine (2.0 mL) was added dropwise Ac$_2$O (0.07 mL, 0.78 mmol). The reaction mixture was stirred at 25° C. for 12 h and then the solvent was removed under reduced pressure. The crude reaction mixture was purified by flash column chromatography (silica gel, 10% MeOH/2% NH$_4$OH/CH$_2$Cl$_2$→16% MeOH/4% NH$_4$OH/CH$_2$Cl$_2$) to furnish the corresponding acid 62 (74 mg, 75% for the two steps) as yellowish viscous oil. 62: R$_f$=0.35 (silica gel, 16% MeOH/4% NH$_4$OH/CH$_2$Cl$_2$); $^1$H NMR: (CDCl$_3$, 600 MHz) δ=8.01 (bs, 1H), 5.76 (d, J=11.2 Hz, 1H), 5.26 (d, J=4.7 Hz, 1H), 4.24 (bs, 1H), 3.31-2.72 (m, 6H), 2.71-2.18 (m, 5H), 2.10 (s, 3H), 1.95-1.79 (m, 1H), 1.79-1.51 (m, 4H), 1.45-1.06 (m, 2H), 0.97-0.65 (m, 7H), 0.64-0.16 (m, 4H) ppm; $^{13}$C NMR: (CDCl$_3$, 150 MHz) δ=172.6, 171.0, 170.0, 169.9, 165.9, 151.9, 125.2, 69.7, 68.6, 54.7, 53.4, 53.1, 42.8, 34.7, 29.8, 29.6, 28.7, 23.9, 22.1, 20.9, 20.0, 19.7, 13.3, 3.9, 2.7 ppm. HRMS calcd for C$_{25}$H$_{39}$N$_4$O$_6$S [M+H$^+$] 523.2590. found 523.2589.

Tb31

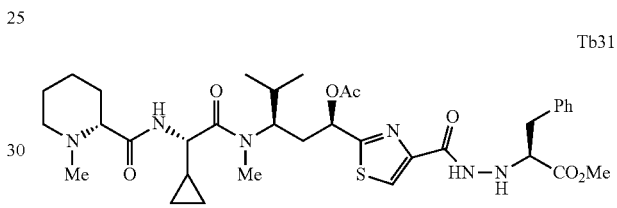

Methyl(2-((1R,3R)-1-acetoxy-3-((S)-2-cyclopropyl-N-methyl-2-((R)-1-methylpiperidine-2-carboxamido)acetamido)-4-methylpentyl)thiazole-4-carboxamido)-L-phenylalaninate (Tb31)

To an ice-cooled stirred solution of the above synthesized acid 62 (70 mg, 0.13 mmol) in CH$_2$Cl$_2$ (1.3 mL) was added DIC (25 mg, 0.16 mmol) followed by pentafluorophenol (37 mg, 0.20 mmol) and the reaction mixture was stirred at 25° C. for 24 h. Filtration through a sintered funnel gave a clear solution, which was concentrated and used in the next step without further purification.

A solution of the pentafluorophenyl ester (0.045 mmol) in DMF (0.2 mL) was added to a stirred solution of hydrazinophenyl alanine[11] (63, 10 mg, 0.05 mmol) and N,N-diisopropylethylamine (0.024 mL, 0.13 mmol) in DMF (0.3 mL) at 25° C. under Ar. The resulting reaction mixture was stirred at 25° C. for 20 h and then concentrated to dryness under reduced pressure. The obtained residue was purified by preparative plate chromatography (silica gel, 10% MeOH/1% NH$_4$OH/CH$_2$Cl$_2$) to furnish Tb31 (22 mg, 73% yield for the two steps) as a white amorphous solid. Tb31: R$_f$=0.61 (silica gel, 10% MeOH/1% NH$_4$OH/CH$_2$Cl$_2$); [α]$_D^{22}$=+122° (c=0.5, CHCl$_3$); FT-IR (neat) ν$_{max}$: 2922, 2852, 1740, 1644, 1496, 1456, 1371, 1219, 1146, 752, 701 cm$^{-1}$; $^1$H NMR: (CDCl$_3$, 600 MHz) δ=8.60 (d, J=5.7 Hz, 1H), 7.95 (s, 1H), 7.33-7.05 (m, 7H), 5.64 (dd, J=11.6, 2.6 Hz, 1H), 4.84 (bs, 1H), 4.50-4.43 (m, 1H), 4.34 (t, J=8.6 Hz, 1H), 4.01-3.96 (m, 1H), 3.67 (s, 3H), 3.12 (dd, J=14.0, 5.4 Hz, 1H), 2.99-2.94 (m, 1H), 2.93 (s, 3H), 2.44-2.36 (m, 2H), 2.25 (ddd, J=15.0, 11.7, 3.5 Hz, 1H), 2.17 (s, 3H), 2.09 (s, 3H), 2.04-1.92 (m, 1H), 1.80-1.42 (m, 5H), 1.38-1.27 (m, 1H), 1.21-1.08 (m, 2H), 0.94 (d, J=6.6 Hz, 3H), 0.74 (d, J=6.7 Hz, 3H), 0.63-0.56 (m, 1H), 0.51-0.44 (m, 1H), 0.41-0.28 (m, 2H) ppm; $^{13}$C NMR: (CDCl$_3$, 150 MHz) δ=171.6, 170.5, 170.3, 168.2, 167.6, 157.7, 145.7, 133.7, 126.7, 126.2, 124.7, 121.4, 67.3, 66.8, 61.6, 53.0, 52.7, 49.7, 42.2, 34.8, 32.2, 32.1, 28.1, 27.2, 26.8, 22.7, 20.8, 18.4, 17.4, 17.0, 11.4, 1.4, 0.0 ppm; HRMS calcd for C$_{35}$H$_{51}$N$_6$O$_7$S [M+H$^+$] 699.3540. found 699.3542.

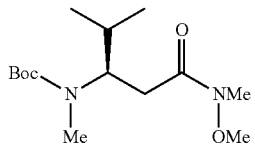

64 tert-Butyl (R)-(1-(methoxy(methyl)amino)-4-methyl-1-oxopentan-3-yl)(methyl)carbamate (64)

To a stirred solution of aldehyde 1 (Sohtome, et al., 2010: In, et al., 2007) (1.0 g, 4.36 mmol) in MeOH (20 mL) at 25° C. was added NaCN (438 mg, 8.94 mmol) and stirring was continued for 15 min. The reaction mixture was then cooled to 0° C. and MnO2 (6.5 g, 75.22 mmol) was added portion wise and the stirring was continue for 24 h while allowing the temperature to slowly rise to 25° C. The reaction mixture was filtered through a pad of celite and washed with MeOH. The solvent was removed under reduced pressure and the obtained residue was purified by flash column chromatography (silica gel, 5→15% EtOAc in hexanes) to afford ester 64a (0.92 g, 82%) as a white amorphous solid; R$_f$=0.5 (silica gel, 10% EtOAc in hexanes); 64a: [α]$_D^{22}$=+12.5 (c=0.5, CHCl$_3$); FT-IR (neat) $\tilde{v}_{max}$: 2967, 1741, 1689, 1436, 1388, 1365, 1251, 1141, 953, 722 cm$^{-1}$; $^1$H NMR: (CDCl$_3$, 600 MHz) δ5=3.91 (s, 1H), 3.63 (d, J=8.3 Hz, 3H), 2.71 (d, J=21.6 Hz, 3H), 2.58 (ddd, J=20.9, 14.4, 4.4 Hz, 1H), 2.53-2.40 (m, 1H), 1.78 (q, J=8.8, 6.7 Hz, 1H), 1.43 (d, J=11.9 Hz, 9H), 0.92 (t, J=5.6 Hz, 3H), 0.86 (d, J=6.7 Hz, 3H): $^{13}$C NMR: (CDCl$_3$, 150 MHz) δ=172.3, 155.8, 79.5, 59.3, 51.6, 36.3, 30.9, 28.5, 28.4, 20.3, 19.6; Diagnostic signals of minor rotamer: $^{13}$C NMR: (CDCl$_3$, 150 MHz) δ=172.1, 155.7, 79.1, 60.3, 51.6, 36.0, 30.5, 28.5, 28.4, 20.1, 19.5; HRMS calcd for C$_{13}$H$_{25}$NO$_4$ [M+Na$^+$] 282.1681. found 282.1667.

To a stirred solution of 64a (1.0 g, 3.85 mmol) in THF (30 mL) at 25° C. was added N,O-dimethyl hydroxylamine hydrochloride (790 mg, 8.09 mmol) and stirred for 15 min. The reaction mixture was then cooled to −20° C. and i-PrMgCl (2 M sol in diethyl ether, 7.7 mL, 15.4 mmol) was added dropwise and the stirring was continue for 3 h while allowing the temperature to slowly rise to 0° C. The reaction was quenched with a saturated aqueous solution of NH$_4$Cl (20 mL). The two phases were separated, the aqueous layer was extracted with EtOAc (3×20 mL), and the combined organic extracts were dried over Na$_2$SO$_4$ and evaporated under reduced pressure. The obtained residue was purified by flash column chromatography (silica gel, 20→80% EtOAc in hexanes) to afford pure Weinreb amide 64 (0.95 g, 86%) as a yellowish oil. 64: R$_f$=0.3 (silica gel, 20% EtOAc in hexanes). [α]$_D^{22}$=−12.5 (c=0.5, CHCl$_3$); FT-IR (neat) $\tilde{v}_{max}$: 2967, 1685, 1444, 1386, 1364, 1149, 1002, 951, 873, 772 cm$^{-1}$; 64: $^1$H NMR: (CDCl$_3$, 600 MHz) δ=3.91 (s, 1H), 3.65 (d, J=11.6 Hz, 3H), 3.10 (d, J=13.9 Hz, 3H), 2.72 (d, J=9.9 Hz, 3H), 2.67 (d, J=18.8 Hz, 1H), 2.62-2.50 (m, 1H), 1.84 (s, 1H), 1.39 (d, J=18.4 Hz, 9H), 0.90 (t, J=6.3 Hz, 3H), 0.83 (dd, J=6.7, 1.9 Hz, 3H); $^{13}$C NMR: (CDCl$_3$, 150 MHz) δ=172.9, 155.8, 79.2, 61.1, 59.8, 34.0, 32.2, 31.0, 28.4, 28.3, 20.2, 19.6 ppm; Diagnostic signals of minor rotamer: $^{13}$C NMR: (CDCl$_3$, 150 MHz) δ=172.3, 155.7, 78.8, 61.1, 33.7, 31.5, 30.3, 28.3, 28.3, 20.1, 19.5 ppm; HRMS calcd for C$_{14}$H$_{28}$N$_2$O$_4$ [M+Na$^+$] 311.1947. found 311.1929.

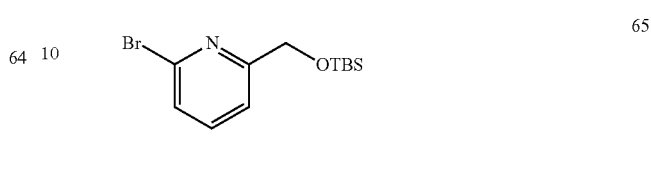

65

2-Bromo-6-(((tert-butyldimethylsilyl)oxy)methyl) pyridine (65)

To a stirred solution of (6-bromopyridin-2-yl)methanol (2.0 g, 10.63 mmol) in CH$_2$Cl$_2$ (20 mL) at 0° C. was added imidazole (0.890 g, 13.08 mmol), followed by TBSCl (2.0 g, 13.08 mmol). The reaction mixture was allowed to warm to 25° C. and stirred for an additional 30 min. The reaction mixture was diluted with H$_2$O (20 mL) and the resulting solution was extracted with CH$_2$Cl$_2$ (3×20 mL). The combined organic extracts were washed with brine (10 mL), dried over Na$_2$SO$_4$ and evaporated under reduced pressure. The obtained residue was purified by flash column chromatography (silica gel, 5→20% EtOAc in hexanes) to afford pure compound 65 (3.2 g, 99%) as a colorless oil. 65: R$_f$=0.5 (silica gel, 10% EtOAc in hexanes); FT-IR (neat) $\tilde{v}_{max}$: 2954, 2929, 2857, 1585, 1559, 1410, 1256, 1151, 1126, 845, 780, 676; $^1$H NMR: (CDCl$_3$, 600 MHz) δ=7.56 (t, J=7.7 Hz, 1H), 7.47 (dd, J=7.7, 1.1 Hz, 1H), 7.34 (d, J=7.8 Hz, 1H), 4.80 (s, 2H), 0.95 (s, 9H), 0.11 (s, 6H); $^{13}$C NMR: (CDCl$_3$, 150 MHz) δ=163.2, 140.9, 139.0, 126.0, 118.6, 65.4, 25.9, 18.3, −5.4: HRMS calcd for C$_{12}$H$_{20}$BrNOSi [M+H$^+$] 302.0576. found 302.0562.

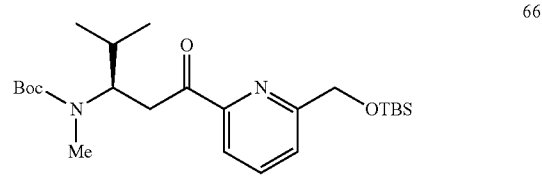 [SMILES: CC(C)[C@@H](CC(=O)c1cccc(CO[Si](C)(C)C(C)(C)C)n1)N(C)C(=O)OC(C)(C)C]

66 tert-Butyl(R)-(1-(6-(((tert-butyldimethylsilyl)oxy) methyl)pyridin-2-yl)-4-methyl-1-oxopentan-3-yl) (methyl)carbamate (66)

To a stirred solution of bromo-pyridine 65 (500 mg, 1.66 mmol) in THF (5.0 mL) at −78° C. was carefully added n-BuLi (2.6 M in hexane, 0.8 mL, 2.0 mmol). After stirring for 30 min at the same temperature, a solution of Weinreb amide 64 (400 mg, 1.386 mmol) in THF (2.0 mL) was added. The reaction mixture was allowed to slowly warm to −50° C., stirred for an additional 2 h and quenched with a saturated aqueous solution of NH$_4$Cl (10 mL). The two phases were separated, the aqueous layer was extracted with EtOAc (3×20 mL), and the combined organic extracts were dried over Na$_2$SO$_4$ and evaporated under reduced pressure. The obtained residue was purified by flash column chromatography (silica gel, 10→30% EtOAc in hexanes) to afford pure ketone 66 (538 mg, 72%) as a colorless oil. 66: R$_f$=0.4

(silica gel, 20% EtOAc in hexanes); [α]$_D^{22}$=+4.7 (c=1.0, CHCl$_3$); FT-IR (neat) $\tilde{v}_{max}$: 3335, 2957, 2929, 1696, 1365, 1255, 1117, 1074, 838, 778 cm$^{-1}$; $^1$H NMR: (CDCl$_3$, 600 MHz) δ=7.80 (ddt, J=21.8, 15.4, 7.7 Hz, 2H), 7.65 (dt, J=18.1, 8.6 Hz, 1H), 4.90-4.77 (m, 2H), 4.32-4.13 (m, 1H), 3.50 (dd, J=14.1, 4.0 Hz, 1H), 3.27-2.93 (m, 1H), 2.70 (d, J=5.1 Hz, 3H), 1.84 (s, 1H), 1.26 (d, J=73.2 Hz, 9H), 1.02 (d, J=6.6 Hz, 3H), 0.95 (d, J=7.5 Hz, 9H), 0.86 (d, J=6.6 Hz, 3H), 0.39-0.29 (m, 1H), 0.19-0.05 (m, 6H); $^{13}$C NMR (CDCl$_3$, 150 MHz) δ=200.3, 160.7, 155.8, 152.1, 137.4, 123.5, 120.0, 79.0, 65.9, 59.9, 39.1, 31.3, 28.1, 25.8, 20.3, 19.6, 18.3, −5.4; Diagnostic signals of minor rotamer: $^{13}$C NMR: (CDCl$_3$, 150 MHz) δ=200.7, 161.3, 157.4, 152.3, 148.5, 136.6, 123.3, 121.7, 78.7, 65.9, 59.1, 38.6, 31.0, 28.3, 26.5, 20.2, 19.5, −6.3; HRMS calcd for C$_{24}$H$_{12}$N$_2$O$_4$Si [M+H$^+$] 473.2812. found 473.2790.

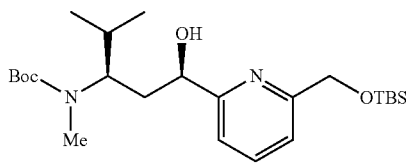

tert-Butyl((1 R,3R)-1-(6-(((tert-butyldimethylsilyl)oxy)methyl)pyridin-2-yl)-1-hydroxy-4-methylpentan-3-yl)(methyl)carbamate (67)

To an ice-cooled stirred solution of (S)—CBS catalyst (1.0 M in toluene, 0.016 mL, 0.016 mmol) in THF (2 mL) was added BH$_3$.SMe$_2$ (2.0 M in THF, 0.08 mL, 0.167 mmol) and stirring was continued for 10 min at 0° C. Then, a solution of ketone 66 (75 mg, 0.167 mmol) in THF (0.5 mL) was added dropwise to the reaction mixture and stirring was continued for 24 h while the temperature gradually increased to 25° C. The reaction was quenched with MeOH (2 mL) and the solvent was removed under reduced pressure. The resulting residue was purified using column chromatography (silica gel, 10→50% EtOAc in hexanes) to furnish alcohol 67 (63 g, 84% yield) as a colorless oil. 67: R$_f$=0.3 (silica gel, 20% EtOAc in hexanes); [α]$_D^{22}$=−2.8. (c=1.0, CHCl$_3$); FT-IR (neat) $\tilde{v}_{max}$: 3425, 2957, 2927, 2855, 1690, 1663, 1461, 1365, 1254, 1153, 1113, 837, 776, 670 cm$^{-1}$; $^1$H NMR: (CDCl$_3$, 600 MHz) δ=7.67 (t, J=7.7 Hz, 1H), 7.39-7.31 (m, 2H), 4.88-4.71 (m, 2H), 4.50 (dd, J=20.9, 3.3 Hz, 1H), 3.91 (brs, 1H), 2.75 (s, 3H), 1.92 (s, 1H), 1.68-1.62 (m, 2H), 1.48 (d, J=14.5 Hz, 9H), 0.95 (d, J=1.4 Hz, 9H), 0.90 (dd, J=12.7, 6.5 Hz, 6H), 0.11 (d, J=2.6 Hz, 6H); $^{13}$C NMR: (CDCl$_3$, 150 MHz) δ=162.1, 160.0, 157.8, 137.1, 118.5, 117.9, 80.0, 71.0, 66.1, 66.0, 58.5, 38.5, 30.0, 28.4, 25.9, 20.1, 18.3, −5.3; HRMS calcd for C$_{24}$H$_{44}$N$_2$O$_4$Si [M+Na$^+$] 475.2968. found 475.2952.

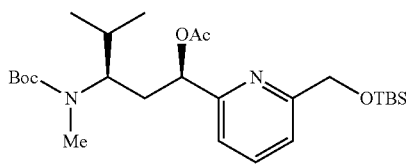

(1R,3R)-3-((tert-Butoxycarbonyl)(methyl)amino)-1-(6-(((tert-butyldimethylsilyl)oxy)methyl)pyridin-2-yl)-4-methylpentyl acetate (68a)

To a stirred solution of alcohol 67 (150 mg, 0.332 mmol) in CH$_2$Cl$_2$ (5 mL) at 0° C. was added Et$_3$N (0.18 mL, 1.33 mmol), followed by acetic anhydride (0.09 mL, 0.99 mmol) and DMAP (4.0 mg, 0.03 mmol). The reaction mixture was allowed to warm to 25° C. and stirred for an additional 2 h. The reaction mixture was diluted with H$_2$O (5 mL) and the resulting solution was extracted with CH$_2$Cl$_2$ (3×10 mL). The combined organic extracts were washed with brine (5 mL), dried over Na$_2$SO$_4$ and evaporated under reduced pressure. The obtained residue was purified by flash column chromatography (silica gel, 10→30% EtOAc in hexanes) to furnish acetate 68a (154 mg, 94% yield) as a colorless oil. 68a: R$_f$=0.5 (silica gel, 20% EtOAc in hexanes); [α]$_D^{22}$=+4.6 (c=1.0, CHCl$_3$); FT-IR (neat) $\tilde{v}_{max}$: 3319, 2959, 2891, 1722, 1662, 1441, 1367, 1190, 1121, 1059, 1035, 923, 840 cm$^{-1}$; $^1$H NMR: (CDCl$_3$, 600 MHz) δ=7.64 (td, J=7.8, 3.7 Hz, 1H), 7.38 (t, J=7.2 Hz, 1H), 7.10 (dd, J=19.6, 7.7 Hz, 1H), 5.54 (dd, J=11.2, 2.9 Hz, 1H), 4.93-4.65 (m, 2H), 4.07 (s, 1H), 2.67 (s, 3H), 2.25-2.15 (m, 1H), 2.11 (d, J=1.5 Hz, 3H), 1.93-1.79 (m, 1H), 1.62 (s, 1H), 1.43 (d, J=1.5 Hz, 9H), 0.94 (s, 12H), 0.84 (d, J=6.5 Hz, 3H), 0.10 (s, 6H); $^{13}$C NMR: (CDCl$_3$, 150 MHz) δ=170.4, 161.0, 158.8, 156.2, 137.1, 118.9, 118.6, 79.0, 73.2, 66.1, 56.8, 34.9, 30.5, 28.4, 28.4, 25.9, 21.1, 20.0, 19.6, 18.3, −5.4; HRMS calcd for C$_{26}$H$_{46}$N$_2$OSi [M+Na$^+$] 517.3074. found 517.3053.

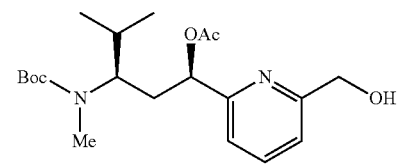

(1R,3R)-3-((tert-Butoxycarbonyl)(methyl)amino)-1-(6-(hydroxymethyl)pyridin-2-yl)-4-methylpentyl acetate (68b)

To a stirred solution of compound 68a (150 mg, 0.30 mmol) in THF (4 mL) at 0° C. was added TBAF (1M in THF, 0.6 mL, 0.6 mmol). The reaction mixture was allowed to warm to 25° C. and stirred for an additional 30 min. The reaction mixture was diluted with H$_2$O (10 mL) and the resulting solution was extracted with EtOAc (3×10 mL). The combined organic extracts were washed with brine (5 mL), dried over Na$_2$SO$_4$ and evaporated under reduced pressure. The obtained residue was purified by flash column chromatography (silica gel, 30→80% EtOAc in hexanes) to afford pure alcohol 68b (110 mg, 96%) as a colorless oil. 68b: R$_f$=0.2 (silica gel, 40% EtOAc in hexanes); [α]$_D^{22}$=+9.6 (c=1.0, CHCl$_3$); FT-IR (neat) $\tilde{v}_{max}$: 3437, 2965, 2922, 1743, 1671, 1578, 1456, 1367, 1228, 1152, 1131, 1044, 752 cm$^{-1}$; $^1$H NMR: (CDCl$_3$, 600 MHz) δ=7.64 (td, J=7.7, 2.2 Hz, 1H), 7.14 (ddd, J=31.2, 13.0, 7.7 Hz, 2H), 5.62 (ddd, J=40.2, 10.5, 3.0 Hz, 1H), 4.72 (s, 2H), 4.24-3.73 (m, 2H), 2.69 (s, 3H), 2.18 (dtd, J=14.9, 7.6, 4.5 Hz, 1H), 2.13 (d, J=4.0 Hz, 3H), 1.93 (ddd, J=14.9, 12.0, 2.9 Hz, 1H), 1.65 (ddd, J=13.2, 10.1, 6.7 Hz, 1H), 1.44 (d, J=2.0 Hz, 9H), 0.94 (dd, J=6.6, 2.2 Hz, 3H), 0.85 (dd, J=6.8, 4.7 Hz, 3H); $^{13}$C NMR: (CDCl$_3$, 150 MHz) δ=170.4, 159.0, 158.3, 156.2, 137.4, 119.4, 118.7, 79.1, 73.0, 63.6, 57.8, 34.9, 30.4, 28.4, 28.4, 21.0, 19.9, 19.6; HRMS calcd for $C_{20}H_{32}N_2O_5$ [M+Na$^+$] 403.2209. found 403.2193.

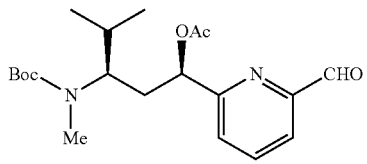

(1R,3R)-3-((tert-Butoxycarbonyl)(methyl)amino)-1-(6-formylpyridin-2-yl)-4-methylpentyl acetate (68c)

To a stirred solution of alcohol 68b (120 mg, 0.315 mmol) in CH$_2$Cl$_2$ (4 mL) at 25° C. was added DMP (201 mg, 0.47 mmol) and stirring continue for 1 h. The reaction mixture was diluted with H$_2$O (10 mL) and the resulting solution was extracted with CH$_2$Cl$_2$ (3×10 mL). The combined organic extracts were washed with saturated aqueous solution of NaHCO$_3$:Na$_2$S$_2$O$_3$ (1:1, 5 mL), dried over Na$_2$SO$_4$ and evaporated under reduced pressure. The obtained residue was purified by flash column chromatography (silica gel, 10→40% EtOAc in hexanes) to afford pure alcohol 68c (106 mg, 89%) as a colorless oil. 68c: $R_f$=0.5 (silica gel, 30% EtOAc in hexanes); $[\alpha]_D^{22}$=+2.4 (c=1.0, CHCl$_3$); FT-IR (neat) $\tilde{v}_{max}$: 2968, 2925, 1744, 1714, 1686, 1590, 1456, 1366, 1226, 1151, 1131, 1046, 754 cm$^{-1}$; $^1$H NMR: (CDCl$_3$, 600 MHz) δ=10.04 (s, 1H), 7.97-7.72 (m, 2H), 7.49 (ddd, J=21.7, 6.3, 2.6 Hz, 1H), 5.69 (ddd, J=36.7, 10.6, 2.9 Hz, 1H), 3.97 (d, J=130.6 Hz, 1H), 2.71 (s, 3H), 2.28-2.19 (m, 1H), 2.15 (d, J=1.6 Hz, 3H), 1.99 (ddd, J=15.0, 11.9, 3.1 Hz, 1H), 1.68 (td, J=6.6, 3.7 Hz, 1H), 1.43 (d, J=3.2 Hz, 9H), 0.95 (dd, J=6.6, 1.9 Hz, 3H), 0.86 (dd, J=6.7, 2.1 Hz, 3H); $^{13}$C NMR: (CDCl$_3$, 150 MHz) δ=193.5, 170.5, 160.9, 156.2, 152.3, 137.7, 124.7, 120.2, 79.2, 73.0, 56.8, 34.8, 30.4, 28.4, 28.3, 21.0, 20.0, 19.6; HRMS calcd for $C_{20}H_{30}N_2O_5$ [M+Na$^+$] 401.2052. found 401.2051.

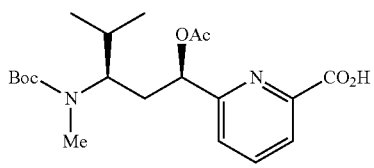

6-((1R,3R)-1-Acetoxy-3-((tert-butoxycarbonyl)(methyl)amino)-4-methylpentyl)picolinic Acid (68)

To a stirred solution of aldehyde 68c (100 mg, 0.264 mmol) in t-BuOH (4 mL) at 25° C. were consecutively added a solution of 2-methyl-2-butene (0.2 mL, 1.98 mmol) in THF (1.0 mL), followed by a solution of NaClO$_2$ (129 mg, 1.42 mmol) and NaH$_2$PO$_4$·H$_2$O (505 mg, 3.24 mmol) in H$_2$O (1.5 mL) and stirring was continued for 1 h at 25° C. The reaction mixture was then diluted with aqueous HCl (1N, 1 mL) and the resulting solution was extracted with ethyl acetate (3×10 mL). The combined organic layers were dried over Na$_2$SO$_4$ and evaporated under reduced pressure. The obtained residue was purified by flash column chromatography (silica gel, 3→18% MeOH in CH$_2$Cl$_2$) to afford pure acid 68 (99 mg, 95%) as a colorless oil. 68: $R_f$=0.3 (silica gel, 10% MeOH in CH$_2$Cl$_2$); $[\alpha]_D^{22}$=+3.4 (c=1.0, CHCl$_3$); FT-IR (neat) $\tilde{v}_{max}$: 2966, 2928, 1742, 1671, 1387, 1367, 1227, 1148, 1046, 750, 666 cm$^{-1}$; $^1$H NMR: (CDCl$_3$, 600 MHz) δ=8.11 (t, J=6.8 Hz, 1H), 7.92 (td, J=7.7, 3.6 Hz, 1H), 7.56 (dd, J=15.8, 7.8 Hz, 1H), 5.66 (ddd, J=33.8, 10.3, 3.1 Hz, 1H), 3.96 (d, J=110.9 Hz, 1H), 2.69 (s, 3H), 2.26-2.15 (m, 1H), 2.14 (s, 3H), 1.93 (ddd, J=14.9, 11.7, 3.2 Hz, 1H), 1.57, (s, 1H), 1.44 (d, J=5.6 Hz, 9H), 0.94 (t, J=7.5 Hz, 3H), 0.85 (d, J=6.6 Hz, 3H); $^{13}$C NMR: (CDCl$_3$, 150 MHz) δ=170.4, 163.9, 159.5, 156.2, 145.7, 139.2, 124.8, 122.7, 79.4, 72.5, 56.9, 34.8, 31.1, 30.4, 28.3, 20.9, 19.9, 19.5. HRMS calcd for $C_{20}H_{30}N_2O_6$ [M+H$^+$] 417.2002. found 417.1984.

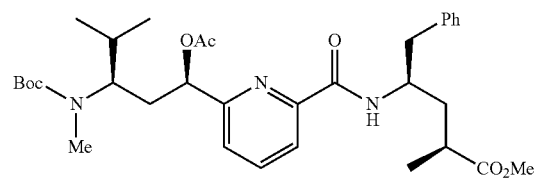

Methyl (2S,4R)-4-(6-((1R,3R)-1-acetoxy-3-((tert-butoxycarbonyl)(methyl)amino)-4-methylpentyl)picolinamido)-2-methyl-5-phenylpentanoate (69)

To a stirred solution of 68 (30 mg, 0.076 mmol) in dry DMF (1.0 mL) at 0° C. were added HATU (87 mg, 0.22 mmol) followed by Et$_3$N (0.06 mL, 1.488 mmol) and the resulting mixture was stirred for 5 min at the same temperature. A solution of 6 (25 mg, 0.114 mmol) in dry DMF (0.2 mL) was then added and the stirring was continue for 24 h while allowing the temperature to slowly rise to 25° C. The reaction mixture was diluted with H$_2$O (2 mL) and the resulting solution was extracted with EtOAc (3×10 mL). The combined organic extracts were washed with brine (5 mL), dried over Na$_2$SO$_4$ and evaporated under reduced pressure. The obtained residue was purified by flash column chromatography (silica gel, 30→90% EtOAc in hexanes) to afford pure dipeptide 69 (43 mg, 94%) as a colorless oil. 69: $R_f$=0.4 (silica gel, 40% EtOAc in hexanes); $[\alpha]_D^{22}$=+12.2 (c=1.0, CHCl$_3$); FT-IR (neat) $\tilde{v}_{max}$: 3377, 2969, 2929, 1738, 1683, 1517, 1453, 1367, 1228, 1157, 1048, 766, 701 cm$^{-1}$; $^1$H NMR: (CDCl$_3$, 600 MHz) δ=8.05 (ddd, J=8.8, 7.7, 1.1 Hz, 1H), 7.80 (td, J=7.8, 4.0 Hz, 2H), 7.39 (ddd, J=16.6, 7.8, 1.1 Hz, 1H), 7.30-7.11 (m, 5H), 5.62 (ddd, J=47.1, 10.6, 2.7 Hz, 1H), 4.43 (qdd, J=10.2, 6.7, 3.7 Hz, 1H), 4.19-3.97 (m, 1H), 3.62 (d, J=9.6 Hz, 3H), 2.98-2.86 (m, 2H), 2.66 (s, 3H), 2.61 (dtt, J=11.5, 8.5, 5.8 Hz, 1H), 2.15 (d, J=1.6 Hz, 3H), 2.13-2.01 (m, 2H), 1.86 (ddd, J=14.9, 11.8, 2.8 Hz, 1H), 1.68 (s, 1H), 1.68-1.59 (m, 1H), 1.45 (s, 9H), 1.18 (dd, J=7.1, 1.8 Hz, 3H), 0.95 (dd, J=6.6, 4.2 Hz, 3H), 0.88 (t, J=7.0 Hz, 3H); $^{13}$C NMR: (CDCl$_3$, 150 MHz) δ=176.6, 170.4, 163.5, 158.9, 156.2, 149.2, 138.2, 137.5, 129.5, 128.3, 126.5, 122.5, 121.1, 79.2, 72.8, 56.7, 51.8, 48.3, 41.0, 37.9, 36.4, 35.1, 30.5, 28.4, 21.0, 20.2, 19.9, 19.6, 17.6; HRMS calcd for $C_{33}H_{47}N_3O_7$ [M+Na$^+$] 620.3312. found 620.3292.

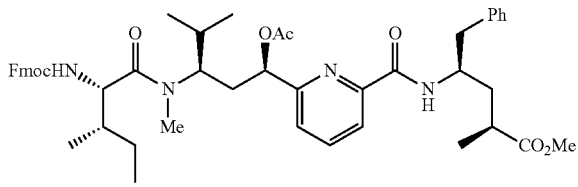

Methyl (2S,4R)-4-(6-((5S,8R,10R)-5-((S)-sec-butyl)-1-(9H-fluoren-9-yl)-8-isopropyl-7-methyl-3,6,12-trioxo-2,11-dioxa-4,7-diazatridecan-10-yl)picolinamido)-2-methyl-5-phenylpentanoate (70)

To an ice-cooled stirred solution of 69 (30 mg, 0.047 mmol) in CH$_2$Cl$_2$ (1.0 mL) was added trifluoroacetic acid (0.16 mL, 2.142 mmol) and the reaction mixture was stirred for 2 h while warming up to 25° C. Evaporation of the volatile components under reduced pressure furnished the crude TFA-ammonium salt (30 mg, quantitative), which was used for the following step without further purification.

To a stirred, ice-cooled solution of crude ammonium salt from the previous step and i-Pr$_2$NEt (0.06 mL, 0.33 mmol) in DMF (1.0 mL) was added dropwise a solution of Fmoc-Ile-F$^8$ (8, 80 mg, 0.22 mmol) in DMF (0.3 mL) and stirring was continued for 18 h at 25° C. The reaction mixture was diluted with ethyl acetate (10 mL), washed with saturated aqueous NaHCO$_3$ solution (10 mL) and brine (10 mL), dried over Na$_2$SO$_4$ and concentrated under reduced pressure. The obtained residue was purified by flash column chromatography (silica gel, 10→50% EtOAc in hexanes) to afford pure tripeptide 70 (40 mg, 96%) as a colorless oil. 70: R$_f$=0.5 (silica gel, 50% EtOAc in hexanes); [α]$_D^{22}$=+3.8 (c=1.0, CHCl$_3$); FT-IR (neat) v$_{max}$: 3291, 2964, 1724, 1678, 1645, 1520, 1452, 1230, 1033, 741 cm$^{-1}$; $^1$H NMR: (CDCl$_3$, 600 MHz) δ=8.06 (d, J=7.7 Hz, 1H), 7.87-7.71 (m, 4H), 7.58 (dd, J=7.6, 4.3 Hz, 2H), 7.44-7.14 (m, 11H), 5.52-5.31 (m, 2H), 4.55 (dd, J=9.7, 6.8 Hz, 2H), 4.50-4.29 (m, 3H), 4.21 (t, J=7.3 Hz, 1H), 3.59 (s, 3H), 2.96 (dd, J=13.8, 6.3 Hz, 1H), 2.93 (s, 3H), 2.70-2.56 (m, 1H), 2.17 (s, 3H), 2.12-2.00 (m, 2H), 1.91-1.57 (m, 6H), 1.18 (d, J=7.1 Hz, 3H), 1.04-0.96 (m, 6H), 0.92 (t, J=7.4 Hz, 4H), 0.82 (d, J=6.6 Hz, 3H); $^{13}$C NMR: (CDCl$_3$, 150 MHz) δ=176.5, 173.5, 170.2, 163.4, 158.7, 156.4, 149.3, 143.9, 141.3, 138.3, 137.5, 129.6, 128.3, 127.7, 127.0, 126.5, 125.1, 122.2, 121.2, 119.9, 73.1, 67.0, 55.8, 51.8, 48.1, 47.2, 40.8, 37.7, 37.4, 37.3, 36.4, 34.8, 30.0, 29.4, 23.9, 20.9, 20.0, 19.6, 17.5, 16.0, 11.2. HRMS calcd for C$_{19}$H$_{60}$N$_4$O$_8$ [M+Na$^+$] 855.4309. found 855.4280.

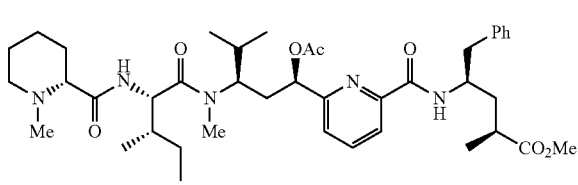

Methyl (2S,4R)-4-(6-((1R,3R)-1-acetoxy-3-((2S,3S)—N,3-dimethyl-2-((R)-1-methylpiperidine-2-carboxamido)pentanamido)-4-methylpentyl)picolinamido)-2-methyl-5-phenylpentanoate (Tb38)

To an ice-cooled stirred solution of Fmoc-derivative 70 (40 mg, 0.048 mmol) in CH$_2$Cl$_2$ (2 mL) was added tris(2-aminoethyl)amine (0.11 mL, 0.769 mmol). The reaction mixture was stirred for 2 h at 25° C. and then diluted with ethyl acetate (10 mL). The solution was washed with saturated aqueous NaHCO$_3$ solution (5 mL), and brine (5 mL), dried over Na$_2$SO$_4$, and concentrated. The crude amine so obtained (30 mg, quantitative) was used for the next step without further purification.

To an ice-cooled stirred solution of N-methyl-(D)-pipecolinic acid 10 (21 mg, 0.147 mmol) in DMF (1.5 ml) at 0° C. was added HATU (56 mg, 0.147 mmol) followed by the above obtained crude amine (30 mg, 0.049 mmol), and Et$_3$N (0.04 mL, 0.295 mmol) and the reaction mixture was stirred at 25° C. for 24 h. The reaction mixture was diluted with H$_2$O (5 mL) and the resulting solution was extracted with EtOAc (3×10 mL). The combined organic extracts were washed with saturated aqueous NaHCO$_3$ solution (5 mL) and brine (5 mL), dried over Na$_2$SO$_4$ and evaporated under reduced pressure. The obtained residue was purified by flash column chromatography (silica gel, 3→18% MeOH in CH$_2$Cl$_2$) to afford analog Tb38 (23 mg, 66%) as a colorless oil. Tb38: R$_f$=0.5 (silica gel, 10% MeOH in CH$_2$Cl$_2$); [α]$_D^{22}$=+16.0 (c=1.0, CHCl$_3$); FT-IR (neat) v$_{max}$: 3377, 2959, 2926, 1738, 1674, 1641, 1516, 1453, 1371, 1229, 1052, 702 cm$^{-1}$; $^1$H NMR: (CDCl$_3$, 600 MHz) δ=8.06 (dd, J=7.7, 1.0 Hz, 1H), 7.81 (t, J=7.8 Hz, 1H), 7.74 (d, J=9.3 Hz, 1H), 7.39-7.32 (m, 1H), 7.26 (t, J=7.3 Hz, 2H), 7.22-7.14 (m, 3H), 7.05 (d, J=9.4 Hz, 1H), 5.39 (dd, J=11.5, 2.2 Hz, 1H), 4.79 (dd, J=9.6, 7.6 Hz, 1H), 4.56 (s, 1H), 4.44 (tdd, J=9.7, 6.8, 4.2 Hz, 1H), 3.59 (s, 3H), 2.95 (s, 3H), 2.94-2.85 (m, 3H), 2.62 (dqd, J=8.9, 7.1, 4.4 Hz, 1H), 2.53 (s, 1H), 2.23 (s, 3H), 2.16 (d, J=5.8 Hz, 4H), 2.09-1.97 (m, 2H), 1.89-1.74 (m, 4H), 1.73-1.46 (m, 7H), 1.44-1.30 (m, 1H), 1.17 (dd, J=7.0, 3.4 Hz, 3H), 0.98 (d, J=6.6 Hz, 6H), 0.90 (t, J=7.4 Hz, 3H), 0.79 (d, J=6.6 Hz, 3H); $^{13}$C NMR: (CDCl$_3$, 150 MHz) δ=176.5, 174.3, 173.4, 170.3, 163.4, 158.7, 149.2, 138.3, 137.4, 129.6, 128.3, 126.5, 122.1, 121.1, 73.2, 69.7, 55.4, 52.9, 51.8, 48.1, 44.9, 40.8, 37.8, 37.4, 37.1, 36.9, 36.4, 35.0, 30.4, 30.0, 29.3, 25.1, 24.5, 23.3, 21.0, 20.0, 19.6, 17.5, 16.0, 10.9; HRMS calcd for C$_{41}$H$_{62}$N$_5$O$_7$ [M+H$^+$] 736.4649. found 736.4666.

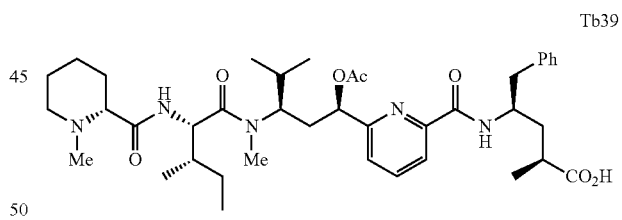

(2S,4R)-4-(6-((1R,3R)-1-acetoxy-3-((2S,3S)—N,3-dimethyl-2-((R)-1-methylpiperidine-2 carboxamido)pentanamido)-4-methylpentyl)picolinamido)-2-methyl-5-phenylpentanoic Acid (Tb39)

To a stirred solution of methyl ester Tb39 (20 mg, 0.027 mmol) in 1,2-dichloroethane (1 mL) was added Me$_3$SnOH (98 mg, 0.544 mmol) at 25° C. The reaction mixture was refluxed for 12 h and the solvent was removed under reduced pressure. The resulting hydroxyl acid (20 mg, quantitative) was used in the following step without further purification.

To an ice-cooled stirred solution of the above obtained hydroxyl acid (20 mg, 0.029 mmol) in pyridine (0.2 mL) was added dropwise Ac$_2$O (0.01 ml, 0.1 mmol). The reaction mixture was stirred at 25° C. for 12 h and then the solvent was removed under reduced pressure. The crude reaction mixture was purified by flash column chromatography (silica gel, 5→15% MeOH in CH$_2$Cl$_2$) to obtained Tb39 (13 mg, 68% yield) as a colorless oil. Tb39: R$_f$=0.32 (silica gel 10% MeOH in CH$_2$Cl$_2$); [α]$_D^{22}$=+20.4 (c=1.0, CHCl$_3$); FT-IR (neat) $\tilde{v}_{max}$: 3286, 2959, 2924, 2853, 1635, 1544, 1497, 1463, 1086, 751 cm$^{-1}$; $^1$H NMR: (CDCl$_3$, 600 MHz) δ=8.30 (s, 1H), 8.06 (dt, J=7.8, 1.7 Hz, 1H), 7.83 (t, J=7.8 Hz, 1H), 7.37 (dd, J=15.1, 7.8 Hz, 1H), 7.32-7.17 (m, 6H), 5.67-5.42 (m, 1H), 4.80 (dd, J=9.6, 8.3 Hz, 1H), 4.57-4.26 (m, 1H), 3.07 (d, J=4.6 Hz, 3H), 3.02 (d, J=6.7 Hz, 1H), 2.98-2.85 (m, 2H), 2.63 (s, 1H), 2.53 (d, J=10.8 Hz, 1H), 2.24 (d, J=13.5 Hz, 3H), 2.15 (d, J=8.0 Hz, 5H), 2.06-1.74 (m, 6H), 1.36 (q, J=12.9 Hz, 6H), 1.23-1.16 (m, 2H), 1.14 (d, J=7.0 Hz, 3H), 0.97 (dd, J=9.4, 6.6 Hz, 6H), 0.94-0.88 (m, 3H), 0.84 (dd, J=6.4, 3.6 Hz, 3H); $^{13}$C NMR: (CDCl$_3$, 150 MHz) δ=177.5, 173.7, 173.3, 170.6, 164.3, 158.8, 148.7, 138.4, 137.6, 129.3, 128.5, 126.6, 122.4, 121.4, 74.0, 69.9, 55.5, 53.2, 48.8, 44.5, 42.2, 41.1, 36.8, 36.1, 34.9, 34.6, 30.1, 30.0, 24.9, 24.6, 23.2, 21.0, 20.1, 20.0, 19.9, 16.7, 15.9, 10.9. HRMS calcd for C$_{40}$H$_{60}$N$_5$O$_7$ [M+H$^+$] 722.4493. found 722.4471.

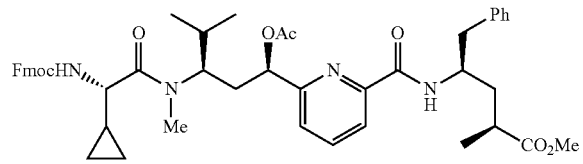

Methyl (2S,4R)-4-(6-((5S,8R,10R)-5-cyclopropyl-1-(9H-fluoren-9-yl)-8-isopropyl-7-methyl-3,6,12-tri-oxo-2,11-dioxa-4,7-diazatridecan-10-yl)picolina-mido)-2-methyl-5-phenylpentanoate (71)

To an ice-cooled stirred solution of 69 (15 mg, 0.023 mmol) in CH$_2$Cl$_2$ (0.5 mL) was added trifluoroacetic acid (0.08 mL, 1.071 mmol) and the reaction mixture was stirred for 2 h while warming up to 25° C. Evaporation of the volatile components under reduced pressure furnished the crude TFA-ammonium salt (15 mg, quantitative), which was used for the following step without further purification.

To a stirred, ice-cooled solution of crude ammonium salt from the previous step and i-Pr$_2$NEt (0.03 mL, 0.33 mmol) in DMF (0.7 mL) was added dropwise a solution of Fmoc-Ile-F (43, 38 mg, 0.11 mmol) in DMF (0.2 mL) and stirring was continued for 18 h at 25° C. The reaction mixture was diluted with ethyl acetate (10 mL), washed with saturated aqueous NaHCO$_3$ solution (5 mL) and brine (5 mL), dried over Na$_2$SO$_4$ and concentrated under reduced pressure. The obtained residue was purified by flash column chromatography (silica gel, 10→70% EtOAc in hexanes) to afford pure tripeptide 71 (18.5 mg, 90%) as a colorless oil. 71: R$_f$=0.3 (silica gel, 50% EtOAc in hexanes); [α]$_D^{22}$=+11.0 (c=1.0, CHCl$_3$); FT-IR (neat) $\tilde{v}_{max}$: 3374, 2924, 2853, 1735, 1643, 1519, 1453, 1372, 1231, 1050, 843, 738, 702 cm$^{-1}$; $^1$H NMR: (CDCl$_3$, 600 MHz) δ=8.07 (dd, J=7.7, 1.1 Hz, 1H), 7.82 (t, J=7.7 Hz, 1H), 7.76 (t, J=9.2 Hz, 3H), 7.60 (dd, J=7.7, 3.4 Hz, 2H), 7.45-7.35 (m, 4H), 7.35-7.28 (m, 3H), 7.24-7.13 (m, 4H), 5.70 (d, J=8.5 Hz, 1H), 5.45 (d, J=11.1 Hz, 1H), 4.50 (s, 1H), 4.45 (dq, J=9.6, 4.2 Hz, 1H), 4.41-4.28 (m, 3H), 4.22 (t, J=7.3 Hz, 1H), 3.58 (s, 3H), 3.06-2.94 (m, 1H), 2.94-2.88 (m, 3H), 2.62 (s, 1H), 2.16 (s, 3H), 2.13-1.99 (m, 2H), 1.85 (t, J=13.5 Hz, 1H), 1.82 (s, 1H), 1.65 (ddd, J=14.1, 9.8, 4.3 Hz, 2H), 1.18 (d, J=7.1 Hz, 3H), 1.01 (d, J=6.5 Hz, 3H), 0.86 (q, J=10.8, 7.8 Hz, 3H), 0.67-0.37 (m, 4H); $^{13}$C NMR: (CDCl$_3$, 150 MHz) δ=176.5, 172.8, 170.3, 163.3, 158.7, 156.1, 149.2, 143.9, 141.3, 138.3, 137.5, 129.6, 128.3, 127.7, 127.1, 126.5, 125.2, 122.2, 121.2, 120.0, 72.9, 67.0, 53.6, 51.8, 48.1, 47.2, 40.8, 37.7, 36.5, 35.0, 29.7, 21.0, 20.0, 19.8, 17.5, 14.2, 3.4, 2.1; HRMS calcd for C$_{48}$H$_{56}$N$_4$O$_8$ [M+Na$^+$] 839.3996. found 839.3374.

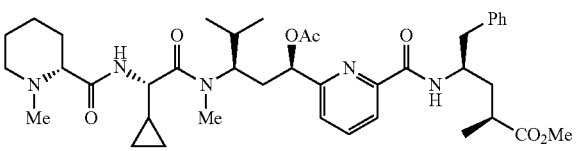

Methyl (2S,4R)-4-(6-((1R,3R)-1-acetoxy-3-((S)-2-cyclopropyl-N-methyl-2-((R)-1-methylpiperidine-2-carboxamido)acetamido)-4-methylpentyl)picolina-mido)-2-methyl-5-phenylpentanoate (Tb36)

To an ice-cooled stirred solution of Fmoc-derivative 71 (12 mg, 0.014 mmol) in CH$_2$Cl$_2$ (2 mL) was added tris(2-aminoethyl)amine (0.03 mL, 0.235 mmol). The reaction mixture was stirred for 2 h at 25° C. and then diluted with ethyl acetate (10 mL). The solution was washed with saturated aqueous NaHCO$_3$ solution (5 mL), and brine (5 mL), dried over Na$_2$SO$_4$, and concentrated. The crude amine so obtained (10 mg, quantitative) was used for the next step without further purification.

To an ice-cooled stirred solution of N-methyl-(D)-pipecolinic acid 10 (4.5 mg, 0.031 mmol) in DMF (1.0 ml) at 0° C. was added HATU (18 mg, 0.047 mmol) followed by above obtained crude amine (10 mg, 0.015 mmol), and Et$_3$N (0.01 mL, 0.094 mmol) and the reaction mixture was stirred at 25° C. for 24 h. The reaction mixture was diluted with H$_2$O (5 mL) and the resulting solution was extracted with EtOAc (3×10 mL). The combined organic extracts were washed with saturated aqueous NaHCO$_3$ solution (5 mL) and brine (5 mL), dried over Na$_2$SO$_4$ and evaporated under reduced pressure. The obtained residue was purified by flash column chromatography (silica gel, 3→18% MeOH in CH$_2$Cl$_2$) to afford analog Tb36 (6.5 mg, 62%) as a colorless oil. Tb36: R$_f$=0.4 (silica gel, 10% MeOH in CH$_2$Cl$_2$); [α]$_D^{22}$=+24.2 (c=1.0, CHCl$_3$); FT-IR (neat) $\tilde{9}_{max}$: 3387, 2960, 2927, 1735, 1646, 1623, 1572, 1522, 1455, 1232, 1028, 840 cm$^{-1}$; $^1$H NMR: (CDCl$_3$, 600 MHz) δ=8.06 (dd, J=7.7, 1.0 Hz, 1H), 7.81 (t, J=7.7 Hz, 1H), 7.76 (d, J=9.3 Hz, 1H), 7.37 (dt, J=7.8, 1.8 Hz, 1H), 7.25 (q, J=6.8, 5.9 Hz, 3H), 7.19 (td, J=5.7, 5.3, 2.4 Hz, 3H), 5.46 (dd, J=11.6, 2.3 Hz, 1H), 4.57 (s, 1H), 4.48-4.34 (m, 2H), 3.58 (s, 3H), 2.93 (d, J=16.5 Hz, 5H), 2.61 (dddd, J=11.6, 8.7, 7.1, 4.3 Hz, 1H), 2.53-2.39 (m, 1H), 2.24 (s, 3H), 2.15 (d, J=6.0 Hz, 4H), 2.04 (ddt, J=16.3, 11.4, 5.6 Hz, 2H), 1.89-1.76 (m, 3H), 1.75-1.49 (m, 5H), 1.34 (s, 1H), 1.27-1.20 (m, 2H), 1.17 (dd, J=7.1, 3.4 Hz, 3H), 0.99 (t, J=6.6 Hz, 3H), 0.82 (d, J=6.6 Hz, 3H), 0.69-0.57 (m, 1H), 0.53 (ddt, J=12.8, 8.6, 3.2 Hz, 1H), 0.46-0.33 (m, 2H); $^{13}$C NMR: (CDCl$_3$, 150 MHz) δ=176.5, 174.0, 172.7, 170.3, 163.3, 158.9, 149.4, 138.3, 137.4, 129.6, 128.3, 126.5, 122.2, 121.2, 72.8, 69.7, 55.4, 52.1, 51.8, 48.1, 44.6, 40.8, 37.7, 36.4, 35.0, 34.9, 30.6, 29.8, 29.1, 25.2, 23.3, 21.0, 19.9, 19.6, 17.5, 13.9, 3.7, 2.5. HRMS calcd for $C_{40}H_{57}N_5O_7$ [M+H$^+$] 720.4336. found 720.4339.

Tb37

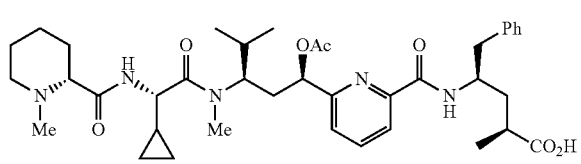

(2S,4R)-4-(6-((1R,3R)-1-Acetoxy-3-((S)-2-cyclopropyl-N-methyl-2-((R)-1-methylpiperidine-2-carboxamido)acetamido)-4-methylpentyl)picolinamido)-2-methyl-5-phenylpentanoic Acid (Tb37)

To a stirred solution of methyl ester Tb36 (12 mg, 0.016 mmol) in 1,2-dichloroethane (1 mL) was added Me$_3$SnOH (60 mg, 0.33 mmol) at 25° C. The reaction mixture was refluxed for 12 h and the solvent was removed under reduced pressure. The resulting hydroxyl acid (12 mg, quantitative) was used in the following step without further purification.

To an ice-cooled stirred solution of the above obtained hydroxyl acid (12 mg, 0.018 mmol) in pyridine (0.2 mL) was added dropwise Ac$_2$O (0.006 ml, 0.072 mmol). The reaction mixture was stirred at 25° C. for 12 h and then the solvent was removed under reduced pressure. The crude reaction mixture was purified by flash column chromatography (silica gel, 5→15% MeOH in CH$_2$Cl$_2$) to Tb37 (7.6 mg, 65% yield) as a colorless oil. Tb37: R$_f$=0.2 (silica gel 10% MeOH in CH$_2$Cl$_2$); [α]$_D^{22}$=+278.0 (c=1.0, CHCl$_3$); FT-IR (neat) $\tilde{v}_{max}$: 3285, 2957, 2927, 2843, 1714, 1638, 1544, 1497, 1463, 1082, 752 cm$^{-1}$; $^1$H NMR: (CDCl$_3$, 600 MHz) δ=8.32 (d, J=8.8 Hz, 1H), 8.07 (dd, J=7.8, 1.0 Hz, 1H), 7.84 (t, J=7.7 Hz, 1H), 7.41 (dd, J=13.9, 7.8 Hz, 2H), 7.33-7.15 (m, 5H), 5.53 (dd, J=11.2, 2.8 Hz, 1H), 4.57-4.28 (m, 2H), 3.00 (d, J=11.3 Hz, 3H), 2.99-2.87 (m, 2H), 2.62 (s, 1H), 2.51 (d, J=11.2 Hz, 1H), 2.25 (s, 3H), 2.21-2.16 (m, 1H), 2.14 (d, J=5.8 Hz, 3H), 2.11-1.76 (m, 6H), 1.53 (s, 4H), 1.47-1.34 (m, 1H), 1.31-1.18 (m, 3H), 1.14 (d, J=7.0 Hz, 3H), 0.96 (d, J=6.6 Hz, 3H), 0.84 (d, J=6.6 Hz, 3H), 0.63 (d, J=8.4 Hz, 1H), 0.53 (t, J=8.7 Hz, 1H), 0.45-0.34 (m, 2H); $^{13}$C NMR: (CDCl$_3$, 150 MHz) δ=177.4, 173.7, 172.6, 170.8, 164.3, 158.7, 148.6, 138.5, 137.5, 129.3, 128.5, 126.6, 122.7, 121.5, 73.9, 69.9, 55.5, 52.4, 48.6, 44.4, 42.2, 41.1, 38.3, 37.0, 36.1, 34.9, 30.4, 29.9, 25.0, 23.3, 21.1, 21.0, 19.6, 16.6, 13.7, 3.6, 2.5; HRMS calcd for $C_{39}H_{56}N_5O_7$ [M+H$^+$] 706.4180. found 706.4186.

72

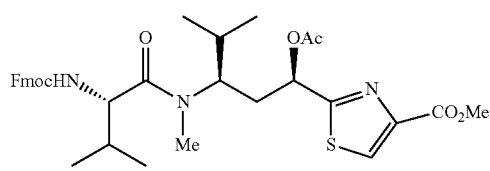

Methyl 2-((5S,8R,10R)-1-(9H-fluoren-9-yl)-5,8-diisopropyl-7-methyl-3,6,12-trioxo-2,11-dioxa-4,7-diazatridecan-10-yl)thiazole-4-carboxylate (72)

According to the procedure described for the synthesis of compound 58, Boc-group was removed through the action of TFA, followed by coupling with compound 46, furnishing compound 72 as an off-white amorphous solid (31 mg, 73% for the two steps). 72: [α]$_D^{22}$=+0.57 (c=1.40, CHCl$_3$); R$_f$=0.53 (silica gel, 50% EtOAc in hexanes); FT-IR (neat) $\tilde{v}_{max}$: 3294, 2963, 2875, 1720, 1638, 1502, 1479, 1450, 1410, 1370, 1323, 1296, 1216, 1099, 1027, 991, 936, 915, 852, 757, 742, 665 cm$^{-1}$; $^1$H NMR (600 MHz, CDCl$_3$) δ=8.13 (s, 1H), 7.75 (d, J=7.5 Hz, 2H), 7.58 (d, J=7.4 Hz, 2H), 7.39 (t, J=7.4 Hz, 2H), 7.33-7.28 (m, 2H), 5.72 (dd, J=11.4, 2.2 Hz, 1H), 5.49 (d, J=9.5 Hz, 1H), 4.51 (dd, J=9.4, 5.5 Hz, 2H), 4.40-4.30 (m, 2H), 4.21 (t, J=7.0 Hz, 1H), 3.94 (s, 3H), 2.97 (s, 3H), 2.41-2.32 (m, 1H), 2.29-2.16 (m, 1H), 2.14 (s, 3H), 2.00 (td, J=13.1, 6.6 Hz, 1H), 1.78-1.71 (m, 1H), 1.03-0.97 (m, 6H), 0.93 (d, J=6.7 Hz, 3H), 0.79 (d, J=6.6 Hz, 3H) ppm; $^{13}$C NMR (150 MHz, CDCl$_3$)=173.5, 171.1, 170.0, 161.6, 156.4, 146.8, 143.8, 141.2, 127.8, 127.6, 127.0, 125.1, 119.9, 69.6, 66.9, 56.2, 52.5, 47.2, 34.3, 30.9, 29.8, 20.8, 20.1, 20.0, 19.6, 17.0 ppm; HRMS calcd for $C_{34}H_{41}N_3O_7S$ [M+Na$^+$] 658.2557. found 658.2553.

73

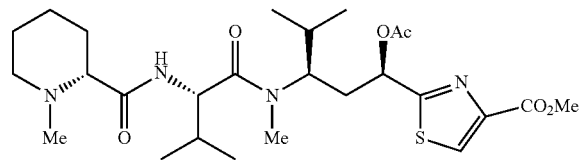

Methyl 2-((1R,3R)-1-acetoxy-3-((S)—N,3-dimethyl-2-((R)-1-methylpiperidine-2-carboxamido) butanamido)-4-methylpentyl)thiazole-4-carboxylate (73)

According to the procedure described for the synthesis of Tb2, compound 73 was obtained as an off-white amorphous solid (22 mg, 78% for two steps). 73: [α]$_D^{22}$=-6.41 (c=1.40, MeOH); R$_f$=0.54 (silica gel, 10% MeOH in CH$_2$Cl$_2$); FT-IR (neat) $\tilde{v}_{max}$: 3386, 2960, 2874, 2794, 1740, 1641, 1485, 1412, 1389, 1371, 1324, 1217, 1100, 1046, 990, 935, 845, 779, 765 cm$^{-1}$; $^1$H NMR (600 MHz, CD$_3$OD) δ=8.37 (s, 1H), 5.71 (dd, J=11.4, 2.3 Hz, 1H), 4.70 (d, J=7.1 Hz, 1H), 4.41 (m, 2H), 3.92 (s, 3H), 3.10 (s, 3H), 3.09-3.06 (m, 1H), 2.87 (d, J=10.3 Hz, 1H), 2.39-2.29 (m, 4H), 2.27-2.19 (m, 1H), 2.15 (s, 3H), 2.14-2.08 (m, 1H), 1.90-1.77 (m, 3H), 1.72 (d, J=13.0 Hz, 1H), 1.68-1.56 (m, 2H), 1.42-1.33 (m, 1H), 1.03-0.99 (m, 6H), 0.97 (d, J=6.8 Hz, 3H), 0.81 (d, J=6.6 Hz, 3H) ppm; $^{13}$C NMR (150 MHz, CD$_3$OD) δ=172.9, 172.1, 171.0, 169.7, 160.9, 145.5, 127.6, 69.3, 67.9, 54.5, 54.1, 50.8, 42.4, 33.7, 29.4, 29.3, 28.8, 23.6, 21.8, 18.8, 18.43, 18.42, 18.3, 16.3 ppm; HRMS calcd for $C_{26}H_{42}N_4O_6S$ [M+Na$^+$] 561.2717. found 561.2700.

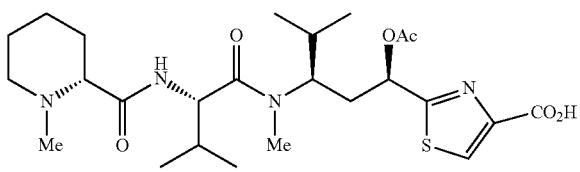

2-((1R,3R)-1-Acetoxy-3-((S)—N,3-dimethyl-2-((R)-1-methylpiperidine-2-carboxamido)butanamido)-4-methylpentyl)thiazole-4-carboxylic Acid (74)

According to the procedure described for the synthesis of 62, acid 74 was obtained as a colorless oil (20 mg, 74% for the two steps). 74: FT-IR (neat) $\tilde{v}_{max}$: 3400, 2961, 2873, 1750, 1637, 1473, 1370, 1222, 1044, 778; $R_f$=0.3 (silica gel, 16% MeOH/4% NH$_4$OH/CH$_2$Cl$_2$); $^1$H NMR: (CD$_3$OD, 600 MHz) δ=7.88 (s, 1H), 5.64 (s, 1H), 4.57 (d, J=7.3 Hz, 1H), 3.16 (s, 2H), 3.03 (s, 3H), 2.63 (s, 1H), 2.46 (s, 3H), 2.27-2.11 (m, 2H), 2.04 (s, 3H), 2.03 (s, 2H), 2.02-1.82 (m, 2H), 1.72 (d, J=17.1 Hz, 2H), 1.61 (qd, J=13.1, 3.6 Hz, 2H), 1.42 (s, 1H), 1.01-0.82 (m, 9H), 0.74 (s, 3H) ppm; $^{13}$C NMR: (CD$_3$OD, 150 MHz) δ=174.5, 171.7, 168.6, 155.0, 124.8, 79.0, 71.6, 68.8, 56.7, 56.2, 43.6, 35.9, 31.2, 30.9, 30.7, 24.8, 23.0, 20.9, 20.6, 20.5, 20.4, 20.3, 18.3 ppm. HRMS calcd for C$_{25}$H$_{41}$N$_4$O$_6$S [M+H$^+$] 525.2747. found 525.2741.

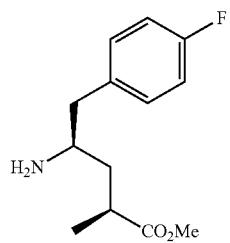

Methyl (2S,4R)-4-amino-5-(4-fluorophenyl)-2-methylpentanoate (75)

According to the procedure described for the synthesis of 6, compound 75 was obtained as its HCl salt as a white solid (90 mg, 52% for the two steps). 75: [α]$_D^{22}$=−7.5 (c=0.1, CHCl$_3$); FT-IR (neat) $\tilde{v}_{max}$: 3389, 2915, 2034, 1734, 1601, 1510, 1435, 1224, 1158, 1090, 826, 815, 769 cm$^{-1}$; $^1$H NMR (CDCl$_3$, 600 MHz) δ=8.46 (s, 2H), 7.27 (s, 2H), 7.03 (s, 2H), 3.64 (s, 3H), 3.14 (d, J=206.4 Hz, 3H), 2.02 (s, 3H), 1.19 (s, 3H) ppm; $^{13}$C NMR: (CDCl$_3$, 150 MHz) δ=175.6, 162.8, 161.2, 131.2, 115.8, 52.5, 52.4, 39.3, 36.1, 18.1, 17.2 ppm; HRMS calcd for C$_{13}$H$_{18}$FNO$_2$ [M+H$^+$] 240.1400. found 240.1400.

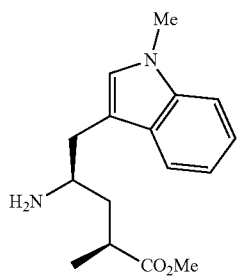

Methyl (2S,4R)-4-amino-2-methyl-5-(1-methyl-1H-indol-3-yl)pentanoate (76)

According to the procedure described for the synthesis of 6, compound 76 was obtained as its HCl salt as a yellowish solid (120 mg, 64% for the two steps). 75: [α]$_D^{22}$=+2.8 (c=0.1, CHCl$_3$); FT-IR (neat) $\tilde{v}_{max}$: 3397, 2935, 1728, 1613, 1509, 1474, 1378, 1330, 1251, 1204, 1159, 1131, 741 cm$^{-1}$; $^1$H NMR (CDCl$_3$, 600 MHz) δ=8.39 (s, 2H), 7.62 (d, 1H), 7.26-7.04 (m, 4H), 3.79 (s, 3H), 3.60 (s, 1H), 3.56 (s, 3H), 3.29-3.0 (m, 3H), 2.24-1.93 (m, 3H), 1.19 (s, 3H) ppm; $^{13}$C NMR: (CDCl$_3$, 150 MHz) δ=176.0, 137.2, 128.8, 127.6, 121.8, 119.1, 118.8, 109.4, 107.4, 52.1, 51.7, 36.5, 36.3, 32.8, 29.4, 17.8 ppm; HRMS calcd for C$_{16}$H$_{22}$N$_2$O$_2$ [M+Na$^+$] 275.1760. found 275.1750.

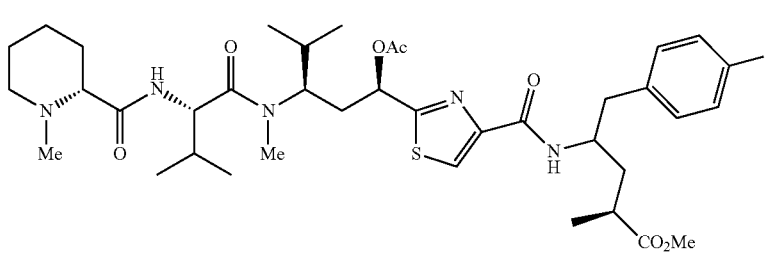

Methyl(2S,4R)-4-(2-((1R,3R)-1-acetoxy-3-((S)—N,3-dimethyl-2-((R)-1-methylpiperidine-2-carboxamido)butanamido)-4-methylpentyl)thiazole-4-carboxamido)-5-(4-fluorophenyl)-2-methylpentanoate (Tb40)

To a stirred solution of acid 74 (10 mg, 0.019 mmol) in dry DMF (0.5 mL) was added HATU (8.3 mg, 0.022 mmol) followed by a solution of fluoro compound 75 (5.2 mg, 0.022 mmol) and Et₃N (0.006 mL, 0.0456 mmol), in DMF (0.1 mL) at 25° C., and stirring continued for 18 h at the same temperature. The reaction mixture was diluted with H₂O (5 mL) and the resulting solution was extracted with EtOAc (3×10 mL). The combined organic extracts were washed with brine (2×5 mL), dried over Na₂SO₄ and evaporated under reduced pressure. The obtained residue was purified by flash column chromatography (silica gel. 3%-15% MeOH in CH₂Cl₂) to furnish analog Tb40 (10.6 mg, 75%) as a light yellow amorphous solid. Tb40: $R_f$=0.5 (silica gel, 10% MeOH in CH₂Cl₂); $[\alpha]_D^{22}$=+5.1 (c=1.0, CHCl₃); FT-IR $v_{max}$ (neat): 2956, 2922, 2852, 1736, 1645, 1542, 1509, 1463, 1371, 1221, 830 cm⁻¹; ¹H NMR: (CDCl₃, 600 MHz) δ=8.01 (s, 1H), 7.22-7.15 (m, 2H), 7.11 (t, J=9.4 Hz, 2H), 7.03-6.91 (m, 2H), 5.68 (dd, J=11.3, 2.7 Hz, 1H), 4.76 (dd, J=9.5, 6.5 Hz, 1H), 4.56 (s, 1H), 4.34 (tdd, J=10.2, 6.7, 3.9 Hz, 1H), 3.63 (s, 3H), 3.03 (d, J=12.8 Hz, 3H), 2.98-2.80 (m, 3H), 2.61 (dqd, J=9.1, 7.1, 4.4 Hz, 1H), 2.49 (q, J=6.8 Hz, 1H), 2.35 (ddd, J=14.8, 11.3, 3.3 Hz, 1H), 2.25 (s, 3H), 2.16 (s, 3H), 2.11-1.92 (m, 4H), 1.86-1.46 (m, 7H), 1.37 (d, J=13.3 Hz, 1H), 1.17 (d, J=7.1 Hz, 3H), 1.06-0.95 (m, 9H), 0.79 (d, J=6.6 Hz, 3H); ¹³C NMR: (CDCl₃, 150 MHz) δ=176.5, 173.4, 170.1, 169.7, 162.5, 160.3, 149.9, 133.2, 130.9, 123.6, 115.3, 115.1, 69.7, 69.3, 55.4, 53.7, 51.7, 48.6, 44.9, 40.3, 37.6, 36.4, 34.5, 30.7, 30.5, 29.9, 29.5, 25.1, 23.3, 20.8, 20.1, 20.0, 19.6, 17.9, 17.6, 17.2; HRMS calcd for C₃₈H₅₆FN₅O₇S [M+Na⁺] 768.3782. found 768.3790.

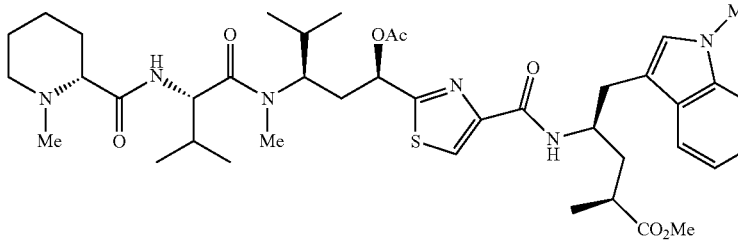

Methyl(2S,4R)-4-(2-((1R,3R)-1-acetoxy-3-((S)—N,3-dimethyl-2-((R)-1-methylpiperidine-2-carboxamido)butanamido)-4-methylpentyl)thiazole-4-carboxamido)-2-methyl-5-(1-methyl-1H-indol-3-yl)pen-tanoate (Tb41)

According to the procedure described for the synthesis of Tb40, analog 41 was synthesized as a yellowish oil. Tb40: $R_f$=0.3 (silica gel, 10% MeOH in CH₂Cl₂); $[\alpha]_D^{22}$=+3.6 (c=1.0, CHCl₃); FT-IR $v_{max}$ (neat): 2922, 2852, 1736, 1644, 1465, 1373, 1221, 742 cm⁻¹; ¹H NMR: (CDCl₃, 600 MHz) δ=8.06 (s, 1H), 7.68-7.56 (m, 1H), 7.29 (dd, J=8.2, 0.9 Hz, 1H), 7.22-7.13 (m, 2H), 7.12-7.03 (m, 2H), 6.92 (d, J=6.5 Hz, 1H), 5.63 (ddd, J=11.6, 7.5, 2.5 Hz, 1H), 4.75 (dd, J=9.5, 6.7 Hz, 1H), 4.51 (td, J=15.1, 12.2, 6.8 Hz, 2H), 3.75 (d, J=1.1 Hz, 3H), 3.61 (s, 3H), 3.16-3.00 (m, 2H), 2.97 (d, J=15.8 Hz, 3H), 2.90 (s, 1H), 2.62 (ddt, J=11.9, 9.0, 5.9 Hz, 1H), 2.48 (s, 1H), 2.29-2.20 (m, 3H), 2.16 (d, J=7.8 Hz, 3H), 2.13-1.91 (m, 4H), 1.83-1.47 (m, 8H), 1.40-1.31 (m, 1H), 1.16 (dd, J=7.1, 2.5 Hz, 3H), 1.07-0.93 (m, 10H), 0.78 (dd, J=6.7, 3.7 Hz, 3H); ¹³C NMR: (CDCl₃, 150 MHz) δ=176.7, 174.4, 173.4, 169.7, 160.4, 150.2, 136.9, 128.4, 127.6, 123.5, 121.6, 119.2, 118.9, 110.0, 109.1, 69.3, 55.4, 53.7, 51.7, 47.9, 45.0, 37.9, 36.6, 34.4, 32.7, 31.5, 30.7, 30.5, 29.9, 29.7, 25.1, 23.3, 20.8, 20.2, 20.0, 19.6, 17.9, 17.6, 17.3; HRMS calcd for C₄₁H₆₀N₆O₇S [M+Na⁺] 803.4142. found 803.4141.

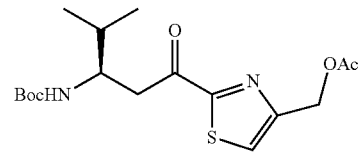

(R)-(2-(3-(tert-Butoxycarbonylamino)-4-methylpentanoyl)thiazol-4-yl)methyl acetate (79)

To a stirred solution of aldehyde 78 (383 mg, 1.78 mmol) and thiazole compound 2 (140 mg, 0.89 mmol) in anhydrous acetonitrile (17.8 mL) at 25° C. was added dropwise over 3 minutes TMSN₃ (0.18 mL, 1.33 mmol) followed by phenyliodobis(trifluoroacetate) (PIFA, 574 mg, 1.33 mmol). After stirring for 12 hours at 25° C., more aldehyde 78 (383 mg, 1.78 mmol), TMSN₃ (0.18 mL, 1.33 mmol) and PIFA (574 mg, 1.33 mmol) were added portion-wise over 3 minutes at 25° C. and stirring was continued for an additional 12 hours. The reaction mixture was cooled to 0° C. and quenched with Et₃N (1.46 mL). The solvent was removed under reduced pressure and the resulting residue was purified by flash column chromatography (silica gel, 10→30% EtOAc in hexanes) to produce ketone 79 (186 mg, 56% yield) as a colorless oil. 79: Rt=0.34 (silica gel, 25% EtOAc in hexanes); $[\alpha]_D^{22}$=−14.4 (c=1.3, CHCl₃); FT-IR (neat) $v_{max}$: 3368, 3104, 2965, 2932, 2876, 1742, 1690, 1512, 1443, 1390, 1365, 1308, 1223, 1168, 1111, 1029, 1009, 935, 866, 779, 725 cm⁻¹; ¹H NMR (600 MHz, CDCl₃) δ 7.61 (s, 1H), 5.26 (s, 2H), 4.85 (d, J=9.0 Hz, 1H), 3.97 (dd, J=9.0, 6.2 Hz, 1H), 3.27 (d, J=4.4 Hz, 2H), 2.13 (s, 3H), 1.91 (dd, J=12.8, 6.4 Hz, 1H), 1.37 (s, 9H), 0.99-0.90 (m, 6H) ppm; ¹³C NMR: (CDCl₃, 150 MHz) δ=192.5, 170.5, 167.1, 155.5, 153.4, 124.8, 79.1, 61.5, 53.1, 41.0, 32.1, 28.3, 20.9, 19.3, 18.4 ppm; HRMS calcd for C₁₇H₂₆N₂O₅S [M+Na⁺] 393.1455. found 393.1459.

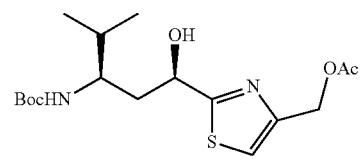

(2-((1R,3R)-3-(tert-Butoxycarbonylamino)-1-hydroxy-4-methylpentyl)thiazol-4-yl)methyl acetate (80)

To an ice-cooled stirred solution of (S)—CBS catalyst (1M in THF, 0.13 mL, 0.13 mmol) in THF (6.5 mL) was added BH$_3$.THF (1M in THF, 0.65 mL, 0.65 mmol) and stirring was continued for 10 minutes at 0° C. Then, a solution of ketone 79 (242 mg, 0.65 mmol) in THF (2.5 mL) was added dropwise to the reaction mixture and stirring was continued for 18 hours while the temperature gradually increased to 25° C. The reaction was quenched with MeOH (5.0 mL) and the solvent was removed under reduced pressure. The resulting residue was dissolved in EtOAc (50 mL) and washed with brine (2×20 mL). The organic layer was dried with sodium sulfate, filtered and concentrated. The residue was purified by flash column chromatography (silica gel, 10→40% EtOAc in hexanes) to furnish alcohol 80 (201 mg, 83% yield) as a colorless oil. 80: R$_f$=0.35 (silica gel, 30% EtOAc in hexanes); [α]$_D^{22}$=+17.7 (c=0.65, CHCl$_3$); FT-IR (neat) $\tilde{v}_{max}$: 3351, 2964, 2931, 1742, 1685, 1525, 1390, 1366, 1312, 1247, 1171, 1027, 868, 776 cm$^{-1}$; $^1$H NMR (600 MHz, CDCl$_3$) δ 7.23 (s, 1H), 5.16 (dd, J=26.4, 12.7 Hz, 2H), 5.09 (s, 1H), 4.97 (d, J=10.6 Hz, 1H), 4.56 (d, J=9.3 Hz, 1H), 3.77-3.70 (m, 1H), 2.11 (s, 3H), 1.99 (t, J=12.7, 1H), 1.81 (t, J=11.6 Hz, 1H), 1.77-1.70 (m, 1H), 1.44 (s, 9H), 0.98-0.91 (m, 6H) ppm; $^{13}$C NMR: (CDCl$_3$, 150 MHz) δ=176.3, 170.7, 157.9, 150.5, 117.6, 80.4, 69.1, 61.8, 52.3, 42.1, 32.2, 28.3, 21.0, 19.4, 18.4 ppm; HRMS calcd for C$_{17}$H$_2$N$_2$O$_8$S [M+Na]$^+$ 395.1611. found 395.1595.

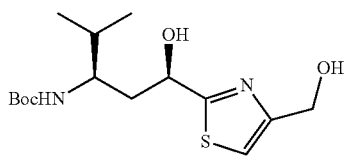

81a tert-Butyl (1R,3R)-1-hydroxy-1-(4-(hydroxymethyl)thiazol-2-yl)-4-methylpentan-3-yl carbamate (81a)

To a stirred solution of alcohol 80 (183 mg, 0.49 mmol) in methanol (15.0 mL) was added K$_2$CO$_3$ (265 mg, 1.92 mmol) at 25° C. The reaction mixture was stirred for 3 h at 25° C. and then quenched with saturated aqueous NH$_4$Cl solution (3.0 mL). The solvent was removed under reduced pressure. The residue was diluted with EtOAc (10 mL) and washed with brine (2×15 mL). The organic layer was dried with Na$_2$SO$_4$. The solvent was evaporated and the obtained residue was purified using flash column chromatography (silica gel, 10→70% EtOAc in hexanes) to furnish the corresponding diol 81a (154 mg, 95% yield) as a colorless oil: R$_f$=0.25 (silica gel, 50% EtOAc in hexanes); [α]$_D^{22}$=+ 7.9 (c=0.61, CHCl$_3$); FT-IR (neat) $\tilde{v}_{max}$: 3332, 2963, 2931, 2874, 1685, 1528, 1467, 1429, 1391, 1366, 1312, 1250, 1170, 1065, 1021, 973, 868, 755 cm$^{-1}$; $^1$H NMR (600 MHz, CDCl$_3$) δ 7.13 (s, 1H), 5.11 (s, 1H), 4.95 (d, J=8.0 Hz, 1H), 4.74 (s, 2H), 4.61 (d, J=9.0 Hz, 1H), 3.78-3.70 (m, 1H), 2.02-1.93 (m, 1H), 1.85-1.78 (m, 1H), 1.74 (dt, J=19.3, 6.6 Hz, 2H), 1.45 (s, 9H), 0.98-0.92 (m, 6H) ppm; $^{13}$C NMR: (CDCl$_3$, 150 MHz) δ=176.3, 157.9, 155.6, 114.5, 80.3, 69.0, 61.0, 52.3, 42.0, 32.2, 28.3, 19.3, 18.3 ppm; HRMS calcd for C$_{15}$H$_{26}$N$_2$O$_4$S [M+Na]$^+$ 353.1505. found 353.1493.

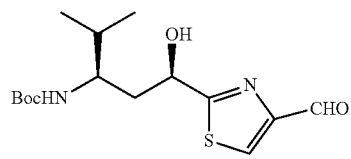

81b tert-Butyl (1R,3R)-1-(4-formylthiazol-2-yl)-1-hydroxy-4-methylpentan-3-ylcarbamate (81b)

To a stirred solution of the diol 81a (154 mg, 0.475 mmol) in CH$_2$Cl$_2$ (5.0 mL) at 25° C. was added TEMPO (7.5 mg, 0.0475 mmol), followed by bis(acetoxy)iodobenzene (BAIB, 153 mg, 0.475 mmol). After stirring for 16 hours at 25° C., the reaction mixture was quenched with aqueous Na$_2$S$_2$O$_3$ solution (5.0 mL). The solvent was removed under reduced pressure. The residue was diluted with EtOAc (80 mL) and washed with saturated aqueous NaHCO$_3$ solution (2×10 mL) and brine (10 mL). The organic layer was dried with Na$_2$SO$_4$. The solvent was evaporated under reduced pressure and the obtained crude aldehyde was purified by flash column chromatography (silica gel, 10→40% EtOAc in hexanes) to give the corresponding hydroxy-aldehyde 81b (153 mg, 98% yield) as a colorless oil; R$_f$=0.37 (silica gel, 30% EtOAc in hexanes); [α]$_D^{22}$=+1.24 (c=0.81, CHCl$_3$); FT-IR (neat) $\tilde{v}_{max}$: 3345, 3099, 2963, 2930, 2874, 1691, 1522, 1488, 1430, 1391, 1366, 1312, 1249, 1169, 1128, 1071, 1020, 1008, 974, 868, 777, 701 cm$^{-1}$; $^1$H NMR (600 MHz, CDCl$_3$) δ 9.97 (s, 1H), 8.14 (s, 1H), 5.30 (d, J=4.3 Hz, 1H), 5.03-4.94 (m, 1H), 4.59 (d, J=9.4 Hz, 1H), 3.79-3.66 (m, 1H), 2.11-2.02 (m, 1H), 1.86-1.78 (m, 1H), 1.75 (dt, J=13.2, 6.6 Hz, 1H), 1.45 (s, 9H), 1.00-0.92 (m, 6H) ppm; $^{13}$C NMR: (CDCl$_3$, 150 MHz) J=184.4, 177.5, 158.1, 154.9, 128.8, 80.5, 69.0, 52.3, 41.7, 32.2, 28.3, 19.4, 18.4 ppm; HRMS calcd for C$_{15}$H$_{24}$N$_2$O$_4$S [M+Na]$^+$ 351.1349. found 351.1344.

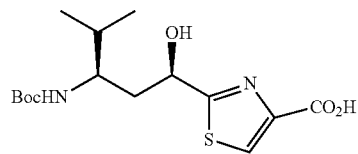

81c

2-((1R,3R)-3-(tert-Butoxycarbonylamino)-1-hydroxy-4-methylpentyl)thiazole-4-carboxylic Acid (81)

To a stirred solution of the aldehyde 81b (121 mg, 0.365 mmol) in t-BuOH (9.0 mL) at 25° C. was consecutively added a solution of 2-methyl-2-butene (0.3 mL, 2.74 mmol) in THF (1.5 mL), followed by a solution of NaClO$_2$ (178 mg, 1.98 mmol) and NaH$_2$PO$_4$.H$_2$O (0.7 g, 4.46 mmol) in H$_2$O (4.5 mL) and stirring was continued for 12 hours at 25° C. The reaction mixture was then diluted with aqueous HCl (1N, 4 mL) and the solvent was removed under reduced pressure. The residue was diluted with EtOAc (200 mL), and washed with brine (2×15 mL). The organic layer was dried with Na$_2$SO$_4$ and evaporated under reduced pressure to give the crude acid which was used in the next step without further purification.

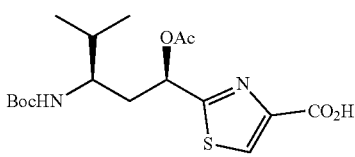

2-((1R,3R)-1-Acetoxy-3-(tert-butoxycarbonylamino)-4-methylpentyl)thiazole-4-carboxylic Acid (81)

To an ice-cooled stirred solution of the crude acid (95 mg) from last step reaction in $CH_2Cl_2$ (2.8 mL) was added DMAP (3.4 mg, 0.03 mmol), $Et_3N$ (0.23 mL, 1.65 mmol), then acetic anhydride (0.08 mL, 0.82 mmol) was added dropwise. The reaction mixture was stirred for 15 h while allowing the temperature to slowly rise to 25° C. The solvent was removed under reduced pressure. The obtained residue was diluted with EtOAc (120 mL) and washed with brine (2×10 mL). The organic layer was dried with $Na_2SO_4$ and evaporated under reduced pressure. The crude acid was purified by flash column chromatography (silica gel, 5→15% MeOH in $CH_2Cl_2$) to give 81 (83 mg, 78% yield in 2 steps) as a colorless oil. $R_f$=0.35 (silica gel, 10% MeOH in $CH_2Cl$); $[\alpha]_D^{22}$=−24.2 (c=1.0, MeOH); FT-IR (neat) $\tilde{v}_{max}$: 3336, 2967, 1751, 1697, 1615, 1486, 1365, 1219, 1170, 1086, 1041, 1015, 974, 919, 865, 828, 800, 773, 701 cm$^{-1}$; $^1$H NMR (CD$_3$OD, 600 MHz) δ 8.10 (s, 1H), 6.85 (s, 1H), 6.21 (s, 1H), 3.73-3.55 (m, 1H), 2.27-2.17 (m, 1H), 2.15 (s, 3H), 2.08-1.99 (m, 1H), 1.74-1.64 (m, 1H), 1.42 (s, 9H), 0.97-0.82 (m, 6H) ppm; $^{13}$C NMR: (CD$_3$OD, 150 MHz) δ=171.9, 169.6, 165.1, 156.4, 150.9, 122.7, 77.8, 69.6, 51.0, 36.5, 32.4, 26.8, 18.8, 17.6, 16.6 ppm; HRMS calcd for $C_{17}H_{26}N_2O_6S$ [M+Na]$^+$ 409.1404. found 409.1412.

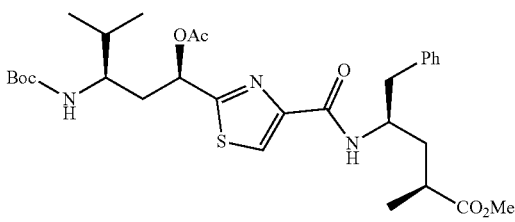

(2S,4R)-Methyl 4-(2-((1R,3R)-1-acetoxy-3-(tert-butoxycarbonylamino)-4-methylpentyl) thiazole-4-carboxamido)-2-methyl-5-phenylpentanoate (82)

To a stirred solution of 81 (20 mg, 0.05 mmol) in dry DMF (0.5 mL) were added amine 6 (26.8 mg, 0.10 mmol), $Et_3N$ (0.04 mL, 0.31 mmol), and HATU (60 mg, 0.16 mmol) was added to the above solution at 0° C. The mixture was stirred at 0° C. for 30 minutes then stirred at 25° C. for 4 h. The reaction mixture was diluted with $H_2O$ (10 mL) and extracted with ethyl acetate (60 mL). The organic layer was washed with brine (10 mL) and dried with $Na_2SO_4$ and evaporated under reduced pressure. The obtained residue was purified by flash column chromatography (silica gel, 10→40% EtOAc in hexanes) to furnish 82 (28.7 mg, 94%) as a colorless oil. 82: $R_f$=0.63 (silica gel, 50% EtOAc in hexanes); $[\alpha]_D^{22}$=+16.6 (c=0.89, CHCl$_3$); FT-IR (neat): 3341, 3110, 2967, 2930, 1736, 1711, 1662, 1540, 1495, 1456, 1435, 1390, 1367, 1303, 1247, 1220, 1171, 1084, 1042, 1018, 974, 921, 867, 833, 774, 753, 702 cm$^{-1}$; $^1$H NMR (600 MHz, CDCl$_3$) δ 8.01 (s, 1H), 7.31-7.27 (m, 2H), 7.23-7.19 (m, 3H), 7.12 (d, J=9.1 Hz, 1H), 6.04 (dd, J=10.8, 2.9 Hz, 1H), 4.50-4.30 (m, 2H), 3.84-3.74 (m, 1H), 3.63 (s, 3H), 2.95 (dd, J=13.7, 5.9 Hz, 1H), 2.87 (dd, J=13.7, 6.7 Hz, 1H), 2.66-2.55 (m, 1H), 2.17 (s, 3H), 2.16-2.11 (m, 1H), 2.01 (ddd, J=13.6, 9.5, 3.8 Hz, 1H), 1.96-1.89 (m, 1H), 1.75 (dt, J=12.9, 6.5 Hz, 1H), 1.62-1.57 (m, 1H), 1.43 (s, 9H), 1.16 (d, J=7.1 Hz, 3H), 1.00-0.90 (m, 6H) ppm; $^{13}$C NMR: (CDCl$_3$, 150 MHz) δ=176.6, 170.3, 170.0, 160.4, 155.6, 150.0, 137.6, 129.5, 128.4, 126.5, 123.3, 79.4, 69.6, 51.8, 51.4, 48.4, 41.2, 37.9, 37.7, 36.4, 32.7, 28.3, 20.8, 19.1, 17.7 ppm; HRMS calcd for $C_{30}H_{43}N_3O_7S$ [M+Na]$^+$ 612.2714. found 612.2697.

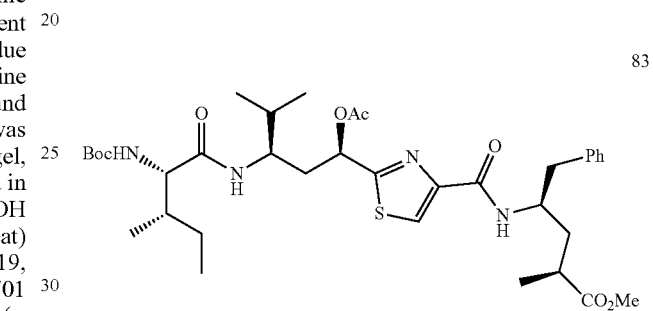

(2S,4R)-Methyl 4-(2-((6S,9R,11R)-6-sec-butyl-9-isopropyl-2,2-dimethyl-4,7,13-trioxo-3,12-dioxa-5,8-diazatetradecan-1-yl)thiazole-4-carboxamido)-2-methyl-5-phenylpentanoate (83)

To an ice-cooled stirred solution of 82 (17.8 mg, 0.03 mmol) in $CH_2Cl_2$ (2.0 mL) was added trifluoroacetic acid (0.40 mL), and the reaction mixture was stirred for 6 hours while warming up to 25° C. The solvent was removed under reduced pressure to give the crude TFA-ammonium salt, which was used for the following step reaction without further purification.

To a stirred, ice-cooled solution of crude ammonium salt from the previous step in DMF (0.50 mL) was added Et$_3$N (0.04 mL, 0.30 mmol) and Boc-Ile-OH (8) (14.0 mg, 0.06 mmol), then HATU (45.6 mg, 0.12 mmol) was added. The reaction mixture was stirred at 0° C. for 30 minutes, then stirred at 25° C. for 12 h. The reaction mixture was diluted with EtOAc (100 mL), washed with saturated aqueous NaHCO$_3$ solution (2×10 mL) and brine (10 mL), dried over Na$_2$SO$_4$ and concentrated. The obtained residue was purified by flash column chromatography (silica gel, 10→70% EtOAc in hexanes) to provide 83 (19.4 mg, 92% yield in 2 steps) as a white amorphous solid. $R_f$=0.43 (silica gel, 50% EtOAc in hexanes); $[\alpha]_D^{22}$=−0.47 (c=0.855, CHCl$_3$); FT-IR (neat) $\tilde{v}_{max}$: 3303, 2965, 2934, 2877, 1738, 1682, 1648, 1536, 1492, 1456, 1368, 1314, 1292, 1228, 1171, 1084, 1044, 1021, 938, 867, 828, 781, 753, 701 cm$^{-1}$; $^1$H NMR (600 MHz, CDCl$_3$) δ 8.01 (s, 1H), 7.30-7.26 (m, 2H), 7.25-7.18 (m, 3H), 7.16 (d, J=9.2 Hz, 1H), 6.05 (d, J=9.7 Hz, 1H), 5.92 (dd, J=10.7, 2.8 Hz, 1H), 4.94 (s, 1H), 4.44-4.36 (m, 1H), 4.15-4.07 (m, 1H), 3.85-3.75 (m, 1H), 3.63 (s, 3H), 2.97 (dd, J=13.8, 6.0 Hz, 1H), 2.88 (dd, J=13.7, 6.8 Hz, 1H), 2.67-2.55 (m, 1H), 2.18 (s, 3H), 2.16-2.10 (m, 1H), 2.05-

1.94 (m, 2H), 1.92 (s, 1H), 1.81 (dt, J=19.1, 6.5 Hz, 1H), 1.62 (ddd, J=14.2, 10.0, 4.3 Hz, 1H), 1.58-1.50 (m, 1H), 1.44 (s, 9H), 1.16 (d, J=7.1 Hz, 3H), 1.14-1.08 (m, 1H), 1.00-0.82 (m, 12H) ppm; $^{13}$C NMR: (CDCl$_3$, 150 MHz) δ=176.6, 171.7, 170.0, 169.9, 160.4, 156.1, 150.0, 137.6, 129.5, 128.4, 126.5, 123.3, 80.1, 69.7, 59.7, 51.7, 50.0, 48.5, 41.3, 37.8, 37.7, 36.4, 35.4, 32.2, 28.3, 24.7, 20.8, 19.1, 17.8, 17.6, 15.8, 11.0 ppm; HRMS calcd for C$_{36}$H$_{54}$N$_4$O$_8$S [M+Na]$^+$ 725.3555. found 725.3553.

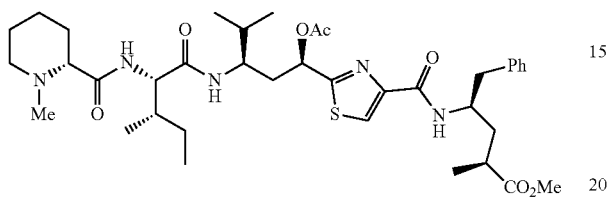

Tb53

(2S,4R)-Methyl 4-(2-((1R,3R)-1-acetoxy-4-methyl-3-((2S,3S)-3-methyl-2-((R)-1-methylpiperidine-2-carboxamido)pentanamido)pentyl)thiazole-4-carboxamido)-2-methyl-5-phenyl pentanoate (Tb53)

To an ice-cooled stirred solution of Fmoc-derivative 83 (16.0 mg, 0.023 mmol) in CH$_2$Cl$_2$ (2.5 mL) was added tris(2-aminoethyl)amine (0.04 mL, 0.3 mmol). The reaction mixture was stirred for 2 h at 25° C. and then diluted with ethyl acetate (5 mL). The solution was washed with saturated aqueous NaHCO$_3$ solution (5 mL) and brine (5 mL), dried over Na$_2$SO$_4$, and concentrated. The crude amine so obtained was used for the next step without further purification.

To an ice-cooled stirred solution of (D)-N-methyl-pipecolinic acid 10 (6.6 mg, 0.05 mmol) in DMF (0.5 ml) at 0° C. was added HATU (26 mg, 0.07 mmol) followed by the above obtained crude amine (10 mg, 0.02 mmol) and Et$_3$N (0.02 mL, 0.14 mmol) and the reaction mixture was stirred at 25° C. for 24 h. The reaction mixture was diluted with H$_2$O (2 mL) and the resulting solution was extracted with EtOAc (3×5 mL). The combined organic extracts were washed with saturated aqueous NaHCO$_3$ solution (2 mL) and brine (5 mL), dried over Na$_2$SO$_4$ and evaporated under reduced pressure. The obtained residue was purified by flash column chromatography (silica gel, 3→15% MeOH in CH$_2$Cl$_2$) to afford analog Tb53 (14.1 mg, 85% for the two steps) as a white amorphous solid. Tb53: R$_f$=0.50 (silica gel, 10% MeOH in CH$_2$Cl$_2$); [α]$_D^{22}$=+4.64 (c=0.69, MeOH); FT-IR (neat) $\tilde{v}_{max}$: 3640, 3401, 2963, 2939, 2878, 1734, 1656, 1545, 1499, 1455, 1383, 1255, 1232, 1147, 1117, 1087, 1050, 1033, 842, 787, 741, 702 cm$^{-1}$; $^1$H NMR (600 MHz, CD$_3$OD) δ 8.09 (s, 1H), 7.34-7.19 (m, 4H), 7.17 (t, J=6.8 Hz, 1H), 5.93 (dd, J=11.0, 2.5 Hz, 1H), 4.39-4.30 (m, 1H), 4.21 (d, J=8.4 Hz, 1H), 4.03-3.95 (m, 1H), 3.59 (s, 3H), 3.06 (d, J=10.1 Hz, 1H), 2.92-2.84 (m, 2H), 2.81 (s, 1H), 2.64-2.56 (m, 1H), 2.34 (s, 3H), 2.32-2.20 (m, 2H), 2.15 (s, 3H), 2.09-2.03 (m, 1H), 1.99 (ddd, J=13.6, 9.8, 3.6 Hz, 1H), 1.93-1.84 (m, 2H), 1.83-1.77 (m, 2H), 1.72 (ddd, J=14.1, 10.4, 3.9 Hz, 2H), 1.68-1.55 (m, 3H), 1.41-1.34 (m, 1H), 1.26-1.17 (m, 1H), 1.14 (d, J=7.1 Hz, 3H), 0.99 (d, J=6.7 Hz, 3H), 0.97-0.73 (m, 9H) ppm; $^{13}$C NMR: (CD$_3$OD, 150 MHz) δ=176.3, 172.1, 171.7, 169.8, 169.7, 160.7, 148.8, 137.4, 128.4, 127.4, 125.5, 123.2, 69.2, 68.1, 57.4, 54.5, 50.3, 49.9, 48.3, 42.3, 40.4, 36.9, 36.1, 35.7, 35.5, 31.9, 29.3, 23.8, 23.7, 21.9, 18.8, 17.6, 16.4, 16.1, 14.3, 9.1 ppm; HRMS calcd for C$_{38}$H$_{57}$N$_5$O$_7$S [M+Na]$^+$ 750.3871. found 750.3860.

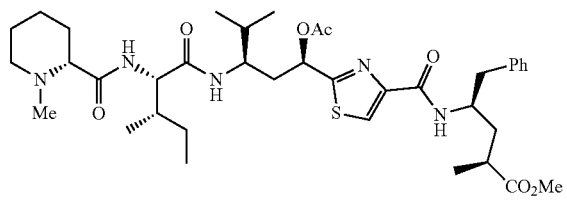

77: tubulysin V (2S,4R)-4-(2-((1R,3R)-1-Hydroxy-4-methyl-3-((2S,3S)-3-methyl-2-((R)-1-methylpiperidine-2-carboxamido)pentanamido)pentyl)thiazole-4-carboxamido)-2-methyl-5-phenylpentanoic Acid: tubulysin V (77)

To a stirred solution of methyl ester Tb53 (11 mg, 0.015 mmol) in dry CH$_2$Cl$_2$ (1.0 mL) was added Me$_3$SnOH (27 mg, 0.15 mmol) at 25° C. The reaction mixture was heated to reflux for 12 hours. The reaction mixture was cooled down and the solvent was removed under reduced pressure. The obtained crude hydroxyl acid was purified by flash column chromatography (silica gel, 3→20% MeOH in CH$_2$Cl$_2$) to provide tubulysin V (77) (6.8 mg, 68% yield) as a white amorphous solid. Tubulysin V: R$_f$=0.40 (silica gel, 10% MeOH in CH$_2$Cl$_2$); [α]$_D^{22}$=-6.49 (c=0.185, MeOH); IR (film) $\tilde{v}_{max}$: 3286, 2962, 2927, 2295, 1647, 1545, 1455, 1312, 1219, 1123, 1082, 771, 700, 663 cm$^{-1}$; $^1$H NMR (600 MHz, CD$_3$OD) δ 8.03 (s, 1H), 7.28-7.19 (m, 4H), 7.18-7.14 (m, 1H), 4.80 (d, J=10.4 Hz, 1H), 4.57 (s, 1H), 4.38-4.32 (m, 1H), 4.20 (d, J=8.8 Hz, 1H), 4.08 (dd, J=8.6, 5.6 Hz, 1H), 3.19 (dd, J=14.6, 7.4 Hz, 1H), 3.10 (d, J=11.7 Hz, 1H), 3.01 (d, J=10.2 Hz, 1H), 2.92 (d, J=6.1 Hz, 2H), 2.56-2.50 (m, 1H), 2.41 (d, J=12.2 Hz, 1H), 2.36 (s, 3H), 2.15-2.10 (m, 1H), 2.01-1.95 (m, 1H), 1.94-1.80 (m, 4H), 1.78 (d, J=13.2 Hz, 1H), 1.73 (d, J=13.8 Hz, 1H), 1.66-1.58 (m, 3H), 1.40-1.37 (m, 1H), 1.33-1.27 (m, 3H), 1.25-1.19 (m, 1H), 1.15 (d, J=6.7 Hz, 3H), 0.99 (d, J=6.7 Hz, 3H), 0.95 (dd, J=6.7, 3.1 Hz, 3H), 0.91 (t, J=7.3 Hz, 3H) ppm; $^{13}$C NMR: (CD$_3$OD, 150 MHz) δ=177.3, 171.7, 171.4, 168.6, 161.2, 148.8, 137.5, 128.5, 127.3, 125.4, 122.4, 67.8, 66.7, 58.0, 54.2, 50.8, 48.8, 41.3, 40.2, 38.8, 37.2, 35.5, 31.8, 28.8, 28.5, 24.0, 22.5, 20.8, 17.6, 16.7, 16.7, 14.2, 9.2 ppm; HRMS calcd for C$_{35}$H$_{53}$N$_5$O$_6$S [M+H]$^+$ 672.3789. found 672.3790.

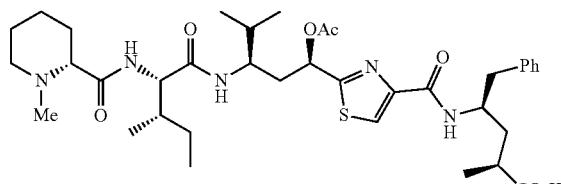

Tb54: tubulysin U

(2S,4R)-4-(2-((1R,3R)-1-Acetoxy-4-methyl-3-((2S,3S)-3-methyl-2-((R)-1-methylpiperidine-2-carboxamido)pentanamido)pentyl)thiazole-4-carboxamido)-2-methyl-5-phenylpentanoic Acid: tubulysin U (Tb54)

To an ice-cooled stirred solution of the above obtained hydroxyl acid tubulysin V (77) (5.0 mg, 0.007 mmol) in pyridine (1.0 mL) was added dropwise Ac$_2$O (0.5 mL). The reaction mixture was stirred at 25° C. for 12 h and then the solvent was removed under reduced pressure. The crude reaction mixture was purified by flash column chromatography (silica gel, 3→15% MeOH in CH$_2$Cl$_2$) to furnish Tubulysin U (Tb54), (4.2 mg, 79% yield) as an amorphous colorless solid. Tubulysin U (Tb545): R$_f$=0.43 (silica gel, 10% MeOH in CH$_2$Cl$_2$); [α]$_D^{22}$=−5.0 (c=0.10, MeOH); FT-IR (neat) $\tilde{v}_{max}$: 3287, 3028, 2960, 2928, 2855, 1748, 1649, 1544, 1496, 1463, 1370, 1312, 1221, 1144, 1087, 1034, 943, 784, 735, 700 cm$^{-1}$; $^1$H NMR (600 MHz, CD$_3$OD) δ 8.07 (s, 1H), 7.28-7.18 (m, 4H), 7.17-7.12 (m, 1H), 5.91 (d, J=9.0 Hz, 1H), 4.36 (s, 1H), 4.21 (d, J=8.4 Hz, 1H), 4.00-3.94 (m, 1H), 3.09 (d, J=11.7 Hz, 1H), 2.99 (d, J=9.7 Hz, 1H), 2.92 (d, J=5.1 Hz, 2H), 2.58-2.51 (m, 1H), 2.37 (s, 3H), 2.28-2.21 (m, 2H), 2.15 (s, 3H), 2.12-2.09 (m, 1H), 2.02-1.96 (m, 1H), 1.92-1.85 (m, 2H), 1.84-1.76 (m, 2H), 1.74-1.69 (m, 1H), 1.68-1.56 (m, 4H), 1.34-1.30 (m, 1H), 1.23-1.19 (m, 1H), 1.16 (d, J=6.3 Hz, 3H), 0.99 (d, J=6.7 Hz, 3H), 0.97-0.80 (m, 9H) ppm; $^{13}$C NMR: (CD$_3$OD, 150 MHz) δ=171.8, 169.8, 169.7, 160.7, 149.0, 137.7, 137.2, 128.4, 127.3, 125.3, 124.1, 123.0, 69.3, 67.8, 57.6, 54.4, 50.0, 49.2, 42.2, 39.8, 36.1, 35.5, 31.8, 29.1, 28.9, 28.8, 23.9, 23.6, 21.7, 18.7, 17.5, 17.0, 16.5, 14.3, 9.0 ppm; HRMS calcd for C$_{37}$H$_{55}$N$_5$O$_7$S [M+H]$^+$ 714.3895. found 714.3901.

Tb44

Methyl (2S,4R)-4-(2-((1R,3R)-1-acetoxy-3-((2S,3S)—N,3-dimethyl-2-(1-methyl-1H-pyrrole-2-carboxamido)pentanamido)-4-methylpentyl)thiazole-4-carboxamido)-2-methyl-5-phenylpentanoate (Tb44)

According to the procedure described for the synthesis of Tb53, Fmoc group was removed through the action of tris(2-aminoethyl)amine, followed by coupling with N-Me-2-pyrrole carboxylic acid 84, furnishing analog Tb44 as a off-white amorphous solid (54 mg, 74% for the two steps). Tb44: R$_f$=0.44 (silica gel, 50% EtOAc in hexanes); [α]$_D^{22}$=−19.0 (c=1.25, MeOH); FT-IR (neat) $\tilde{v}_{max}$: 2966, 2876, 1736, 1630, 1540, 1492, 1435, 1371, 1285, 1220, 1170, 1095, 1054, 731, 702, 673 cm$^{-1}$; $^1$H NMR (CD$_3$OD, 600 MHz) δ=8.08 (s, 1H), 7.27-7.20 (m, 4H), 7.19-7.13 (m, 1H), 6.85-6.80 (m, 1H), 6.76 (dd, J=3.9, 1.7 Hz, 1H), 6.06 (dd, J=3.9, 2.6 Hz, 1H), 5.72 (dd, J=11.3, 2.4 Hz, 1H), 4.87 (d, J=8.9 Hz, 1H), 4.48 (m, 1H), 4.35 (m, 1H), 3.86 (s, 3H), 3.59 (s, 3H), 3.14 (s, 3H), 2.88 (m, 2H), 2.65-2.57 (m, 1H), 2.38 (ddd, J=14.5, 11.3, 2.9 Hz, 1H), 2.25 (m, 1H), 2.16 (s, 3H), 2.02-1.94 (m, 2H), 1.89-1.80 (m, 1H), 1.74 (ddd, J=14.3, 10.5, 4.0 Hz, 1H), 1.66 (m, 1H), 1.33-1.17 (m, 2H), 1.14 (d, J=7.1 Hz, 3H), 1.02 (d, J=6.6 Hz, 3H), 1.00 (d, J=6.7 Hz, 3H), 0.94 (t, J=7.4 Hz, 3H), 0.82 (d, J=6.6 Hz, 3H) ppm; $^{13}$C NMR: (CD$_3$OD, 150 MHz) δ=176.3, 173.7, 169.83, 169.79, 161.8, 160.7, 148.8, 137.5, 128.5, 127.7, 127.4, 125.5, 124.3, 123.2, 112.4, 106.4, 69.3, 53.0, 50.3, 48.2, 47.6, 40.3, 36.8, 35.7, 35.6, 34.7, 33.7, 29.1, 23.7, 18.8, 18.5, 18.0, 16.1, 14.4, 9.3 ppm; HRMS calcd for C$_{38}$H$_{53}$N$_5$O$_7$S [M+Na]$^+$ 746.3558. found 746.3564.

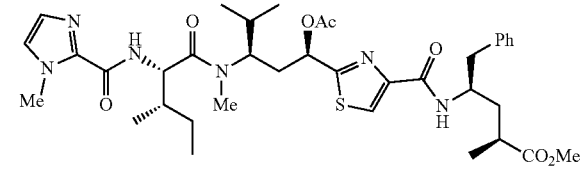

Tb45

Methyl (2S,4R)-4-(2-((1R,3R)-1-acetoxy-3-((2S,3S)—N,3-dimethyl-2-(1-methyl-1H-imidazole-2-carboxamido)pentanamido)-4-methylpentyl)thiazole-4-carboxamido)-2-methyl-5-phenylpentanoate (Tb45)

According to the procedure described for the synthesis of Tb53, Fmoc group was removed through the action of tris(2-aminoethyl)amine, followed by coupling with N-Me-2-imidazole carboxylic acid 85, furnishing analog Tb45 as a off-white amorphous solid (54 mg, 74% for the two steps). Tb45: R$_f$=0.33 (silica gel, 50% EtOAc in hexanes); [α]$_D^{22}$=−26.2 (c=1.50, MeOH); FT-IR (neat) $\tilde{v}_{max}$: 3389, 2965, 2876, 1735, 1646, 1536, 1496, 1474, 1370, 1285, 1220, 1084, 1047, 1033, 752, 702 cm$^{-1}$; $^1$H NMR: (CD$_3$OD, 600 MHz) δ=8.08 (s, 1H), 7.27-7.21 (m, 5H), 7.19-7.14 (m, 1H), 7.01 (d, J=0.5 Hz, 1H), 5.72 (dd, J=11.2, 2.5 Hz, 1H), 4.90 (d, J=7.1 Hz, 1H), 4.46 (m, 1H), 4.36 (m, 1H), 4.00 (s, 3H), 3.59 (s, 3H), 3.14 (s, 3H), 2.95-2.83 (m, 2H), 2.60 (m, 1H), 2.38 (ddd, J=14.6, 11.3, 2.9 Hz, 1H), 2.26 (dd, J=15.3, 11.2 Hz, 1H), 2.15 (s, 3H), 2.07-1.91 (m, 3H), 1.90-1.83 (m, 1H), 1.74 (m, 1H), 1.67 (m, 1H), 1.26-1.18 (m, 1H), 1.14 (d, J=7.1 Hz, 3H), 1.03 (m, 6H), 0.94 (t, J=7.4 Hz, 3H), 0.81 (d, J=6.6 Hz, 3H) ppm; $^{13}$C NMR: (CD$_3$OD, 150 MHz) δ=176.8, 176.3, 172.8, 169.8, 160.7, 158.4, 148.8, 137.7, 137.5, 128.5, 127.4, 126.7, 125.53, 125.45, 123.2, 69.2, 53.1, 50.3, 48.2, 40.4, 36.8, 36.1, 35.7, 33.9, 33.7, 29.0, 23.1, 18.8, 18.5, 18.1, 16.1, 15.7, 14.5, 9.5 ppm; HRMS calcd for C$_{37}$H$_{52}$N$_6$O$_7$S [M+Na]$^+$ 747.3510. found 747.3492.

Tb46

Methyl (2S,4R)-4-(2-((1R,3R)-1-acetoxy-3-((S)-2-cyclopropyl-N-methyl-2-((R)-1-methylpiperidine-2-carboxamido)acetamido)-4-methylpentyl)thiazole-4-carboxamido)-cubane-1-carboxylate (Tb46)

To a stirred solution of 62 (11 mg, 0.02 mmol) in dry DMF (0.5 mL) at 0° C. were added HATU (38 mg, 0.1 mmol) followed by Et₃N (0.03 mL, 0.2 mmol) and the resulting mixture was stirred for 5 min at the same temperature. A solution of 29 (30 mg, 0.1 mmol) in dry DMF (0.2 mL) was then added and the stirring was continue for 16 h while allowing the temperature to slowly rise to 25° C. The reaction mixture was diluted with H₂O (5 mL) and the resulting solution was extracted with EtOAc (3×10 mL). The combined organic extracts were washed with brine (5 mL), dried over Na₂SO₄ and evaporated under reduced pressure. The obtained residue was purified by flash column chromatography (silica gel, 05→20% MeOH in CH₂Cl₂) to furnish Tb46 (9.6 mg, 70%) as a white amorphous solid. Tb46: $R_f$=0.55 (silica gel, 10% MeOH in CH₂Cl₂); $[\alpha]_D^{22}$=+6.38 (c=0.345, MeOH); FT-IR (neat): 2935, 1722, 1646, 1532, 1491, 1371, 1311, 1217, 1092, 1044, 749 cm⁻¹; ¹H NMR: (CD₃OD, 600 MHz) δ=8.16 (s, 1H), 5.79 (dd, J=11.4, 2.5 Hz, 1H), 4.57 (s, 1H), 4.46 (s, 1H), 4.24 (dd, J=6.2, 3.9 Hz, 3H), 4.21 (d, J=9.1 Hz, 1H), 4.17 (dd, J=6.2, 4.0 Hz, 3H), 3.71 (s, 3H), 3.06 (s, 3H), 2.95 (d, J=11.6 Hz, 1H), 2.61 (dd, J=11.2, 2.4 Hz, 1H), 2.40 (ddd, J=14.8, 11.5, 3.3 Hz, 1H), 2.29 (d, J=12.0 Hz, 1H), 2.22 (s, 3H), 2.15 (s, 3H), 2.14-2.09 (m, 1H), 1.88-1.82 (m, 1H), 1.80-1.74 (m, 2H), 1.65 (dd, J=18.3, 8.6 Hz, 1H), 1.61-1.53 (m, 1H), 1.36-1.30 (m, 1H), 1.23-1.15 (m, 1H), 1.02 (d, J=6.5 Hz, 3H), 0.84 (d, J=6.6 Hz, 3H), 0.71-0.64 (m, 1H), 0.63-0.57 (m, 1H), 0.53 (td, J=9.8, 4.9 Hz, 1H), 0.37 (td, J=9.8, 5.0 Hz, 1H) ppm; ¹³C NMR: (CD₃OD, 150 MHz) δ=173.1, 172.9, 172.5, 169.9, 169.8, 160.6, 148.7, 123.4, 68.9, 68.4, 66.2, 55.4, 54.7, 52.9, 50.1, 49.5, 47.6, 44.3, 42.6, 33.6, 29.4, 28.8, 24.1, 22.3, 18.8, 18.4, 18.2, 12.3, 2.4, 1.5 ppm; HRMS calcd for C₃₅H₄₇NSO₇S [M+Na]⁺ 704.3088. found 704.3091.

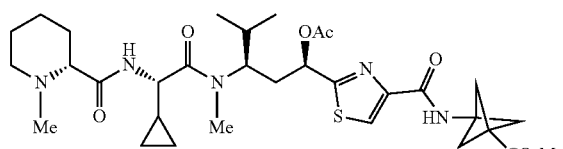

Methyl 3-(2-((1R,3R)-1-acetoxy-3-((S)-2-cyclopropyl-N-methyl-2-((R)-1-methylpiperidine-2-carboxamido)acetamido)-4-methylpentyl)thiazole-4-carboxamido)bicyclo[1.1.1]pentane-1-carboxylate (Tb47)

To a stirred solution of 62 (11 mg, 0.02 mmol) in dry DMF (0.5 mL) at 0° C. were added HATU (38 mg, 0.1 mmol) followed by Et₃N (0.03 mL, 0.2 mmol) and the resulting mixture was stirred for 5 min at the same temperature. A solution of 29 (25 mg, 0.1 mmol) in dry DMF (0.2 mL) was then added and the stirring was continue for 16 h while allowing the temperature to slowly rise to 25° C. The reaction mixture was diluted with H₂O (5 mL) and the resulting solution was extracted with EtOAc (3×10 mL). The combined organic extracts were washed with brine (5 mL), dried over Na₂SO₄ and evaporated under reduced pressure. The obtained residue was purified by flash column chromatography (silica gel, 05→20% MeOH in CH₂Cl₂) to furnish Tb47 (9.3 mg, 72%) as a white amorphous solid. Tb47: $R_f$=0.54 (silica gel, 10% MeOH in CH₂Cl₂); $[\alpha]_D^{22}$=+9.58 (c=0.24, MeOH); FT-IR (neat): 3309, 2929, 1742, 1645, 1535, 1489, 1349, 1205, 1049 cm⁻¹; ¹H NMR: (CD₃OD, 600 MHz) δ=8.15 (s, 1H), 5.77 (dd, J=11.5, 2.5 Hz, 1H), 4.57 (s, 2H), 4.47 (s, 1H), 4.21 (d, J=9.1 Hz, 1H), 3.70 (s, 3H), 3.06 (s, 3H), 2.93 (d, J=11.6 Hz, 1H), 2.57 (d, J=8.9 Hz, 1H), 2.44 (s, 6H), 2.42-2.37 (m, 1H), 2.26 (dd, J=21.6, 8.9 Hz, 1H), 2.20 (s, 3H), 2.13 (s, 3H), 2.11-2.06 (m, 1H), 1.86-1.81 (m, 1H), 1.80-1.74 (m, 2H), 1.67-1.62 (m, 1H), 1.61-1.54 (m, 1H), 1.32 (m, 1H), 1.19 (ddd, J=13.3, 8.3, 4.2 Hz, 1H), 1.02 (d, J=6.5 Hz, 3H), 0.84 (d, J=6.6 Hz, 3H), 0.70-0.65 (m, 1H), 0.62-0.57 (m, 1H), 0.52 (td, J=9.9, 5.0 Hz, 1H), 0.36 (td, J=9.8, 5.0 Hz, 1H) ppm; ¹³C NMR: (CD₃OD, 150 MHz) δ=173.2, 172.9, 169.8, 169.7, 169.6, 161.6, 148.8, 123.5, 68.8, 68.4, 54.6, 53.4, 52.8, 50.3, 47.5, 44.7, 42.5, 35.2, 33.5, 29.4, 28.7, 24.1, 22.3, 18.8, 18.3, 18.2, 12.3, 2.3, 1.4 ppm; HRMS calcd for C₃₂H₄₇N₅O₇S [M+Na]⁺ 668.3088. found 668.3081.

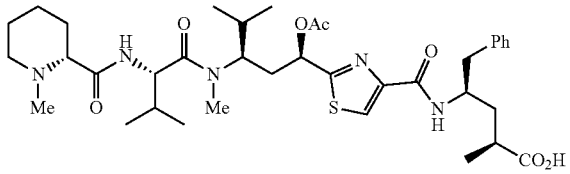

(2S,4R)-4-(2-((1R,3R)-1-Acetoxy-3-((S)—N,3-dimethyl-2-((R)-1-methylpiperidine-2-carboxamido)butanamido)-4-methylpentyl)thiazole-4-carboxamido)-2-methyl-5-phenylpentanoic Acid (Tb48)

According to the procedure described for the synthesis of Tb54, methyl ester and OAc was removed through the action of trimethyltinhydroxide, followed by reacetylation with acetic anhydride, furnishing acid analog Tb48 as a off-white amorphous solid (12 mg, 50% for the two steps). Tb48: $R_f$=0.33 (silica gel, 50% EtOAc in hexanes); $[\alpha]$=−6.9 (c=0.75, MeOH); FT-IR (neat) $\tilde{v}_{max}$: 2962, 2303, 1752, 1642, 1543, 1496, 1408, 1370, 1221, 1087, 1034, 749, 704 cm⁻¹; ¹H NMR: (CD₃OD, 600 MHz) δ=8.08 (s, 1H), 7.25-7.22 (m, 4H), 7.18-7.14 (m, 1H), 5.73 (dd, J=10.8, 2.7 Hz, 1H), 4.68 (d, J=7.2 Hz, 1H), 4.41-4.32 (m, 2H), 3.14-3.11 (m, 1H), 3.09 (s, 3H), 3.00 (d, J=10.4 Hz, 1H), 2.95-2.88 (m, 2H), 2.53 (m, 1H), 2.46-2.41 (m, 1H), 2.38 (s, 3H), 2.37-2.33 (m, 1H), 2.28 (dd, J=25.0, 12.7 Hz, 1H), 2.15 (s, 3H), 2.12-2.06 (m, 1H), 2.00 (ddd, J=13.5, 9.7, 3.9 Hz, 1H), 1.94-1.90 (m, 2H), 1.81 (d, J=13.2 Hz, 1H), 1.75 (d, J=13.6 Hz, 1H), 1.72-1.59 (m, 3H), 1.45-1.36 (m, 1H), 1.16 (d, J=7.0 Hz, 3H), 1.02 (m, 6H), 0.98 (d, J=6.7 Hz, 3H), 0.82 (d, J=6.6 Hz, 3H) ppm; ¹³C NMR: (CD₃OD, 150 MHz) δ=181.6, 173.0, 172.9, 169.8, 169.5, 160.7, 149.1, 137.8, 128.6, 127.2, 125.3, 122.9, 69.2, 68.3, 54.6, 54.0, 49.4, 42.6, 39.8, 38.2, 37.8, 33.5, 29.5, 29.4, 29.0, 24.0, 22.1, 18.8, 18.5, 18.4, 18.3, 17.2, 16.5 ppm; HRMS calcd for C₃₇H₅₅N₅O₇S [M+H]⁺ 714.3895. found 714.3871.

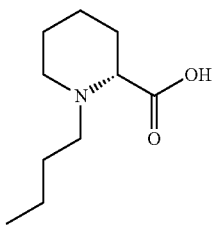

(R)-1-Butylpiperidine-2-carboxylic Acid (78)

To a stirred solution of D-Pipecolinic acid 78a (200 mg, 1.5 mmol) in anhydrous methanol (3 mL), under argon condition were added 10% Pd/C (50 mg) followed by cyclopropanecarboxaldehyde (0.12 mL, 1.7 mmol) at 25° C. The argon balloon was replaced with hydrogen, additionally aldehyde (0.06 ml, 0.08 mmol) was added and the reaction mixture was stirred for 20 h at 25° C. The reaction mixture was filtered through celite, wash with methanol and evaporated under reduced pressure. The obtained residue was purified by flash column chromatography (silica gel, 5→20% MeOH in $CH_2Cl_2$) to afford acid 78 (11.4 mg, 86%) as a white solid. 78: $R_f$=0.5 (silica gel, 15% MeOH in $CH_2Cl_2$); 1H NMR: ($CDCl_3$, 600 MHz) δ=4.07 (s, 1H), 3.58 (d, J=12.7 Hz, 1H), 3.37-3.25 (m, 1H), 3.25-3.13 (m, 1H), 2.81 (td, J=12.7, 12.1, 5.5 Hz, 1H), 2.61 (t, J=11.8 Hz, 1H), 2.16 (d, J=14.2 Hz, 1H), 1.90-1.71 (m, 3H), 1.68-1.58 (m, 3H), 1.39 (t, J=12.4 Hz, 1H), 1.31-1.17 (m, 2H), 0.84 (t, J=7.3 Hz, 3H); $^{13}C$ NMR: ($CDCl_3$, 150 MHz) δ=171.0, 68.0, 55.7, 51.3, 28.0, 25.4, 22.4, 21.6, 19.8, 13.2; HRMS calcd for $C_{10}H_{19}NO_2$ [M+H$^+$] 186.1494. found 186.1489.

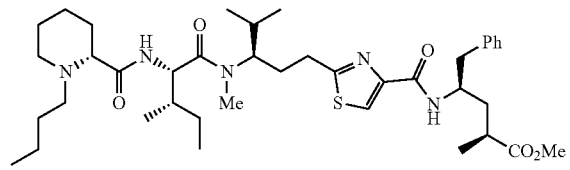

PTb-D49

Methyl(2S,4R)-4-(2-((R)-3-((2S,3S)-2-((R)-1-butylpiperidine-2-carboxamido)-N,3-dimethylpentanamido)-4-methylpentyl)thiazole-4-carboxamido)-2-methyl-5-phenylpentanoate (PTb-D49)

To an ice-cooled stirred solution of Fmoc-derivative 16 (15 mg, 0.02 mmol) in $CH_2Cl_2$ (1 mL) was added tris(2-aminoethyl)amine (0.04 mL, 0.3 mmol). The reaction mixture was stirred for 2 h at 25° C. and then diluted with ethyl acetate (5 mL). The solution was washed with saturated aqueous $NaHCO_3$ solution (5 mL) and brine (5 mL), dried over $Na_2SO_4$, and concentrated. The crude amine so obtained (10 mg, quantitative) was used for the next step without further purification.

To an ice-cooled stirred solution of (R)-1-butylpiperidine-2-carboxylic acid 79 (10 mg, 0.05 mmol) in DMF (0.5 ml) at 0° C. was added HATU (21 mg, 0.05 mmol) followed by the above obtained crude amine (10 mg, 0.02 mmol) and $Et_3N$ (0.01 mL, 0.11 mmol) and the reaction mixture was stirred at 25° C. for 24 h. The reaction mixture was diluted with $H_2O$ (2 mL) and the resulting solution was extracted with EtOAc (3×5 mL). The combined organic extracts were washed with saturated aqueous $NaHCO_3$ solution (2 mL) and brine (5 mL), dried over $Na_2SO_4$ and evaporated under reduced pressure. The obtained residue was purified by flash column chromatography (silica gel, 3→15% MeOH in $CH_2Cl_2$) to afford analog PTb-D49 (11.4 mg, 82%) as a colorless oil. PTb-D49: $R_f$=0.4 (silica gel, 10% MeOH in $CH_2Cl_2$); $[α]_D^{22}$=+10.8 (c=1.0, $CHCl_3$); FT-IR (neat) $\tilde{v}_{max}$: 3292, 2958, 2928, 2873, 1735, 1671, 1636, 1541, 1497, 1460, 1260, 1198, 1096, 700 cm$^{-1}$; $^1H$ NMR: ($CDCl_3$, 600 MHz) δ=7.88 (s, 1H), 7.36 (d, J=9.3 Hz, 1H), 7.26-7.16 (m, 5H), 4.78 (t, J=9.0 Hz, 1H), 4.47-4.33 (m, 2H), 3.63 (d, J=8.0 Hz, 3H), 3.07 (dt, J=12.4, 3.9 Hz, 1H), 3.02 (s, 3H), 2.97 (dd, J=13.8, 6.6 Hz, 1H), 2.91-2.78 (m, 3H), 2.71 (dd, J=10.3, 3.6 Hz, 1H), 2.65-2.52 (m, 2H), 2.16-2.08 (m, 2H), 2.04 (ddd, J=13.9, 9.4, 4.1 Hz, 1H), 1.94 (td, J=11.6, 2.7 Hz, 1H), 1.89-1.50 (m, 9H), 1.41 (ddt, J=17.1, 12.9, 5.8 Hz, 3H), 1.27 (dt, J=24.3, 7.5 Hz, 4H), 1.16 (d, J=7.1 Hz, 3H), 0.97 (dd, J=6.7, 5.3 Hz, 6H), 0.90 (td, J=7.3, 1.6 Hz, 6H), 0.79 (d, J=6.6 Hz, 3H); $^{13}C$ NMR: ($CDCl_3$, 150 MHz) δ=176.6, 174.8, 173.1, 169.6, 160.7, 149.8, 137.8, 129.5, 128.3, 126.4, 122.3, 68.0, 57.2, 53.1, 51.7, 51.4, 48.6, 41.2, 38.2, 37.4, 36.5, 30.2, 30.1, 29.8, 29.7, 29.4, 24.7, 24.6, 23.4, 20.6, 20.1, 19.6, 17.9, 16.5, 15.8, 14.1, 11.3, 11.1; HRMS calcd for $C_{40}H_{63}N_5O_5S$ [M+Na$^+$] 748.4448. found 748.4437.

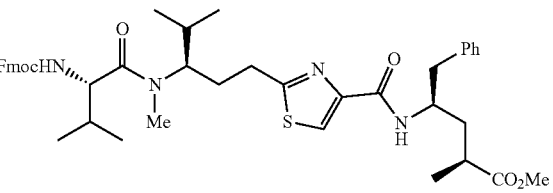

86

Methyl(2S,4R)-4-(2-((R)-3-((S)-2-((((9H-fluoren-9-yl)methoxy)carbonyl)amino)-N,3-dimethylbutanamido)-4-methylpentyl)thiazole-4-carboxamido)-2-methyl-5-phenylpentanoate (86)

To an ice-cooled stirred solution of 15 (40 mg, 0.15 mmol) in $CH_2Cl_2$ (2 mL) was added trifluoroacetic acid (0.25 mL, 3.31 mmol) and the reaction mixture was stirred for 2 h while warming up to 25° C. Evaporation of the volatile components under reduced pressure furnished the crude TFA-ammonium salt (38 mg, quantitative), which was used for the following step without further purification.

To a stirred, ice-cooled solution of crude ammonium salt from the previous step and i-$Pr_2NEt$ (0.1 mL, 0.51 mmol) in DMF (0.5 mL) was added dropwise a solution of 86a (255 mg, 0.722 mmol) in DMF (0.2 mL) and stirring was continued for 18 h at 25° C. The reaction mixture was diluted with ethyl acetate (5 mL), washed with saturated aqueous $NaHCO_3$ solution (5 mL) and brine (5 mL), dried over $Na_2SO_4$ and concentrated under reduced pressure. The obtained residue was purified by flash column chromatography (silica gel, 10→70% EtOAc in hexanes) to afford pure tripeptide 86 (53 mg, 95%) as a white amorphous solid. 77: $R_f$=0.3 (silica gel, 50% EtOAc in hexanes); $[α]_D^{22}$=−12.4 (c=1.0, $CHCl_3$); FT-IR (neat) $\tilde{v}_{max}$: 3300, 2962, 2926, 1721, 1638, 1541, 1495, 1451, 1296, 1235, 1085, 1029, 758, 741, 701 cm$^{-1}$; $^1H$ NMR: ($CDCl_3$, 600 MHz) δ=7.89 (s, 1H), 7.76 (d, J=7.6 Hz, 2H), 7.63-7.55 (m, 2H), 7.39 (q, J=8.3, 7.9 Hz, 2H), 7.31 (dt, J=15.0, 8.5 Hz, 4H), 7.24-7.12 (m, 4H), 5.55 (d, J=9.4 Hz, 1H), 4.54 (dd, J=9.4, 6.2 Hz, 1H), 4.44-4.33 (m, 3H), 4.30-4.16 (m, 1H), 3.63 (s, 3H), 2.96 (s, 3H), 2.94-2.74 (m, 3H), 2.72-2.56 (m, 1H), 2.17-2.09 (m, 1H), 2.09-1.99 (m, 2H), 1.72 (d, J=6.6 Hz, 1H), 1.68-1.55 (m, 3H), 1.17 (d, J=7.1 Hz, 3H), 1.02 (d, J=6.7 Hz, 3H), 1.00-0.89 (m, 6H), 0.82 (d, J=6.6 Hz, 3H); $^{13}C$ NMR: ($CDCl_3$, 150 MHz) (=176.6, 173.1, 169.5, 160.6, 156.5, 149.8, 143.9, 141.3, 137.8, 129.5, 128.3, 127.7, 127.0, 126.4, 125.1, 122.3, 120.0, 67.0, 58.8, 56.4, 51.7, 48.6, 47.2, 41.2, 38.1, 36.5, 31.2, 30.2, 30.0, 29.3, 20.4, 20.1, 19.8, 19.7, 17.8, 17.3; HRMS calcd for $C_{44}H_{54}N_4O_6S$ [M+Na$^+$] 789.3662. found 789.3631.

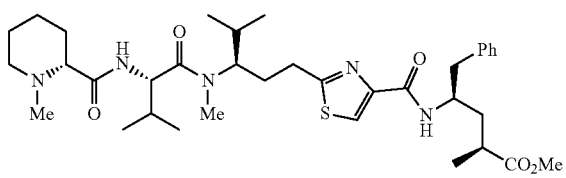

PTb-D50

Methyl(2S,4R)-4-(2-((R)-3-((S)—N,3-dimethyl-2-((R)-1-methylpiperidine-2-carboxamido)butanamido)-4-methylpentyl)thiazole-4-carboxamido)-2-methyl-5-phenylpentanoate (PTb-D50)

To an ice-cooled stirred solution of Fmoc-derivative 86 (15 mg, 0.02 mmol) in $CH_2Cl_2$ (1 mL) was added tris(2-aminoethyl)amine (0.04 mL, 0.3 mmol). The reaction mixture was stirred for 2 h at 25° C. and then diluted with ethyl acetate (5 mL). The solution was washed with saturated aqueous $NaHCO_3$ solution (5 mL) and brine (5 mL), dried over $Na_2SO_4$, and concentrated. The crude amine so obtained (10 mg, quantitative) was used for the next step without further purification.

To an ice-cooled stirred solution of N-methyl-(D)-pipecolinic acid 10 (8 mg, 0.05 mmol) in DMF (0.5 ml) at 0° C. was added HATU (21 mg, 0.05 mmol) followed by the above obtained crude amine (10 mg, 0.02 mmol) and $Et_3N$ (0.01 mL, 0.11 mmol) and the reaction mixture was stirred at 25° C. for 24 h. The reaction mixture was diluted with $H_2O$ (2 mL) and the resulting solution was extracted with EtOAc (3×5 mL). The combined organic extracts were washed with saturated aqueous $NaHCO_3$ solution (2 mL) and brine (5 mL), dried over $Na_2SO_4$ and evaporated under reduced pressure. The obtained residue was purified by flash column chromatography (silica gel, 3→15% MeOH in $CH_2Cl_2$) to afford analog PTb-D50 (10.6 mg, 81%) as a colorless oil. PTb-D50: $R_f$=0.5 (silica gel, 10% MeOH in $CH_2Cl_2$); $[\alpha]_D^{22}$=+10.8 (c=1.0, $CHCl_3$); FT-IR (neat) $\tilde{v}_{max}$: 3300, 2926, 2853, 1735, 1670, 1636, 1541, 1497, 1370, 1260, 1198, 1169, 1033, 745, 700 cm$^{-1}$; $^1$H NMR: ($CDCl_3$, 600 MHz) δ=7.87 (s, 1H), 7.40 (d, J=9.3 Hz, 1H), 7.24 (d, J=2.1 Hz, 3H), 7.22-7.16 (m, 2H), 7.13 (d, J=9.4 Hz, 1H), 4.81-4.70 (m, 1H), 4.40 (tdd, J=10.2, 7.0, 4.2 Hz, 2H), 3.63 (d, J=10.0 Hz, 3H), 3.01 (s, 3H), 2.97 (q, J=9.0, 8.0 Hz, 1H), 2.89 (dq, J=16.2, 9.8, 7.5 Hz, 2H), 2.84-2.78 (m, 2H), 2.66-2.57 (m, 1H), 2.53-2.47 (m, 1H), 2.26 (s, 3H), 2.06 (dddd, J=39.1, 21.0, 9.7, 4.5 Hz, 4H), 1.87-1.78 (m, 2H), 1.74-1.64 (m, 2H), 1.62 (ddd, J=14.2, 9.9, 4.5 Hz, 3H), 1.55-1.49 (m, 1H), 1.40-1.33 (m, 1H), 1.23-1.14 (m, 3H), 1.04-0.93 (m, 9H), 0.79 (d, J=6.6 Hz, 3H); $^{13}$C NMR: ($CDCl_3$, 150 MHz) δ=176.6, 174.4, 173.1, 169.5, 160.7, 149.9, 137.9, 129.5, 128.3, 126.4, 122.2, 69.7, 58.5, 55.4, 54.1, 51.7, 48.6, 45.0, 41.2, 38.2, 36.5, 30.9, 30.5, 30.2, 30.0, 29.7, 29.4, 25.1, 23.3, 20.1, 19.9, 19.6, 18.2, 17.9; HRMS calcd for $C_{36}H_{55}N_5O_8S$ [M+H$^+$] 670.4002. found 670.3997.

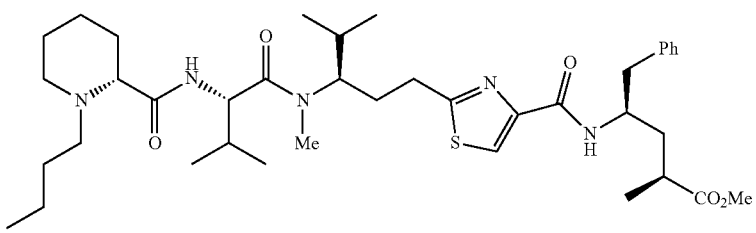

PTb-D51

Methyl(2S,4R)-4-(2-((R)-3-((S)-2-((R)-1-butylpiperidine-2-carboxamido)-N,3-dimethylbutanamido)-4-methylpentyl)thiazole-4-carboxamido)-2-methyl-5-phenylpentanoate (PTb-D51)

To an ice-cooled stirred solution of Fmoc-derivative 86 (15 mg, 0.02 mmol) in $CH_2Cl_2$ (1 mL) was added tris(2-aminoethyl)amine (0.04 mL, 0.3 mmol). The reaction mixture was stirred for 2 h at 25° C. and then diluted with ethyl acetate (5 mL). The solution was washed with saturated aqueous $NaHCO_3$ solution (5 mL) and brine (5 mL), dried over $Na_2SO_4$, and concentrated. The crude amine so obtained (10 mg, quantitative) was used for the next step without further purification.

To an ice-cooled stirred solution of (R)-1-butylpiperidine-2-carboxylic acid 78 (10 mg, 0.05 mmol) in DMF (0.5 ml) at 0° C. was added HATU (21 mg, 0.05 mmol) followed by the above obtained crude amine (10 mg, 0.02 mmol) and $Et_3N$ (0.01 mL, 0.11 mmol) and the reaction mixture was stirred at 25° C. for 24 h. The reaction mixture was diluted with $H_2O$ (2 mL) and the resulting solution was extracted with EtOAc (3×5 mL). The combined organic extracts were washed with saturated aqueous $NaHCO_3$ solution (2 mL) and brine (5 mL), dried over $Na_2SO_4$ and evaporated under reduced pressure. The obtained residue was purified by flash column chromatography (silica gel, 3→15% MeOH in $CH_2Cl_2$) to afford analog PTb-D51 (10.6 mg, 76%) as a colorless oil. PTb-D51: $R_f$=0.5 (silica gel, 10% MeOH in $CH_2Cl_2$); $[\alpha]_D^{22}$=+12.2 (c=1.0, $CHCl_3$); FT-IR (neat) $\tilde{v}_{max}$: 3298, 2958, 2928, 2857, 1735, 1671, 1636, 1542, 1497, 1260, 1169, 1094, 744, 700 cm$^{-1}$; $^1$H NMR: ($CDCl_3$, 600 MHz) δ=7.88 (d, J=2.9 Hz, 1H), 7.36 (d, J=9.2 Hz, 1H), 7.25-7.17 (m, 5H), 4.75 (t, J=8.5 Hz, 1H), 4.47-4.31 (m, 2H), 3.64 (s, 3H), 3.08 (d, J=11.8 Hz, 1H), 3.01 (s, 3H), 3.00-2.93 (m, 1H), 2.89 (dd, J=13.7, 6.8 Hz, 1H), 2.85-2.81 (m, 1H), 2.80 (s, 1H), 2.73 (dd, J=10.4, 3.7 Hz, 1H), 2.66-2.56 (m, 2H), 2.21-1.90 (m, 6H), 1.89-1.50 (m, 8H), 1.43 (d, J=11.4 Hz, 2H), 1.37-1.22 (m, 3H), 1.16 (dd, J=7.2, 3.4 Hz, 3H), 1.04-0.94 (m, 9H), 0.90 (t, J=7.4 Hz, 3H), 0.79 (d, J=6.6 Hz, 3H); $^{13}$C NMR: ($CDCl_3$, 150 MHz) δ=176.6, 174.8, 173.2, 169.6, 160.7, 149.9, 137.8, 129.5, 128.3, 126.4, 122.3, 67.9, 57.0, 54.1, 51.7, 51.3, 48.6, 41.2, 38.6, 38.2, 36.5, 31.0, 30.2, 30.1, 29.7, 29.6, 29.4, 24.5, 23.4, 20.7, 20.4, 20.1, 19.8, 19.6, 18.2, 17.9, 14.1; HRMS calcd for $C_{36}H_{55}N_5O_5S$ [M+Na$^+$] 734.4291. found 734.4298.

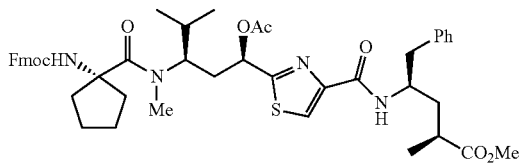

89

Methyl (2S,4R)-4-(2-((1R,3R)-3-(1-((((9H-fluoren-9-yl)methoxy)carbonyl)amino)-N-methylcyclopentane-1-carboxamido)-1-acetoxy-4-methylpentyl)thiazole-4-carboxamido)-2-methyl-5-phenylpentanoate (89)

According to the procedure described for the synthesis of compound 9, Boc-group was removed through the action of TFA, followed by coupling of the resulted amine with compound 88, furnishing compound 89 as a off-white amorphous solid (20 mg, 56% for the two steps). 89: $R_f$=0.33 (silica gel, 50% EtOAc in hexanes); $[\alpha]_D^{22}$=+19.5 (c=0.21, CHCl$_3$); FT-IR (neat) $\tilde{v}_{max}$: 3312, 2960, 2874, 1732, 1644, 1541, 1495, 1451, 1370, 1224, 1087, 1047, 741, 702 cm$^{-1}$; $^1$H NMR: (CDCl$_3$, 600 MHz) δ=8.02 (s, 1H), 7.75 (dd, J=7.4, 3.9 Hz, 2H), 7.59 (m, 2H), 7.38 (dd, J=16.3, 7.9 Hz, 2H), 7.32-7.26 (m, 3H), 7.22-7.16 (m, 3H), 7.12-7.06 (m, 1H), 5.83-5.75 (m, 1H), 5.20-5.14 (s, 1H), 4.50-4.42 (m, 2H), 4.41-4.35 (m, 1H), 4.20 (t, J=6.5 Hz, 1H), 3.62 (s, 3H), 2.90 (s, 3H), 2.86-2.82 (m, 1H), 2.60-2.53 (m, 1H), 2.38-2.27 (m, 3H), 2.18 (s, 3H), 2.15-2.11 (m, 1H), 2.00-1.93 (m, 1H), 1.85-1.77 (m, 2H), 1.72-1.67 (m, 2H), 1.63-1.54 (m, 6H), 1.11 (d, J=7.1 Hz, 3H), 1.02 (d, J=6.4 Hz, 3H), 0.86 (d, J=6.4 Hz, 3H) ppm; $^{13}$C NMR: (CDCl$_3$, 150 MHz) δ=176.6, 172.8, 170.9, 170.3, 160.4, 154.4, 150.0, 143.9, 141.4, 137.6, 129.6, 128.4, 127.7, 127.0, 126.5, 125.0, 123.4, 120.0, 99.8, 69.1, 67.7, 66.1, 51.8, 48.3, 47.4, 41.0, 37.6, 36.4, 34.8, 29.9, 24.5, 24.4, 21.0, 20.3, 19.8, 17.7 ppm; HRMS calcd for $C_{47}H_{56}N_4O_8S$ [M+Na]$^+$ 859.3711. found 859.3694.

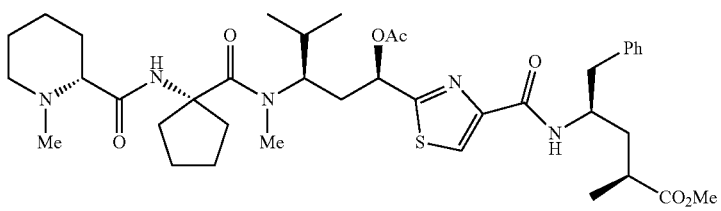

Methyl (2S,4R)-4-(2-((1R,3R)-1-acetoxy-4-methyl-3-(N-methyl-1-((R)-1-methylpiperidine-2-carboxamido)cyclopentane-1-carboxamido)pentyl)thiazole-4-carboxamido)-2-methyl-5-phenylpentanoate (Tb52)

According to the procedure described for the synthesis of Tb53. Fmoc-group was removed through the action of tris(2-aminoethyl)amine, followed by coupling of the resulting amine with N-methyl-(D)-pipecolic acid (10), furnishing analog Tb52 as a off-white amorphous solid (3.0 mg, 69% for the two steps). Tb52: $R_f$=0.35 (silica gel, 10% MeOH in CH$_2$Cl$_2$); $[\alpha]_D^{22}$=+2.3 (c=0.13, CHCl$_3$); FT-IR (neat) $\tilde{v}_{max}$: 3381, 3186, 2956, 2930, 2873, 1736, 1676, 1640, 1542, 1492, 1453, 1401, 1370, 1258, 1222, 1169, 1086, 1046, 933, 751, 701, 659 cm$^{-1}$; $^1$H NMR: (CD$_3$OD, 600 MHz) δ=8.08 (s, 1H), 7.28-7.20 (m, 4H), 7.19-7.15 (m, 1H), 5.75-5.70 (m, 1H), 4.37-4.32 (m, 1H), 3.76 (d, J=10.9 Hz, 1H), 3.59 (s, 3H), 3.48-3.44 (m, 1H), 3.12-3.07 (m, 1H), 3.00 (s, 3H), 2.88 (ddd, J=25.5, 13.6, 6.9 Hz, 2H), 2.79 (s, 3H), 2.62-2.53 (m, 3H), 2.34-2.30 (m, 1H), 2.29-2.19 (m, 3H), 2.15 (s, 3H), 2.13-2.10 (m, 1H), 2.08-2.03 (m, 1H), 2.00-1.89 (m, 4H), 1.83-1.69 (m, 6H), 1.62 (d, J=12.6 Hz, 2H), 1.15 (d, J=7.1 Hz, 3H), 1.02 (d, J=6.6 Hz, 3H), 0.86 (d, J=6.4 Hz, 3H) ppm; $^{13}$C NMR: (CD$_3$OD, 150 MHz) δ=176.3, 170.2, 170.1, 166.0, 160.8, 156.7, 148.8, 137.5, 128.4, 127.4, 125.5, 123.1, 66.9, 54.3, 50.3, 48.3, 41.0, 40.3, 36.9, 36.7, 35.7, 35.1, 33.6, 28.7, 28.6, 28.1, 23.2, 23.0, 22.0, 20.4, 18.9, 18.8, 18.7, 16.1 ppm; HRMS calcd for $C_{39}H_{57}N_5O_7S$ [M+Na$^+$]+ 762.3871. found 762.3855.

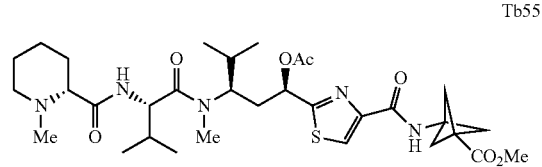 [SMILES: COC(=O)C12CC(NC(=O)c3csc([C@@H](C[C@H](C(C)C)N(C)C(=O)[C@@H](NC(=O)[C@H]4CCCCN4C)C(C)C)OC(C)=O)n3)(C1)C2]

Tb55

Methyl 3-(2-((1R,3R)-1-acetoxy-3-((S)—N,3-dimethyl-2-((R)-1-methylpiperidine-2-carboxamido)butanamido)-4-methylpentyl)thiazole-4-carboxamido)bicyclo[1.1.1]pentane-1-carboxylate (Tb55)

To a stirred solution of acid 74 (5 mg, 0.01 mmol) in dry DMF (0.4 mL) was added HATU (4.3 mg, 0.012 mmol) followed by a solution of amine 30 (1.6 mg, 0.012 mmol) and Et$_3$N (0.003 mL, 0.024 mmol), in DMF (0.1 mL) at 25° C., and stirring continued for 18 h at the same temperature. The reaction mixture was diluted with H$_2$O (5 mL) and the resulting solution was extracted with EtOAc (3×10 mL). The combined organic extracts were washed with brine (2×5 mL), dried over Na$_2$SO$_4$ and evaporated under reduced pressure. The obtained residue was purified by flash column chromatography (silica gel, 3%→15% MeOH in CH$_2$Cl$_2$) to furnish analog Tb55 (10.6 mg, 75%) as a light yellow amorphous solid. Tb55: $R_f$=0.4 (silica gel, 10% MeOH in CH$_2$Cl$_2$); $[\alpha]_D^{22}$=+12.2 (c=1.0, CHCl$_3$); FT-IR $v_{max}$ (neat): 2924, 2853, 1742, 1674, 1644, 1533, 1489, 1349, 1204, 1049, 754; $^1$H NMR: (CDCl$_3$, 600 MHz) δ=8.04 (s, 1H), 7.65 (s, 1H), 5.68 (dd, J=11.2, 2.8 Hz, 1H), 4.74 (t, J=7.7 Hz, 1H), 4.56 (s, 1H), 3.71 (s, 3H), 3.02 (s, 3H), 2.91 (s, 1H), 2.49 (s, 6H), 2.38-2.30 (m, 2H), 2.25 (s, 3H), 2.16 (s, 3H), 2.08-1.99 (m, 2H), 1.57 (d, J=42.2 Hz, 6H), 1.43-1.15 (m, 2H), 1.01 (dd, J=6.7, 1.7 Hz, 6H), 0.98 (d, J=6.7 Hz, 3H), 0.79 (d, J=6.6 Hz, 3H): $^{13}$C NMR: (CDCl$_3$, 150 MHz) δ=173.4, 170.1, 170.0, 169.9, 161.1, 149.8, 123.7, 69.7, 69.5, 55.4, 54.9, 54.6, 53.7, 51.8, 51.7, 45.7, 44.9, 36.2, 34.9, 30.7, 30.5, 30.0, 29.7, 25.1, 23.2, 20.8, 20.1, 20.0, 19.6, 17.9; HRMS calcd for C$_{32}$H$_{49}$N$_5$O$_7$S [M+Na$^+$] 670.3250. found 670.3241.

Methyl 2-(3-((tert-butoxycarbonyl)amino)bicyclo[1.1.1]pentan-1-yl)acetate (79b)

To a stirred solution of 3-((tert-butoxycarbonyl)amino)bicyclo[1.1.1]pentane-1-carboxylic acid 22 (10 mg, 0.04 mmol) and Et$_3$N (0.006 mL) in THF (1 mL) at −20° C. was added isobutyl Chloroformate (0.006 mL, 0.05 mmol). After stirring for 30 min at the same temperature, precipitated Et$_3$NH$^+$Cl$^−$ was filtered off. Acetonitrile (0.5 mL) and TMSCHN$_2$ (2M in hexane, 0.04 mL, 0.08 mmol) were added to the filtrate at −20° C. and the mixture was stirred for 18 h, allowing the temperature to gradually rise to room temperature. Diethyl ether (5 mL) was then added and the mixture was extracted with 10% aqueous citric acid and saturated NaHCO$_3$. Combined organic extracts were dried over Na$_2$SO$_4$ and evaporated under reduced pressure. The obtained residue was purified by flash column chromatography (silica gel, 10→80% EtOAc in hexanes) to afford diazoketone 79a (quantitative yield) as a yellowish solid. 79a: R$_f$=0.3 (silica gel, 50% EtOAc in hexanes); $^1$H NMR: (CDCl$_3$, 600 MHz) δ=5.29 (s, 1H), 4.97 (s, 1H), 2.24 (s, 6H), 1.44 (s, 9H); $^{13}$C NMR: (CDCl$_3$, 150 MHz) δ=190.7, 154.7, 79.9, 54.0, 53.4, 45.3, 40.4, 28.4.

The above obtained diazoketone 79a was suspended in MeOH (0.6 mL) and a solution of silver benzoate (2 mg, 0.01 mmol) in Et$_3$N (0.2 mL) was gradually added while the mixture was sonicated in an ultrasound bath. The reaction was completed in 30 min. at room temperature. Methanol was evaporated and the residue was dissolve in EtOAc (5 mL), extracted with saturated aq. NaHCO$_3$. Combined organic extracts were dried over Na$_2$SO$_4$ and evaporated under reduced pressure. The obtained residue was purified by flash column chromatography (silica gel, 10→50% EtOAc in hexanes) to afford pure homologated ester 79b (7.6 mg, 68%) as a yellowish solid. 79b: R$_f$=0.4 (silica gel, 30% EtOAc in hexanes); FT-IR ν$_{max}$ (neat): 3359, 2977, 2918, 1705, 1502, 1366, 1271, 1253, 1204, 1172, 1154, 1015, 781; $^1$H NMR: (CDCl$_3$, 600 MHz) δ=4.92 (s, 1H), 3.66 (s, 3H), 2.58 (s, 2H), 1.99 (s, 6H), 1.44 (s, 9H); $^{13}$C NMR: (CDCl$_3$, 150 MHz) δ=171.8, 118.9, 53.5, 51.5, 45.8, 35.6, 32.9, 28.4.

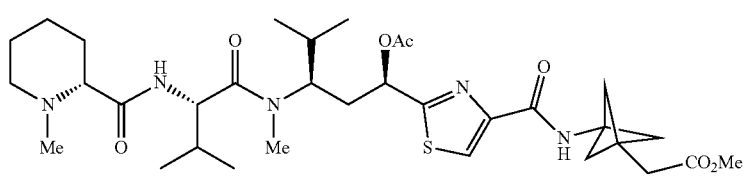

Methyl 2-(3-(2-((1R,3R)-1-acetoxy-3-((S)—N,3-dimethyl-2-((R)-1-methylpiperidine-2-carboxamido)butanamido)-4-methylpentyl)thiazole-4-carboxamido)bicyclo[1.1.1]pentan-1-yl) (Tb56)

To a stirred solution of carbamate 79b (12 mg, 0.05 mmol) in CH$_2$Cl$_2$ (0.5 mL) at 0° C. was added TFA (0.16 mL, 2.1 mmol) and the mixture was stirred for 30 min while the temperature gradually rise to 25° C. The reaction mixture was evaporated under reduced pressure to furnish crude amine 79 (10 mg, quantitative), which was used in the next step without further purification.

To a stirred solution of acid 74 (5 mg, 0.01 mmol) in dry DMF (0.4 mL) were added HATU (5 mg, 0.012 mmol) and Et$_3$N (0.003 mL, 0.024 mmol) at 0° C. and the reaction mixture was stirred for 30 min at 25° C. A solution of the previously synthesized amine 79 (2 mg, 0.012 mmol) in dry DMF (0.2 mL) was then added and stirring was continued at the same temperature for 18 h. The reaction mixture was diluted with H$_2$O (5 mL) and the resulting solution was extracted with EtOAc (3×10 mL). The combined organic extracts were washed with brine (5 mL), dried over Na$_2$SO$_4$ and evaporated under reduced pressure. The resulting residue was purified using flash column chromatography (silica gel, 2→15% MeOH in CH$_2$Cl$_2$) to produce analog Tb56 (5 mg, 79%) as a colorless amorphous solid. Tb56: R$_f$=0.4 (silica gel, 10% MeOH in CH$_2$Cl$_2$); [α]$_D^{22}$=+11.2 (c=1.0, CHCl$_3$); FT-IR (neat) ν̃$_{max}$: 2922, 2851, 1741, 1671, 1644, 1535, 1489, 1466, 1371, 1259, 1220, 1046, 934 cm$^{-1}$; $^1$H NMR: (CDCl$_3$, 600 MHz) δ=8.02 (s, 1H), 7.58 (s, 1H), 7.08 (s, 1H), 5.67 (dd, J=11.4, 2.6 Hz, 1H), 4.74 (s, 1H), 4.53 (s, 1H), 3.69 (s, 3H), 3.02 (s, 3H), 2.90 (d, J=11.3 Hz, 1H), 2.64 (s, 2H), 2.53 (s, 1H), 2.33 (ddd, J=14.8, 11.3, 3.2 Hz, 1H), 2.24 (s, 3H), 2.20 (s, 6H), 2.16 (s, 3H), 2.03 (d, J=34.2 Hz, 2H), 1.61 (d, J=10.9 Hz, 6H), 1.23 (d, J=27.9 Hz, 2H), 1.06-0.95 (m, 9H), 0.79 (d, J=6.6 Hz, 3H); $^{13}$C NMR: (CDCl$_3$, 150 MHz) δ=173.4, 171.7, 170.1, 170.0, 160.9, 150.2, 123.5, 69.7, 69.5, 55.4, 53.9, 53.7, 51.5, 45.9, 45.0, 35.6, 34.8, 34.0, 30.7, 30.5, 30.0, 29.7, 25.1, 23.3, 22.7, 20.8, 20.2, 20.0, 19.6, 17.9 ppm; HRMS calcd for C$_{33}$H$_{51}$N$_5$O$_7$S [M+Na$^+$] 684.3407. found 684.3404.

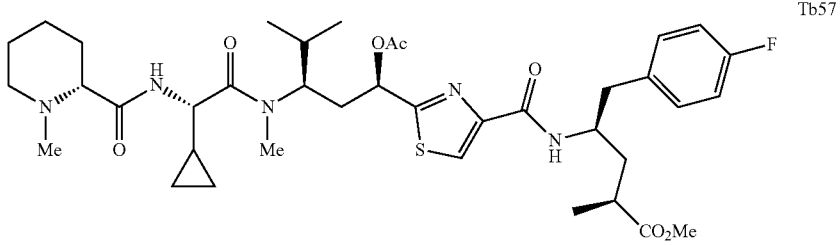 [SMILES: COC(=O)[C@@H](C)C[C@H](Cc1ccc(F)cc1)NC(=O)c1csc([C@@H](C[C@H](C(C)C)N(C)C(=O)[C@@H](NC(=O)[C@H]2CCCCN2C)C2CC2)OC(C)=O)n1]

Tb57

Methyl (2S,4R)-4-(2-((1R,3R)-1-acetoxy-3-((S)-2-cyclopropyl-N-methyl-2-((R)-1-methylpiperidine-2-carboxamido)acetamido)-4-methylpentyl)thiazole-4-carboxamido)-5-(4-fluorophenyl)-2-methylpentanoate (Tb57)

To a stirred solution of acid 62 (10 mg, 0.019 mmol) in dry DMF (0.5 mL) was added HATU (35 mg, 0.09 mmol) followed by a solution of fluoro compound 75 (22 mg, 0.09 mmol) and Et$_3$N (0.05 mL, 0.2 mmol), in DMF (0.1 mL) at 25° C., and stirring continued for 16 h at the same temperature. The reaction mixture was diluted with H$_2$O (5 mL) and the resulting solution was extracted with EtOAc (3×10 mL). The combined organic extracts were washed with brine (2×5 mL), dried over Na$_2$SO$_4$ and evaporated under reduced pressure. The obtained residue was purified by flash column chromatography (silica gel, 3%→15% MeOH in CH$_2$Cl$_2$) to furnish analog Tb57 (10.6 mg, 75%) as a colorless oil. Tb57: R$_f$=0.4 (silica gel, 10% MeOH in CH$_2$Cl$_2$); $[\alpha]_D^{22}$=+26.6 (c=1.0, CHCl$_3$); FT-IR $\nu_{max}$(neat): 2939, 1735, 1645, 1542, 1509, 1222, 1160, 844, 754 cm$^{-1}$; $^1$H NMR: (CDCl$_3$, 600 MHz) δ=8.02 (s, 1H), 7.22-7.14 (m, 2H), 7.09 (d, J=9.2 Hz, 1H), 7.01 (t, J=8.6 Hz, 1H), 6.97 (td, J=8.7, 2.7 Hz, 2H), 5.74 (dd, J=11.6, 2.8 Hz, 1H), 4.53 (s, 1H), 4.42-4.30 (m, 2H), 3.63 (s, 3H), 3.00 (s, 3H), 2.97-2.79 (m, 4H), 2.59 (dddd, J=32.2, 14.5, 7.0, 3.8 Hz, 3H), 2.38 (ddd, J=15.0, 11.5, 3.4 Hz, 1H), 2.31 (s, 3H), 2.16 (d, J=4.9 Hz, 3H), 2.04 (dddt, J=36.0, 13.8, 9.4, 4.8 Hz, 2H), 1.92-1.38 (m, 8H), 1.17 (d, J=7.1 Hz, 3H), 1.02 (d, J=6.6 Hz, 3H), 0.83 (d, J=6.6 Hz, 3H), 0.74-0.65 (m, 1H), 0.58 (tt, J=9.1, 4.9 Hz, 1H), 0.44 (ddt, J=29.7, 9.8, 4.8 Hz, 2H); $^{13}$C NMR: (CDCl$_3$, 150 MHz) δ=176.57, 170.08, 160.36, 149.93, 133.26, 130.91, 130.62, 123.58, 115.81, 115.67, 115.30, 115.16, 69.01, 56.27, 55.44, 51.89, 51.77, 48.56, 41.86, 40.29, 39.89, 38.92, 37.55, 36.44, 34.54, 29.80, 29.69, 20.85, 19.95, 19.52, 18.11, 17.62, 13.71, 3.84, 2.56 Diagnostic signals of minor rotamer: $^{13}$C NMR: (CDCl$_3$, 150 MHz) δ=176.4, 169.8, 160.9, 133.1, 130.8, 130.6, 115.7, 115.4, 115.2, 52.0, 51.6, 48.7, 41.2, 37.4, 37.0, 34.6, 18.3, 17.3 ppm; HRMS calcd for C$_{38}$H$_{54}$FN$_5$O$_7$S [M+Na$^+$] 766.3626. found 766.3599.

Methyl (1R,4r)-4-(2-((1R,3R)-1-acetoxy-3-((tert-butoxycarbonyl)(methyl)amino)-4-methylpentyl)thiazole-4-carboxamido)cyclohexane-1-carboxylate (92)

To a stirred solution of 5 (100 mg, 0.25 mmol) in dry DMF (2.0 ml) at 0° C. were added HATU (285 mg, 0.75 mmol) followed by Et$_3$N (0.2 ml, 1.5 mmol) and the resulting mixture was stirred for 5 min at the same temperature. A solution of 91 (60 mg, 0.37 mmol) in dry DMF (0.5 ml) was then added and the stirring was continue for 18 h while allowing the temperature to slowly rise to 25° C. The reaction mixture was diluted with H$_2$O (5 mL) and the resulting solution was extracted with EtOAc (3×10 mL). The combined organic extracts were washed with brine (5 mL), dried over Na$_2$SO$_4$ and evaporated under reduced pressure. The obtained residue was purified by flash column chromatography (silica gel, 10→50% EtOAc in hexanes) to furnish 92 (113 mg, 84%) as a white amorphous solid. 92: R$_f$=0.5 (silica gel, 50% EtOAc in hexanes); $[\alpha]_D^{22}$=−3.6 (c=1.0, CHCl$_3$); FT-IR (neat): 2936, 1735, 1687, 1663, 1540, 1492, 1368, 1220, 1154, 1130, 1040, 771, 732 cm$^{-1}$. $^1$H NMR: (CDCl$_3$, 600 MHz) δ=8.02 (d, J=2.1 Hz, 1H), 7.12-7.01 (m, 1H), 5.82 (dd, J=11.6, 2.9 Hz, 1H), 4.14-3.84 (m, 2H), 3.67 (d, J=1.5 Hz, 3H), 2.71 (s, 3H), 2.35-2.20 (m, 2H), 2.15 (s, 2H), 2.15-2.11 (m, 3H), 2.10-1.98 (m, 3H), 1.62 (d, J=15.2 Hz, 2H), 1.44 (s, 9H), 1.37-1.22 (m, 3H), 0.97 (dd, J=8.3, 6.5 Hz, 3H), 0.86 (dd, J=6.6, 2.9 Hz, 3H); $^{13}$C NMR: (CDCl$_3$, 150 MHz) δ=175.7, 170.4, 160.0, 150.1, 139.7, 128.2, 123.3, 79.4, 69.2, 56.4, 51.6, 48.4, 47.7, 42.4, 35.0, 32.1, 31.9, 30.4, 28.3, 27.8, 20.9, 20.0, 19.5; Diagnostic signals of minor rotamer; $^{13}$C NMR: (CDCl$_3$, 150 MHz) δ=175.6, 170.1, 156.3, 150.3, 142.4, 131.0, 123.1, 79.8, 70.9, 51.6, 47.4, 42.3, 35.4, 32.0, 31.7, 30.5, 28.4, 27.8, 21.0, 19.7 ppm; HRMS calcd for C$_{26}$H$_{41}$N$_3$O$_7$S [M+Na$^+$] 562.2563. found 562.2572.

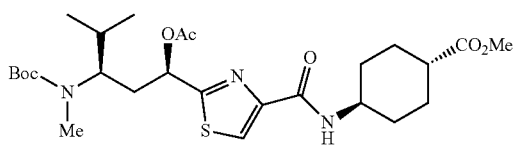

92

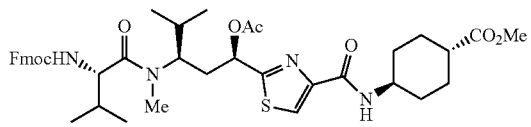

82

Methyl (1R,4r)-4-(2-((5S,8R,10R)-1-(9H-fluoren-9-yl)-5,8-diisopropyl-7-methyl-3,6,12-trioxo-2,11-dioxa-4,7-diazatridecan-1-yl)thiazole-4-carboxamido)cyclohexane-1-carboxylate (93)

To an ice-cooled stirred solution of 92 (100 mg, 0.18 mmol) in $CH_2Cl_2$ (4 mL) was added trifluoroacetic acid (0.57 mL, 7.4 mmol) and the reaction mixture was stirred for 2 h while warming up to 25° C. Evaporation of the volatile components under reduced pressure furnished the crude TFA-ammonium salt (96 mg, 0.17 mmol, quantitative), which was used for the following step without further purification.

To a stirred, ice-cooled solution of crude ammonium salt from the previous step and i-$Pr_2$NEt (0.2 mL, 1.11 mmol) in DMF (1.2 mL) was added dropwise a solution of Fmoc compound 46 (253 mg, 0.74 mmol) in DMF (0.3 mL) and stirring was continued for 18 h at 25° C. The reaction mixture was diluted with ethyl acetate (10 mL), washed with saturated aqueous $NaHCO_3$ solution (10 mL) and brine (10 mL), dried over $Na_2SO_4$ and concentrated under reduced pressure. The obtained residue was purified by flash column chromatography (silica gel, 20%-40% EtOAc in hexanes) to provide 93 (120 mg, 92% yield for the two steps) as a white amorphous solid. 93: $R_f$=0.3 (silica gel, 60% EtOAc in hexanes); $[\alpha]_D^{22}$=−7.3 (c=1.0, $CHCl_3$) FT-IR (neat) $\tilde{v}_{max}$: 2959, 1724, 1647, 1538, 1493, 1450, 1370, 1256, 1221, 1037, 910, 760, 732 $cm^{-1}$; $^1$H NMR: ($CDCl_3$, 600 MHz) δ=8.04 (s, 1H), 7.75 (d, J=7.6 Hz, 2H), 7.58 (d, J=7.5 Hz, 2H), 7.39 (t, J=7.5 Hz, 2H), 7.34-7.27 (m, 2H), 7.06 (d, J=8.4 Hz, 1H), 5.67 (dd, J=11.4, 2.6 Hz, 1H), 5.48 (d, J=9.5 Hz, 1H), 4.52 (dd, J=9.6, 5.6 Hz, 2H), 4.43-4.30 (m, 2H), 4.21 (t, J=7.3 Hz, 1H), 3.92 (tdt, J=12.1, 8.4, 4.1 Hz, 1H), 3.67 (s, 3H), 2.98 (s, 3H), 2.40-2.23 (m, 2H), 2.16 (s, 3H), 2.14 (d, J=3.9 Hz, 2H), 2.12-1.99 (m, 5H), 1.69-1.56 (m, 2H), 1.40-1.28 (m, 2H), 1.02 (dd, J=10.0, 6.7 Hz, 6H), 0.95 (d, J=6.8 Hz, 3H), 0.81 (d, J=6.6 Hz, 3H); $^{13}$C NMR: ($CDCl_3$, 150 MHz) &=175.7, 173.4, 169.9, 159.9, 156.4, 150.2, 143.9, 143.7, 141.2, 127.6, 127.0, 125.0, 123.4, 119.9, 69.4, 67.0, 60.3, 56.2, 51.6, 47.7, 47.2, 42.3, 34.6, 32.1, 30.9, 29.9, 27.8, 21.0, 20.8, 20.1, 20.0, 19.6, 17.1, 14.2 ppm; HRMS calcd for $C_{41}H_{52}N_4O_8S$ [M+Na$^+$] 783.3404. found 783.3413.

Methyl (1R,4r)-4-(2-((1R,3R)-1-acetoxy-3-((S)—N,3-dimethyl-2-((R)-1-methylpiperidine-2-carboxamido)butanamido)-4-methylpentyl)thiazole-4-carboxamido)cyclohexane-1-carboxylate (Tb58)

To an ice-cooled stirred solution of Fmoc-derivative 93 (50 mg, 0.065 mmol) in $CH_2Cl_2$ (2 mL) was added tris(2-aminoethyl)amine (0.16 mL, 1.05 mmol). The reaction mixture was stirred for 2 h at 25° C. and then diluted with ethyl acetate (20 mL). The solution was washed with saturated aqueous $NaHCO_3$ solution (10 mL) and brine (10 mL), dried over $Na_2SO_4$, and concentrated. The crude amine so obtained (30 mg, quantitative) was used for the next step without further purification.

To an ice-cooled stirred solution of N-methyl-(D)-pipecolinic acid 10 (24 mg, 0.17 mmol) in DMF (0.5 mL) at 0° C. was added HATU (64 mg, 0.17 mmol) followed by above obtained crude amine (30 mg, 0.055 mmol) and $Et_3N$ (0.04 ml, 0.33 mmol) and the reaction mixture was stirred at 25° C. for 24 h. The reaction mixture was diluted with $H_2O$ (5 mL) and the resulting solution was extracted with EtOAc (3×10 mL). The combined organic extracts were washed with saturated aqueous $NaHCO_3$ solution (5 mL) and brine (5 mL), dried over $Na_2SO_4$ and evaporated under reduced pressure. The obtained residue was purified by flash column chromatography (silica gel, 5→10% MeOH in $CH_2Cl_2$) to furnish Tb58 (31 mg, 72% yield for the two steps) as a white amorphous solid. Tb58: $[\alpha]_D^{22}$=+10.2 (c=0.1, $CHCl_3$); $R_f$=0.4 (silica gel, 10% MeOH in $CH_2Cl_2$); FT-IR (neat) $\tilde{v}_{max}$: 2938, 2859, 1737, 1645, 1540, 1493, 1371, 1258, 1221, 1128, 1036, 753 $cm^{-1}$; $^1$H NMR: ($CDCl_3$, 600 MHz) δ=8.03 (s, 1H), 7.07 (d, J=8.3 Hz, 2H), 5.67 (dd, J=11.4, 2.5 Hz, 1H), 4.75 (dd, J=9.4, 6.6 Hz, 1H), 4.54 (s, 1H), 3.92 (dtt, J=12.0, 8.3, 4.1 Hz, 1H), 3.68 (s, 3H), 3.02 (s, 3H), 2.89 (d, J=16.1 Hz, 1H), 2.48 (d, J=10.7 Hz, 1H), 2.39-2.28 (m, 2H), 2.24 (s, 3H), 2.16 (s, 3H), 2.14 (s, 1H), 2.11-1.97 (m, 5H), 1.84-1.46 (m, 8H), 1.40-1.14 (m, 4H), 1.06-0.95 (m, 9H), 0.78 (d, J=6.6 Hz, 3H); $^{13}$C NMR: ($CDCl_3$, 150 MHz) δ=175.7, 174.3, 173.4, 170.0, 162.5, 160.0, 150.2, 123.4, 69.7, 69.5, 55.4, 53.7, 51.7, 47.7, 44.9, 42.4, 34.8, 32.1, 32.1, 30.7, 30.5, 29.9, 29.7, 27.8, 25.1, 23.3, 20.8, 20.2, 20.0, 19.6, 17.9 ppm; HRMS calcd for $C_{33}H_{53}N_5O_7S$ [M+Na$^+$] 786.3563. found 786.3559.

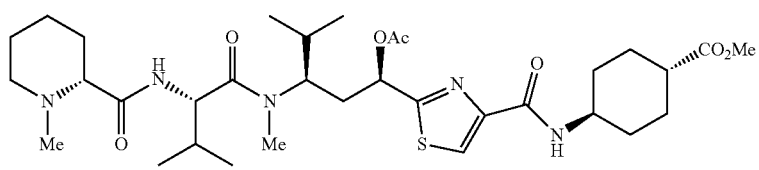

Tb58

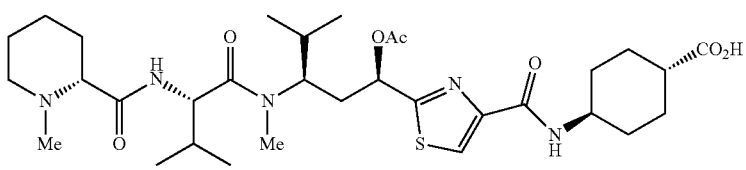

Tb59

(1R,4r)-4-(2-((1R,3R)-1-Acetoxy-3-((S)—N,3-dimethyl-2-((R)-1-methylpiperidine-2-carboxamido)butanamido)-4-methylpentyl)thiazole-4-carboxamido)cyclohexane-1-carboxylic Acid (Tb59)

To a stirred solution of methyl ester Tb58 (10 mg, 0.01 mmol) in 1,2-dichloroethane (1 mL) was added Me$_3$SnOH (136 mg, 0.75 mmol) at 25° C. The reaction mixture was refluxed for 12 h and the solvent was removed under reduced pressure. The resulting hydroxyl acid (10 mg, 0.01 mmol, quantitative) was used in the following step without further purification.

To an ice-cooled stirred solution of the above obtained hydroxyl acid (10 mg, 0.01 mmol) in pyridine (0.5 mL) was added dropwise Ac$_2$O (0.01 ml, 0.1 mmol). The reaction mixture was stirred at 25° C. for 12 h and then the solvent was removed under reduced pressure. The crude reaction mixture was purified by flash column chromatography (silica gel, 10→20% MeOH in CH$_2$Cl$_2$) to furnish Tb59 (6.6 mg, 68% yield) as a colorless oil. Tb59: R$_f$=0.2 (silica gel 10% MeOH in CH$_2$Cl$_2$); $[\alpha]_D^{22}$=+11.2 (c=0.1, CHCl$_3$); FT-IR (neat) $\tilde{v}_{max}$: 3290, 2934, 2857, 1750, 1645, 1542, 1495, 1454, 1412, 1371, 1259, 1222, 1125, 1044, 766 cm$^{-1}$; $^1$H NMR: (CDCl$_3$, 600 MHz) h=8.05 (s, 1H), 7.24-7.02 (m, 2H), 5.68 (dd, J=11.4, 2.6 Hz, 1H), 4.75 (dd, J=9.3, 6.7 Hz, 1H), 4.54 (s, 1H), 4.05-3.84 (m, 1H), 3.04 (s, 3H), 2.93 (d, J=9.5 Hz, 1H), 2.54 (s, 1H), 2.34 (ddd, J=14.9, 11.4, 3.2 Hz, 2H), 2.26 (s, 3H), 2.19 (d, J=3.8 Hz, 1H), 2.17 (s, 3H), 2.13 (d, J=13.6 Hz, 2H), 2.07 (q, J=7.3 Hz, 3H), 1.65 (t, J=20.2 Hz, 7H), 1.47-1.29 (m, 4H), 1.23 (s, 1H), 1.06-0.94 (m, 9H), 0.79 (d, J=6.6 Hz, 3H); $^{13}$C NMR: (CDCl$_3$, 150 MHz) δ=179.1, 174.9, 173.5, 170.1, 170.1, 160.1, 150.1, 123.5, 69.5, 55.4, 53.9, 47.7, 44.7, 42.0, 34.8, 32.1, 32.0, 30.6, 30.3, 29.9, 29.7, 27.7, 25.0, 23.2, 20.8, 20.5, 20.1, 20.0, 19.6, 18.0 ppm; HRMS calcd for C$_{32}$H$_{51}$N$_5$O$_7$S [M+Na$^+$] 772.3407. found 672.3380.

mixture was stirred for 2 h at 25° C. and then diluted with ethyl acetate (20 mL). The solution was washed with saturated aqueous NaHCO$_3$ solution (10 mL) and brine (10 mL), dried over Na$_2$SO$_4$, and concentrated. The crude amine so obtained (30 mg, quantitative) was used for the next step without further purification.

To an ice-cooled stirred solution of acid 78 (31 mg, 0.17 mmol) in DMF (0.5 mL) at 0° C. was added HATU (64 mg, 0.17 mmol) followed by above obtained crude amine (30 mg, 0.055 mmol) and Et$_3$N (0.04 ml, 0.33 mmol) and the reaction mixture was stirred at 25° C. for 24 h. The reaction mixture was diluted with H$_2$O (5 mL) and the resulting solution was extracted with EtOAc (3×10 mL). The combined organic extracts were washed with saturated aqueous NaHCO$_3$ solution (5 mL) and brine (5 mL), dried over Na$_2$SO$_4$ and evaporated under reduced pressure. The obtained residue was purified by flash column chromatography (silica gel, 5→10% MeOH in CH$_2$Cl$_2$) to furnish Tb60 (21 mg, 77% yield for the two steps) as a white amorphous solid. Tb60: $[\alpha]_D^{22}$=+12.8 (c=0.1, CHCl$_3$); R$_f$=0.4 (silica gel, 10% MeOH in CH$_2$Cl$_2$); FT-IR (neat) $\tilde{v}_{max}$: 2929, 2857, 1736, 1646, 1541, 1493, 1454, 1370, 1323, 1258, 1221, 1129, 1048, 767 cm$^{-1}$; $^1$H NMR: (CDCl$_3$, 600 MHz) δ=8.02 (s, 1H), 7.21 (d, J=9.7 Hz, 1H), 7.06 (d, J=8.4 Hz, 1H), 5.66 (dd, J=11.4, 2.6 Hz, 1H), 4.74 (dd, J=9.5, 6.7 Hz, 1H), 4.53 (s, 1H), 3.91 (dtt, J=12.0, 8.2, 4.1 Hz, 1H), 3.67 (s, 3H), 3.11-3.03 (m, 1H), 3.01 (s, 2H), 2.78 (s, 3H), 2.69 (td, J=10.0, 6.5 Hz, 1H), 2.57 (td, J=11.7, 5.7 Hz, 1H), 2.30 (dddd, J=23.7, 15.9, 11.8, 3.5 Hz, 2H), 2.15 (s, 3H), 2.11-1.96 (m, 5H), 1.92 (t, J=11.3 Hz, 1H), 1.74 (dd, J=23.8, 10.0 Hz, 2H), 1.66-1.48 (m, 5H), 1.45-1.18 (m, 8H),

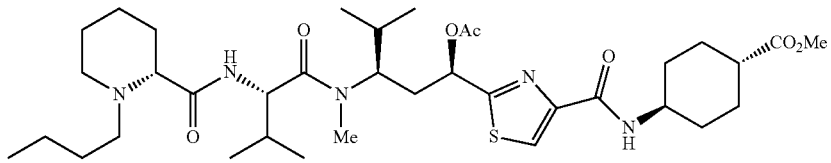

Tb60

Methyl (1R,4r)-4-(2-((1R,3R)-1-acetoxy-3-((S)-2-((R)-1-butylpiperidine-2-carboxamido)-N,3-dimethylbutanamido)-4-methylpentyl)thiazole-4-carboxamido)cyclohexane-1-carboxylate (Tb60)

To an ice-cooled stirred solution of Fmoc-derivative 82 (50 mg, 0.065 mmol) in CH$_2$Cl$_2$ (2 mL) was added tris(2-aminoethyl)amine (0.16 mL, 1.05 mmol). The reaction 0.99 (dd, J=6.6, 2.0 Hz, 6H), 0.94 (d, J=6.7 Hz, 3H), 0.88 (t, J=7.4 Hz, 3H), 0.77 (d, J=6.6 Hz, 3H); $^{13}$C NMR: (CDCl$_3$, 150 MHz) δ=175.7, 174.8, 173.4, 170.0, 162.4, 159.9, 150.2, 123.3, 69.5, 68.0, 57.1, 55.3, 53.6, 51.6, 51.3, 47.7, 42.3, 38.5, 34.8, 32.1, 30.7, 29.9, 29.8, 29.6, 27.7, 24.6, 23.4, 20.8, 20.6, 20.0, 20.0, 19.6, 17.8, 14.1 ppm; HRMS calcd for C$_{36}$H$_{59}$N$_5$O$_7$S [M+Na$^+$] 728.4033. found 728.4009.

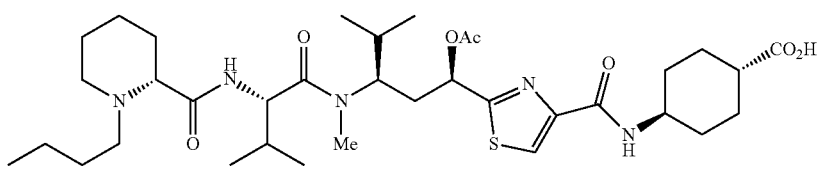

Tb61

(1R,4r)-4-(2-((1R,3R)-1-Acetoxy-3-((S)—N,3-dimethyl-2-((R)-1-methylpiperidine-2-carboxamido)butanamido)-4-methylpentyl)thiazole-4-carboxamido)cyclohexane-1-carboxylic Acid (Tb61)

To a stirred solution of methyl ester Tb60 (10 mg, 0.01 mmol) in 1,2-dichloroethane (1 mL) was added Me$_3$SnOH (128 mg, 0.71 mmol) at 25° C. The reaction mixture was refluxed for 12 h and the solvent was removed under reduced pressure. The resulting hydroxyl acid (10 mg, 0.01 mmol, quantitative) was used in the following step without further purification.

To an ice-cooled stirred solution of the above obtained hydroxyl acid (10 mg, 0.01 mmol) in pyridine (0.5 mL) was added dropwise Ac$_2$O (0.01 ml, 0.1 mmol). The reaction mixture was stirred at 25° C. for 12 h and then the solvent was removed under reduced pressure. The crude reaction mixture was purified by flash column chromatography (silica gel, 10→20% MeOH in CH$_2$Cl$_2$) to furnish Tb61 (7.7 mg, 74% yield) as a colorless oil. Tb61: R$_f$=0.4 (silica gel 20% MeOH in CH$_2$Cl$_2$); [α]$_D^{22}$=+10.5 (c=0.1, CHCl$_3$); FT-IR (neat) $\tilde{v}_{max}$: 3398, 2957, 2933, 2861, 1755, 1645, 1572, 1543, 1497, 1451, 1411, 1371, 1220, 1046, 755 cm$^{-1}$; $^1$H NMR: (CDCl$_3$, 600 MHz) δ=8.06 (s, 1H), 7.32 (d, J=10.4 Hz, 1H), 7.10 (d, J=8.6 Hz, 1H), 5.68 (d, J=11.3 Hz, 1H), 4.76 (dd, J=10.4, 6.2 Hz, 1H), 4.55 (s, 1H), 3.93 (d, J=10.3 Hz, 1H), 3.10 (d, J=12.6 Hz, 1H), 3.03 (s, 3H), 2.77 (dd, J=10.4, 3.3 Hz, 1H), 2.60 (td, J=12.1, 5.6 Hz, 1H), 2.39-2.28 (m, 2H), 2.16 (s, 3H), 2.12-1.92 (m, 7H), 1.83-1.69 (m, 2H), 1.64 (d, J=14.0 Hz, 5H), 1.48-1.21 (m, 9H), 1.01 (d, J=6.8 Hz, 6H), 0.96 (d, J=7.0 Hz, 3H), 0.90 (t, J=7.3 Hz, 3H), 0.79 (d, J=6.9 Hz, 3H); $^{13}$C NMR: (CDCl$_3$, 150 MHz) δ=174.6, 173.5, 170.1, 170.1, 160.0, 150.1, 123.5, 69.6, 67.9, 56.9, 55.5, 53.8, 51.3, 47.8, 42.3, 34.8, 32.1, 30.7, 30.0, 29.7, 29.7, 29.4, 27.8, 24.5, 23.3, 20.8, 20.6, 20.1, 20.0, 19.6, 17.8, 14.1 ppm; HRMS calcd for C$_{35}$H$_{57}$N$_5$O$_7$S [M+Na$^+$] 714.3876. found 714.3849.

Example 4—Biological Activity i. Cytotoxic Assay

Cells were cultured in a T75 flask to ~50-80% confluency and harvested with trypsin into a single cell suspension. Five hundred (500) cells per well were seeded in tissue culture plates in 50 µL/well culture media and incubated at 37° C. for 18-24 hours. Compounds were diluted as 400× final desired concentrations in DMSO. Serial dilutions in DMSO were then diluted in culture media for a final DMSO concentration of 0.25% and 50 µL/well of the final dilution was added to the cells (Vf=100 µL). Upon plating and treatment, cells were returned to the incubator for an additional 72 hours. CellTiter-Glo reagent was prepared per manufacturer's instructions and added at 100 µL/well to the cultures. CellTiter-Glo allows for relative enumeration of metabolically active cells by quantifying intracellular ATP concentrations. After 5 minutes of incubation with CellTiter-Glo at ambient room temperature, 125 µL/well of the Cell Titer Glo/cell lysate solution was transferred into black assay plates, which were then read in a luminometer within 30 minutes. Luminescence readings obtained from cultures that did not receive any treatment (cell culture media only) were set as 100% control and all other luminescence values were normalized to these controls (e.g., Normalized RLU, relative luminescence unit).

ii. Cell Lines

MES SA and MES SA/Dx cells are uterine sarcoma. MES SA Dx cell line was generated from MES SA to achieve upregulation of MDR1. MES-SA/Dx cells exhibit marked cross-resistance to a number of chemotherapeutic agents (including daunorubicin, dactinomycin, vincristine, taxol, colchicine) and moderate cross-resistance to mitomycin C and melphalan. 293T cells are human embryonic kidney cell line.

iii. Activity

A number of the synthesized compounds (i.e. Tb1-Tb23) were evaluated for their activity against a variety of cancer cell lines, namely the NCI-60 human cancer cell line panel representing leukemia, melanoma, lung, colon, brain, ovary, breast, prostate and kidney types of cancer through the In Vitro Cell Line Screening Project (IVCLSP) of the National Cancer Institute (NCI), and a summary of the results is shown in Table 1. As seen from these data, tubulysins Tb12, Tb15, Tb17-Tb19 and Tb22 failed to pass the one-dose test (10 µM) while the rest (Tb1-Tb11, Tb13, Tb14, Tb16, Tb20, Tb21 and Tb23) advanced to further testing at lower concentrations. Among the most potent were Tb1, Tb2, Tb11, Tb14 and Tb20 which exhibited consistently potent activities against leukemia, non-small cell lung, colon, CNS, melanoma, ovarian, renal, prostate and breast cancer cell lines as shown by their selected GI$_{50}$ values presented in Table 1. The most impressive activities were exhibited by tubulysin Tb11 (leukemia: GI$_{50}$=159 pM; non-small cell lung cancer: GI$_{50}$=331 pM; colon cancer: GI$_{50}$=1140 pM; CNS cancer: GI$_{50}$=1150 pM; melanoma: GI$_{50}$=349 pM; ovarian cancer: GI$_{50}$=489 pM; renal cancer: GI$_{50}$=768 pM; prostate cancer: GI$_{50}$=1130 pM; breast cancer: GI$_{50}$=428 pM), Tb14 (leukemia: GI$_{50}$=64 pM; non-small cell lung cancer: GI$_{50}$=156 pM; colon cancer: GI$_{50}$=433 pM; CNS cancer: GI$_{50}$=382 pM; melanoma: GI$_{50}$=137 pM; ovarian cancer: GI$_{50}$=256 pM; renal cancer: GI$_{50}$=364 pM; prostate cancer: GI$_{50}$=449 pM; breast cancer: GI$_{50}$=267 pM), and Tb20 (leukemia: GI$_{50}$=98 pM; non-small cell lung cancer: GI$_{50}$=247 pM; colon cancer: GI$_{50}$=263 pM; CNS cancer: GI$_{50}$=345 pM; melanoma: GI$_{50}$=35 pM; ovarian cancer: GI$_{50}$=49 pM; renal cancer: GI$_{50}$=270 pM; prostate cancer: GI$_{50}$=211 pM; breast cancer: GI$_{50}$=44 pM). As there was interest in the activity in certain other cell lines, these and the remaining compounds (Tb1-Tb41, PTb-D42 and PTb-D43) were subjected to further testing against MES SA (uterine sarcoma cells), MES SA DX (multidrug resistant uterine sarcoma cells), and HEK 293T (human embryonic kidney cells). As shown in Table 2 several of these compounds exhibited picomolar potencies, with the most potent being Tb1 (MES SA: IC$_{50}$=340 pM; HEK 293T: IC$_{50}$=20 pM), Tb2 (MES SA: IC$_{50}$=200 pM; HEK 293T: IC$_{50}$=30 pM), Tb11 (MES SA: IC$_{50}$=840 pM; HEK 293T: IC$_{50}$=260 pM), Tb14 (MES SA: IC$_{50}$=350 pM; HEK 293T: IC$_{50}$=110 pM), Tb20 (MES SA: IC$_{50}$=46 pM; HEK 293T: IC$_{50}$=47 pM), Tb26 (MES SA: IC$_{50}$=200 pM; HEK 293T: IC$_{50}$=120 pM), Tb32 (MES SA: IC$_{50}$=12 pM; HEK 293T: IC$_{50}$=2 pM), Tb33 (MES SA: IC$_{50}$=66 pM; HEK 293T: IC$_{50}$=48 pM), Tb36 (MES SA: IC$_{50}$=308 pM; HEK 293T: IC$_{50}$=631 pM), Tb38 (MES SA: IC$_{50}$=357 pM; HEK 293T: IC$_{50}$=574 pM) and Tb39 (MES SA: IC$_{50}$=891 pM; HEK 293T: IC$_{50}$=194 pM). Particularly impressive are the potencies exhibited by compounds Tb20, Tb32, and Tb33. Tubulysins are known to be substrates for Pgp pumps (Xiangming, et al., 2013; Kaur, et al., 2006; Szakacs, et al., 2006) as supported by the observed low activities of all tubulysins tested except Tb28, Tb32 and Tb33. In that regard, the latter analogues are notable for their relatively high potencies (Tb28: MES SA DX: IC$_{50}$=81.72 nM; Tb32: MES SA DX: IC$_{50}$=1.29 nM; Tb33: MES SA DX: IC$_{50}$=101 nM) against the MDR cell line MES SA DX.

TABLE 1

Selected NCI-60 Cytotoxicity Human Cancer Cell Line Panel Data [(GI$_{50}$ nM)[a] for Tubulysins Tb1-Tb23

| compound | one dose[c] | leukemia | non-small cell lung cancer | colon cancer | CNS cancer | melanoma | ovarian cancer | renal cancer | prostate cancer | breast cancer |
|---|---|---|---|---|---|---|---|---|---|---|
| Tb1 | — | 0.264 | 0.347 | 0.269 | 0.305 | 0.074 | 0.234 | 0.548 | 0.339 | 0.147 |
| Tb2 | — | 0.078 | 0.280 | 0.158 | 0.219 | 0.030 | 0.042 | 0.218 | 0.162 | 0.043 |
| Tb3 | — | >1000 | >1000 | >1000 | >1000 | >1000 | >1000 | >1000 | >1000 | >1000 |
| Tb4 | — | >1000 | >1000 | >1000 | >1000 | >1000 | >1000 | >1000 | >1000 | >1000 |
| Tb5 | — | >1000 | >1000 | >1000 | >1000 | 416 | >1000 | >1000 | >1000 | 514 |
| Tb6 | — | 286 | 164 | 339 | 439 | 83.9 | 127 | 154 | 689 | 71.4 |
| Tb7 | — | 17.6 | 57.8 | 61.3 | 219 | 31.4 | 48.5 | 134 | 105 | 42.8 |
| Tb8 | — | 9.62 | 96.7 | 121 | 105 | 33.3 | 75.0 | 164 | 125 | 52.1 |
| Tb9 | — | 24.2 | 83.6 | 331 | 246 | 46.6 | 61.0 | 238 | 459 | 53.2 |
| Tb10 | — | 61.3 | 60.2 | 355 | 271 | 49.5 | 92.6 | 413 | 500 | 66.4 |
| Tb11 | — | 0.159 | 0.331 | 1.14 | 1.15 | 0.349 | 0.489 | 0.768 | 1.13 | 0.428 |
| Tb12 | 84.90 | — | — | — | — | — | — | — | — | — |
| Tb13 | — | 13.8 | 142 | 122 | 117 | 40.2 | 111 | 167 | 167 | 136 |
| Tb14 | — | 0.064 | 0.156 | 0.433 | 0.382 | 0.137 | 0.256 | 0.364 | 0.449 | 0.267 |
| Tb15 | 94.38 | — | — | — | — | — | — | — | — | — |
| Tb16 | — | 15.1 | 85.0 | 98.1 | 127 | 46.1 | 99.1 | 186 | 303 | 123 |
| Tb17 | 97.37 | — | — | — | — | — | — | — | — | — |
| Tb18 | 98.48 | — | — | — | — | — | — | — | — | — |
| Tb19 | 100.82 | — | — | — | — | — | — | — | — | — |
| Tb20 | — | 0.098 | 0.247 | 0.263 | 0.345 | 0.035 | 0.049 | 0.270 | 0.211 | 0.044 |
| Tb21 | — | 1.65 | 6.62 | 23.9 | 24.1 | 2.23 | 5.79 | 23.2 | 34.6 | 4.04 |
| Tb22 | 49.38 | — | — | — | — | — | — | — | — | — |
| Tb23 | — | 16.3 | 84.5 | 204 | 119 | 45.1 | 54.9 | 181 | 308 | 44.7 |

[a]GI$_{50}$ = Concentration at which compound that inhibits growth by 50%;
[b] mean growth %.

TABLE 2

Cytotoxicity Data Against Cancer Cell Lines MES SA, MES SA DX and HEK 293T[a] for Tubulysins Tb1-Tb41, PTb-D42 and PTb-D43 IC$_{50}$ Value in nM.

| compound | MES SA | MES SA DX | HEK 293T |
|---|---|---|---|
| Tb1 | 0.34 | >10 | 0.02 |
| Tb2 | 0.20 | >10 | 0.03 |
| Tb3 | >50 | >50 | >50 |
| Tb4 | >50 | >50 | >50 |
| Tb5 | >50 | >50 | >50 |
| Tb6 | >50 | >50 | >50 |
| Tb7 | >50 | >50 | >50 |
| Tb8 | >50 | >50 | >50 |
| Tb9 | >50 | >50 | >50 |
| Tb10 | >50 | >50 | >50 |
| Tb11 | 0.84 | >50 | 0.26 |
| Tb12 | >50 | >50 | >50 |
| Tb13 | >50 | >50 | >50 |
| Tb14 | 0.35 | >50 | 0.11 |
| Tb15 | >50 | >50 | >50 |
| Tb16 | >50 | >50 | >50 |
| Tb17 | >50 | >50 | >50 |
| Tb18 | >50 | >50 | >50 |
| Tb19 | >50 | >50 | >50 |
| Tb20 | 0.046 | <200 | 0.047 |
| Tb21 | 16.830 | >50 | >10 |
| Tb22 | >50 | >50 | >50 |
| Tb23 | >50 | >50 | >50 |
| Tb24 | 13.1 | >100 | 9.69 |
| Tb25 | >50 | >100 | >50 |
| Tb26 | 0.20 | >100 | 0.12 |
| Tb27 | 2.46 | >100 | 1.96 |
| Tb28 | 1.13 | 81.72 | 0.69 |
| Tb29 | 2.61 | 499.8 | 2.24 |
| Tb30 | 4.09 | >100 | 0.35 |
| Tb31 | 8.16 | >100 | 7.28 |
| Tb32 | 0.012 | 1.29 | 0.002 |
| Tb33 | 0.066 | 101 | 0.048 |
| Tb34 | >1,000 | >1,000 | >500 |
| Tb35 | >1,000 | >1,000 | >500 |

TABLE 2-continued

Cytotoxicity Data Against Cancer Cell Lines MES SA, MES SA DX and HEK 293T[a] for Tubulysins Tb1-Tb41, PTb-D42 and PTb-D43 IC$_{50}$ Value in nM.

| compound | MES SA | MES SA DX | HEK 293T |
| --- | --- | --- | --- |
| Tb36 | 0.308 | >1,000 | 0.631 |
| Tb37 | 14.430 | >1,000 | 3.524 |
| Tb38 | 0.357 | <500 | 0.574 |
| Tb39 | 0.891 | <500 | 0.194 |
| Tb40 | 15.56 | >1000 | >1000 |
| Tb41 | >1000 | >1000 | 21.12 |
| PTb-D42 | >1000 | >1000 | >1000 |
| PTb-D43 | 408.8 | >1000 | 109.0 |

[a]IC$_{50}$ = 50% inhibitory concentration of compound against cell growth; MES SA = uterine sarcoma cell line; MES SA DX = MES SA cell line with marked multi-drug resistance; HEK 293T = human embryonic kidney cell line.

TABLE 3

IC$_{50}$ of Compounds in nM for HEK 293T and MES SA Cell Lines

| Compound | HEK 293T IC$_{50}$ (nM) | MES SA IC$_{50}$ (nM) |
| --- | --- | --- |
| PTb-D49 | >100 | >100 |
| PTb-D50 | >100 | >100 |
| PTb-D51 | >100 | >100 |
| Tb-52 | 5.78 | 7.18 |
| Tb-53 | 0.56 | 0.92 |
| Tb-54 | 0.73 | 6.21 |
| Tb-55 | 0.35 | 0.93 |
| Tb-56 | 1.79 | ~2.732 |
| Tb-57 | ~105.4 | ~89.31 |
| Tb-58 | 3.83 | 6.164 |
| Tb-59 | >100 | >100 |
| Tb-60 | >100 | >100 |
| Tb-61 | >100 | >100 |

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

V. REFERENCES

The following references, to the extent that they provide exemplary procedural or other details supplementary to those set forth herein, are specifically incorporated herein by reference:

Anderson, N. G., *Practical Process Research & Development—A Guide For Organic Chemists*, 2$^{nd}$ ed., Academic Press, New York, 2012.
Balasubramanian et al., Bioorg. Med. Chem. Lett., 18, 2996-2999, 2008.
Burkhart et al., Eur. J. Org. Chem., 3050-3059, 2011.
Burkhart et al., RSC Advances, 2, 3785-3790, 2012.
Chai et al., Chem. Biol., 2010.
Chatgilialoglu et al., Chem. Rev., 99, 1991-2070, 1999.
Corey and Helal, Angew Chem., Int. Ed., 37:1986, 1998.
Corey, et al., J. Am. Chem. Soc., 109:5551, 1987.
Deloux and Srebnik, Chem. Rev., 93:763, 1993.
Dömling and Richter, Molecular Diversity, 9, 141-147, 2005.
Dömling et al., Angew. Chem. Int. Ed., 45, 7235-7239, 2006h.
Dömling et al., Angew. Chem., 118, 7393-7397, 2006a.
Eirich et al., Mol. BioSyst., 8, 2067-2075, 2012.
EP 2 174 947 A1
EP2409983A1
Falkiner, et al. Org. Process Res. Dev., 17:1503-1509, 2013.
Floyd et al., ChemMedChem, 6, 49-53, 2011.
Fulmer et al., Organometallics, 29, 2176-2179, 2010.
Greene's Protective Groups in Organic Chemistry, Wuts and Greene, Ed., 1973
Hifle et al., Pure Appl. Chem., 75, 167-178, 2003.
In, et al., Arch. Pharm. Res., 30:695, 2007.
Ingalsbe, et al., Synthesis, 1:98-102, 2010.
Kaur, et al., Biochem J., 396:235, 2006.
Kazmaier et al., The Open Natural Products Journal, 6, 12-30, 2013.
Khalil et al., ChemBioChem, 7, 678-683, 2006.
Khemnar et al., Synlett, 25 (1), 110-114, 2014.
Kubicek et al., Angew. Chem. Int. Ed., 49, 4809-4812, 2010b.
Kubicek et al., Chem., 122, 4919-4922, 2010a.
Li et al., C. Adv. Synth. Catal., 352, 2588-2598, 2010.
March's Advanced Organic Chemistry: Reactions, Mechanisms, and Structure, 2007.
Matcha and Antonchick, Angew. Chem. Int. Ed., 52, 2082-2086, 2013
Neri et al., ChemMedChem, 1, 175-180, 2006.
Nicolaou, et al., Angew. Chem., Int. Ed., 44:1378, 2005.
Nicolaou, et al., ChemMedChem, 2015. In Press.
Pando et al., B. Org. Lett., 11, 5567-5569, 2009.
Pando et al., J. Am. Chem. Soc., 133, 7692-7695, 2011.
Pangborn et al., Organomerallics, 15, 1518-1520, 1996.
Patterson et al., Chem. Eur. J., 13, 9534-9541, 2007.
Patterson et al., J. Org. Chem., 73, 4362-4369, 2008.
Patzel, et al., Eur. J. Org. Chem., 493-498, 2004.
Peltier et al., J. Am. Chem. Soc., 128, 16018-16019, 2006.
Raghavan et al., J. Med. Chem., 51, 1530-1533, 2008.
Rath et al., Br. J. Pharmacol., 167, 1048-1061, 2012.
Reddy et al., B. Synthesis, 4203-4207, 2009.
Remington's Pharmaceutical Sciences, 15$^{th}$ Ed., 1035-1038 and 1570-1580, 1990.
Remington's Pharmaceutical Sciences, 15$^{th}$ Ed., 3:624-652, 1990.
Sandmann et al., Chem. Biol., 11, 1071-1079, 2004.
Sani et al., Angew. Chem. Int. Ed., 46, 3526-3529, 2007b.
Sani et al., Angew. Chem., 119, 3596-3599, 2007a.
Sasse et al., J. Antibiot, 53, 879-885, 2000.
Sasse et al., Nat. Chem. Biol., 3, 87-89, 2007.
Shankar et al., Org. Biomol. Chem., 11, 2273-2287, 2013.
Shankar et al., Synlett, 1673-1676, 2011.
Shibue et al., Bioorg. Med. Chem. Lett., 21, 431-434, 2011.
Shibue et al., Chem. Eur. J., 16, 11678-11688, 2010.
Sohtome, et al., Angew. Chem., Int. Ed., 49:7299, 2010.
Steinmetz et al., Angew. Chem., 116, 4996-5000, 2004.
Stepan, et al., J. Med. Chem., 55:3414, 2012.
Still et al., J. Org. Chem., 43, 2923-2925, 1978.
Szakacs, et al., Nature. Rev. Drug Disc., 5:219, 2005.
Telvekar et al., H. M. Tetrahedron Lett., 50, 5056-5058, 2009.
Ullrich et al., Angew. Chem. Int. Ed., 48, 4422-4425, 2009b.
Ullrich et al., Angew. Chem., 121, 4486-4489, 2009a.
U.S. Patent Application 2010/0240701 A1

U.S. Patent Application 2011/0027274 A1
U.S. Pat. No. 7,816,377 B2
Viret, et al., Tetrahedron, 43:891, 1987.
Wang et al., Chem. Biol. Drug Des., 70, 75-86, 2007.
Wang et al., V. Chin. J. Chem, 31, 40-48, 2013.
Wipf and Wang, Org. Lett., 9, 1605-1607, 2007.
Wlochal, et al., Org. Lett., 16:4094-4097, 2014.
WO 2004/005326 A2
WO 2004/005327 A1
WO 2008/106080 A2.
WO 2009/012958 A2
WO 2009/055562 A1
WO 2012/010287 A1
WO 2012/019123 A1
WO 2013/149185 A1
Xiangming, et al., Mini Rev. Med. Chem., 11:1572, 2013.
Yang et al., Chem Asian J., 8, 1213-1222, 2013.
Yang et al., Tetrahedron Lett., 54, 2986-2988, 2013.
Yeung et al., Chem. Rev., 111, 1215-1292, 2011.
Zhou et al., Angew. Chem. Int. Ed., 48, 7094-7097, 2009.

What is claimed is:
1. A compound of the formula:

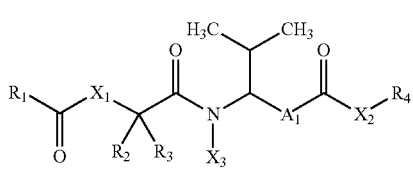

wherein:
$R_1$ is heterocycloalkyl$_{(C \leq 12)}$ or substituted heterocycloalkyl$_{(C \leq 12)}$;
$R_2$ is isopropyl, cycloalkyl$_{(C \leq 12)}$, or substituted cycloalkyl$_{(C \leq 12)}$;
$R_3$ is hydrogen;
$R_4$ is cycloalkyl$_{(C \leq 12)}$, fused cycloalkyl$_{(C \leq 12)}$, aralkyl$_{(C \leq 12)}$, substituted cycloalkyl$_{(C \leq 12)}$, substituted fused cycloalkyl$_{(C \leq 12)}$, substituted aralkyl$_{(C \leq 12)}$, fused cycloalkylamino$_{(C \leq 12)}$, substituted fused cycloalkylamino$_{(C \leq 12)}$, or a structure of the formula:

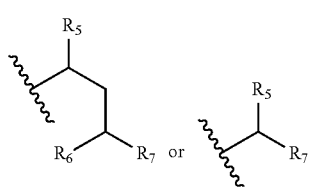

wherein:
$R_5$ is aryl$_{(C \leq 12)}$, aralkyl$_{(C \leq 12)}$, heteroaryl$_{(C \leq 12)}$, heteroaralkyl$_{(C \leq 12)}$, or a substituted version of any of these groups; or is -alkanediyl$_{(C \leq 6)}$-arenediyl$_{(C \leq 12)}$-$Y_3$ or a substituted version of any of these groups; wherein:
$Y_3$ is alkoxy$_{(C \leq 12)}$, aryloxy$_{(C \leq 12)}$, an oxygen linked antibody, —C(O)-alkoxy$_{(C \leq 12)}$, —C(O)-alkylamino$_{(C \leq 12)}$, —C(O)-dialkylamino$_{(C \leq 12)}$, —C(O)-aryloxy$_{(C \leq 12)}$, —C(O)-arylamino$_{(C \leq 12)}$, —C(O)—$Y_4$; or a substituted version of any of these groups; wherein:
$Y_4$ is a nitrogen linked antibody or an oxygen linked antibody;
$R_6$ is hydrogen, alkyl$_{(C \leq 8)}$, or substituted alkyl$_{(C \leq 8)}$;
$R_7$ is —C(O)—$Y_5$; wherein
$Y_5$ is amino, hydroxy, alkoxy$_{(C \leq 12)}$, substituted alkoxy$_{(C \leq 12)}$, alkylamino$_{(C \leq 12)}$, substituted alkylamino$_{(C \leq 12)}$, dialkylamino$_{(C \leq 12)}$, substituted dialkylamino$_{(C \leq 12)}$, an oxygen linked antibody, or a nitrogen linked antibody;
$X_1$ and $X_2$ are each independently selected from a covalent bond, —O—, —S—, —$NR_8$—, or —$NR_9NR_{10}$—, wherein:
$R_8$, $R_9$, and $R_{10}$ are each independently selected from hydrogen, alkyl$_{(C \leq 12)}$, substituted alkyl$_{(C \leq 12)}$, cycloalkyl$_{(C \leq 12)}$, or substituted cycloalkyl$_{(C \leq 12)}$;
$X_3$ is hydrogen, alkyl$_{(C \leq 12)}$, or substituted alkyl$_{(C \leq 12)}$; and
$A_1$ is —C(O)$NR_{13}$-fused cycloalkanediyl$_{(C \leq 12)}$, -alkanediyl$_{(C \leq 12)}$-heteroarene-diyl$_{(C \leq 12)}$, -alkanediyl$_{(C \leq 12)}$-heteroarenediyl$_{(C \leq 12)}$, wherein the alkanediyl is substituted with an amido$_{(C \leq 8)}$ or acyloxy$_{(C \leq 8)}$ group, or a substituted version of any of these groups, wherein:
$R_{13}$ is hydrogen, alkyl$_{(C \leq 12)}$, substituted alkyl$_{(C \leq 12)}$, cycloalkyl$_{(C \leq 12)}$, or substituted cycloalkyl$_{(C \leq 12)}$;
provided that $X_3$ is not hydrogen, methyl, hydroxymethyl, or acetoxymethyl, when $R_2$ or $R_3$ is sec-butyl, $R_5$ is benzyl, $R_7$ is —$CO_2H$, and $R_1$ is 2-N-methylpiperidinyl;
or a pharmaceutically acceptable salt thereof.
2. The compound of claim 1, wherein the formula is further defined as:

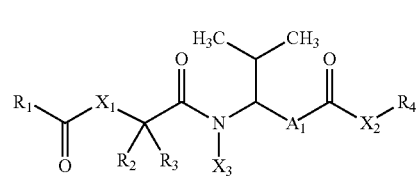

wherein:
$R_1$ is heterocycloalkyl$_{(C \leq 12)}$ or substituted heterocycloalkyl$_{(C \leq 12)}$;
$R_2$ is isopropyl, cycloalkyl$_{(C \leq 12)}$, or substituted cycloalkyl$_{(C \leq 12)}$;
$R_3$ is hydrogen;
$R_4$ is fused cycloalkylamino$_{(C \leq 12)}$, substituted fused cycloalkylamino$_{(C \leq 12)}$, or a structure of the formula:

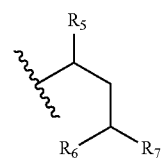

wherein:
$R_5$ is aryl$_{(C \leq 12)}$, aralkyl$_{(C \leq 12)}$, heteroaryl$_{(C \leq 12)}$, heteroaralkyl$_{(C \leq 12)}$, or a substituted version of any of these groups; or is -alkanediyl$_{(C \leq 6)}$-arenediyl$_{(C \leq 12)}$-$Y_3$ or a substituted version of any of these groups; wherein:

$Y_3$ is alkoxy$_{(C≤12)}$, aryloxy$_{(C≤12)}$, an oxygen linked antibody, —C(O)-alkoxy$_{(C≤12)}$, —C(O)-alkylamino$_{(C≤12)}$, —C(O)-dialkylamino$_{(C≤12)}$, —C(O)-aryloxy$_{(C≤12)}$, —C(O)-arylamino$_{(C≤12)}$, —C(O)—$Y_4$; or a substituted version of any of these groups; wherein:
  $Y_4$ is a nitrogen linked antibody or an oxygen linked antibody;
$R_6$ is hydrogen, alkyl$_{(C≤8)}$, or substituted alkyl$_{(C≤8)}$;
$R_7$ is —C(O)—$Y_5$; wherein
  $Y_5$ is amino, hydroxy, alkoxy$_{(C≤12)}$, substituted alkoxy$_{(C≤12)}$, alkylamino$_{(C≤12)}$, substituted alkylamino$_{(C≤12)}$, dialkylamino$_{(C≤12)}$, substituted dialkylamino$_{(C≤12)}$, an oxygen linked antibody, or a nitrogen linked antibody;
$X_1$ and $X_2$ are each independently selected from —O—, —S—, —NR$_8$—, or —NR$_9$NR$_{10}$—, wherein:
  $R_8$, $R_9$, and $R_{10}$ are each independently selected from hydrogen, alkyl$_{(C≤12)}$, substituted alkyl$_{(C≤12)}$, cycloalkyl$_{(C≤12)}$, or substituted cycloalkyl$_{(C≤12)}$;
$X_3$ is hydrogen, alkyl$_{(C≤12)}$, or substituted alkyl$_{(C≤12)}$; and
$A_1$ is —C(O)NR$_{13}$-fused cycloalkanediyl$_{(C≤12)}$, -alkanediyl$_{(C≤12)}$-heteroarene-diyl$_{(C≤12)}$, -alkanediyl$_{(C≤12)}$-heteroarenediyl$_{(C≤12)}$, wherein the alkanediyl is substituted with an amido$_{(C≤8)}$ or acyloxy$_{(C≤8)}$ group, or a substituted version of any of these groups, wherein:
  $R_{13}$ is hydrogen, alkyl$_{(C≤12)}$, substituted alkyl$_{(C≤12)}$, cycloalkyl$_{(C≤12)}$, or substituted cycloalkyl$_{(C≤12)}$;
  provided that $X_3$ is not hydrogen, methyl, hydroxymethyl, or acetoxymethyl, when $R_2$ or $R_3$ is sec-butyl, $R_5$ is benzyl, $R_7$ is —CO$_2$H, and $R_1$ is 2-N-methylpiperidinyl;
or a pharmaceutically acceptable salt thereof.

3. The compound of claim 1, wherein the formula is further defined as:

(II)

wherein:
  $R_1$ is heterocycloalkyl$_{(C≤12)}$ or substituted heterocycloalkyl$_{(C≤12)}$;
  $R_2$ is cycloalkyl$_{(C≤12)}$ or a substituted cycloalkyl$_{(C≤12)}$;
  $R_3$ is hydrogen;
  $R_5$ is aryl$_{(C≤12)}$, aralkyl$_{(C≤12)}$, heteroaryl$_{(C≤12)}$, heteroaralkyl$_{(C≤12)}$, or a substituted version of any of these groups; or is -alkanediyl$_{(C≤6)}$-arenediyl$_{(C≤12)}$-$Y_3$ or a substituted version of any of these groups; wherein:
    $Y_3$ is alkoxy$_{(C≤12)}$, aryloxy$_{(C≤12)}$, an oxygen linked antibody, —C(O)-alkoxy$_{(C≤12)}$, —C(O)-alkylamino$_{(C≤12)}$, —C(O)-dialkylamino$_{(C≤12)}$, —C(O)-aryloxy$_{(C≤12)}$, —C(O)-arylamino$_{(C≤12)}$, —C(O)—$Y_4$; or a substituted version of any of these groups; wherein:
      $Y_4$ is a nitrogen or an oxygen linked antibody;
  $R_6$ is hydrogen, alkyl$_{(C≤8)}$, or substituted alkyl$_{(C≤8)}$;
  $R_7$ is —C(O)—$Y_5$; wherein
    $Y_5$ is amino, hydroxy, alkoxy$_{(C≤12)}$, substituted alkoxy$_{(C≤12)}$, alkylamino$_{(C≤12)}$, substituted alkylamino$_{(C≤12)}$, dialkylamino$_{(C≤12)}$, substituted dialkylamino$_{(C≤12)}$, an oxygen linked antibody, or a nitrogen linked antibody;
  $X_1$ and $X_2$ are each independently selected from —O—, —S—, —NR$_8$—, or —NR$_9$NR$_{10}$—, wherein:
    $R_8$, $R_9$, and $R_{10}$ are each independently selected from hydrogen, alkyl$_{(C≤12)}$, substituted alkyl$_{(C≤12)}$, cycloalkyl$_{(C≤12)}$, or substituted cycloalkyl$_{(C≤12)}$;
  $X_3$ is hydrogen, alkyl$_{(C≤12)}$, or substituted alkyl$_{(C≤12)}$; and
  $X_4$ is amino, hydroxy, acyloxy$_{(C≤8)}$, substituted acyloxy$_{(C≤8)}$, amido$_{(C≤8)}$, substituted amido$_{(C≤8)}$;
or a pharmaceutically acceptable salt thereof.

4. The compound of claim 1, wherein the formula is further defined as:

(III)

wherein:
  $R_1$ is heterocycloalkyl$_{(C≤12)}$ or substituted heterocycloalkyl$_{(C≤12)}$;
  $R_2$ is cycloalkyl$_{(C≤12)}$ or substituted cycloalkyl$_{(C≤12)}$;
  $R_3$ is hydrogen;
  $R_5$ is aryl$_{(C≤12)}$, aralkyl$_{(C≤12)}$, heteroaryl$_{(C≤12)}$, heteroaralkyl$_{(C≤12)}$, or a substituted version of any of these groups; or is -alkanediyl$_{(C≤6)}$-arenediyl$_{(C≤12)}$-$Y_3$ or a substituted version of any of these groups; wherein:
    $Y_3$ is alkoxy$_{(C≤12)}$, aryloxy$_{(C≤12)}$, an oxygen linked antibody, —C(O)-alkoxy$_{(C≤12)}$, —C(O)-alkylamino$_{(C≤12)}$, —C(O)-dialkylamino$_{(C≤12)}$, —C(O)-aryloxy$_{(C≤12)}$, —C(O)-arylamino$_{(C≤12)}$, —C(O)—$Y_4$; or a substituted version of any of these groups; wherein:
      $Y_4$ is a nitrogen or an oxygen linked antibody; and
  $R_6$ is hydrogen, alkyl$_{(C≤8)}$, or substituted alkyl$_{(C≤8)}$;
  $R_7$ is —C(O)—$Y_5$; wherein
    $Y_5$ is amino, hydroxy, alkoxy$_{(C≤12)}$, substituted alkoxy$_{(C≤12)}$, alkylamino$_{(C≤12)}$, substituted alkylamino$_{(C≤12)}$, dialkylamino$_{(C≤12)}$, substituted dialkylamino$_{(C≤12)}$, an oxygen linked antibody, or a nitrogen linked antibody;
  $X_1$ and $X_2$ are each independently selected from —O—, —S—, —NR$_8$—, or —NR$_9$NR$_{10}$—, wherein:

$R_8$, $R_9$, and $R_{10}$ are each independently selected from hydrogen, alkyl$_{(C \leq 12)}$, substituted alkyl$_{(C \leq 12)}$, cycloalkyl$_{(C \leq 12)}$, or substituted cycloalkyl$_{(C \leq 12)}$;
or a pharmaceutically acceptable salt thereof.

5. The compound of claim 1, wherein the formula is further defined as:

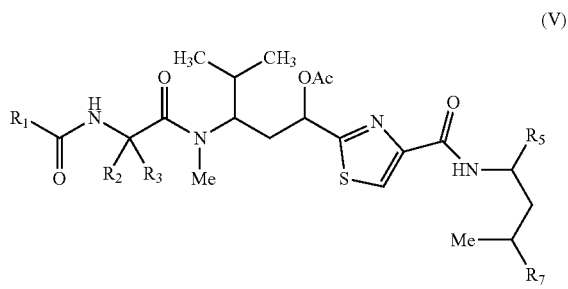

(V)

wherein:
- $R_1$ is heterocycloalkyl$_{(C \leq 12)}$ or substituted heterocycloalkyl$_{(C \leq 12)}$;
- $R_2$ is cycloalkyl$_{(C \leq 12)}$ or substituted cycloalkyl$_{(C \leq 12)}$;
- $R_3$ is hydrogen;
- $R_5$ is aryl$_{(C \leq 12)}$, aralkyl$_{(C \leq 12)}$, heteroaryl$_{(C \leq 12)}$, heteroaralkyl$_{(C \leq 12)}$, or a substituted version of any of these groups; or is -alkanediyl$_{(C \leq 6)}$-arenediyl$_{(C \leq 12)}$-$Y_3$ or a substituted version of any of these groups; wherein:
  - $Y_3$ is alkoxy$_{(C \leq 12)}$, aryloxy$_{(C \leq 12)}$, an oxygen linked antibody, —C(O)-alkoxy$_{(C \leq 12)}$, —C(O)-alkylamino$_{(C \leq 12)}$, —C(O)-dialkylamino$_{(C \leq 12)}$, —C(O)-aryloxy$_{(C \leq 12)}$, —C(O)-arylamino$_{(C \leq 12)}$, —C(O)—$Y_4$; or a substituted version of any of these groups; wherein:
    - $Y_4$ is a nitrogen or an oxygen linked antibody; and
  - $R_7$ is —C(O)—$Y_5$; wherein
    - $Y_5$ is amino, hydroxy, alkoxy$_{(C \leq 12)}$, substituted alkoxy$_{(C \leq 12)}$, alkylamino$_{(C \leq 12)}$, substituted alkylamino$_{(C \leq 12)}$, dialkylamino$_{(C \leq 12)}$, substituted dialkylamino$_{(C \leq 12)}$, an oxygen linked antibody, or a nitrogen linked antibody;

or a pharmaceutically acceptable salt thereof.

6. The compound of claim 1, wherein the formula is further defined as:

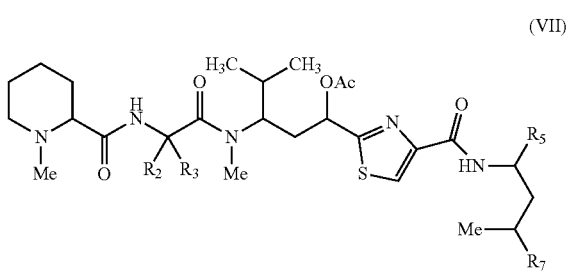

(VII)

wherein:
- $R_2$ is cycloalkyl$_{(C \leq 12)}$ or substituted cycloalkyl$_{(C \leq 12)}$;
- $R_3$ is hydrogen;
- $R_5$ is aryl$_{(C \leq 12)}$, aralkyl$_{(C \leq 12)}$, heteroaryl$_{(C \leq 12)}$, heteroaralkyl$_{(C \leq 12)}$, or a substituted version of any of these groups; or is -alkanediyl$_{(C \leq 6)}$-arenediyl$_{(C \leq 12)}$-$Y_3$ or a substituted version of any of these groups; wherein:
  - $Y_3$ is alkoxy$_{(C \leq 12)}$, aryloxy$_{(C \leq 12)}$, an oxygen linked antibody, —C(O)-alkoxy$_{(C \leq 12)}$, —C(O)-alkylamino$_{(C \leq 12)}$, —C(O)-dialkylamino$_{(C \leq 12)}$, —C(O)-aryloxy$_{(C \leq 12)}$, —C(O)-arylamino$_{(C \leq 12)}$, —C(O)—$Y_4$; or a substituted version of any of these groups; wherein:
    - $Y_4$ is a nitrogen or an oxygen linked antibody; and
  - $R_7$ is —C(O)—$Y_5$; wherein
    - $Y_5$ is amino, hydroxy, alkoxy$_{(C \leq 12)}$, substituted alkoxy$_{(C \leq 12)}$, alkylamino$_{(C \leq 12)}$, substituted alkylamino$_{(C \leq 12)}$, dialkylamino$_{(C \leq 12)}$, substituted dialkylamino$_{(C \leq 12)}$, an oxygen linked antibody, or a nitrogen linked antibody;

or a pharmaceutically acceptable salt thereof.

7. The compound of claim 1, wherein $R_2$ is cycloalkyl$_{(C \leq 12)}$ or substituted cycloalkyl$_{(C \leq 12)}$.

8. The compound of claim 1, wherein $R_4$ is:

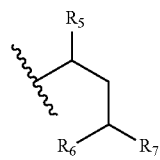

wherein:
- $R_5$ is aryl$_{(C \leq 12)}$, aralkyl$_{(C \leq 12)}$, heteroaryl$_{(C \leq 12)}$, heteroaralkyl$_{(C \leq 12)}$, or a substituted version of any of these groups; or is -alkanediyl$_{(C \leq 6)}$-arenediyl$_{(C \leq 12)}$-$Y_3$ or a substituted version of any of these groups; wherein:
  - $Y_3$ is alkoxy$_{(C \leq 12)}$, aryloxy$_{(C \leq 12)}$, an oxygen linked antibody, —C(O)-alkoxy$_{(C \leq 12)}$, —C(O)-alkylamino$_{(C \leq 12)}$, —C(O)-dialkyl-amino$_{(C \leq 12)}$, —C(O)-aryloxy$_{(C \leq 12)}$, —C(O)-arylamino$_{(C \leq 12)}$, —C(O)—$Y_4$; or a substituted version of any of these groups; wherein:
    - $Y_4$ is a nitrogen linked antibody or an oxygen linked antibody;
- $R_6$ is hydrogen, alkyl$_{(C \leq 8)}$, or substituted alkyl$_{(C \leq 8)}$;
- $R_7$ is —C(O)—$Y_5$; wherein
  - $Y_5$ is amino, hydroxy, alkoxy$_{(C \leq 12)}$, substituted alkoxy$_{(C \leq 12)}$, alkylamino$_{(C \leq 12)}$, substituted alkylamino$_{(C \leq 12)}$, dialkylamino$_{(C \leq 12)}$, substituted dialkylamino$_{(C \leq 12)}$, an oxygen linked antibody, or a nitrogen linked antibody.

9. The compound of claim 8, wherein $R_5$ is aralkyl$_{(C \leq 12)}$ or substituted aralkyl$_{(C \leq 12)}$.

10. The compound of claim 8, wherein $R_6$ is alkyl$_{(C \leq 12)}$ or substituted alkyl$_{(C \leq 12)}$.

11. The compound of claim 8, wherein $R_7$ is —CO$_2$H, —C(O)—$Y_5$ wherein $Y_5$ is alkoxy$_{(C \leq 12)}$ or substituted alkoxy$_{(C \leq 12)}$, or —C(O)—$Y_5$ wherein $Y_5$ is an oxygen linked antibody or a nitrogen linked antibody.

12. The compound of claim 1, wherein $X_1$ or $X_2$ is —NR$_8$—, wherein $R_8$ is hydrogen, alkyl$_{(C \leq 12)}$, substituted alkyl$_{(C \leq 12)}$, cycloalkyl$_{(C \leq 12)}$, or substituted cycloalkyl$_{(C \leq 12)}$.

13. The compound of claim 1, wherein $A_1$ is -alkanediyl$_{(C \leq 12)}$-heteroarenediyl$_{(C \leq 12)}$, wherein the alkanediyl is substituted with an amido$_{(C \leq 8)}$ or acyloxy$_{(C \leq 8)}$ group or a substituted version thereof.

14. The compound of claim 1, wherein the formula is further defined as:

319
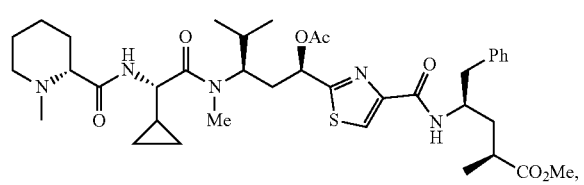 [SMILES: COC(=O)[C@@H](C)C[C@H](Cc1ccccc1)NC(=O)c1csc([C@@H](C[C@H](C(C)C)N(C)C(=O)[C@@H](NC(=O)[C@H]2CCCCN2C)C2CC2)OC(C)=O)n1]
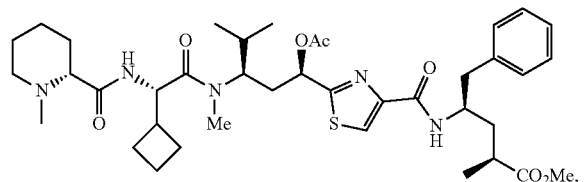
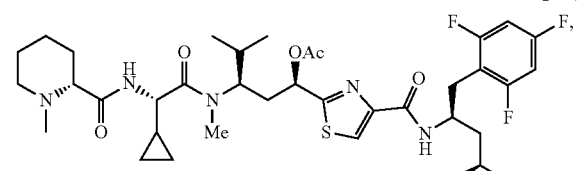
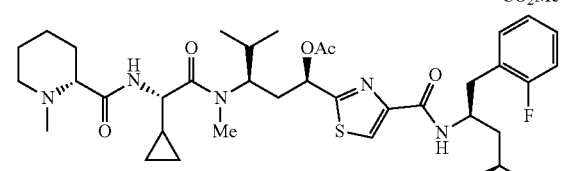
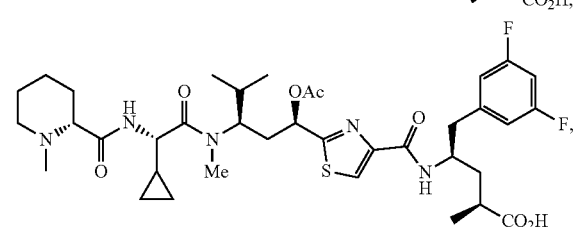
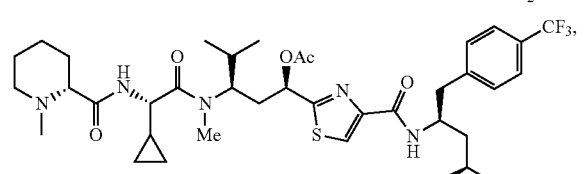
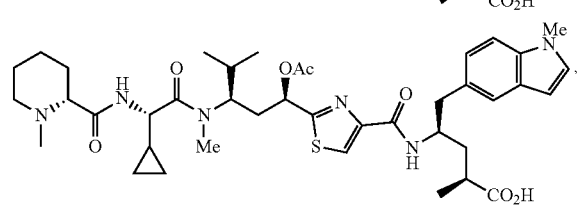
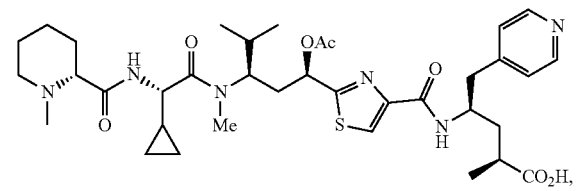
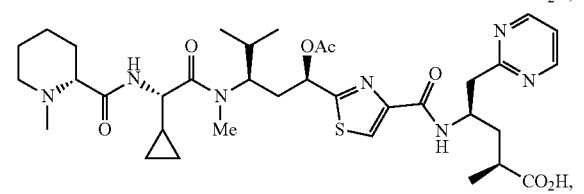
320
-continued
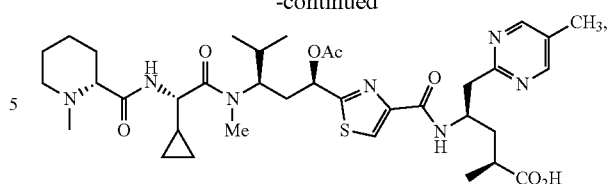
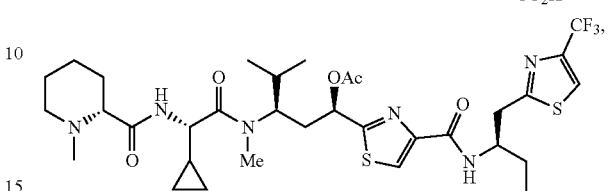
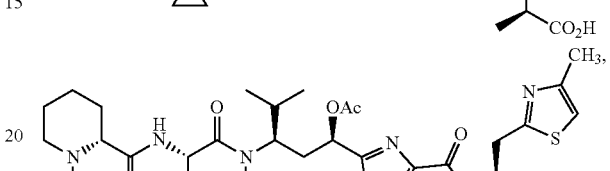
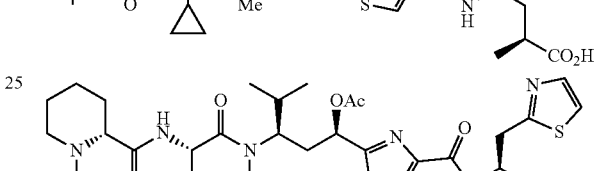
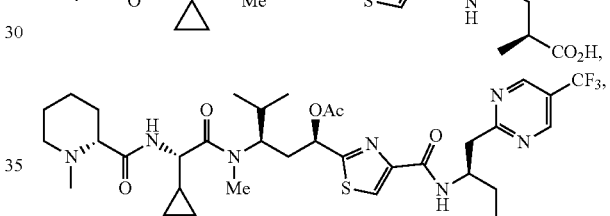
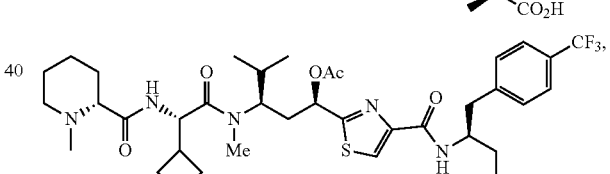
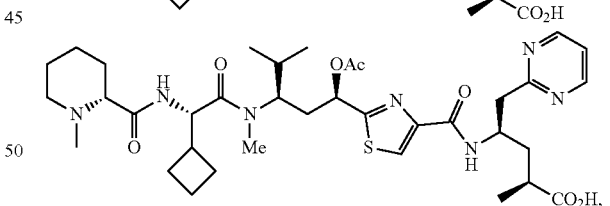
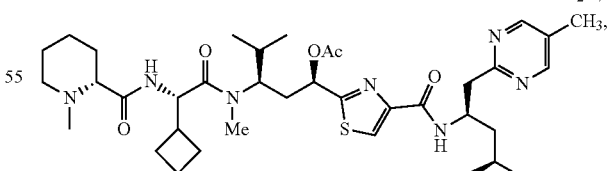
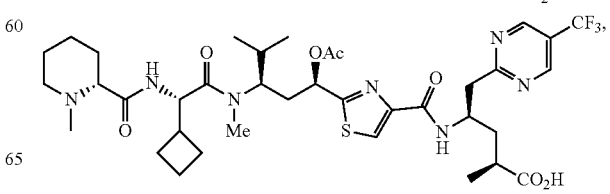

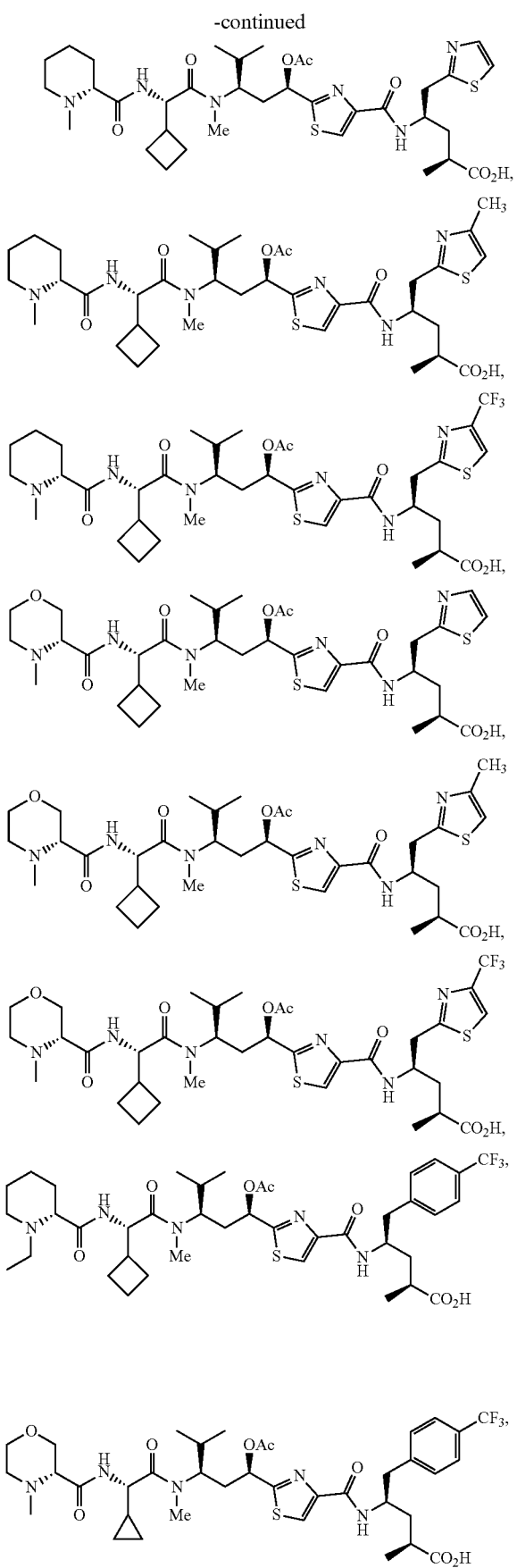
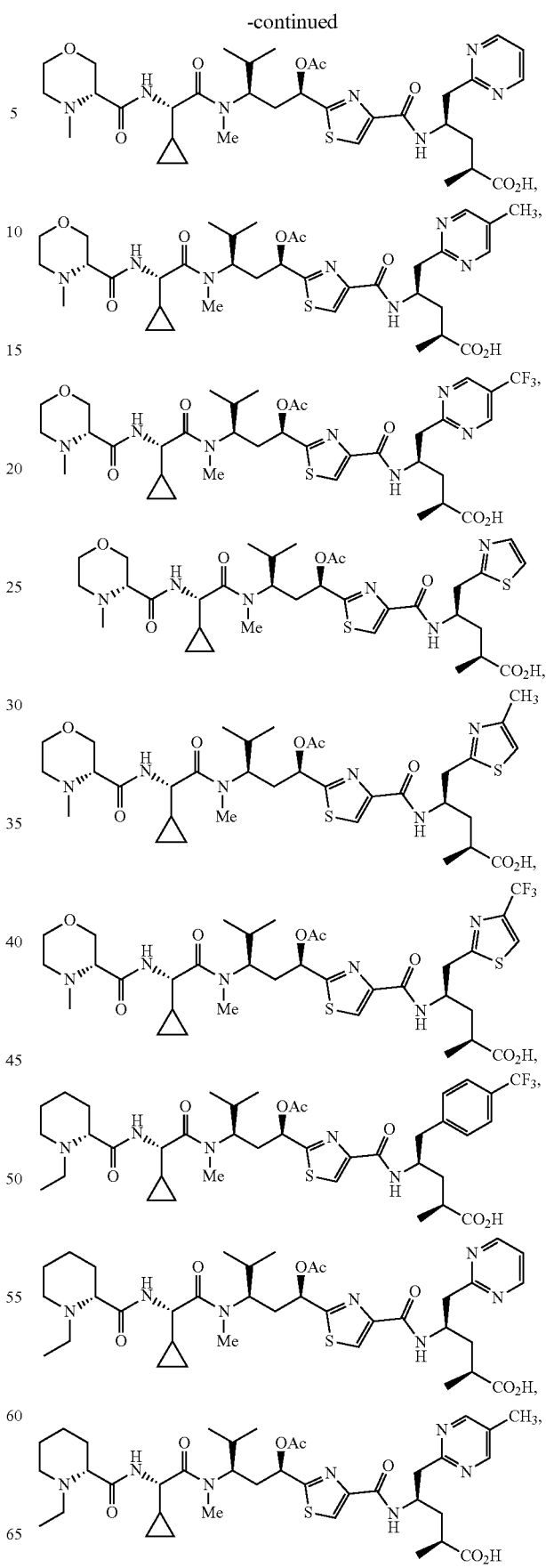

323
-continued
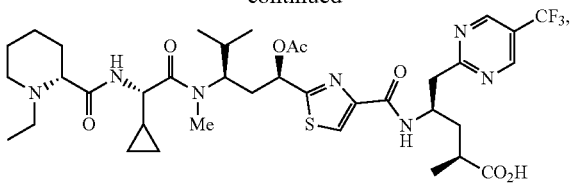
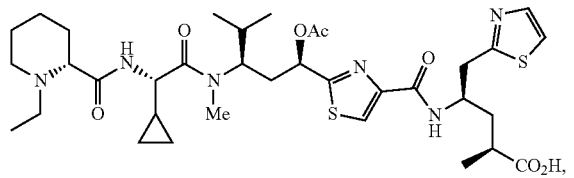 [SMILES: CC(=O)O[C@H](C[C@H](C(C)C)N(C)C(=O)[C@@H](NC(=O)[C@H]1COCCN1C)C1CCC1)c1nc(C(=O)N[C@@H](Cc2nccs2)C[C@H](C)C(=O)O)cs1]
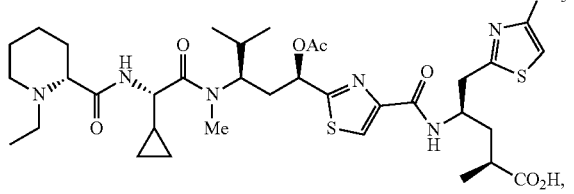
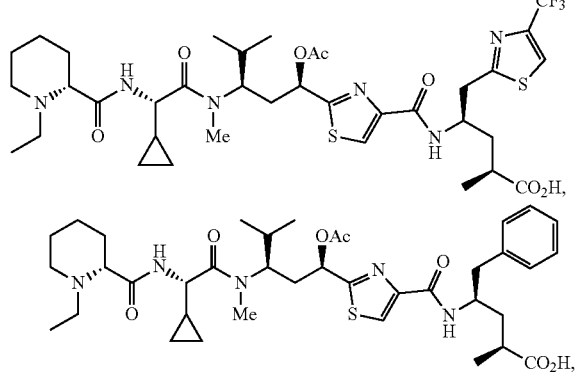
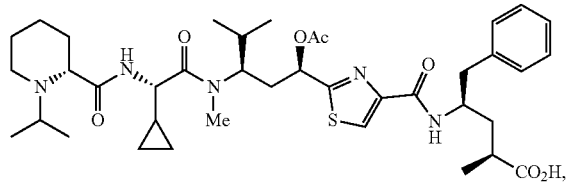
324
-continued
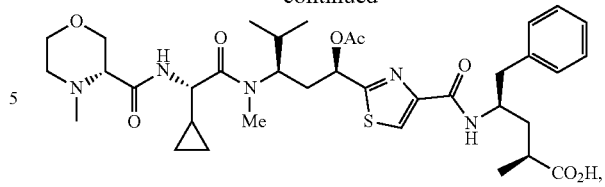
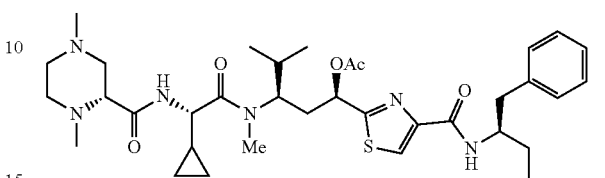
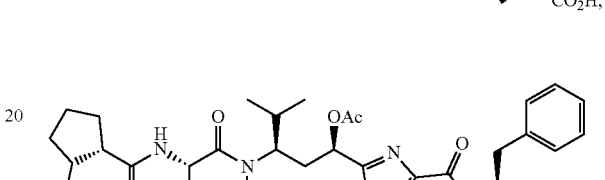
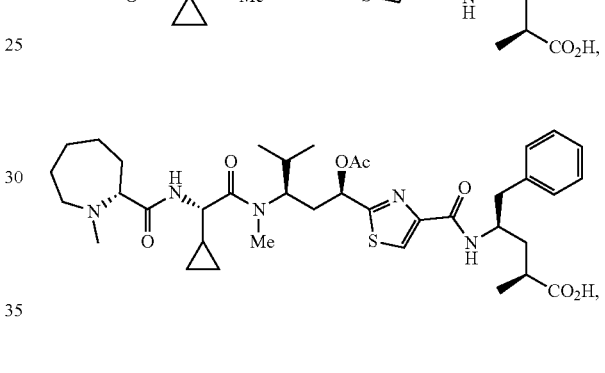
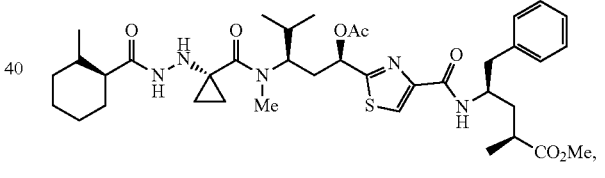
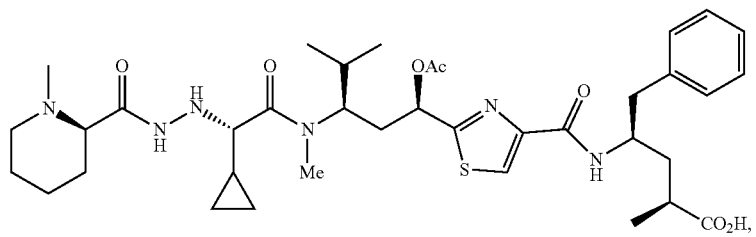
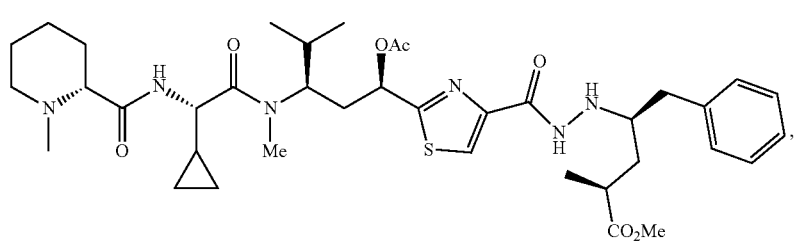

-continued
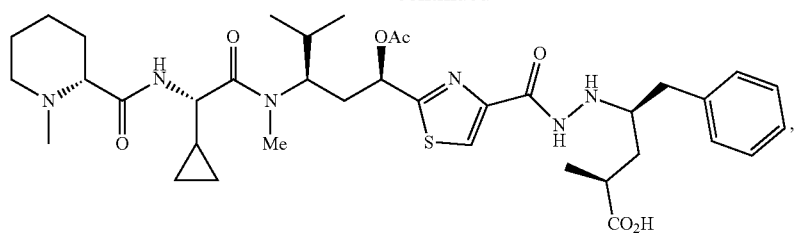
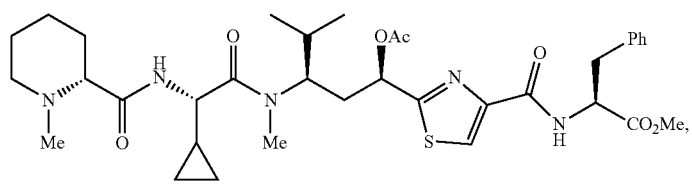
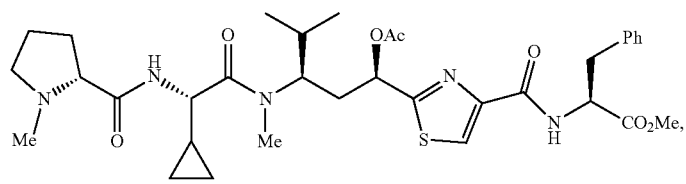
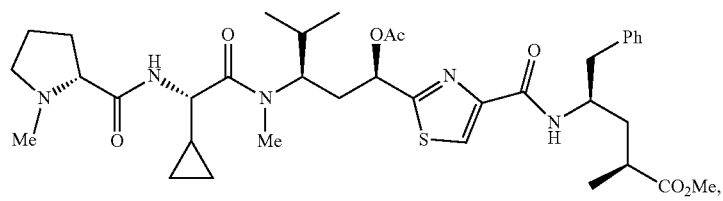
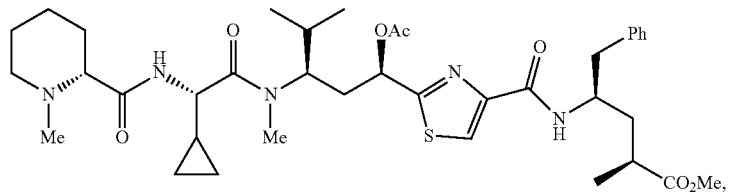
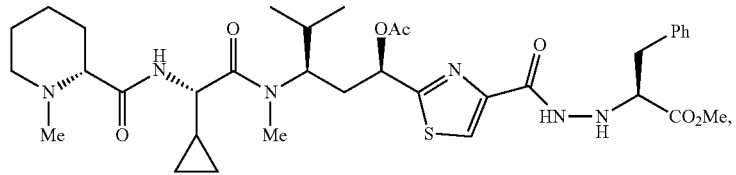
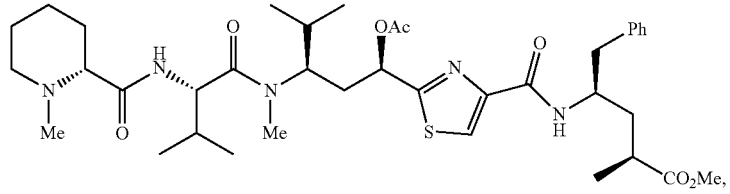
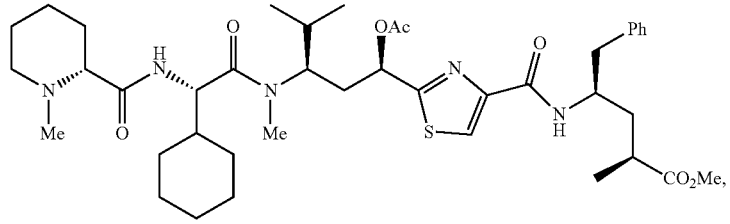

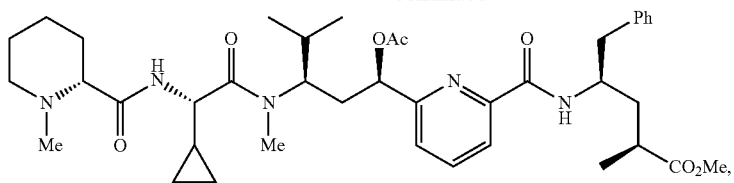
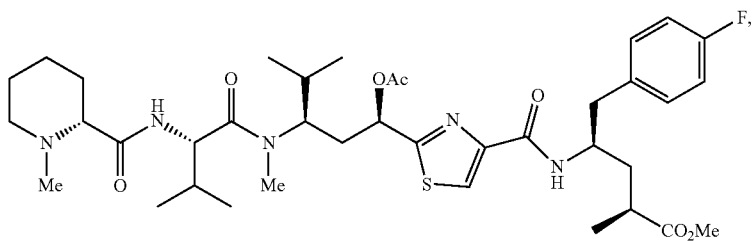
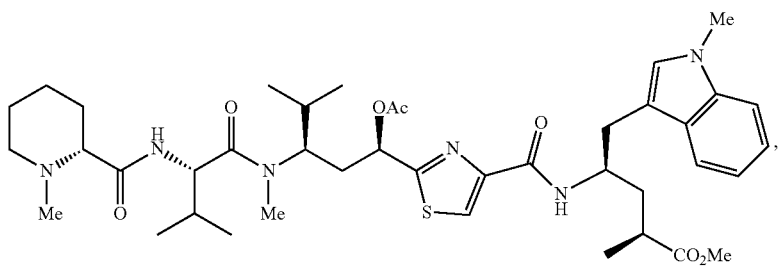
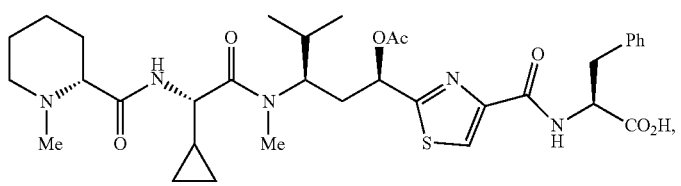
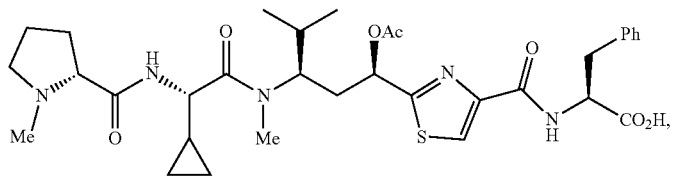
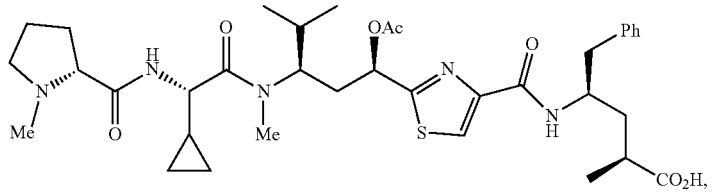
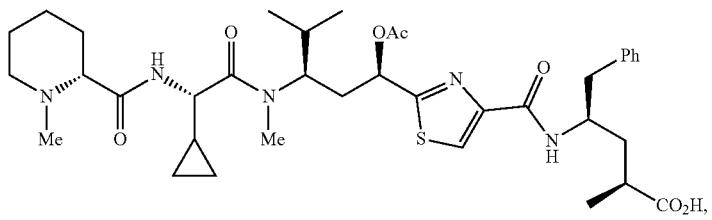
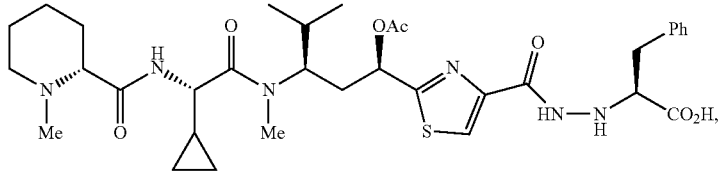

-continued
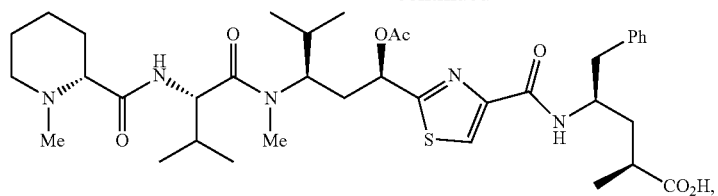
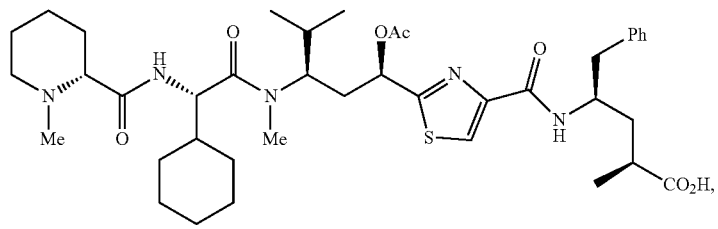
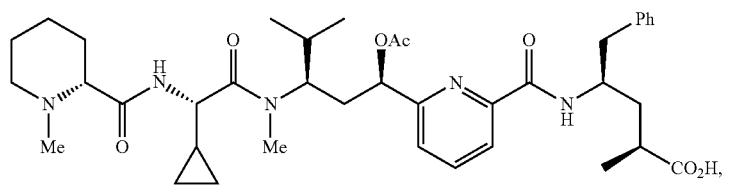
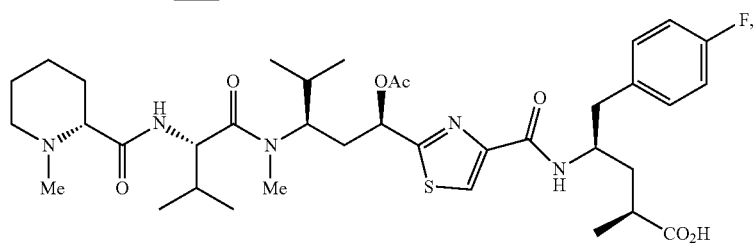
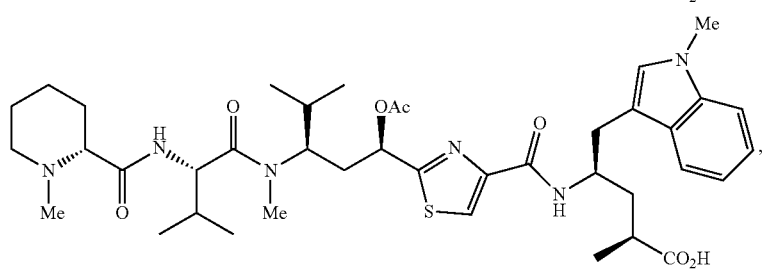
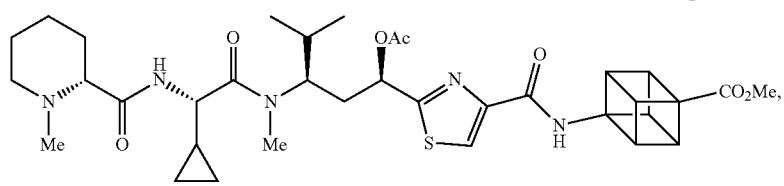
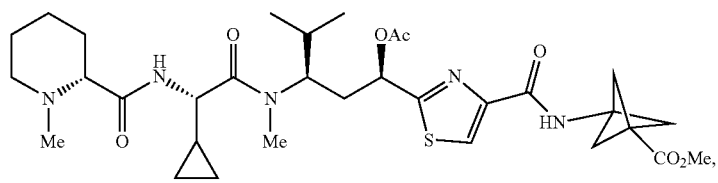
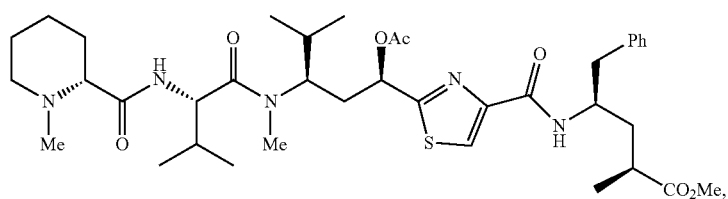

-continued
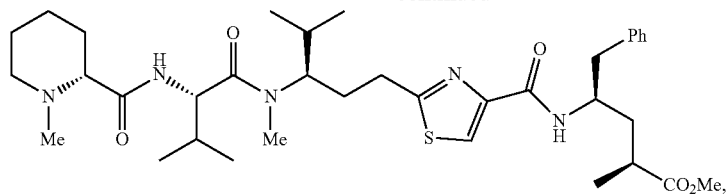
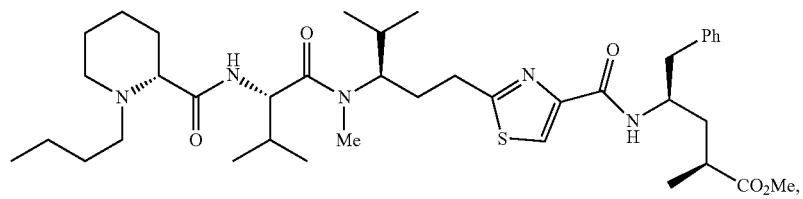
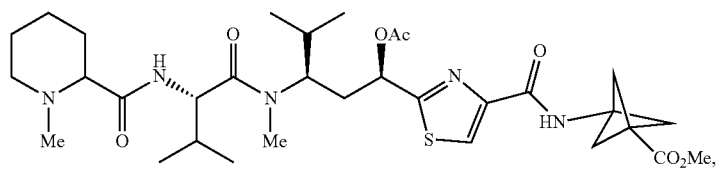
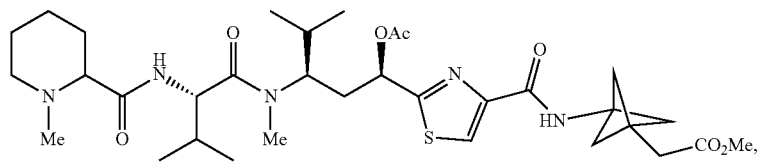
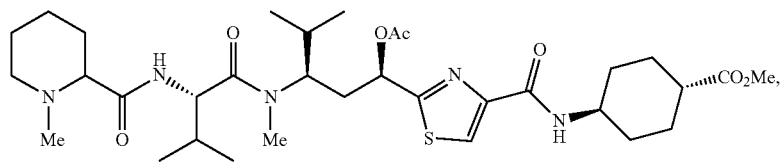
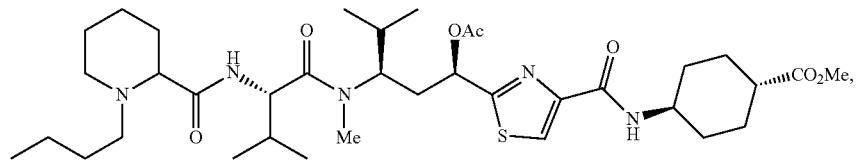
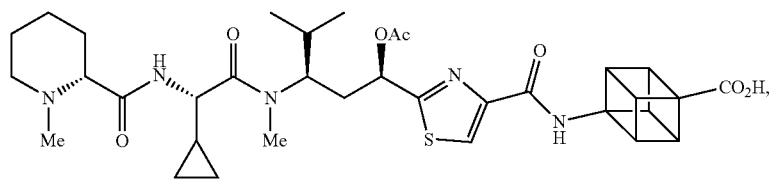
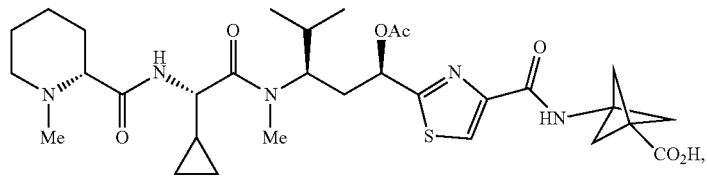
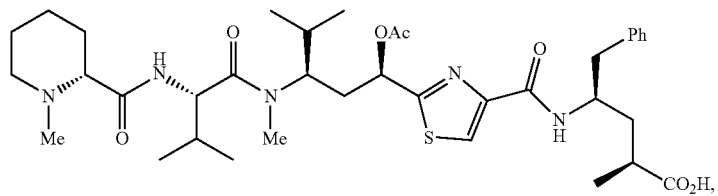

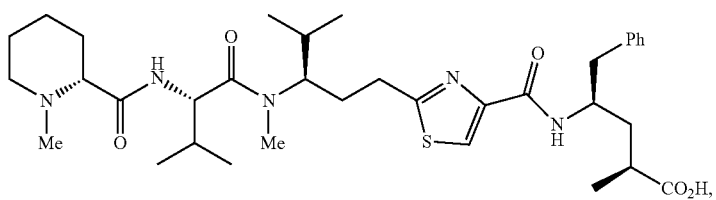
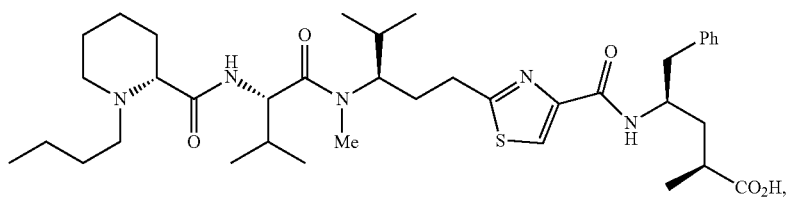
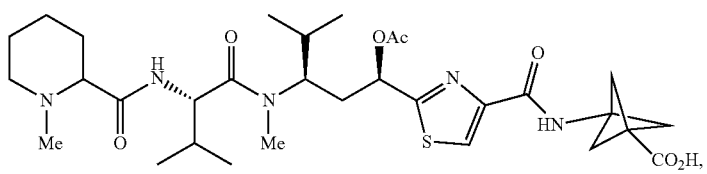
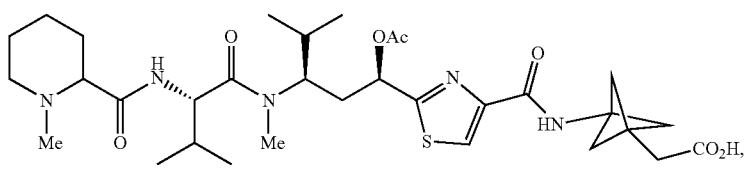
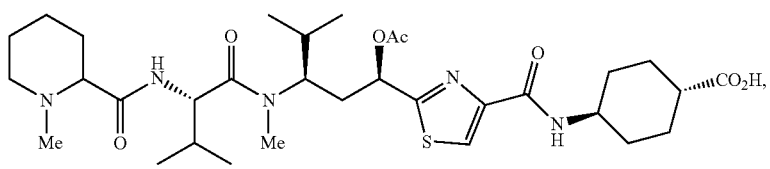
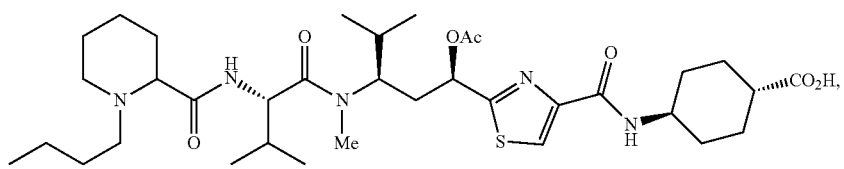
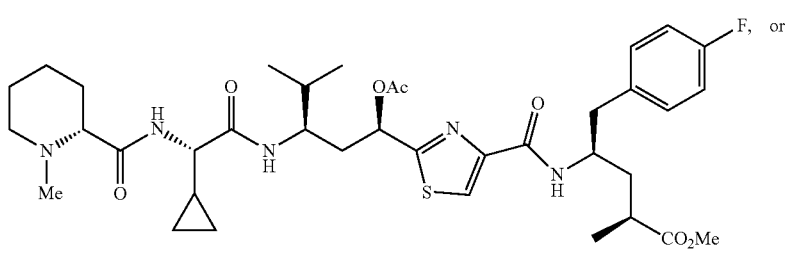

-continued

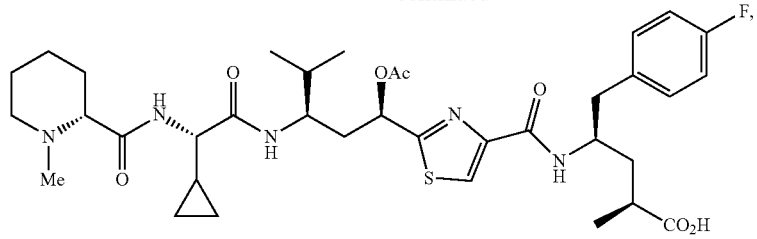

or a pharmaceutically acceptable salt thereof.

15. A pharmaceutical composition comprising a compound of the formula:

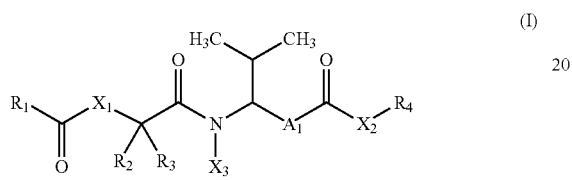

(I)

wherein:
R$_1$ is heterocycloalkyl$_{(C≤12)}$ or substituted heterocycloalkyl$_{(C≤12)}$;
R$_2$ is isopropyl, cycloalkyl$_{(C≤12)}$, or substituted cycloalkyl$_{(C≤12)}$;
R$_3$ is hydrogen;
R$_4$ is cycloalkyl$_{(C≤12)}$, fused cycloalkyl$_{(C≤12)}$, aralkyl$_{(C≤12)}$, substituted cycloalkyl$_{(C≤12)}$, substituted fused cycloalkyl$_{(C≤12)}$, substituted aralkyl$_{(C≤12)}$, fused cycloalkylamino$_{(C≤12)}$, substituted fused cycloalkylamino$_{(C≤12)}$, or a structure of the formula:

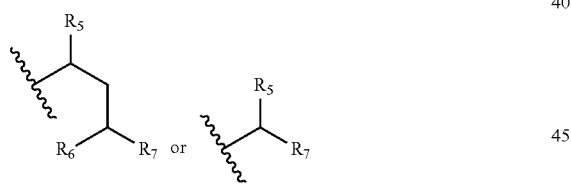

wherein:
R$_5$ is aryl$_{(C≤12)}$, aralkyl$_{(C≤12)}$, heteroaryl$_{(C≤12)}$, heteroaralkyl$_{(C≤12)}$, or a substituted version of any of these groups; or is -alkanediyl$_{(C≤6)}$-arenediyl$_{(C≤12)}$-Y$_3$ or a substituted version of any of these groups; wherein:
Y$_3$ is alkoxy$_{(C≤12)}$, aryloxy$_{(C≤12)}$, an oxygen linked antibody, —C(O)-alkoxy$_{(C≤12)}$, —C(O)-alkylamino$_{(C≤12)}$, —C(O)-dialkylamino$_{(C≤12)}$, —C(O)-aryloxy$_{(C≤12)}$, —C(O)-arylamino$_{(C≤12)}$, —C(O)—Y$_4$; or a substituted version of any of these groups; wherein:
Y$_4$ is a nitrogen linked antibody or an oxygen linked antibody;
R$_6$ is hydrogen, alkyl$_{(C≤8)}$, or substituted alkyl$_{(C≤8)}$;
R$_7$ is —C(O)—Y$_5$; wherein
Y$_5$ is amino, hydroxy, alkoxy$_{(C≤12)}$, substituted alkoxy$_{(C≤12)}$, alkylamino$_{(C≤12)}$, substituted alkylamino$_{(C≤12)}$, dialkylamino$_{(C≤12)}$, substituted dialkylamino$_{(C≤12)}$, an oxygen linked antibody, or a nitrogen linked antibody;

X$_1$ and X$_2$ are each independently selected from a covalent bond, —O—, —S—, —NR$_8$—, or —NR$_9$NR$_{10}$—, wherein:
R$_8$, R$_9$, and R$_{10}$ are each independently selected from hydrogen, alkyl$_{(C≤12)}$, substituted alkyl$_{(C≤12)}$, cycloalkyl$_{(C≤12)}$, or substituted cycloalkyl$_{(C≤12)}$;
X$_3$ is hydrogen, alkyl$_{(C≤12)}$, or substituted alkyl$_{(C≤12)}$; and
A$_1$ is —C(O)NR$_{13}$-fused cycloalkanediyl$_{(C≤12)}$, -alkanediyl$_{(C≤12)}$-heteroarene-diyl$_{(C≤12)}$, -alkanediyl$_{(C≤12)}$-heteroarenediyl$_{(C≤12)}$, wherein the alkanediyl is substituted with an amido$_{(C≤8)}$ or acyloxy$_{(C≤8)}$ group, or a substituted version of any of these groups, wherein:
R$_{13}$ is hydrogen, alkyl$_{(C≤12)}$, substituted alkyl$_{(C≤12)}$, cycloalkyl$_{(C≤12)}$, or substituted cycloalkyl$_{(C≤12)}$;
provided that X$_3$ is not hydrogen, methyl, hydroxymethyl, or acetoxymethyl, when R$_2$ or R$_3$ is sec-butyl, R$_5$ is benzyl, R$_7$ is —CO$_2$H, and R$_1$ is 2-N-methylpiperidinyl;
and an excipient.

16. A method of treating cancer in a patient in need thereof comprising administering to the patient a therapeutically effective amount of a compound of the formula:

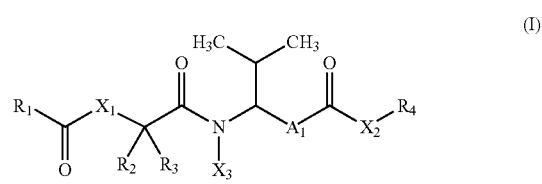

(I)

wherein:
R$_1$ is heterocycloalkyl$_{(C≤12)}$ or substituted heterocycloalkyl$_{(C≤12)}$;
R$_2$ is isopropyl, cycloalkyl$_{(C≤12)}$, or substituted cycloalkyl$_{(C≤12)}$;
R$_3$ is hydrogen;
R$_4$ is cycloalkyl$_{(C≤12)}$, fused cycloalkyl$_{(C≤12)}$, aralkyl$_{(C≤12)}$, substituted cycloalkyl$_{(C≤12)}$, substituted fused cycloalkyl$_{(C≤12)}$, substituted aralkyl$_{(C≤12)}$, fused cycloalkylamino$_{(C≤12)}$, substituted fused cycloalkylamino$_{(C≤12)}$, or a structure of the formula:

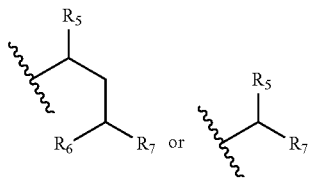

wherein:
R$_5$ is aryl$_{(C\leq12)}$, aralkyl$_{(C\leq12)}$, heteroaryl$_{(C\leq12)}$, heteroaralkyl$_{(C\leq12)}$, or a substituted version of any of these groups; or is -alkanediyl$_{(C\leq6)}$-arenediyl$_{(C\leq12)}$-Y$_3$ or a substituted version of any of these groups; wherein:
Y$_3$ is alkoxy$_{(C\leq12)}$, aryloxy$_{(C\leq12)}$, an oxygen linked antibody, —C(O)-alkoxy$_{(C\leq12)}$, —C(O)-alkylamino$_{(C\leq12)}$, —C(O)-dialkylamino$_{(C\leq12)}$, —C(O)-aryloxy$_{(C\leq12)}$, —C(O)-arylamino$_{(C\leq12)}$, —C(O)—Y$_4$; or a substituted version of any of these groups; wherein:
Y$_4$ is a nitrogen linked antibody or an oxygen linked antibody;
R$_6$ is hydrogen, alkyl$_{(C\leq8)}$, or substituted alkyl$_{(C\leq8)}$;
R$_7$ is —C(O)—Y$_5$; wherein
Y$_5$ is amino, hydroxy, alkoxy$_{(C\leq12)}$, substituted alkoxy$_{(C\leq12)}$, alkylamino$_{(C\leq12)}$, substituted alkylamino$_{(C\leq12)}$, dialkylamino$_{(C\leq12)}$, substituted dialkylamino$_{(C\leq12)}$, an oxygen linked antibody, or a nitrogen linked antibody;
X$_1$ and X$_2$ are each independently selected from a covalent bond, —O—, —S—, —NR$_8$—, or —NR$_9$NR$_{10}$—, wherein:
R$_8$, R$_9$, and R$_{10}$ are each independently selected from hydrogen, alkyl$_{(C\leq12)}$, substituted alkyl$_{(C\leq12)}$, cycloalkyl$_{(C\leq12)}$, or substituted cycloalkyl$_{(C\leq12)}$;
X$_3$ is hydrogen, alkyl$_{(C\leq12)}$, or substituted alkyl$_{(C\leq12)}$; and
A$_1$ is —C(O)NR$_{13}$-fused cycloalkanediyl$_{(C\leq12)}$, -alkanediyl$_{(C\leq12)}$-heteroarene-diyl$_{(C\leq12)}$, -alkanediyl$_{(C\leq12)}$-heteroarenediyl$_{(C\leq12)}$, wherein the alkanediyl is substituted with an amido$_{(C\leq8)}$ or acyloxy$_{(C\leq8)}$ group, or a substituted version of any of these groups, wherein:
R$_{13}$ is hydrogen, alkyl$_{(C\leq12)}$, substituted alkyl$_{(C\leq12)}$, cycloalkyl$_{(C\leq12)}$, or substituted cycloalkyl$_{(C\leq12)}$;
provided that X$_3$ is not hydrogen, methyl, hydroxymethyl, or acetoxymethyl, when R$_2$ or R$_3$ is sec-butyl, R$_5$ is benzyl, R$_7$ is —CO$_2$H, and R$_1$ is 2-N-methylpiperidinyl.

17. A antibody-drug conjugate comprising:

A-L-(X)$_y$  (XI)

wherein:
A is an antibody;
L is a covalent bond or a difunctional linker;
X is a compound of the formula:

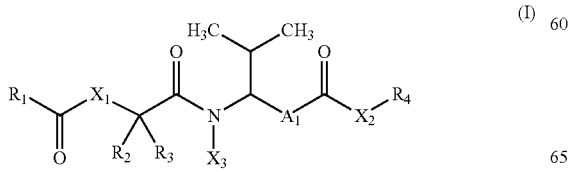

(I)

wherein:
R$_1$ is heterocycloalkyl$_{(C\leq12)}$ or substituted heterocycloalkyl$_{(C\leq12)}$;
R$_2$ isopropyl, cycloalkyl$_{(C\leq12)}$, or substituted cycloalkyl$_{(C\leq12)}$;
R$_3$ is hydrogen;
R$_4$ is cycloalkyl$_{(C\leq12)}$, fused cycloalkyl$_{(C\leq12)}$, aralkyl$_{(C\leq12)}$, substituted cycloalkyl$_{(C\leq12)}$, substituted fused cycloalkyl$_{(C\leq12)}$, substituted aralkyl$_{(C\leq12)}$, fused cycloalkylamino$_{(C\leq12)}$, substituted fused cycloalkylamino$_{(C\leq12)}$, or a structure of the formula:

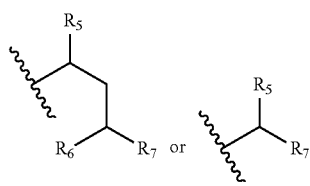

wherein:
R$_5$ is aryl$_{(C\leq12)}$, aralkyl$_{(C\leq12)}$, heteroaryl$_{(C\leq12)}$, heteroaralkyl$_{(C\leq12)}$, or a substituted version of any of these groups; or is -alkanediyl$_{(C\leq6)}$-arenediyl$_{(C\leq12)}$-Y$_3$ or a substituted version of any of these groups; wherein:
Y$_3$ is alkoxy$_{(C\leq12)}$, aryloxy$_{(C\leq12)}$, an oxygen linked antibody, —C(O)-alkoxy$_{(C\leq12)}$, —C(O)-alkylamino$_{(C\leq12)}$, —C(O)-dialkylamino$_{(C\leq12)}$, —C(O)-aryloxy$_{(C\leq12)}$, —C(O)-arylamino$_{(C\leq12)}$, —C(O)—Y$_4$; or a substituted version of any of these groups; wherein:
Y$_4$ is a nitrogen linked antibody or an oxygen linked antibody;
R$_6$ is hydrogen, alkyl$_{(C\leq8)}$, or substituted alkyl$_{(C\leq8)}$;
R$_7$ is —C(O)—Y$_5$; wherein
Y$_5$ is amino, hydroxy, alkoxy$_{(C\leq12)}$, substituted alkoxy$_{(C\leq12)}$, alkylamino$_{(C\leq12)}$, substituted alkylamino$_{(C\leq12)}$, dialkylamino$_{(C\leq12)}$, substituted dialkylamino$_{(C\leq12)}$, an oxygen linked antibody, or a nitrogen linked antibody;
X$_1$ and X$_2$ are each independently selected from a covalent bond, —O—, —S—, —NR$_8$—, or —NR$_9$NR$_{10}$—, wherein:
R$_8$, R$_9$, and R$_{10}$ are each independently selected from hydrogen, alkyl$_{(C\leq12)}$, substituted alkyl$_{(C\leq12)}$, cycloalkyl$_{(C\leq12)}$, or substituted cycloalkyl$_{(C\leq12)}$;
X$_3$ is hydrogen, alkyl$_{(C\leq12)}$, or substituted alkyl$_{(C\leq12)}$; and
A$_1$ is —C(O)NR$_{13}$-fused cycloalkanediyl$_{(C\leq12)}$, -alkanediyl$_{(C\leq12)}$-heteroarene-diyl$_{(C\leq12)}$, -alkanediyl$_{(C\leq12)}$-heteroarenediyl$_{(C\leq12)}$, wherein the alkanediyl is substituted with an amido$_{(C\leq8)}$ or acyloxy$_{(C\leq8)}$ group, or a substituted version of any of these groups, wherein:
R$_{13}$ is hydrogen, alkyl$_{(C\leq12)}$, substituted alkyl$_{(C\leq12)}$, cycloalkyl$_{(C\leq12)}$, or substituted cycloalkyl$_{(C\leq12)}$;
provided that X$_3$ is not hydrogen, methyl, hydroxymethyl, or acetoxymethyl, when R$_2$ or R$_3$ is sec-butyl, R$_5$ is benzyl, R$_7$ is —CO$_2$H, and R$_1$ is 2-N-methylpiperidinyl; and
y is an integer selected from 1, 2, 3, 4, 5, 6, 7, 8, 9, 10, 11, 12, 13, 14, 15, 16, 17, 18, 19, or 20.

18. The compound of claim 1 further defined as:

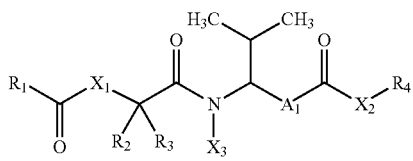

(I)

wherein:
- $R_1$ is heterocycloalkyl$_{(C \le 12)}$ or substituted heterocycloalkyl$_{(C \le 12)}$;
- $R_2$ is isopropyl, cycloalkyl$_{(C \le 12)}$, or substituted cycloalkyl$_{(C \le 12)}$;
- $R_3$ is hydrogen;
- $R_4$ is a structure of the formula:

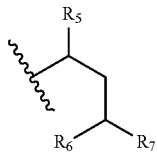

wherein:
- $R_5$ is aralkyl$_{(C \le 12)}$, heteroaralkyl$_{(C \le 12)}$, or a substituted version of any of these groups;
- $R_6$ is hydrogen, alkyl$_{(C \le 8)}$, or substituted alkyl$_{(C \le 8)}$;
- $R_7$ is —C(O)—$Y_5$; wherein
  - $Y_5$ is amino, hydroxy, alkoxy$_{(C \le 12)}$, substituted alkoxy$_{(C \le 12)}$, alkylamino$_{(C \le 12)}$, substituted alkylamino$_{(C \le 12)}$, dialkylamino$_{(C \le 12)}$, substituted dialkylamino$_{(C \le 12)}$, an oxygen linked antibody, or a nitrogen linked antibody;
- $X_1$ and $X_2$ are each independently selected from —O— or —NR$_8$—, wherein:
  - $R_8$ is hydrogen, alkyl$_{(C \le 12)}$, substituted alkyl$_{(C \le 12)}$, cycloalkyl$_{(C \le 12)}$, or substituted cycloalkyl$_{(C \le 12)}$;
- $X_3$ is alkyl$_{(C \le 12)}$ or substituted alkyl$_{(C \le 12)}$; and
- $A_1$ is -alkanediyl$_{(C \le 12)}$-heteroarenediyl$_{(C \le 12)}$, -alkanediyl$_{(C \le 12)}$-hetero-arenediyl$_{(C \le 12)}$, wherein the alkanediyl is substituted with an amido$_{(C \le 8)}$ or acyloxy$_{(C \le 8)}$ group, or a substituted version of any of these groups;
- provided that $X_3$ is not methyl, hydroxymethyl, or acetoxymethyl, when $R_2$ or $R_3$ is sec-butyl, $R_5$ is benzyl, $R_7$ is —CO$_2$H, and $R_1$ is 2-N-methylpiperidinyl;

or a pharmaceutically acceptable salt thereof.

* * * * *

UNITED STATES PATENT AND TRADEMARK OFFICE
CERTIFICATE OF CORRECTION

| | | |
|---|---|---|
| PATENT NO. | : 10,808,007 B2 | Page 1 of 1 |
| APPLICATION NO. | : 15/553674 | |
| DATED | : October 20, 2020 | |
| INVENTOR(S) | : Nicolaou et al. | |

It is certified that error appears in the above-identified patent and that said Letters Patent is hereby corrected as shown below:

In the Claims

In Claim 14, Column 324, Lines 18-25, delete

"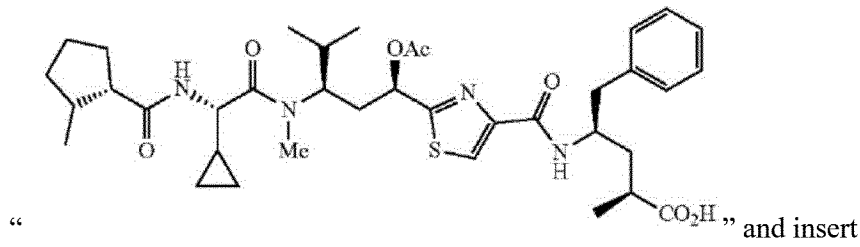" and insert

--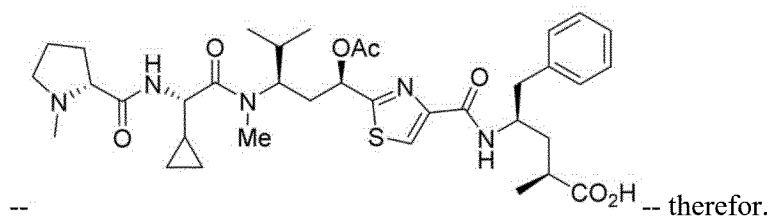 -- therefor.

In Claim 14, Column 324, Lines 36-43, delete

"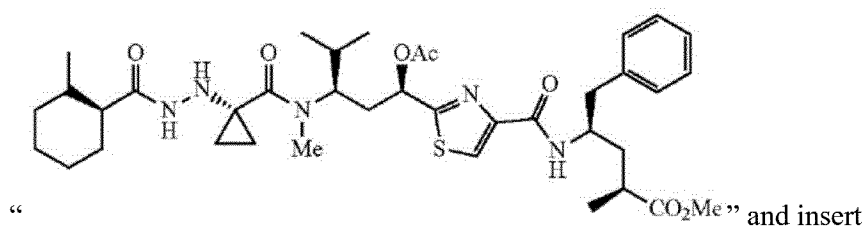" and insert

--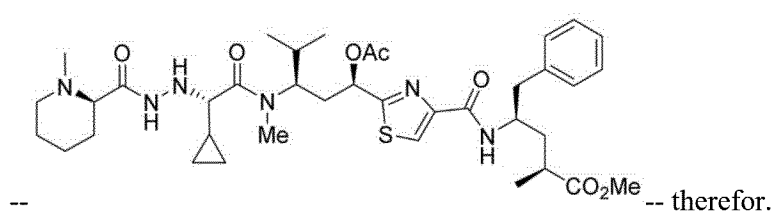 -- therefor.

Signed and Sealed this
Sixth Day of April, 2021

Drew Hirshfeld
*Performing the Functions and Duties of the
Under Secretary of Commerce for Intellectual Property and
Director of the United States Patent and Trademark Office*